United States Patent
Achiron et al.

(10) Patent No.: US 10,993,948 B2
(45) Date of Patent: *May 4, 2021

(54) RNA POLYMERASE I INHIBITORS AND USES THEREOF

(71) Applicant: Tel HaShomer Medical Research Infrastructure and Services Ltd., Ramat-Gan (IL)

(72) Inventors: Anat Achiron, Tel-Aviv (IL); Roi Mashiach, Kiryat-Ono (IL); Michael Gurevich, Rechovot (IL)

(73) Assignee: Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/996,544

(22) Filed: Jun. 4, 2018

(65) Prior Publication Data

US 2018/0264002 A1  Sep. 20, 2018

Related U.S. Application Data

(63) Continuation of application No. 15/626,198, filed on Jun. 19, 2017, now Pat. No. 10,022,382, which is a continuation of application No. 14/742,907, filed on Jun. 18, 2015, now Pat. No. 9,688,697, which is a continuation-in-part of application No. PCT/IB2014/066402, filed on Nov. 27, 2014.

(60) Provisional application No. 61/910,060, filed on Nov. 28, 2013.

(51) Int. Cl.
| | | |
|---|---|---|
| A61K 31/551 | (2006.01) | |
| A61K 31/428 | (2006.01) | |
| A61K 31/4375 | (2006.01) | |
| A61K 31/4748 | (2006.01) | |
| C07D 413/14 | (2006.01) | |
| C07D 471/12 | (2006.01) | |
| C07D 513/14 | (2006.01) | |
| C12Q 1/6876 | (2018.01) | |

(52) U.S. Cl.
CPC .......... *A61K 31/551* (2013.01); *C07D 513/14* (2013.01); *C12Q 1/6876* (2013.01); *C12Q 2600/136* (2013.01); *C12Q 2600/158* (2013.01); *Y02A 50/30* (2018.01)

(58) Field of Classification Search
CPC ............... A61K 31/551; A61K 31/425; A61K 31/4375; A61K 31/4745; C07D 413/14; C07D 471/12; C07D 513/14
USPC ......................................... 514/218; 540/575
See application file for complete search history.

(56) References Cited

U.S. PATENT DOCUMENTS

| | | | |
|---|---|---|---|
| 9,688,697 B2 | 6/2017 | Achiron et al. | |
| 2007/0117770 A1 | 5/2007 | Drygin et al. | |
| 2008/0248001 A1 | 10/2008 | Bourke | |
| 2009/0093455 A1 | 4/2009 | Nagasawa et al. | |
| 2009/0093465 A1 | 4/2009 | Pierre et al. | |
| 2014/0086839 A1 | 3/2014 | Achiron et al. | |
| 2015/0284410 A1 | 10/2015 | Achiron et al. | |
| 2017/0290842 A1 | 10/2017 | Achiron et al. | |

FOREIGN PATENT DOCUMENTS

| | | |
|---|---|---|
| EP | 0983256 | 3/1997 |
| WO | WO 98/52933 | 11/1998 |
| WO | WO 03/081201 | 10/2003 |
| WO | WO 2007/022474 | 2/2007 |
| WO | WO 2008/081435 | 7/2008 |
| WO | WO 2008/131134 | 10/2008 |
| WO | WO 2009/046383 | 4/2009 |
| WO | WO 2010/113096 | 10/2010 |
| WO | WO 2012/123938 | 9/2012 |
| WO | WO 2015/079411 | 6/2015 |

OTHER PUBLICATIONS

Office Action dated Jul. 18, 2018 From the Israel Patent Office Re. Application No. 245839 and Its Translation Into English. (6 Pages).
Advisory Action Before the Filing of an Appeal Brief dated Mar. 28, 2016 From the US Patent and Trademark Office Re. U.S. Appl. No. 14/005,583.
Applicant-Initiated Interview Summary dated Mar. 14, 2017 From the US Patent and Trademark Office Re. U.S. Appl. No. 14/005,583 (4 pages).
Communication Pursuant to Article 94(3) EPC dated Apr. 5, 2016 From the European Patent Office Re. Application No. 12710797.7.
Communication Pursuant to Article 94(3) EPC dated Jan. 17, 2018 From the. European Patent Office Re. Application No. 14865441.1. (5 Pages).
International Preliminary Report on Patentability dated Jun. 9, 2016 From the International Bureau of WIPO Re. Application No. PCT/IB2014/066402.
International Preliminary Report on Patentability dated Sep. 26, 2013 From. The International Bureau of WIPO Re. Application No. PCT/IL2012/050061.
International Search Report and the Written Opinion dated Jul. 9, 2012 From the International Searching Authority Re. Application No. PCT/IL2012/050061.

(Continued)

*Primary Examiner* — Brenda L Coleman

(57) ABSTRACT

Provided are novel compounds which are capable of inhibiting an activity of RNA polymerase I, and uses thereof in treating diseases or disorders modulated by RNA polymerase I, preferably autoimmune diseases such as multiple sclerosis and proliferative diseases.

5 Claims, 16 Drawing Sheets

Specification includes a Sequence Listing.

(56) References Cited

OTHER PUBLICATIONS

International Search Report and the Written Opinion dated Feb. 15, 2015. From the International Searching Authority Re. Application No. PCT/IB2014/066402.
Notification of Office Action dated Sep. 30, 2014 From the State Intellectual Property Office of the People's Republic of China Re. Application No. 201280023297.2 and Its Translation Into English.
Office Action dated Jan. 17, 2016 From the Israel Patent Office Re. Application No. 228464 and Its Translation Into English.
Office Action dated Jul. 17, 2016 From the Israel Patent Office Re. Application. No. 228464 and Its Translation Into English.
Office Action dated Jun. 24, 2015 From the State Intellectual Property Office of the People's Republic of China Re. Application No. 201280023297.2 and Its Translation Into English.
Official Action dated Apr. 3, 2015 From the US Patent and Trademark Office Re. U.S. Appl. No. 14/005,583.
Official Action dated Oct. 3, 2017 From the US Patent and Trademark Office. Re. U.S. Appl. No. 15/626,198. (10 pages).
Official Action dated Jan. 11, 2017 From the US Patent and Trademark Office. Re. U.S. Appl. No. 14/005,583. (28 pages).
Official Action dated Jul. 12, 2016 From the US Patent and Trademark Office Re. U.S. Appl. No. 14/742,907.
Official Action dated Dec. 13, 2016 From the US Patent and Trademark Office Re. U.S. Appl. No. 14/742,907. (8 pages).
Official Action dated Apr. 14, 2016 From the US Patent and Trademark Office Re. U.S. Appl. No. 14/005,583.
Official Action dated Dec. 31, 2015 From the US Patent and Trademark Office Re. U.S. Appl. No. 14/005,583.
Restriction Official Action dated Nov. 28, 2014 From the US Patent and Trademark Office Re. U.S. Appl. No. 14/005,583.
Search Report dated Sep. 30, 2014 From the State Intellectual Property Office of the People's Republic of China Re. Application No. 201280023297.2 and Its Translation Into English.
Supplementary European Search Report and the European Search Opinion dated. Mar. 17, 2017 From the European Patent Office Re. Application No. 14865441.1. (11 Pages).
Achiron et al. "Zinc-Ion Binding and Cytokine Activity Regulation Pathways Predicts Outcome in Relapsing-Remitting Multiple Sclerosis", Clinical and Experimental Immunology, 149: 235-242, 2007.
Banti et al. "Synthesis and In-Vitro Antitumour Activity of New Naphthyridine Derivatives on Human Pancreatic Cancer Cells", Journal of Pharmacy and Pharmacology, JPP, 61: 1057-1066, First Published Jan. 8, 2010. Abstract.
Bratrude "The Anti-Inflammatory Diet and Multiple Sclerosis", Swedish Medical Center, 4 Pages, Aug. 12, 2013.
Cavanaugh et al. "Mammalian Rrn3 is Required for the Formation of a Transcription Competent Preinitiation Complex Containing RNA Polymerase I", Gene Expression, 14(3): 131-147, 2008.
Cavanaugh et al. "Rrn3 Phosphorylation is a Regualtory Checkpoint for Ribosome Biogenesis", The Journal of Biological Chemistry, 277(30): 27423-27432, Jul. 26, 2002.
Costelloe et al. "Long-Term Clinical Relevance of Criteria for Designating Multiple Sclerosis as Benign After 10 Years of Disease", Journal of Neurology, Neurosurgery, and Psychiatry, 79(11): 1245-1248, Nov. 2008.
Drygin et al. "Targeting RNA Polymerase I With an Oral Small Molecule CX-5461 Inhibitis Ribosomal RNA Synthesis and Solid Tumor Growth", Cancer Research, XP002678820, 71(4): 1418-1430, Published Online Dec. 15, 2010.
Drygin et al. "The RNA Polymerase I Transcription Machinery: An Emerging Target for the Treatment of Cancer", Annual Review of Pharmacology and Toxicology, 50: 131-156, 2010.
Haddach et al. "Discovery of CX-5461, the First Direct and Selective Inhibitor of RNA Polymerase I, for Cancer Therapeutics", ACS Medical Chemistry Letters, XP055350883, 3(7): 602-606, May 8, 2012. p. 602, Compound 7c.
Haegert "Multiple Sclerosis: A Disorder of Altered T-Cell Homeostasis", 2011: Article ID 16130, . 6 pages, 2011.
Kalita et al. "Inhibition of Nucleolar Transcription as a Trigger for Neuronal Apoptosis", Journal of Neurochemistry, 105(6): 2286-2299, Jun. 1, 2008.
Leuenroth et al. "Triptolide-Induced Transcriptional Arrest is Associated With Changes in Nuclear Substructure", Cancer Research, 68: 5257-5266, Jul. 1, 2008.
Liu et al. "Triptolide, A Component of Chinese Herbal Medicine, Modulates the Functional Phenotype of Dendritic Cells", Transplantation, 84(11): 1517-1526, Dec. 15, 2007.
Pittock et al. "Benign Multiple Sclerosis: A Distinct Clinical Entity With Therapeutic Implications", Current Topics in Microbiology and Immunology, 318: 1-17, 2008.
Reagan-Shaw et al. "Dose Translation From Animal to Human Studies Revisited", The FASEB Journal, 22: 659-661, 2007.
Russell et al. "RNA-Polymerase-I-Directed rDNA Transcription, Life and Works", Trends in Biochemical Sciences, 30(2): 87-96, Feb. 2005.
Wang et al. "Triptolide Modulates T-Cell Inflammatory Responses and Ameliorates Experimental Autoimmune Encephalomyelitis", Journal of Neuroscience Research, 86: 2441-2449, 2008.
Communication Pursuant to Article 94(3) EPC dated Sep. 19, 2018 From the European Patent Office Re. Application No. 14865441.1. (5 Pages).

RNA POLYMERASE I INHIBITORS AND USES THEREOF

RELATED APPLICATIONS

This application is a continuation of U.S. patent application Ser. No. 15/626,198 filed on Jun. 19, 2017, which is a Continuation of U.S. patent application Ser. No. 14/742,907 filed on Jun. 18, 2015, now U.S. Pat. No. 9,688,697, which is a Continuation-in-Part (CIP) of PCT Patent Application No. PCT/IB2014/066402 having International Filing Date of Nov. 27, 2014, which claims the benefit of priority under 35 USC § 119(e) of U.S. Provisional Patent Application No. 61/910,060 filed on Nov. 28, 2013. The contents of the above applications are all incorporated by reference as if fully set forth herein in their entirety.

SEQUENCE LISTING STATEMENT

The ASCII file, entitled 74029SequenceListing.txt, created on Jun. 4, 2018, comprising 574,287 bytes, submitted concurrently with the filing of this application is incorporated herein by reference.

FIELD AND BACKGROUND OF THE INVENTION

The present invention, in some embodiments thereof, relates to therapy and, more particularly, but not exclusively, to novel RNA Polymerase I inhibitors and to uses thereof in methods of treating medical conditions including, for example, autoimmune diseases multiple sclerosis and proliferative diseases such as cancer.

Autoimmune diseases are caused by an autoimmune response, i.e., an immune response directed to a substance in the body of the subject. The characteristics of the autoimmune diseases vary and depend on the site affected by the autoimmune response.

Multiple sclerosis (MS) is the most common demyelinating disease of the central nervous system (CNS) affecting young adults (disease onset between 20 to 40 years of age) and is the third leading cause for disability after trauma and rheumatic diseases, with an estimated annual cost of 34,000 USD per patient (total life time cost of 2.2 million USD per patient).

The disease is characterized by destruction of myelin, associated with death of oligodendrocytes and axonal loss. The main pathologic finding in MS is the presence of infiltrating mononuclear cells, predominantly T lymphocytes and macrophages, which surpass the blood brain barrier and induce an active inflammation within the brain and spinal cord. The neurological symptoms that characterize MS include complete or partial vision loss, diplopia, sensory symptoms, motor weakness that can worsen to complete paralysis, bladder dysfunction and cognitive deficits, which eventually may lead to a significant disability. The associated multiple inflammatory foci lead to myelin destruction, plaques of demyelination, gliosis and axonal loss within the brain and spinal cord and are the reasons which contribute to the clinical manifestations of neurological disability.

The etiology of MS is not fully understood. The disease develops in genetically predisposed subjects exposed to yet undefined environmental factors and the pathogenesis involves autoimmune mechanisms associated with autoreactive T cells against myelin antigens. It is well established that not one dominant gene determines genetic susceptibility to develop MS, but rather many genes, each with different influence, are involved.

Clinically, in 85% of MS patients the illness is initiated with a relapsing-remitting course (RRMS), and in about 10-15% of MS patients have an a-priori primary progressive course (PPMS) without relapses. RRMS is characterized by inflammatory attacks associated with neurological deficits with periods of remissions between the relapses that vary in time. After a period of 10 years, about 50% of RRMS patients will progress to a secondary progressive MS (SPMS) course, characterized by permanent neurological dysfunction, with or without relapses and progressive disability.

Benign MS (BMS) is a clinical variant of RRMS in which the patients develop low neurological disability if at all after a disease duration of at least 10 years. Accordingly, this group of MS patients do not experience devastating accumulating disability over-time and when these patients are examined neurologically and scored by the Expanded Disability Status Scale (EDSS) they receive a score that is equal to or lower than 3.0. This low EDSS score signifies mild disability and when this low disability occurs more than 10 years after disease onset, the course of MS is defined as benign. Prediction of patients that will have BMS is currently impossible and the definition of these patients is retrospective. The molecular events accountable for the BMS variant of disease are not understood.

WO 2008/081435 discloses methods and kits for predicting the prognosis of a subject diagnosed with multiple sclerosis and methods of selecting a treatment regimen of a subject diagnosed with multiple sclerosis.

Achiron A, et al., 2007 [Clinical and Experimental Immunology, 149: 235-242] describe genes of the zinc-ion binding and cytokine activity regulation pathways which predict outcome in relapsing-remitting multiple sclerosis.

WO 2010/113096 discloses methods of predicting clinical course and treating multiple sclerosis.

Current approved drugs for the treatment of MS are either general anti-inflammatory agents or immunomodulators and consequently result only in moderate beneficial effects suppressing disease activity.

CX-5461 (see, Table 1 hereinunder) is a small molecule that was designed to selectively inhibit rRNA synthesis by inhibiting RNA Polymerase I (POL I or POL1), without affecting mRNA synthesis by RNA Polymerase II (POL II), and without inhibiting DNA replication or protein synthesis (Russell J, Zomerdijk J C. Trends Biochem Sci 30:87-96, 2005; Drygin D, et al. Annu Rev Pharmacol Toxicol 50:131-156, 2010).

The inhibition of POL1 results in nucleolar stress which causes the release of ribosomal proteins (RP) from the nucleolus and subsequent activation of p53, resulting in cell apoptosis [Kalita K, et al. J Neurochem 105:2286-2299, 2008]. In a previous study [Drygin D, et al. Cancer Res 71:1418-1430, 2011], the antiproliferative activity of CX-5461 was studied in cell lines and it was shown that CX-5461 inhibited POL-I activity in human cancer cell lines.

Recent studies indicate that disruption of the SL1/rDNA complex by CX-5461 results from the interference between SL1 and rDNA. SL1, a protein complex containing TATA binding protein-associated factors, is responsible for POL1 promoter specificity. SL1 performs important tasks in the transcription complex assembly, mediating specific interactions between the rDNA promoter region and the POL1 enzyme complex, thereby recruiting POL1, together with a collection of POL1-associated factors like RRN3 to rDNA (Cavanaugh A, et al. *Gene Expr* 14:131-147, 2008).

U.S. Patent Application Publication No. 2009/0093465 discloses a family of compounds, including CX-5461, as kinase modulators useful in the treatment of proliferative diseases such as cancer.

Recently, a role for inhibition of RNA polymerase I (POL1) pathway in the regulation of MS disease activity by suppression of inflammation and enhancement of apoptosis of autoreactive lymphocytes has been uncovered. The suggested mechanism by which POL1 pathway inhibition affects the disease process is demonstrated in Background Art FIGS. 1 and 2A-2B.

The above findings have supported a basis for direct targeting of RNA Polymerase-I transcription pathway as a strategy for selective induction of apoptosis in MS in order to transform the active disease of RRMS to the preferable BMS subtype. Administration of a specific POL1 inhibitor (POL1-I) was demonstrated to prevent animal Experimental Autoimmune Encephalomyelitis (EAE) when administered at disease induction and to reduce the disease severity when administered at clinical disease onset [Achiron et al. 2013, J Neuroimmunol 263:91-97], thus confirming that a POL1 inhibitor acts specifically by inhibiting the polymerase I associated molecules.

WO 2012/123938 discloses uses of family of compounds, including CX-5461 and derivatives thereof, in the treatment of autoimmune diseases such as MS.

Additional background art includes Leuenroth S J and Crews C M (Triptolide-induced transcriptional arrest is associated with changes in nuclear substructure. Cancer Res. 2008; 68:5257-5266); Liu Y, et al. (Triptolide, a component of Chinese herbal medicine, modulates the functional phenotype of dendritic cells. Transplantation. 2007; 84:1517-1526); Wang Y, et al. (Triptolide modulates T-cell inflammatory responses and ameliorates experimental autoimmune encephalomyelitis. J Neurosci Res. 2008; 86:2441-2449; EP 0983256; PCT/US1998/008562; WO9852933A1; Alice H. Cavanaugh, et al., 2002 (Rrn3 Phosphorylation is a regulatory checkpoint for ribosome biogenesis J. Biol. Chem., 2002; 277: 27423-27432); PCT Pub. No. WO 03/081201.

SUMMARY OF THE INVENTION

Based on the findings that inhibition of RNA Polymerase-I plays a role in regulation of MS and other autoimmune diseases, as well as cell proliferation, the present inventors have searched for POL-1 inhibitors (denoted herein as POL1-I) that would exhibit an improved effect as compared to the presently known POL1 inhibitors (e.g., POL1-I and structural analogs thereof).

The present inventors have uncovered that by modifying a structural feature of CX-5461 or analogs thereof, so as to reduce or even reverse its capability of participating in hydrogen bond formation, inhibitors which exhibit improved performance are obtained.

According to an aspect of some embodiments of the present invention there is provided a compound represented by general Formula I:

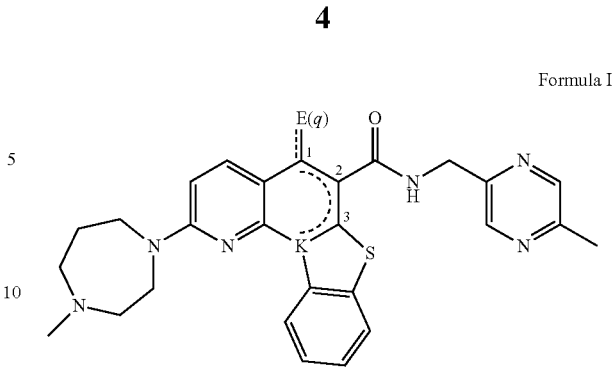

Formula I wherein ══ or the dashed line each independently indicates an optionally unsaturated bond, depending on the nature and valency of E;

E forms a chemical moiety other then carbonyl, capable of interfering with a hydrogen binding capacity of the compound;

Q equals 1 or 2; and

K is N or $N^{(+)}$, depending on the nature and valency of E.

According to some embodiments of the present invention, E forms a chemical moiety selected from the group consisting of thiocarbonyl and a substituted or unsubstituted imine.

According to some embodiments of the present invention, q is 1, K is N, E is linked to carbon 1 of the ring via an unsaturated double bond, and another unsaturated double bond is present between carbons 2 and 3 of the ring, the compound being represented by Formula Ia:

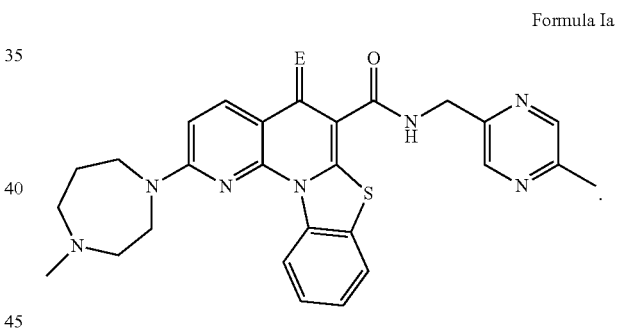

Formula Ia

According to some embodiments of the present invention, E forms a substituted or unsubstituted imine, the compound being represented by Formula Ib:

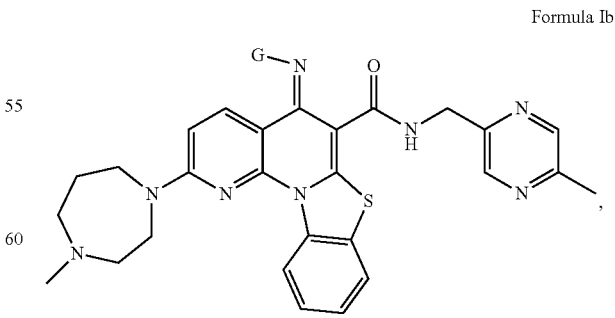

Formula Ib wherein G is selected from the group consisting of hydrogen, alkyl, cycloalkyl, aryl, heteroaryl, heteroalicyclic, alkoxy, thioalkoxy, thiol, hydroxyl, aryloxy, and thioaryloxy.

According to some embodiments of the present invention, G is aryl.

According to an aspect of some embodiments of the present invention there is provided a compound as described herein, for use in the treatment of an autoimmune disease.

According to an aspect of some embodiments of the present invention there is provided a compound as described herein, for use in the manufacture of a medicament for treating an autoimmune disease.

According to an aspect of some embodiments of the present invention there is provided a method of treating an autoimmune disease in a subject, the method comprising administering to the subject a therapeutically effective amount of the compound of Formula I as described in any one of the respective embodiments herein.

According to some embodiments of the present invention, the autoimmune disease is multiple sclerosis.

According to some embodiments of the present invention, the multiple sclerosis is a relapsing-remitting multiple sclerosis (RRMS) or benign multiple sclerosis (BMS).

According to some embodiments of the present invention, treating the multiple sclerosis comprises changing the course of the disease from the RRMS to BMS.

According to some embodiments of the present invention, the autoimmune disease is treatable by inhibiting an activity of RNA Polymerase I.

According to an aspect of some embodiments of the present invention there is provided a compound as described herein, for use in the treatment of a proliferative disease or disorder.

According to an aspect of some embodiments of the present invention there is provided a use of the compound as described herein, in the manufacture of a medicament for the treatment of a proliferative disease or disorder.

According to an aspect of some embodiments of the present invention there is provided a method of treating a proliferative disease or disorder, the method comprising administering to a subject in need thereof a therapeutically effective amount of the compound as described herein.

According to some embodiments of the present invention, the proliferative disease or disorder is treatable by inhibiting an activity of a protein kinase.

According to an aspect of some embodiments of the present invention there is provided a compound as described herein, for use in inhibiting an activity of RNA Polymerase I and/or for treating a disease or disorder treatable by inhibiting an activity of RNA Polymerase I.

According to an aspect of some embodiments of the present invention there is provided a use of a compound as described herein, in the manufacture of a medicament for inhibiting an activity of RNA Polymerase I and/or for treating a disease or disorder treatable by inhibiting an activity of RNA Polymerase I.

According to an aspect of some embodiments of the present invention there is provided a method of inhibiting an activity of RNA Polymerase I, the method comprising contacting the RNA Polymerase I with an effective amount of a compound as described herein.

According to some embodiments of the present invention, contacting is effected in vitro.

According to some embodiments of the present invention, contacting is effected in vivo.

According to some embodiments of the present invention, the method is being for treating a disease treatable by inhibiting an activity of RNA Polymerase I.

According to an aspect of some embodiments of the present invention there is provided a compound as described herein, for use in inhibiting an activity of a protein kinase and/or for treating a disease or disorder treatable by inhibiting an activity of a protein kinase.

According to an aspect of some embodiments of the present invention there is provided a use of a compound as described herein, in the manufacture of a medicament for inhibiting an activity of a kinase and/or for treating a disease or disorder treatable by inhibiting an activity of a protein kinase.

According to an aspect of some embodiments of the present invention there is provided a method of inhibiting an activity of a protein kinase, the method comprising contacting the protein kinase with an effective amount of a compound as described herein.

According to some embodiments of the present invention, contacting is effected in vitro.

According to some embodiments of the present invention, contacting is effected in vivo.

According to some embodiments of the present invention, the method is being for treating a disease treatable by inhibiting an activity of a protein kinase.

According to some embodiments of the present invention, there is provided a method of monitoring an efficiency of the compound of claim 1 in treating a disease associated with a subject, the method comprising:

(a) administering to the subject a therapeutically effective amount of the compound, and (b) comparing a level of expression of at least one gene involved in the RNA polymerase I pathway in a cell of the subject following treating with the compound to a level of expression of the at least one gene in a cell of the subject prior to treating the subject with the compound, (i) wherein a decrease above a predetermined threshold in the level of expression of the at least one gene following treating with the compound relative to the level of expression of the at least one gene prior to treating with the compound indicates that the compound is efficient for treating the subject;

(ii) wherein an increase above a predetermined threshold in the level of expression of the at least one gene following treating with the compound relative to the level of expression of the at least one gene prior to treating with the compound indicates that the compound is not efficient for treating the subject; or (iii) wherein when a level of expression of the at least one gene following treating with the compound is identical or changed below a predetermined threshold as compared to prior to treating with the compound then the treatment is not efficient for treating the subject;

thereby monitoring the efficiency of the compound in treating the disease in the subject.

According to some embodiments of the present invention, the disease is selected from the group consisting of an autoimmune disease and a proliferative disease or disorder.

According to some embodiments of the present invention, the compound is:

Compound 10

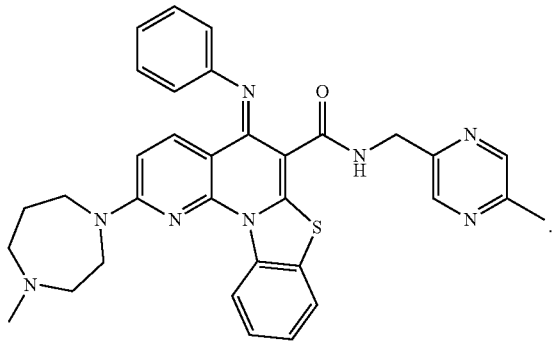

According to some embodiments of the present invention, the at least one gene involved in the RNA polymerase 1 pathway is selected from the group consisting of POLR1D, LRPPRC, RRN3, pre-rRNA and NCL.

According to some embodiments of the present invention, the at least one gene involved in the RNA polymerase 1 pathway is selected from the group consisting of POLR1D, LRPPRC, RRN3 and pre-rRNA.

According to some embodiments of the present invention, the cell is comprised in a biological sample.

According to some embodiments of the present invention, the biological sample is a blood sample.

According to some embodiments of the present invention, the level of expression of the at least one gene is determined using an RNA and/or a protein detection method.

According to some embodiments of the present invention, the detection method is selected from the group consisting of RT-PCR, oligonucleotide microarray, immunoprecipitation, Western blot analysis and FACS.

According to some embodiments of the present invention, the level of expression of the at least one gene is determined by hybridizing the cell or fractions or extracts thereof of the subject with an oligonucleotide which specifically hybridizes with a polynucleotide expressed from the at least one gene and/or by contacting the cell or fractions or extracts thereof of the subject with an antibody which specifically binds a polypeptide expressed from the at least one gene.

A "compound" as described herein refers to a compound having Formula I as described in any one of its respective embodiments, and further to any other compound described in the following description as being contemplated by embodiments of the present invention.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIG. 6A shows the results of a representative experiment and FIGS. 6B-6D show the mean results of 3 independent experiments. Error bars represent mean±SEM.

DESCRIPTION OF SPECIFIC EMBODIMENTS OF THE INVENTION

Figure 1:
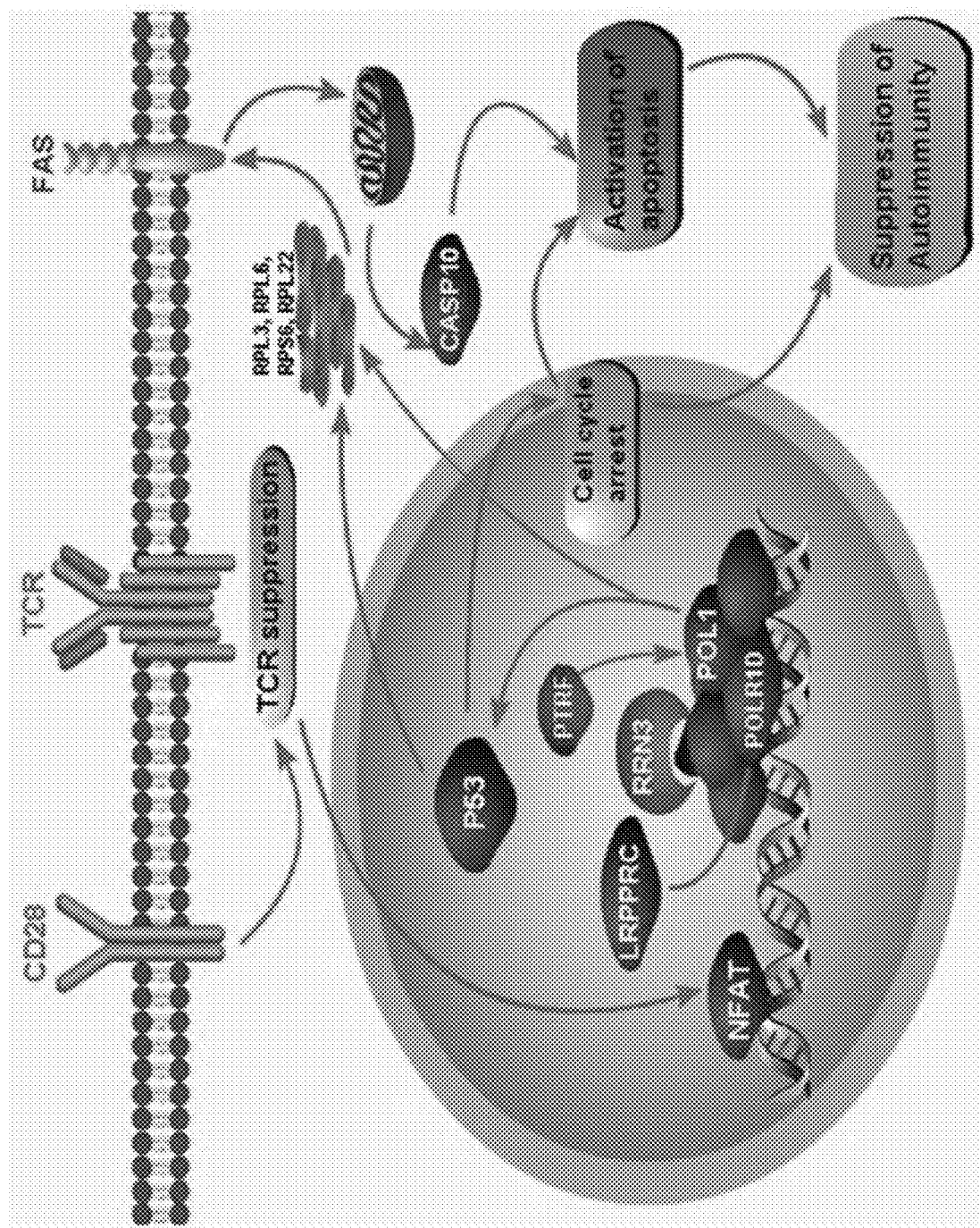
FIG. 1 (Background Art) presents a schematic illustration of POL1 molecular mechanism, showing the effect of POL1 on apoptosis and proliferation.
Figure 2B:
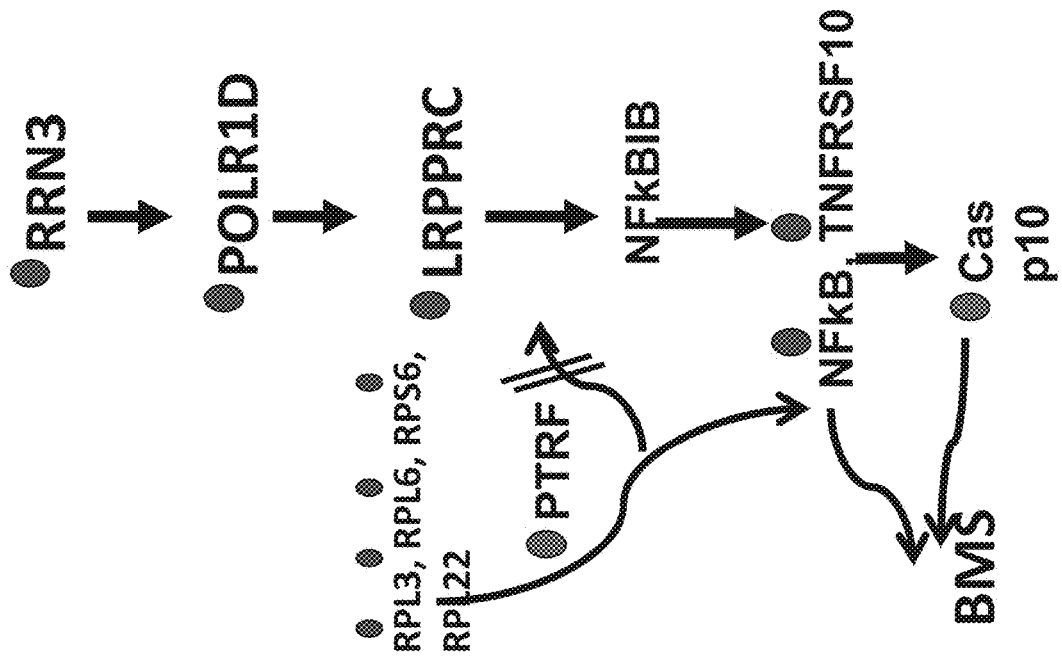
FIGS. 2A-2B (Background Art) present schematic illustrations of the effect of POL1 inhibition on multiple sclerosis.
Figure 2A:
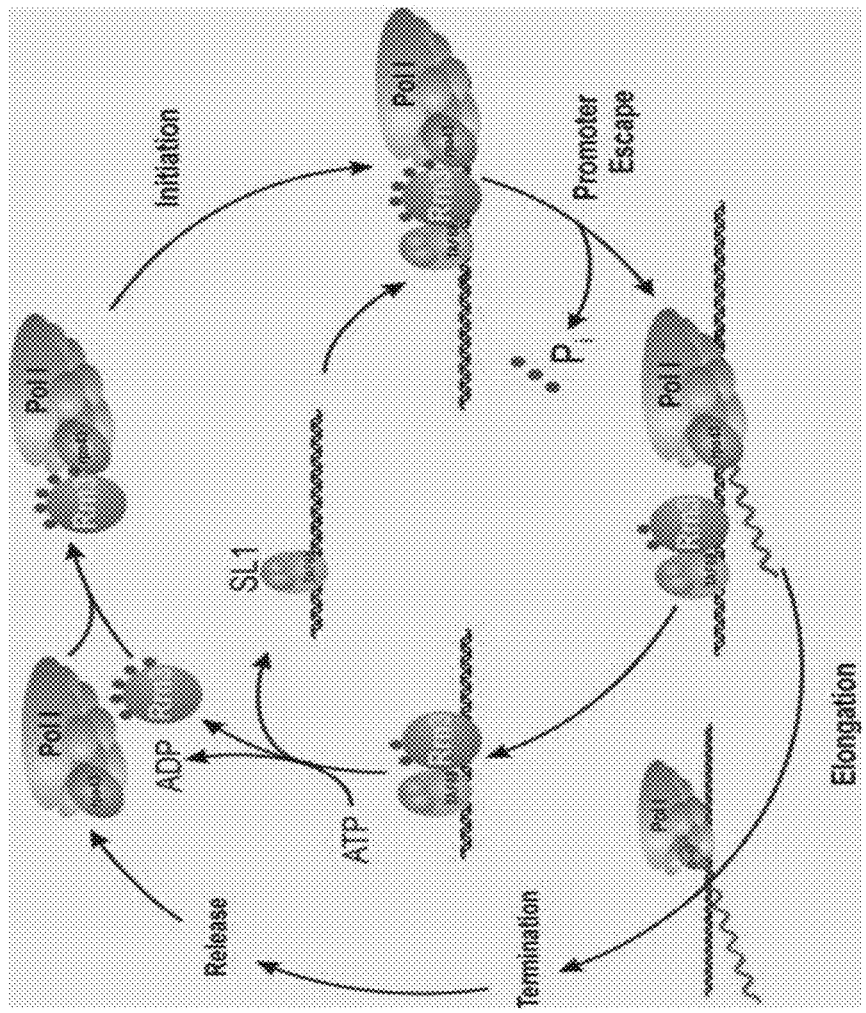

The present invention, in some embodiments thereof, relates to therapy and, more particularly, but not exclusively, to novel RNA Polymerase I inhibitors and to uses thereof in methods of treating medical conditions including, for example, autoimmune diseases multiple sclerosis and proliferative diseases such as cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Embodiments of the present invention stem, at least on part, from previous findings that demonstrated a characterizing gene expression signature in blood sample of RRMS and BMS subjects, whereby the major operating pathway was RNA Polymerase I (POL1). These findings have previously led the present inventors to explore a role for POL1 inhibitors in the treatment, and optionally personalized treatment, of MS.

Led by the fact that the current commercial products for the treatment of autoimmune diseases, and particularly MS, are used intramuscularly, intradermally or as intravenous injections for drug delivery, and lead to uncontrolled plasma peaks, undesired side effects such as flu like reactions and painful local reactions, and thus are accompanied by a high rate of non-compliance to these treatments, the present inventors have explored utilizing inhibitors of POL1-I, which are characterized by oral bioavailability, and improve patients' compliance and benefit patients in the aspect of side effects and pain relief.

As described hereinabove, a POL1 inhibitor, termed CX-5461, and structural analogs thereof, and their use in inhibiting a protein kinase activity and an abbrant cell proliferation, has been previously disclosed. See, for example, U.S. Patent Application Publication No. 2009/0093465.

A family of such POL1 inhibitors, including CX-5461, for use in the treatment of autoimmune diseases has been disclosed in WO 2012/123938.

In a search for POL1 inhibitors that exhibit an improved therapeutic effect, such as, for example, an improved (wider) therapeutic window, the present inventors have devised and successfully prepared and practiced a novel family of POL1 inhibitors, which can be used to treat autoimmune diseases such as multiple sclerosis, proliferative diseases such as cancer, and other medical conditions which are associated with inhibition of POL1 and/or a protein kinase.

According to an aspect of some embodiments of the present invention there are provided compounds which can be collectively represented by Formula I:

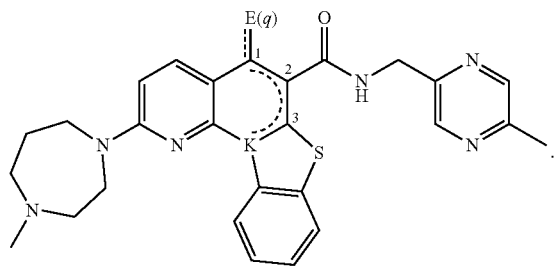

Formula I wherein ---- or the dashed line each independently indicates an optionally unsaturated bond, depending on the nature and valency of E;

E forms a chemical moiety other then carbonyl, capable of interfering with a hydrogen binding capacity of the compound;

Q equals 1 or 2; and

K is N or $N^{(+)}$, depending on the nature and valency of E.

Compounds represented by Formula I feature structural similarity of CX5461 (POL1-I, RAM-0, Compound 1; See, for example, FIG. 3A and Table 1 hereinbelow), yet the structure of CX5461 is modified so as to longer include a carbonyl (oxo substituent) at a position equivalent to variable E in Formula I.

The variable E therefore represents a chemical group that, when attached to the carbon marked as carbon "1" in Formula I of the quinazoline ring, forms a chemical moiety other than carbonyl (C=O). E is therefore a chemical group other than oxo (=O).

The chemical group of variable E in Formula I herein can be attached to carbon "1" via a double (unsaturated bond), in which case, q is 1. In such cases, the valency of E is such that is suitable to be attached via an unsaturated bond to carbon "1" (as in the case of, for example, an oxo group =O that forms a carbonyl C=O group.

In such cases, the electronic structure of the quinazoline ring of CX-5461 is maintained, such that an unsaturated (double) bond also exists between carbons "2" and "3" of the ring, and K is nitrogen in a neutral form (N).

Compound exhibiting such structures are represented by Formula Ia:

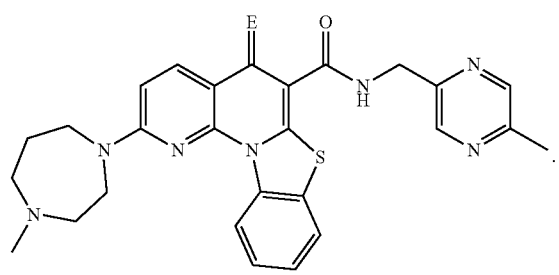

Formula Ia

Exemplary chemical groups formed by "E" in such cases include, but are not limited to, thiocarbonyl (C=S), formed of thioxo (=S) group; and imine (e.g., C=N-G, with being as defined hereinafter), formed of e.g., a corresponding =N-G group.

Alternatively, the group represented by variable E is attached to carbon "1" via a single bond, and q is 2. Thus each E group is attached to the ring via a single bond (saturated bond). In such cases, the electronic structure of the quinazoline ring is maintained, such that an unsaturated (double) bond also exists between carbons "2" and "3" of the ring, and K is nitrogen in a neutral form (N).

Compound exhibiting such structures are represented by Formula Ic:

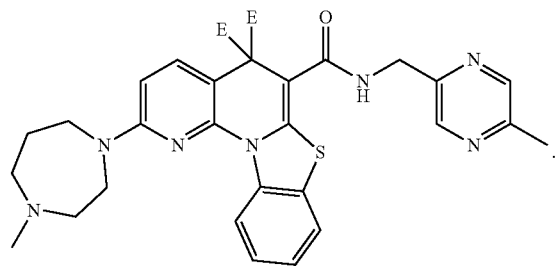

Formula Ic

Exemplary chemical groups formed by "E" in such cases include, for example, two halides, preferably two fluorides, as explained hereinafter.

Further alternatively, the group represented by variable E is attached to carbon "1" via a single (saturated) bond, and q is 1. In such cases, the electronic structure of the quinazoline ring undergoes a rearrangement (a tautomerization rearrangement), such that an unsaturated bond exists between carbons "1" and "2" of the ring, and between carbon "3" and K, and K is a positively charged nitrogen N⁺.

Compound exhibiting such structures are represented by Formula Id:

Formula Id

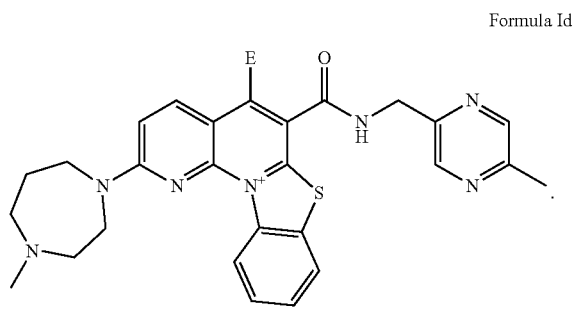

Exemplary chemical groups formed by "E" in such cases include, for example, halides, preferably a chloride.

While the above formulae provide an exemplary illustration for some preferred embodiments of the invention, generally, the chemical moiety formed by variable E is selected so as to modulate the hydrogen bonding capacity of the compound.

As used herein and known in the art, a "hydrogen bond" is a relatively weak bond that forms a type of dipole-dipole attraction which occurs when a hydrogen atom bonded to a strongly electronegative atom exists in the vicinity of another electronegative atom with a lone pair of electrons.

The hydrogen atom in a hydrogen bond is partly shared between two relatively electronegative atoms.

Hydrogen bonds typically have energies of 1-3 kcal mol⁻¹ (4-13 kJ mol⁻¹), and their bond distances (measured from the hydrogen atom) typically range from 1.5 to 2.6 Å.

A hydrogen-bond donor is the group that includes both the atom to which the hydrogen is more tightly linked and the hydrogen atom itself, whereas a hydrogen-bond acceptor is the atom less tightly linked to the hydrogen atom. The relatively electronegative atom to which the hydrogen atom is covalently bonded pulls electron density away from the hydrogen atom so that it develops a partial positive charge (δ⁺). Thus, it can interact with an atom having a partial negative charge (δ⁻) through an electrostatic interaction.

Atoms that typically participate in hydrogen bond interactions, both as donors and acceptors, include oxygen, nitrogen and fluorine. These atoms typically form a part of chemical group or moiety such as, for example, carbonyl, carboxylate, amide, hydroxyl, amine, imine, alkylfluoride, F₂, and more. However, other electronegative atoms and chemical groups or moieties containing same may participate in hydrogen bonding.

By "modulating the hydrogen bonding capacity" it is meant altering the number and/or strength of hydrogen bonds that the compound may form intramolecularly or intermolecularly, as compared to a carbonyl moiety at the same position.

For example, the group formed by variable E can be, for example, a stronger donor for a hydrogen bond compared to carbonyl, a weaker donor for a hydrogen bond, compared to carbonyl, or be a stronger or a weaker acceptor of a hydrogen bond, compared to carbonyl.

Without being bound by any particular theory, it is assumed that hydrogen bonds may form upon a keto-enol-type tautomerization of the amide group attached to carbon "2" in Formula I, which results in a hydroxyl group (—OH), the latter participates in hydrogen bonding.

The hydroxyl group thus formed is a strong donor of a hydrogen bond and may form a hydrogen bond intermolecularly, with, for example, a hydrogen bond acceptor group of a targeted molecule (e.g., a targeted enzyme such as POL1).

The hydroxyl group may also form hydrogen bond with a carbonyl, when it is the substituent of carbon "1", so as to form a six-membered ring structure, by intramolecular hydrogen bonding.

Alternatively, both a carbonyl at carbon "1" and the hydroxyl group may participate in hydrogen bonds with compatible groups of a targeted biomolecule (e.g., a targeted enzyme).

The modification of substituent E so as to no longer include a carbonyl group may therefore alter the compound's hydrogen bonding capacity by, for example, reducing or increasing the probability of hydrogen bond formation intramolecularly, reducing or increasing the probability of hydrogen bond formation intermolecularly, and/or reducing the strength of an intermolecular or intramolecular hydrogen bond.

In some embodiments, group E is selected such that the chemical moiety formed therewith increases the probability of forming a hydrogen bond intermolecularly and reduces the probability of forming a hydrogen bond intramolecularly (e.g., due to the formation of a group that forms a less stable hydrogen bond with the hydroxyl).

In some embodiments, E is such that the energy of a hydrogen bond formed between a highly electronegative atom therein and hydrogen of the neighboring hydroxyl is lower than the energy of a hydrogen bond formed with the same hydroxyl by carbonyl's oxygen.

In some embodiments, the energy is lower by at least 0.1 kcal/mol, and can be lower by, for example, 0.1, 0.2, 0.3, 0.5, 0.7, 0.8, 1, 1.5, or 2 kcal/mol, including any subranges and intermediates between these values. A person skilled in the art would recognize which groups are encompassed by this definition based on art-recognized tables that define the energies of hydrogen bonds formed with a hydroxyl group.

In some embodiments, the electron density on such an electronegative atom is lower than an electron density of carbonyl's oxygen, that is, the atom is less electronegative than the oxygen in carbonyl.

Without being bound by any particular theory, it is assumed that by interfering with the hydrogen bond capacity of the compound, by e.g., reducing the number (e.g., from 1 to 0) and/or strength of intramolecular bonds, and at the same time increasing the number and/or strength of intermolecular bonds, the compound may better interact with the targeted biomolecule (e.g., POL1), even more electively, and also may have a weaker or no interaction with an unknown off-target protein. It may also further exhibit improved water dissolution kinetics, which facilitates its administration.

In some embodiments, E is an imine group, which can be substituted or non-substituted, as depicted for compounds represented by Formula Ib:

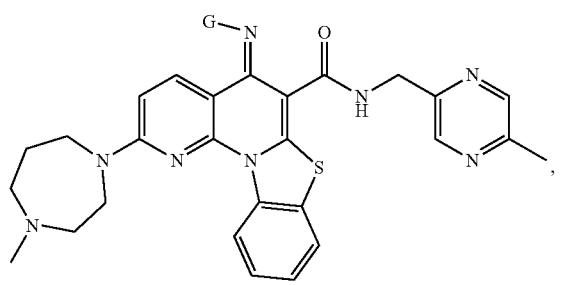

Formula Ib wherein G can be, for example, hydrogen, alkyl, cycloalkyl, aryl, heteroaryl, heteroalicyclic, alkoxy, thioalkoxy, thiol, hydroxyl, aryloxy, or thioaryloxy.

Exemplary such compounds are presented in Table 1 hereinafter as Compounds 3, 4, 5, 6, 7, 8 and 10.

In some embodiments, G is an electron withdrawing group.

Without being bound by any particular theory, it is assumed that electron withdrawing groups reduce the electronegativity of the imine's nitrogen and hence result in a weaker hydrogen bond intramolecular interaction with the presumably formed neighboring hydroxyl described hereinabove, and increase the hydrogen bond intermolecular interactions of the hydroxyl group.

In some embodiments, G is a bulky group as defined herein.

As used herein, the phrase "bulky" describes a group that occupies a large volume. A bulkiness of a group is determined by the number and size of the atoms composing the group, by their arrangement, and by the interactions between the atoms (e.g., bond lengths, repulsive interactions). Typically, lower, linear alkyls are less bulky than branched alkyls; cyclic moieties are more bulky than liner moieties; bicyclic molecules are more bulky than cycloalkyls, etc.

Exemplary suitable electron-withdrawing substituents of an imine include, but are not limited to, substituted or unsubstituted aryls, which, when substituted, preferably are substituted by chemical moieties and at position which strengthen the electron-withdrawing nature of the aryl; heteroaryls in which the heteroatom is positioned such that it exhibits electron-withdrawal with respect to the imine nitrogen; and bulky cycloalkyls substituted by one or more electron withdrawing substituents.

The phrases "electron-withdrawing substituent" or "electron-withdrawing group" are well known to those of skill in the art and are used herein interchangeably as their standard meaning which is a functional group that draws electrons to itself more than a hydrogen atom would if it occupied the same position in the molecule, as described in J. March, Advanced Organic Chemistry, third edition, Pub: John Wiley & Sons, Inc. (1985).

Exemplary electron-withdrawing substituents include, but are not limited to, halogen, pseudohalogen, haloalkyl, haloalicyclic, haloaryl, haloheteroaryl, carbonyl, ester, —C(=O)H and any combination thereof.

Figure 3A:
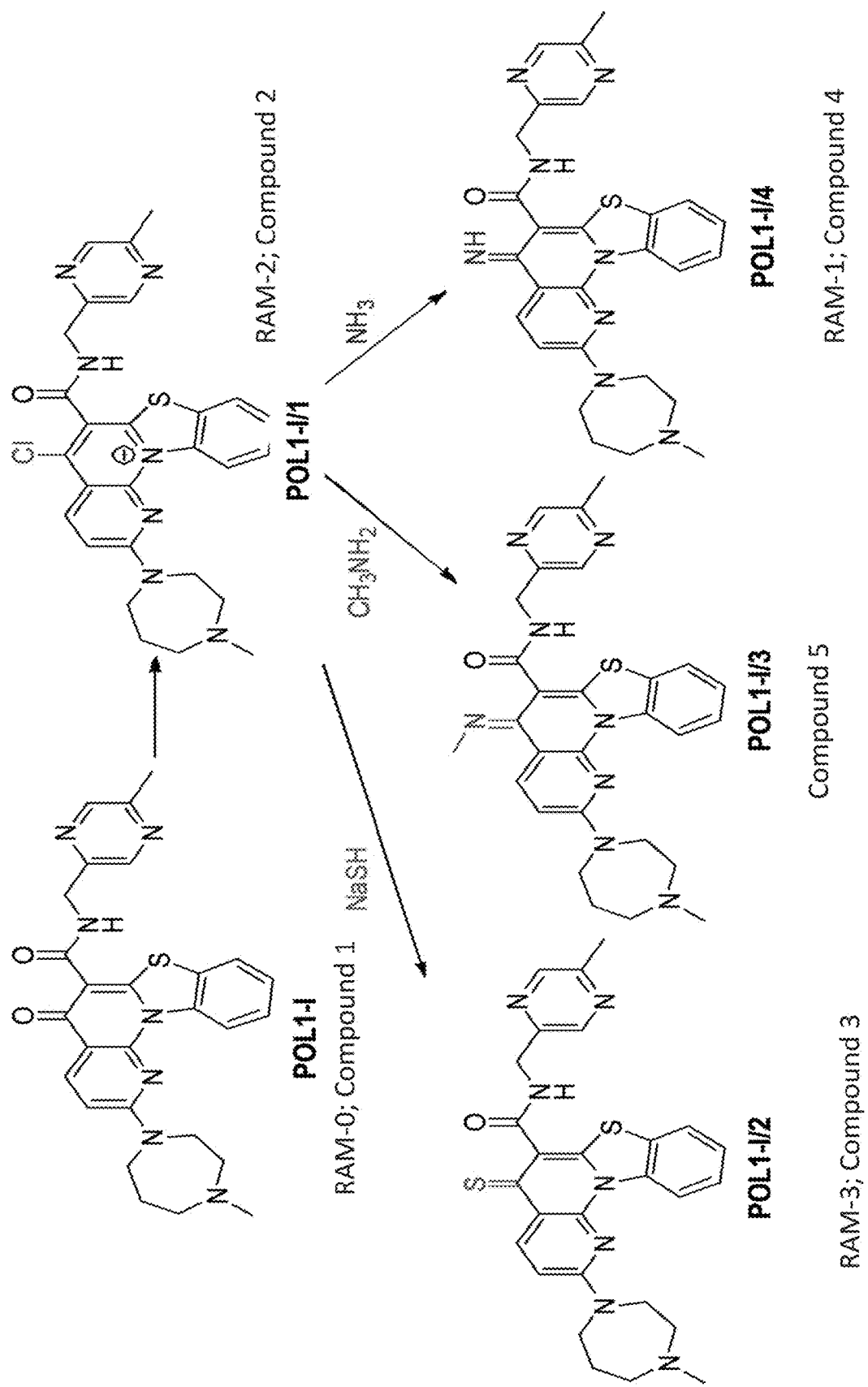
FIGS. 3A-3B present chemical structures and synthetic pathways of exemplary compounds according to some embodiments of the present invention.
Figure 3B:
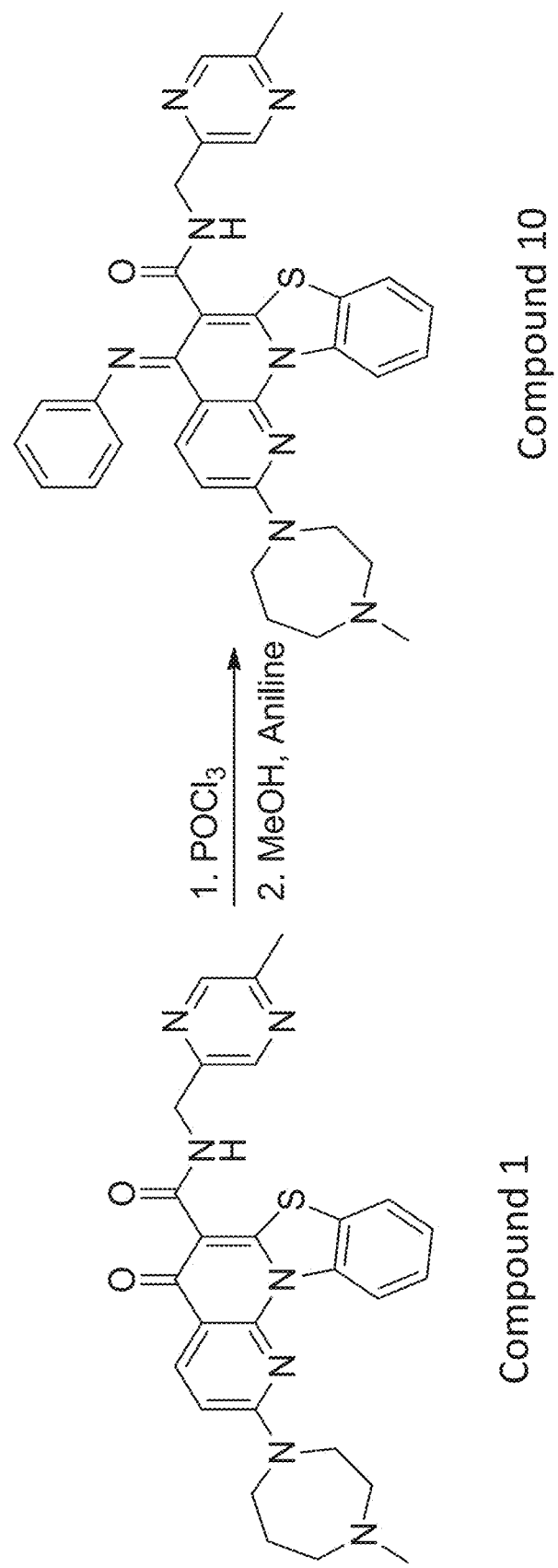

In some embodiments, G is aryl and the compound is Compound 10 (see, Table 1 and FIG. 3B).

It is to be noted that an inclusion of moieties that enhance the hydrophobicity of the compound, such as, for example, aryl, are assumed, without being by bond by any particular theory, to enhance the bioavailability of the compound, compared to compounds featuring a carbonyl moiety at the same position.

Thus, in some embodiments, there are provided compounds having Formula I as described herein, or Formula Ia or Ib, as described herein, which are characterized by higher hydrophobicity compared to corresponding compound in which E is oxo.

The term "hydrophobic" thus often translates into values such as Log P, which describes the partition coefficient of a substance between an aqueous phase (water) and an oily phase (1-octanol).

In some of these embodiments, the group denoted as E in these formulae increases the Log P of the compound, compared to CX-5461, by at least 0.5, or by at least 0.6, 0.7, 0.8, 0.9, 1, 1.2, 1.5, 2, 3, or 4 and any intermediate value therebetween.

According to some embodiments of the present invention, additional compounds, featuring or encompassing the main structural features described herein for compounds represented by Formula I are encompassed by the present embodiments.

According to some of these embodiments, there are provided compounds represented by Formula II:

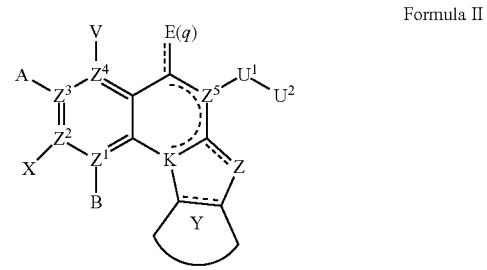

Formula II wherein E, q and K are as defined for any one of the embodiments of Formula I hereinabove;

⸺ indicates an optionally unsaturated bond;

each of B, X, A or V is absent if $Z^1$, $Z^2$, $Z^3$ and $Z^4$, respectively, is N; and each of B, X, A and V is independently H, halo, azido, —CN, —CF$_3$, —CONR$^1$R$^2$, —NR$^1$R$^2$, —SR$^2$, —OR$^2$, —R$^3$, —W, -L-W, —W$^0$, -L-N(R)—W$^0$, A$^2$ or A$^3$, when each of $Z^1$, $Z^2$, $Z^3$ and $Z^4$, respectively, is C;

Z is O, S, CR$^4$$_2$, NR$^4$CR$^4$, CR$^4$NR$^4$, CR$^4$, NR$^4$ or N;

each of $Z^1$, $Z^2$, $Z^3$ and $Z^4$ is independently C or N, provided any three N are non-adjacent;

$Z^5$ is C; or $Z^5$ may be N when Z is N;

Y is an optionally substituted 5-6 membered carbocyclic or heterocyclic ring;

U$^1$ is —C(=T)N(R)—, —C(=T)N(R)O—, —C(=T)-, —SO$_2$N(R)—, —SO$_2$N(R)N(R$^0$)—, —SO$_2$—, or —SO$_3$—, where T is O, S, or NH; or U$^1$ may be a bond when $Z^5$ is N or U$^2$ is H;

U$^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or U$^2$ is —W, -L-W, -L-N(R)—W$^0$, A$^2$ or A$^3$;

in each —NR$^1$R$^2$, R$^1$ and R$^2$ together with N may form an optionally substituted azacyclic ring, optionally containing an additional heteroatom selected from N, O and S as a ring member;

R$^1$ is H or C1-C6 alkyl, optionally substituted with one or more halogens, or =O; R$^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided one of $U^2$, V, A, X and B is a secondary amine $A^2$ or a tertiary amine $A^3$, wherein the secondary amine $A^2$ is —NH—$W^0$, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring, optionally containing an additional heteroatom selected from N, O or S as a ring member.

According to some embodiments of the invention, $Z^1$ is N, and each of $Z^2$, $Z^3$ and $Z^4$ is C.

According to some embodiments of the invention, U is —W or -L-W, where W is an optionally substituted 5-6 membered unsaturated or aromatic azacyclic ring, optionally containing an additional heteroatom selected from N, O and S; or W is an optionally substituted 5-7 membered saturated azacyclic ring containing an additional heteroatom selected from N and S.

According to some embodiments of the invention, $U^2$ is -L-N(R)—$W^0$.

According to some embodiments of the invention, Y is an optionally substituted phenyl ring.

According to some embodiments of the invention, the compound with the proviso that when $Z^1$ is N, $Z^2$ and $Z^4$ are C, $Z^5$ is C, $U^1$ is —C(O)NH—, $U^2$ is -L-W, and L is an ethylene linker, one of V, A, and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

According to any one of the embodiments of the invention, compounds having a general structure represented by Formula III, are also contemplated:

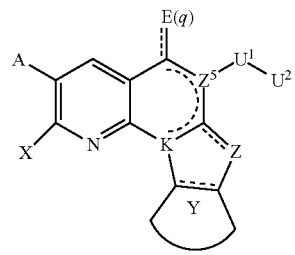

Formula III wherein E, q and K are as defined for any one of the embodiments of Formula I hereinabove;

and wherein:

⚌ indicates an optionally unsaturated bond;

each of A and X is independently H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$;

Z is O, S, $CR^4{}_2$, $NR^4CR^4$, $CR^4NR^4$ or $NR^4$;

Y is an optionally substituted 5-6 membered carbocyclic or heterocyclic ring;

$U^1$ is —C(=T)N(R)—, —C(=T)N(R)O—, —C(=T)-, —$SO_2$N(R)—, —$SO_2$N(R)N($R^0$)—, —$SO_2$—, or —$SO_3$—, where T is O, S, or NH; or $U^1$ may be a bond when U2 is H;

$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or $U^2$ is —W, -L-W, -L-N(R)—$W^0$, $A^2$ or $A^3$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O; R2 is H, or C1-C10 alkyl, C1-C10 hetero alkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—W0;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl; W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided that one of $U^2$, A, and X is a secondary amine $A^2$ or a tertiary amine $A^3$, wherein the secondary amine $A^2$ is —NH—$W^0$, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring optionally containing an additional heteroatom selected from N, O or S as a ring member.

According to some embodiments of the invention, with the proviso that when $U^1$ is —C(O)NH—, $U^2$ is -L-W, and L is an ethylene linker, one of A and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

According to some embodiments of the invention, at least one of A and X is a tertiary amine $A^3$.

According to some embodiments of the invention, $A^3$ is selected from the group consisting of imidazole, imidazoline, pyrroline, piperidine, piperazine, morpholine, thiomorpholine and homopiperazine.

According to some embodiments of the invention, $U^1$ is a —C(=T)N(R)—, T is O, and $U^2$ is -L-W or -L-N(R)—$W^0$.

According any one of the embodiments of the invention, compounds having a general structure represented by Formula IV, are also contemplated:

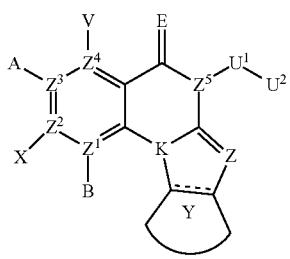

Formula IV wherein E is as defined for any one of the respective embodiments of Formula I, and K is N; and wherein $=\!=\!=$ indicates an optionally unsaturated bond; and each of B, X, A or V is absent if $Z^1$, $Z^2$, $Z^3$ and $Z^4$, respectively, is N; and each of B, X, A and V is independently H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$, when each of $Z^1$, $Z^2$, $Z^3$ and $Z^4$, respectively, is C;

each of $Z^1$, $Z^2$, $Z^3$ and $Z^4$ is independently C or N, provided any three N are non-adjacent;

Y is an optionally substituted 5-6 membered carbocyclic or heterocyclic ring; $U^1$ is —C(=T)N(R)—, —C(=T)N(R)O—, —C(=T)-, —$SO_2$N(R)—, —$SO_2$N(R)N($R^0$)—, —$SO_2$—, or —$SO_3$—, where T is O, S, or NH; or $U^1$ may be a bond when $Z^5$ is N or $U^2$ is H;

$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or $U^2$ is —W, -L-W, -L-N(R)—$W^0$, $A^2$ or $A^3$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O; $R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided that one of $U^2$, V, A, X and B is a secondary amine $A^2$ or a tertiary amine A3, wherein the secondary amine $A^2$ is —NH—$W^0$, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring, optionally containing an additional heteroatom selected from N, O or S as a ring member.

According to any one of the embodiments of the invention, compounds having a general structure represented by Formula V, are also contemplated:

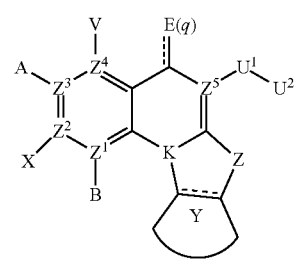

Formula V wherein E, q and K are as defined for any one of the embodiments of Formula I hereinabove;

and wherein:

$=\!=\!=$ indicates an optionally unsaturated bond;

A and V independently are H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$;

Z is O, S, $CR^4_2$, $NR^4CR^4$, $CR^4NR^4$ or $NR^4$;

Y is an optionally substituted 5-6 membered carbocyclic or heterocyclic ring;

$U^1$ is —C(=T)N(R)—, —C(=T)N(R)O—, —C(=T)-, —$SO_2$N(R)—, —$SO_2$N(R)N($R^0$)—, —$SO_2$—, or —$SO_3$—, where T is O, S, or NH; or $U^1$ may be a bond when U2 is H;

$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or $U^2$ is —W, -L-W or -L-N(R)—$W^0$, $A^2$ or $A^3$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O; $R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or R4 may be —W, -L-W or -L-N(R)—$W^0$;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided one of $U^2$, A, and V is a secondary amine $A^2$ or a tertiary amine A3, wherein the secondary amine $A^2$ is —NH—W0, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring optionally containing an additional heteroatom selected from N, O or S as a ring member.

According any one of the embodiments of the invention, compounds having a general structure represented by Formula VI, are also contemplated:

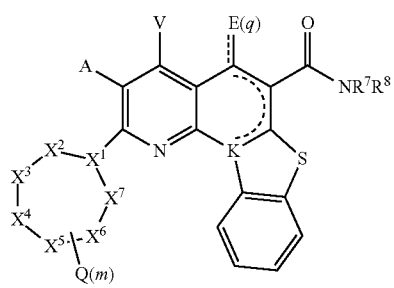

Formula VI wherein E, q and K are as defined for any one of the embodiments of Formula I hereinabove;

and wherein:

$X^1$ is CH or N;

$X^2$, $X^3$, $X^4$, $X^5$, $X^6$ and $X^7$ independently are $NR^4$, $CH_2$, CHQ or $C(Q)_2$, provided that: (i) zero, one or two of $X^2$, $X^3$, $X^4$, $X^5$, $X^6$ and $X^7$ are $NR^4$; (ii) when $X^1$ is N, both of $X^2$ and $X^7$ are not $NR^4$; (iii) when $X^1$ is N, $X^3$ and $X^6$ are not $NR^4$; and (iv) when $X^1$ is CH and two of $X^2$, $X^3$, $X^4$, $X^5$, $X^6$, $X^7$ are $NR^4$, the two $NR^4$ are located at adjacent ring positions or are separated by two or more other ring positions;

A and V independently are H, halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

in each —$NR^1R^2$, $R^1$ and $R^2$ together with N may form an optionally substituted azacyclic ring, optionally containing one additional heteroatom selected from N, O and S as a ring member;

$R^1$ is H or C1-C6 alkyl, optionally substituted with one or more halogens, or =O;

R is H, or C1-C10 alkyl, C1-C10 hetero alkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or R4 may be —W, -L-W or -L-N(R)—$W^0$;

each R is independently H or C1-C6 alkyl;

$R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in $NR^7R^8$, $R^7$ and $R^8$ together with N may form an optionally substituted azacyclic ring, optionally containing an additional heteroatom selected from N, O and S as a ring member;

m is 0, 1, 2, 3 or 4;

n is 0, 1, 2, 3, 4, or 5;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

According to some embodiments of the invention, $X^1$ is CH and two of $X^2$, $X^3$, $X^4$, $X^5$, $X^6$ and $X^7$ are $NR^4$.

According to some embodiments of the invention, wherein $X^1$ is CH and one of $X^2$, $X^3$, $X^4$, $X^5$, $X^6$ and $X^7$ are $NR^4$.

According to some embodiments of the invention, $X^1$ is CH and none of $X^2$, $X^3$, $X^4$, $X^5$, $X^6$ and $X^7$ are $NR^4$.

According to some embodiments of the invention, wherein $X^1$ is N and none of $X^2$, $X^3$, $X^4$, $X^5$, $X^6$ and $X^7$ are $NR^4$.

According to some embodiments of the invention, $X^1$ is N and one of $X^4$ or $X^5$ is $NR^4$.

According any one of the embodiments of the invention, compounds having a general structure represented by Formula VIII, are also contemplated:

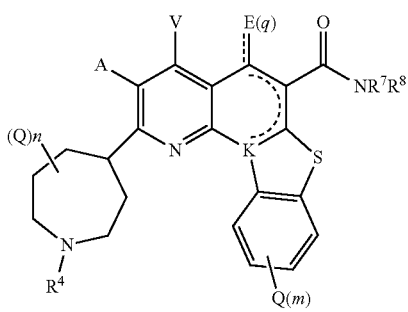

Formula (VIII)

wherein E, q and K are as defined for any one of the embodiments of Formula I hereinabove;

and wherein:

A and V independently are H, halo, azido, —CN, —CF$_3$, —CONR$^1$R$^2$, —NR$^1$R$^2$, —SR$^2$, —OR$^2$, —R$^3$, —W, -L-W, —W$^0$, or -L-N(R)—W$^0$;

each Q is independently halo, azido, —CN, —CF$_3$, —CONR$^1$R$^2$, —NR$^1$R$^2$, —SR$^2$, —OR$^2$, —R$^3$, —W, -L-W, —W$^0$, or -L-N(R)—W$^0$;

in each —NR$^1$R$^2$, R$^1$ and R$^2$ together with N may form an optionally substituted azacyclic ring, optionally containing an additional heteroatom selected from N, O and S as a ring member;

R$^1$ is H or C1-C6 alkyl, optionally substituted with one or more halogens, or =O; R$^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R$^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R$^4$ is independently H, or C1-C6 alkyl; or R4 may be —W, -L-W or -L-N(R)—W$^0$;

each R is independently H or C1-C6 alkyl;

R$^7$ is H and R$^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —NR$^7$R$^8$, R$^7$ and R$^8$ together with N may form an optionally substituted azacyclic ring, optionally containing an additional heteroatom selected from N, O and S as a ring member;

m is 0, 1, 2, 3 or 4;

n is 0, 1, 2, 3, 4 or 5;

p is 0, 1, 2 or 3;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and W$^0$ is an optionally substituted 3-4 membered carbocyclic ring, or a C1-C6 alkyl group substituted with from 1 to 4 fluorine atoms.

According to some embodiments of the invention, R$^7$ is H and R$^8$ is a C$_{1-4}$ alkyl substituted with an optionally substituted aromatic heterocyclic ring.

According to some embodiments of the invention, the optionally substituted aromatic heterocyclic ring is selected from pyridine, pyrimidine, pyrazine, imidazole, pyrrolidine, and thiazole.

According to some embodiments of the invention, R$^7$ and R$^8$ together with N in —NR$^7$R$^8$ form an optionally substituted azacyclic ring selected from the group consisting of morpholine, thiomorpholine, piperidine or piperazine ring.

According to any one of the embodiments of the invention, compounds having a general structure represented by Formula VII are also contemplated:

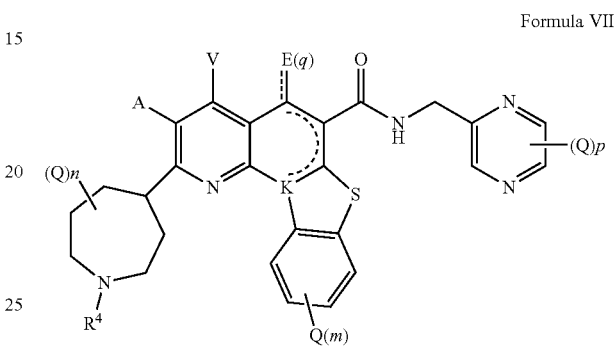

Formula VII wherein E, q and K are as defined for any one of the embodiments of Formula I hereinabove;

and wherein:

A and V independently are H, halo, azido, —CN, —CF$_3$, —CONR1R2, —NR1R2, —SR$^2$, —OR$^2$, —R$^3$, —W, -L-W, —W$^0$, or -L-N(R)—W$^0$;

each Q is independently halo, azido, —CN, —CF$_3$, —CONR$^1$R$^2$, —NR$^1$R$^2$, —SR$^2$, —OR$^2$, —R$^3$, —W, -L-W, —W$^0$, or -L-N(R)—W$^0$;

in each —NR$^1$R$^2$, R$^1$ and R$^2$ together with N may form an optionally substituted azacyclic ring, optionally containing an additional heteroatom selected from N, O and S as a ring member;

R$^1$ is H or C1-C6 alkyl, optionally substituted with one or more halogens, or =O; R2 is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R$^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R$^4$ is independently H, or C1-C6 alkyl; or R$^4$ may be —W, -L-W or -L-N(R)—W$^0$;

each R is independently H or C1-C6 alkyl;

m is 0, 1, 2, 3 or 4;

n is 0, 1, 2, 3, 4 or 5;

p is 0, 1, 2 or 3;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and W⁰ is an optionally substituted 3-4 membered carbocyclic ring, or a C1-C6 alkyl group substituted with from 1 to 4 fluorine atoms.

According to some embodiments of the invention, A and V are independently H or halo.

According to some embodiments of the invention, $R^4$ is H or C1-4 alkyl.

According to some embodiments of the invention, m and n are each 0.

According to some embodiments of the invention, p is 0 or 1.

Methods of synthesizing the compounds of some embodiments of the invention are described in Example 1 in the Examples section the follows.

According to some embodiments, compounds represented by Formula I as described herein, or by any one of Formulae II-VIII are prepared by converting a compound encompassed by these formulae into a corresponding chloride such as depicted for Compound 2 herein (see, Table 1) and the chloride is thereafter reacted with a suitable precursor (e.g., an amine) to form the desired compound (e.g., a corresponding imine).

For use as pharmaceutical agents, the compound of some embodiments of the invention is sterile.

According to some embodiments of the invention, the compound is purified using known methods.

According to some embodiments of the invention, the compound has 95-99.9% purity.

For any of the embodiments described herein, the compound may be in a form of a salt, for example, a pharmaceutically acceptable salt, and/or in a form of a prodrug.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be an acid addition salt comprising at least one basic (e.g., amine) group of the compound which is in a positively charged form (e.g., an ammonium ion), in combination with at least one counter-ion, derived from the selected acid, that forms a pharmaceutically acceptable salt.

The acid addition salts of the compounds described herein may therefore be complexes formed between one or more amino groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

Depending on the stoichiometric proportions between the basic or acidic charged group(s) in the compound (e.g., amine group(s)) and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

As used herein, the term "prodrug" refers to a compound which is converted in the body to an active compound. A prodrug is typically designed to facilitate administration, e.g., by enhancing absorption. A prodrug may comprise, for example, the active compound modified with ester groups, for example, wherein one or more hydroxy groups of the active compound is modified by an acyl (e.g., acetyl) group to form an ester group, and/or wherein one or more carboxylic acid of the active compound is modified by an alkyl (e.g., ethyl) group to form an ester group.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, except in embodiments wherein a specific stereoisomer is explicitly required, as well as any isomorph thereof.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein. Representative examples are piperidine, piperazine, tetrahydrofuran, tetrahydropyran, morpholine and the like.

A "hydroxy" group refers to an —OH group.

As used herein, the terms "amine" and "amino" refer to either a —NR'R" group, wherein R' and R" are selected from the group consisting of hydrogen, alkyl, cycloalkyl, heteroalicyclic (bonded through a ring carbon), aryl and heteroaryl (bonded through a ring carbon). R' and R" are bound via a carbon atom thereof. Optionally, R' and R" are selected from the group consisting of hydrogen and alkyl comprising 1 to 4 carbon atoms. Optionally, R' and R" are hydrogen.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "disulfide" group refers to both a —S-thioalkoxy and a —S-thioaryloxy group.

A disulfide bond describes a —S—S— bond.

A "carbonyl" group refers to a —C(=O)—R' group, where R' is defined as hereinabove, or where R' and C form a part of a cyclic moiety such as cycloalkyl, aryl, heteroaryl and heteroalicyclic, as defined herein.

A "thiocarbonyl" group refers to a —C(=S)—R' group, where R' is as defined herein.

A "C-carboxy" group refers to a —C(=O)—O—R' groups, where R' is as defined herein.

An "O-carboxy" group refers to an R'C(=O)—O— group, where R' is as defined herein.

An "oxo" group refers to a =O group.

A "thioxo" group refers to a =S group.

A "carboxylate" or "carboxyl" encompasses both C-carboxy and O-carboxy groups, as defined herein.

A "carboxylic acid" group refers to a C-carboxy group in which R' is hydrogen.

A "thiocarboxy" or "thiocarboxylate" group refers to both —C(=S)—O—R' and —O—C(=S)R' groups.

An "ester" refers to a C-carboxy group wherein R' is not hydrogen.

An ester bond refers to a —O—C(=O)— bond.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

A carbamate bond describes a —O—C(=O)—NR'— bond, where R' is as described herein.

An "O-thiocarbamyl" group refers to an —OC(=S)—NR'R" group, where each of R' and R" is as defined herein.

An "N-thiocarbamyl" group refers to an R'OC(=S) NR"— group, where each of R' and R" is as defined herein.

A "thiocarbamyl" or "thiocarbamate" group encompasses O-thiocarbamyl and N-thiocarbamyl groups.

A thiocarbamate bond describes a —O—C(=S)—NR'— bond, where R' is as described herein.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

An amide bond describes a —NR'—C(=O)— bond, where R' is as defined herein.

A "urea" group refers to an —N(R')—C(=O)—NR"R'" group, where each of R' and R" is as defined herein, and R'" is defined as R' and R" are defined herein.

A "nitro" group refers to an —NO₂ group.

A "cyano" group refers to a —C≡N group.

The term "hydrazine" describes a —N(R')—N(R")R'" group, with each of R', R" and R'" as defined hereinabove.

Treatment of Autoimmune Diseases:

According to an aspect of some embodiments of the present invention any one of the compounds as described herein is for use in the treatment of an autoimmune disease in a subject in need thereof.

According to an aspect of some embodiments of the present invention any one of the compounds as described herein is for use in the manufacture of a medicament for treating an autoimmune disease in a subject in need thereof.

According to an aspect of some embodiments of the present invention there is provided a method of treating an autoimmune disease, which is effected by administering to the subject a therapeutically effective amount of any one of the compounds as described herein.

As used in the context of this aspect of the present embodiments, the phrase "treating" refers to inhibiting or arresting the development of the autoimmune disease (e.g., multiple sclerosis) and/or causing the reduction, remission, or regression of the autoimmune disease and/or optimally curing the autoimmune disease. Those of skill in the art will understand that various methodologies and assays can be used to assess the development of autoimmune disease, and similarly, various methodologies and assays may be used to assess the reduction, remission or regression of the autoimmune disease.

As used herein, the term "subject" includes mammals, preferably human beings at any age which suffer from the pathology (the autoimmune disease) or which have been diagnosed as being afflicted by the pathology.

According to some embodiments of the invention, the term "subject" encompasses individuals who are at risk to develop the pathology or are suspected of having the pathology. As used herein the phrase "autoimmune disease" refers to any disease caused by an autoimmune response, i.e., an immune response directed to a substance in the body of the subject.

It should be noted that since autoimmunity can affect any organ or tissue of the subject, e.g., the brain, skin, kidney, lungs, liver, heart, or thyroid of the subject, the clinical expression of the disease depends upon the site affected.

Following is a non-limiting list of autoimmune diseases or disorders (including autoimmune-related diseases or disorders) which can be treated by the compound of some embodiments of the invention: Acute Disseminated Encephalomyelitis (ADEM); Acute necrotizing hemorrhagic leukoencephalitis; Addison's disease; Agammaglobulinemia; Alopecia areata; Amyloidosis; Ankylosing spondylitis; Anti-GBM/Anti-TBM nephritis; Antiphospholipid syndrome (APS); Autoimmune angioedema; Autoimmune aplastic anemia; Autoimmune dysautonomia; Autoimmune hepatitis; Autoimmune hyperlipidemia; Autoimmune immunodeficiency; Autoimmune inner ear disease (AIED); Autoimmune myocarditis; Autoimmune pancreatitis; Autoimmune retinopathy; Autoimmune thrombocytopenic purpura (ATP); Autoimmune thyroid disease; Autoimmune urticaria; Axonal & neuronal neuropathies; Balo disease; Behcet's disease; Bullous pemphigoid; Cardiomyopathy; Castleman disease; Celiac disease; Chagas disease; Chronic inflammatory demyelinating polyneuropathy (CIDP); Chronic recurrent multifocal ostomyelitis (CRMO); Churg-Strauss syndrome; Cicatricial pemphigoid/benign mucosal pemphigoid; Crohn's disease; Cogans syndrome; Cold agglutinin disease; Congenital heart block; Coxsackie myocarditis; CREST disease; Essential mixed cryoglobulinemia; Demyelinating neuropathies; Dermatitis herpetiformis; Dermatomyositis; Devic's disease (neuromyelitis optica); Discoid lupus; Dressler's syndrome; Endometriosis; Eosinophilic fasciitis; Erythema nodosum; Experimental allergic encephalomyelitis; Evans syndrome; Fibrosing alveolitis; Giant cell arteritis (temporal arteritis); Glomerulonephritis; Goodpasture's syndrome; Granulomatosis with Polyangiitis (GPA) see Wegener's; Graves' disease; Guillain-Barre syndrome; Hashimoto's encephalitis; Hashimoto's thyroiditis; Hemolytic anemia; Henoch-Schonlein purpura; Herpes gestationis; Hypogammaglobulinemia; Idiopathic thrombocytopenic purpura (ITP); IgA nephropathy; IgG4-related sclerosing disease; Immunoregulatory lipoproteins; Inclusion body myositis; Insulin-dependent diabetes (type1); Interstitial cystitis; Juvenile arthritis; Juvenile diabetes; Kawasaki syndrome; Lambert-Eaton syndrome; Leukocytoclastic vasculitis; Lichen planus; Lichen sclerosus; Ligneous conjunctivitis; Linear IgA disease (LAD); Lupus (SLE); Lyme disease, chronic; Meniere's disease; Microscopic polyangiitis; Mixed connective tissue disease (MCTD); Mooren's ulcer; Mucha-Habermann disease; Multiple sclerosis; Myasthenia gravis; Myositis; Narcolepsy; Neuromyelitis optica (Devic's); Neutropenia; Ocular cicatricial pemphigoid; Optic neuritis; Palindromic rheumatism; PANDAS (Pediatric Autoimmune Neuropsychiatric Disorders Associated with *Streptococcus*); Paraneoplastic cerebellar degeneration; Paroxysmal nocturnal hemoglobinuria (PNH); Parry Romberg syndrome; Parsonnage-Turner syndrome; Pars planitis (peripheral uveitis); Pemphigus; Peripheral neuropathy; Perivenous encephalomyelitis; Pernicious anemia; POEMS syndrome; Polyarteritis *nodosa*; Type I, II, & III autoimmune polyglandular syndromes; Polymyalgia rheumatica; Polymyositis; Postmyocardial infarction syndrome; Postpericardiotomy syndrome; Progesterone dermatitis; Primary biliary cirrhosis; Primary sclerosing cholangitis; Psoriasis; Psoriatic arthritis; Idiopathic pulmonary fibrosis; Pyoderma gangrenosum; Pure red cell aplasia; Raynauds phenomenon; Reflex sympathetic dystrophy; Reiter's syndrome; Relapsing polychondritis; Restless legs syndrome; Retroperitoneal fibrosis; Rheumatic fever; Rheumatoid arthritis; Sarcoidosis; Schmidt syndrome; Scleritis; Scleroderma; Sjogren's syndrome; Sperm & testicular autoimmunity; Stiff person syndrome; Subacute bacterial endocarditis (SBE); Susac's syndrome; Sympathetic ophthalmia; Takayasu's arteritis; Temporal arteritis/Giant cell arteritis; Thrombocytopenic purpura (TTP); Tolosa-Hunt syndrome; Transverse myelitis; Ulcerative colitis; Undifferentiated connective tissue disease (UCTD); Uveitis; Vasculitis; Vesiculobullous dermatosis; Vitiligo; Wegener's granulomatosis (now termed Granulomatosis with Polyangiitis (GPA).

According to some embodiments of the invention, the autoimmune disease is multiple sclerosis.

According to some embodiments of the invention, the subject is diagnosed with multiple sclerosis.

The diagnosis of "multiple sclerosis" can be made when a subject has experienced at least one neurological attack affecting the central nervous system (CNS) accompanied by demyelinating lesions within the brain or spinal cord, which may have, but not necessarily confirmed by magnetic resonance imaging (MRI). The neurological attack can involve acute or sub-acute neurological symptomatology (attack) manifested by various clinical presentations like unilateral loss of vision, vertigo, ataxia, incoordination, gait difficulties, sensory impairment characterized by paresthesia, dysesthesia, sensory loss, urinary disturbances until incontinence, diplopia, dysarthria, various degrees of motor weakness until paralysis, cognitive decline either as a monosymptomatic or in combination. The symptoms usually remain for several days to few weeks, and then partially or completely resolve.

Further details on the diagnosis of multiple sclerosis according to 2010 McDonald Criteria for Diagnosis of MS are provided in Polman C H., et al., 2011 ("Diagnostic criteria for multiple sclerosis: 2010 revisions to the McDonald criteria" Annals of Neurology, vol. 69 (2): pages 292-302) which is fully incorporated herein by reference in its entirety.

For example, the diagnosis of multiple sclerosis can be made upon (I): Clinical presentation of ≥2 attacks, with objective clinical evidence of ≥2 lesions or objective clinical evidence of 1 lesion with reasonable historical evidence of a prior attack; (II): Clinical presentation of ≥2 attacks, with objective clinical evidence of 1 lesion, additional data have to include dissemination in space, demonstrated by: ≥1 T2 lesion in at least 2 of 4 MS-typical regions of the CNS (periventricular, juxtacortical, infratentorial, or spinal cord); (III): Clinical presentation of 1 attack, with objective clinical evidence of ≥2 lesions, additional data have to include dissemination in time, demonstrated by: Simultaneous presence of asymptomatic gadolinium-enhancing and nonenhancing lesions at any time; or A new T2 and/or gadolinium-enhancing lesion(s) on follow-up MRI, irrespective of its timing with reference to a baseline scan; (IV): Clinical presentation of 1 attack, additional data have to include dissemination in space and time, demonstrated by: For DIS: ≥1 T2 lesion in at least 2 of 4 MS-typical regions of the CNS (periventricular, juxtacortical, infratentorial, or spinal cord) and for DIT: Simultaneous presence of asymptomatic gadolinium-enhancing and nonenhancing lesions at any time; or A new T2 and/or gadolinium-enhancing lesion(s) on follow-up MRI, irrespective of its timing with reference to a baseline scan; (V): Clinical presentation of Insidious neurological progression suggestive of MS (PPMS), additional data have to include 1 year of disease progression (retrospectively or prospectively determined) plus 2 of 3 of the following criteria: 1. Evidence for DIS in the brain based on ≥1 T2 lesions in the MS-characteristic (periventricular, juxtacortical, or infratentorial) regions 2. Evidence for DIS in the spinal cord based on ≥2 T2 lesions in the cord 3. Positive CSF (isoelectric focusing evidence of oligoclonal bands and/or elevated IgG index).

According to some embodiments of the invention, the subject has relapsing-remitting multiple sclerosis (RRMS).

According to some embodiments of the invention, the subject has a primary progressive multiple sclerosis (PPMS).

According to some embodiments of the invention, the subject has a secondary progressive MS (SPMS).

According to some embodiments of the invention, the subject has benign multiple sclerosis (BMS).

According to some embodiments of the invention, the subject has a progressive-relapsing course of MS.

According to some embodiments of the invention, treating the subject refers to changing the disease course of the subject from a typical RRMS course to a BMS course.

According to some embodiments of the invention, treating the subject refers to suppressing the activity of typical RRMS course.

According to some embodiments of the invention, administering the compound is performed after diagnosing the subject as having the autoimmune disease.

According to some embodiments of the invention, the autoimmune disease is multiple sclerosis and the diagnosis comprises appearance of brain lesions characteristics of the multiple sclerosis.

According to some embodiments of the invention, the compound prevents the appearance of additional neurological attack(s) and/or brain lesion(s) as compared to the number of neurological attack(s) and/or brain lesion(s) present at time of diagnosing multiple sclerosis.

According to an aspect of some embodiments of the present invention the compounds as described herein, in any one of the embodiments thereof are useful in inhibiting an activity of RNA Polymerase I, or in modulating a RNA Polymerase I pathway. These compounds are therefore useful in the treatment of any disease or disorder that is associated with the RNA Polymerase I or which is treatable by modulating (e.g., inhibiting), a RNA Polymerase I activity or pathway, as is described in further detail hereinafter.

Such diseases and disorders include, in addition to autoimmune diseases as described herein, also proliferative diseases or disorders, as described herein, and any other medical conditions which would be recognized by any person skilled in the art.

Treatment of Proliferative Diseases or Disorders:

According to some embodiments of the invention, any of the compounds described herein are useful in treating a proliferative disease or disorder and/or in modulating (e.g., inhibiting) a protein kinase activity.

As used herein the phrase "proliferative disease" refers to diseases manifested by abnormal cell proliferation, and includes, for example, benign tumors, pre-malignant tumors, and malignant tumors, such as cancer.

As used herein the terms "cancer" and "malignant tumor" are interchangeably used. The term refers to a malignant growth or tumor caused by abnormal and uncontrolled cell proliferation (cell division). Exemplary cancers include, without limitation, cancers of the colorectum, breast, lung, liver, pancreas, lymph node, colon, prostate, brain, head and neck, skin, liver, kidney, blood and heart (e.g., leukemia, lymphoma, carcinoma).

The terms "treat" and "treating" and "treatment" as used herein refer to ameliorating, alleviating, lessening, and removing symptoms of a disease or condition. In some embodiments, "treating" is effected by a compound as described herein, which, when administered to a subject in need thereof, exhibit a biological effect such as apoptosis of certain cells (e.g., cancer cells), reduction of proliferation of certain cells, or lead to ameliorating, alleviating, lessening, or removing symptoms of a disease or condition. "The terms "treat" and "treating" and "treatment" as used herein in some embodiments, also can refer to reducing or stopping a cell proliferation rate (e.g., slowing or halting tumor growth) or reducing the number of proliferating cancer cells (e.g., removing part or all of a tumor). The terms "treat" and "treating" and "treatment" as used herein also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

Also provided herein are methods and uses of any one of the compounds described herein, for modulating the activity of a protein kinase, which are effected by contacting a system comprising the protein kinase with a compound as described herein in an amount effective for modulating (e.g., inhibiting) the activity of the kinase. The system in such embodiments can be a cell-free system or a system comprising cells. Also provided are methods and uses utilizing the compounds as described herein for reducing cell proliferation, and optionally inducing apoptosis, which are effected by contacting cells with a compound as described herein in an amount effective to reduce proliferation of the cells. The cells in such embodiments can be in a cell line, in a tissue or in a subject (e.g., a research animal or human). Protein kinases are a family of enzyme which catalyze the transfer of a gamma phosphate from adenosine triphosphate to a serine or threonine amino acid (serine/threonine protein kinase), tyrosine amino acid (tyrosine protein kinase), tyrosine, serine or threonine (dual specificity protein kinase) or histidine amino acid (histidine protein kinase) in a peptide or protein substrate. Thus, included herein are methods and uses which are effected by contacting a system comprising a protein kinase with a compound as described herein in an amount effective for modulating (e.g., inhibiting) the activity of the protein kinase. In some embodiments, the activity of the protein kinase is the catalytic activity of the protein (e.g., catalyzing the transfer of a gamma phosphate from adenosine triphosphate to a peptide or protein substrate). Systems in such embodiments can be a cell-free system or a system comprising cells (e.g., in vitro).

In some embodiments, the protein kinase is a serine-threonine protein kinase or a tyrosine protein kinase. In some embodiments, the protein kinase is a protein kinase fragment having compound-binding activity.

In some embodiments, the protein kinase is, or contains a subunit (e.g., catalytic subunit, SH2 domain, SH3 domain) of, CK2, Pim subfamily protein kinase (e.g., PIM1, PIM2, PIM3) or Flt subfamily protein kinase (e.g, FLT1, FLT3, FLT4).

In some embodiments the protein kinase is a recombinant protein. The protein kinase can be from any source, such as cells from a mammal, ape or human, for example. In some embodiments, the protein kinase is a human protein kinase.

In some embodiments, any of the compounds described herein is also useful in the treatment of a condition related to inflammation or pain. Conditions associated with inflammation and pain include without limitation, acid reflux, heartburn, acne, allergies and sensitivities, Alzheimer's disease, asthma, atherosclerosis, bronchitis, carditis, celiac disease, chronic pain, Crohn's disease, cirrhosis, colitis, dementia, dermatitis, diabetes, dry eyes, edema, emphysema, eczema, fibromyalgia, gastroenteritis, gingivitis, heart disease, hepatitis, high blood pressure, insulin resistance, interstitial cystitis, joint pain/arthritis/rheumatoid arthritis, metabolic syndrome (syndrome X), myositis, nephritis, obesity, osteopenia, osteoporosis, Parkinson's disease, periodontal disease, polyarteritis, polychondritis, psoriasis, scleroderma, sinusitis, Sjogren's syndrome, spastic colon, systemic candidiasis, tendonitis, urinary tract infections, vaginitis, inflammatory cancer (e.g., inflammatory breast cancer) and the like.

In some embodiments, any of the compounds described herein is also useful for modulating angiogenesis in a subject, and for treating a condition associated with aberrant angiogenesis in a subject.

Pharmaceutical Compositions:

In any one of the methods and uses described herein, and any one of the embodiments thereof, a compound as described herein can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compound of some embodiments of the invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to some embodiments of the invention, the compound is administered by oral administration.

Conventional approaches for drug delivery to the central nervous system (CNS) include: neurosurgical strategies (e.g., intracerebral injection or intracerebroventricular infusion); pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (the compound of some embodiments of the invention) effective to prevent, alleviate or ameliorate symptoms of a disorder (e.g., an autoimmune disease such as multiple sclerosis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide tissue or blood levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The doses shown herein with respect to the mouse animal model can be converted for the treatment other species such as human and other animals diagnosed with the autoimmune disease. Conversion Table approved by the FDA is shown in Reagan-Shaw S., et al., FASEB J. 22:659-661 (2007).

The human equivalent dose is calculated as follows: HED (mg/kg)=Animal dose (mg/kg) multiplied by (Animal $K_m$/human $K_m$).

According to some embodiments of the invention, the compound is provided at an amount equivalent to a range of from about 3-30 mg/kg/day in mice, including any intermediate subranges and values therebetween.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is detailed herein.

Monitoring Treatment Efficacy:

As shown in Examples 2 and 3 in the Examples section which follows, treatment with the compound of some embodiments of the invention (e.g. Compound 10) suppresses transcription of genes of the RNA polymerase pathway e.g. pre-rRNA. Thus, the teachings of the invention can be also used to determine efficiency of the compound of some embodiments of the invention in treating a disease, e.g. autoimmune disease (e.g., multiple sclerosis) and/or a proliferative disease, by determining the effect of the compound on the expression level of at least one gene of the RNA polymerase I pathway. This can be used to develop a tailored treatment of a disease by monitoring drug efficacy. This system is based on measuring the level of genes of the RNA polymerase I pathway during treatment with the compound and the ability to perform an ongoing fine-tuning drug efficacy assessment.

Thus, according to an aspect of some embodiments of the invention, there is provided a method of monitoring treatment efficiency of the compound of some embodiments of the invention, the method comprising:

(a) treating the subject with the compound according to the method of some embodiments of the invention, and (b) comparing a level of expression of least one gene involved in the RNA polymerase I pathway in a cell of the subject following treating with the compound to a level of expression of the at least one gene in a cell of the subject prior to treating the subject with the compound, (i) wherein a decrease above a predetermined threshold in the level of expression of the at least one gene following treating with the compound relative to the level of expression of the at least one gene prior to treating with the compound indicates that the compound is efficient for treating the subject;

(ii) wherein an increase above a predetermined threshold in the level of expression of the at least one gene following treating with the compound relative to the level of expression of the at least one gene prior to treating with the compound indicates that the compound is not efficient for treating the subject; or (iii) wherein when a level of expression of the at least one gene following treating with the compound is identical or changed below a predetermined threshold as compared to prior to treating with the compound then the treatment is not efficient for treating the subject;

thereby monitoring treatment efficiency of the subject having disease or disorder as described herein.

As used herein, the phrase "level of expression" refers to the degree of gene expression and/or gene product activity in a specific cell. For example, up-regulation or down-regulation of various genes can affect the level of the gene product (i.e., RNA and/or protein) in a specific cell.

It should be noted that the level of expression can be determined in arbitrary absolute units, or in normalized units (relative to known expression levels of a control reference). For example, when using DNA chips, the expression levels are normalized according to the chips' internal controls or by using quantile normalization such as RMA.

As used herein the phrase "a cell of the subject" refers to at least one cell (e.g., an isolated cell), cell culture, cell content and/or cell secreted content which contains RNA and/or proteins of the subject. Examples include a blood cell, a cell obtained from any tissue biopsy [e.g., cerebro-spinal fluid, (CSF), brain biopsy], a bone marrow cell, body fluids such as blood, plasma, serum, saliva, spinal fluid, lymph fluid, the external sections of the skin, respiratory, intestinal, and genitourinary tracts, tears, saliva, sputum and milk. According to an embodiment of the invention, the cell is a blood cell (e.g., white blood cells, macrophages, B- and T-lymphocytes, monocytes, neutrophiles, eosinophiles, and basophiles) which can be obtained using a syringe needle from a vein of the subject. It should be noted that the cell may be isolated from the subject (e.g., for in vitro detection) or may optionally comprise a cell that has not been physically removed from the subject (e.g., in vivo detection). According to specific embodiments the cell is comprised in a biological sample (e.g. a blood sample). Thus, according to a specific embodiment, the method further comprises obtaining the biological sample from the subject. It should be noted that a specific cell type may be further isolated from the biological sample directly obtained from the subject e.g. a white blood can be isolated from a blood sample. Methods of isolating specific cell types are well known in the art including, but not limited to, density gradient centrifugation, flow cytometry and magnetic beads separation.

According to some embodiments of the invention, the white blood cell comprises peripheral blood mononuclear cells (PBMC). The phrase, "peripheral blood mononuclear cells (PBMCs)" as used herein, refers to a mixture of monocytes and lymphocytes. Several methods for isolating white blood cells are known in the art. For example, PBMCs can be isolated from whole blood samples using density gradient centrifugation procedures. Typically, anticoagulated whole blood is layered over the separating medium. At the end of the centrifugation step, the following layers are visually observed from top to bottom: plasma/platelets, PBMCs, separating medium and erythrocytes/granulocytes. The PBMC layer is then removed and washed to remove contaminants (e.g., red blood cells) prior to determining the expression level of the polynucleotide(s) therein.

According to some embodiments of the invention, the level of expression of the gene(s) of the invention is determined using an RNA and/or a protein detection method.

According to some embodiments of the invention, the RNA or protein molecules are extracted from the cell of the subject. Thus, according to specific embodiments, the method further comprises extracting a RNA or a protein from the cell prior to the comparing.

Methods of extracting RNA or protein molecules from cells of a subject are well known in the art. The extracted RNA can be further processed to a cDNA. Methods of and commercially available kits for converting RNA to cDNA are well known in the art and include e.g. the use of the enzyme reverse transcriptase. Once obtained, the RNA, cDNA or protein molecules can be characterized for the expression and/or activity level of various RNA, cDNA and/or protein molecules using methods known in the arts.

According to specific embodiment, the expression of the POL1 pathway gene can be determined at the nucleic acid level using RNA or DNA detection methods.

Thus, according to some embodiments of the invention, detection of the expression level of the RNA of the POL1 pathway is performed by contacting the biological sample, the cell, or fractions or extracts thereof with a probe (e.g. oligonucleotide probe or primer) which specifically hybridizes to a polynucleotide expressed from the gene of the POL1 pathway (e.g., including any alternative spliced form which is known in the art). Such a probe can be at any size, such as a short polynucleotide (e.g., of 15-200 bases), an intermediate polynucleotide of 100-2000 bases and a long polynucleotide of more than 2000 bases.

The probe used by the present invention can be any directly or indirectly labeled RNA molecule [e.g., RNA oligonucleotide (e.g., of 17-50 bases), an in vitro transcribed RNA molecule], DNA molecule (e.g., oligonucleotide, e.g., 15-50 bases, cDNA molecule, genomic molecule) and/or an analogue thereof [e.g., peptide nucleic acid (PNA)] which is specific to the RNA transcript of the gene involved in the POL1 pathway. According to specific embodiments, the probe is bound to a detectable moiety.

Oligonucleotides designed according to the teachings of the present invention can be generated according to any oligonucleotide synthesis method known in the art such as enzymatic synthesis or solid phase synthesis.

According to specific embodiments, the contacting is effected under conditions which allow the formation of a complex comprising mRNA or cDNA of a gene involved in the POL1 pathway present in the cell and the probe. The complex can be formed at a variety of temperatures, salt concentration and pH values which may vary depending on the method and the biological sample used and those of skills in the art are capable of adjusting the conditions suitable for the formation of each nucleotide/probe complex.

Thus, according to an aspect of the present invention there is provided a composition of matter comprising a biological sample of a subject, and a probe capable of detecting a polynucleotide expressed from a gene involved in the POL1 pathway.

Non-limiting examples of methods of detecting RNA and/or cDNA molecules in a cell sample include Northern blot analysis, RT-PCR [e.g., a semi-quantitative RT-PCR, quantitative RT-PCR using e.g., the Light Cycler™ (Roche)], RNA in situ hybridization (using e.g., DNA or RNA probes to hybridize RNA molecules present in the cells or tissue sections), in situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface [e.g., a glass wafer) with addressable location, such as Affymetrix microarray (Affymetrix®, Santa Clara, Calif.)].

For example, the level of RRN3 in a sample can be determined by RT-PCR using primers available from Santa Cruz Biotechnology Inc. (sc-106866-PR), or Taqman Gene Expression Assay HS00607907_m1 (Applied Biosystems, Foster City, Calif., USA), according to manufacturer's recommendation.

For example, the level of human pre-rRNA (Accession No: NR_046235, SEQ ID NO: 68) in a sample can be determined by RT-PCR using the RT2 qPCR Primer Assay for Human RNA45S5 (330001, Cat. N PPH82089A-200, Qiagen).

As mentioned, according to specific embodiments, the expression of the POL1 pathway gene can be determined at the amino acid level using protein detection methods.

Thus, according to some embodiments of the invention, detection of the expression level of the protein of the POL1 pathway is performed by contacting the biological sample, the cell, or fractions or extracts thereof with an antibody which specifically binds to a polypeptide expressed from the gene of the Pol I pathway (e.g., including any variants thereof which is known in the art). According to specific embodiments, the contacting is effected under conditions which allow the formation of a complex comprising polypeptide of a gene involved in the POL1 pathway present in the cell and the antibody (i.e. immunocomplex).

The immunocomplex can be formed at a variety of temperatures, salt concentration and pH values which may vary depending on the method and the biological sample used and those of skills in the art are capable of adjusting the conditions suitable for the formation of each immunocomplex.

Thus, according to an aspect of the present invention there is provided a composition of matter comprising a biological sample of a subject, and an antibody capable of detecting a polypeptide expressed from a gene involved in the POL1 pathway. According to a specific embodiment, the composition further comprises a secondary antibody capable of binding the antibody.

The antibody used by the present invention can be any directly or indirectly labeled antibody. According to specific embodiments, the probe is bound to a detectable moiety.

The detectable moiety used by some embodiments of the invention can be, but is not limited to a fluorescent chemical (fluorophore), a phosphorescent chemical, a chemiluminescent chemical, a radioactive isotope (such as $[^{125}I]$iodine), an enzyme, a fluorescent polypeptide, an affinity tag, and molecules (contrast agents) detectable by Positron Emission Tomography (PET) or Magnetic Resonance Imaging (MRI).

Non-limiting examples of methods of detecting the level and/or activity of specific protein molecules in a cell sample include Enzyme linked immunosorbent assay (ELISA), Western blot analysis, immunoprecipitation (IP), radio-immunoassay (RIA), Fluorescence activated cell sorting (FACS), immunohistochemical analysis, in situ activity assay (using e.g., a chromogenic substrate applied on the cells containing an active enzyme), in vitro activity assays (in which the activity of a particular enzyme is measured in a protein mixture extracted from the cells) and molecular weight-based approach. For example, in case the detection of the expression level of a secreted protein is desired, ELISA assay may be performed on a sample of fluid obtained from the subject (e.g., serum), which contains cell-secreted content.

As described above, the level of expression of least one gene involved in the RNA polymerase I pathway in a cell of the subject following treating with the compound is compared to the level of expression of the at least one gene in a cell of the subject prior to treating the subject with the compound.

As used herein the phrase "following treating with the compound" refers to any time period after administering the compound to the subject, e.g., from a few minutes to hours, or from a few days to weeks or months after drug administration.

According to some embodiments of the invention the level of expression is determined following administration of the first dose of the compound.

According to some embodiments of the invention the level of expression is determined following administration of any dose of the compound.

As used herein the phrase "prior to treating with the compound" refers to any time period prior administering the compound to the subject, e.g., from a few minutes to hours, or from a few days to weeks or months prior to drug administration.

According to some embodiments of the invention the level of expression is determined prior any dose of the compound (e.g., when the subject is naïve to treatment).

According to some embodiments of the invention prior to treating refers to when the subject is first diagnosed with autoimmune disease, e.g., multiple sclerosis.

According to some embodiments of the invention prior to treating refers to when the subject is suspected of having the autoimmune disease (e.g., multiple sclerosis), or diagnosed with probable autoimmune disease (e.g., probable multiple sclerosis).

According to some embodiments of the invention prior to treating refers to upon the onset of the autoimmune disease.

According to some embodiments of the invention the effect of the treatment on the subject can be evaluated by monitoring the level of expression of at least one of the polynucleotides described hereinabove and below. For example, downregulation in the level of RRN3 in the subject following treatment can be indicative of the positive effect of the treatment on the subject, e.g., switching from a typical RRMS to a BMS course of multiple sclerosis.

As described above, a decrease above a predetermined threshold in the level of expression of the at least one gene following treating with the compound relative to the level of expression of the at least one gene prior to treating with the compound indicates that the compound is efficient for treating the subject.

As used herein the phrase "a decrease above a predetermined threshold" refers to a decrease in the level of expression in the cell of the subject following treating with the compound which is higher than a predetermined threshold such as a about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times, higher than about 350, higher than about 500 times, higher than about 1000 times, or more relative to the level of expression prior to treating with the compound.

As described, an increase above a predetermined threshold in the level of expression of the at least one gene following treating with the compound relative to the level of expression of the at least one gene prior to treating with the compound indicates that the compound is not efficient for treating the subject.

As used herein the phrase "an increase above a predetermined threshold" refers to an increase in the level of expression in the cell of the subject following treating with the compound, which is higher than a predetermined threshold such as about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times, higher than about 350, higher than about 500 times, higher than about 1000 times, or more relative to the level of expression of the at least one gene prior to treating with the compound.

As described, a level of expression of the at least one gene following treating with the compound which is identical or changed below a predetermined threshold as compared to prior to treating with the compound is indicative that the treatment is not efficient for treating the subject.

As used herein the phrase "changed below a predetermined threshold as compared to prior to treating with the compound" refers to an increase or a decrease in the level of expression in the cell of the subject following treating with the compound, which is lower than a predetermined threshold, such as lower than about 10 times, e.g., lower than about 9 times, e.g., lower than about 8 times, e.g., lower than about 7 times, e.g., lower than about 6 times, e.g., lower than about 5 times, e.g., lower than about 4 times, e.g., lower than about 3 times, e.g., lower than about 2 times, e.g., lower than about 90%, e.g., lower than about 80%, e.g., lower than about 70%, e.g., lower than about 60%, e.g., lower than about 50%, e.g., lower than about 40%, e.g., lower than about 30%, e.g., lower than about 20%, e.g., lower than about 10%, e.g., lower than about 9%, e.g., lower than about 8%, e.g., lower than about 7%, e.g., lower than about 6%, e.g., lower than about 5%, e.g., lower than about 4%, e.g., lower than about 3%, e.g., lower than about 2%, e.g., lower than about 1% relative to the level of expression of the at least one gene prior to treating with the compound.

Non-limiting examples of genes involved in the RNA polymerase I pathway which can be used according to the method of the invention include RRN3, LRPPRC, POLR1A, POLR1B, POLR1C, POLR1D, POLR1E, PTRF, NIP7, ISF1, TAF1A, TAF1B, TAF1C, TAF1D, UBTF, TTF1 NCL and RNA45S5 (45S Pre-rRNA).

Sequence information regarding gene products (i.e., RNA transcripts and polypeptide sequences) of the genes of RNA polymerase I pathway which can be used for detection thereof can be found according to the following access numbers.

| Affymetrix ProbSet/SEQ ID NO: | Representative Public ID/SEQ ID NO: | Representative polypeptide Public ID/SEQ ID NO: | Gene Symbol | Gene Title |
|---|---|---|---|---|
| 216902_s_at/1 | AF001549/18 NM_018427/19 | NP_060897/38 | RRN3 | RRN3 RNA polymerase I transcription factor homolog |
| 211971_s_at/2 | AI653608/20 NM_133259/21 | NP_573566/39 | LRPPRC | leucine-rich PPR-motif containing |
| 220113_x_at/3 | NM_019014/22 | NP_001131076/40 NP_061887/41 | POLR1B | polymerase (RNA) I polypeptide B, 128 kDa |
| 207515_s_at/4 | NM_004875/23 | NP_976035/42 | POLR1C | polymerase (RNA) I polypeptide C, 30 kDa |
| 218258_at/5 | NM_015972/24 | NP_057056/43 NP_689918/44 | POLR1D | polymerase (RNA) I polypeptide D, 16 kDa |
| 200610_s_at/6 | NM_005381/25 | NP_005372/45 | NCL | nucleolin |
| 222704_at/7 | W93584/26 | NM_015425/46 | POLR1A | polymerase (RNA) I polypeptide A, 194 kDa |
| 218997_at/8 | NM_022490/27 | NP_071935/47 | POLR1E | polymerase (RNA) I polypeptide E, 53 kDa |
| 218859_s_at/9 | NM_016649/28 | NP_001263309/48 NP_057733/49 | ESF1 | ESF1, nucleolar pre-rRNA processing protein, homolog (S. cerevisiae) |
| 206613_s_at/10 | NM_005681/29 | NP_001188465/50 NP_005672/51 NP_647603/52 | TAF1A | TATA box binding protein (TBP)-associated factor, RNA polymerase I, A, 48 kDa |
| 214690_at/11 | AA004579/30 | NP_005671/53 | TAF1B | TATA box binding protein (TBP)-associated factor, RNA polymerase I, B, 63 kDa |
| 203937_s_at/12 | AW015313/31 | NP_001230085/54 NP_001230086/55 NP_001230087/56 NP_001230088/57 NP_001230089/58 | TAF1C | TATA box binding protein (TBP)-associated factor, RNA polymerase I, C, 110 kDa |
| 218750_at/13 | NM_024116/32 | NP_077021/59 | TAF1D | TATA box binding protein (TBP)-associated factor, RNA polymerase I, D, 41 kDa |
| 214881_s_at/14 | X56687/33 | NP_001070151/60 NP_001070152/61 NP_055048/62 | UBTF | upstream binding transcription factor, RNA polymerase I |
| 204771_s_at/15 | NM_007344/34 | NP_001192225/63 NP_031370/64 | TTF1 | transcription termination factor, RNA polymerase I |
| 208790_s_at/16 | AF312393/35 | NP_036364/65 | PTRF | polymerase I and transcript release factor |

-continued

| Affymetrix ProbSet/SEQ ID NO: | Representative Public ID/SEQ ID NO: | Representative polypeptide Public ID/SEQ ID NO: | Gene Symbol | Gene Title |
|---|---|---|---|---|
| 219031_s_at/17 | NM_016101/36 | NP_001186363/66 NP_057185/67 | NIP7 | NIP7, nucleolar pre-rRNA processing protein |
| Not Applicable | NR_046235/37 | Not Applicable | RNA45S5 | 45S rRNA precursor for the 18S, 5.8S and 28S rRNA |

According to some embodiments of the invention, the at least one gene involved in the RNA polymerase 1 pathway is selected from the group consisting of POLR1D, LRPPRC, RRN3, pre-rRNA and NCL.

According to some embodiments of the invention, the at least one gene involved in the RNA polymerase 1 pathway is selected from the group consisting of POLR1D, LRPPRC, RRN3, and NCL.

According to some embodiments of the invention, the at least one gene involved in the RNA polymerase 1 pathway is RRN3.

According to some embodiments of the invention, the at least one gene involved in the RNA polymerase 1 pathway is LRPPRC.

According to some embodiments of the invention, the at least one gene involved in the RNA polymerase 1 pathway is POLR1D.

According to some embodiments of the invention, the at least one gene involved in the RNA polymerase 1 pathway is pre-rRNA.

According to some embodiments of the invention, the at least one gene involved in the RNA polymerase 1 pathway comprises RRN3 and POLR1D.

According to some embodiments of the invention, the at least one gene involved in the RNA polymerase 1 pathway comprises RRN3 and LRPPRC.

According to some embodiments of the invention, the at least one gene involved in the RNA polymerase 1 pathway comprises POLR1D and LRPPRC.

According to some embodiments of the invention, the at least one gene involved in the RNA polymerase 1 pathway comprises RRN3, LRPPRC and POLR1D.

According to some embodiments of the invention, the at least one gene involved in the RNA polymerase 1 pathway is RRN3 and NCL.

According to some embodiments of the invention, the at least one gene involved in the RNA polymerase 1 pathway is LRPPRC and NCL.

According to some embodiments of the invention, the at least one gene involved in the RNA polymerase 1 pathway is POLR1D and NCL.

According to some embodiments of the invention, the at least one gene involved in the RNA polymerase 1 pathway comprises RRN3, POLR1D and NCL.

According to some embodiments of the invention, the at least one gene involved in the RNA polymerase 1 pathway comprises RRN3, LRPPRC and NCL.

According to some embodiments of the invention, the at least one gene involved in the RNA polymerase 1 pathway comprises POLR1D, LRPPRC and NCL.

According to some embodiments of the invention, the at least one gene involved in the RNA polymerase 1 pathway comprises RRN3, LRPPRC, POLR1D and NCL.

According to some embodiments of the invention, the at least one gene involved in the RNA polymerase 1 pathway comprises pre-rRNA and RRN3.

According to some embodiments of the invention, the at least one gene involved in the RNA polymerase 1 pathway comprises pre-rRNA and LRPPRC.

According to some embodiments of the invention, the at least one gene involved in the RNA polymerase 1 pathway comprises pre-rRNA and POLR1D.

According to some embodiments of the invention, the at least one gene involved in the RNA polymerase 1 pathway comprises pre-rRNA and NCL.

According to some embodiments of the invention, the at least one gene involved in the RNA polymerase 1 pathway comprises pre-rRNA, RRN3 and LRPPRC.

According to some embodiments of the invention, the at least one gene involved in the RNA polymerase 1 pathway comprises pre-rRNA, RRN3 and POLR1D.

According to some embodiments of the invention, the at least one gene involved in the RNA polymerase 1 pathway comprises pre-rRNA, LRPPRC and POLR1D.

According to some embodiments of the invention, the at least one gene involved in the RNA polymerase 1 pathway comprises pre-rRNA, RRN3, and NCL.

According to some embodiments of the invention, the at least one gene involved in the RNA polymerase 1 pathway comprises pre-rRNA, LRPPRC and NCL.

According to some embodiments of the invention, the at least one gene involved in the RNA polymerase 1 pathway comprises pre-rRNA, POLR1D and NCL.

According to some embodiments of the invention, the at least one gene involved in the RNA polymerase 1 pathway comprises pre-rRNA, RRN3, LRPPRC and POLR1D.

According to some embodiments of the invention, the at least one gene involved in the RNA polymerase 1 pathway comprises pre-rRNA, RRN3, LRPPRC and NCL.

According to some embodiments of the invention, the at least one gene involved in the RNA polymerase 1 pathway comprises pre-rRNA, RRN3, POLR1D and NCL.

According to some embodiments of the invention, the at least one gene involved in the RNA polymerase 1 pathway comprises pre-rRNA, LRPPRC, POL1RD and NCL.

Qualifying the compound as being suitable for treating the autoimmune disease in the subject can be also performed by an in-vitro method.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Chemical Syntheses and Characterization of POL1 Inhibitors

Materials and Methods:
2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (also referred to herein interchangeably as CX-5461, POL1-I, RAM-0 or Compound 1; see, chemical structure as presented in FIG. 3A and Table 1 below) was synthesized according to known procedures (see, for example, U.S. Patent Application Publication No. 2009/0093465 and WO 2012/123938).

All of the reagents were obtained from Sigma Aldrich.
$^1$H NMR analyses were performed using a Bruker Avance DPX-400 Ultra shield or alternatively Bruker Avance DMX-500. All the chemical shifts are referenced to the residual solvent signal.

All Mass Spectra analyses were performed on a Thermo Scientific LCQ Fleet mass spectrometer with an ESI source. All the spectra were recorded in the positive mode (unless mentioned otherwise) and were analyzed by the Thermo Scientific Xcalibur software.

General Synthetic Procedure:
POL1-I (CX-5461, Compound 1) is refluxed in phosphoryl chloride for several hours to afford the chlorinated analog 5-chloro-2-(4-methyl-1,4-diazepan-1-yl)-6-(((5-methylpyrazin-2-yl)methyl)carbamoyl)benzo[4,5]thiazolo[3,2-a][1,8]naphthyridin-12-ium (also referred to herein interchangeably as POL1-I/1, RAM-2, RAM Cl or Compound 2; see, FIG. 3A and Table 1 below).

The phosphoryl chloride is thereafter removed by evaporation and the crude product 2 is dissolved or suspended in an alcoholic solvent (e.g., methanol or ethanol). An amine or thiol compound, as desired, is then added and the resulting reaction mixture is stirred, possibly under reflux, until reaction completion. The solvent is then removed by evaporation and the resulting crude is purified, typically by preparative HPLC.

The chemical structure of the obtained product was verified by MS [ESI] and/or $^1$H NMR, as detailed hereinbelow.

An exemplary synthetic pathway of exemplary compounds according to some embodiments of the present invention is presented in FIGS. 3A-3B.

5-chloro-2-(4-methyl-1,4-diazepan-1-yl)-6-(((5-methylpyrazin-2-yl)methyl) carbamoyl)benzo[4,5]thiazolo[3,2-a][1,8]naphthyridin-12-ium (POL1-I/I; Compound 2)

MS [ESI]: calcd. 532.1. found [M+H] 532.2.

Preparation of 2-(4-methyl-1,4-diazepan-1-yl)-N-((5-methylpyrazin-2-yl)methyl)-5-thioxo-5H-benzo[4,5]thiazolo[3,2-a][1,8]naphthyridine-6-carboxamide (referred to herein interchangeably as POL1-I/2; RAM-3; or Compound 3)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. Sodium hydrosulfide was then added (100 mg) and the resulting solution was stirred for 5 minutes. The obtained compound 3 was purified by preparative HPLC to yield 82.4 mg 80% yield).

$^1$H NMR (500 MHz, CDCl$_3$): δ=13.02 (t, J=5.58 Hz, 1H), 9.50 (d, J=7.01 Hz, 1H), 9.23 (d, J=9.38 Hz, 1H), 8.64 (d, J=1.13 Hz, 1H), 8.43 (s, 1H), 7.75 (m, 1H), 7.45 (m, 2H), 6.82 (d, J=9.42 Hz, 1H), 4.89 (d, J=5.61 Hz, 2H), 4.17-3.64 (m, 4H), 2.88-2.79 (m, 2H), 2.64-2.57 (m, 2H), 2.56-2.53 (s, 3H), 2.39 (s, 3H), 2.11 (m, 2H) ppm.

MS [ESI]: calcd. 530.6. found [M+H] 530.2.

Preparation of 5-imino-2-(4-methyl-, 4-diazepan-1-yl)-N-((5-methylpyrazin-2-yl)methyl)-5H-benzo[4,5]thiazolo[3,2-a][1,8]naphthyridine-6-carboxamide (referred to herein, interchangeably, as POL1-I/4; RAM-1 or Compound 4)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. Gaseous ammonia was then bubbled into the methanol for 1 minute and the resulting solution was stirred for 5 minutes. The obtained compound 4 was purified by preparative HPLC to yield 64 mg (64% yield).

$^1$H NMR (400 MHz, CDCl$_3$ ppm): 9.28 (d, J=8.21 Hz, 1H), 8.58 (m, 1H), 8.44 (m, 1H), 8.04 (d, J=8.72 Hz, 1H), 7.64 (dd, J=7.62, 1.35 Hz, 1H), 7.34 (m, 2H), 6.68 (d, J=9.23 Hz, 1H), 4.86 (s, 2H), 3.98-3.74 (m, 4H), 2.84 (m, 2H), 2.66-2.60 (m, 2H), 2.54 (s, 3H), 2.41 (s, 3H), 2.12 (m, 2H), MS [ESI]: calcd. 513.2. found [M+H] 513.3.

Preparation of (E/Z)-2-(4-methyl-1,4-diazepan-1-yl)-5-(methylimino)-N-((5-methylpyrazin-2-yl)methyl)-5H-benzo[4,5]thiazolo[3,2-a] [1,8]naphthyridine-6-carboxamide (referred to herein, interchangeably, as POL1-I/3; or Compound 5)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. Methylamine was then added (3 mL) and the resulting solution was stirred for 5 minutes. The obtained compound 5 was purified by preparative HPLC to yield 74 mg (73% yield).

MS [ESI]: calcd. 527.6. found [M+H] 527.3.

Preparation of Compounds 6 and 7 (see, Table 1) was performed similarly to Compound 5, using propylamine and isopropylamine, respectively, and yielding 82 mg (76% yield) and 85 mg (79% yield), respectively.

MS [ESI]: calcd. 555.7. found [M+H] 555.4, MS [ESI]: calcd. 555.7. found [M+H] 555.3.

Preparation of Compound 8 (see, Table 1):

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. 3 mL of Triethylamine and 100 mg of [Methoxylamine hydrogen chloride] were then added and the resulting solution was stirred for 5 minutes. The obtained compound 5 was purified by preparative HPLC to yield 34 mg (32% yield).

MS [ESI]: calcd. 543.6. found [M+H] 543.2.

Preparation of Compound 9 (see, Table 1):

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. 100 mg of urea were added and the resulting solution was left to stir for 4 hours. The title compound was purified by preparative HPLC to yield 78 mg (75% yield)

MS [ESI]: calcd. 537.2. found [M+H] 537.6.

Preparation of (E)-2-(4-methyl-1,4-diazepan-1-yl)-N-((5-methylpyrazin-2-yl)methyl)-5-(phenylimino)-5H-benzo[4,5]thiazolo[3,2-a][1,8]naphthyridine-6-carboxamide (Compound 10; See, Table 1 and FIG. 3B)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (100 mg) was suspended in 3 mL of phosphoryl chloride, and the resulting mixture was refluxed for 3 hours. The phosphoryl chloride was thereafter removed by evaporation and the resulting crude product was dissolved in MeOH. Aniline was then added (2 mL) and the resulting solution was stirred for 5 minutes. The compound was purified by preparative HPLC to yield 56 mg (50% yield).

MS [ESI]: calcd. 589.7. found [M+H] 589.4.

Compound 11 (see, Table 1) was prepared similarly to Compound 10, using 3-fluoroaniline instead of aniline.

MS [ESI]: calcd. 607.2. found [M+H] 607.5.

Solubility:

The solubility of Compounds 1 and 10 was determined by dissolving 50 mg of the tested compound in 0.5 mL of mQ water, at room temperature.

Compound 10 immediately dissolved in the aqueous solution, whereby Compound 1 dissolved only in a pH 4.5 buffered solution after vigorous stirring for 30 minutes.

Example 2

Cell Viability Assay

Cell viability was assessed by the 2,3 bis [2-Methoxy-4-nitro-5-sulfophenyl]-2H-tetrazolium-5-carboxanilide (XTT) assay (Biological Industries, Kibbutz Beit Hemeek, Israel), which measures the reduction of a tetrazolium component (XTT) into soluble formazan product by the mitochondria of viable cells. The intensity of the dye obtained is proportional to the number of metabolic active cells. On the day of measurement, cells were washed and XTT was added according to the manufacturer's instructions. Plates were incubated at 37° C. for 2-5 hours. The absorbance was read at 450 nm.

Mouse splenocytes were removed and spleenocytes were plated (250,000 cell/well) in DMEM+10% FCS+P/S+Q and 10 mg/ml Phytohaemaglutinin (PHA), in the presence of elevated concentrations (25-400 nM) of RAM-0 (Compound 1), RAM-1 (Compound 4), RAM-2 (Compound 2) or RAM-3 (Compound 3) for 72 hours. Cells cultured without PHA served as control. Control mice at zero are mice splenocytes with PHA stimulation.

Following incubation, cell viability was determined by XTT assay, as described above.

RNA samples from similar cultures were also prepared and tested by Q-RT-PCR for pre-rRNA expression levels as described in Example herein below.

Figure 4A:
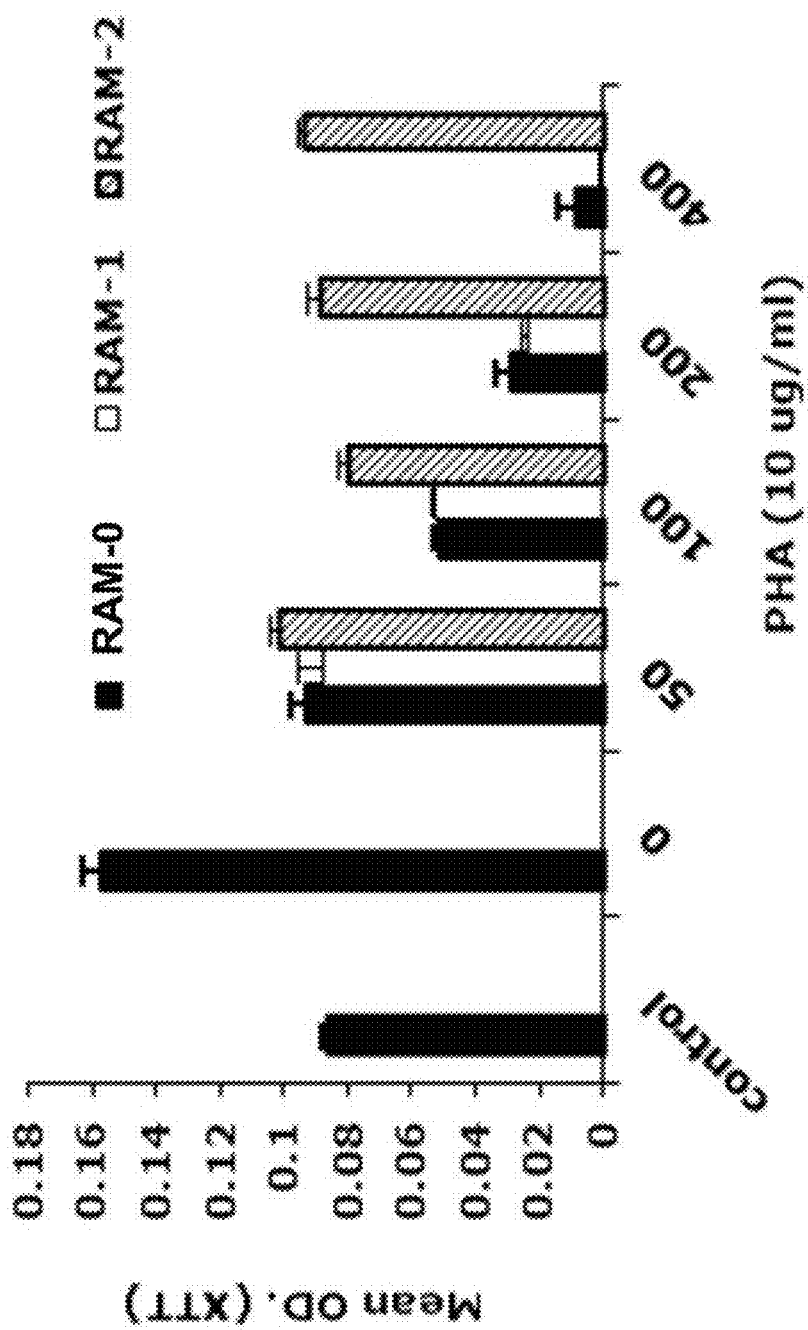
FIGS. 4A-4C present bar graphs showing the effect of exemplary compounds according to some embodiments of the present invention in suppressing proliferation of mouse splenocytes, as determined in an XTT assay.
Figure 4B:
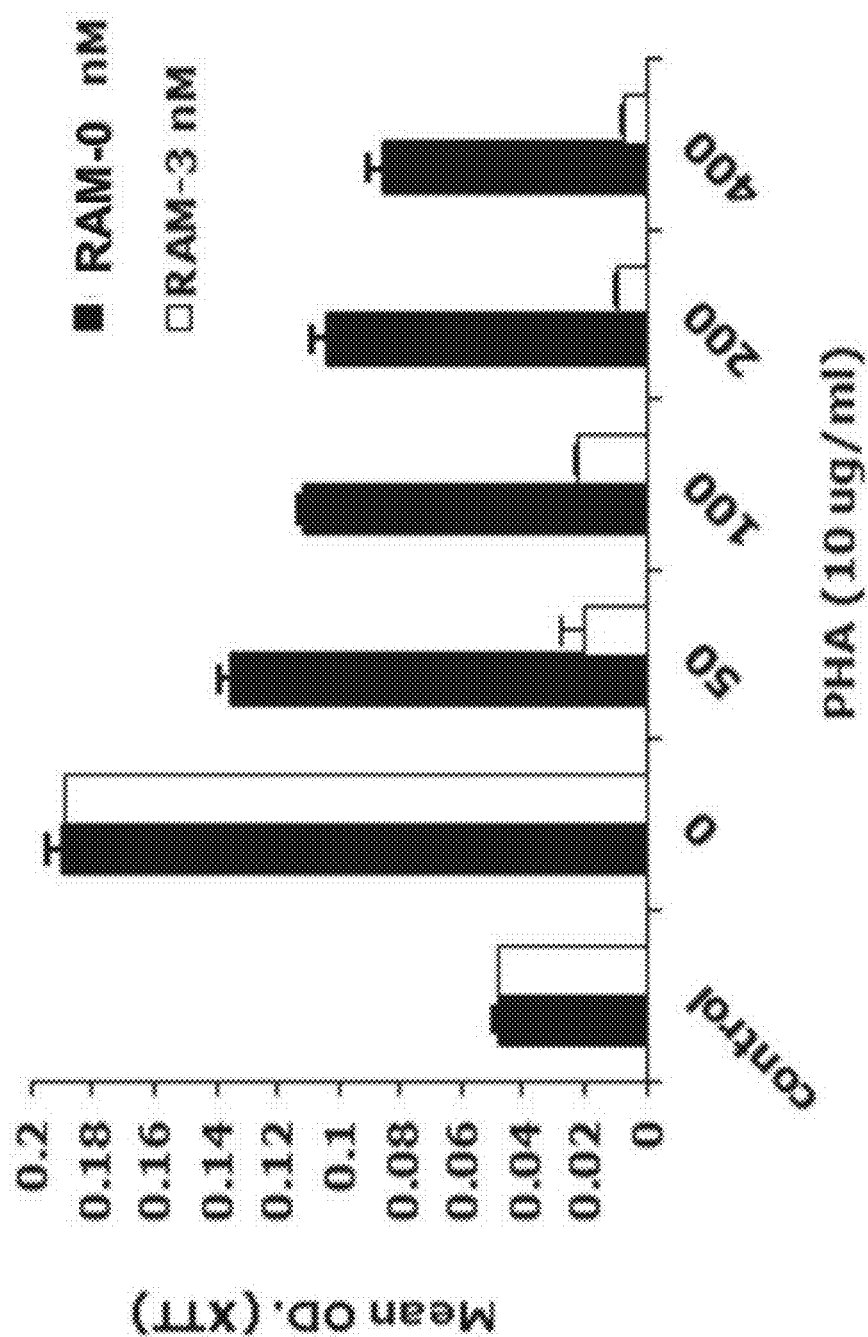
Figure 4C:
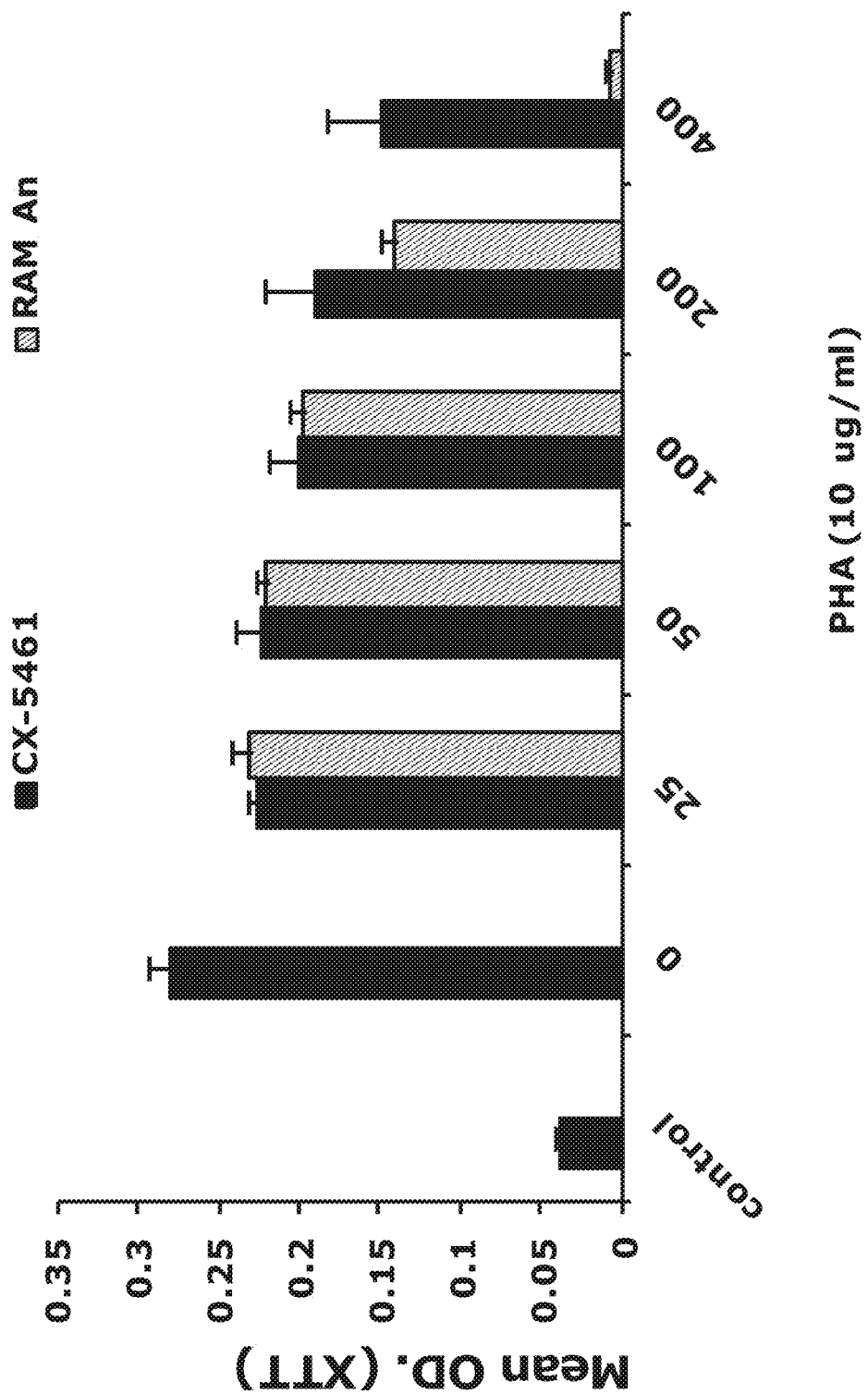

The obtained XTT data is presented in FIG. 4A (for Compound 1 compared with Compounds 2 and 4), in FIG. 4B (for Compound 1 compared with Compound 3), and FIG. 4C (for Compound 1 compared with Compound 10).

As shown, PHA stimulation resulted in substantial increase in proliferation as compared to control. As shown in FIG. 4A, Compound 4 (RAM-1) exhibited a dose response curve similar to RAM-0 (Compound 1), while RAM-2 (Compound 2) showed no substantial effect. As shown in FIG. 4B, RAM-3 (Compound 3) was 6-folds more effective in suppressing proliferation compared to Compound 1 (RAM-0), suggesting much lower therapeutic doses of this compound. As shown in FIG. 4C, Compound 10 exhibits an improved performance is suppressing proliferation compared to Compound 1. As indicated below, this compound was also found to feature a larger therapeutic window and improved solubility and pharmacokinetic properties, compared to Compound 1.

$IC_{50}$ values as determined in these assays for Compounds 1-4 and 10, and for all other tested compounds, are presented in Table 1 below.

Figure 5:
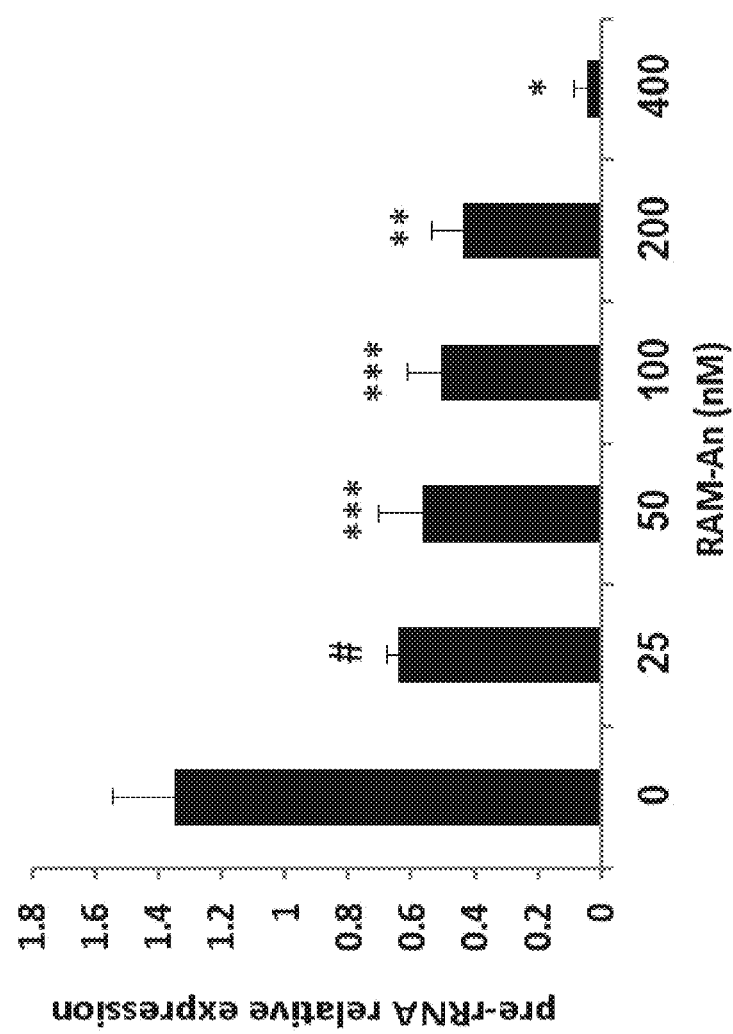
FIG. 5 is a graph showing mRNA levels of pre-rRNA in splenocytes of naïve mice following 72 hours stimulation with PHA in the presence of elevated concentrations of Compound 10. Bars represent mean±SEM; *p=0.0003, **p=8.8*10$^{-5}$, ***p<0.009 and #p=0.03.

The effect of Compound 10 on splenocytes proliferation was accompanied by suppression of pre-rRNA transcription, a key gene representing overall activity of the RNA polymerase I pathway. As shown in FIG. 5, 72 hours incubation with Compound 10 in concentrations of 25 to 400 nM resulted in a significant dose dependent decrease in pre-rRNA mRNA levels expressed by the splenocytes.

TABLE 1

| No. | Structure | Mw | Name | XTT |
|---|---|---|---|---|
| 1 | 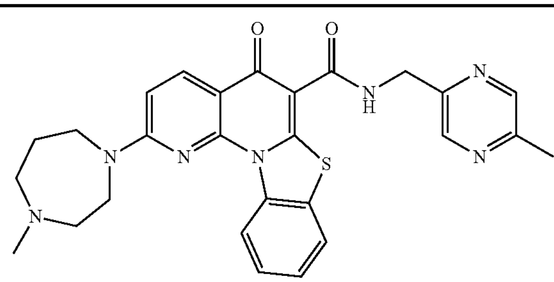 | 513.2 | CX-5461; RAM-0; POL1-I | $IC_{50}$ = 50 nM |
| 2 | 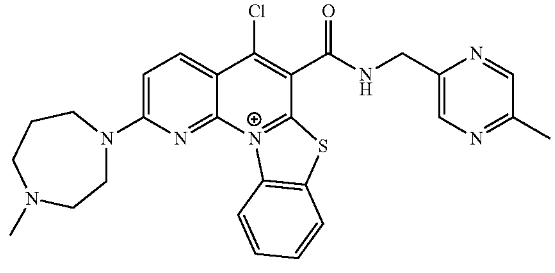 | 532.7 | RAM-2 POL1-I/1 | No Effect |

TABLE 1-continued

| No. | Structure | Mw | Name | XTT |
|---|---|---|---|---|
| 3 | 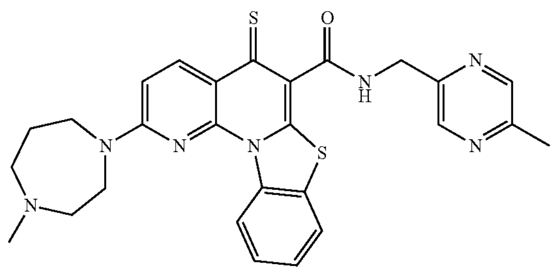 | 529.6 | RAM-3; POL1-I/2 | IC$_{50}$ = 20 nM* |
| 4 | 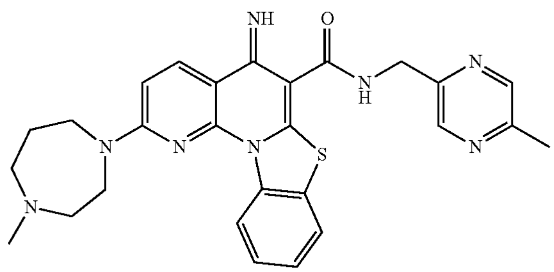 | 512.6 | RAM-1; POL1-I/4 | IC$_{50}$ = 50 nM |
| 5 | 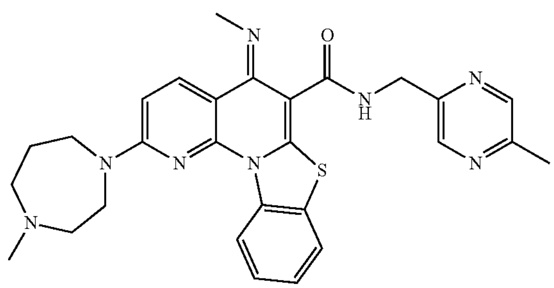 | 526.2 | RAM Me | IC$_{50}$ = 50 nM |
| 6 | 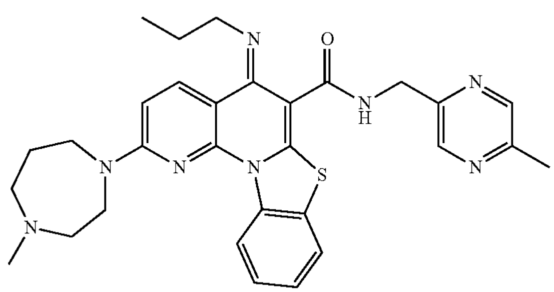 | 554.2 | RAM Pr | IC$_{50}$ = 50 nM |
| 7 | 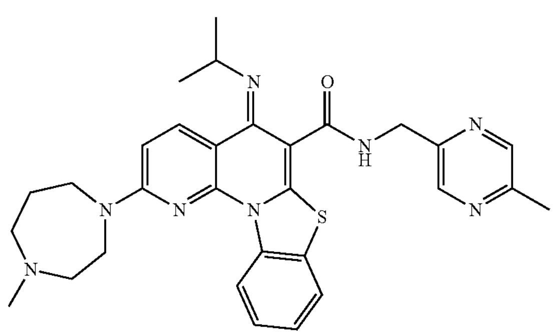 | 554.3 | RAM iPr | IC$_{50}$ = 50 nM |

TABLE 1-continued

| No. | Structure | Mw | Name | XTT |
|---|---|---|---|---|
| 8 | 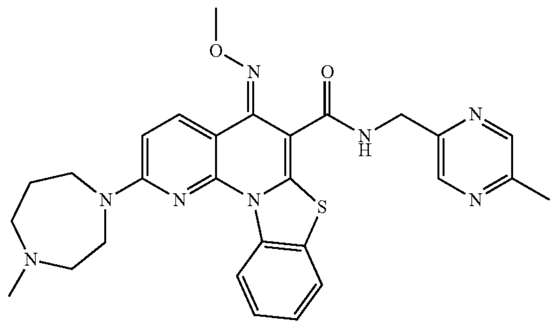 | 542.2 | RAM MeAM | $IC_{50} = 50$ nM |
| 9 | 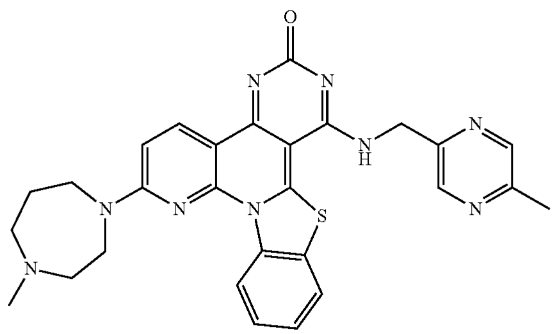 | 555.2 | RAM urea | No Effect |
| 10 | 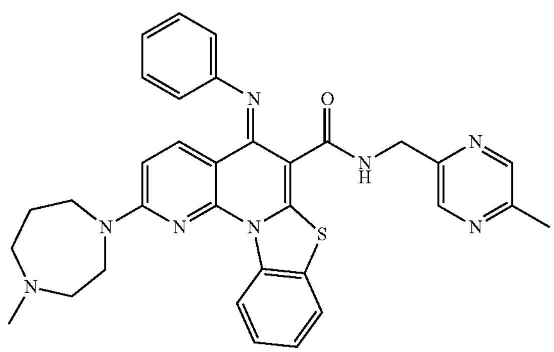 | 588.2 | RAM An | $IC_{50} = 40$ nM |
| 11 | 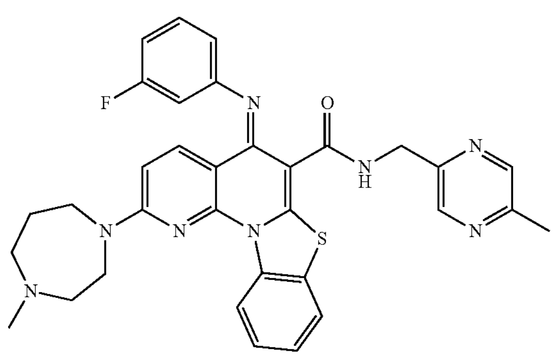 | 606.2 | RAM 3Fan | ND |

*Compound 2, although effective, was found to decompose in some of the experiments conducted.

Example 3

In Vivo Assays

Experimental Methods:

Mice: Eight-weeks-old female C57BL/6J mice (15-20 g, Harlan laboratories, Rehovot, Israel) were used in all experiments. Animal maintenance and experimental protocols were performed in accordance with the Israeli Council for Animal Care guidelines and approved by Sheba IRB Animal Care Committee. Mice were kept in an SPF environment, maintained on a 12-h light/dark cycle at a constant environmental temperature with free access to food and water in their home cages.

Induction of MOG35-55 EAE (Prevention Model): EAE (Experimental Autoimmune Encephalomyelitis) was induced in 8 week old female C57BL/6J mice (15-20 g, Harlan laboratories, Rehovot, Israel) by immunization with an emulsion containing 300 µg of purified myelin oligodendrocyte glycoprotein (MOG) peptide (MEVGWYR-SPFSRVVHLYRNGK, corresponding to residues 35-55; obtained from (Difco, Detroit, Mich.) in saline and an equal volume of complete Freund's adjuvant containing 5 mg H37RA (Difco, Detroit, Mich.). 0.2 ml of the inoculum was injected subcutaneously. In addition, 300 ng of *Bordetella pertusis* toxin (Sigma) in 0.2 ml saline was injected intraperitoneally at the day of induction and two days later.

Oral gavages with the tested compound, at various concentrations ranging from 3 mg/kg-30 mg/kg in PBS or 50 mM $NaH_2PO_4$ (PH 4.5), or with vehicle only, were initiated at day of immunization. Mice were monitored daily for clinical signs of EAE, scored as: 1, flaccid tail; 2, forelimb weakness and poor righting ability; 3, hind limb paralysis; 4, quadriplegia; 5, moribund. Animal reaching a score of 4 were scarified using $CO_2$.

Treatment was stopped once 30% of the vehicle-treated animals scored 1 on the EAE score. The experiment was terminated after 28 days.

Toxicity: The lethal dose for 50% of animals ($LD_{50}$), was determined for the EAE model, and was estimated in a continuous administration model. The animals were evaluated for signs of acute toxicity and survival during the entire administration period in the EAE model. Various concentrations were evaluated for efficacy, and when 50% mortality was observed in a specific concentration, this concentration was determined as the $LD_{50}$.

The therapeutic index ($LD_{50}/ED_{50}$), which is also referred to herein as Safety Margin (SM), was then determined based on the EAE model. $ED_{50}$ is the minimum effective dose observed for 50% of the tested animals.

Bioavailability: Determination of the level of the tested compound in serum was done following oral gavage. Blood samples (0.5 mL) were collected and immediately centrifuged at 5,000 rpm for 10 minutes. The serum was separated and stored at −20° C. until fluoprometric analysis by Tecan SpectraFluor, based on the specific excitation/emission values of the tested compound was conducted. The pharmacokinetic parameters including serum maximum concentration (Cmax), the time needed to reach Cmax (Tmax), and half-life (T½), were calculated to evaluate oral bioavailability. The serum concentration after oral gavages was calculated according to a calibration curve for each compound in the serum.

The Pharmacokinetic properties of compound 10 were quantified by the LCMS method described below. The concentration of Compound 10 was calculated with a calibration curve. The serum was prepared for analysis using protein precipitation. 15 µL of water were added to 15 µL of serum and a $H_2O:MeOH:CHCl_3$ (90:120:30) solution was added. The supernatant was subjected to LCMS analysis equipped with a PHENOMENEX® C-18 RP column.

RNA extraction: For in vivo experiments spleens from EAE mice were isolated at day 17 post immunization and splenocytes were re-stimulated for 72 h hours in the presence of 5.0 µg/ml MOG35-55. For in-vitro experiments spleens from intact mice were isolated and splenocytes were stimulated with for 72 h in the presence of PHA. RNA was extracted from splenocytes of both the in-vitro and in-vivo experiments by robotic ABI PRISM, Applied biosystem 6100 Nucleic Acid Prep Station. To avoid genomic DNA contamination samples were treated with DNase I (Roche). The quality and integrity of the total RNA preparation was confirmed using a NanoDrop 2000c Spectrophotometer (Thermo Scientific).

Quantitative RT-PCR of pre-rRNA: Complementary DNA was obtained from the extracted RNA by the High capacity cDNA reverse transcription kit (Applied Biosystems, CA, USA) following manufacturer's instructions. To confirm the role of POL1 pathway suppression by POL1-Inhibitors, the expression level of pre-rRNA transcript, a key gene of the RNA polymerase I pathway, was evaluated by Q-RT-PCR (n=3 per group). All PCR reactions were performed on a Light Cycler 480 instrument (Roche Diagnostic). The pre-rRNA, specific primers used were Forward: tttcttgtaagcgtcgaggtg (SEQ ID NO: 69) and Reverse: agcaggcacctaggagacaa (SEQ ID NO: 70) with a quantification probe (Roche, Probe ID #1, cat. no. 04684974001). For sample normalization, actin expression level was used as an internal control.

Statistical analysis: All statistical analyses to evaluate differences between groups are performed by T-test and p value <0.05 is considered significant.

Figure 6A:
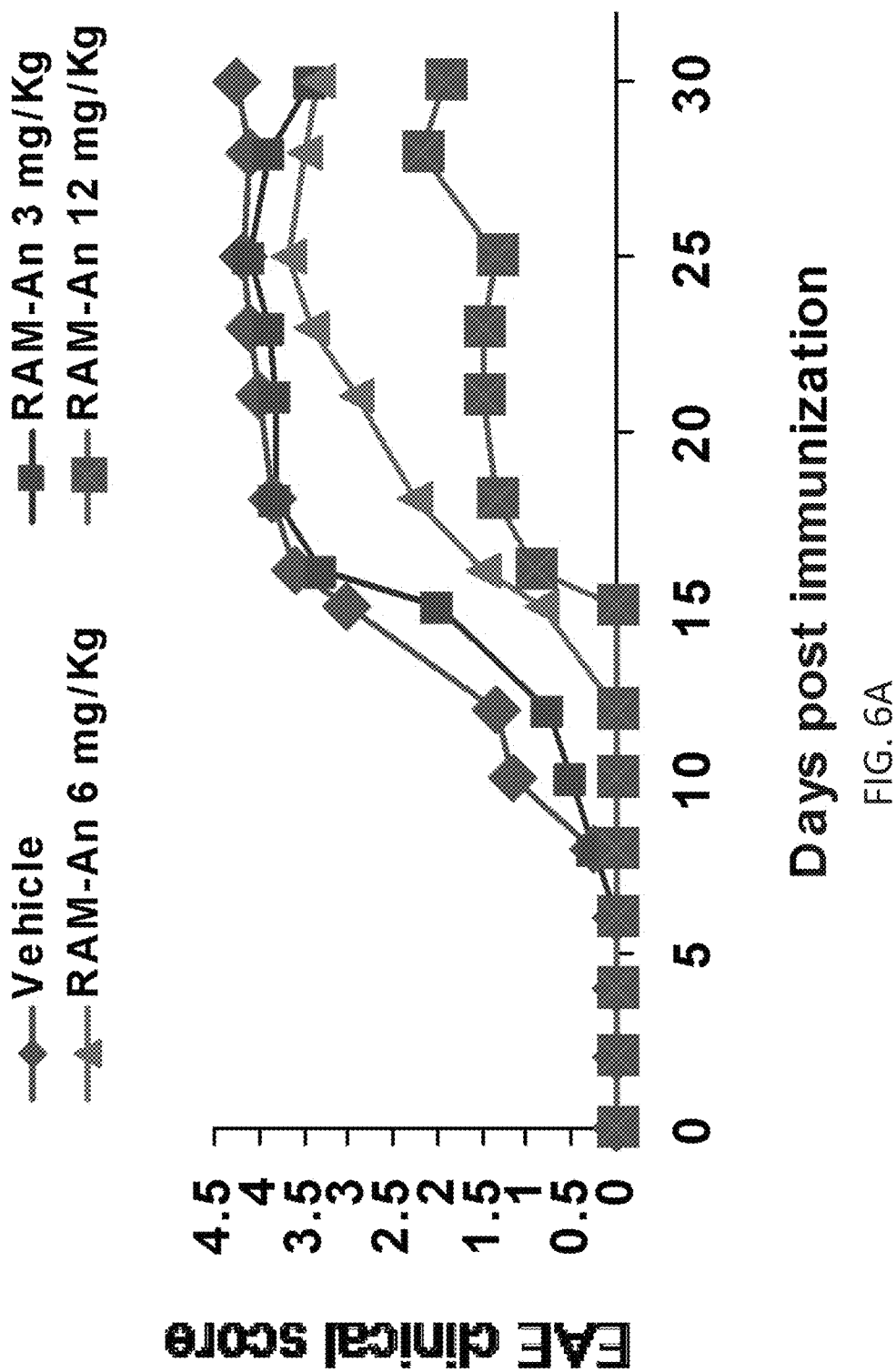
FIGS. 6A-6D present plots showing the effect of various concentration of Compound 10 (RAM-An) on the EAE clinical score and disease incidence, as observed in an EAE prevention mice model, following daily (FIG. 6D) or every other day administration (FIGS. 6A-6C).
Figure 6B:
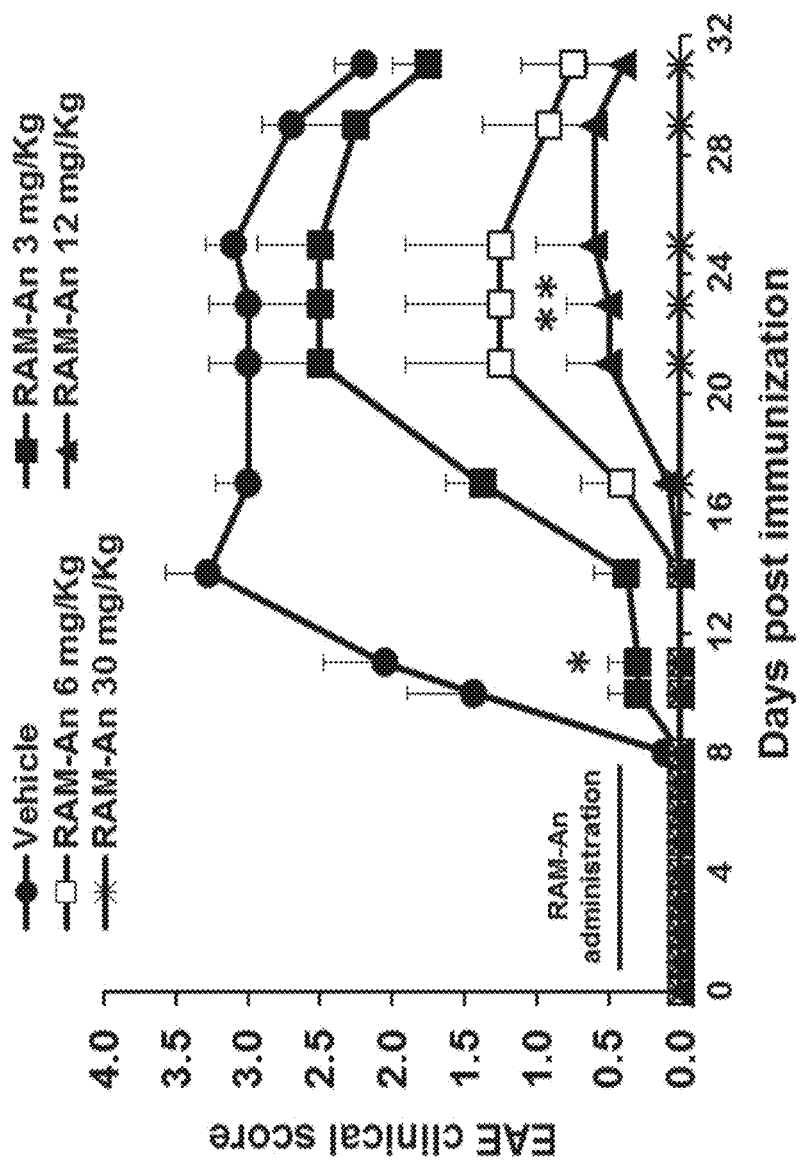
Figure 6C:
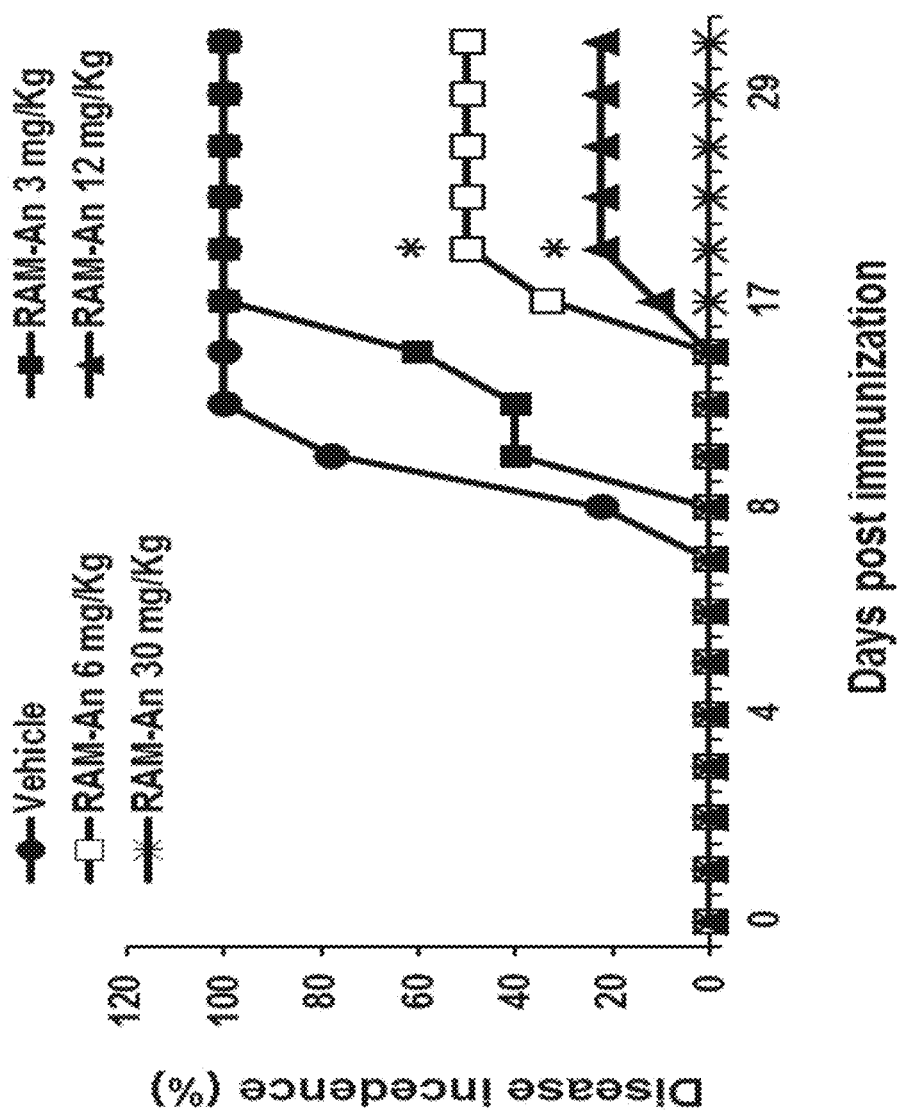

Experimental Results:

FIGS. 6A-6C present the minimal clinically effective dose and optimal dosing schedule for Compound 10 by evaluating its efficacy in an EAE immunization model by oral administration at alternate days starting at the day of immunization. As shown in FIG. 6A administration of 12.0 mg/kg of Compound 10 significantly delayed disease development by 10 days; p<0.001, and suppressed EAE severity (as shown by decreased activity at 23 day post immunization, p=4.57E-05).

As also evident in FIG. 6B, the disease incidence gradually decreased with elevation of the dose and ranged between 98% at a dose of 3 mg/kg and 22% at a dose of 12.5 mg/kg (p<0.0001 for 6.125 and 12.5 mg/kg as compared to the vehicle treated group). Moreover, administration of 30 mg/kg completely inhibited disease development. Notably, mice in all treated groups showed 100% survival without apparent signs of toxicity.

As summarized in Table 2 below, analysis of 15 mice per group showed that mice treated with Compound 10 remained free of disease for 10 additional days as compared to mice treated with vehicle. Even following disease onset, the treated mice reached the peak of disease 6 days following the vehicle treated group and the peak itself was significantly lower in the Compound 10 treated animals ($p=4.8*10^{-6}$).

TABLE 2

Effects of Compound 10 in EAE, immunization model

| Treatment | No. of mice | EAE onset (dpi) | Peak of EAE (dpi) | Max clinical score | Cumulative disease score * |
|---|---|---|---|---|---|
| Vehicle | 15 | 9.5 ± 0.4 | 14.4 ± 1.2 | 3.8 ± 0.1 | 30.3 ± 2.4 |
| RAM-An/589.555 12.5 mg/Kg | 15 | 19.2 ± 0.6 | 20.4 ± 0.7 | 1.2 ± 0.4 | 7.2 ± 1.9 |
| p-value | | $1.3*10^{-12}$ | $2*10^{-4}$ | $4.8*10^{-6}$ | $3.3*10^{-7}$ |

* The cumulative scores represent the summation of each single score recorded for each mouse from the day of immunization (day 0) to the day of sacrifice (day 31).
dpi—days post immunization As shown in FIG. 6A, the minimal effective dose was 6 mg/kg.

Figure 6D:
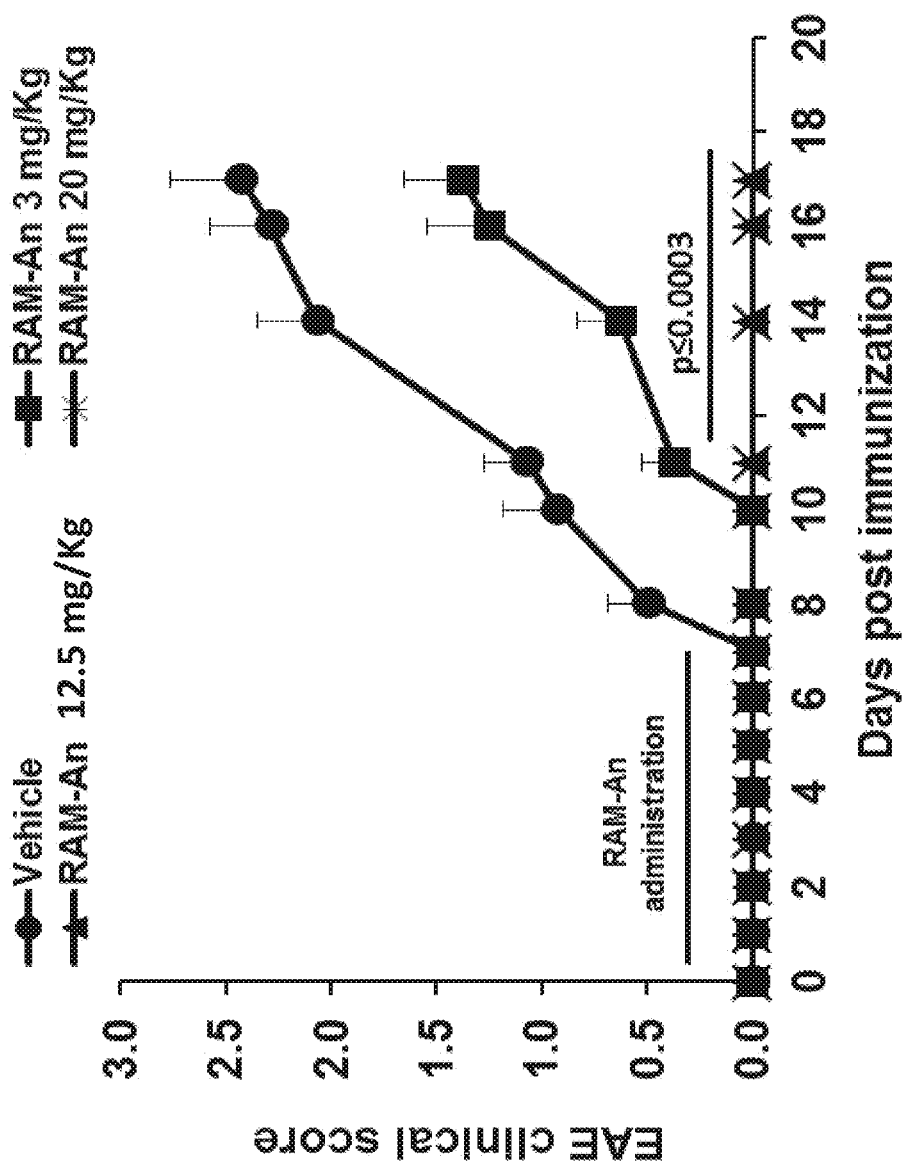

FIG. 6D demonstrated that the minimal effective dose was even lower in daily administration regimen in which efficacy of Compound 10 was evaluated using daily doses of 3.0, 6.0, 12.5 and 20 mg/kg starting at the day of immunization until disease onset at the vehicle treated group. Thus, daily administration of Compound 10 at a dose of 12.5 mg/kg resulted in complete inhibition of EAE ($p \leq 0.0003$ as compared with vehicle treated at 11-17 days post immunization and the minimal effective dose was 3.0 mg/kg.

Table 3 below presents comparative data for the effective and toxic doses as determined in the EAE prevention model assay described hereinabove, as determined for Compounds 1 and 10.

TABLE 3

Compounds effective and toxic doses as determined in the EAE prevention model

| No. | Structure | EAE $ED_{50}$ | $LD_{50}$ | SM |
|---|---|---|---|---|
| 1<br>CX-5461;<br>RAM-0;<br>POL1-I | [structure] | 12.5 mg/kg | 25 mg/kg | 2 |
| 10<br>RAM An | [structure] | 3 mg/kg | 30 mg/kg | 10 |

Compounds 2 and 9 were not tested; Compounds 3-7 were found relatively toxic during these preliminary studies.

It is shown in Table 3 that Compound 10 exhibits a substantially superior therapeutic index compared to CX-5641 (Compound 1).

Figure 7:
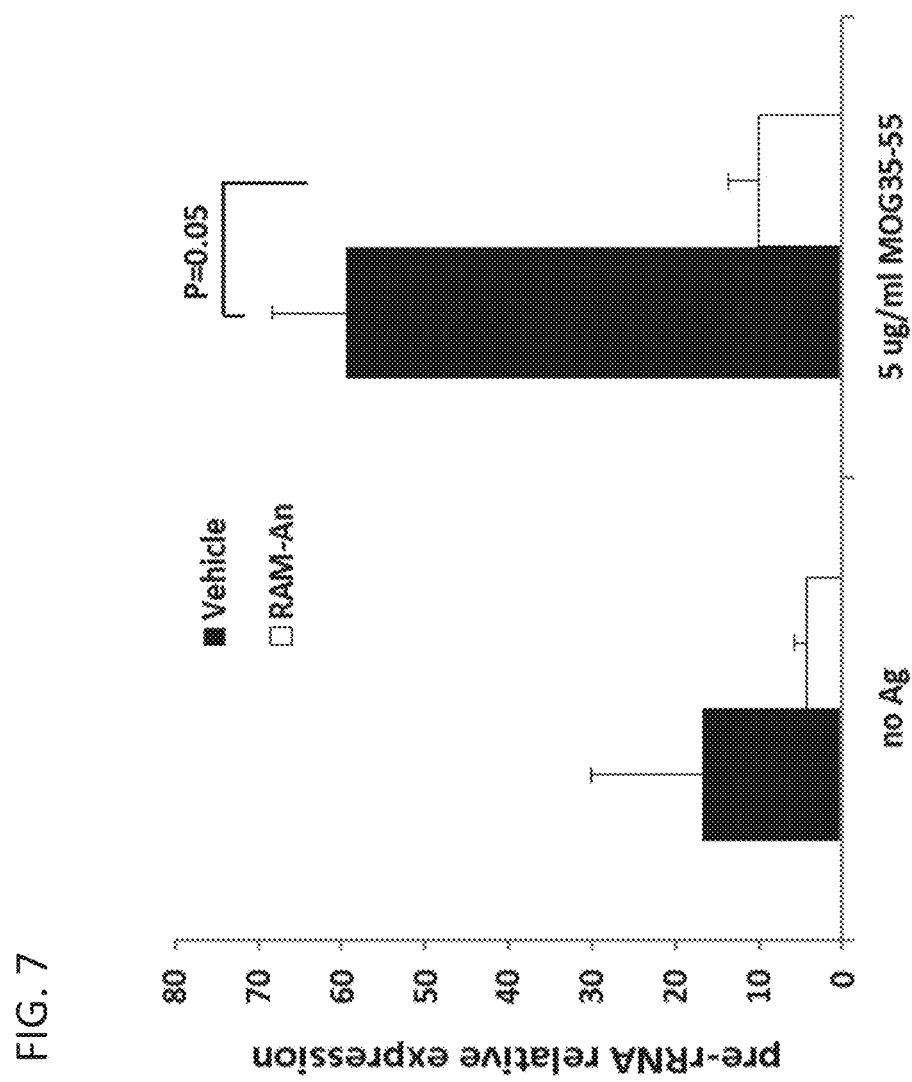
FIG. 7 is a graph showing mRNA levels of pre-rRNA in splenocytes isolated from spleens of EAE mice treated with 12.5 mg/Kg Compound 10 (RAM-An) for 17 days following immunization with MOG 35-55, as compared to vehicle-treated control mice. Bars represent mean±SEM.

The effects of Compound 10 in the EAE mouse model were accompanied by suppression of pre-rRNA transcription. As shown in FIG. 7, treatment with Compound 10 resulted in a significant decrease (5.9 folds) in pre-rRNA mRNA levels expressed by splenocytes 17 days following immunization, as compared to treatment with vehicle-control ($p = 0.05$).

Figure 8A:
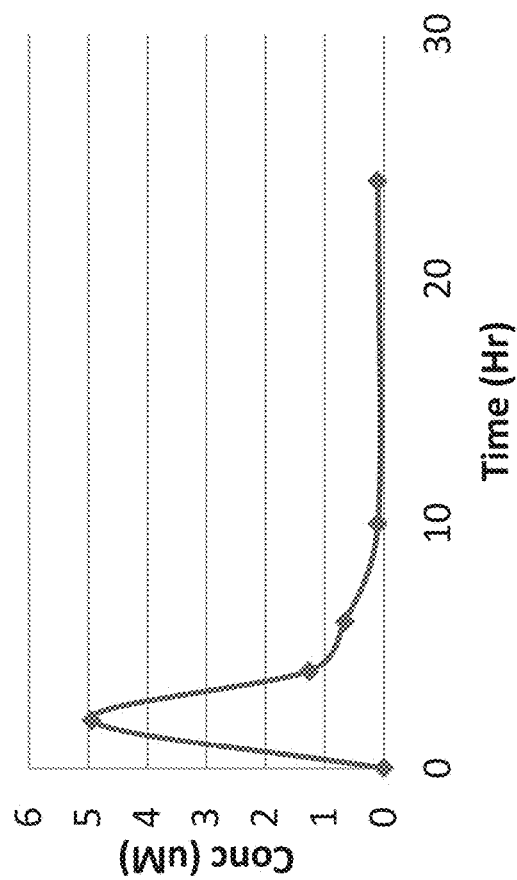
FIGS. 8A-8B present graphs showing the time-dependent profile of Compound 10 (FIG. 8A) and Compound 1 (FIG. 8B) in mice serum following administration by oral gavage.
Figure 8B:
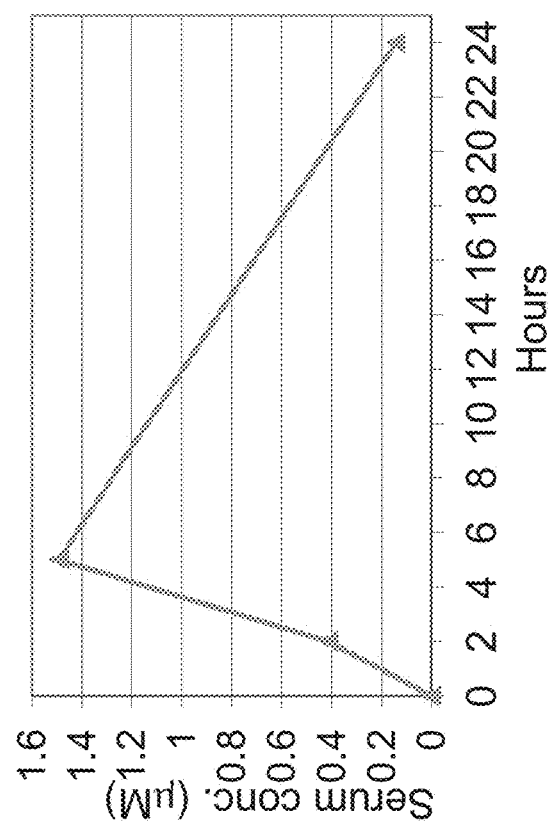

FIGS. 8A-8B present the data obtained in the bioavailability assay for Compounds 1 and 10. As shown therein, Compound 10 exhibits a more favorable pharmacokinetic compound to Compound 1, as reflected by the higher Cmax, the lower Tmax, and the faster clearance.

Figure 9A:
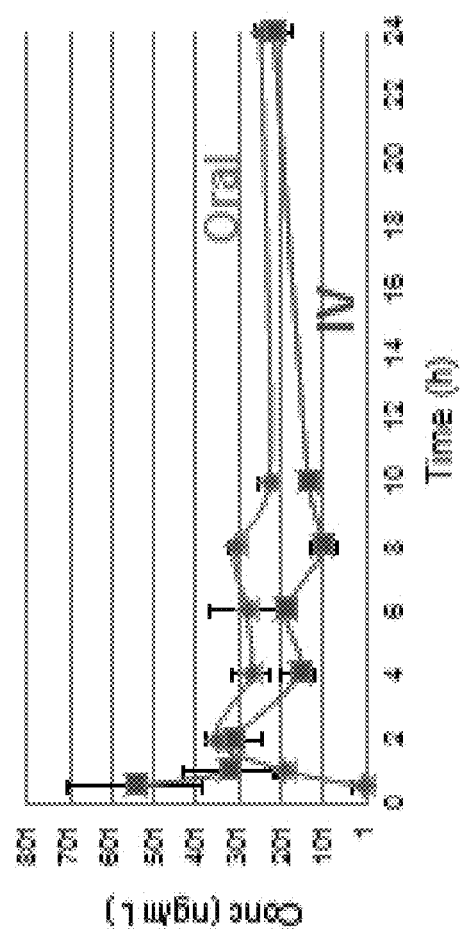
FIGS. 9A-9B present graphs showing the bioavailability profile of Compound 10 for 24 (FIG. 9A) and 168 hours (FIG. 9B) in the serum of naive C57B1 female mice following single administration of 12.5 mg/kg by IV and of 12.5 mg/kg by oral gavage.

FIG. 9A presents the data obtained in the bioavailability assay for Compound 10 after oral and IV administration up to 24 h. As shown therein, Compound 10 is rapidly absorbed following both oral and IV administration; Compound 10 reaches maximal concentration after 0.5 h following IV administration and maximal concentration after 2 h following oral administration in healthy C57B6J, female mice.

Figure 9B:
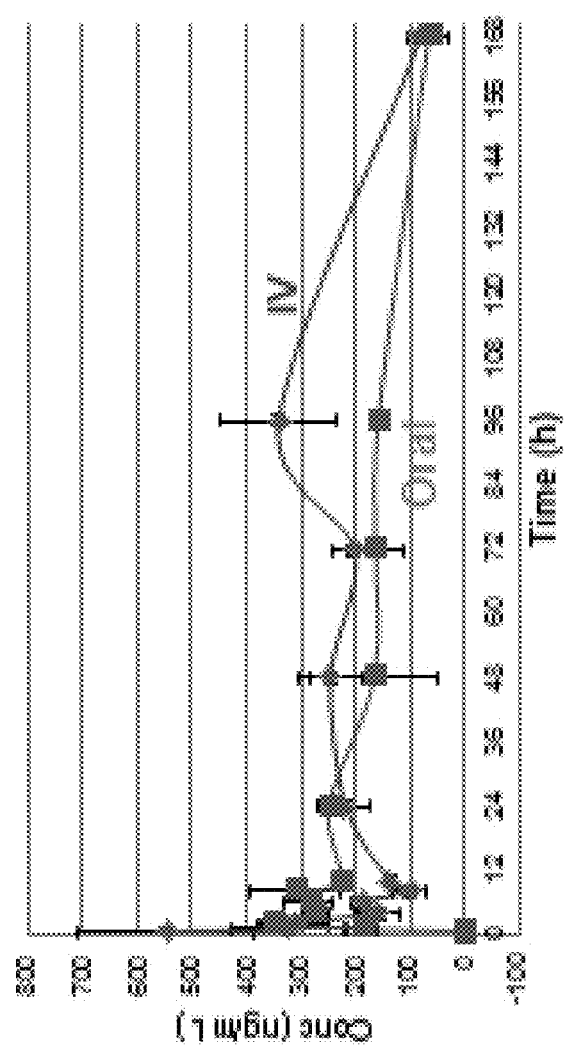

FIG. 9B presents the data obtained in the bioavailability assay for Compound 10 after oral and IV administration up to 168 h. As shown therein, the calculated bioavailability of Compound 10 is AUC(oral)/AUC(IV)=72%.

Compound 10: Single Dose Toxicity

The toxicity of oral administration of a single dose of Compound 10 was tested in naïve mice using range from 3 mg/kg to 500.0 mg/kg. No effect on survival was observed at 24 h. No behavioral changes were observed at 24 h.

Compound 10 Chronic Toxicity

Compound 10 was well tolerated when administered to EAE mice every alternate day until disease onset at a dose of 30 mg/kg. No effect on survival was observed. No behavioral changes were observed.

Example 4

Experimental Methods:

Cell-free Polymerase I transcription assay: Cell-free Pol I transcription assay was performed according to Drygin et al. (2010). Briefly, a reaction mixture consisting of 8 units of HeLa scribe nuclear extract (Promega) in transcription buffer and $MgCl_2$ (4 mM) was combined with POL1-Inhibitor (200 nM) and 10 mg/ml α-amanitin (Sigma) for 20 minutes at ambient temperature. Following, 10 ng DNA template (GENEWIZ, Inc.; http://www(dot)genewiz(dot)com(dot)cn) corresponding to the (−160/+350) region on human rDNA was added and the reaction was incubated for 5 minutes at ambient temperature. Transcription was initiated by adding rNTPs mix to a final concentration of 1 mM and the reaction was incubated for 1 hour at 30° C. Afterward, DNase I (Ambion kit) was added and the reaction was further incubated for 25 minutes at 37° C. DNase activity was terminated with adding an inactivation solution according the manufacturer's protocol. The samples were then subjected for RNA isolation (following the same procedure described in Example 3 hereinabove). Pellets of RNA were re-suspended in DEPC-treated double distilled water and subjected for reverse transcription by a High capacity kit (Applied Biosystems). The resultant transcripts were analyzed by qRT-PCR in a Light cycler 480 system using primer pairs (Sigma) and probe for real-time PCR. Primers were designed from the Assay Design Centre of the Universal ProbeLibrary (Roche Applied Science, USA) as follows: Pol I forward primer: tcaggcgttctcgtctcc (SEQ ID NO: 71), Pol I reverse primer: caccacatcgatcacgaaga (SEQ ID NO: 72).

Transcription by polymerase II from CMV promoter was tested similarly using the template provided HeLa scribe kit of Promega, further processing as described above and analysis of transcript with template specific primers: POL II forward primer: ctatgcgcacccgttctc (SEQ ID NO: 73), Pol II reverse primer: gtagcgaagcgagcagga (SEQ ID NO: 74). Probe ID: #70, cat. no. 04688937001 (Roche), was used for both reactions.

Figure 10:
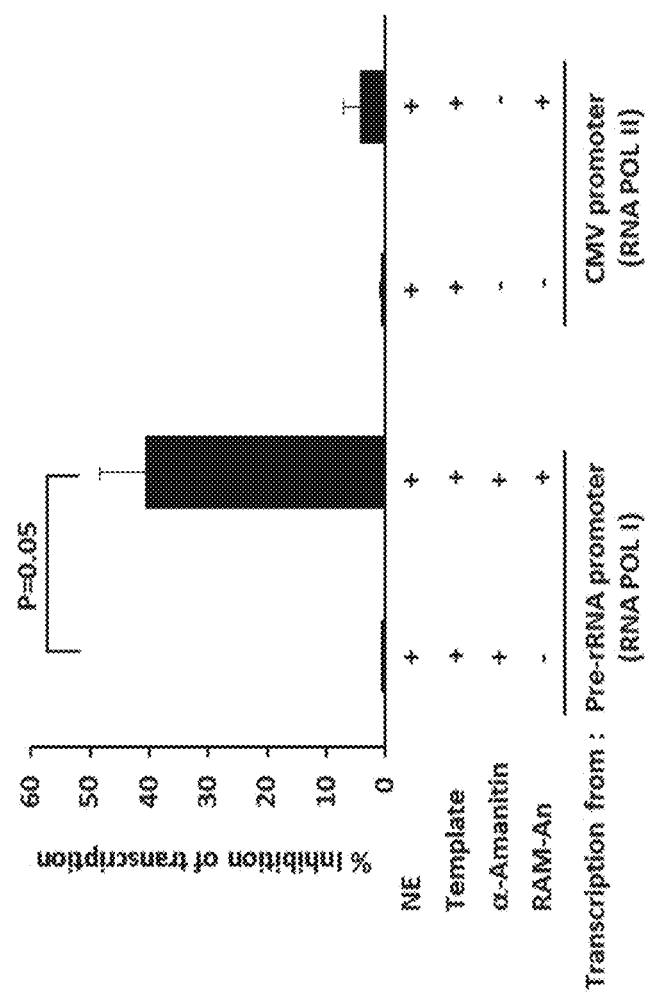
FIG. 10 is a graph shown effect of Compound 10 (RAM-An) on POL1 activity in cell-free transcription assay.

Experimental Results:

The analysis of the POL1 cell free assay showed that addition of 200 nM Compound 10 resulted in about 40% inhibition of Pol I transcription from the pre-rRNA promoter (p=0.05, FIG. 10), whereas Compound 10 only minimally affected Pol II transcription by 5% from the CMV promoter. These data indicate that Compound 10 directly targets the Pol I machinery.

In addition, viability, proliferation and apoptosis of splenocytes isolated from mice 14 days post immunization and incubated for 72 h with MOG 35-55 were assessed by XTT, BrdU and flow cytometry (Annexin V and propidium iodide double staining) assays, respectively. The results indicated that treatment with Compound 10 (Ram-An lot no. 589.555) reduced viability, suppressed cell proliferation specifically more affecting cells with high proliferation index, and induced apoptosis in CD4+ lymphocytes, as compared to treatment with the vehicle (data not shown).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating cancer in a subject in need thereof, said cancer being selected from pancreatic cancer, colon cancer, brain cancer, lymphoma, leukemia, prostate cancer and breast cancer, the method comprising administering to the subject a therapeutically effective amount of the compound:

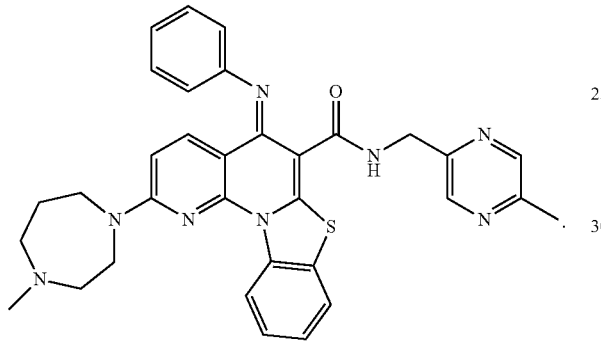

Compound 10

2. The method of claim 1, wherein said therapeutically effective amount is an amount equivalent to a range of from about 3-30 mg/kg/day in mice.

3. The method of claim 1, wherein the compound has 95-99.9% purity.

4. The method of claim 1, wherein said cancer is a pancreatic cancer.

5. A method of reducing tumor growth or of reducing the number of proliferating cancer cells in a subject in need thereof, the method comprising administering to the subject a therapeutically effective amount of the compound:

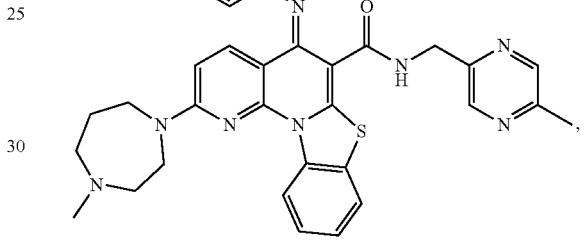

Compound 10 wherein said tumor or proliferating cancer cells comprise breast, pancreas, lymph node, colon, prostate, brain, or blood cancer cells.

* * * * *

SEQUENCE LISTING

```
<160> NUMBER OF SEQ ID NOS: 74

<210> SEQ ID NO 1
<211> LENGTH: 296
<212> TYPE: DNA
<213> ORGANISM: Artificial sequence
<220> FEATURE:
<223> OTHER INFORMATION: Affymetrix ProbSet target nucleotide sequence

<400> SEQUENCE: 1
gatgaccaga tcatcaactg gctgctagaa ttccgttctt ctgtcatgta cttgacaaaa      60
gactttgagc aacttatcag tattatattg agattgcctt ggttgaatag aagtcaaaca     120
gtagtggaag agtatttggc ttttcttggt aatcttgtat cagcatagac tgtttcctc     180 agaccgtgtc tcagcatgat tgcttcccat tttgtgcctc cccgagtgat cattaaggaa     240
ggcgatgtag atgtttcaga ttctgatgat gaagatgata atcttcctgc aaattt        296

<210> SEQ ID NO 2
<211> LENGTH: 476
<212> TYPE: DNA
<213> ORGANISM: Artificial sequence
<220> FEATURE:
<223> OTHER INFORMATION: Affymetrix ProbSet target nucleotide sequence
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t

<400> SEQUENCE: 2
```

```
tttccttcaa cttgtggatg caggcaaggt ggatgatgcc agagctctcc tacagagnat    60
gtggtgcnaa ttgctgaaca aaccccgatt ttgttgttgt tcctccttag gaattctagg   120
aaacaaggaa aggcatcaac tgtgaaatct gtgttagaat tgattcctga attaaatgaa   180
aaggaagaag catacaattc cctcatgaaa agctatgtct cagagaaaga tgtcacatct   240
gctaaagcac tgtatgaaca tttgactgca aagaatacaa aattggatga tctgtttcta   300
aagcgttacg catctttgct gaagtatgct ggagagcctg tcccttttcat tgaaccccct   360 gaaagctttg aattttatgc acagcagcta agaaaattga gggaaaactc ttcttgaaat   420
aaccaggcga actttgtttt tgtatatatt tgtgattctg tgtctacatg ttatttt      476

<210> SEQ ID NO 3
<211> LENGTH: 533
<212> TYPE: DNA
<213> ORGANISM: Artificial sequence
<220> FEATURE:
<223> OTHER INFORMATION: Affymetrix ProbSet target nucleotide sequence

<400> SEQUENCE: 3
aggcttagca ggatgggcgc agtggctcac gccactaatc ccaacatttt aggaggccta    60
ggcaggagca atcacttgtg cctgggagtt ctagactagc ctgggcgaga cttcatctct   120
acaaaaaaag caacaacgac aaaaaaaatt agccaagcat agtggcacac ccctgtagtc   180
ccagctactt gggaggctga ggtgggagga ttgcttgaac ccaagaggtc gaggctgcag   240
tgagccaaga ttgtgccact gcactccagc ctgggtgaca gagcaggacc ctgtctctat   300
tttataaatt aaaaaaggct gggtgtggtg gctcacaccc ataatcccaa cactttggct   360
cagcagattg cttgaaccca ggaattcaag tccaatctgg gcaacatggg gaaaccccag   420
ctctacaaaa aaaattagcc tggtgtggtg gcacatgcct gtagttccag ctactcagga   480
ggctgaggtg ggagaatctc ctgagcctgg aaggtccagg cagtgagcca aga           533

<210> SEQ ID NO 4
<211> LENGTH: 411
<212> TYPE: DNA
<213> ORGANISM: Artificial sequence
<220> FEATURE:
<223> OTHER INFORMATION: Affymetrix ProbSet target nucleotide sequence

<400> SEQUENCE: 4
ccaggcatat gacatggatc cccctgggga accaggctga tctctttcca gagggcacta    60
tccgaccagt gcatgatgat atcctcatcg ctcagctgcg gcctggccaa gaaattgacc   120
tgctcatgca ctgtgtcaag ggcattggca agatcatgc caagttttca ccagtggcaa   180
cagccagtta caggctcctg ccagacatca ccctgcttga gcccgtggaa ggggaggcag   240
ctgaggagtt gagcaggtgc ttctcacctg gtgttattga ggtgcaggaa gtccaaggta   300
aaaaggtggc cagagttgcc aaccccccggc tggatacctt cagcagagaa atcttccgga   360
atgagaagct aaagaaggtt gtgaggcttg cccgggttcg agatcattat a             411

<210> SEQ ID NO 5
<211> LENGTH: 441
<212> TYPE: DNA
<213> ORGANISM: Artificial sequence
<220> FEATURE:
<223> OTHER INFORMATION: Affymetrix ProbSet target nucleotide sequence

<400> SEQUENCE: 5
gcacgaggaa gaccataccc taggaaattc tctacgttac atgatcatga agaacccgga    60
```

```
agtggaattt tgtggttaca ctacgaccca tccttcagag agcaaaatta atttacgcat    120
tcagactcga ggtacccttc cagctgttga gccattcag agaggcctga atgagctcat    180
```

```
agtggaattt tgtggttaca ctacgaccca tccttcagag agcaaaatta atttacgcat    120
tcagactcga ggtacccttc cagctgttga gccattcag agaggcctga atgagctcat    180
gaatgtctgc caacatgtgc ttgacaagtt tgaggccagc ataaaggact ataaggatca    240
aaaagcaagc agaaatgaat ccacattcta gtcctttatg cagtatacaa ggagaactgt    300
cctgtaggat attctcttcc tgatggtgca gaacccagaa ttagaagttt gtggttacag    360
catactctgt ccttcagaaa ggcgtgattc tagctgttga ccccttgcag ctgttggaat    420
ctctgcaaga acctctgtat t                                             441

<210> SEQ ID NO 6
<211> LENGTH: 528
<212> TYPE: DNA
<213> ORGANISM: Artificial sequence
<220> FEATURE:
<223> OTHER INFORMATION: Affymetrix ProbSet target nucleotide sequence

<400> SEQUENCE: 6
ggtttggttt tgtagacttc aacagtgagg aggatgccaa ggaggccatg gaagacggtg     60
aaattgatgg aaataaagtt accttggact gggccaaacc taagggtgaa ggtggcttcg    120
ggggtcgtgg tggaggcaga ggcggctttg gaggacgagg tggtggtaga ggaggccgag    180
gaggatttgg tggcagaggc cggggaggct ttggagggcg aggaggcttc cgaggaggca    240
gaggaggagg aggtgaccac aagccacaag gaaagaagac gaagtttgaa tagcttctgt    300
ccctctgctt tcccttttcc atttgaaaga aaggactctg gggttttttac tgttacctga   360 tcaatgacag agccttctga ggacattcca agacagtata cagtcctgtg gtctccttgg    420
aaatccgtct agttaacatt tcaagggcaa taccgtgttg gttttgactg gatattcata    480 taaactttt aaagagttga gtgatagagc taacccttat ctgtaagt                  528

<210> SEQ ID NO 7
<211> LENGTH: 488
<212> TYPE: DNA
<213> ORGANISM: Artificial sequence
<220> FEATURE:
<223> OTHER INFORMATION: Affymetrix ProbSet target nucleotide sequence

<400> SEQUENCE: 7
aagagtcccc atcaagactt cttccctgag tcaagtacag cgtagcatag tcctccaccc     60
acccaacctc tctgcctggc cagggtcctg gccctgccac tgtgtggcga ggtgtccttc    120
tagaccacat cagccccaag gctgggagca gtcgctccag ggccgcagca gttcactccc    180
acacatagaa cccaggtcac tgctggggcg attgaacagg ttgcctggct tttctctgct    240
gtcagtttgg tgtggaggcc tatgttctgc cccatacacc ccacaggccc tgcttatggg    300
aaggaacaca ggcctccagc ccagaggact gtgccgccct gttcttggcc gtccacgttt    360
cctctccctc tagcaccagc aatacatttc cctggcatgg acagaaaaga cagagaggac    420
ttgtacaaag gctttgtaaa accagaggct agcttctatc tttgtctact gttatttcag    480
ctcagggc                                                            488

<210> SEQ ID NO 8
<211> LENGTH: 566
<212> TYPE: DNA
<213> ORGANISM: Artificial sequence
<220> FEATURE:
<223> OTHER INFORMATION: Affymetrix ProbSet target nucleotide sequence
```

<400> SEQUENCE: 8

```
gtggccgccg gcagtgaaga agatcacaaa ctgggcaccc tgtccctccc gctgcctcca    60
gcccagacct cagaccgcct ggcaaagcgg aggaagatta cctagacgca tgctttccag   120
acagggcgtt ttggctgcat cacagccact ggctggtcct attcatttcc atttttatgt   180
atgttttgaa aagaaaaggt ccggggatgg tggctcacac ctgaaatccc agcactttgg   240
gaggccgagg caggaagatc attgagctca ggagtttgaa accagtctgg acaacatggg   300
gagaccccat ctctaccgga ggaaaaaaaa aagagtcagg cctggtggtg tgcgcctgta   360
atcccagcta ctcgggaggc tgaggcagga cgattacttg agcttgggaa atcaaggttg   420
cagtgagcta tgattgtgtg gccacactcc atcctgggtc acagagtgag accttgtctc   480
aaaaaagtaa cataaggaaa aagaagcct tgctttagca caggtatgaa gccagaagcc   540
agcatctcaa ctgtgcttgt cttatg                                        566
```

<210> SEQ ID NO 9
<211> LENGTH: 459
<212> TYPE: DNA
<213> ORGANISM: Artificial sequence
<220> FEATURE:
<223> OTHER INFORMATION: Affymetrix ProbSet target nucleotide sequence

<400> SEQUENCE: 9

```
gggaacatca acggtggaaa tcacttggga tgagactgat catgaaagaa ttacaatgct    60
caacaggaag tttaaaaagg aagagctttt ggacatggat tttcaagcct acttagcttc   120
ctctagtgaa gacgaagagg agatagaaga ggagctacaa ggtgatgatg gagtcaatgt   180
agaagaagat gggaaaacaa agaaaagtca gaaggatgat gaagagcaaa ttgctaaata   240
caggcagctc ttgcaggtta ttcaagaaaa agaaaagaaa ggcaaagaaa atgatatgga   300
aatggaaatt aaatgggttc caggtcttaa agaaagtgca gaagagatgg tcaaaaacaa   360
attggaagga aaggataaac tgacccttg ggaacaattt ttagaaaaga agaaagagaa   420
aaaaagactg aaaaggaaac agaaggctct tgctgaaga                           459
```

<210> SEQ ID NO 10
<211> LENGTH: 387
<212> TYPE: DNA
<213> ORGANISM: Artificial sequence
<220> FEATURE:
<223> OTHER INFORMATION: Affymetrix ProbSet target nucleotide sequence

<400> SEQUENCE: 10

```
gagtcttaga ttttgccgga tgcactaaga atataactgc ttggaaatac ttggcaaaat    60
atctgaaaaa tatcttaatg ggaaaccacc ttgcgtgggt tcaagaagag tggaactcca   120
ggaaaaactg gtggccaggg tttcatttca gctacttttg ggcaaaaagt gattggaagg   180
aagatacagc tttggcctgt gagaaagctt ttgtggctgg tttactgtta ggaaaaggtt   240
gtagatattt ccggtatatt ttaaagcaag atcaccaaat cttagggaag aaaattaagc   300
ggatgaagag atctgtgaaa aaatacagta ttgtaaatcc aagactctga tactgaattt   360
tagttatttc acagttgtag ctacaca                                        387
```

<210> SEQ ID NO 11
<211> LENGTH: 530
<212> TYPE: DNA
<213> ORGANISM: Artificial sequence
<220> FEATURE:
<223> OTHER INFORMATION: Affymetrix ProbSet target nucleotide sequence
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (452)..(455)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t

<400> SEQUENCE: 11
gaaagtgaga cgacattgag aaaatgaaat agaaactttc tgganaaata ttttaatagt     60
gataataaca tcagatttta atataacatt ccagagaatt gtggaaaata ctgcatatat    120
atgtatagac tctgacacat atttacatat atatcaagtg tgcttagaaa aatgtatatt    180
gtaaagcagg tgagcttcat ttgattttat ttttcagagt atgaacattc taagagaaag    240
ttaaaacaat agcaaattgt ataattgtat ccagaaatgt atactcatcn tattttaaag    300
ctaaatttat ttttaaact agatcccttc attattcttt atgccccaga gtaaatccca    360
gatggatcaa agatctaaac ataatctttc atatgtaaaa atataaaagt attagtagaa    420
aacanatatg aatgctttga tgatcttgga annnnaangt caattttttgc agcatatggt    480 ggacaaagga gataatttct ttaatgtatc aatagctctt gcaaagcaaa              530

<210> SEQ ID NO 12
<211> LENGTH: 407
<212> TYPE: DNA
<213> ORGANISM: Artificial sequence
<220> FEATURE:
<223> OTHER INFORMATION: Affymetrix ProbSet target nucleotide sequence
<220> FEATURE:
<221> NAME/KEY: misc_feature
<222> LOCATION: (52)..(54)
<223> OTHER INFORMATION: n is a, c, g, or t
<220> FEATURE:
<221> NAME/KEY: misc_feature
<222> LOCATION: (57)..(59)
<223> OTHER INFORMATION: n is a, c, g, or t

<400> SEQUENCE: 12
ccctcccagg agttgactcc ggatgcatgc gcccagggcg tcccatcaga gnnncgnnng     60
atgctccgtg actacatggc caagctacca ccccagaggg acaccccagg ctgtgccacc    120
acacctcccc actcccaggc ctccagcgtc cgggccactc gctcccagca gcacacaccc    180
gtcctctcta gctctcagcc cctccggaag aagcctcgaa tgggcttctg aggacacaag    240
gtgggctgcc ctcaagcccc agagagcccc tcatccttcc tctgggacca gatgtgcctt    300
ccacagttga aacttgagaa gcagagctcg ccaccttctg gaggccactg tgatgatgag    360
ccaagcaatt tggagccaag ttgaagggac agggcaacaa aatacag                 407

<210> SEQ ID NO 13
<211> LENGTH: 427
<212> TYPE: DNA
<213> ORGANISM: Artificial sequence
<220> FEATURE:

<223> OTHER INFORMATION: Affymetrix ProbSet target nucleotide sequence

<400> SEQUENCE: 13

| gtatgggtca | tttcaaagag | ggcttatgag | gctgtgaaac | ccagagctct | taacgctgtg | 60 |
| accaaagatg | gaagttctct | ataggaagcc | atagcactcc | taatgtttgg | tgctatgttt | 120 |
| tcctgaggag | atataaaacg | taataatcca | tgattgttgc | catgtgagag | ttttaaaggt | 180 |
| taatcaaaat | ttctcttctt | cagggcaaac | ttgaagataa | atcttttgac | tccagctctt | 240 |
| tagaggatct | aaagtgacct | tgatggacag | tggaagaaat | cacaacatgg | aattcctcga | 300 |
| ataacaattt | attgacttta | aataattttg | tctaatgcta | catatacaca | attaaaaaac | 360 |
| ctttacacta | tttctagaaa | gtcagcatgt | attttggct | cgaagtttct | ctagtgtttt | 420 |
| ctgtgga | | | | | | 427 |

<210> SEQ ID NO 14
<211> LENGTH: 413
<212> TYPE: DNA
<213> ORGANISM: Artificial sequence
<220> FEATURE:
<223> OTHER INFORMATION: Affymetrix ProbSet target nucleotide sequence

<400> SEQUENCE: 14

| ggagcactac | aaaaagctgg | ccgaggagca | gcaaaagcag | tacaaggtgc | acctggacct | 60 |
| ctgggttaag | agcctgtctc | cccaggaccg | tgcagcatat | aaagagtaca | tctccaataa | 120 |
| acgtaagagc | atgaccaagc | tgcgaggccc | aaaccccaaa | tccagccgga | ctactctgca | 180 |
| gtccaagtcg | gagtccgagg | aggatgatga | agaggatgag | gatgacgagg | acgaggatga | 240 |
| agaagaggaa | gatgatgaga | atggggactc | ctctgaagat | ggcggcgact | cctctgagtc | 300 |
| cagcagcgag | gacgagagcg | aggatgggga | tgagaatgaa | gaggatgacg | aggacgaaga | 360 |
| cgacgacgag | gatgacgatg | aggatgaaga | taatgagtcc | gagggcagca | gct | 413 |

<210> SEQ ID NO 15
<211> LENGTH: 514
<212> TYPE: DNA
<213> ORGANISM: Artificial sequence
<220> FEATURE:
<223> OTHER INFORMATION: Affymetrix ProbSet target nucleotide sequence

<400> SEQUENCE: 15

| gcaggtgtta | cagttgtcct | tgtggataaa | gaaaatatta | caacacacc | aaagcatttt | 60 |
| agaaaggatg | ttgatgttgt | ttgtgttgat | atgagcatag | aacagaagtt | accaagaaag | 120 |
| cctaaaacag | acaaatttca | ggtacttgct | aagtcacatg | cacataaatc | agaagccctg | 180 |
| cacagtaaag | ttagggagaa | aaagaataaa | aagcatcaga | ggaaagctgc | atcctgggag | 240 |
| agccagcggg | caagggacac | cctgcctcag | tcagaatccc | accaggagga | gtcctggctt | 300 |
| tctgtgggtc | caggggggtga | aattacagaa | ctaccagcat | ctgctcataa | aaacaagtct | 360 |
| aagaaaaaaa | agaaaaagtc | cagtaaccgg | gaatatgaga | cactggccat | gcctgaagga | 420 |
| tcgcaagcag | gcagagaggc | cgggactgat | atgcaggaat | cccagcctac | tgtgggcttg | 480 |
| gatgatgaaa | ctccacaact | actaggacct | actc | | | 514 |

<210> SEQ ID NO 16
<211> LENGTH: 529
<212> TYPE: DNA
<213> ORGANISM: Artificial sequence
<220> FEATURE:
<223> OTHER INFORMATION: Affymetrix ProbSet target nucleotide sequence

<400> SEQUENCE: 16

```
ccccgcttgg acacagtccg agtggaatgg gaagggaatg gtcaatccct gtcctggttg      60
tccaagtcgg gatctcagag gaaattgcag tgattccacg gttaggcccc cctggggggg     120
ctgccttccc ctcagcctct ccccacacca cccacccagc tgctgtcatt ccgctcactg     180
agctcttctt cattctcacc ctgatccctg ggggactcaa agccaaaact gcccaaagag     240
gaaagattga atcctaaagg ggatccttgc ccccatggga ggcccctac tagaaggacg      300
tgaaagcagc ttttggggga aactgaggca gtggggaaga cagagcagaa tgagccctca     360
ccctggctgg gggtccagca caggctgtat ctgcagaggg tcccagagga acgctggagc     420
caagagaagc cctgggaagg agggtgggg aacgacatgc atgtgaggga tggcacactg      480
atgtgtttat gcacctgtac acaggagcgc atggccatgg ctttggaaa                 529
```

<210> SEQ ID NO 17
<211> LENGTH: 481
<212> TYPE: DNA
<213> ORGANISM: Artificial sequence
<220> FEATURE:
<223> OTHER INFORMATION: Affymetrix ProbSet target nucleotide sequence

<400> SEQUENCE: 17

```
atggggtttc agatctttgt gacgaaatag aatactgttt catatttgaa tcagagggct      60
tcttgttctg agaaataggt tcaaaatcat tggaaccagg aacaagaata gcttattgtt     120
atctgtgata acactgtttt ctaaacacaa ggatttcctt ttttattaat atgcaacata     180
gacattgcca taacagaata taaaccaca tgtgggggttt taaaaatgaa atttggctaa     240
taggagcaat tcagctattt ttctatacag taattggtgt gtggtataga agaaaaacgg     300
gttcaaaccc cacttctgcc acctaccagc tatatggcct tgaatgagtc attcagcttt     360
aataaggttc atttcttct gtttaaaaag acacaaaact tgaaaatcag ctttggccat      420
ctacctgaga attagaaagt ctgattttg gaattagaaa tcatgattgt aggctgggca     480
c                                                                     481
```

<210> SEQ ID NO 18
<211> LENGTH: 202004
<212> TYPE: DNA
<213> ORGANISM: Homo sapiens

<400> SEQUENCE: 18

```
aagcttgcag taagccgaga tcgcgccact gcactccagc ctgggtgaca gagggagact      60
ccatctcaaa aaaaaagag agaaagtaaa ggaataaaag aatggctacc ccatagacgg     120
agcagccgtg agggctgctg gttgcccatt tttatggtta tttgttgatg atatgctaaa     180
caaggagtgg attttcatg cctcctcttt ttagaccata tagggtaact tcttgatgtt     240
gccgtggcat ttgtaaactg tcatggtgct ggtaggagtg tagcagggag gatgatggga     300
ggtcagtctt gtctctattt tggttttggt gggttttggc cagctccttc actgcaacct     360
gttttatcag caaggtcttt atgactggta ttttgtgctg accttctatg tcatcctgtg     420
acttagaatg ccttaaccat cagggaatgc agcccagtag tttcagcctc attttttccg     480
gctcctattt aagatggagt tgctctggtt cacacacctc tgacatgatc attgcccact     540
gcggcttcca cctcccgggt tcaagagatc ctcctgcctc accctcccaa ggtgctggga     600
ctacaggtgt gtgccaccag ctcagctaat ttttgtattt tttgtagaga tggtgttttt     660
```

-continued

```
ccatgttgcc caggctggtc tcaaactcct gggctcaagc aatccttctg tctcagcctc    720
ccaaagtact gggattacag gcatgtccca ccatgcccag actaatattt acttttaatc    780
agactaagat agggttacta cttgagttgc tatggctcca gctgaaagaa agcccgtgca    840
gtcatatcac gcgtaaacat ttgctttatg ctaaaaatat ggtggacctg gcattacagc    900
tattacaaat ctcctaagat gtctcgggta gtgtattagt tacttttcat actgctatga    960
agaaatactg gaaactgggt aatttataaa gaaaaagagg tttaatgtac tcacagttcc   1020
acaaggctgg agaggcctca gaatcatggt ggaaggcaaa gaaggagcaa aaggtatgt    1080 cttccatggc agcaggcaag agagcacgtg cagggaaact gccctttata aaccatcag    1140 atttagtgag atgtattcac tatcacgaga acagtatggg aaaaacctgc ccccatgatt   1200
cgattacctc ctaccgggtc cctcccacga cacatgggga ttatgggaac tacaattcaa   1260
gatgaaattt gggtggggac gcagccaaac catatcgggt agcaacaacc tagggtcagt   1320
tttgcaggtg gtaaagccat ttaccaagat agttgtgggt aaagaagggc agatttatta   1380
gagaaattgt gaaatatgt tgcagtgggc agctcagcag agaaggggct acctgcaaag    1440
aggcaagggc tggaggaaag ttttataggg tcctgctgaa gggtgctacg tgtggaatga   1500
ggtcattgtg cccgcaggtt gtttgtgatt agctgtctct aacaattgtt catacaataa   1560
ttgttcatta ttgttctcaa cttggggctc tccccaacct ggggacccct ccttattgtt   1620
gcttacttat caggtctcca cataaaggtg tggaaacttc attcattcat atcttcaaca   1680
caaattgtag gtagcctgtt ttttaaaaca tttattcaac aaatatttag tccaagccac   1740
tattacttac taccttctct actattgtat ggacttttaa ctatctctga cactattcac   1800
tattcttcca cattctctat tatttatacc tatggtaaaa tttgccagtt tgaccataca   1860
actaatactc acagggaata tatagagtct agaagaaaat atacaggtcc ttaaaggctg   1920
ccctgccaac aaaaccataa cgcaggaaca aacatcacaa ctatgccaaa taatcaatcc   1980
tacaatgtcc aaaattttac tttaaaactg gaattaccag acttcctttc tgcattaacc   2040
agtttaacta gacagtaacg aaatattcct actttatgct gtgatagttt gtttgtttgt   2100
ttgtttgttt atttatttat ttatttattt aagacagagt ttcgctcttg ttgcccaggc   2160
tggagtgcag tggcacgatc tcagctcacc acaacctccg cctcccaggt tcaagcgatt   2220
ctcctgcctc agcctcccga gtagctggga ttacaggcat gtaccaccac gcccgggtaa   2280
ttttgtattt ttagtagaga cgggggggttt ctccatgttg gtcaggctgg tctagaactc   2340
cagacctcag gtgataccc tgcctcagcc tcccaatgtg ctgggattac agctgtgaag    2400
ccaccgcgcc cggctgctgt gatagttgag atgtaaacca aaaataaaat tctaagccac   2460
ccaatccgac tgaatggacc cttcctgttg agcaaggaca ttccaaagta aactgaaaag   2520
accagcttag gccatgatgg aaggggagg tgtcaacatg cctcattcta ccttcctccc    2580
tctggaatcc agacacaact gaccagcatt aacattaaaa cagagatctt aagctgggca   2640
cagtggctca tgcctgtaat cccagcactt tgggaggcca aggtgggatc acctgaggtc   2700
agaagttcaa gaccagcctg gccagtatgg tgaagccatg tctctactaa aaatacaaaa   2760
ttagccggac attgtggtgc acgtctgtca tcccagcaag gcaggcgaat cacttgaacc   2820
caggaagcag aggttgcagt gagccaggat catgccattg cactccagcc tggtcaacag   2880
agcgagactc cgcctcatta aaaaaaaaa aaaaaaaaa ttagccgggc gtggtggcgg   2940
gcacatgtag tcccagctac tagggaggct gaggcaggaa aatggtgtga accagggagg   3000
cggagcttgc agtgagccga gattgtgcca ctgcactcca gcctggacag aagtgcattt   3060
```

```
cataatgcat tttaattgca ttagcagtga tttaattttt ttagatgcta aaacttatgg   3120
gtgaaagtgg attaaatgta gccaaatgca acatcaaaat cttcaggcac aaaaacccat   3180 taacttttc atactctcag aaggtgaacc taatttcaaa tgaaagctgc ctccagaata    3240
tattgttaag cgtattctag atataattca ttttggcaaa catactgtag aaattcacat   3300
aacattttac tgtactaaaa gtaaattgcc catgtaacaa aaaatatctt ttcagagctt   3360
gaaatgaatt ttaaaggatg actgatggtc cctggaagag aaacagtaaa caaataaggt   3420
ttgtagcaat gatgtatgag ttagaaattg cagttccaga tgatctcttt attaaagaga   3480 cgatctcac ttaatttgat caagtgttat aacatagtt catgttaagt ctccatttaa     3540
atacaacctg aaataccaaa gttaattttc ttttctttct ttctttttttt tttttttag    3600 aaggagtctt gctctgttgc ccttcctgga gtgcagtgac gtgatcttgg ctcactgcaa   3660
cctccacctc ctgggcttga gcgatcctac tgcctcagcc ccccaagtag ctgggaggac   3720
aggcgcaagc cacggcactc agctaatttt tgtattttc gtagagatag ggtttcacca    3780
tgttgcccaa tttggtctcg aactcctgag ctcaagtgat ccgcccgcct tggcctccca   3840
aagtgctggg attacaggca tgagccaccg tgcctggcca gaaaattgta aacacacaca   3900
aactctcaag tggcctaatt ccctctcacc aaaccaatca caatacagat aaaagagaat   3960
aacttgtgtt catttttgta caaacaaaaa agatataaat tgtgaatgat gcatgatttt   4020
taattacaag taaactgggc aaatgcttct gcattattta aagctaaaag gtgatcagtg   4080
gaaactttcc tctgttagta ctctaatact ttttatattt atcggctcac tacaacctgt   4140
gcctaccagg ttcaagcgat tctcctgtct cagccacctg agtagccgag accacaggca   4200
cgcactacca tgtccggcta attttgtatt tttaatagag acagggtttc accgtgttgg   4260
ccatgctggt cttgaactcc tgacctcaac cgatccgcct gccttggcct cccaaagttc   4320
tgggattaca gcgtgagcc acagcgccca gccttattat aattgttact atttaaatct    4380
cttttgctct ctccttcaag agagacctca tcccattcag ttgcttccat ttatttattc   4440
atcttctgcc tcctgggctc gagagatcct ccagcgtgag tctcccaagt agctgggact   4500
acaggctcac accaccaagc ttggctaaat tttgtaggtt ttggagagac aggctcttgc   4560
cacgttgcct aggctggtct caaactcctg ggctcagatg atccacctgc cttcgcctcc   4620
caaagcactg gacatgagc caccgcgccc agccgcaagt acttttacac aaaatgcaaa    4680
caccattctt ccatcataaa agtgatacca cagcttccgt gaagttttgc caggtagtac   4740
tcataattac cttgggtaaa cttttgatg ttaaactgta tcttcttatt acgagttttt    4800
ccattgtatt aactgctttt acaacaacac aaataacaag ttatttaca aaccatttag    4860 aaatttctgt actatggtcc cagtaatgta aaatatatta atgcctatta cattcagata   4920
aattatacac ttggaaacca catacttatg acttacagaa acttacataa acaaattata   4980
gaaattacat gctcaatttt taggtatata gtcttaaatt aagcttaaat atacattctc   5040
aagataaatt aacagttcag ggcttcacaa cttgaaatct gtggaagatg acattggaga   5100
caacagaact ctggtggaat tcttagatgg aatttgccga aactttttt tttttttttt    5160 tttgagatgg agtgtcgctc tgtcgcccag gctggagtgc agtggcgcaa tctcagctca   5220
ctgcaagctc tgcctcccgg gttcacgcca ttcttctgcc tcagcctccc gagtagctgg   5280
gactacaggc gcccaccgcc acgcccggct aatttttat attttttagta gagatggggt   5340 tttactatgt tagccaggat ggtctcgatc tcttgacctt gtgatctacc cgccttggcc   5400
```

```
tcccaaagtg aaacttttct ttaaaataga gatgggatct tgctgtattg cccaggctgg    5460
tctcagactc cttgccttaa gcagtcctcc caccctcagcc tcctaaagtg ctgggattac   5520
aagcgtgaag cattacatcc aagtgaaact tcttgagatg gttacataat gtctaaatct   5580
gctggtgtag aagttaataa agtgtagaac tgaataacta ttaaatatta gatcaagttt   5640
ctcatgttta tcttaacgta taacgattta tcttaaagca ctgattttca caaaataaca   5700
tcagtgtgaa attggaaaag aagccaaata ttttatttca cgtatctggg aaatgaggtg   5760
ctttagtcaa ctgaatctgc ccaaaactaa aaagcattaa ttaaaagta cttaactcag    5820 aaattataaa ataggagac atcaataaaa tacattctac acagaatacg ccaaccatac    5880
actactcttt tttgataata aaaatgtat ttactgagcc agttgtggtg gctcacgcct    5940
ataatcccag caccttggaa ggccaatgag agtggatcag ttgaggccag gagtttgaga   6000
ccagcctggc caacatggtg aaatgccgtc tctactaaga atacaaaaat gagccgggca   6060
cggtggcacg cacctgtaat cccaggtact ccgaaggatg aggcaggata attgtttgaa   6120
ctcaggaggt ggaggttgca gtgagccaaa atcatgccac tgcactccag cctgggtgac   6180
agagtgagtc tctgtctcaa aaaaaaaaa aaaaaaaag aaaaaaagtc agttgcagtg    6240
gctcacgcct gtaatcccag cactttggga ggctgaggca ggcggattac aaggtcagga   6300
gatcgagacc accctggcca acatggtgaa acctcctctc tactaaaaat gcaaaaatta   6360
ggctgggcac ggtggctcac acctgtaatc ccagcacttt gggaggccga ggcgcggaga   6420
tcacgaggtc aggagattga ccatcctg gctaacacag tgaaaccctg tctctactaa    6480
aaatacaaaa aattagctgg atgtggtggc agcacttgta gtcccagcta cttgggtggc   6540
tgaggcagga gaatggcgtg aacccgggag gcagagtttg cagtgagccg agatcccacc   6600
actgcactcc agcttaggcg acagagccag actgtgtctc aaaaacagga aagaaaacaa   6660
aagaaatttt ggactattgc caattacaaa tattttaga gaagaattca aaacagtaac   6720
tgtggatgat ggaaacaata gttatgataa aagtctgatg aaacttccca gttcacaagg   6780
aaatttaatt acttatgtgc agcattttaa gacagtaatc agaatcatga ctgacagcat   6840
catatcaggg ccagcagact tttataaatt tcatacaatc ttcagaaata ataacttttt   6900
tttttttttt tggatagatt ctacctttgt cacccaggcg ggagtgcagt ggcatgatct   6960
cggctcacta caacctccgc atcctgggtt caagcagttc tcctgtctca gcctcccgag   7020
tagctgagat tacaggcatg tgccaccagg catggctaat ttttgtattt ttagtggaga   7080
cagggtttca ctctattagg ctggtctgga actcccgacc tcaggtgatc cacgtgcctt   7140
tgtctcccaa agtgctggga ttacaggcat gagtgacagt gcccagccat tcgtgacatg   7200
tttatacaaa tataacttta gcaaatattt agcataacta tcaaaattac aaatcatatt   7260
aaatttgtat aaatgtatgc aattttcgga acacgcatat caacaacata cccataaata   7320
taactgagat gagatctaat gtcacctcac ttgacagtgc cctcccatgc agtatcgcca   7380
catttgacaa tgcctgccca tttaatctac caaataaatc gaatcactta atacctctac   7440
aagatgagag atacattctt tagactcccc aagggatgca gctgaaaaaa atcccaaagt   7500
tagttttaag ccaaaaagac ttgatttagg attttgacac tggagaaacc catcaaagat   7560
gtcaagtttg aaaacacttg atcaaaacag aatcacaggt cactattaaa agagtattaa   7620
tttaaccaga gacttccaaa gcaatacaga aacttacatg gatataaaaa ccctaaccct   7680
tttaaaggtc agatttgcta agtgatcaaa aggggtactt gaattgaatc gacacaggaa   7740
gagtgtgtac agggttatga gtgtaggcag gtggttactt tggtcatatc tccatttgcc   7800
```

```
acctgattac acatgagaat ggcatcttta ctcaccagaa agccagtatt ataggaggtg   7860
taggaggcat tcttggactt gagacaagaa cattgttgtg tagaaatttc attgactgtg   7920
ttaaaattat tctccatggg ctggagaaca cataacatgg cctttagaat gagacgggca   7980
ttgattggat gcaaggtctc cacacttact agctgtgtga cattggacag agtgcttcat   8040
cattccgaga ctcagttttt aaaggaaaaa caactaacta ccttgcaagc ttgctagcag   8100
gtttaagtgt aataatgtgt gggaatgact gcaccgtgac taacatgcag tgacagctta   8160
attaatgtta acccttatca ttatcatata agaatgtgag ttacataaga gaggagtcct   8220
gtcagttcgt tctctgctgt gtccccaaga ccatgaatca tggctggcat gtagtaggca   8280
tttaataata tatgttcaac aagtatttgg cagtcttgga gggcagaaaa ggaggtgggg   8340
aagattttta aataacattc tttaaaaagt cacattgtcc tacaataccg atttttcttg   8400
catatttagg aaattgaggg ttttttttcta aaacatgcgg acatatggga aataggatgc   8460
aacatttgca ctaatgtttc agacacagtt agaggtttcc aagagatttt gcgctgggga   8520
ggctgcttgc tacaagctcc caaagctctg ggaggacata gtattcattc ctccctcagc   8580
agaagcggtg aggcaagaag ctctggggag cacccagcgt tggacttta gcatagtgtg   8640 tcaggtcttc atagtttggg cccagggcac agagaagtca cagctctccg gcatcctgtg   8700
acctttaccc tctttgccaa gggaaaatgt ggcccaccaa agcaagaaac ttgagggcat   8760
gggtcacccc agccctggca tctgcccaga gcccgagaag gaaggaacaa tgatcctcca   8820
gctacctcac ggggctggca caggtgacca ctgccctggc atcacccagc tgtgtccggc   8880
agcctgaacc ccatctgtgg ggatgcgagg aggaaaatac aaaagtcctt aggtgaacac   8940
tgagaaggca gatgcagcag aaacctccag gccagaacta cccagtcttg gacctatggt   9000
ggagatagag catagctggc gatcatgtgt acttacactc taaggtcacc tggttgcact   9060
atggcctcat ctgtggctct gaaaatgaag atttggaagg agatcatcac agctaatgtt   9120
taacaagccc ctcctgtgtg ccaaatcatt caccoctcac cacaaccgaa tgagctaagg   9180
attctcatta tatatagttt atggagaggg aagtgcagac ataaagaggt gaattatctt   9240
acccagatca cacagctgat aagtggtgga ggcagaatag aatctaaaca gtgtggctcc   9300
ggagcccaca tgcattgatt cgacaagtgt ttattgagca cctgccgcgg acaaggcctt   9360
gtgtgattaa ataggggttat aattagtaat ataaaaatga gaaatcacta atgcttttta   9420
gacttaacat tttgttttttt tgtaggtttc aggcacagaa ctgtatatcc aataatagtg   9480
aaatggatcc cactaattat gacagaaatg atgatacatt taaatgactt ggatgtttta   9540
taggtatgat ctcgtgaaat cttgagagaa actgaatgac gaatgaaact attgttcctg   9600
tttcacacag aagaaaactg aggttaaaag gggtaaagta attttgcatg gcatgaagta   9660
gaaattcaaa gtacaggaat ttgaacttgg ttctgtcctt ttctgaagcc cttgaccact   9720
atagactcaa acatcacctt gttttttccac tcattcaaca cttttttttt taaattatct   9780
aataggttgg cactcatcat gagcccctgt tctcattctg caaatggtga agctctctat   9840
tgtcctgacc ccacagttcc tgtcccatga ccagggccag ctcaccaagg agctgcagca   9900
gcatgtaaag tcagtgacat gcccatgcga gtacctgagg aaggtgagtg agtgcagaca   9960 gatgggggcct ggtgcccttg agcagttccc gggtctcagc tgccacacat ctcatagccg  10020
gtgatgctgg gggaagctta cgcagtcaca gtactggctt cttcctcttt ttcttttccat  10080 acaagtggct tagggatggg gtagagtagt tgacttattt ggatgaaaac cactatcttc  10140
```

```
tgtcagaaac tcaaaaggaa tcattgctgg catggtaacc taaagaaaaa caaccagaca  10200
agtgcccaac gacacttaaa aaggtgattt attatcttgc caagtttagg ctgggcatgg  10260
tgactcatgc ctctaatccc agcattttgg gaggctgagg ctggtggatc accggaggcc  10320
aggactttga gaccagcctg accaatatgg caaaacctcg tccctactaa aaatacaaaa  10380
attagccggg catggtggtg tgagcctgta gtcccagcta ctcaggaggc tgagacagga  10440
gaattgctta gattcaggag gtgggggttt tagtgggccg agatcacgcc attgcactcc  10500
agactgtgcg acagagcgag actctgtcaa aaaaaaaaa aaaaaattat cctgcaaaat  10560
ttgaaaagga aattcaaatc aacagcttct aaactacttt ttaacatgac tcataataat  10620
acattctata gtacatatgt atgttctata actttgaata aaagagttaa ccacatcaca  10680 tttatttat aacatgtaat acatattttt tattctcctt catttgtttt gaatgctctg  10740
tgcagtctac aaaaagtcca atagtaataa ttaaattagt cattaagttg aacattatct  10800
tgtcttttaa aatgataatc tcaaaaatga tcttttattt ttgagattta tatagataca  10860
cacacacaca cacacacaca cacacacaca cacacacaca cacacacaca catatttttt  10920
gagacagagt ttcactctgt cccccaggct ggagtgcaat ggcacaatct tggctcactg  10980
caacctctgt ctcccgggtt caagcaattc ctctgcctca gcctctgagt agctgggact  11040
acaggtgtgt gccaccatgc ccagctaatt tttgtattct tagtagagat ggggtttcac  11100
catattggcc aggctcgtgt caactcctga cctcgtgatc tgcccaccgc ggcctcccaa  11160
agtgctggga ctataggtgt gagccgctgc accggtcca agtaaaatta ttttaacaat  11220
atactatgaa gagaaaaaca ctggctatga agaatatgc atagttttac ctgttttaaa  11280
aataaagatt gaaagaatac atatgcaaat aagtttactt ttattttgg taacacttta  11340 ctgcattgtc tgaatattga caatcagtat gcattatgaa gctacctggc taacattgtg  11400
tactcactgt gtgtgccagg ccctgggttc aatgctctac atgcacttat atttcattta  11460
attctctctg caacctgaga tggtatagcc acctcatttt acagagttga aactgaggct  11520
cagagactga aagttaagcc tgaggttgca gtcaataaga ggcagagctg gaactgaaac  11580
ctacctgtgt ctgaccacca gttcgtgttc tgacggcagg ctagtctgca tcacagagtg  11640
tggagtagat ggtgcatgcc tgctaggatg ggctaggtat cactgtaggt aagaaacagc  11700
cccaaactat ggaaatgtac accactgaag gctcttttcc tgcccatgct gcacatcctc  11760
catggctctc ctgtgccctg tgccccacat gccctcatcc tgccacgaga ataaaggagc  11820
agcctccata tgggagctgt cagctgctct aagagatgaa ggagagagtg gcccgtctca  11880
atggctccca actcttttgc ctcgaggtga cacgcttcac ttccacgcac atctcctggg  11940
tcaaagcaaa tcccatgggt acatccactt tcaagtggcc caggagagaa cctgaaatac  12000
tcggtggact ccattaaggc cgtcatatgg tgtcagcctg catgggagac tgtggagggg  12060
cagaggagga gagtggggaa ctgatgggaa atgacaggag gactaagtca ccgcagattt  12120
gctttatctt cagccaggtg gagtttgtcc cagagccgca caaaatcatc accagcatga  12180
ttaaacggag tagacttcag aaaaagcagt ttggtcggat gtaatcagca gtgaactcag  12240
aatcaattga gtgacattga gtcagtaaat ctctgactgc ctcagttacc ccatatgata  12300
gttttgagga tgggaacatt gagagagttg atttggaagg atatcaagag taaaaattcc  12360 aacatttta gttcctttaa gttaaatcca ggcactgtct ttcctgcaag tctcctgttc  12420 cttttcagatt gcacaggtga gagtgctcag attagggctg gaggttgtaa accattgctc  12480
ccacactgac agtgccccg tgtcgtgcgt gtattctgcg cattttcctg tgctaaacac  12540
```

```
tctcccaaaa catcgtgggg cctgattctt cctctttgtt ccaatggccc tgggtgactc    12600
aagtgcccat tcaatgacca ggacacagag gtcttagaga gatgctcctt gaggcccag     12660 gtgcgagcct gtaccctgcc ggagcatgag gcaagggaca gggcatcgtc tgtggggata    12720
gtgggggtag tgggggtagt ggtcagccag atttggtgac tctacttgct caccagacga    12780
tcctacacct gccacctccg atggatccac tgcctctgtg cctgcctgta ctgctgatgc    12840
tccagtggat aactcagcat cccagcctag gcccaatgcc actgaagatg gacctgcccc    12900
ctggggaccc aggagtccta ccactcagct gtccccagga gtgcccagac cctcattctt    12960
atccaggacc taggagccct accctggcc ttccctcatc agccgtaaat gatgatttac      13020
tgctgttacc atcatcactg ccttcagtga ccaagggcct tccaaggtgc cagctctgga    13080
acgaaggatg cccttgggag gtgatgacac tcaggtacac gggtgctcaa cagattgctt    13140
cctcctatcc tcagacggtc tttgcatgca tgcagccatt ggcactccca ttgtgtggaa    13200
ggaaaccagc ccagggtcac acagctggtc agcagcaaca tagctggtct caaatctaag    13260
gtgcctgacc atgcctccat gagggaccgc ctccaaggga ggttgatcct ggctttgggg    13320
agcctttcct gggctgcacg aataacctcc attgttcgag accccaaact ctgctcacat    13380
cttcctttcc ctatctctgc ttgggctatg atcacggtga ctctagcagc ccttcatgga    13440
cattatagta ctctctgcca ttcacttttg ctctaatctg acttcaaccc ccacttactt    13500
ggtctctcct tttacaacca ccacaaccga aatctagggc tgctttttttt tttttttttt    13560 tttgagacag agtctcattc cattctgtca cccaggctgg agtgcaatgg tacgatctcg    13620
gctcactgca acctccgcct cccgggtcca agggattgtc ctgcctcagc ctcctgagta    13680
gctgggatta caggcgtgtg ccaccatgcc tggctaattt ttgtattttt agtagagacg    13740
gggtttcacc atgttggtca ggctggtctc gaactcctaa cctcgtgatc cgcctgcctc    13800
agcctcccaa agtgctggga ttacaggcgt gagccaccat gcccagccaa atctagggca    13860
ggaacatggc tgcagcatat aaaaagaatt gaattccata cttttgttaa ccctgttttt    13920
tgtttgtttg tagttgttgc tgttttgag acagagtctc gctctgtcgc ctaggctgga     13980
gtgcagtggt gcaatctcgg ctcactgcag actctgcctc ccgggttcaa actattctcc    14040
tgcctcagcc tcccaagtag gtgggactac aggcgcccac caccacaccc ggctaatttt    14100
tgtattttat tagagacagg gtttcaccat attggccagg ctggtctgga actcctgacc    14160
ttgtgatccg cccacctcgg cctcccaaag tgctgggatt acaggcgtga gccaccacac    14220
ccagcccctg ttttgttttt gttttgcttg cttcttaggg ttgttttctt ctatttatggta   14280 aaggcattgg ctttccattt gtagcatcaa tagaatattt cctgtttaca ataaccttat    14340
gtcatagtaa atggtaaagg gatttaaagc agtggttttc agctgccaga ggcctgagag    14400
agtttgggca tactctgtgt gatcgggcag aaggcctgtg ggaagtttag cagaggacag    14460
ggccaggaaa ggtgatggac agtgggggtc tgtcctggtc accaggcccc tgggtcctgc    14520
ccacctgctt ggagctcccc acccatcaca catgatgctg ccaagccctc tgggtattgt    14580
gggcaaatac cttaggagag aagctgatga actttgtttc ttgaaatgca cagattcctt    14640
ggacgtccct gagagctcag tcatgaaagt caacttggtt ttctccccct catttgggtt    14700
cagaatttaa agtccacaca cacaggcagt aagatgatat agataaggac gtcatcactc    14760
ggtttcggat gttaaaatgt ctaggtgggt tagcggtgat ttgagatcac acaaccttgt    14820
gccacaaaga ggaattccca ggccagaggg agacatttta ttgccatgtt atgatctcat    14880
```

```
cattgagttg aaaggcaatc ttgtttcatt ttggattctt tcttatgttt atgtcttata    14940
agggcacttt gaatttccaa gcaaataata attttgaatt agcttttaat cattgacttc    15000
tagcacagtt atatgatcag aaacatgctg tgtgatttga ttgctctcaa atatattgag    15060
atttgctgga acaaaataag tcaggttaat ttttgtaaat gtaccaggca tgcttaaaat    15120
gaatgtatct acatttgttc ccgagataca ggttgatgga cggatggcta catggatgtg    15180
atggagatgg tttactatcg ggaccttccg caccctgctg atgttttgtt gcttaggata    15240
tgaatggctg agcggaggct gtaaaacctg gcactctgct tgggtatgag gttcttcctg    15300
ccatcctgcc atcatttgtt ttttatgttt tgtcgccata agtgaccttg aggaaccctg    15360
ggagctcagg aaggaaggag cgcccagaag cagggacagg gagctggttg gggaggacca    15420
gaaatcaggt ttgtgaaggt tccagagagg acctgtcttt ggaggagtg tgggagactg    15480 agatggggga ggggtcattg gaatgatgcg ggcgctactt ggcattgtcc attgtgaggc    15540
actgtccatt gtgaggcacc accggggtca tcagggattg gtggagaggg agtataaagc    15600
cccagggttg gtaaggagg gcccagaccg aagaaggttt ggtggatagc agaaccttt    15660 tgtctccctc tgattgctcc taagcctcac gctcccttgc cccgcgtgtc ctgttgcttc    15720
cctgatcttc tccgtgacct gtagctaaac cttccaccag cgcttgagaa cttaatttga    15780
accggatcct ttcccagacc cctttcttct tctcctcctc ctcctccacc tcctccaggt    15840
gcccaacagc ccccttctcc tccttccct tcccttactt cccccttcc cctcccttc    15900 ccctcccct ccctcccc tccctcccc ctccctccc caactcagat ccggccccgg    15960
tccccgtccc cttccctccc ccctgcccta agccacctcc acctctgtcc tggccgcctc    16020
agggcgccct gaaaggacca ggacatgcgg gtgcggtgga tgctctttg gctcctcttt    16080 gggctcctac tggaatttat cagccatcag tgcatctctg tgagtagacg ctggacccgt    16140
ggggtttctt ccttttact gggctgtatc acgtggcatg aaattacaca gctcaggcct    16200
gtaatcccag cactttaggg ggccgaggtg ggcagatcac ttgagtccag gagttgaaga    16260
ctagccaggg catcatagcg aaacccccatc tctacaaaaa attccaataa agattagtcg    16320
ggcctggtgg tgcgtacctg ttatcccagt tactggagag gctgaggtgg gaggatcgct    16380
tgggcccagg agctggacgt tgcagtgagc cgagatggcc ccgctgcact cttgttttta    16440
acaaagaaaa tggaccaaaa caaagtgaaa tgtcatttga tttgtgtcat ctggtttgat    16500
gacttttttt ttttttttt tttttttaga cagagtctca ctctgtcgcc caggctggag    16560
tgcagtggca agatctcggc tcactgcaac ctccgcttct ggggttcaag caattgtcct    16620
gcctcagcct cctgagtagc tcagattaca acgcctggct aatttttgta tttttagtag    16680
accaccacgc ctggctaatt tttgtgtttt tagtagagat ggggtttcac catgttcgcc    16740
aggatagtct ccatctcttg acctcgtgat ctgcctgcct cagcctccca gtgctgggat    16800
tacaggcgtg agccaccgcg cctggccaaa atatataacc ttaagtgtaa gtttactaac    16860
tttggaaagt acatacacca gcataaacca accccctttc aagatctaca ttatttatt    16920 tatttattta tttatttga gacagtttct cccttgttgc ccaggctgga gtgcaatggg    16980
gcaatatcag ctcaccgcaa cctctgcttc ccaggttcga gcgattctcc tgcctcagcc    17040
tcccgagtgg ctgggattac agacatgtgg caccactccc agctaatttt gtattttag    17100 tagagatagg gttctccat gttggtcagg ctggttttga actcccgacc tcaggtgatc    17160
cgcccgcctc ggcctcccaa agcgtttggga ttacaggcgt gaaccaccat gcccagccaa    17220
gatctacact attatgtcac cccagaaagt gaactctcag tcttcccagc cagtctcttt    17280
```

```
cttatcatag gttagcttgc ttattctgga atttcgcgta tacagatgca tgccatgcca   17340
taggtactct tttgtgtctg ctttgttctg ctcaacacca tgtttctgaa atcattacca   17400
ttgttgtatg gttctctaac ttcatcattt ccatttcaga ctcagcatat gctgagttca   17460
acctgttgaa gggctatctc tgtttaattc accatcttga aagaaacatt taaaattgag   17520
atgttttcaa gaatatatag ttaaatcctg aggaatcgac gtagaaatgt tatcacaagc   17580
tgtctgaact tactcagggg aagtcttcgt cttcactcac ataagagtct aatgaatta    17640 atatcaacaa tcttagagaa atcccacact attcatgcca ttttcatgat ctccaccttg   17700
ataatttttt tttttttttt tttttttttt tttttttttt tttgagacag agtctcgctc   17760
tgtcacccag gctgaagtgc agtggtgcga tctcggctca ctgcaacctc tgcctcccgg   17820
gttcaagtga ttcttctgcc tcagcctccc aagtagctgg aactataggc atgtgccacc   17880
atgccctgct aatttttgt atttttagta gagacgggtt tcaccgtgtt agctaggatg    17940
gtctcaatct cctgatctcg tggtccaccc acctcggctt cccaaagtgc tgggattgca   18000
ggcgtgagcc accacgccca gcccaccttg ttaatttta agcactaaaa tttgatactt    18060
atttgtgaat gaagtaatct cttcattgta tttttttttt tttttactta tgctgagatt   18120
taaatgacaa agattcatat aatccaagag agaagtatta tttagaggga ttcttttacc   18180
atgtgatata taataaatgc atccaatgtt atacatcaat ttaaaaaaca agtaaataac   18240
tttaaagaaa agataactac tggccaggtg cagtggctca cacctgtatt cccagcactt   18300
tgggaggcca aggcaggtgg atcatgaggt caggagttgg agaccagcct ggccaagatg   18360
gtgaaaccct gtttctacta aaaatacaaa aattagccga gcgtggtggc aggcgcctgt   18420
aatcccagtt actcagtagc tgaggcagga gaatcgcttg aacccgggag gcggaggttg   18480
cagtgagttg agatcatgcc actgcaatct agcctgggtg acagagcaaa actttgtctc   18540
aaaacaaaaa gaaagaaaaa gataagataa ttactttata cttagcttgt cttacccatg   18600
agtgacgggc tgcatgtggc ccaggacagt tttgaatgca gttcaacaca aatttgtaaa   18660 cttttcttaaa acattaggag attttggcca ggtacagtgg ctcatgcgtg taatcccagc   18720
actttgggag gctgaggcgg gcagattacc tgaggtcagg agttcgagac caccctgacc   18780
aacatggcaa aaccccatct ccacaaaaaa tacaaaaatt tgctgagtgc actgtcaggc   18840
acctgtactc ccagctactc aggaggctga ggcaggagaa tcacttgaac ctgagaggca   18900
gaggttgcag tgagccggga gcacaccact gcactccagc ctgggtgaca gagtgagacc   18960
ccatctcaaa aacaacaaac aaaaacaaaa acaaaaaaat ggctgggcac ggtggctcac   19020
acctgtaatc ccagcacttt gggaggccga ggcaggcaga tcgcctgtca ggagttcaag   19080
gccagactgg ccaacatggt gaaacctcat ctctactaaa aatacaaaaa tgagtcggc    19140 atggtggcag agacctgtaa tctcagctac tcggaggct gaggcaggag aatggcttga    19200
gcccaggagc tggaggttgc agtgagccga gattgcacca ctgcactcca gcctgggcga   19260
ctgagtggag cggaactctg tctcaaaaaa aaaaagagg ttttttttag atcatcagct    19320
attgttagtg ttagtgtatg ttatgtgtgg ctcaagacaa ctttgcttct tttaatatag   19380
gcagggaagt caaaagattg gatatccctg ctttataccca agaaagacaa cacccccacat  19440 ttgcaatgcc tgaaaacact accagccatc tgaaaaacat gtgacttcta acttctgttc   19500
ttttttgtag cagtggaatc ccacggtgat atctgaggga tgtggttacc ttttggagga   19560
ggttgacggt ttctaaggat gattctttct gagtgaaata ttgtcagtgt cattgacctt   19620
```

```
ttcattattt caactattat tattccaggt tatcaatact ctggctgacc atcatcatcg    19680
tgggactgac tttggtggaa gtccttggtt acatgtcatt attgcatttc cgacaagtta    19740
taaagttgtc attaccctct ggatagttta cctttgggtg agtatactaa ctttctgtag    19800
aggtatactt gtaatcacaa ataagaataa attatataaa acaattcaca tttctggact    19860
tcattatgaa tatgtggttt tacccaaaaa atcagggaaa tgatttatta gtataagaat    19920
tatgaaaaca tctgccattt gcattatgaa aattaaatag gtcggtgttt gtttaataga    19980
atgtcaacag agcttttggt caaaaataag ttttttttaac ctttgtgcta tttatcacaa    20040
atggagtatg aggtttcgtc acttaaatag gaaattcttt ctaaactctt ctgctttata    20100
gttctatcgt atgggtggaa ggaaagcttc aatctcctc tctgaagatt cactgcagaa     20160
atgagctgac aacagacagc ttaacaggaa agaaaaaca tagaacaggc ataaacatgg     20220
gaaccagctg aaaaatgaga ctgctagaag ggccggatgg ctgatgctta aagagcaccc    20280
tcttctgagg ggagagggag atagatggag atgtaggcca tttagagggg cagcaaatga    20340
tttttagggg aaatgaaaga ggccaaggaa caaacaattg gcctgagaca aagttcctgt    20400
gaggtcatag ggacgaggtg acaaactgcc ggaaggtgaa gggcagaact gcactgcgtc    20460
tcatgatgca gagaaagccc cagagactct tagaactgcc ctccaagaga atcaatgaaa    20520
agtgtgtctg ggcagggtaa ttttgaatga catcattcaa agtgcatgtt ccgacttgga    20580
actggagaga gatcagtatg tcaaaagtct gtacttggta agaatttggc tgctaagttg    20640
tgccataatt tgtcttttga gccttttttc ctttgggtaa gttgagctct acattttgtc    20700
ttgccattca tgacagtaaa aatgtggttg tctgggggct gaacctcctt ctgaacaatg    20760
atccaagata aaagtactaa taccacaatg ctttttttata ttcaagggaa gaggaagtat    20820
gtttcagttt taccacctag ataattacac gtcatttggc actgcctttc aagatatgta    20880
gaaaacagaa aatatatgag ttatgaagat atctaggcac atttaacatt ctctatgcca    20940
cttagtcctg aacagagaat tttcggtata aattggagga agcttttttc ttttttttt     21000 ttcttttctc accccgaaga cgagtctcct tctgttgccc aggctggagt ataatggtgt    21060
gacctcggct cactgcaacc tccacctcct ggcttcaagt gattcccctg cctcagcctc    21120
tcaagtagct gggattgcag gtgcccacca ccatgcccag ctaattttg tatttttagt     21180 agagtcgggg ttttaccatg ttggccaggc tagtctcaaa acccgacctc aaatgatcca    21240
ccaacctcag cctcccaaag tgctgggatt acaagcgtga gccaccacgt gagccagggg    21300 aagttttaa atttaccact ttttaacaat tccacttagg aaagttcagt tgagctgttg     21360
gacttggaca acttcgcacc tctcatcttt gtccttgtca tctagtcatc tataccatta    21420
cctccttagc agggacatca tgggtgccat gaagcattca tgcgtgatgg catttcttgg    21480
cttctcattt cttcatgtgt ttgacatttc ccctagctcc aaactgggcc agctaccttt    21540
cctatgaaat ctagcagtag ctgtgggatt gacgtggttg ctctttcat cttttttagat    21600 tacccattgc ttctctcgaa atcctagtac atgattttt ttttatccta tgtgcagaaa     21660
tcaggaaaaa acaaattcta caaagaattt gaaagatatt atttcaggcc aggtgtggtg    21720
gctcatgcct gtaatcccag cactttggga ggctgaagca gatggatcat tgaggtcag     21780 gagttcaaga ccagatgggc caacatggtg acaccccatc tctactaaaa agacaaaaat    21840
tagccaggca tggtagcagg cacctgtaat cccagctact tgggaggctg aggcacaaga    21900
atcgcttgaa tctgggaggt ggaggttgcc gtgagccaag gtagcgccac tgcacttcag    21960
cacggttgag agtgacactc tgtctcaaga aaaaagtcat ttcaatgacc acctcaggag    22020
```

```
attcataggt atctgaccca catctgagat gggatttgca ttgcatttta gctatgatga    22080
gaagaaatat ttaatatctt agaagattaa aagcatactg tgataaatatg gaaatcttgg   22140 tgggaattca gtcattagtg agaatgtttt gcgttaagtt caaaccagcc tcaatgaagc    22200
tgatgtgagg gaagggaaag tgaactctga gtagagcagg gacagaagga agatgctcca   22260
gtgcagatca ggaaggagca ggggatgaaa tgttacaaat tctagaactc agagagctga   22320
aggtaattac ttccttttca agttgtgaaa catgttaacc tgtggtaaaa tacttataag   22380
atgataatta ccatctaacc gtgttgaagt gtacagttca gttgtgtgaa gtatattcat   22440 gtcattttt ttttttttt ttttttgag acgaagtctc actctgtcac caggctggag     22500
tgcagtggtg ggatcttggc tcactgcaac ctctgcctcc tgggttcaag cagttctcct   22560
gcctcagcct cccgagtagc tgggactaca ggcgtgcatc accatgctca gctaattttt   22620
gtatttttag tagagacggg gtttcaccat gttgcccagg atggtctcca tctcttgacc   22680
ttgtgattca cccgcctcgg cctcccaaag tgctgggatt acaggcgtga gctaccgcat   22740
ctggcctatt ttttttttt tttttttttt ttttttgag acagagtttc aattttgttg    22800
cccaggttgg agtgcaatgg cacaatctca gctcaccaca agcttttcct gctgggttca   22860
agtgattctc ctgcctcagc ctcccgacta gctgggatta caggcatgca ccaccatgcc   22920
tggctaattt tgtatttta gcagagacag cgtttctcca tgttggtgag gctggtctca    22980
aactcccgac ctcaggtgat ccgcctgcct cggcctccca aagtgctggg attacaggag   23040
tgagccaccg tgccagcctc atgtcattct tgtgtgtgtg tgtgtgtatg tgacagagtc   23100
tcattctgtc gctcaggctg gagtgcagtg gtgtgatctc ggctcactgc aacctccgcc   23160
tcccagcttc aaacggttct ctgcctcagc ctcccgagta gcttggatta caggcgcccg   23220
ctgccatgcc cggctaattt ttgtattttt agtagagacg gggtttcacc atcttggcca   23280
ggctggtctt gaactcctga ccccgtgatc cacctgcctc ggcctcccga agtactggga   23340
ttatacgcat gagccaccgt gcccagccgt cattcttata ttattatttc ctaggtgtct   23400
ctcctgaaga ctatcttctg gtctcgaaat ggacatgatg gatccacgga tgtacagcag   23460
agagcctgga ggtccaaccg ccgtagacag gaaggtatgg ctctgttgga atccgcatag   23520
tgtggaaatg agtttgccct ggaaagggaa agaacagctt cttgccctca ggtttctcac   23580
cttctcctct cctcactctc accaagggct gaggtccatt tgtatgcaca caaagaaaag   23640
agtttcttcc tttcgaggaa ataaaattgt cctgaaagac gtcattactc tacggagaca   23700
tgtggaaaca aaagttagag ctaaaatccg taagaggaag gtgacaacga aaatcaacca   23760
tcatgacaaa atcaatggaa agaggaagac cgccagaaaa cagtaagatg tgccttgaca   23820
caaatactgt tgtatgaacc atgtgccaat caaagtagac aactgtaaag tccttgagaa   23880
tattttctac aatatttgtg gcaaattcag tgggttcaaa attgagtttg tcctttctgc   23940
ttcattagtt taagctgtat aattcctttc ccttcctaca ttcttgtttt catttttcg    24000 gaggaagagg agttgctagt actggcattg gttttccttt ctcttttttt tttttttt    24060 ttcctgagat ggagctttgc tgttgttgcc caggctgtag tgcaatggca caatctcagc   24120
tcactgcctt ttgggttcaa gcaattctcc tgcctcagcc tcccaagtag ctgggattac   24180
aggtgcccac caccacgccc agctaatttt tgtatttta ctagagatgg ggtttcacca    24240
tgttgtccag gctggtctcg aacttctgac ctcaggtaat ccacctgcct cagcctccca   24300
aagtgctggg attagaggcg tgagccacca cagccagcct ttttttttt ttttttttt    24360
```

```
tttaattttg cgatagagtc tcgctctgtc gcccaggctg gagtgctatg gtgcaatctt    24420
ggctcactgc aacctctgcc tcccagtttg aagcaattct gcctcagctt cccgagtagc    24480
ttggattaca ggtgtgtgcc accacatttg accattttt tttttttttt ttttttttga    24540
gacagagtct cactctgtca cccaggctag agtgcagtgg catgatcttg gctcactgca    24600
acctccacct cccaggttca agcgattctt atccctcagc ctcttgagta gctgggacta    24660
caggcatatg ccaccatgcc cggataattt ttgtatttt agtagaggcg gggtttcacc    24720
atattggcca agctggtcta gaactcctga catgatccgc acacctcggc ctcccaatgt    24780
gctgggatta caggcgtgag ccaccgtgcc cggcccaatt tttgtatttt tagtagagac    24840
aggggttcac catgttggcc aggctagtct tgaactcctg acctcaggtg atctgcctac    24900
ctcagcctcc cagtgtgagc caccgcaccc agcctggatt gttgaattca atgcttgggt    24960
cacctccaga ttcattttca cagtctttca tgttttggtc atatgacatt gtattttgct    25020
gccatatgac tgatcttttt ttgttaaatg tgagatactt gttaaaaaat gtttagcaat    25080
gaattgaggc ctagtagcat gttatcttgc tgcagaagag atgggagtct acttctgggg    25140
gatggtcagg ggtcctccat acaagctgca attgaagtcg tcggtgcagg ctcagtccct    25200
acaaaggcca gggtatttcc tgtccacctt tattctgatg catgactctt ctgggtctca    25260
accagagcca gcggacttca gtatgggtcg cttcattgg cagaccctca atccacttgt    25320
tttccatcta atcccacgca tgtgtgcaaa agctgctgtg cttctttgca tctcagtagt    25380
tccttctgga attcagcaat gaaactcagg gaaatgggtt ccaaatgcga ggctgacttt    25440
cgtcctgggt ttccttcttc tccatcttca cctcatgtct gtttactgcc atgttagcaa    25500
tttgatgtat tcaatcatgg gttttatatt ctgtttggtg tcccccattg ttctcattgg    25560
agatcagaag cttcagatgc acttatgtca actcaagagt agaatgcttc cttagcttcc    25620
ctccagagtc aggttttgtg tttctagttc ccaagtgcac agcaggagta gtgatgtcct    25680
cactggcttc tcatttgcat taagctgtga gcttctttag cgtggggaca ggaccctgct    25740
cccattgcat tctcagcacc acaccacaca ctccttgttt gaggccactc cagacagcat    25800
gtgctgaagg atgccttgtg gtcagaaaca agttcattaa ctttctcttt gaagtgtttt    25860 cgccctgtt tcctagcgtt ctgggaattt tacacatcct tcctataaag ccaagtatca    25920
ggtgagatcc ttaggatcag gaccatgaat caagtggtgt gagggcaaca cagcaaactt    25980
acccttttta ggccgtttcc tttttctgcc ctcaatctct gtgaactgaa ccttgttaaa    26040
gtcagtcaac accagggtgg atggtttgcc gttgtcacct attttcagga cataacaccc    26100
tgacttagga gccattccga tcatttctaa ttcaatagat gcgcccagca ttcagattgc    26160
cttttctctc aaccaggatc tttaaagttg atgacaagag ttccagtcct gaatcatggc    26220
aaagtgcagt agtgaactgc ggggttattc tggaaggatc tctctatggc tgatggtctc    26280
agttccggca tcagcctctg actgagaatc aggtctcaca caggaggagt cagatgagga    26340
gcaatcctct gcttccgatg gagttagttg tgatgaattg gtgaggtctg gttttcaca    26400 ctgaactaaa atgagctttc gctgtgtcaa gcacaagact gaccccagag acacacatag    26460
tgcacctcat agaagctttt aatagtcttt atatttacta aagaatagga ctaactatgg    26520
aactatgaag atgagctgga aatgacaggt gacttgccag caggccagag tgtgactttt    26580
ttttgtccct caatgggagg tgtcaattct cccttcggtt gtgagaatca gttggttcat    26640
ttgtgggaag gttgcagggg ggaatctttg aatcacagcc ttcagatgcc agaagggcag    26700
agggaatccc acacgggctg gtggatcatg tgtgtgcatt tctctcccctt ctaatctgag    26760
```

```
gaaactaagc gtgaaagaat gtgagcatgc agaaaaggag aggcaggtat cagaggcaga    26820
ggaaaatggg aaattggata tgaaagaaat acacacctac aagtgagttc agaaactgta    26880
ccccaccctc ttgggaaacg cccattggag tgttgttttt aacctttgta cagtatttag    26940
acccagtaaa tgcagaaata gaaacaaacg gtcagaagac atatcgtgag agagagcgag    27000
agagagttca caaaacagaa aacaaagtac cttaatattt accagtgacc aaaagatgtg    27060
aagtagcaaa acgtctcctg accccattgc cagctagact gtgtggaaac tcggttcata    27120
ccagccattc taggggtggg gtgagttgtt gtcatcctta ggaaagtgtg ttgttgtagg    27180
atcaaccaca tccttcaaaa ggactatgcc tgtttataag cccagctgtt tctgccctgt    27240
gaaacacggt aaggatatta atacaaagag aatacagctt tatgataaaa gatgctcaat    27300
gaaggatgaa ttagggatgt actgagaatg gggaaggaaa ctatcatctc agaagtcagc    27360
aggcagtaag caagaggagg aatcaataca gcaacagttt ggatcagact gtacagtttt    27420 tttgttttg tttttgtttt tctgagatgg agtctcgctg tgtcacccag gctggagtgc    27480
aatgacgtga tcttggctca ctgcaacctc cgcctcccag gttcaagtga ttcccctgcc    27540
tcagcctccc gagtagctgg gattacaggt gcctgccacc acgcctggct aatttttgt    27600 attttagta gagaaggggt ttcaccatat tagccacaat ggtctcaatc tcctgacctc    27660
gtgatccatc cgccccgccc tcccagagtg ctgggattac aggcgtcagc caccgtgacc    27720
ggctcagact gtactcttct agccatctga aatacgtttt ctaggtagag atagattgtg    27780
taagggtaca gttgtgagga taacagaaac atggcagatt attaaaatc atcctgaaag    27840 tggtgcttta tctgatgaaa gtgattgtaa tccataggaa aatgtttcaa cgtgcgcaag    27900
agttgcggcg gcgagcagag gactaccaca aatgcaaagt aaggagcttc ctccctgcag    27960
ttgcaggata gttcagtgct gatgcagatg atgccacggc ccttagactc tctcaacatt    28020
caatttctca tgtgttggct ttttcagatc cccccttctg caagaaaggc tctttgcaac    28080
tgggtaagtt tgcttgtttt ccttgctttt ggacatagtc tgccaggtca ggacatggat    28140
acatttttct ccctacagct ctgtgctcaa gccctgcaga gggagatggc agagagaaag    28200
gctgcctaca agcatcacag tcccatccct gttggtaacc gtgttgcgca aaaacacctt    28260
catccccacc cagtgggggcc cctgatctaa tattctaagt gtcagaggtt ccgtatttgt    28320
aatagcagat gggccctgac tgtaaactag tgaagagtga atgtaactta ttacccacag    28380
ggacaattcc aaatgaaggc cttaaatgat gctcagctaa gctggttctt gtgtggcctc    28440
tgtaccttca aaagctgccg agtcctatga ttacacgtga tgggacttgt acacttgaag    28500
tgaaacacag ttttaaaact tgctttgttt agaattccca cctcattttt ccatggacaa    28560
aagtattctt tatgtcctag tgcacttaca atttggtatt acctgggagt gaaagaaat    28620 attacagcca tgcctaagtg acttcttgag gtgagattgt tctgtcagaa acccctctcc    28680
cagttcccct gcagctcttc aggaatccac atctctccag agctctttgt tctcatgggt    28740
ggcacctcca gagtgaagaa gatcctttgt caagaaggga aacagagggg aaatgagagg    28800
gtcctgcagg cagagctgga atcaacttcc actctgcctc ttgcaagctg tgtgaccctg    28860
ggcacaattt ctccttcctc tggaaacctc tgttttctta gatttggagc agggtggtca    28920
cactgacctt gcagagttct gagaatcaga gacagaacat aaaaggcctg gaaacattc    28980 tccaaaaaga agctgcaaca tgtgtggaca gtgggctttt catgcctctc ttactgtctc    29040
ttactgtctg ttgacctggt gcaagaaaca tgctctggta atggctgtga gggaggaatg    29100
```

```
aggatagaca tagacactcc tgtgtctcaa acatgcttct ttattactct gttatgactc    29160
tgtcttccct ggggcaggac cccagcctgc ctacatttgc agacagacac agtggcatgt    29220
ggagacaaca gtgtgtccca atgactttcc tttaccctcc agctgtcggc agtactcagt    29280
ggaagggtga tattatgaca ctgatacttc tattttgaaa cctggaggat ggaaaggtgc    29340
aaaaatctat caccagcaac agaaggtgca gactgtgttg gtggcggtaa ttttgtccat    29400
caaatgaata tgtgtgaaaa cattccctcc tttggcccta caggtcagaa tggcggcagc    29460
ggagcatcgt cattcttcag gattgcccta ctggccctac ctcacagctg aaactttaaa    29520
aaacaggatg ggccaccagc cacctcctcc aactcaacaa cattctataa ctgataactc    29580
cctgagcctc aagacacctc ccgagtgtct gctcactccc cttccaccct cagcggatga    29640
taatctcaag acacctcccg agtgtgtgct cactccccct ccaccctcag cggatgataa    29700
tctcaagaca cctcccgagt gtgtgctcac tcccccttcca ccctcagcgg atgataatct    29760
caagacacct cctgagtgtc tcctcactcc ccttccaccc tcagcggatg ataaactcaa    29820
gacacctccc gagtgtctgc tcactcccct tccaccctca gctctaccct cagctccacc    29880
ctcagcggat gataatctca agacacgtgc cgagtgtctg ctccatcccc ttccaccctc    29940
agcggatgat aatctcaaga caccttccga gcgtcagctc actcccttc caccctcagc    30000 tccaccctca gcagatgata atatcaagac acctgccgag cgtctgcggg ggccgcttcc    30060
accctcagcg gatgataatc tcaagacacc ttccgagcgt cagctcactc ccttccacc    30120 ctcagctcca ccctcagcag atgataatat caagacacct gccgagcgtc tgcgggggcc    30180
gcttccaccc tcagcggatg ataatctcaa gacaccttcc gagcgtcagc tcactcccct    30240
tccaccctca gctccaccct cagcagatga taacatcaag acacctgcct tccaccctca    30300
gcggatgata atctcaagac accttccgag cgtcagctca ctccccttcc accctcagct    30360
ccaccctcag cagatgataa tatcaagata cctgctgagc gtctgcggat tccgcttcca    30420
ccatcagccg atgataatct caagacacct tccgagcgtc agctcactcc ccttccaccc    30480
tcagctccac cctcagcaga tgataatatc aagacacctg ccgagcgtct gcgggggccg    30540
cttccaccct cagcggatga taatctcaag acaccttccg agcgtcagct cactccccctt    30600 ccaccctcag ctccaccctc agcagatgat aatatcaaga cacctgccga gcgtctgcgg    30660
gggccgcttc caccctcagc ggatgataat ctcaagacac cttccgagcg tcagctcact    30720
ccccttccac cctcagctcc accctcagca gatgataata tcaagacacc tgccgagcgt    30780
ctgcgggggc gcttccaccc tcagcggat gataatctca agacaccttc cgagcgtcag    30840
ctcactgccc ttccaccctc agctccaccc tcagcagatg ataatatcaa gacacctgcc    30900
gagcgtctgc gggggccgct tccaccctca gccgatgata atctcaagac acctcccttα    30960 gctactcagg aggctgaggc agaaaaacca cgcaaaccca agaggcagag ggcggctgag    31020
atggaaccac ctcccgaacc caagaggcgg agggtcggtg acgtggaacc gtcacgcaaa    31080
cccaagaggc ggagggccgc tgacgtggaa ccatcatcac ccgaacccaa gaggcggagg    31140
gtcggtgatg tggaaccgtc acgcaaaccc aagaggcgga gggccgctga cgtggaacca    31200
tcatcacccg aacccaagag gcggagggtc ggtgacgtgg aaccgtcacg caaacccaag    31260
aggcggaggg ccgctgacgt ggaaccatca ttacccgaac ccaagaggcg gaggttgagc    31320
tgagaagagg ccagtgcact caagcctgag caataagaat aaaaccgagt agaacaaaat    31380
aaaaaattca aaaaacaaaa caaacccac actccaaaaa ctaacaaaga ataaataaat    31440
aatataaaaa taaaataaat actgcagtcc ttatgttatt gctttgtttc gatatctggt    31500
```

```
atgattgcct gagggacctg aggtttttaa tcatagggt  ttttttttaa tctttagaag   31560
tggttggtta tgtaaaatat tattatttt  tttttgaga  ctggattttg ctgtgtcacc   31620
caggctggag tgcagtggct cgatcacagc tcactgcagc ctcaacctcc tgggcttcaa   31680
gcaatcctcc tgcctcagcc tcccaagtag ctgggatcac agatatgtgc caccacgcct   31740
ggccaatgtt aaaaaatcct ttaactttt  tgtagagatg cactcctgga ctcaagcgat   31800
cctcctactt gtcccgacca ccagccctt  tctgataaac aaacatttac actgtttatt   31860
atctgatgcc atttctatct tcttccttgt cgtccagaca tcgaataatt aggtttcttc   31920
agggtttct  ttttcaagtg ctcagtgtta aagatcactc acattagggc cagacaccat   31980
ggctcatgcc tgtaatccca gcactttggg aggccgaggc gggcagagca cttgaggtgg   32040
ggagtttgag accagcccgg ccaacttggg gaaaccccac ctctactgaa aaaaatacaa   32100
aaattagctg ggcgtgatgg tgcatgtctg tagtcctagc cacttgggag gctgaggcat   32160
gagaatcgct tgaacccagg aggcagaggt tgtagtgagc caagatcacg tcagcacact   32220
ctagcctggg tgacagagtg agactctgac tcaaaaaata aataaaataa atatcactta   32280
catgagatat acccaagggg tggtctacag agacttggaa gcagtggtta ttgcaacagg   32340
ggcacggaag tcatctggct atgccagggt gcccagggga tactcggggt gggtggcatg   32400
gtgctgctgg ggactcatcg cacaggacgc tctgattgac gcactgccag gagtagcgct   32460
ctgtcttggg gctgcagccg gcctcctcag ctcgagtgta acatcagtcg tggccatggc   32520
agcacctgcg gatgtcacat gggcaggaca gcaggtgggt gaagctctct cctggccctc   32580
ctctcttgcc aggaccatgg gtgactgaag acccccaggg aggcacagca tcctcttatc   32640
taagattttt ttttttttaa gagacagggt ctttaaaaaa gtcctgcagt ctgcagtcgc   32700
ccaggctgga ctgcagaggc acaatcatag ctcacggcag ccttgaactc ctgggctcaa   32760
gcgatcctcc cacttcagtg tcccaagtag ctgagactac aggcacacgc cagcatgtcc   32820
ggctggtttt ttagtttgta tttcctttga gacagcatat ctctctgtcg ctcaggctgg   32880
ggtgcaatgg ctcaatcagc tcactttagc cttgaactcc cgggctcaag tgatactgcc   32940
acctcaactt cccaagtatg ctactacagg aacacaaact ccttttttaa attttttgtg   33000
gatatggggt ctcactatgt tgcctaggct ggtcttgaac tcccaggctc aagcagtcct   33060
acctcagcct ccccaaatgc tgggattaca ggtgggagct actgtacgcc tggccttatc   33120
taagctgttt ccctgaaaat gcccgtcttg ggtaatgatt ccattggccc caccatgccc   33180
tgtcctgcct tcctggctgt gcccaagctt ggtccctgcc tgcctgcctc actctctggg   33240
tctcgagctc ctgtgacaca tgactcctct ctcttcctgg agtgatccaa gccctgccac   33300
ttcctgactt tgcccacact gtaccctctg cctggggcaa cttcatgtct gcccattgtc   33360
ccttaggcct cagcccaggc acaagcccct gcctccggag gtcatccagg cctcaccagg   33420
ctacaccctc tcgtaaaatt ggattccctc ccttcagggc aggtttataa tgaaatcctc   33480
ctcagaggcc aggtgcggtg cacccatct  gtaatcccag cactttggga ggctgaggtg   33540
ggaggatcac ttgaggccag ggggtcgaga ccagcctggg caacataaga gagactcttg   33600
tctctcttgt ctctataaca aatttaaaaa ttagctcacc aggccaggct cagtggctca   33660
tgcctgtaat cccaacactt tgagaggccg aggcaggtgg atcacgaggt caggagttcg   33720
agagcagcct gaccaacacg gcgaaaccct gtctctacta acatacaaaa ttagccagg   33780
catggtggca cgcacctgta atcccagcta ctcgggaggc tgaggtagga gaattgcttg   33840
```

```
aaccccggag gtggaggttg cggtgagcca agatcacgcc attgcagtcc agcctgagca   33900
acagagcaag actctgtctc gagagaataa aaacacacaa aaaattaact cgccaggatg   33960
gcacatgcct atagtcctaa ctacttggga ggctgaggtg ggaggattcc cttcagccca   34020
ggagtttgag gctgcagtga gccactgtga ttgtgccact gcactctaac ctgggcaaaa   34080
gcgagacccc aggctagagt gcatgatttt gggtcactgc aacctccacc tcccaggttc   34140
aagtgattct cctgcctcag cctcttgagt agctgggact acaggcatgt gccaccacgt   34200
ctgggtaatt tttgtatttt tagtagagac agggtttagt agagaccatg gtgaaacccc   34260
atctctatta aacaaatctc tactaacccc atctctacaa aaaacagctg ggcgtggtag   34320
tgcacacctg taattccagc tacttgggag gctgaggcac gagaatcatt tgcatcttgg   34380
aggcagagtt tgcagtgagc tgagatcgca ccactgcact ccagccggga tgacagagca   34440
agaccctgtc tcaaaaaaaa aaaaagggcc gggcgcggtg gctcacgcct gtaatcccag   34500
cactttggga ggccgaggcg ggcggatcac gaggtcagga gatcgagacc atcctggcta   34560
acacggtgaa accccgtctc tactaaaaat acaaaaaatt agccgggcgt ggtggcgggc   34620
gcctgtagtc ccagctactc gggaggctga ggcaggagaa tggcgtgaac ctgggaggcg   34680
gagcttgcag tgagccgaga tcgcgccact gcactccagc ctgggcgaca gagcgagact   34740
ccgtctcaaa aaaaaaaaa aaaaaaaaa aagaaaaaag aacaaacaac agcaacaaca   34800
acaaaaaaac ctctgtgtca atcacagcct tcgagctagg ggagaggcgg ccgaattctg   34860
ccctccgcta acgagctata gctttgtgga aatgggcgag tggcgtgccc ttgtgagcct   34920
cagggccgca tctgtaaaat gggcataact gtcatgcctg tctttaagaa cagccttggg   34980
ggtaaatgag tggaactaat ggaaagatct cagcccacaa ccttccacag aacaggcgct   35040
tctcacacag taagtagcag gagtgcagag gctgcaggca tgaatccagt cagactgcag   35100
actgcctggg ttcaagtccc agctcccacg tcttggtaac taagtggcct cagacaagtt   35160
acttagtatt tcttcttctt cttttttttt tttttcaga cggagttttg ctctgtcacc   35220
caggctggag tgcagtggtg tgatctcggc tcactgcaac ctccgcctcc cgggttcaag   35280
caattctcct gcctcagctt cctgagtagc tggaattaca ggcacctgcc accacatcca   35340
gctaattttt gtatttttag tagagacagg gtttcaccat attggccagg atggtctcga   35400
actcctgacc tcgtgatctg cctgcctcag cctcccaaag tactgggatt ataggcgtga   35460
gccaccgcac ctggacacat tacttaatat ttctgtgcct tggtttcttc atctgtgaaa   35520
tgggattgtt gtgagaatgc aaagggattc ccagggcagt tcctagtgca tagtctggct   35580
gcctttgtgt gtgtgtgtgt gtgtgtgcat gtgtgtgtgt gtttaatata gagacagggt   35640
ctcactatgt tgcctaggct ggtttcaaac tcctgggctc cagtgatcct cctgcttcca   35700
cccaaagtgg tgggataaca ggtgtgagtc accacacctg gtcactttat attatttttt   35760
tcttttgaga cagggtctcg cactgttgcc gaggttggaa tgcagtggtg caatctcaac   35820
tcactgcaaa ctccgcctcc cgggttcaag tgtttctcct gcatcagcct cttgagtagc   35880
tggtactata gtcaccgggc tccttgcctg gctaagtttt gtattttag tagagatgcg   35940 gtttagtgat tctcctgcat cagcctcttg agtagctggt actataatca cttagctcct   36000
tgcccagcta attttgtat tgttagtaga gatgcggttt cctttttttt tttttttt   36060 gagatggagt ttcgctcttg ttgcctaggc tggagtgcag tggtgctatc tcggttcacc   36120
acagcctccg cctcctgggt tcaagcgatt ctcctcctca gcctcccgag tagctgggat   36180
tacaggcatg tgccaccgca cctggctaat tttgtatttt tagtagagac ggggtttccc   36240
```

```
catgttggtc aggctagtct cgaactcctg atgtcaggtg atctgccttc cttggcctcc   36300
caaagtgctg ggattacagg catgagccag catgccaggc tggcccgttt tttttttttt   36360
ttaatcactt aacatatatc ttggagaact ttccattttg ggagttaaag agatttgttt   36420
gtttgtttgt tttgagacag gtctccctc tgtgcccag gctggagctg gaccttggct    36480
cagtccaact tccaccccc gggctcaagc aatcctccca cttcagcctt ccaagtagct    36540
gggtctatgg gcacatgcca ccacatcccg ctacttttta tagttttgt agagatagga    36600
ttttaccatg ttgcccaggc tggtcttgaa ctcctgagct caagtgatcc acctgcttca   36660
gcctcccaaa ttactgggat tacaggcatg agccatcttg cccagcctgt tttttatta    36720
atatctacta agtgccaact accatagagg acataaagat gattcagtct ctgcagaagt   36780
cattttcttt ctctttcctg ttgtacagca caaaattaat ggactaaata gtctgtcact   36840
agataaagaa gccctaagta atcaggcact tgctgcagtt tttacaaagt ttaaaaagcc   36900
atatgaaaca cagtatactc caagtaataa gaggcaaaat atgtgaagtg ttactgctgg   36960
ggaatttacg gactattctt ttctacaata tatctgctgt ggtctgaatg tgttccccaa   37020
gattcatatg ttaaaactta accaccagtc tggtagtatt aagaggtggg gcatcattaa   37080
gtcatgaggg catgggatta gtaacctcat aaaaaggttg gcgggaacga gctaggccct   37140
ttcattgccc ttcatccct ctgtcacttg aagacacagc actggtcccc ccggaggac    37200
atagcagcaa ggtgccgtat tggaaatggc caccatgccc tcaccagata ccaacctgct   37260
ggtaacttaa tcttggcctt cctagcctcc agaactgtga gaaagaaatt tctgggtttt   37320
gtttgtttgt atgagacagg gtctctgtca cctaggctgg agtgcagtgg cacgatctcg   37380
gctcactgca acctctgcct cctgggttca agtgattctc ccacctcagc ctcccgagta   37440
gctgggatta caggtatgca ccaccacacc cagctttttt tttttttcat agcgttgtac   37500
agatagggtt tcgtcatgtt gcccaggctg atctcgaact cctaaggtca cacgatccac   37560
ctgccctggc ctcccagcat gctgggatta aaggcgtgag ccactgtgcc tggccaaaat   37620
ttccgttttt tataaataac ccagtctctg gtactttctt atagccgcac gaacagataa   37680
agactgtacc tatctgttga ctgggcgcag tggctcacgt ctgtaatccc agcacttcgg   37740
gaggcttaga caggtggatc acgaggtgag gagatcgaga ccatcctggc taatatggtg   37800
aaacccgtc tctactaaaa atacaaaaaa tttagctggg ctcggtggcg ggcgcctgta    37860
gtcccagcta ctcaggaggc tgaggcacga gaatggcatg aacccgggag gcggagcttg   37920
cagtgagccg agatcatgcc actgcagtcc gtcctgggcg aaagagcgag actccgtctc   37980
aaaaaacaaa caaacaaaca aacaaacaaa aagaccgtg cctttctgtc tgtctccctc    38040
ataggtcagt ttccacctga ttgtaaccac atcaagtatc ctagtatatt tcatatttac   38100
agaaaaataa atgggcaaat actgtcattt acagagaacc tgccctgtcc tgtacactgt   38160
gacatatttt gtggtttgtg attatgtgct ctgatcctta cgatagctct aaaatagctc   38220
aaaaagttat tcccatttg tacataagaa aattgaagtt ctggaaacat aaggcaattg    38280
cccaaagtaa tagagtaaat gacaaagcta ggatttctttt ctttcttcca ttaattaatt   38340
aattatttga gatagggtcc ctgttgtggg atgcagtggg gagatcatag ctcactgcag   38400
tctcgacctc ctgggctcaa ctgatcctca cgtctcagcc tcctgagtag ccgggactac   38460
aggtgcacac caaacactatg gctaattctt gtattttct gtagaggtct gcctaggcta    38520
ggcagagatt ctggctaggc tggtctcaaa ctcctgggct caagcaattc tcctgcctca   38580
```

| | |
|---|---|
| ccctcccata tagctgggac cgcaggtgtg tgccaccact cccagctgac ttgtttatac | 38640 |
| cagtggttct taattggaag agttttgtac cccgggggaca tttggcaaca tctggagatg | 38700 |
| ttttttgaatg ttacagtggg gaggagggga atgctactgt cacctactgc gtagaggcaa | 38760 |
| gggatgctgc tgaacatccc acaatgcaca gaacagcctc ctccccaccc aacagagaag | 38820 |
| tatctggttg gcccaaaatc tcaatgatgc caagtctaag aaactgcttt gtatttctct | 38880 |
| gagatactgg gatgaggaac gctctaaatt agttgtcttt gaggataatg tatgcataca | 38940 |
| tacacatata tgtgtataca tgtatataac taaagatata tagttgagat cttgcatttg | 39000 |
| tgttaatgaa tgtagttttt ataaagataa ttgactcata cattaattgt tgactctttg | 39060 |
| gaaaggaaaa aggacaaatg agatacatgc tattggtttt gttatttaga aattgttcgt | 39120 |
| gtggatcctc cctaccattc agccatttgc aaaccattag ttgagcataa cttaatccct | 39180 |
| tctagttcac agcaaagatt catcaaaagc catttggtat actgtcacct catctctcta | 39240 |
| ccagtgttga ttagattaca ggagggttac aggagggcac cttatccaaa ttggccaatg | 39300 |
| ataaattctt ttttggtacc ttactatata tttgtatcct cagaacaaat tctccttcct | 39360 |
| gcttaagctg gcttgacttc atttcttcca ctagcaagct aagaggcttt ggccaacaga | 39420 |
| actactctag gggtagctgt aaaatttatc tctaaggaaa ggctgctctt ttgaaaaacac | 39480 |
| agtttaatgg gtcttctggg tatatgacga tagtaaagca aaattttgtt ctggaatgaa | 39540 |
| gaagctgatt acattgttgt attacaaaca atatattact cagtgaagtg aaaggccaca | 39600 |
| ctgtgggcag ggtggtgact ttgcagatag catgttaatc cttgcatgct ttttgttgtt | 39660 |
| tctcttttg gaggggggagg gtcttaattt tcttttggccc tcccccaccc cctttatttt | 39720 |
| ctctggggaa ggcaagactg gataaggagg cttttatcct gccaagatga gttggcccac | 39780 |
| aggacaattt gactgaatag aggctccaca aagaacggac atggccaaag aattacaaca | 39840 |
| ggaaattatg catttagttt taaggcttcc ttttttctcct tttttttttt tttttttga | 39900 |
| gaccgagtct tgctctgttg cccaggctgg agtgcagtgt tgcgatctca gctcactgca | 39960 |
| acctctgcct cccgggtcca agcgattctc cagcctcagc ctcccgagta gctgggatta | 40020 |
| caggtacctg ccaccacacc tggctaattc gtattttttgg tagagatggg gtttcaccat | 40080 |
| gttggcccgg ctggtcttga actcctggtc tcaagtgatc cacccgcctc agcctcccaa | 40140 |
| agtacaggga ttacaggcat gagccacagg gcctggccag tattttttctt gtataatgct | 40200 |
| cagagtttcc tttaaatctt tttaaaaact tggcagcctt agtcttagct gtgctttggg | 40260 |
| aaaataagga gctgcactca agcttaagaa gatattgctg gaagtgtaca ttggcacagc | 40320 |
| cttcgaagct tcttggtgcc ctcctgtaac ccaatcgaca ctggctagag agatgaggtc | 40380 |
| atattgcatc aaatggcttc cagtgattct ttgctgtgga caagaaagtt gctcttttc | 40440 |
| tttgagaaag ttgctctttt tctttgagag ggagttttga tgcctaggct ggagtgcaat | 40500 |
| ggcagtgatg tcggctcact gcaacctctg cctcccaggt tcaagtgatt ctcctgcctc | 40560 |
| agcctcccga gtagctggga ttacaggaat gtgccaccat gccaggctaa ttttgtattt | 40620 |
| ttagtagaga cagggttttt ccatgttggt caggctggtc tcgaactccc gacctcaggt | 40680 |
| gatccaccca tgtggcctc caaaagtgct gggattacag gcgtgagcca ccacgccag | 40740 |
| ccaagaaggt cactctttat gctcaacaaa tgtattgcaa atggctgaaa ggtagggagg | 40800 |
| atccagatga acaatttcta aataggaaaa ctaatagcca gacacgatgg ctcacacctg | 40860 |
| taatcccagc attttaggag gtcgaggcag gcagatcacc tgatgtcagg catttgagac | 40920 |
| cagcctgggc aacacggaga aacccccatgt ctactaaaaa tacaaaaatt agccaggtgt | 40980 |

```
ggtggcgggc atgtgtagtc ccagctactc aggaggctga ggcaggagaa tcacttaaac   41040
ccgggaggca gaggttgcag tgagctgagc ttgtgccact gtactccagc ctgggcaaca   41100
gagagagact ctgtctcaaa aaaaaaaaaa aaaatcgta gatatccaat ttgttccttt    41160
ctcctttcct aaaagctttt tgtgccccct ccaacccaac agttccaccc tagaaaaaca   41220
cttgtacaca tacatcagga aacgatacaa gaatattcag gctggtcgcg gtggcttgcc   41280
tataatctca gcatttgggg aggccgaggt gggaggacgg cgagagatca tgccactgcg   41340
ctccagcctg ggcaacagag ggagactccg tctcaaaaaa aaaaaaaaa aaaagcataa    41400 tgttgaaaac aaacagcagt ataatacagc atggagataa ctttataaaa tgcaaagaca   41460
aataaaagta aatatagtgc attgtttagg agtataaata tggtaattat gcaaagaaaa   41520
ctaaaatgac ttttaaaaat catgatggtg actatttttg ggaggaaagc aggtagaagg   41580
tgggatctga gagcagcaca cagtaagtgt caattgtcct agttaatgtt cggcttctta   41640
aattgggtga tatgttcaca ggtgttcatt atgttctttt tttttttttt tttttgaga    41700 cggagtctga ctctgttgcc caggctgggg tgcagtggtg cgatctcggc tcactgcaag   41760
ctccacctct tgggttcatg ccattctcct gcctcagctt cccaagtagc tgggactaca   41820
ggtgcccgcc accacacccg ctaattttt tttttttttg tattttagt agagacgggg     41880 tttcaccgtg ttagccagga tggtctcgat ctcctgacct cgtgatccac ctgcctcggc   41940
ctcccaaagt gctgggatta caggcgggag ccgctgcgcc cagcccatta tgttcttata   42000
acttacatta acatattatt ttatatatgt caagcttttt ttcccttttt tttttttaag   42060
agatgagatt ttgctttgtc acccaggcca gagagtgtcg tggtgcagtc atagctcaca   42120
gcagcctcca actcctgggt tcaagtgatt ctcccacctc tgtctgccaa ataattggaa   42180
ctacaggcat gtgccaccat gcctgggtaa gttttttttt ttaattttt atttattatt   42240 atactttaag atttagggta catgtgcaca atgtgcaggt tagttacata tgtatacatg   42300
tgccatgctg gtgcgctgca cccactaact cgtcatctag cattaggtat atctccgaat   42360
gctatccctc ccccctcccc ccaccccaca acagtcccca gagtgtgatg ttcccccttcc   42420 tgtgtccatg tgttctcatt gttcaattcc cacctatgag tgagaatatg cagtgtttgg   42480
ttttttgttc ttgcgatagt ttactgagaa tgatgatttc caatttcatc catgtcccta   42540
caaaggatgt gaactcatca ttttttatgg ctgcatagta ttccatggca tatatgtgcc   42600 acatttctt aatccagtct atcattgttg gacatttggg ttggttccaa gtctttgcta    42660
ttgtgaataa tgccgcaata acatatgtg tgcatgtgtc tttaaaacag catgattttat  42720 agtcctttgg gtatcctggg taagtttttt aaaagtgtta tttgtagaga cggagtctgg   42780
ctgtgttgcc tgggctggtc tcaaactcct ggcttcaagg tatcctcctg cctcagcctc   42840
ccaaagctct ggcattacag gtgtgagcca ctgcacccag actcagactt tttttaaggg  42900
aaagaatggg agtgtaggtg gggagacaca ctttgggagg ccaaggtggg aggatcactt   42960
gggccggggg ttcaagacca gtctgggcaa caaagtgaga cctcgtattt accaaaaata   43020
caaaaaatta gctgggcttg gtggtgtggg tttgggaggc tgaggtgaga ggattgcata   43080
agctgtagga gcccgaggct gcaacgagct gtgatcgcgc cattgcgctc taacttgggc   43140
tagacaatga gatcctgtct caaaccaaaa caaaacaaaa cagataattg tcaaattgct   43200
gttttgctat tgttgctttt tgtttttgct tcgctttgcc ttggaagtga agaagagatt   43260
ctcatttaaa cagttatctt gaagtatctt tgtgaactag ggtgcaatta tttcctctgt   43320
```

```
ccttgagaca cagatgattc ctgtccaaca ttcccaagga actcagtaag gaccaaatag   43380
agactcagga aagacagtta ctgattttac actgttgcaa aacagagcta tggtttatgt   43440
ttaacaaact gctggtgggg cgtggtggct catgtctgta atcccagcac tttgggatgc   43500
caaggtgggt ggatcacttg aggtcaagag ttcgagacca gcctggccaa catggtgaaa   43560
ccctgtctct actaaaaata caaaaattag cagggcatgg tggtgcatgc ctgtaatcct   43620
agctactggg gagggtgagg cacaagaatc gcttgaacct gggaatcgga ggatgcagtg   43680
agccgagatc acgacactgt actccatcct gggtgacgga gcgagactgt ctcaaaaaaa   43740
acacaaaaaa caaaaaaacc aaattgctgt attttatttt gtgaaatagg gtctagctct   43800
gttgtccagg ctggagtgca ggggtgcaat cacagctcac tgcagccttg acctccaggg   43860
ctcaatcgat cctccctcct cagttttcaa gtagctgaga ctacaggtat gcaccaccat   43920
atgctgccca ggctggtctt gaactcctgg agagagatac atacacacac acacacacac   43980
acacacacac acacacacac actttttttt tttttttgag acacagtttc gctcgtcacc   44040
caggctggag tgcaatggca caatcttggc tcattgcaac ctctgcctcc tgggttcaag   44100
ctattatcct gcctcggcct cccaagtagc tgggattagt aaggcactgc caccatgcct   44160
ggctaatttt gtattttag tagagacagg gttttgtcat gttggccagg ctggtctcaa   44220
acttctggcc tcaggtgatc cacttgcctc ggcctcccaa agtgttggga taacaggcat   44280
gagccactgc gccgggccca tacatatgca ttttaaaaaa tttatttatt tatttcgaga   44340
cagggtctca ctctgttgcc caagcaggag tgcagtggtg ctatctccca ggctcaagca   44400
atcctcagcc tcccgagtag ctgggactac aggtgtgtgc catcacaccc agataatttt   44460
tattattttt atttttaaa ttttttgtag agatggagtt tcaccgtgtc acccaggctg   44520 gatattttg tattttgat aggcctgtac agtttccaaa gttgcaacct ttccccctcc   44580
ctgagagtag gggcagcccc ggctctccct ctacatcctc cacagtcccg aggttttggc   44640 ctctgttttcc tctgtttcct atgcttggaa caccagtcgc tcttttgttg gtctggctga   44700
cttctgttcc tcttttaaaa atttaagttt ggccgggtgc ggtggctcac gcttgtaatc   44760
ccagcacttt gggagtccga ggcgggtgga tgacctgagg tcatgagttc aagaccagcc   44820
tggccaacac agtgcaaccc cgtctccact aaaaatacga aaattagccg ggtgtggtgg   44880
catgcgcctg taatcccagc tacttgggag gctgaggcaa gagaattgct tgaactgggg   44940
aggcggaggt tgcagtgagc tgagatcacg ccactgcact ccacctgggc aacagggcaa   45000
gactcggtct caaagaaaaa taataaata aataaataaa taaataaata aataaataaa   45060 gtcaagggg taacacctct tggtaactct cctgttgttt ctcatgccag catcatcaca   45120
gccttgaggc tctggggtag gtcacttcgt cgagctcgtt tccatgagga taacgttatc   45180
ttgggtgtct gtgagaatgc tgcactgagt atagagccca ggctcctggg tcagccgggt   45240
tcgaatcccc tttcctccgt gaagatctgg gtcagtcaca agtgcttcag tttcttcgat   45300
ctgactgagg gaggctttga ctccaaaaaa ttaacacttg agtgtacctg ccacagcttt   45360
agcacatcca gggtgtttcc acccttctt tgggatcctc agggctggat ggagccgatc   45420
cttcccgtct ctccttacac tcgcgcactc acgctggctg gaacaagtcc tccaagtaga   45480
acgaagagcg cgttttagcg gcgctctagc ccgccgagag catacgccct ccccacacgg   45540 ggccctgat tgtctgaagg ttgcgctggc acgcgcaact tccgggacag aggctgtggc   45600
tggaaggagc tgggcatccg gcctgaggcg cagcggtcgc gttagttcgg cccaatggcc   45660
gcaccgctgc ttcacacgtt gtttgtcggg agatgcggcc gcttcgtcct ctgcagtcaa   45720
```

```
gacgctgggc gcgtcgagga ctgggtaaga ttcaggccgc ttccttctgc gcgtctggga      45780
ccaaagctca ggaccgcgct tagaggagcg gattgaaagg atgtgggaca aagctaatgg      45840
cgtgtgatag gagcacgggg tcgagggtca tctcacgttc acagaaatga gctcattcct      45900
cctaactggg taatagacat gggtgggggcc tggaaaagtg agtatgttct ctgttctgga     45960
ggcccacttt cccgactgtg tctcttcgtg atttcccagg cctgggtact gccttctgcg      46020
ccttgacccc tcttccttcc ctcttcttcg tccaaatttg gaagggattt ccctgggcta      46080
tgtgggttat cagccgaacg ttgtcactca tggcaaattg aatattacat ctttttttgtt     46140 tgaaatttgt ttcgacacac gtatttgttt cgcagtcttt attttgctcc acttttaaaa      46200
tccctaaccc ccatagcact cttggcgttt aactttcaga gtcattagga tgctatgttt      46260
tttcattaat ttactacgtg taagtgaagc aaaccttgta aaacaattag cgtaatatga      46320
ttcctaatat ttatcgagct cctgcttact gtgttaaaca ctggggacag tggtttatcc      46380
aaagacacta atgtccctgc tttctacaga gcttacagca tagggtggga aggcagtaca      46440
caggccaata ataaacgaa cacgatgatt tcagttatac aacaaggtaa tgggggaggg       46500
agaagggaga gaaggagtgt tcgagatttc tcattgggaa gacatctgtc atttcagctt      46560
ctacttgaat gaagacaaaa atctaggccg ggcgcggttg ctcacgcctg taatcccagc      46620
actttgggag gccgaggtgg gcggatcacc tgaagtcagg agttcgagac cagcctggcc      46680
aacatgcgaa acctcgtctc tactgaaaat acaaaaatta gccaggcgtg gtggcagggt      46740
gcctgtaatc ccagctactc aggaggctga ggcaggagaa ttgcttgaac ccggagatgg      46800
aggttgcagt taagctgaga tcacaccact gcactccagc ctgggcagca gagcaagact      46860
ccatctcaaa aaaaaaaaa aatccagcca cgtagagatt tgggaaaaga gtatttccaa       46920
tagagtgaac agtaagtgaa atgagaaaca gcttggcttg tttgaagagc agaaaagaca      46980
tgatggctgt agtaaaacaa gttgttggag atgaggtgag agaggtaggc gggggccaga      47040
ttaatgtagg atttttaaaga ccacactgag agatttggat tgttactgta agtgcagtgg     47100
gaagacagtt attggttgct gagcaaagga gggattgttg gttaagagtg aagcaggga      47160 gaccagtaaa gaggccttaa caatagtccc actgaattat gttggttcaa taaaggttgg      47220
ctattataat ttttattatt ttcatgaact taatagcttg ttaatcttgg ttccacagga      47280
tttcaaatat gcgtgcatta gagaatgatt ttttcaattc tcccccaaga aaaactgttc      47340
ggtttggtgg aactgtgaca gaagtcttgc tgaagtacaa aaaggtaaga ggagataatg      47400
tgtgaggttt gcttttggtc aggtcagaat acaactattg ctgttatact aaagaccaat      47460
agaaatagca agattaatta agataccagt tgaaatcaaa tatttaataa tagcatgatg      47520
ccgtcagtgc aaaattagag taatagtgtc ctttttttcc cccaccttgg cccatttcac      47580
aggtaataat gagagagtaa taatgtcttt actgaggttt cacctcttca aatgctttat      47640
ttacaaagca tcttttaact ttagcaagtg ctagaattaa aaacaattac agcatttat      47700 ttatttattt atttgtgctg gagtcttcct ctgtcaccca ggctggagtg cagtggcgtg      47760
acctcagctc actgcatcct ccacctccca ggttcaagca attctcctgc ctcagtcttc      47820
tgaatagctg gggttacagg cacgcaccac cacacctggc taatttttta atttttttaa      47880
tagagacggg gtttcaccat gttggcctgg ctggtctcaa actcctgagc ttgtgatcca      47940
cccgccttgg cctcccaaag tgctgggatt acagatgtga gccaccatgc ctggcctaca      48000 gcatttatt ttttgaggaa cttacctaag cattactttg ggacagtaaa ccggttctct       48060
```

```
gaatagggat ttttgttttt gtggtagttt agaagcattt ctactatatc tcagcagtag    48120
agggaaaatg ttaagtaacc gtatgtttat atgaaatatc catttgtatc catatttgag    48180
tgaatacttt tttagatcct cctgaattag atcattagag ctggctgttt tttcccctca    48240 tgcttttttga gaattcgcag gagtatcaac tattatattc aaatgtcaat acagaagtat    48300
agctaaatgt agtttatcat tttccttttt ccaagccctc tggctgcact aacatgagtg    48360
tttaaatttt tgtagtcatg attttataat ccgcaattga catgtgaaag ttagtgttcc    48420
ttttataatt tcatctgatg ttaaagtacg gttaaaagtc ttgctgttga tactaaacag    48480
gaaacaaaag cataacttaa ttcttttcccc ttcttgttaa gggtgaaaca aatgactttg    48540
agttgttgaa gaaccagctg ttagatccag acataaaggt aattaatttt gtgtttgatc    48600
attagcaaaa ttattgccac tttatacaga catagtttgc tctttgggtc ccattctgtt    48660
ctgcagaact tgctctctcc atggtcctcc cttactttaa tctggtggtt ctcaaccagg    48720
gacagtttta cccctagaa gacatttggt gatggctgca gatattttg tcacaactgg    48780 gaggaaaggg tgctactggc atctagtggg tgaatgacag agatgctgct aaacatctca    48840
cagtgcacag ggcagcctcc cataaccaag agtgatccag ccccaaatga caacagtgtt    48900
gaggctggga aaccctgctc taatgcttcc tttctattag attactacct ctttcctcca    48960
tgctgcatgc aactctttg tctctttaaa gctaaaacaa accaaaaaaa aaaaacaaac    49020
cactgtttca gcatttccag gttcgagata cacctatcat gtagtaaaac cttaatacat    49080
tttgtttcac cattcttcct ttactgccca gttttgaaga gaatggttta ttaccatggc    49140
agtggtagtt agattgcctg gaatgaaatt ccaattttat tatccagtgt gtgatcttga    49200
gcaaattgtt ttaacctctc tgcctctatt ttccactgtg tgaaaccaag aaaacaatag    49260
agatttaaaa aatatggagt gttttgtttt ttaagagatg tggtcttgct gtgttgctct    49320
agctattcac aggtgtgatc atagtgcact acagccttga actcctggcc tcaaatgatc    49380 cttttctcttc agccttctaa aaagctggga ctataggtgc atgccactgt gcctggcttt    49440
aaacatggaa atacttaaca aggattcaat gagctaatat gcaagaagca cttagaacag    49500
tctctgactc aaagtaaggg cagtaattgt catctgttgt ttttgttcca gctgactgtg    49560
ctgtatcatt tctcactcac atttaagtcc actgttctta tcactgtagt aattaccctg    49620
acagattacc catgtttttt ttttacatgc tgatttcagt ggacttttttt tgagacaaag    49680 tctccttctt gtcacccagg ctggagtgca gtggtgtgat atgggctccc tgcaaccttt    49740
gcctcctggg ttcaagcaat tctcctgcct cagcctccca aatagctgag attacaggca    49800
cccgccacca tgcctggtta atttttttat ttttagtaga acggggttt caccatgttg    49860 gccaggctgg tcttgaactc ctgacctcag gtgacctgcc tgcctcggcc tcccaaagtg    49920
ctgggattac aagtgtgagc cactgagccc agcctcagtg gacttacttt tttaagcctt    49980
gtattccttg tatcagccga cactgttggc cacccacttc ttaaaacttc agtgtttctg    50040
atcctcctgt cttctgatcc tttaatctct ctcttttttt tttttttttt tttttgctc    50100 tgtcgcccag gctggagtgc aatgacgcaa tcttggctca ctgcaagctc cacctcccga    50160
gttcaagtga ttctcctacc tcagcctccc gagtagctgg gactacacgc gcccgccacc    50220 accccagct aattttttgt attttagta gagatggggt ttcaccatgt tagccaggat    50280
ggtatcgatc ttctgacctc gtgatccacc cgccttggac tcccaaagtg ctaggattag    50340
aggtgtgagc caccacaccc ggccagtgat cctttaagct ctagtatctc tcgataggtt    50400
cttgatctta aatttggtgt tgattgggct tcaaaacttg actcttttct cactctgttg    50460
```

```
attcttctgt gtgatctcct catctcccctt catggctttg aaatctacct gtgtcctaat    50520
atatttgtgt ctgtagccaa gattgctctt gtgggctcca gacttatttc attttcattt    50580
ttggggatgg gcagaacaga gtcttgctct gtcacctagg ctgtagtgta gtgggatgat    50640
cttggctcac tgcaacctct gcctcctggg ttcaagccat cctcccacct cagcctcctg    50700
agtagctgtg ccaccacgcc cagctaattt ttttgtattt tcagtagatt tggggtttca    50760
ccatgctggc caggctggtc tcgaactcct gacctcaagt gatccacccg cctcagcctc    50820
ccaaagtgct gggattatag acgtgagcca ctgcacccgg cctagacttg tttcttaact    50880
gtctgttaga tgcatttacc cagaatcatc atagatgctc caaacttatc atgtccactc    50940
ttggctgggc tccatctttc atggagcttt ccctggttct ctctaagcac atggttgttc    51000
cttcattgag tctatttccc acacttccag atctctctag ttacagatct ggtttacaag    51060
gccctccatg gtctatttgg tgcttctttg ttccccagat ttattatctg ttggcttggt    51120
cactatacat gccagccata ctgaacattt ttcagttttc tgaaaacata cttttccttc    51180
tgtaagaagc agaacttcca gaaaagactc aactgtgtta ctgtttaaag acagctgaag    51240
catcactttc tctttaaagc ttttcctgac ccctgcctcc tttcccagat acaaagggac    51300
attttctttg tgttccactg tattttgtat cagcagttct cattcttggt attttgacat    51360
accaagaatt gcactagttg tgtggagtgt tgcaagtaga acttttttcg tcttgagaca    51420
gggtctcgct gtgtcaccca ggctggagtg taatgggccc gatcatggct cactgcagcc    51480
tcaacctccc aggctcaagc aatcttccca cctcaggctc ccgagcacct gggaccacaa    51540
gcatgtgcta ccatgcctgg ctaattttc tagagacgag gtctccctat gttgcccagg    51600
ctggtctcaa attcctgggc tcaagcagtt tcctcctgcc ttggcctccg aaaagtgctg    51660
ggattacagg catgagccac tgttcctgcc tgctagtaga aataataata gttcagtact    51720
aaagcatcaa agtctgcaac tgatttactt tttttttttt cttttgaga catagttttg    51780 ctcttgttgc ccaggctgga gtgcagtggc atgatcttgg ctcactgcaa cctctgcctc    51840
cgagtttttt aagtaattct cctgcctcag cctcccgagt agctgggatt atgggcatgc    51900
accaccacgc ccagctaatt ttgtattttt agtagagacg gggtttctcc atgttggtta    51960
ggctcgtctc gaactcccaa cctcaggtga tccacccacc tcggcctccc aaagtgttgg    52020
gattacaggt gtgagccacc acccccagcc tgatttactt ttaaaaatgg tacagtttaa    52080
atgttatcct tatagttttg ttgcagtctt tttagtggaa agagatagg atagattatt    52140 ttatttacac actaacttag cttgtttct acatgccttt ggccttagtg agctaccgtt    52200
aatgttatcc ttaacagttt tggacatatg aaattaccat agtacaaatg agttgtggtt    52260
ttactttatt ttactgccag gctacttggg atttcatcag aaaatggttg atctgtggga    52320
gtttgacaca tggatatggc atagtaagca ctcagtagct gaattaaggt ggggaaaagg    52380
ggacagcttc ttctccgcat atagggaggc atgtgggatg gtggacagag gatagccttg    52440
accgagacag atgggtttgg acctgcttct ttactggcct cttggttggg cagattgctt    52500
attaatcgtt cttagcctca gcttcctgaa cagcaaaatg gaataacta aacatcttgc    52560 agagttctta ggattagaag aagatatata tgcggagtgt caggcaccat gcctggcata    52620
tggtgtattc tcactaaatg ataactccat atgaatatcc ctgtaggtat gatgaccttg    52680
tgttgctttt atttatatgt ctaagccttc cacaaattag gggcttttc ttaatggttt    52740 ttgtcctgtg cagtatatat gcatgaatat aattaatata gtaatatttt acataattga    52800
```

| | |
|---|---|
| cactgtattt tataccttgc gtttcaaatt tagcagttct tctcatgtca ctaacaatta | 52860 |
| ctatgaacag taatttgatt gcctgaaaaa tatttcatgg aggaatgggg ctatcattta | 52920 |
| tacagaacaa acacatcata atatatttaa actcagccac agatttggtt tagaaaagtt | 52980 |
| atgtttattc atgaccccaa ttgatcagcc tagactgaat tttatcagca tgcttcctgg | 53040 |
| tcagcttgaa tatagaggaa atagaggtag ctattgttcc tttgtgatct tctaatattt | 53100 |
| caatctgcta gaattctgca gttttttaaaa gtcccaggtg tcaacatttg aggtgatttc | 53160 |
| acttttcag ggcaaacaaa agtgatcagg ctgaagtatt gcatttaagt ctttctcctg | 53220 |
| tgtattagag ttactagatt actttcttaa aacgattaag tttattgtga catctttttc | 53280 |
| tgttttaata cccagttttg atttccttcc aagtttgtga ccttttcccc ccaacctatt | 53340 |
| cttgataaat gattgatata agatagctgt aaatttctgt tatcttagag gatttgtgat | 53400 |
| tttgaaagta ctctttgttt aacttaagga tgaccagatc atcaactggc tgctagaatt | 53460 |
| ccgttcttct gtcatgtact tgacaaaaga ctttgagcaa cttatcagta ttatattggt | 53520 |
| aagttcacca tttatttac tgtcaagtat gtaattcaga actttggtaa tagtatatgt | 53580 |
| tatattaata acatgctgct tttatctttc ttccccact ctagagattg ccttggttga | 53640 |
| atagaagtca aacagtagtg gaagagtatt tggcttttct tggtaatctt gtatcagcat | 53700 |
| agactgtttt cctcagaccg tgtctcagca tgattgcttc ccatttgtg cctcgtaagt | 53760 |
| cattactctt tgcttgcttg gaattttctt ttcttttctt tttaatactt ctttgttaaa | 53820 |
| ataccacctt cccttatat atgagagact gctaccatgg aagattccag atgcatattg | 53880 |
| gcaccaggtc tggtagacat atattccccg taatgacccc tatggaggtg tctagattca | 53940 |
| tttgttgctg tgagtttgat gaattataac ttgctttatt gaactcctgg tgaaatctag | 54000 |
| gaattttag ccatttaaaa actataaagt tgcattactt tttttcagat tgtgcattta | 54060 |
| attaatcatt gggctaactt tggattatgg aaaaataact ttttttatag ctgttcattg | 54120 |
| tctaggtcaa taactttttt tgtatagcca ttcattgtct agatcaatga cagaacaaca | 54180 |
| tattttcttt ttccctcaaa agcccgagtg atcattaagg aaggcgatgt agatgtttca | 54240 |
| gattctgatg atgaagatga tagtaagtat aaaaaggttt aaagcctggg cacagtagct | 54300 |
| tacacccata atcccagcat tttgggaggc caagatggga ggatcacttg aggccaagag | 54360 |
| tttgagacca gcctgggcaa catagtgaga ccttgtctct gcaaaaaaac attttttttc | 54420 |
| aaatatttc ttaaaaaagg cttaaagtag aactaggcag ggtagtgtgt gtctttagtc | 54480 |
| acagctacct gggaggctta agtgggtgga ttgcttgagc ccaggagttc aagctctgcc | 54540 |
| tggtggcaag actctgtctt ctttaaaaaa aaaaaagtaa agcacagaat acctggcatc | 54600 |
| tattctaata agtagactgc aacaaatgac aacttttgat gtaatctttt tgttatattt | 54660 |
| accattgata tgcagtcagt tgtcctgaat gcattattta tataattagt ccatttaatt | 54720 |
| ttcattgatg ctggtggaga aaagtcttga aattattatt tctctgataa attattccgt | 54780 |
| tttggttagc atgtgttttt agcttcaagt atgtcacttt ttgtttgttt gtttgttttt | 54840 |
| tgagacagag tctcgctctg ttgcccaggc tggagtacag tggtgtgatc ttggttcgct | 54900 |
| gcagccttca cctcctaggt tcaagtgatt ctcctgcttc agcctcctga gtagatggga | 54960 |
| ctacaggcgt ttgccaccat gcccggctaa ttttttgtatt tttagtagag atggggtttc | 55020 |
| accatattgg tcaggctggt ctcgaactcc tgacctcagg tgatccaccc acctcggcct | 55080 |
| cccagagtgc tgggattaca ggcgtgagcc actgtgcccg gccagcattt attttttagtt | 55140 |
| tcaagcatgt cgcccttcag ttttgttttg atgctcatac tctgaacttt tcttctttca | 55200 |

```
gatcttcctg caaatttttga cacatatcac agagccttgc aaataatagc aagatatgta  55260
ccatcatgag tatactttc cttattttga atgtttaatt ctcaagaaaa ttgtaatcaa   55320
ttagtaaaaa ttataaaatg ttaatagtat taaagcttga gtcttacatt gcatttttt   55380 tttttgtatc cacttgagga aacattacat tctacaaaaa gtggcatttc cattttctat  55440
ttattctctt taattgtttt tcaaagttcg tatgcagatt ctcccccaat tttgtatggt  55500
ggttggaatt ttgtttttat cttcaacaga tatgctatcc aaaattttc agtgagaaac   55560 ccctgggtgt gtttgtgtca tgccatatga ataaaaattg cacttctaag aaaagctttt  55620
caggtttgtg ggtttctttt ggaggggtgg atttctagtt ccctctgtct gttgattatt  55680
tgttaactta aaaaaatcca acttgattat tttttcttct tttaaaaata atatacatgt  55740
gtagtgggaa atgtcagcaa aagtgctgtt atgtttctgt gggagagaag ctccctcttt  55800
gatttgctgt tgatatcaga gttaacagaa gcttatttc tctaagttgt tatagacttt   55860
ctcagaagct atacattgta agttccagtt ctggccgggc gcggtggctc acacctgtaa  55920
tcccagcact ttgggaggct gaggcgggcg gatcacctga ggtcgggagt tcgagactag  55980
cctgaccaac atggagaaac cccgtctcta ctaaaaatac aaaattaggt gggcgtggtg  56040
gcgcatgcct gtaatcccag ctgtttgggg ggctgaggca ggagaatcgc ttgaacccgg  56100
gaggcagagg ttacagtgag ccgagattgt accactgcac tccagcctgg caacaagag   56160 cgaaactccg tctcaaaaaa caaaaaaagt tccagttctt tgaggtaagg gttcctgttt  56220
gcctcctatg tctatcgata tttgctttta gaatggtagt tttccttttt attccttttc   56280
tagaaagtaa agtcaacatg gattgattta attttttaaa aatagggcac cgtggtttct  56340
catgccaata ctggtggaaa aatttccatt tgttcgaaaa tcagagagaa cactggtaag  56400
aaatcttttc attgagaaca tcatggaaaa gttgtttgta tgatttcatt ttagatgata  56460
ttaggtcttt ttcttttcttt ttctgtcttt attttttattt ttcttttttg agaccgagtc  56520
tcactctatc gcccaagctg gagtgcaatg gcgtcatctt ggctcactgc aacctctgcc  56580
tctcgggttc aagcaattct cctgcctcag cctccccatt agctgggact gcaggcacct  56640
accaccatgc ccagctaatt tttgtatttt tagtagagac aaggtttcac catattggcc  56700
acactgttat cgaacgcctg accttgtgat ctgcctgcct cggcctccca agtgctggg   56760 attggtgaac caccgtgccc ggctgatgtt aggtcttttt cttaaaggtt actttgtctt   56820 ctagactta aactgatgtc taagaatttg actcagattc ctttcttata aagcggctat    56880
tggggattcg cagtgccttt ttctgttatt actatgtgca agtcaaggtc tgagttcatt  56940
tccggaatat ctgtagtggc tttatgctca tacgggcaag aattactaga agataatagt  57000
tcatgtatta ctaattgtga acatgcctta ttttaacctg aaaacaaagc cttccataga  57060
agaattctgc ttaagttttt gtacaatgtt cagatcatct gtgcagtttt taataattaa  57120
tagtggttgc cttagtagaa aaccgaatct agtagcatac aaaaagaatt acgtaccatg  57180
accaagtgcg actgatgtta ggaatgcaag attgattttt tttttcgggg gtgggggggac  57240 agtctctgtc tgtcacccag gctggagtgc agtggcacca tctcagctca ctgcagcctc  57300
tgcctccagg gttcaagtga ctctcccacc tcagcttccc aagtaggtgg gactatagac  57360
atggggcacc acaccccact aatttttgtg ttttttggtag agatgggggtt ttgccatgtt  57420 ggccagactg gtcttgaact cctgacctca agcgatctac ccgtctccac ctcgcaaagt  57480
gttgggatta gaggcgtgaa ccaccgtgac cggctgagat tgagttagta cctgaaaatg  57540
```

```
aattaataaa atattttgta gcaatagaac aaaggacaaa aaccacataa tcatctcagt    57600
agatgcagaa gtgtgtgaca acaccaata tccctttatg agaaaaacag aaggaaattt    57660
tctcaacctg ataaagggca tctgaaaaac ccacagctaa catcatattc agtggtgaaa    57720
gaccaaaagt ttttcctaa gacaaagaac aaaacaagga tttccgctct tgctgcttgt    57780
ctagccaagg cagttaggca agaaaaagaa ttaaaagcat ccagatggaa aggaaggcgt    57840
aaactctctt tgcatggtg atttatatg tcattctaag aagttacac acacacaaga    57900 aattttagag ataataaatg agttcagcat ggttacggga cagaagacta acatacacta    57960
accagttgtt caagacaatt gaatagggga gaatagtcat ttcaacaaat gctgctggca    58020
gaagtggata tgaacatgca aaagagtgaa gcatatggat atccatatac aaaaatgaac    58080
tcaataaaag ccctacatga agtgtaaaaa ctgtaaaact ctgagaagaa aacgagtaca    58140
ttttcataat gttggattag gcagtaattt ccagatttga tgcctaagca caagcaacca    58200
aagaaaaaat gcatcaattg tacttcaaaa ttaaacgttg ttatgcttca taggacatct    58260
tcaagaagat gaaaagaatc cccaaataat gggaggaaat atttctaaat tttatgtctg    58320
gtaatggact tgtatatgta aagaactctt ataattgaat aataaagggg caaatagccc    58380
aactgaagag ggcaaaggat ctgaataggc atttctgcaa aacacatgaa aagaagctca    58440
acatcattag ccatcaggga aatgatttca cttaatgccc acaaggatgg ctataatcag    58500
aacgagaaga cagtaacaag tgttcacaag gatatgagaa aatgggaacg ttggaactgt    58560
catatgttgc tgtgagaatg taaaatggtg cagccgtttt ggaaaatagc ctggcatttc    58620
ttcaaggtta aatgtagaat taacacgtga ctcagcagtt ccatttctgg gtttataccc    58680
aagagaaatg aaaatatatg tccacagaaa aacttgtaca tggatgttca tagcagcagc    58740
atccataata gcctcaagta gaagcaactc aaatgtctgt caactgatga acagatgaca    58800
aaacatggta caatggaata ttactcagca atgaaaagga atgctttata tgttacaaca    58860
tgattggacc ctaaaaacat gccaaaaggc tgtgtattat atgactccat tgataggaaa    58920
ggaatggttt acatgttaca acatgattga accttaaaaa catgccacaa actgtgtatg    58980
actccattga tatgagagga atggtttaca tgttacaaca tgattgaacc ctaaaaacat    59040
gtattatatg actccatttta tatgaaatgt ctcaaagagg cagattcata gaaagactag    59100
tggttgccaa ggtcttcatt ttttaggggt gcactaatgg atgtaggatt tcttttaga    59160 gtgattaaaa tgttacaaaa ttgctggctg ggtgcagtgg cttatgccca taatcacagc    59220
acttcgggag gctgaagtgg gaagatccag gagttgaaga ccagcctggg caacatagtg    59280
agaaaatgtc tccctaaaag gaagaattaa cctcatgtgg tggtgtgcac ctgtagttct    59340
agctactagg gaggctgagg aggaaggatt gcttatcccg ggaattcaag gttgcagtga    59400
gctatgattg cacccactgt acctcatcct gagagagaga gcaagaccct gtctctaaaa    59460
gaaaaataaa tgttctgaaa ttgattatgt tgacggtcac ataactgaat atattaaaaa    59520
cttaaattgt atactttaag ttggtgattg tatgatatat gagttttatc aatacagcta    59580
cttaaaaacc tatagttatg caaattaaaa atttcattta ctgggataa ttgaaatgat    59640 tataccgaac ataatacatg tagaaacagt atagttttg tattgctgga tagtctgttt    59700
ttttcttttt caatatttga aactaaaggt catgtaattg atgttttct tacataactg    59760 tgaaatattt attctctgtt gaaatgtttt atcttacgtt ttctccttta ggaatgttac    59820
gttcataact tactaaggat tagtgtatat tttccaacct tgaggcatga aattctggag    59880
cttattattg aaaaactact caagctggat gtaagtattg agtaatctat tttattttc    59940
```

```
ttttttttat ttttttatttt tttattttca tttactgact tgaatttgtt ataatcacag    60000
tatgtggaaa caatagtcag tgatagaaaa gaatccactt ggccaggcat ggtggctcat    60060
gcctttattc ccagcacttt gggaggccga ggcaggcaga tcacctgagg tcaggagttc    60120
aagaccagcc tggccaacat ggcgaaaccc cgtctctata aaaaaaaaaa aaaaaaatta    60180
gccaggcatg atggtgggtg cctgtaatcc cagctactca ggaggctgag gtgggagaat    60240
tgcttgaatc cggaggcag atcttgcagt gagctgagat cgtgccactg cactccagcc    60300
tgggcgacag agcgagactc catctcaaaa aaaaaaaag aaaagaaaag aaaagaaacc    60360
actagcacca ttctttgctt cctttctttg aatgtgtctt gaactccatc tgtgcatgtg    60420
ctgggagttg tagacagttc cttctcatga ttggagaaca aggcgttaaa tacatagtta    60480
tccaaatgta aaagtatggt tgtggaaaat gccatgaatg aaacatacat tatgagttag    60540
agaacctgat agaatcacag tggggtcagg aagggattcc tacggaagtg attttttcctg   60600 tttggccttt cttaagggca gattataatt ataaacagtt aaaactttgt ttaaggaggc    60660
ccgcactaag gtgcagtggg aatgaaagga agtggtagat tctagtgaca ttgtgaggaa    60720
aggtgaactg gtccttgaga ctggtttgga ggaggggagg cagacagtaa gggaaaggaa    60780
tccttcaata gttgctccct gtggaatcga atcttggtgt tgccattaat ggtagttaga    60840
aatatgaaga ggaggctggg tgtggtggct cacgcatgta atcccagcac tttgggaggc    60900
cgaggcgggc ggatcacgag gtcaggagat cgagaccatc ctggctaaca tggtgaaact    60960
ctgtctcact aaaaatataa aaaattggcc gggtatggtg gtgggcacct atagtcccag    61020
ctactcggga ggctgaggca ggagaatggt gtgaacctgg gaggtggagc ttgcagtgag    61080
cccagattgt gccactctgc tccagcctgg gtgacagagc aagactctgt ctcaaaaaaa    61140
aagaaaaaaa aaatatgaag aggaggcagt tggaagagta gttccatctt ggccaggttc    61200
agttgctggt gggcagccta ccagagaata ctcacaggca gtcgtggctg cagatgggga    61260
cctgagcata aacctttgga aagatgcagt ttaggacagg ggaggagaag ggtgatcaga    61320
agtatgggga aaaccaagag tctggatgct caggaagaat ccgctggaag gaggagtttg    61380
gtcagcagca tcagatactg ctgtcatttt ttagaaagat gaaaagagca acagtccttg    61440
gatttagtgg ttagaaggta gtcttttgttg cttctggag gaccatgtca gtgaagacgc    61500
agaaactgca tttcgggaga ggatgtggat ggtggggaag cagaattggg gctgttagag    61560
accttggtgc agggttgtgg tggaaggagg ggatggagca gggctaagag gcgtggttta    61620
ggagtgggga gatgtgagca ggtttgtgga ctgagggag aggagctttg gtggaggaaa    61680
acattgatgc tataggaaag caggaagatg gaacaaggtc ttagaagagc tggagcttgg    61740
gctcactggt gcagtgctcc cttggagttg cacctctctg gccaactgta tatgtactct    61800
ttatagtctt tctctggtat atacttaagg aacattttag aatgtttaca agaaggtca     61860 ggcatagtta ataaaaaatg gcatggtttg agtggtatgt taagatattt gaatggtgat    61920
ataccaaaat aaatattgca tcatgcacat ttggcttgca gttcatcatt tttctgctca    61980
attgattgac gatatgttta ttacacaatg tgtctgtgag tgtcttgtgc atagagattg    62040
tattagtcca ttttcacact gctgataaag acatagctga gcctgggaag aaaaagagat    62100 gttttttgttt gtttgtttga gatggtgtct cgctctgttg cccaggctgg agtgcagtgg    62160
tgcgatctcg gctcactgca acctccacct cccgggttca agcagttctc ctgcctcagc    62220
ctcctgatta gctgggatta caggcacgtg ccaccatgcc cggctaattt tttgtatttt    62280
```

| | |
|---|---|
| tagtagagat ggggtttcac tgtgttagcc aggatggtct caatctcctg acctcatgat | 62340 |
| ccatccacct cggcctccca aagtgctggg attacaggcg tgagccactg cacctggcca | 62400 |
| aaaaagaggt ttaattggac ttacagttcc acatggctgg ggagccctca gaatcatggc | 62460 |
| gggaggtgaa aggcacttct tacatggtgg cggcaagaga aaatgaggaa gatgtaaaag | 62520 |
| tggaaacccc tgataaaacc atcagatctc gtgagactta ttcactatca tgagaacagt | 62580 |
| atggggaaa cctaccctat gattcaaatt atctcccacc agtcccccccc ccaacaacat | 62640 |
| gtgggactta caggagtaca attcaagatg agatttgggg ccaggcgtgg tggctcatgc | 62700 |
| ctgtaattcc agcactttgg gaagctgagg ccggtggatc acctgaggtc aggagttcga | 62760 |
| gaccagcctg actaacatgg agtaaccccca tctctactaa aaatacaaaa ttagctgggc | 62820 |
| acagtggcac atgcctgtaa tcccagctac tcaggaggct gaggcaggag aatctcttga | 62880 |
| acctgggggg cggagtttgc ggtgagccaa gatcttgcca ttgtattcca gcctgggcaa | 62940 |
| caagagcaaa actctgcctc aaaaaaaaaa aaaaaaaaa gtgagatttg ggtggggaca | 63000 |
| cagagccaga ccatatcaga gctagaataa atgttgaatt tgttgaggct acctgacata | 63060 |
| gagcatcatg tgatagttgt cgattttata taagtatgta gtaaaagggg cttggttttat | 63120 |
| tatatttaaa ttccttcatg acctaggtca gtttacaggc ttgcaccata attgtgtatt | 63180 |
| gtgttggggt gtgatataag gcactaatct ggacaccttg aacgtgtgta tatcagatga | 63240 |
| atttccatcc caaataaca tagttgtatt tttttaaatcc ttttattctt ttttccccccc | 63300 |
| cctttgttat aggtgaatgc atcccggcag ggtattgaag atgctgaaga aacagcaaat | 63360 |
| caaacttgtg gtgggacaga ttccacggaa ggattgttta atatggttag cagtttatta | 63420 |
| atgaaagtgg agatgaagtt tatcataatc aaagggtgga aacagctagt gctgctcatc | 63480 |
| tttgttaagg ctttagattg aaagaattaa aatagtttag caaacttgaa aacgattcct | 63540 |
| tatatgagta atttgctgcc atgtcattta gcacttagca taattggtct atttccaagg | 63600 |
| ctttgaattt gggtttggtg aagtatgttt cacttttgtt gttgtaactt tcagtgtttg | 63660 |
| tttttgtaag ccagatgctg tctgtgaggg cgtggctaat ggaaaagcat aactgtttaa | 63720 |
| tttctgcatt ttaccacttg tacactttat agcattactt cttacgagta gctgggacca | 63780 |
| cagattacca tgcctggcta atttttgtgt ttttagaaga ggcgggggttt caccatgttg | 63840 |
| gccagactgg ttgtgaactc ctgaccgcaa gtgatctgcc cgcctcctgc cccgcaaagc | 63900 |
| gttgggatta caggtgtgaa caactgtgcc tggcccacgt tcccttctca gtacacttgg | 63960 |
| agagaaaaca gattgctgcc tgccagccca gctaggtgct ctgaaaatgt catcctgcct | 64020 |
| ttggtcacta ggtggtggtc ttcccttaag cctttctcta ttaaaatctc atatggggta | 64080 |
| attaacagta tttcctttat tctttccaag ggttgagttg taactagccc aaaccaactt | 64140 |
| attaatctag aattttaaaa actttaggct ttgacttttc ttcttcttct tcttttttt | 64200 |
| tttggtgggg gaaagaatat agaaggcttt tccttctctg caacgatttt gtggcttcct | 64260 |
| agaggtcagg agagtgttgg tcatgggaaa gaaggttgaa ttcagtctgc ccacatgggc | 64320 |
| gtgcctagct ttagaacagc gctatttagg agaagttgga agttacaccc tttggtgaga | 64380 |
| agctgtgtct gtttttttcc atgattggca taattaactc aaataccagc tgtacattag | 64440 |
| tccgtatttc tgttcatggt tgagttcagt gtgtccagag accggaaggt gctttgcact | 64500 |
| cacaggagtg cccatgtgga gctccatggg atgtgaatta ttgttggtca ctagttctgg | 64560 |
| ctgacattgg aatcacttga agagtttta taatatgtgg attccaaagc cctgtcacaa | 64620 |
| acctattgaa tttgtaccctc ccaggttgaa tttttttgttg tttttttgttt gtttgttttt | 64680 |

```
tgagatggag tctcactctg tcacccaggc tggagtgtag tggcatgatc tcagctcact   64740
gcaacctctg cctcctgggt tcaagtgatt ctcctgcctc aacctcccaa gtagctggga   64800
ttacaggcac ctgccaccac gcctggctaa ttttttgtatt tttagtagag agagggtttc   64860
tccatgttgg ccagtctggt ctcgagctcc tgaccttggg tgatccaccc gcctcggcct   64920
cccaaagtgc tgggattaca tttacaggcg tgagccactg tgcctggccc tgggttgatt   64980
ttgatgctta gctaggtttg ggatccattg gattatttaa cacccgaggt gccttttgtt   65040
tctaatgata ttctctcaac gtgttttaaa aatgaagccc atgagatagt tatgagatag   65100
tagaactttt ccctacattg gtgaagtaaa aatcttggga ttttgatagt cagattatct   65160
taggcattaa aaaatatcac accgatgccc tctcttttta tagggattcg cagaggcatt   65220
tttggaacat ctttggaaaa acttgcagga tccaagtaat cctgccatca tcaggcaggc   65280
tgctggaaat tatattggaa gcttttggc aagagctaaa tttatttctc ttatgtaagt    65340
agcctaattt gccgagtact ttttaatatc atgcttaaa aagagtatag cattgtctca    65400
agtcagaaat atctcccata tgttttggc atgttttaa agtgaataaa attcctactc     65460
tgtgcaagat gtttatattt ctaagtggtg attttagaat aaagtgtctc cttttttata   65520 tataaaccc tgtatgtaag gcttttgtca tctcttttgt gtggttgcac ttaaagatcc     65580
atttgttttg tggatagagg acagtgttgt atactgtttt gattcttttt gtaggtttgt   65640
catttttttc atttgcattc caaatctatt gtatctgtta aagctgaaga aaaacccttt   65700
taaaggtaat agacctatct aggaggccag tttctttcag tggcccatga agatatcttt   65760
ggacaaggat gctgttgaaa cccttcccca agaacaaaat tattcaccca taggacttga   65820
ctggatgcat cagggaatac tgaagtccac cagactgtct ttctcttgag acgtgttggt   65880
gaacatgtcc tatttggcca atcaccctaa gagggggtgcc tttgagatgg ttaggagaac   65940
ctgctttcca tcccttggga cgttcttagg ggctcacctg ttcctagaag gtcagagcta   66000
ctctgccttg taattggaag gttgtcttcc tacgcaccca tccttatcct tccttctttt   66060
gcttttcctc tgtacccatg ggtattattt aaagaaacct atgaacttac ttagcatggt   66120
ttgtaatgaa aggcagttgt gtgttttttat gttattctgg tttttttatg aagtgtaaag   66180
ttgacttgaa ttttctttt ctctagtact gtaaaaccat gcctagatct tttggttaac    66240
tggctgcaca tataccttaa taaccaggat tcgggaacaa aggcattctg cgatgttgct    66300
ctccatggac cattttactc agcctgccaa gctgtgttct acacctttgt ttttagacac    66360
aagcagcttt tgagcggaaa cctgaaagaa ggtcagtgtt gtgggagtgc tggactggat    66420
tttccttgtg ttcttgtcac ccttcagaat ggtgattcat tactttttg agatttttat    66480 aaaaactgga ttcagaaaac tgcatgtaca ctcaaacttc taataataat ttcaagcagc    66540
tcataggccc ctacaaaccc cttaagatag atttgagctt gagaaccta caaacccctt     66600 aagatggatt tgaggttaag aaagaggttt ctgcctttga aggtttgaaa tgtgaagatg    66660
tctccagagg tgaggctgag ccctgggctg tgccagcgcc ctgtacaaag cttcagttgg    66720
atgcaccttc tctttgttgt ccttgtaaca gcccagtaaa tggcaggtat tctcccttta   66780
cagacagcac caaagcacgg ggaagtcatt ttcccaagat cacatggtta ctgcaggat     66840 tagaaaactg aagccaggtt cagctgaccc taaagtttga gtttatatag attacactct    66900
gcctgaagcc ttgagactta attgaccagt attgttttgc taatttctaa gagttactta   66960
taattcaaat ctatcagttg aaacttacta gattagcgta ttttagttga agagagtctc   67020
```

```
caagaacagt gtttataagt cattgtaaat tgttctgttt atgtttatga ataattcata    67080
tggttttgtg ggtcacttcc tctaaaccag ggtctgtcaa ccctgcatga ttgccatttg    67140
ggctgcatca tccttcatcg tcggggggctg tcctctgcac tgtaggatgt ttaacagcct   67200
ccacctacta gctgccaaca gcagtccctg accaccccca gctgtgacaa ctaaaagtgt    67260
ctccagacac tgccaggtgt cctctgtggg ggttgcagtc tccttaggtt aacagccaca    67320
gctctaaact gacagttgta cgtgttgcat tatatatgtt tacctacatc ctacatgctt    67380
ctaaaagatg ttgtatgaac tagtaggatg aggttttatc acaaggtaag taaatacaag    67440
ctctgctttt ctttgtataa attaatgcca ggaatctgaa ttaaatatct tgttttgta     67500 agcagtgaca tcccatttag gtaattttta ttgaaatatg catcaaagaa actcctaaga    67560
aaatatactt aagtacaagt tggtcagctt gcctcttaaa ataaatgtga tgtctttatt    67620
ttactcatgt aggaaagaat tgtattcact aagtctaaga aagtggcttc tgtctaaatt    67680
tgccgtccgt tgaggtagaa ggcaaatttg gagttttctt gtttagaaaa aaaactacag    67740
atgactactg tgcacctgaa aacagcactc agcttcacta acgagacatg caagctagaa    67800
tcaaattgct gttttgtttt gttgcctgtc gtgattgtta gctgaaacca aatcacaagg    67860 tcttttctc cctctgtatt agctcagcat acactgagct tacaaacgta tgaacttcac     67920
gttgtcgtgg aatcttacag cctgctactt cctaagtttc ctttagagaa gctgccttgg    67980
tgaccaatga atgtggttag cctagtgata ctcttctggg ccatatactg tgtgactatc    68040
tgcatggacc tttattgaaa gcatttctgc aaataatttt tttaagtttt tttaaatgt     68100 gtgataattt gtgcttttaa agatatctta cacttttcac ttatttgtac ctttaaaaat    68160 ctttttttt tttaaaccaa aggtttgcag tatcctcaga gtctgaattt tgagcggata     68220
gtgatgagcc agctaaatcc cctgaagatt tgcctgccct cagtggttaa ctttttttgct   68280 gcaatcacaa agtaagttat ttatgctttc ttgatgggag ttatttaaaa tatttttatt    68340
tatgtttctc tagtattgta agagtctgtt aaatttctat gaaattagta acattataaa    68400
aggccaggcg tggtggctga cgcctgtaat ctcaacattt gggaggctg aggtgggagg     68460 attgcttgag gccaggagtt aaaagaccag cttgagcaac atagtgagac cctatctcta    68520
taaaaaaatt ttaaaaatta gctgggtgtg gttgcctgtg cctgtagtcc caactactca    68580
ggaggctgag gtaggagaat cacttgaacc caggaggcag aggttgcagt gagctgagat    68640
cgtgccattg cactccagcc tgggtgacaa gggcaagact ccatcaaaaa aaaaaaaaaa    68700
aaaaggaatt tctgcaatac gctacaacat gaatgatttt gtaggacatt acgctaagta    68760
aaataagcca gtcacagaaa aacaaatact gtatggttct acttaaagga agcccataga    68820
gttgtcaaaa ttagagagac agaaagtaga atggtggtcc ccagcggctg cagaaagaca    68880
gagtggggaa attattgttt aatgggtaca gagttttcat tttacaggat gaagacttgt    68940
ggatatggat ggtggtgatg gttgcacaac aatatcaatt tatttatac cactgaaccg     69000 tgcacttcaa aatggttaag atggtaagtt ttatgttgtg tattttacca taataaaaaa    69060
aattgtagag ggaaaaacag tctgcctcca cttttgatat gggactgcta acatcttcca    69120
ccctccctct cccctctgc cccacatctg ggcaagctaa gaaagcctgc tgctctctcc     69180
tctggcacca gctggaaatt catcccaac aagccctagc cctcccacca gacccacatt     69240
tcatccccat ccccatcgca tcccatccc catcccatc cctaaccacc ataaatgcta      69300
agggagtttc cttgcctggt tttctgaaac cattttggga cctgcttggg aatctgccct    69360
gctctctcag aaagcttcat tatatgagca ataaaccttt tcctacctc ttggtgcatg     69420
```

```
tggtgtatca tcagtcttga catctaaaac aaattttggg tggtggggtc catgtctttg    69480
cagggtgacc acaatagtac ctggcacatt atgtgtttaa taaacagaga ttactgtcat    69540 attttatttta ttttattttt tgagatgaaa tttcactctt ttttcctagg ctggggtgta    69600
gtggtgcgat cttggctcac tgcaacctcc acctcccggg ttcaagtgat tctcctgcct    69660
cagcctccca aggagctgag attacaggca tgcgccacca cacctggcta attttgtatt    69720
tttagtaggg atggggtttc accacgttag ccagactggt ctcgaactcc tgacctcaga    69780
tgatccaccc accttgacct cacttacagg cgtgagccac cgcgccttgt ctctgttata    69840
tttatttctc tatttaaatt gatggatata tgcaaacctg atcattatca tacttatgcc    69900
ttgacacaag agaggcaata aactaatcta agtgatgctt gtgatgccaa agatgtcaga    69960
acactttctg ggccaatggc agatacctca tgtcaccaga tgctaagggt ccacaataaa    70020
aagcgttgaa tgaaaatttt gaggataaat atctccaggt tgaggaagaa ggttgcacat    70080
atcgggtgct caataaatat ttgtcgaatg aatgaatgag tgaatggccc cagtgtgtgg    70140
ggcttgggaa gtgattggat ataggcagag aaaaggaaca agtcaaaaat aattcagaaa    70200
tcaagaacaa gcaagttgcc ttgatatact tcattcctac acttggcaaa ctttagtgat    70260
taaggaaaca atgttttaaa aaaagttttg gtgatgagac attcaggaag atctatcaat    70320
aaatagcaaa cctggtcctt tttaagacac tgtgtataaa aaaattccaa aaagattaaa    70380
atcagtgcag aaaccaaaga accatttttt tctatatcat attgatcatt tcaagtggaa    70440
ctgttagcta tcttagaaaa attgtggttc tcaattggtt ttgcctctat ctctgaacca    70500
ccattcctaa aggaaaacat tcaaccagaa aatttcagca catcacaatc tctctgaaga    70560
ttaagaagtc tctgtgaagg actgaatgta taaattgaaa aattttttgct gtcacattta    70620 ggtaaaagag aaatcgttct tcatatcccc ttcctttcca tctgtagctc acctatgtca    70680
actttcctct cagaagtgaa ataaaattaa agctatgaca ctgagtgtca gtcatggagg    70740
gacacgttcc ccacttagcc tttgctgaag tgtttccaga gacaactgtc taatgccagg    70800
tccccactta gtgggctgca cttttctact catttgcaca taatccagaa gtcacatttt    70860
gggttcacag tttccactgg ggtaacctca ttaggcctgg ccacctctgt gcttcttgtg    70920
aagtctctga tttgaaggat tagtatcctt tccagactgt gtgggttgac tttcacccat    70980
ctggagttgc ttggaacaaa gataactacc tcaactcctt gtcatgaaag caaaaaaaaa    71040
atagcattag agttctgaga acaggatgtc attacgggtt gtgccttgtc agctacaggt    71100
aagatatttg agtggctcct caagcctccc caactccctc tccaacctcg ctacacagtc    71160
ttcccaggtc tggtatttga cctccagact gccgcccaga aagcaactca gagctcagca    71220
acaccatgat gatgaaacac aaatatgtgg ccccccaact ttggagactc cactggttgc    71280
ttttgtgcag ctctttctat atatgacttt caaaatggca gccaacccctc tcaactgttg    71340 gttgatctga atatgtaaag ttcagccttc aaacccagca aacagtcagc tataggatag    71400
agttcaggtg ctggggaatg accacggttg gctgctacgt tgggaaccct ggtgacatca    71460
tatatggacc tgggaatgta aagaaacgta ggaaatctga atttatgact tttctaatct    71520
ctctatcggg atccttttttt ggaatcaaga tgatttttcct tctaaaaggt cattttatta    71580
cagtaatggg cagggtagac atacctcact agcgtactct caaaatttct tgcatgcata    71640
tgctttctcc ggcatgcata tgctttctac tacaatgtga acaagcctac gaaagctagc    71700
ctaatggagg atgagagacc acgtggagga gagctgaagt gccccagcca gcagctagcc    71760
```

```
tacacccaca gctattttgc ttgtgttcca ctcgtcctat ttgcataata ttgttcttta    71820
agttaaccca ttcttaattt attgttttaa tcttaagcaa taatattcaa gaactaatga    71880
gttttgtgta ttcattatat ttttccataa tatatattat actaataaat gcccattcaa    71940
atttttgttt gagtgctcaa gtgggtatca tttaaaataa tcttatatac tatatataac    72000
agccaaggtt tgggcaacac aacagaaact gcatgagttt atttttatcag aatttttaa    72060 acggtatggg agaactaaaa aagtaaaaaa gggaacccctt gagttaacaa ggagataaga    72120
actacgtaaa gcagttactg tcctgaagga ataaagggaa gagcatgggg ttattagaac    72180
ctagaagttt ggaaccacca ggagctggga ccctatgagg agagggttgg cccctgacaa    72240
tgctggtgtc tctaagggag ctcctgaggc tgattctagc agtgtaggga agaaactgg    72300 aaactggaac aatttcctct gtaatcaatg acccttgcca gggtaaagaa tcactgctga    72360
agagatgcta ctggaaaagc aagcaaacaa aaaggagggt gtcccttccc cttcttcctt    72420
ccttccagtc tccctcatga cagagcatct ggctggtgac gggaaaaggt gctccacaga    72480
gcaccacccc aacatcacac gggcatctgc tgacccacag ctgactgcag atgaggaagc    72540
tcagcctagg tcacacaaac gcctcccagc tgagtctagc ctaaattgcc aacctgccaa    72600
atcatgaact aataagtgac tattgtttta agccactacc tttaagggaa ttcagtatgc    72660
agcaatagct atctgatcca tataggccta caaggctata gaaaaactat cacatgtaat    72720
cccagcactt tgggaggcca gggcgggtgg atcaactgag gtcaggagtt cgagaccagc    72780
ctgaccaaca tggagaaacc tcgtccctac taaaaacaca aaattagcca ggcatggtgg    72840
tgcatgcctg taatcccagc tacttgggag gctgaggcag gagaatcact tgaacctggg    72900
aggcagaggt ttcagtgagc caagatcgca ccattgcact ccagcctggg caaaagagc    72960 gaaactctgt caaaaaaaag aaaagaaag aagagagag agagagagag aaagcagaga    73020
ggctactgca gagaaaagtc tagaaggatg ggttcatggg ttcatcgaga gacaatagct    73080
taacaaccag cacaccatag ttggcaaaac actatcattg aaaaaaaaac atgctcaaaa    73140
ggggaaatgc cagtttgggt aaatatgctt ttgtgttgga gagaaagaat ttggaacagg    73200
cttttcagac ccccttaagg cccaacaaac aaattataat ttagacaagt ctgggattct    73260
tcacagctca gcttgtggtg atggtattag cttcacaact ccaaacaagt taagctgtct    73320
gtgtgaaatc tcctcaacaa cacctcactg gcaaacctgg aggtgctgaa acagagctt    73380 tcaattcttg tttgcaacca agggagttga gttggcagat gggcactgtg tccagccttg    73440
ggaaaggaca tcgcagactt tgcatcctaa gaactcataa ccacaacggc aaggtaagac    73500
acaagctctt gaaagttttcc atcacagtgc agcacaaatg accttggcta tgtgccctgt    73560
tattgctggt ccctgcttaa aaatctcctg tgacttccaa ccacacaaat ttcctacctg    73620
gttgcaaaaa tgcccttgat aattcacccc tccctctatc ttgcccccctt tacaatgtgg    73680 cttggcagct cctcccatca agagttaaaa tctatttcct cacccccttga atctaggctg    73740 gccatgggac ttgctttggc caatagatgt ggcagaaatt atggcgtgac agttctaagc    73800
atgagtctca agaggctttg catgcagcaa cttttctctta gaaccctgcc accatgtgaa    73860
caatcctgcc tgggctagcc taatggagga tgagagacca tgtggaagag agctgaggtg    73920
ccccagccaa caaccagcct accccagaag cagaggcatc tgctgaccca cagctgactc    73980
cagatgcata agggagctca gcctagatcc agaacgcctc ccagctgagt ctagcctaga    74040
ctgccagcct gccaaatcat gaagtaataa gggactattg ttttaagtca ctacctttttg    74100 ggggaatttg atatgcaaca atagctctct gatacatata ggcctacaag tctatagaaa    74160
```

```
aactatgctg cctctctctc cagccacaca atttctttct cttctcattt actattctaa  74220
ttcctctgtg ttatagtctg tgtcccaaaa ttcatgtcaa aatcctaatc tccaaggtaa  74280
tggtattaga aggtaaatct ttggtaggtg atcaggtcat gagggtggag ccctcatgaa  74340
tgggattagt aaccttataa aagagaaccc agagagctca tttgctgctt ctgccatgtg  74400
aagatacagt gaaaaagaa gcaggccctt gccagatacg agtttgccaa tgccttgatc  74460
ttggaattcc cagcctccag aactgtgagc agtaagtttc tattgtttat aagctaccca  74520
gcctatggca ttttgttacg gcagcctgaa tggactaaga cagtctacct agaccattat  74580 ttcccttttca tcatccacca gccaattcca gcacatcttt tagatctcag cttaaatact  74640
ccctccaaga cctccctcta tctctaatat gaatgaaatc catatctcaa gttcttcaca  74700
gaatcctcta ctcttttcctt catggcattt gtcataattt gtaattatat atctagcaaa  74760
gttctttgtt gttaaacatc tacctcctcc actctcctag aaactccaca aggacatccc  74820
tgcacccagt gcctaggcaa tgccagacac atagcagatg ctccattaat tatctgtcga  74880
atgactgaat ggcttccaag ttagttaact gggcacccctt gataacagat tctggcctat  74940
ttgaaggatc aaagaagaaa gtggtgctac cttctcccct gccactatct tgcccacttg  75000
tggtgccagt tcaggaggtt tggaatggat gtggctaatg atagacgtag acctattgcc  75060
tttcttggat cataattctg ccaggctctg agtccatgtg gcatcgatgg ctaattgtcc  75120
tccaaaattt atcctctctt cttccattta taccctccca tggagttttta acagggcatg  75180 tggtcaccct actgggatct cacttctcag cttcccttgc aactggatgt ggccttgtga  75240
ctaaattctc atgaacagaa tgtgagtgca agtgatgtgt cagtatcttc atcactttcc  75300
taaaaaggga actgctggtc ctccacttcc tctctttcac ccttccaatg agccagaaca  75360
tgcatgtgat gctggtgagt cagcttcagt cacatgaata aaaacaaact ccaggagatg  75420
actaagcaat aagacagaag gaacccaagt ccctagacga gttcacagaa ccaagctacc  75480
tatccaaccc tgggcccacc tggattataa catgagaaaa acataagtcc taatcatatt  75540
tttgaagcac tgcattttag ggcttctttg tgacagcagc ctaccctcta gtctaatcaa  75600
tatacctcac caagtctcct gctcctaagg gagacaaaga agcaaaatga gtctcaaaac  75660
atcatccaaa tggaatagat acagacctgt aatcccaaca ctgtgggtgc caaggcggg  75720 tggatcactt gaggtcagga gtttgagacc aacctggcca acatggcaaa accctgtctc  75780
cactaaaaat acaaaaatta gccggacgtg gtgttgtgca cctgtaatcc cacctaccca  75840
cgaggctaag ccgggagaat tgcttgaacc caggaggggg aggttgcagt gagccgagat  75900
catgccactg cactccagcc tgggtaacag agtgagactc tgtctcaaaa aaataaataa  75960
aaataaaaat aaatagacca ttaattaata gatatagcct tggtctgtga ccaaagctca  76020
gaatgttatg atattccttt cctatgtcac ctcaacttgc ccctgtcatc agacaggaca  76080
aattccccac tggtccttttg cactcacagc tgttacattt gaaatgggag cttagccttc  76140
cctgccctgg ttcctcctta gactcatttg ggaaaacagg aaacgtaatt atttctgcca  76200
ttacctttat ctcatggagc ctgacagagt gtaaccaatg gtaggaatta aaacattcta  76260
attgccaact cacaacaact cccgaaaaaa atcatttttaa ctcattatac atattaaatt  76320
atgacatgct taatgtccaa acctaataga ttcagtactc aggaaatccc ttatacaggt  76380
agacaccttt cctcctgtac tttaagaaaa tcttacatca atatgcggga cttctcaaat  76440
ttttctatca cagtttttctt aataggaagg agaatttgtg ccaaaagatg tatggaaatt  76500
```

```
tagcacaaag tagccctcta caagcggagg atttctttaa agcattgtgt tttatctcaa   76560
gattccatgg caaatgttta tcttctctgc ttgttttagt atgaaatagt tttcatttgc   76620
ttgtcatcat ttttaaggag ttgaaaatac aatcaacctc actcatcata aaataaaagc   76680
aaattaaaac tactatgaca tattttcacc tacaaaattg agaacatttt aaaatgtgat   76740
aatagttcta ttaacaaggg tgtgagaaga caattctcag gcagggcatg gtggctcaca   76800
cctgtcatcc cagagctttg ggaggctaaa gtgggaggat cgcttgagct caggaattca   76860
agatccacct aggcaacata gtgagactct gtctctacaa aaagtaaaat ataaattagc   76920
tgggtgtggt ggcatgcggc tatcatccca gctactgggg aggctgaggc gggaggattg   76980
cttgaactgg ggaagaccag gttgccatga gccatgatca cgccactgta ttctagcctg   77040
ggtggcagga ccggaccctg tcccaaaaaa aaaaaaaaa aaaaaaaaat ccctcttccc   77100
tgattggtgg gactgtaagc tggtgcaacc tcttgggagg agcaggtggt tagaaaacat   77160
gtatcaaatt tttatgcaaa atttaaatag acccacaatt agaccctagg aatttattct   77220
ccagatattc tcatgcatgc gtgcaaggta tatttgcaaa gatttgtatc cagcactatc   77280
tgtaattgca aaaatccaga agcaacctca gtgtcaatcc ttagaagact gtgtacatga   77340
gatactgtac atgttggttg ggttctccga gaagcgcatg cccggataga atgcaaagaa   77400
ttcattaggg agtaacacct ctgccagaaa agcagaagag ataggattgg gcaggagggg   77460
ccattagagc acaatttaga gctaccacca tttcagaagg cagcaaagat tgcctgttag   77520
agaaatggtc aggcccttgt accctcagtc actggatggg agccactcca agaagagcat   77580
gaccatgact taacagctaa ggggaccctg aaagagctgc caggttaagg ctatcagctc   77640
ctcactcccc acagctggac agagagcctt tgtttaagga ggatctgagc agctcatctc   77700
caggtctggc acaagggtta cccataggat gaagatggaa gacatgaatc tatatgtatt   77760
agtatggaac aatctccatg atagattttt aagtgaaaga gcaatagtaa attgcaaaag   77820
agaacataac gttttgggac taggcagaag tgataaccga acaacagtgt gaatggagta   77880
aaatgtcacc gaattgtaca ctttaaagtg gctaattttg ctatgtgaat ttcacctcaa   77940 ttttttttt ttttttgag atggtgtttc actcttgttg tccaagctgg agtgcaatgg   78000
caaagtctcg gctcaccaca acctccgcct cctgggttca agcaattctc ctgcctcagc   78060
ctcttgagta gctgggatta caggtgcgtg ccaccacgcc cggctaattt tgtattttta   78120
gtagagacgg ggtttctcca tgttagtcag gctggtcttg aactcccgat ctcaggagat   78180
ctgcctgcct cggcctccca aagtgtggga ttacaggcgt gagccaccgc gcctgacccc   78240
atctcaatgt tttaaaagag agagaataca gcatgctgtc atttgtgtta attttaaaaa   78300
ggaaatgaat ttatgtgcat gtataaatgc tagacatgga atctctctga aaggagccat   78360
gaaacactca tactatgatc tccagtcagg aaagagactt aattttcact gtacgccctt   78420
ggtgctgctt aaattttat catgtgcatg taattacacc ctgtctttaa aaatcattaa   78480
agatgtttaa ttgttctgat gaaggaatac attacttgcc atcaagaaaa atgaatgaaa   78540
aattttctgc gagacaattt ttagcaagac actgttgtat tgatcattca agttcagaaa   78600
attcagcctc cgtcaagggg cacaaacatc atatatcagg ttcagtttgt cctctctctc   78660
agagtcaaag tgctttagga acatagacac aataagtttc tggaaccaaa tggcaaatat   78720
caaaacttgc tagaacagga gaaaagtgta tcttattgaa aattcaccag ctgctatacc   78780
attcagcatt gggaaaatca gcataccttc ttagacttca ttattttaaa gatggcaaaa   78840
tagccaagtc atggatgtct cccccttttca tcaaaatgta aagaactagc tgcctctggg   78900
```

```
actctccacc aattttcaag cacgtctttt gaacccattt gatggtgtca ctcaataagg    78960
gcaccttttt caacttggct gcctcttttt gacccaaaat aatttcaacc cttttctgca    79020
gctccgggct tcaccaggct ttctattatt gcatatacct ttcatagtga ttctaaaccg    79080
acctcgaatg aagagacaaa tgattttta  tctattggtt tgattgcact tctccttgta    79140
ctgctccaag acaaggcttg tcttttgagt tgcaaaaaat actagcgctc tatttccaaa    79200
gtcaaacaag tggcttttca atgtctctgc aagtgttttg tttcatgcag tcagtgctga    79260
cttttctcga tggagagaca tatggtttgg gcccatttta gcaactctat aataaaactg    79320
attataaaaa taagcatcta agaatatctt aggcttttaa gattgacacc actgcttgct    79380
actcaattgc tagttgtggt tggcagtgca cgcagtgtct ttgtggtcaa gttcattgtg    79440
gcaagctcag aggtcatgtc agatcacaac acagggactt gaattgggt  ggacatccat    79500 tcattacgtg gcacacgtca cgagcttcaa ggttttgctt caaaaactct tctgtcttct    79560
aggtgaaagt ataagtttaa acttactgct ctttaagaaa gtaaatgaaa aatgacacta    79620
aagtcccaaa agccagaatt gtcagcaatc ctaggtgcag ttcattcatt cattcattca    79680
cgtattcatt caataaatat ttatggaggg cctatttacc tggcagcact tcatgaggcc    79740
ctggaaatac aatagtgagc aataaaaaca cactccttca ccaggtggag ctatagtcta    79800
ctagggagat atagatgtta aacaaattat cacacaggcc gggcatggtg gctcacacct    79860
gtaatcccag cactttggga ggccgaggca ggtggatcac ctgaggtcag gagtaggagt    79920
tcaagaccag gctgactaac atggtgaaac cccatcttta ctaaaaatac aaaattagct    79980
aggcatggtg gtgcatgcct gtgatccaag ctacttggga ggctgaggca ggagaattgc    80040
ttgaaccggg gaggcagagg ttgcaatgag ctgagatcgc accattgcac tccagcctgg    80100
gcaacaagag cgaaactcca actcaaaaaa aaaaaaaat  tatcacacaa acaagtacat    80160
aattctatat tgtgaagtgt cccaagaaa  aatatgccac tcttaataag tacaggaggc    80220
ttaatttgga aagttagaaa agtgatgttt aaagtgagaa ctgtaagaca agtcactttg    80280
tcagtgcaaa gtggaaagaa agtattttaa gtagcaagga gagcatgagt aaagaccacg    80340
gagaaggaaa gcgaggatgc agttagagac atgaaaggac tgcattggtg gggcaccggg    80400
atgaaggaga tgatgaagaa gatgtaacca gaaaggctgg cagggacaag gtcatgctgg    80460
gtcttgcagg ccagcatgag cacttgagat tcttaaagta attgcaaggg agcctttgag    80520
ggttttaatg agggcagtat ctttatcaga tgtgcacttg tttggggttt ctctggattt    80580
tgttgaaaga acaatttaag cagaaggcag attaggaaat aggagaatcg agaggctgta    80640
tatgttgaga cgcagtggta gtctagggtg acaatgcagg aaatgggaag cagtggatga    80700 actgggata  tgttttgaag gtagaataga tgatggctgg gaagacagtg actattcaag    80760
ggcagggggg ttggggagg  tatcaagaat gtttagaata tagctaacca catacccttt    80820
tagaaacagt cttctctgaa catttctcct gtctccaagc ctcagtttcc tcatctatga    80880
aataagaaca ctactacttc ctttttaagg ttgttaaact ggttaaatga gattatgcag    80940
ggaaagcatc actagtcagt gctcaaaaat gtgctttta  aatttcctcc ctttgcctct    81000
tattctcaac tttgtccttt gtaatattat tgttctttaa gtgggcttgg ttttgtccta    81060
tcttgtccca ttcactcact gctccccatc cacccaaatc ccctctgtat tctgtttatg    81120
caagactgag tttaccccktt ctcagtccat tgacttatct ctcctcactc attgacttgt    81180
cccaggcaat ttattctgca atcttggaca aaaatctgga ttttcagcca ggtgcagtgg    81240
```

```
ctcacacctg taaacccagc actttgggag gccaaggcgg gtagatcatt tgaggtcagg   81300
agtttgagac cagcctgacc aacatgacga aaccctgtct ctactagaaa tacaaaaatt   81360
agctgggtgt ggtgacgtgt gcctgtaatt ccaggcatgc ctgtaatccc agctactcgg   81420
gaggctgagg caggagaatc gcttgaaccc aggagacgga ggttgcagtc aggcgagctc   81480
acgccactgt attccagcct gggcaacaaa gcgagacttc atctcaaaaa aaataataa    81540 taattcatta tgtaatccag ctttgaaaca ctctttggct acacttttgt atgctttaag   81600
gaggaacaaa acacagatgg tctccaactt acattggtta aatctacaat ttttcagctt   81660
tacaatggtg caaaaacaat gtgcattcag tagaaactgt acttcaagta cccatacaac   81720
cattctggtt tgccccttca gtacaatgtt caatgaatta tgtgagatat tcaacacttt   81780
attataaaac aggctttatt ttagatgatt ttgcccaacc ttaggctaat gtaagtgttc   81840
taagcatgtt taaggtaggc taggctaagc tatgatgttc agtaggttag gtgtattaaa   81900
gcaagtttta cttaagatat tttcaagtta cagtgggttt attgagatgc aacctcattg   81960
taagtcaagg aacatctgta cttcagaagt catcaaagct gcatgagcag gacacaagtc   82020
atatgaaaag ccaggtagac ataatgctat aaaaaatccc tccattgggc cgggcacggt   82080
ggctcatgcc tgtaatccca gcactttggg aggccgggga gggtggatca cgaggtcagg   82140
agattgagac catcctgact aacacagtga aaccccgtct ctactaaaaa tacaaaaaat   82200
tagccaggca tggtggcggg cacctgcagt cccagctact cgggaagctg aggcaggaga   82260
atggcaagaa cccgggaggc ggagcttgca gtgagccgag atcacgccac tgcactccag   82320
cctgggtgac agagcaagac tccatcaaaa aaaaaaaaaa atccctccat tgtcagagtg   82380
tgagcttcca gctcattatc ccagaagccc gagatagcag cagttctcag atcttgtgat   82440
aaaggtcatc tcctatcctg gggctctcag gaccataatg caagagtctc cctctaaacc   82500
tgccagcccc agggcttttc ccgccttcct catcctaagt cctgaaaagt tcactgggcc   82560
aaatggtgaa ccacgcactt attgccccat aacccttggt acaaatgtct ccaaatatat   82620
ccatcaagcc tacaggtagt actgagaata caacagtag ctaacattga ttggacactt    82680
ctaagcccct taaatccatt atcttactta attctcacaa cactgatcaa gagttggata   82740
aaataatcca ctctcaagcc agcaaatcta aaccagccac tcttccgtat ggattcctgc   82800
tcttatggta acaagggctt gccttcccca cctttattct taaccttct ggaaaacctc    82860 tgctcctcct tttctgagat ggaaaaattt ataagtgaaa aaccattcca tctttcgagg   82920
tgtggaggga ggaaaacaat cactcctgcc ttcaactaag agtgtgaaaa ataagcttaa   82980
ctaaacctga aatacatttt caaatgcctt tgaaaagact tataaatcaa atcacatttg   83040
tccatctctc tgctcttcaa aattatcatg catgcacctg aagtttaagc aaagaaatcc   83100
attaaacaaa caaacctaaa atcataaaac ccagatttag agatttatcc gctcagtcta   83160
atgaatgccc aattcagaat acaattttgt cttcaaagag ccctgaaggt tcttatctt    83220 cttatctttc tatagtgtta acagaaatat tacatctttg aaaagaagaa aaacattatt   83280
cccagagcta aaacagaaaa ggctttgaac tattttaggg ataaatcaac tcacagttac   83340
caataaacca aaaagaataa aaaagactgt ttcaaaccaa gttgactact cttacatata   83400
ttcaagtgtc aacttacaaa tcagtctttta aatatacacg tacactttct aactctcctg   83460
aaatgtcacc caagccccca ttcaatcagc taaaaacaat ttaattcttt ctctagggag   83520
gaaatcaggt tatcagataa gtaaacctta aataccattt ctaggcctga tgtggtggct   83580
catgcctgta atcccagcac tttgggaggc taaggcaggt ggatcacttg aggtcaggag   83640
```

```
tttgagaaca gcttggccac atggtgaaac cctatctcta ctaaaaatac aaaacttagc   83700
caggcatggt gacaggcacc tgtaatccca actactcaag ataatctgca taccaattgt   83760
gggtagacat aggttttgt ccagagccct ccacagaccc atcccttacc taccattgtc    83820
tctcgggctt caaccttatt tgaaagtctt aatttgcagt tccacatact gcaaacacaa   83880
gacccagtct ttctggttct tattttacct ggagattaaa atacaggctg ggcgtggtgg   83940
ctcatgcctg taatcctagc actttgggag gccaaggtgg gtggattgct tgaggccagg   84000
agtttaagac cagcctgggc aacatggtga accccctgtc tctactaaaa atacaaaaat   84060
catccgggtg tggtggtgtg tgccgacagt cccagctact caggtagctg aggcataaga   84120
atcgcttgaa ccaggaggc agaggttgca gtgagctgaa atctcaccac tgcactccag    84180
cctgggcaac aaggcaagac tgtctccaaa aaaaaaatta agtttctgtc ttacaatatc   84240
ataagaaaat ggctggacag gttttcacca aagttggagg gtacttttgt gatgggtttg   84300
gtttaaattg gtttaaaata taagacacat agtccataga gaattcacct atggactatg   84360
ctgctaagag aatctcaaag agatgcactg ttatgctcca gagttttgtg agaggccact   84420
aaggtcagga gacacatgcc atatatatca agatgctgtc aacagagaaa accagtgagg   84480
tttcaaacag aagccccgct ccattcaacc aggcagccac tcctcattgc aggtgctgac   84540
ctgggctttg gctgcttctc acatgggcaa ctctatacac tctattcctg ggagaagggc   84600
agcaaagacc cacttattaa atgatgttta acaatcctcg gccgggcgcg gtggctcacg   84660
cctataatcc cagcactttg ggaggccgag gtgggcggat catgaggtca ggagatcgag   84720
accatcctgg ctaacaaggt gaaaccctct ctctactaaa aatacaaaaa aattagccgg   84780
gcgtggtgtc gggcacctgt agtcccagct acccaggagg ctgaggcagg agaatggtgt   84840
gaacctggga ggtggagttt gcagtgagcc gagatcatgc cactgcactc cagcctgggt   84900
gacggccgtc tcaaaaaaaa aaaaaaaata tcctccaggc aattgtgtga cagctggaat   84960
gaaaaatcag gggcaaattg tacatataag ggaacaattg ttcatatttg tgtaagctac   85020
cctccggagt ctacaagtta aaaggcacac tttaatcaat ttggcaactt gcatggcatt   85080
ttcctccact atttgtagga tgctggtatc tccttaacag ctactgtttt cctatgcaac   85140
acacaatgac ttcttgaaca catggcagct tttcatttgt tcatttaaca aatacttatt   85200
gagttactac tatgtgccaa acaccattat aaaggtactg aggatacagc ggtgaacaag   85260
atggacaaaa tccctgcct ttgtactaca ttcttgagtg ggtgtgagga gacaatgaac    85320
caaagaatga acaaactgtg tattgtgcag gtgtgtcatg gaaaaaaat gaaggaggga    85380 agaaaagcgg aaaagcagaa aatgtcagga atgcacttcc gtggcgggtg gccagacagg   85440
tggccaagaa gtgacatttg aactaaagaa ggtataagtg agcaagctat gagggaattt   85500
ggcaaaacaa tttcggaggc ggaggtcaca gccagcaggt gcaaaggcct ggggcaggag   85560
tgggtccagg gcatgggacg gatggggaga aggtcagcat ggctgaagga agtaggggt    85620 aagctcaaac aagtcgcagg tgggaaactg agtgtattgg accttgtagg caattttaag   85680
aactttagtt tccactcatt aacatggaaa accactggaa ggttttgagc aaaggaataa   85740
cataatctgc cttttttct tcaaatgctg tgaaacaaat acttatttga ccctatcacc    85800
atttctacct ttggaaaggc tatggtgtgt tactggatgt tgaggatagc ttactcttca   85860
atgtgcagta accaaactga attcattctt tctcaagatg agagaaagat aagccaggta   85920
tggtggcttt cttagataag ccaggtatgg tggctcacgc ctgtgagctg aggcgagagg   85980
```

| | |
|---|---|
| atcacttgag gccaggagtt gaagaccagc ctgggcaaca tagtgagacc cctcatctct | 86040 |
| taaaaatttt tttttagtta gccagacatt gtggcatccg cctgtaatcc cagctctttg | 86100 |
| ggaagctgaa gtgagctatg atcacgccac tgcacccag cctgggtgac agagtgagac | 86160 |
| ccccatctct aattttgaaa aaagactgg atagggcctg gttaatacaa ctaactcccc | 86220 |
| aaaattcaag tttttcatat aggtcttttt taaaaaatag ctttaattga cataaaattc | 86280 |
| acccatttaa agtttacaat tcaatggatt tttatatatt cacaatgtag tacaaccatc | 86340 |
| attataattt tttttttttt tttagacaga gtctagctct attgtccaga gctggagtgc | 86400 |
| agtggcgtga tctcagctca ctgcaacctc catctcctga gttcaagcga tcctcccact | 86460 |
| ttggcctccc aagtaactag gattacaggc atgtgccatc acgcctggct aagttttgta | 86520 |
| tttttagtag agatggggtt tcaccacgtt ggccacgctt gtctcaaact cctggcttca | 86580 |
| agtgatccac ctgcctcggg tccaaagtgc tgggattaca ggcatgagcc acagcacctg | 86640 |
| cccgtaatct acgttagaac ttttttatcat cccatcaccc atttaagtct ttacccatta | 86700 |
| gccatcactc cccattttct caaccctcc cgcaaaaccc ctacccagcc ttgggcaacc | 86760 |
| actaatctac tttctataca tttgcctatt ctgaacattt catatcaatg gaatcatact | 86820 |
| acatgtgaca ttttgcatct ggcttcttag aataagattt tcaaggttcg tctatgttgt | 86880 |
| agcatatatc agcacttcag tccttttgag ttttttttta acaatcttta ccattttcaa | 86940 |
| gtgtatcgtt tcatggcagt aagtatattc acactgttgt gtaaccatac ccaccatcca | 87000 |
| tctccagaac tcttgtcacc tctccaaact gaaactctgt acccattaaa caacaattcc | 87060 |
| cattccccac cccaccccag tccctggtat ggcaaccacc attgtactt ctgtctctat | 87120 |
| aaatatgact actcatactt catttttaa attgccaagt aatgtttcat tgtatggata | 87180 |
| tactgtacaa caatttaact atccattcag ctaatggaca tttggggttt ttttaacctt | 87240 |
| ttggctatca tgaataatgt tctgatactt cgtgtgtgtg tatagataga tagataaatt | 87300 |
| aaatagaaga tagaagagag agagagagat tggagacagg gtctcactct gtcactcagg | 87360 |
| ctggaatgca gtggcaggga cacatctccc tgcagcctca acctcccagg ctcaagtgat | 87420 |
| cctcccacct cagcctccca agcagctggg actacacgca tgtgccacca cacctgacta | 87480 |
| atgtatgtat ttacttattt atttatgtat tgtaaagaca gagtctagct atgttgccca | 87540 |
| ggctggtctc aaactcctga cctcaagtga tccttcctac ctcagcctcc caaagtacca | 87600 |
| agattacagg catgagcccc cgtgcccagc ctgatacttt ttttttttaag tattattcca | 87660 |
| gttgccttgt tgaaaataga ccccaagaaa gcaaatctca aacagagaaa actgctagga | 87720 |
| agttcttgct ggaatccagg tgagaacgga tagaggctca catttaaatg aagtagtcag | 87780 |
| aaatagccac atttggatgt atttttatac aattcctgct cctgaagtct tccccactcc | 87840 |
| tttttttttt tttttaacca ttactacaat tgctttgctg ccttttttgct gatttattgg | 87900 |
| atcacgtgtt taaaccctg atgtgaacac ctacatttat ccttcttact gggtatgtgt | 87960 |
| taggtattta acaaagtctt agttctcctg gagtctgcct gcatgaacca accaaatata | 88020 |
| aatctgcaaa atgggaactc tacagtgtct cttcagtttt gctgtcaaga tttcacagcc | 88080 |
| tcagcttcta aaattatttc atcaagttca atggatacat attcttgaac tctttttctag | 88140 |
| cctatatttt ccaacaatgt tgctaactat atttccatac cagccttctt atctaacata | 88200 |
| ctggttaaaa tgtcaaaaag cagagggttt aaaaagcttt tctcggtgga atgtgcttct | 88260 |
| ccttcataca tgatataact tgatttgaac aatgtcacaa agatattttc tctgttagat | 88320 |
| taaaattttg tttgcatgaa ttttttcaata gctttaagca gttgaatagc aatatatgca | 88380 |

```
ggaagaagct gagagactta tgtaatagat atttcatgta tctataaccc acactgctgc   88440
ccaggaaatg tgcgctgcat taatagagag gatttttttcc tgctgaatac cttgaggagt  88500
tggccaacac gtttgggagt agaagtagaa agggccaggt gtgatggctc atgcctgtaa   88560
tcccagcact ctgggaggcc aagtggggag gattgcttaa gcccaggact ttgaggccag   88620
cctgggcaac agagtgagac tccatctcta aagaaaaaaa atcataaaaa actaaaattc   88680
tctgccaaaa tggacacaga aaaaactgac aatccagaga aagataatat gcaatgaagc   88740
tagacatggc caaattagaa aatgatattg agagagaaca agagcaagaa agaggagccc   88800
tcagcattga gagggctgag gaagcacaga aatgactgat gggttggtta gttagttact   88860
ttttgtgaag tgtgcaatgt aaatttcact ttggtctccc caccggaatc atcaactaaa   88920
gtctacactg ctatatcggc tatctattgc tgtgtaacaa attattccaa aactcagtgg   88980
cttaaaacaa cacatttatt atctcacagt ttctgtgggt taggaattcg aagatgggcc   89040
ccctgcttca gggtctccca tgggttgcta tctaggtgta agctaggtct catctcaaga   89100
ctcaactggg gcaggatcca cttccaagtg cacccacatg attattggca ggattcgttt   89160
cccatgaact gttgtcagaa gccgctttca gatccttgcc acgtgggcct ctccgaaggg   89220
cagctcacaa cacaacagct tgatttatca gagcaagcag gcaatgaggc agaacaggga   89280
cctctcttag ggacatgcag cactcccacc ctcaaacata gaaataaaga aaaatcttaa   89340
gttcctttaa gaaaaattcc aggcacttag ctagcccttaa aaaataaat aaggccgggc   89400 acggggctc atgcctgtaa tcctagcact ttgggaagcc gaggcagttg gatcacttga    89460
agtcaggagt tcaagaacag cttggccaac atgacaaaac cccatctcta ctgaaaatac   89520
aaaattagcc aggagtggtg gcgcatgcct gtagtcccag ctactcagga ggctgaagca   89580
ggagaattac ttgaacccag gaggtggagg ttgcagtgag ccgagatcat gccattgcac   89640
tccagcctgg gcaatggaga aagactctgt ctcagaaata aataaataca tcaataaaca   89700
acttaataag caagaagata atagtagctt agaataatgg gcaaaaaagt taaaatcatg   89760
ggatgtttgg cttccctata aaactaatg ttcatagatt gttttttcaaa aatgaggact   89820 ccccactaaa tgggtccagc aacacacaag gtccagcaac acaactcaga taaggggggac  89880 ctgaaggcta aactcttaac acttttctca gttctaaatt tcttcctaag gggagtagag   89940
gaagtcacac cccaggccag aactaacatt ccactgatct caaattttta gacaaggctt   90000
ctcctcctaa gccaattaca aatcaaaaca tctttaaatc tacctttgac ccatgggttc   90060
ccactttgag acgtcctgcc tttttaggtc aaaccaatgt agagcctccc atatattgat   90120
ttataacttt gcatgtaacc tctgccttcc tgcaattaca aatccttacc tataagccat   90180
ccgggagctt gggacttaag cattaactaa ttatctttgc ttggtgcccc tccaataaat   90240
accccacttc ctcttgctac aatcccaata tcaatgtttg gttttgctgt gctgggcagg   90300
gggacccaag ttaggttcag tatcagcaag aaggcaagac agagtgtgtg ctagcaagac   90360
agaagtccgt gtgtttggta acctaatctc aaactgaaat gccatcacct ttgctgtgtt   90420
ctactgatta aaagctagtc acccatatgt tcattgcagc actattcaca aaagcaaaga   90480
cattgaatca acctaggtgc ccatcaatgg agaattggaa aaagaaaatg tggtacatat   90540
ataccatgga atactacaca tccataaaaa ggaacaaaat catacccttt gcagctacat   90600
agatgcagct ggcagccatt ttcctaggtg aattaacgta ggaatggaaa accaaatact   90660
gcatgttctc atttataagc aagagctaaa cgttgggtac acatggatat aaacatatga   90720
```

| | |
|---|---|
| acaataaaaa ctggggacta cagctgggca tggtggctca cacctataat cccagcactt | 90780 |
| tgggaggcca agctgggcgg atcacttgag gtcaggagtt caagaccagc ctggccaaca | 90840 |
| tggcaaaacc ctgtctctac taaaaataca aaaattagca gggcgtggtg gcaagcacct | 90900 |
| gtaatcccag ctactcagga ggctgaggca tgaggatcac ttgaatttgg aaggtggagg | 90960 |
| ttgcagtgag ccaagatcat gccactgcac tccagcctgg gcaacagagc aagactctgt | 91020 |
| ctcaaaaaaa aaaaaaaaaa aaaaaaaaaa aaaaaaacg gggactgcta gatgagagag | 91080 |
| aaagggagag acaaaagggc tgacaaacta tgctcactat ttggatgaca gaaccagtca | 91140 |
| taccccaaac atcagcaaca gacaacatac ccatgtaaca aacctgcaca tgtatcccct | 91200 |
| acatctaaaa taaaagttga aattataggc tgttcgcagt ggctcatgcc agtaacccca | 91260 |
| gcactttggg aggctgggc agaaggatca cttgagccta ggaaatcaag accagcctgg | 91320 |
| gcaacatagg gagacttcct ctctacaata aaattaaaaa ttagccaggc attgtgatgt | 91380 |
| gcacctgtgg tcccaactac ttggaaggct gaggtgggag gattgcttga gcccaggagt | 91440 |
| tcaaggctgc agtgagccgt gattgtgtca ctgtactcat cctgggccac agagcaagac | 91500 |
| cctgtctcaa aaaagagac agctcactgt cagctcactg caaccccac ctcctggatt | 91560 |
| caagcgattc tcctgcctca gcctcccaag tagctgggac tacaagagcg caccaccata | 91620 |
| cccagctaat ttttgcattt ttttttttta gtagagacaa ggtttcacta tgttggccag | 91680 |
| gctggtcttg aactcctgac ctcgtgatcc gcccgcctca gcctcccata gtgctaggat | 91740 |
| tacaggcgtg agccaccgta cctggccgag aaattatttt ttaagtgaaa ataaaaaaat | 91800 |
| aaaagctagt cactaggtcc agcccacagt cagggcaagg ggtcacaaaa ggacgtgaat | 91860 |
| atgaggtggc agggatcatt tggggtcatc ttagaagctg tctaccacaa tgttccacta | 91920 |
| tgaattattt cagaggattc acacctgggg caaggaggta catcgatagc atgcaaccag | 91980 |
| aaggagtcct gagacagtca tttgcagaaa ccctggtgaa gttttggttt tccttggcca | 92040 |
| tgcaatcagg ggctactcac tggctgatgg actcagctga cacccagatt aatttgagaa | 92100 |
| ctgtatccac agtcattaac tacggggcag tgcccaactg tccccaagcc agaagtaaga | 92160 |
| ggtatgcatc ttcacgacct caatgacaaa cttgatcata taaaataggc agcattaatt | 92220 |
| gacctggttc aggctacgcc ggaggtggac taccacctgg aaacagagag acattgcaga | 92280 |
| agcttccctg aggttcccct tgcagccttc aggggtgaat tctttgacac tgggtgtttg | 92340 |
| aaatggagca atcaaggccc cagcaaaaaa cagatgcaca ctccaatggg gtaattgagg | 92400 |
| acagtttagg aaagagatta tttacagaag tgtggacagg attaagagaa acaaggatg | 92460 |
| tggagcacgc tggtattatc aacagtgggg tctaaaaggg aaggagagag agagagagaa | 92520 |
| tcctggaacc cagagagagc tgtcgctgta agacagaact gcccaacagg aactgtggcc | 92580 |
| tttagggaga aactgagcta ctgcaaactc tcagcccgga aggaaagaag ccaaaggaat | 92640 |
| aaataccctg acctcccctt ccaccctcca atctcctact gggtccccac tggccagtct | 92700 |
| ggctccctgg gcacaccaga gttgagaaga acggacagcg gatttggagg cgcaagaaga | 92760 |
| aagtatccaa aacctagaca gaaagccagg cagcttcaca tgagcttttt aaaagtgtag | 92820 |
| aagtcataaa aattctcctg gaaatgagca aacacatggg ctttcagaag atgaacacaa | 92880 |
| aatagctttt aaaatgaaag tctgctctgg aagggaaaag gtggttcctg gcaatgtgca | 92940 |
| gaggaggatt aaagtcccca ccctcaactc cagcctgctg cgtcttccaa gagagaattc | 93000 |
| cccagagcct ggactaggga agcattggcg ccactgggaa aagctgctac agcccttgtt | 93060 |
| gggcggctct ttctcacagc tactgaagct gcctttgcaa agattatgac agtgagagaa | 93120 |

```
tctggtgttg ctgactccat cttgtttcta gcctcacagg ctaactgtcc tcactcattc    93180
ctgggcatag gccaagttaa tcatgagatg aattttttta ttttatttat ttgcttttg     93240 agacaaggcc tcactctgtc gcccaggatg gagtgcagtg gcatgatcac ggctcaccac    93300
agcctcgaac tccctggtct cagggtggtc ctcccacctc agcctccaga gtagctagga    93360
ctgcaggcgc atgttaattt ttttgtattt tttgtggaga tggggcttcg ccatgttgcc    93420
cagtctggtc ttgaactcct gggctcaagc gatctgcctg ccttggcatc caaagtgct     93480 gagattgcag gtgtgagcta ctgcacctgg ataggtattt agtttatagt ttaatttgaa    93540
agcaaggatg ataatagtgt tccactaaaa ctgattccct cattgtttca gggctgaaac    93600 caccttгta aaactaagga aaggccacaa gattagggag gggcctgaat tctgctaaaa     93660
tggaggcata gtcttaggca tagttttaga accagccatt gttctataag tcacaagatt    93720
tgtgacttcc ccaattgctc ctatagataa catcactatt atagaaccta ggattggtct    93780
tttgagatgt ttttcagact ttgcattctg gcaaataact gaccccacct ggacttgtaa    93840
ctcatgactc aactggtcct gtggccccta cccagaggtg gactcagagc accaggacca    93900
tttcccacac ctctattgca tccccaacta atcagcagca tccattgcct agtcctctgc    93960
ccaccaaact attttgaaa aaccacaggc tgggtgcggt ggctcatacc tgtaatctca     94020 gcactгggg aggccaaggt gaggggatca cctgaggtca ggagttcgag accagcctga    94080
ccaacatgga gaaacctgt ctctaccgaa aatacaaaat tagccgggca tggtggcaca    94140
tgcctgtaat cccagctact tgggaggctg aagcaggaga atcacttgaa cccgggggc     94200 ggaggttgtg gtgagccaag agcacaccat tgcacaccag cccaggcaac aagagcaaaa    94260
ctccacctca aaagaaaag aaagaaaaa ccacaacctc caagttttt gggagactga      94320 tttgagtgat aactccagtt cttccacatg gccagcctca agttaattaa actctttctt    94380
cactgcaata ccacagtctc agcaaactgg ttttgtctat gcagtgggta ggaaggttga    94440
gtaatcacac tacagttctt tctggattcc aggagtctct ctccccttcc cttttagacc    94500
tggttggtaa gggctctgtg ctgttgacag ttccagagta cctcacatcc tttgtttcat    94560
ttaacccagt ccatgcttct gtaaatactc tctttgctaa actctcctca agtaattgat    94620
tttaatgtgc atccattgcc tgccaggacc tgattagtcc atttcaagca tccaatatca    94680
aagaatgcac ccaaaacaaa gacgctgtta ggaaacacag aactgggcac tgcaaaggtc    94740
tttgagcatg acacaaggat gttgcaagag cggcaggccc agaaggcaag tggggatgga   94800
agaaccttaa cagcatattc acggggctca gtcctaggat tcagcatcat gacatatcac    94860
ctccaagctt ccatgctttc atttgtatag ctaagacttg acaagactag tgagggtgtc    94920
cgatgatgag gacagtcaag gatgttaaat tcctgactat acattaacaa ggaggaaaaa    94980
aactaacaaa cctgcatcag tgtgaagacc agaaaggcct gtccacagag ccagatgaca    95040
aggtacaaca ggatgctgtt gaaaaaaatc agactagata agagcaggtt gctgtgtgag    95100
caaactcaga ccatacaaga gaactatagg cccctctcct ccagcccaga attcctgccc    95160
tgagtgatgc taaatcagaa ggaagaaaag caggagatga tattggctac cctccgggga    95220
caggaagcat cacctggttg gactaccaga ctgccattca cacttatata catggagtca    95280
gtcgggtatg actcagtccc ctgaggccaa atgtcagcga ggagagtggg aggagcaaat    95340
ctctctcctc cattagagtt gtctccggaa caaacccagg tctcaaggca aaggcctcac    95400
acactatttt gctattttgt cacccacgta aagttttcag aaacaggatc cctgtagctc    95460
```

```
atcaggcact caggtgcatc aaagctgaat tcagggtaaa gattgatgct gtggcccagt    95520
gaagctgaga tgcccatact ctctctgttc aggttataga gaaatgggc actttgtgat     95580 cacttatacc cataataaaa aacaatttgt gtgcatctca tgagcaagaa aaataaacag    95640
gaaaaaagaa agcaacccaa ctacttgtaa gtataaggaa atccaaccca tatttgttca    95700
tataactgaa aggtccaggg gcaaacctgc aggtatggtt tgatgcaggt gccaacatct    95760
tttgccagga cccagtgttt ctcacaccct ttctttttc ttttttctt tccttctttc      95820 tttcttttc tttttgtctt tccttctttc tctttttttt ttttaacagg atctcactct     95880
gtcacccaag ctggagtgca atggtgcaat ctcagctcac tatagcctca acctcccagg    95940
ctcaagcaat cctcccacct cagcctcctg agtggctagg accacaggca tgcaccacaa    96000
tgcccagcta attcttttca ttatttatag aaacagggag tctcactatg ttgccagggc    96060
tggtctcgaa ctcctgggct catgtaatcc tcccacccac ctaagcctcc caaagttctg    96120
ggattacagg tgtcagccac catgcctgac ctcacaccat ttcttaactc cattcttctc    96180
actccatttc ttaatttcat tcctttataa agcttctctt cttactattt caagatggct    96240
gcccaattca tgtgcagagg aaagagaagt tctttctctt tactctgaca gttgaataaa    96300
aaatccaaag cctggctctc tttggtccat ccctgaatca gtcattatgg cctggggaat    96360
ggagtatgct aattgactta agggaatcag ggcccagcac tggagtgaag gtggggctaa    96420
tgccacctaa tccactggag agtaccaaaa gtgtgcttcc ccaaaggaaa ttcacaatac    96480
tgtgggaaag gatgaattga tgctgagtca ctatgaatga caaatgcaaa agataaacat    96540
accaggcccc actccttgca ggaagcaaaa gatcctagag ggagaggctg acatggaaca    96600
ggatgtctga ccaataaaac ttcttccaat gaggattcac agacatagtc ataccttcca    96660
ggttaagtaa ggctcaattc caggcagctg tctgtctcag ctcctcatgc acatccgtcg    96720
cttctgtcta cccagcattt gtttctccct tattcagttc tcattgctgt gtaacaaatt    96780
gacagaagtg catcaactaa agcaacacaa atgtattatc tcacagctct ataggtcaaa    96840
atccaagcac ggctcaaccg gattctctgc tcagggtctc atggggctga aatcaaggtg    96900
tcagctggag ctgtagtctt atctaaagct caggtcttc ttccaggatg attggttgtt     96960
ttcagacttc cgctccttct gattatcttg agataggagg caggacttga ctctggaggt    97020
ggggcttgga caccggacca agttcaggac taactaaaac agagctggga gggaagcagc    97080
tttccctaag acacacccac cagtgtgcca ggtcagttta ccattgacac ggcaatacct    97140
gggagttacc accccttttcc atggcaatga cctgatgacc taaagttact accccttctc   97200
tagaaagttc tgcagaaacc acccttgaat ctgcatataa ttaaaagcag gtataaatat    97260
gactgcaaaa ctgcccagag atgccactct ctggttacag ggtagccctg ctctgcagga    97320
gccgtcatgg agctgtaaca ctgcaggagc tgtaacacca ccgcttcagt aaagctgttt    97380
tcttctacct ccagcttgcc cttgaattct ttcctgggca aggccaagaa ccctcacagg    97440
ctaagcccca gtttggagtt catctaccct gcatcaatat gactgaggtc ttttttcttg    97500
ctggctatcg accagagacc tctctcacct cctaaagaca aacctaggtc cttgccctgt    97560
ggcctctcca taggctttct cacactttga gcatctctga cttcaggaag ggcctagtcc    97620
cttttaaagg tgcacctgat taggtcaggc ccacccagat gctctcccctt ttgattaact   97680 caaaatcaac taactagtag cccagtcagg gcagggctat tccatcacat cctctaattg    97740
tgcagcactg gagaggagga gattgcacag attgtgcaca ccaggagca gggatcttgg     97800 gggccatctc agaattctgc ctaccacatg ttagtaattg atctcttctg gaatcagtcc    97860
```

```
tttcctgctc agtcaatgtt atttgtggta ggatttaggg taatcagacc tagccttggc   97920
caattggtgt aaccattgtc tgggccacag tggtcagatc agaaatgggc acctgcctca   97980
agcaagccca atcagaccta acctggggac ttttgctgaa gtaactagga aagatctctc   98040
tctctctctc tctctctctc tctctctctc tctctttctt gttattgcgg aagtgttagg   98100
ctgtaaactt agagctgatg gtggacacca tgtgctttga ttcaaatgac cccccaaaac   98160
tcatgttgaa actgaatccc aaaagtggga gcattgagag gtgggacctt taagaagcga   98220
ttgtatccct cttgagggca gagcctttac tgaccaccta atgtttttatt aaagcttgtt   98280 ctgcaccacc cctatcccta ccatcaccat ctggagctct cgatcctttc ctccagattt   98340
ctttgctcca taatatttat cactatctga tacaggggtg tgtggatgtg aacatgtata   98400
tgtgtgcatg tgtgtgttta tggtccgcct ctcccagtcc ccggtagact gtaagcttca   98460
tgaaagcagg gctttgtgta ctgttgtttc tgtagcatga ggtctgccaa aaaagtaggt   98520
tccccataaa tgtttgttaa atgaatatat tctgattcta tctcccccctc ctccagaatg   98580 gatctaaagc ttcccaatct ttgcctgagt gagtgtccta ctgagttcaa ttttgtttca   98640
gaaaggacgt gtgtatgttc acccatatgc tgcacaaata tgtaatggac accagccatg   98700
accagcctac tggggactgc ttggcagtag caacatggca gcgaacaaga cagatgagcc   98760
tcctgcccac agaagcttac attcgggtgg aatacaggct ggtgagttgt catgccgatt   98820
cctccaaccc aaaacccttg ccagtatggc aggtcctgga gctggactgg ccaccattga   98880
gaatccaccc aactgcccat cagcatctca agttccctgt tgcaagatgc cagggagcat   98940
gagagaggac cgtgggggag agtgagctct caatgaacct ggtgtggcag ggagaagacg   99000 aagatgtgggc agatccccag ggggaagaca acttaagggc agatttgttg aactaagtta   99060
cttcaaaggg tcttccatct tccagcatga gcagagaaga tgaccacaca cctgggggag   99120
agtcagatgg cttcttcaat tggaacgttc ttccctaagg atgagctaat atagcacatg   99180
acctgaaaat ccttctggga gactccaggt aaaagggcct tgactgcacc agggagagaa   99240
gctaagttgt agatttgggg gaaatgagtg ttagaacagt gagtgctcaa gggaagtagt   99300
taagtgagcc atgagataca aagtctgcca tggcaaagta ggtggaacaa ccatgttatg   99360
agtataagtt ctgaccccag cttttcctgtg atttctacga cccttggtct tgaagatggg   99420 aaataaaatgg gtgcatgaca gaagttaaag actattatcg ggtatcaagt accatagcac   99480
tttttggagg cagaagagct tgacaaatgg gcatagtgta catagtaaat gatggtaagg   99540
gtaaaggata aaatgtatca tcttcctgtc atcagaatgg gaccagcact gtgtaaggtg   99600
ggcatgttaa tgacatgata tataagacag cttttgctac aataacaagg aactccctag   99660
gcctggcacg gtggctcatg cctataaccc cagcactttg ggaggctaag gcgggtggat   99720
tacctgaggt caggagtttg agaccagcct ggccatcatg gcgaaaccct gtctctacca   99780
aaaaatacaa aaattagcca agcaaggtgg cactgcctgt aatcccagat actcgggagg   99840
ctgaggcact agtggtgctt gaacccagga ggcagaggtt gcagtgagcc gagatcactc   99900
cactgcactc cagcctgggt gacaaagtga gactccatct caaaaaataa caataactta   99960
aaaaaagaga aatagctctc aaatcccaat agatccctat aacaaatatt tgtttcttgc  100020
ttctgagtct tcagattggc tgtgattaca ctgggtttgg cttggctgag ctcagctagg  100080
ttctgctgag ctcagcttgg ctccaaggtt tgggttgagt tcaggtctgc tccacatgtc  100140
ccttcacatg agaagcaatt gccaagaggt caagtcaaat catgcagcac atttaaaact  100200
```

```
tctgctgggg gaaaatgtgt ctgctcacat tccaatgacc aaagcccaaa gttagaaggg    100260
caaggaatta gactctacct attgagatgt actacaaagt cacatggcaa aaagcttata    100320
attctaataa aggaactaag cagaatcact aggagcaatc acctagtccg ccacacatgg    100380
agatgtgcca cagggactca gagactggaa ggaattcccc agggccagag ttctcctggg    100440
aaactacagc ctccaccatt gcctcccaga tttcatcagc atctctgtag tctggctcat    100500
cagaggccac aacggagata aaggcaaata aagacttcag ctgctggcaa gctgcagata    100560
tctccatgga tcagccaagc ccatgtctct ttctgaaaca atcagtaatc ggggaagcga    100620
ccacagaaaa gcgtaataca aactacctat ggtattggaa gaatcccagg aatcgttgga    100680
ggtcttgaat gaatttgaag agggtactca gttcaagact actttaagac acacactttg    100740
tagatgtccc aactagatac tgtgtggcct gggaattctg caatgtttac ttttttttcaa    100800 ttatattatg ttataatata tttataagaa atatatatca tatataagat tatatatagc    100860
ttatatatct atatataatc tagatatatt atatatctaa atataatctt tgatatatat    100920
ctcatatatt atcttataca tatgatatat tatcatatac atgagttata cgtatctcat    100980
atatattatt ttcttatata tatgaaatat atctcatata tataagatat gagagctata    101040
tatctcatat atagatagat atagatatct atctacatct atattcccag ccacacagt     101100 gtctagttgg gacatctaca aaatgtgtgt cttaaactag tcttgaacga gtaccctctt    101160
caaattcatt caagacctcc aacgattcct gggattcttc aataccata ggtagttgt      101220 attacgcttt tctgtatatg agatatatat ctcatacaca gatagatata gatcattcca    101280
tcacccaggc tggagtgcag tggcacaatc atagttcatt gcagcctcaa aattctgggc    101340
tcaaccgatc ctcccacttc agcctcctga gtggctggga ctacaggtgt gtgccaccag    101400
gcgggggcta atttttcttt ttttggagac agagtctcac tctgttgccc agactcagat    101460
gtagtggtgc aatctcagct cactgcaacc tccacctccc aggttcaagc agttctcctg    101520
cttagcctcc caagtagctg ggactacagg cacgtgcaac cactcccagc taatttttt     101580 tatttactta gagacgaggt ttcaccatgt tgcccaggct ggtcttgaac tcctgagctc    101640
agatacctgc ccgcctcagc ctcctaaaat actgggatta caggagtgac ccacccactg    101700 ccccccagcct tttttttttt tttttttttt ttttttttt ttggtaggga caggatttcc    101760
ctatgttgcc catgctggac atgaactcct ggcctcaagt gatcctcctg cctcagcctc    101820
ccaaagtgct aagattatag gtatgagcca ccacgcctgg cccaatattt ctaaaggccc    101880
ctcaagaggc aaaagtgggc aaaggacttt taaggacaaa aaatgcctag tattgaatat    101940
taagttgttt actgtgttgt aactctcttc catgacttca gtaaagcaga gtaagcacac    102000
acatgcccca agacacagta acctctgttt ggtagtacag cccatcacaa gcagctgtgg    102060
ctgaacccct gggtaccagg actagagagg ataacttcat tgtaagttcc actggatgtt    102120
aggctgaagt tgcagccccc atcaagccag gcttggtgtc tggagcgggc ctgaaggtag    102180
agattctgca aaaggatcta actggggtga tattcaaaaa atttagaagc cagaatggca    102240
caggtcctga ctgataagaa ccagagccaa catgctgtga tctgcataca agtgccagtg    102300
atccctgcct ccagctgagg agggctgtga aggatggagg ctagaaatcc atcaggagag    102360
ctgacattga aaggtgaatg ggagcagcac ctgccagcgt gacctgctgc tttcctgcat    102420
gcaaaggact gtgcatttca acctgagacc ctggggttcc tgcagggcat cagctagatt    102480
tgtcttcctg cctggggcga tcaccaatta tatgtgctgt gaggcaaact gtcctcccac    102540
cagaggagga ggtgaaggga tttacagaat ctctctctga tctgacttat tagagaagtt    102600
```

```
aaaggacacc tgtccaggag gcagcacagt gcagagataa agaagtcagg attcaaattt  102660
gtcctatctg ggaagcttag acaagagctc cttaacctct ctcacactca gtccctcat  102720 ctggaaaatg ggaatcctaa cagtgcctac ctggcaggag catggccaca atgaaatgag  102780
ctaatgacac agtgaaagcc cttagacagc ctgacccaga gtcagccctc tgtaatggga  102840
gtcattattc aagatgggag gaaagaaaca ggaattagat cagaaacaaa tgaccagaaa  102900
gagagatgaa atacaaaagc tacatgaagt cggcagtgtg aagcctgact cgcaggagag  102960
tggattttgt tactgtttgc ttttcttgt ccaggataat ccaagactgg cagaaagtga  103020
gaataccgat tgagatccaa ggacatcctc atgggagtct gtgcagacac gttttcatca  103080
agaacccctc tccaagcagc tggtccagcc cagctaaact gggggctgct gtttgtaaga  103140
aaattaatgc tctgggccaa gcacggtggc tcatgcctgt aatctcagca ctttaggagg  103200
ccaaggcagg cggatcactt gaggccagga gttcaagacc agcctggcca acgtggtgaa  103260
atcccgtctc caccaaaaat gcaaaactta gctgggcatg gtggcgcatg cctgtaatcc  103320
cagctactca ggaggctgag gcaggagaat cacttgaacc cgggaggtgg atgttgcagc  103380
gaaccaagat catgccactg cactccagcc tgggtgacag agtgaggctc catctcaaaa  103440
acaaaaacaa aaaaattaa tgttctgtac ctgaggagca cccatttgct gctacttccc  103500
tgccaggatg aaggaaaacc aagtcagaca ttaaataaca cgtgcaggat cacaggatca  103560 caccttcac actgcagtct tagttttcta taaaaccacg tgacctctga aaatacactc  103620
cagcctctgc aacacctact catgacgctt tgtaaaatcc accgccttt agggacacca  103680 agattttcgg aaacatgcag ttttcttacc tccagatgag atgtctactg tggataggtg  103740
actaggagga gaacccaagg tgtgctgatg gcagaacaga agcacctagg atgccaccag  103800
ggaaacgccc tgacaagcag ctgtgatgct gtcttcgaga aggtgtttgc aaacaccact  103860
gctgcccccc ttccctgagc cctgacttcc taaacctaag gctaaaagca tcctggcaat  103920
tcccggaagt aacttcattc tagcaggatc gagccagtgg gtggagtttt ctcagcccgc  103980
caggatcaca tcagtgactg acttacccaa tgtacttta ttttttattt caaccaattc  104040
cccaaagccc agagcaactt aaaaccagaa gagccaccac catctccacc aaaaacaggg  104100
aatattttga gagtttaatg ataacttcac agccatccat tcagctgagt cccaaggaaa  104160
tggaagacac ctgaaaaatg tatttttaaa ttgatttaac gttgagccat gttaaatgtt  104220
ttaacttcca accaatgcaa tgcccaccaa aacatcaatt agtcccagca atcaggcaag  104280
aatattggct tctgctcagg gattcattta tttcagctct gctaaatatc gtagaggaga  104340
aatccaatgt agcctgtagc ttcaagaaag tgaaattaag cccaagtaga aactagatga  104400
ggccctggct aaaatggtgc ctttttcttgc actgcctctc tctggtatct ctctaaagtg  104460
agggcagcaa cttgattgta agggtctcgt gctgttaaca gaaaacaccc ttccttcccc  104520
acaggttctc tgtctccaag ctggaaaaca aagaggctg caatgggaca gagaagggct  104580
tcctgctgag gagatgagtg ggcttaagaa tttgcaagat caaaaatcaa acaattaaa  104640 cccatggaga tagagtagaa ggagagtgaa cagaggctgg gaagggtaat gggagagttg  104700
gtggggagga ggcagatggt taacgggtac aaaaaaaaca gaaagatgag taagacctac  104760
ttttccatag cacaacagga tgactatagt caacagtaat tttttttttt tttgagataa  104820
cgtcactctg tcacccaggc tagagagcag tggcatggtc tctgcccact gcaacttctg  104880
gctcctcagt tcaagcgatt ctcctgcctc agcctcccga gtagctggaa ttacaggcgc  104940
```

```
acaccaccat gtccagctaa tttttgtatt tttatagaga tggggtttca ccatgttggc   105000
caggctggtc ttgaactcct gacctcaggt gatccacctg cttcggcctc ccacagtgct   105060
gggattacag gcatgagcca ctgcacccga ccctatagtc aataataatt taatcgcaca   105120
ttttaaaata actaaaagag tacaattgga ttgtttgtaa cacaaaggat aaaggtttga   105180
ggtaatggat accccatttt acatgatgtg attattacac atcgcatgcc tgtatcaaaa   105240
catctcatgt accccataaa tatatatacc tactatgtac taatgaaaat taaaatttaa   105300
aaaaattaaa aataatttgc aagatcattt ttaataatta ttttcatttt ggggtgcatt   105360
ttcaccatca aggccccagg gtttccctgc cctagatgag ggtctggatc cagggaaggg   105420
tgtcccacca tctggagcat cctgtctcta cacatgttgg ccagctgctt ggggcaacac   105480
aggacgatgc gctcaggcca ctcaccacag gagcttggcc attagaacca gcagggggaca  105540 accaagccaa agaccccacg actggagagc tcctaaaagc aaatacaaaa taagagtaca   105600
catgaagttc tggcagcaag cagaaggtag acacatgatg tccaactccc cgagtctctc   105660
tctggggcca cttgatgcag agccttgatt tgttcgtctc ttaaatggga acaatgatcc   105720
ccaaagagga ggaggggtgg gggagtgaga attaaatgag attgtgtcag tcagcatgta   105780
ctagggagct tgttagaaac accaattcca ggatccctg gagattctga tttagcaagt    105840
ctgccaggag acccaggaat ttgtatttta agcatctctc ccaggtgatt ctgataatta   105900
agcaacttta ggaagaaaaa gattagggct ctggtccata ggaagggttc atccaatggc   105960
agccctcact taggcccttg gggtgaatga aggaggggca tccaggatct tgcccagcca   106020
gggacatgca ggaaacatct ttttaagggg ccctcatcac tttctgacac tgctgtttca   106080
agggaaaact ggtcacacct ttctgcaggg gatttgacaa catccattaa aaaaaaaat    106140 ttaagacaga gtctcgccct gtcacccagg atggagtgca atggcgccat ctcggctcac   106200
tgtagcctct gtctcccagg ttcaagcgat tcctctgcct cagcttccct agtaactggg   106260
actaaggcat gtgccaccac acctggctaa ttttttgcatt tttagtagag acggggtttc   106320
accatattgg ccaggctcat ctcaaattc taaccccaag tgatccacct gcctcagcct    106380
cccaaagtgc tgggattaca ggcataagct gccacatccg accacatcc atcaaaatta    106440 taaatgcaga ccctgtgatc tagcaatctc actttgaaga gtttatccta cagacatact   106500
tgcacagatg caaattatat caggtcagga gctgcagcat tgttcataac agcaaaaaaa   106560 aaaaaaaat agaaacaact gcaaggtcca tctacagacc tctggttgaa tacagttacg    106620
gcatagccat aaaaccaaca atggcacagc tcctgtgcac agatacagaa ctccctccaa   106680
agtatattgt taggtgaaaa atacaaggtg cagaataagg tgtataataa gcttttgtga   106740
aaagtgcaga gatcatctat atttgatttg ctgtgtatgc atagaatatc tctgacaaa    106800 tacacaagaa gctgctaaca ttggttgcct ctggggaggg aacagggtgg ctgggggaca   106860
ggggctggag gaaagagattt caccacatgc cttgcagact ttatatattc ggaaccctgt   106920
gcattatcta ttgcacatat tatctattca tgcaaaacgc tataacattt acaaataact   106980
ttcaaatata tgcatatcat atttcaatgg aaagtttttt ttgttgctgt tgtttgttt    107040 gtgatggagt tttgctcttt tgcccaggct ggagtgaact ggcatgatct cagctcactg   107100
caacctctgc ccccagtgtt caagcaactc tcctgcctta gcctcccgaa tagctgggat   107160
tacaggtgcc ccccaccaca cccggctaat ttttgtattt ttagtagaga cggggttttg    107220
ccatgttggc caggctggtc tcaaaactcc tgacctcagg tgatccgccc acctcggcct   107280
cccaaagtgc taggattaca ggcatgagcc aatgtgccca gcctcaatga aaagtgtttt   107340
```

```
aaagtaataa tataatacat caaaaggcat gatttatgtt ttcaagtgcc acctctggcc 107400
acttgtggct gtagaaatgg ggaatactcc aattcaccat ccctatgtga aggcaggaca 107460
gggagacatt caagtcagga aaaggtggag tggaggtttt agtcaagcac caagtcctct 107520
gacttctctg ggcacttgcc catgccggta cctactcctg agacactgtc tacctcgcta 107580
agcccatctt cttctcacct tgtgtctcac ctgagacatc actgacttta ggaggtttcc 107640
tgacccatgt gtgttcccca tctcagcacc cagcacctgc ctcatgttca ccagggtaca 107700
tgtcttccct ccccgccagg ctgcactgag agctcaatga gggcagggaa catctctgtt 107760
ccccatcttg ttagaagcta tctccccaga gcatggtcca aatgtggtgt taagaacaga 107820
agttatcaca aagaagtgag aaagtgaagg ggaaatgggg agagctgtaa gaaaggcatg 107880
ggggagaaaa aggaaagaag gccatgttcc caggatccaa tgccactccc tggggaggct 107940
tctctatctt agctcagccc tcagtcacta tcaccctccc tggtcttgtc agatttgaaa 108000
tatcttcttc atttacaaga gggccttatc tatcttggtc acctctgtat tcccagcccc 108060
tactgcggac ttgaacata gtaggtgccc agtaaacatg ggttgaatta attaatattg 108120
gacaggccag gcttggtggc tcgcgcctgt aatcccaaca ctttgggagg ctgaggtggg 108180
cagatgacct gaggtcagga gttcaagacc agcttggcca acatggtgaa gccccatctc 108240
tactaaaaat acaaaaatta accaggtgtg gtggcacaca cctgtgatcc tagctactgg 108300
gaggctgagg tgggaggatc gcttgagcct gggaggtgga ggttgcagtg agccgagatc 108360
gcggcactgc actccagcct gggcgacagg gcgagactct gagtcaaaat aataataata 108420
ataatagttc attattattg gatagtgagg agggagtttg caaggagcg gctaaaatga 108480 aattagtcct gagtttctga tgttatgcgt tctgggtagg ggcgggagaa ctggaagatg 108540
tttaatgccc cccacccaag ggcagccata gttgagaatc actaattctg aagcttggta 108600
gggaagcttg atagggactt tgggtttttc actgagggca gaatcccag tgactgtcag 108660 agacctcgct ctgaatctta agaacctccc caccccaggc ctgacaggga ggacaaggaa 108720
ggagagtggg gctgggacgc ggggcagagg gcggctctgc tcacctgcgg gagaacgcga 108780
ggatgaggtt ctagtgggac cggcgctagc gggcgcgtcc tgccaggagt gagtcttggc 108840
gccatctagc gcctgctgga ggctctgcag ctgcagtgga ctgagccgcc ggcgctgggc 108900
gtgggtcacc gccgcggcgt tctccggacc cagggaggcg atctgctccg cggacagctc 108960
ctgcaggagg caaaggggca gcaccctcac acggggcccc tccccggatt tcccacatct 109020
cgggcgtccg cgcaggatgc acacaacttt gccatcccct tgtgtgtatc atgtgtggtc 109080
ctctttaaga tatttcctta aaattagatc actcttgcac taccaaagta aatgcattta 109140
aaaatagaaa atttaaaatg gaagtttcca aaaatgaaaa gccggcagac ttgccataag 109200
caagcattaa ataggagccg caaaataaaa ataaaacaat attgttgaat cctagctaga 109260
tttgtccgcc aacaatatct gaaccctgg cctcttggaa aaaaagaga gagagagaga 109320 atataaaatg tactatacag ggttaaattg acacttcctt cttgaagtat ttagaagtac 109380
taatggagag ttgaaaaggg aagcatgatt tcctccctat gtggcaatgt tgtttaatgc 109440
aatgcaggac agcttcccag tgcttcaagt cttccacctc ctgaaacact gatgtggagg 109500
gggaaacaca ggccttaaag atcagaggcc tgaattcgag cccctgctct gccacatact 109560
tgctgtgtca ccttgaacaa attacacagc ctccgtgggc tttggggata aatgtgagac 109620
ggcatagaga actcatctcc tctgctgact gattctgatc ctttggtttg actgcctgag 109680
```

```
caccatgtga tgagctctgt gagggctcca tggagggaaa atgcagtcat ctattggtga 109740
tatctgctat ggacaacatg agttggaaat tctgccagcc agactatgtc ttcaaggact 109800
gtgaacaagg tgtcttctga agtcacttcc agatcaaagg acttggtgac tcgttccaat 109860
gggactggaa tacgaagggg actctatatc atcatgttta ttttctaaag gccctgaaga 109920
atctgggaaa gatgcttatg ctccctcatc ccttcctctc ctgtcagtca ccctctcctc 109980
ctcttttgtc caggtagata cttccctgga atcatatccc tctgtgtaaa gcccttccag 110040 gaacccccact ccagaacaca gttcaggctc ctggaaaaaa ctctgccac ctctccagcc 110100 tcacacatgg cattcttcac tccaggagag tgggtgccaa tatttacagt tccctagagg 110160
cagcatcttc ctgtgcacct ctttctgcct ggaacactgt ttcttcttca tcgccagctg 110220
ttctccaaga ttcagcatct ggtcggtcaa gcgccatggc tcatgcctac aatcccagca 110280
ctttaggagg ctgaggcaga atgattaacg gagctcagga gttcgagacc agcctgggca 110340
acacagtgag accccccttc tctacaaaaa gttttttttaa ttagccaagt gtgtagtcct 110400
agttacttag gctgacgtga gaggattgct tgagcccagg ggatcaaggg tgcagtgagc 110460
catcattgtg ccactgcact cccttgggca acagagtgag actttgtctc aaaaaaatta 110520
aaattcagca tcacctcctc tcctctcact acacacacac acacacacac acacacacac 110580
acacacacac ggtggggtgg tcagagaggt acttttttgg cttccatata ccattaacac 110640
agagtctgta ttctaaaaat tatctctttt atcaatgttg ctgacttgcg acccacaggc 110700
cagattgaat ctctaggcct acggcactgt gttttcaaaa ataaattcag attggctgcc 110760
aacatttaat tatcaagcaa ttccatatga aaatgaagat ttctgacttc ttctcgaaaa 110820
aagtgaaaag gaaaattcag caatcttggg cccacatggc cacactgcat gaatgtgcta 110880
ggaatgagaa gcagcctcca catttagaca aggctctcca gttcacttcg gtctctaccc 110940
agcctactgc accttatgtt accttttagg cccctgaagg cactatgtga taacccttc 111000 acctgtgcat ccttaggtgc acctaccctg gagcctgcca caatgtaggt gatcagtagg 111060
gatttctgga atagataaat acctgtacaa ggaagcagca caacagcact ccaaacaaga 111120
ccaagagaaa gtgcttagca aaatgccagc atccaagacc aagctgcttg tcccatgcag 111180
agtgccccag aggggaagca ggtatttgct caatggcttt gaggactgct atttattgcc 111240
ctcaaacagc tattatgcct gcaatgtgct cggaactgtc caggatgctg aagtgattga 111300
aggttggctt tcttttttttt ttttttgagac agagtctcgc tctgtcgccc aggctagagt 111360
gtagtggagc gatcttggct cactgcaagc tccgccccc gggttcacac cattctcctg 111420
cctcagcctt ctgagtagct gggactacag gcacatgtga ccaccccagc taatttttttt 111480 gtatttttag tagagacagg gttttaccat gttagccacg atggtctcaa tctcctgacc 111540
tggtgatcca ccctcctcgg cctcccaaag tgctgggatt acaggtgtga gccactgcac 111600
ccggcctcag ctatctttct tgaaatgaac aagtgatgtg gcactggggg agttgtcga 111660 gcctggtttg tgtgttttat ccagaagtgc tggacaaaat gtgttccac attacgcagc 111720 aaacaggaac accagaatga ctgcctcctc atcagagcag actattccca ccaaacactc 111780
ccctaatctt gtatacagac agaaaaaaag gacctgtcat tagataccct gcttcccttc 111840
cttcaaatga tccaatttca ccctctcaat ttttcatag cagttttca cctgtcctct 111900 tgtgattttc ctaatacttt tctttaaatc aactaaaaat atatatatat agaaaaaaat 111960
atatatatat agagagagag agatggtttc gctcttgttg cccaggctgg agtgcaatgg 112020
tgtggtcttg gctcattgca acctctgtct cccgggttca agtgattctc ctgcctcagc 112080
```

```
ctcccaagta actgggatta caggcatcca ccaccacgcc cagctaattt tgtattttc    112140 atagagatgg ggtttcacca cattggccag gctggtctca gactcctgac ctcaggtgat    112200
tggcctgtct cagcctccca aaatgttggg attacaggtg tgagccacca tgcctgacct    112260
aaatcaacta aaatatttt  atttaattat atcttaaaag gaaatgttac agaggtccac    112320
aatccctcat ctgcaattcc aaagtccaaa aataatctga aaactgcaag ttttccccca    112380
aagtttaagt caaacttatt tatcagcaaa acttgacctg aagtaatgtg aggctattta    112440
tttatagtct ctatttattc caattagtgt ggcttgtcac agatttcttc acagaaatat    112500
taatgtgttt gcttacaagg tgcttcccca gacactgctg ggggtatgaa gttacataca    112560
gtaaatgtac agggtgatct tttcaaaatc tgagaaattc tgaattctga actatatctg    112620
tccccagggg ttttcgtaag ggtttatgaa cctgtcatac caccataagt agaaaatcag    112680
taccacctgc tagaagaaga gaagatgacc gtaaaaataa atataattaa actacatatt    112740
gtaattttaa gaaaaatgtt ttttaaaaac acctaaactc acacagatct cctctgaccc    112800
catcagcaga gcctggtcac aagcctctaa attccaaggc ccatcacctg tttccctgtg    112860
tgatttgaaa tggggtcaag ctcccatttc tccttgaaga actgagcacc tactttgaat    112920
atctcatcag gaaggcattt tattgctgat ggctggaaat atggcatcaa atccttgtca    112980
agcatccgga gctctgcctt agttaatcca gctggggaga aaaggaatc  acggggtttt    113040 agttcaagcc atcagaactc cgcttgtttt attaatggtg ctgcataatg ttcagatctg    113100
agtgttctag gcaggcatca ttccttacaa aaggccctgg aaatcacact ggggaatcaa    113160
gttccttcat caactcagaa aaaaaaaatg tgggtcacat tagccctgat tggcctccta    113220
cagtgaaacg catgcccaga aggaacttca atttacacac tttcaaattt tgtataaacc    113280
tacttagggg ccaattaaat cacattctaa actagcggtt ttccaaactt tagtgtacac    113340
aagaatctcc aaaagagctt gttttaaaag cagatttgca gacccaccct ctgcaacttc    113400
aaatcatgaa atgtaggttc tactgtaacg ccactgatgt ttgctacaca tggccaagga    113460
taatgtttta ttttgtgtcc ccacatttaa gtttggaaag agagagaaag gtatgctcag    113520
ggtgagtctt acctgcaatg gtcccaagct cctgcaagac agaactggtc cactcagtgg    113580
gatccccaaa cacaacttca gccttcctct taaactcggc taagacatgt gtgctgcaga    113640
gcagggtccc aattctggcc actaccaccc tggtagtggt taaagaggga gggatataat    113700
atgagcttgg actcttcagc caaaaacaaa caaacacaca cacacacaca cacatacac    113760 cacacacact gcacagtagg ctcagcaggg acagcagatc cagcttatcc cattagccca    113820 gtgggattt  agcccagaaa ggtgccaagt gtcaggaggt ggaatatctg gatggatgga    113880
tggatggatg gatggatgga tggatggatg gatggatgaa ttaacccatt tgccattttg    113940
cacattcata ttttagttac ctgaattctg agatctttat aagtgggatt tcagtgatgt    114000
ttatagcaca cagggttgca ccaagtccta ccaaatgaaa gctcttcagg tcctggatac    114060
tgtatcctga atcatccagg taccctttgca aaatggattc agcctaaaaa atagtaagaa    114120
taaaagataa accatccagg aatgatcaag gtccccaggc ctgaggggat aaataagctg    114180
ttgctgtagt ctcctgactg atctcccatc ctactcctct ggaatcccca ctccaaacca    114240
tcctggcctc tgcatccaag ttcatgtcct taagatacta cttcaactga gtatgtcccc    114300
taatctatga aagtgtcttc aggcaatgaa tctcttacat ccttcaccaa tattaaaggc    114360
acttgtgtcc tgtgtgtctg ctgcttattt ccttcagtca ctcttatgac cctcagacag    114420
```

```
tttggacata caacttcttc tgcatcagga tccaaacttt tccagcatct ttttccacaa    114480
cgtttcttct cccttttttt ttttttttc gttttttgga gacggagtct tgctctgtca    114540
cccaggctgg agtgcagtgg cacagctcgc tgcaacctcc acctcccag gttcaagcaa    114600 ttctcgtgct ttagccaccc aagtagctag aattacaggt gcacatcacc acatctggct    114660
ttttgtattt tttgtagaga cggggtttca ccatgttgcc caggctggta tcaaactcct    114720
gacctcaagt gatccaccca cctcggcctc ccaaagtgct gggattatag gcatgagcca    114780
ccgcacccag cctttccaca acctccaaca aaaccttata atttcctgtc tctttgcctt    114840
tgttcaaacc agtcctttca tctgaaatgc ccttctgcac ttccaagtgc agacattctt    114900 ttttttttt ctttggttca actcaaatgt caccttcttc atgaggtttc agccagaatg    114960 atttttctt cctctatggt cctacagaaa tatgtttacc ccttaatgat ttttcttcc    115020 tctgtggtcc tacagaaata tgttcacccc ttcaattcca atgtttactc ttcaattcca    115080
agagtagcac acaaaatgct ttggtgttaa actattttaa actaagcctt gatttaaggc    115140
ggctgacaca taagtctcca taattctagc acagtggcta ttcatcattc ataacttcct    115200
ctggagaacc acctctcttg tattcctgct tcatgtggtt cagtcaaagc taactgcacc    115260
aagttccagg agtgatgaat ttcaattcat accttagcct agctgcagtc actggttctg    115320
gattggacat gtgatttaac cagagtcaac cagaactttg agtggagcat taggggaaga    115380
gctttcttta ctctggactt gaacttagaa ggatatacac aaggatctgc tggaacctac    115440
cacatgcagg catagagcct gtctctcaat gaagccaaca caaagaaaag caaagttcaa    115500
aaacatgata agagacagat tcccacccag agtgttgaag atcctggatc cagctgtatc    115560
tgaacactac ccctgaactt tccagtaatg ggagtcaata aattcctttt tttttttttt    115620 ttttgagac aaggtctcac tctgtcaccc agcctggagt gcagcggcat gatctctgct    115680
cactacaacc tccctctccc aggttcaagc gattctcatg cctcagcctc cccagtagct    115740
gggattacag gcaggcatga acatgcctgg ctgattttg tatttttagt agagaagtag    115800
tttcactgtt gggccaggct ggtctcaaac tcctgacctc aagtgatctg cccgtttcag    115860
cctcccaaag ttctaggact acaggtatga gccactgcac agtgcaccca gccccttat    115920 ttgttcaagc cagtttgtgt tgggttttct gccacttgta actaaacatg tgctgattca    115980
ttttatctac ctatgtagga cctgaggagg catccaagcc aatcctatga agatcagcta    116040
caaaataaag tctgggctgg gcacggtggc tcacacctgt aatcccagca ctttgggagg    116100
ccgaagcagg aggatcactt aaagtcagga gtttgagacc agcctggctg acatggtgaa    116160
agcttgtctc taccaaaaaa tacaaaaatt agccaggcat ggtggcacgt gcctgtggtc    116220
ccagctactt gggaggctga ggtgggagga ttgcttgagc ctgggaggtg gaagttgcag    116280
tgatccaaga ttgtgccact gcactccagc ctgggtgaca gagggagact ctgtctcaca    116340
aaataaagtc tggttccttc agtgctcatg ggagcaagta aaagagatta taagacctca    116400
caaggcaaag atgaggagac atccaaggag agacccctaa gtggaagcga aaatcacagg    116460
ctatagtcaa tcttcccaac tctctttgct tttttttgtt ttttttttt gagacagcgt    116520 ctcactgtgt cacccaggct ggagtgcagt gacatgatct tggcttactg caacctccat    116580
cccccagggt tcaagtaatt cttatgcctc tgactcccaa gtagctggga ttacaggcgc    116640
ccgccaccac acccaactaa tttttgtgt tttagtaga cagggtttt caccattttg    116700 gccaggctgg tctcaaactc ctggcctcaa gtgatctacc cacctcagcc tcccaaagtg    116760
ctgggatcac aggcatgagc caccatgccc gaccccatc tccgtttaat gttagtcatc    116820
```

```
cccatcacac aatatagatc attaaggtgt tgagagaaag tgttgaggaa gattgtgaaa   116880
tgttgcaatg aaattccgtc ttcatgggct ggtgcttccc accccctcagg tgtgtttaaa  116940
```



```
cccatcacac aatatagatc attaaggtgt tgagagaaag tgttgaggaa gattgtgaaa   116880
tgttgcaatg aaattccgtc ttcatgggct ggtgcttccc accccctcagg tgtgtttaaa  116940 tgctacctac tcagagaaaa ctgccctctg gactctttca tctcaaacag cccttcttcc   117000
cactattccc atgagcacct tgtccatttt ccgcatcact tatcgtgatt tttcaaattt   117060
ttcactttga ttactcactt ttttgtctgt atcaccaagt aggctcccaa aagaaaagga   117120
ccatatccag gtagtttacc aatgagtccc cagcacctag cataatgcct gccacagagt   117180
aggagttcaa taagtacttc ttgagtaagt aaatgaatga gtgaatgaat gaatgaatga   117240
aacaacatct gagtgagtga cttacaaaag tcgtgggcaa tatatattat ttgacatgct   117300
tcattttgct gccttcatgt aatagactgg cttcaggaag atttctcatg tttctgaaaa   117360
tcggactggt cagtgtcctc atcaagttgt cctccatgat tacaaagctc acagctacta   117420
tgggggcggg ggatgcagta acaccatgct tagacttata tgtctttgac ttaatgggac   117480
tgtatatcca aagtggtaat agctaacatt tattgtagct aacatttctt gagtgcatac   117540
tgtgtgctgg caccactttg accactttac acatactatc tcatctaatc ctcctaaata   117600
acactatgag gtaagtatta atagtatccc tagtttgcag atgagcaaac tgaggcaagg   117660
agaggttaag taactaggcc aagatcacac agctagaaaa tgatcgttct ggccaggcgc   117720
cgtagctcct gcccgtaatc ccagcacttt gggagacaaa ggcgggcaga tcacctgagg   117780
tcgggagttg gagaccagcc tgaccaacat ggagaaaccc cgtctctact aaaaatacaa   117840
aataagcagg gtgtgatgat gcatgcctgt aatcccagtt actcaggagg ctgaggcagg   117900
agaattgctt gaacccggga ggcagaggtt gcagtgagtg gagattacac tccagcctgg   117960
gcaacaagag caaaactcat tctaaaaaaa aaaagaaga agaagaaaga gaaagaaaa    118020 tgatggttct aggatcaaaa cccaggcagt ctgattccag ggcccatact cttagccagt   118080
gaaggtgttt ggctatggag aaaagatgga gattcaagtt agttttcaaa tttttcttat   118140
taagtcttca taatcaggtt tcactagttg actcagagca atttgggctc ctcaactatc   118200
aggcacgctc acttttaaaat gaaagtgcaa aaatacaatt taaataaaat tactttgaag   118260
atatggtatt aaattgtcct tgccactgaa acccggaaaa tgcaagctca gcctgcaagg   118320
tgataagtta aaataaattt ccttgagtga cgagaccagt gtatatgtaa tgattccaag   118380
acaattaata ccaacacttt taggcaatat taactgttga aaaatgaata gctttaagat   118440
ttcaatctct ctgttcatcc ctctggcttc tataatagtt ttttccctta tattggtttt   118500
tgagctgaac tatctgttaa tgtagttccg tcaggtctga ctattaatct agaaacctgc   118560
atttaaggtt gattgggagc taaagttgaa gaactgacta caaatgatac atgcaaatgt   118620
taggttttca tatcctcttc aaacatattg ataaatctca ctgccatcca tgagaattaa   118680
aatcggtgcg aagggaagga gatacccctag tttctgcatg tattttttctg tttctccgag  118740 cctgcaaata gaatgatttt aatagcacag tgtgatgtgg cacttctcaa actagtcaaa   118800
accagtttta gagtcaaaga accatgggat tatagaatat cagactggaa ggaacctcag   118860
attgttgggg ctaaccctct catcttgcaa aggaggagac taacccagag aaaggggctg   118920
taatgatgat aatgttgatg atgacaatgc aatgatgtca atatcaacat aaaaacagct   118980
aattttattt gactactatg taccagacat tgttcaaaat gttttcaagt attaactcat   119040
gtaatcttca tggccaggat ctgcatgttg cccagctcca ggggtgcacc attcacagtg   119100
tattctgttt gaatggtgcc actcagagtt atgaaacatg gccaccgtga ttacaaaaag   119160
```

```
ctcaaaagag taggggggaca ttcattggtt ttggctgctc agcgtccaca cttttctttt  119220
ggaaaattac cctccattag cttcctattg ctactctacc aaattacccc aaacatagtg  119280
gctttaaaac tacacgttta ttctcttata gttctggaga ctgtatgtcc taaaatggac  119340
tagaaggatg ggttccttct gggagttcta agaagaattc attttcttgc tttttctagc  119400
ttcaagaggc cacctgcatt tccttggctc atagccccat cctccatctc caaaatcagc  119460
agcagagcac cttcagatct cttttctaggt ccctctgctt ccattatcat gtcaccttct  119520
ctatctatga ccctccttgc tccttcttaa aaggacccctt gtgattacat tgggcccacc  119580
caaataatcc aagataacct cctcatctca agatccttaa tcgcatcttc aaagtccctt  119640
ttgctccata agttaacata gtcacagctt ccaggggttc agacatggac atctttcggg  119700
gaccttaatc agcccaccac atatccttcc ccactcggct catgtggtca tgagatgctg  119760
ataagatgga ctccgctccc tgatgcaggc ctcgccaacc aacatattca acccctgacc  119820
agagtggttg ctcaggggcg ggcaactaca tgagtggagt caatgctgag gcttttccaa  119880
aaactaataa agaagaggca cattttttatg ggcttgttaa ttaggttgta tataagccta  119940
gtgctgaaaa tgaccactga gagagctgcc taagaacgaa gataacatgg aagggctaac  120000
acttcccttt ccagcagtac agtggattag acaccctaaa ctcctctccc aatcaaaaca  120060
attaaaattc tgggaagaac ttcttcttta gcccatgaag gattaattaa cataggaatt  120120
ggccacccac cataaacaac tagaaaattt aacaaaatac atcagacaac tgcatccgga  120180
tatggaacaa cagaatcata atcccagaag aagaaaaaca aacaagatga gccttaaaat  120240
taccctcact tactgccaaa aagcagtttc caagacatgg atcaggaaga ggaaccaaaa  120300
caagcccagt ggcccagctg agtggaggat acagatatcc aagttcagag aggccacggc  120360
acttatcact tgggcaaagt attggagagg aggaaactgc agagggttcc agaaagctgc  120420
agagatgtct agtactgact gctatttttgc acatgcaaag agtgaaactc cacataggca  120480
ggaaaagagt catcagtaat cagaaaggat taggctgagc aacttccaga gctcatatgg  120540
agctggaaat agttcacatt ctccaccagcc aaagtagaga gatcttgaaa tacatggagc  120600
attaggtaac atcctcaaag gaatcatgtc acagtaatga tgataaatta acaacagaat  120660
aaaggtcact ctggttttac cctaacaaaa ctcaaaagga agcatcaaaa ggatcaagct  120720 gattttgaaag taacttaagt gtatgacaga acaaagccca atactcttca aagaaataca  120780
actaaatcaa atactcaaca atgtaaaatc cacaatgctc atcacccaat caaaattgct  120840
aggcttgcaa acaaaaaaag aaaatatgac tcataactaa gagaaaaatc agtcaacaga  120900
aacagactca aaaatgacca tcatgaggaa attaacagta aggatatgaa ggcagctctt  120960
ataaatatgg aatagttaaa agacccagaa acatccaccc acctgtcccg gggtccattc  121020
tgtttgccag cttagggaag ccacagtgtc tatggagctg aggtccagct gctccagctc  121080
actctcatta agagccagag caatgcgccc cagggagacg atatggtgtt ctctccagta  121140
agatggcatg tcccaaacct ttaggcaaaa aaagaaaata gattagactg aacactgtga  121200
tggtatttac aatgatttga atgtttgtgc ccctctaaaa tgcatatgtt aaaacctaat  121260
ctccaatgtg atagtattgg aaggttgggc cttgggagat gattaggtca taagggtgga  121320
gccctcatga gtgggattag tgcccttgta aaagagaccc cagagagcta gctacaagct  121380 agtcccttttc caccatgtga ggacacagtg agaaagcacc atctatgaaa acaagtcct  121440 taccagatac tggatctgcc agtgcttcaa ttttttgatt tctcaccccccc agaactgtga  121500 gaaataaatt tctgtttata agttaccagt ctatgatatt ttgttatagc agcctgaatg  121560
```

```
gacaaaggca gtatctaaaa tagacataag gaggctaggt gcggtggctc acacttggaa   121620
tctcagcatt tttggaggcc aaggcatgca gatcacatga ggccaggagt tcaagaccag   121680
cctggccaac ataacgaaac cctgcctcta ctaaaaatac aaaaaaaaaa aattagctgt   121740
gcatggtggc gcacatctgt aatcccagcc acttgggtgg ctgaggcaca agactcactt   121800
gcagaagttg cagttagcca agatggtgcc actgtactcc agcctgggtg acagagcgag   121860
accctgtctc aaagaaataa aaataaaaca gacataggga aacctattgt gcagcatggt   121920
gaccacagtt gataataatg tgttgaatgg ttgaaaattg tgaagagagt agatgttaaa   121980
tattctcaca acaaaaactg acaacggaca agtatgaaag gtgattgaca tgttagcttg   122040
ctttaaccat tccccaatgt atacatacat caaaacatca tattgtatat atgtatacac   122100
cataaatata tataatttgt atttgtcaac tatcccttaa taaaaaataa ataaaaatta   122160
aaaagacata gggtaaatct taatataaag ctctctttta aatcaataat aaaaacatga   122220
ctatatttgt tttaaaaaaa agatagacaa aagacatcaa caaggaattc acaaaagaaa   122280
aattaaatgt atggggaaaa ctttattctc agtcataatt aaagaaatat acattaaaaa   122340
caatcagacc atgttgattc atcacatgtc aagaagtata aagacttatc accatttacg   122400
atactggaaa gatacaaggt aagggatacc ctcatttgtt gtagttgaga atataagttg   122460
gtacatactc ttgagagggc aatttggcta tctgtatcaa aagcttttaa agtatttata   122520
ttctttgacc cagaaattcc acctctggga atttagcctg agtaaatgag acaagtaccc   122580
aacagtatat gtataaaggc atacattgag gcattttttt aatgcaacct gaaagtctaa   122640
caattagcta aataaataag aactaaccat aaataaaatg aagttgcccc tgtggatacc   122700
tccaccaagg attggttcca ggacttctta aagataccaa atccatgga tattcaagtc   122760 ccttatataa aatagtgtag tatttgcata taatctatgc acatcctcat gtatactttta  122820 aatcatctct agattagtta taatacctga tgcaatataa gtgctatgta aatatgtaca   122880
aaatgttatg tcaaaaatgc tactgtattt ttatgtgtat tgtttttttat tgttatattg   122940 ttatttggat cattttttct aaatacattc tacctgaggt tggttgaatc tgcagatgtg   123000
gaacccactg atatggaagg ctaattgtat tacaaagcta tttaaaatac tgatataggc   123060
tagatgctgt ggcttacgcc tgtaatccca cactttggg aggccaggca gacagatcac    123120
ttgaggtcag gagttcgaga ccagcctggc caacattgtg aaaccccatc tctactaaaa   123180
atacaaaaat tagccgggca tggtggcgga tgcctgtaat ctcagctact gggaggatg    123240 aggcaggaga attgcttgaa cctgggaggc agaagttgca gtaagccaag accacactat   123300
tgtactccag cctgggcaac aagaacaaaa ctccatctca aaaataaat aaataaataa    123360 aatactgaca tagatgtaca ttttggatat gaaaaaatat gcagtctgta ctgttgggtg   123420
tagaaagcaa gttattgaat agtaggtaag tataatatca ttttgtaaa acatgagata    123480 tatgtatgaa atatataaaa taatatttt tatatacata gttttggagt ctggtaagct    123540
tcaagtgaat ataccaaaat atcaacagtg cttatctgct gaacagtgct tatcaaaata   123600
tcaacagtga gtaaaagatt atcactgatt ttcttcttta ttatttttctg acttttctac   123660 aataaacttg aagtactcat ataatacata aatacagtta tatttataat tttaagacat   123720
tgaattgttt aacccttgag ggtaactaga tattccacaa ccatgtaaag agctaaaaca   123780
gggctgggtg cagtggctca tgcctgtaat cccagcactg tgggaggcca aggtgagcag   123840
atctcttgag gctaggggtt tgagacaagc ctggccaaac aaacccccgtc tctactaaaa  123900
```

```
tacaattatt agccaggcat ggtggcttgt gcctgtagtc ccagctactc aggtggctga   123960
gacacaagaa tcacttgaac ccgggaggca gagtttgcag tgaacaacag atcgcgctgc   124020
tgccctccag cctgtacgac agagcaagac tctgtcttaa aagaaaaaga aaaaaaaag    124080 aaagaaaagc taaacaggc cacaaaggga ccttttcctt ttatttattt atttgagaca    124140
gagtctcgct ctatcaccag gctggagtgt agtgacgcaa tctcggctca tggcagcctc   124200
cgcctcccgg gttcaagcaa ttctcctgcc tcagcctccc gagtagctgg aactacaggt   124260
gcatgccacc tgtagagatg gggtttcacc atgtgggcca ggctggtctc gatctcttga   124320
cctcgtgatc cgcctcccaa agtgctggga ttataggcat gagccactgc acccagccta   124380 tttttatttta tttttgagac aaggtatcag ctctgacgcc taggctagag tgcactggcg   124440
caatcttggc ttactgcaac ctccacctcc cgggttcaag ccattctcct gcctcagcct   124500
cctgagtagc tggaactaca ggcacatgac accacgcctg gctaatgttt gcattttgag   124560
tagagacagg gtttcaccat gttggccagc ctggtctcga actcctgacc tccgtgatc    124620 cgcccgcctc ggcctcccaa agtgttggga ttacaggcat aagccactgc acccagccaa   124680
caaagggacc tttttaaaga tggaaagcta cttccagtcc tcttttttact cctttctgtt   124740 atattttcag acaaatttgc aaatgattct gagaaaacct gctgtgagca gcagctgggg   124800
ctctccaggt gaaggaataa agcctaattc ctgcaaaccg ccttggtcag aggcactggg   124860
acatccacag aacttgattc actgagcatc tgctagatgc caagacacat ctcatcccat   124920
tctctgccac agccctaaga gggaggaact ggaaatttcc tcctttctca gataaggaga   124980
tcacaatatc actgagctga tgcagtaaaa tttcaagatg atgtatggga aaactgctcg   125040
aggagggttc tatgtgcaga aatgctgaac tggttttggt gttttctttt tttcctctgt   125100
ttaatgtttc ctccctgagg tgggcttcac ctgtattgct ttctccttca gggtcatcag   125160
ctgaggccgg ctgaaaccct ggacagctcc cagcagttcc acggtcctga tgaatgtgtc   125220
ttcctccatg caccgcaggt cctccagggc ccagcaggcg ttggcttcgg ccaacttgaa   125280
gatgtcatca gaagagggg ccacgactcc atggcaacct gaagaaagga gagatgcagg   125340
gaaggagaag aggaaagaga atttcaggaa atgttagtgt attgaaatga gtaacattct   125400
ttgccagtca gatttatgca tggaagggac tacagagtaa aagcagagag caggaggcag   125460
ggaccagttt gaatcccact tctgccattt cttgctaatt actgggtaac aaagtcatgg   125520
aaatgccagc ttttttgcaca tccacatgca caaactagga gcggtgcaac attacaatta   125580
aactacaaat tccttgaggg cagtaagagc tggtggtgaa cagtcctgac tttcgattca   125640
aatccaaggc tatttaacct ctctgtattt cagttttctt gtctataaaa tggaaataaa   125700
atcgcctcat aggatggttg tgaaaactaa atgtgttata tgtaaagcac ttagaacagt   125760
gccacgcata cagtaagcac tcgatacaca atttctgttg cctatcttac cccctatgcc   125820
tttgagtttg cagcccagca taagattcc aaaattatgc agcagccttc ctataaaaat    125880
gggaagatgg gctgtgcggt ggcgcatgtc tttaatccca gcactttggg aggccaaggc   125940
agaaggatca cttgagccca ggaattcaag accagcctgg gcagcatggt aagacctcac   126000
ctctaaaaaa aaaaaaacta caaaatatta gctaggcatg gtggcacatg cctgtagtcc   126060
cagctaccca gcaggctgag gtgggaggat cacctgagcc tgggaggtca agattgcagt   126120
gagccgtgat cacacctatt ctccagcctg ggtaacggtg agaccctgtg tcaaaataaa   126180
ataaaaaata aaaaccagga agatgagttg ctgtccatga aaatcatagt gggggttgtg   126240 gcttcccat cccaagagaa aagagaaatg agcctattgc atttctcttg gcaacaggaa    126300
```

```
aaacatccat ttcggtcttt gaataatgtg aaccttacct actcaaacca gctaccaacc   126360
aacatgcaag tgagatattg tctttgctgg atctgatgtg cccaacctgg agaaaactc   126420 taggatcctt aagagcaacc ctggatttct tatcttagcc gcagaccacc actgatgctg   126480
acagatgcac caaccccacc caaggccagg gtatttcccg agcccatgg cctctctctt   126540 ctcattgcac cttcaatgga aattcactgc attccaatca cgaggcaaaa gtagaccaga   126600
tcaaagatgc cagttgtggt cctcaaacat ctttatcata agccacttgg agaggactaa   126660
agacccatcc ctccctaggc caaccccag cccaccctct agtgaaaaca acatcagtga   126720
tagcacagaa ctagagaggg cagaatggtt gactagtata tcaggaactt ggtcttatca   126780
ctgtgtctgt ccagggctta aatagagcc tggtacatcg taggtgttca gcaaatatct   126840
gtggagtgag tgaacacaca cacacaaatt aatataaaac caagcggtaa ttctgctaat   126900
ccatcaatca ctaaagcaca gcagcaatta atacccagaa ccaactaaag aacactcaaa   126960
ctatgcactg ataccagagc ttccttcccc tgagcatgga aagccttatt ttgtgtacca   127020
catgcacaca gtaagagctc tgcaatatga tgacatggac tgctagacct tgagggcagt   127080
gggagccagt ggtggtcacc accaactttg ggtacaaatc caagaactgc catttactaa   127140
ctctgtgact ttagacaagt cccttagtct cctaagcccc agtttccttc atttaaaaaa   127200
caagagaaca cccaagcctg gaaatctgca gccctaaatg ggaataggca ttcctgtttt   127260
cacgcccaaa tgttaggttt tggcctgcca catcccacta tcctgtaccc atataaaccc   127320
caaaccccag gctccatgag catacaagca gatgagcaga tgaacagaag agaagaggag   127380
cagaagagca gcatggcaga gaaggagca tctgaaggcc aagaagagtt tggctgggga   127440
cagttggaga ggagattggt cacaggacag ccaaactcca ggggaagatc atcttcccac   127500
tccatcccct ttctagctcc ccatccatcc caccgagagc cacctccatt acccaataaa   127560
accccacatt caccaagaaa aaaaaaaaac gggagaacaa gataatgcat ggagggataa   127620
tcacccaagg tagacacaaa tccaattgtg atacttcttt gctcgatgtc acacgatgcc   127680
tccacccaga gtaaaagcca aagtcattag ggtttccttt aacagtcact acatggctgg   127740
ccttgtctct cactcccctc caaacacact ggcccttacc tcccactcat ggaagtggtc   127800
ctgttgcact ctctgcctgg aagactctaa ttgaaaatat ccacatggcc cactctccct   127860
tgggtcttca ttcaaatgtc accttctcaa taagatgttc cttcatgatt ctcttttcac   127920
atgacagtcc cctctcaaca ctcgtggtgc attcccttgc tttatttcc ttcttggcac   127980 ttttcataca atataccata tattttactt atgtatggaa atttattgtc ttgctaccct   128040
ccatttgaaa gtaagctctt tatttacaaa attggtgctt aacgaatatt tgttgggtgg   128100
atgaaagcaa gcactgactg tcaactacta tcactggggg tgattaactt tgtctcctca   128160
tgcctggccc cagtctgcac ttagtaggtg catggtaata ataataaaat atctaacact   128220
tggacaggca tggtagctca catctataat cccagcacta tggagaccaa aggcaggagg   128280
atcacttgag gctcagagtt caagatcagc ctgggcaaca cagtaagacc ctatctctac   128340
aaaaaaataa aaaattatcc agatgtggtg gttcatgcct gtagtcccaa ctacttgtga   128400
agctgaggtg ggaggatccc ttgagtccag gaggtcgagg ctgtagtgaa ccatgattgc   128460
tgcactccag cctgggtggc agagcgaggc cctgcctcta taaatcaaa ttttaggccg   128520 ggggcagtgg ctcacgcctg taatcccagt atttcgggag gccaaggcag gtggatcacc   128580
tgaggccagc gttcaagacc agcctggcca acattgtgaa accccgtctt tactaataat   128640
```

```
acaaaactta gccaggcgtg gtggcacatg cctataatcc cagctagtca ggaggctgag   128700
gcaggagagt tgctgtaatc tgggaggtgg aggttgcagt gggccgagat catgccacta   128760
tactccagcc tgggtgacac tccagcaaga ctccatctca aaaataaaa aaaatcaaat   128820 tttaaaaata tataatactt attaaagatc tgctacatgc caggcattcc ggtaaacatg   128880
tttctgggtt taaacccatt aattctcaca ataacccagt gaggtagaga ctttcattat   128940
ccccatttga taaggatga aaactgaggc acacagaggt taaagagctt acccaaagcc   129000
acacagccag taagtggcag actcaggagt gaaatgtagc cagcccggcc ctgtcactgc   129060
tatgttaaac cactaatcca tgttggtcct ctaagtcaat cctactgaaa tgtttgttac   129120
acatattcac gcattaaacc tactagcctg ggtatggagt atgggacatg attccaggtc   129180
actttacaaa agtgtaactc ttttttttt gagacagagt ctcgctgtca cccaggctgg   129240
agtgcagtgg tgccatctca gctcactgca accttcacct cctgggttca agcaatcctc   129300
gtgtctcagc ctcctgagta gctgagacta caggtatgca ccaccacacc cggctaattt   129360
ttgtgtttct agtagagaca gggtttcgcc atgttggcca ggctggtctc gaactcctga   129420
cctcaagtga tctgcctgcc tcaacctcac aaagtgctag gattacaggc ttgagcaacc   129480
gcacctgaac caaaagtgta attcttttgc ttatagattt tgtcattcta ttgctttgca   129540
gacatttcat ccagttccct gcataaggag gcctcttgat gtcagggacc ctgcccaaaa   129600
cattaattac tatgtcagca atggctcaga taccctgaaa acactcacca ggcatagggt   129660
catagctggg gatcttatca ctgctgttcc gaacagactg aaagacagcc cagaggaatt   129720
ctttagtggg cagggtcctg gccatcttgg aagctgcttg cagaaggatc tcaggaaact   129780
gtgtgaaaga agatgaaaga agaggaataa taattaaaac cccttaaata cagattgaaa   129840
ttagagttga aactgtcaca ctacttactg ccttcattct ttgttatagc aacttctcat   129900
ataaatctat tccctagtcc cactaatgtg gtctctataa agaatcctat aaaatgatac   129960
tcaacttcaa taaaaatcca ataaagtcta aaaaacataa gtaaatcact tttcacccat   130020
cagattgtca aaaataaaat gaagtgctaa tacttaatgc tgggcacatt catttttccg   130080
tgggactgtc aaactgtgca ctattagcag agcaatctgg taatatcgac aaaaaatgta   130140
ggttaggcga ggtgtggtgg ctcatacctg taatcccagc attttgggag gtcgaggcag   130200
gcaaatcact tgaggtcagg agctcaagac tggcctggcc aacatggtga acccccatct   130260
ctactaaaaa tacaaaaatt agtcagtcgt ggtggcatga gcctgtcatc ccagctactt   130320
aggaggctga gacagaagga tcaccagagc ccaggaggct gaggttgtag tgagtcgaga   130380
gcatgccact gcactccagc ctgggtgatg ggagtacaac cctgtctcag aaaaaaacaa   130440
aaaaaatgta tgtgtaccta cccctttttt ggtttggtgc tatttctaag ttttttactaa   130500 acttatatt tgacatagtt tggatgtgta ccccacccaa atcttattga aatgtaatcc   130560
ccagtgttgg aggtggggcc cagtgagagg tgattggatc atgggggcag atttctcatg   130620
aatggttaaa tacaatcccc ttggtactgt cctcacaata gtgcgtgcgt tctctcgaga   130680
tcttgttgtt taaatgcatg tagcacctcc cccatcacgc tcttgctcct gtgtcggcca   130740
agtaagatgt gtctgctccc ccttcgcctt ccgccgatgt tgtaagtttc ctgaggcctt   130800
cccagaagct gggcagatgc cagcatcatg cttcctgtac agtcggcaga gccatgagcc   130860
aatcaatcct cttttcttgt ctctttttt tttttttttt ttcagagtct tgttctgttg   130920
ctcaagctgg aatacagtgg tgtgatctcc actcactgca acctccacct cccaggctca   130980
agtaattctc gtgcctgagc ctcctgagta gctgggatta catgcatgca gcaccaagcc   131040
```

```
aggctaattt ttttttattt ttattgtaga caaggtttca ctatcttggc ctggctggtc  131100
tcaaactcct ggcctcaagt gattcgccca cctcggcctc ccaaagtgct gggattacag  131160
atgtgagcca ctgtgcctgg cagtgtttgt ttgtttgttt gtttagacgg agtctcgctc  131220
tatcacccag gctggagtgc agggcacgat ctcggctcac tgcaagctct gcccctggg   131280
ttcacgccgt tctcctacct cagcctcccg agtagctggg actacatgtg cccaccacca  131340
cgcccggcta attttttgta ttttttagta gagacgggt  ttcaccctct tagccaggac  131400
ggtctcaatc tcctgacctc gtgatctgcc cgcctcggcc tcccaaactg ctgggattgc  131460
aggcatgagc cactgcacct ggccctttt  atttatttt  ttttaattta acttttattt  131520
taagttcagg ggtacatggc aggtttgtta tataggtaag cttgtgtcat ggaggtttgt  131580
tgtacaaatt atttaatcac ccaggtatta agcctagtac ccattagtta tttttgctga  131640
tcttctccct cctcccacct ttcactctcc aataggcccc agtatctgct gttccattct  131700
atgtgacaac gtgttctcat catttagctc ccacttataa gtaagaacat gcggtatttg  131760
gttttctgtt tctgcattag tttgctaagg atgatggcct ccagctccat ccatgtccct  131820
gcaaagaaca cgatctcatt cttttttatg gccacatagt attccatgta aacctccttt  131880
ctttataaat tacccagtct caggtatttc tttatagcaa tgcaagaatt gcctaacaca  131940
ggtcaggtgc ggtggctcac acctgtaatc ctagcacttg ggaggcccaa gcaggcagat  132000
cacctgaggt caagggttca agaccagcct ggccaacacg gtgaaacccc gtttctacaa  132060
aaaatacaaa aattcactcg gcatggtggt gtatgcctat aatccctgct actcaggagg  132120
ctgaggcagg agaatcactt gaacccagga ggtggaggtt gcagtgagcc gaaatcgtgc  132180
cactgcattc cggcctgggc aacacagcta gactccatct caaaaaagag aaagaaaaa   132240
agaattgcct aacacaacat ttgtcatgaa aaggaggtga agaagggttg tctcaacatc  132300
ctgggtggag actagcaatg aggggactta ggggactttg ggttgccttg gagaaagtgc  132360
catttctcat ctagaacgaa tacactttgt caagacttgg gattttatta gaaggcctgc  132420
ccatgggccc agataatcca tcaggctcta caaacagcta tgcctcactg ggtcccggct  132480
cacccagaga gcaagcctct cagcctatgt agctcccctt tctagtctca tcttcagaat  132540
tagagtcaca gtctaagcca gcagttcttc aaccctggct gtacctaaga gtcacctggg  132600
acacccagag ccagccccta aagattctga ctcagtcggg ctgggctgga taccatggat  132660
tggtccctct tggaatctcc ccaggtgatt ctaatgtgca gctgaggctg aaggcaacca  132720
ctctaagaca gttaactttt agaaagcaat atgcatagcg gagtgaatgg cattttccat  132780
tttgtatttt ctaaagaaga gtgtgtatat gctcttgtgt ttttagtaga cagggttt    132840
cgccatgttg gcgaggcttg ttatataggt attttttatac ctatataaaa cttgttatat  132900
agatattcag gatatttctg aaaggatgca gaagagattg gggacagcaa ttgcctctga  132960
agagggaggc tagggaacta gaagtctggg gtgggaggga gacttgcttc tcatcctatt  133020
acctttggtg cgattgggat ttgttaacca ggagcatgta ttacttgctt tattaaacat  133080
ttccagtatt taaaaaaaga gtatacagaa taatacaaca aaacacccat gtcctcacaa  133140
cccaacttaa gaaataaaac atcacaatat aaataataag tccctccttc actctttgcc  133200
ttcctccttc cccagaagta actgtcactc tgaatttggc attcacttt  acacttctct  133260
tacatataaa cttggcttac atttgcttta aattaattca gctactattt atttatttac  133320
tttgtatcct actatagata ttcttttgca atctgggttt tttttaact  ctacactgtg  133380
```

```
tttttgagat ttcacagtgt tgatgcaaga cttttttcaat ttcagaagtt gattttttta    133440
agattagata gatatatgga tgttctcact gatatgtggg agctaaacta tgaggaccca    133500
aaggcataag aatgatacaa tgggctttgg ggacttggat ggaagagtgg gaggggccaa    133560
gggataaaag actacaaata tgttgcagtg tatactgttc aggtgatggg tgcaccaaaa    133620
tctcacaaat caccactaaa gaacttactc atgtaaccaa acaccacctg taccccaata    133680
ccttatggaa aaataaaaat aataataaac atctaaacat aagaaaaaca aggaaggaaa    133740
aaaaatagat ggatatataa catttgtgca tcagggccgg gcatggtggc tcacgcctgt    133800
aatcccagca cttgggaggc cgaggcgggc agatcacttg aggtcaggag ttcaagacca    133860
ggctggccaa catggtgaag ccccatatct actaaaaata taaaaattag ctgggcatag    133920
tggcaggggc ctgtaatccc agctactcgg gaggctgagg caggagaatc acttgaaccc    133980
aggaagcaga ggttgcagtg agccgagatt gcatcactac actccagcct gggcaacaga    134040
gggagactcc atcgcaaaat aaaataaaat aataaaataa aaataaacat gtgtgcatca    134100
actgcttata actatatatt cagacatcca gaatatgatt ttactgtgac tggacttcag    134160
aatgtgctgc gtgtgatcct aggtgaagtt gtgtgtgttc aggccctgct gagcatgtgt    134220
gaccatgtgc accttgtgcc tgcaagtgca ggtatgagag tgtgtggatg tgctttgtgt    134280
gggatctgat tgtcattcag caaacattca ctccttttcct gccctccacc tccatggaag    134340
gagactcctt cctgccccat taaagttggt cttggtcatg taacttactt tggccattgg    134400
agtgtggcag aagtgacagc gtgccaactt ccaacctagg acttaaggag aattgtactt    134460
atcccttccc ttttttggta gtttcatacc ttcatggtaa gaaaaacaag ttctagagca    134520
gggctgcccc agcgacccac aaatcaggca gcaaggaaca tatgcgaatt gttctatgcc    134580
cttgagattg tgtggctttg ttatgcagca caaatgacta attcatgctt attttgcatg    134640
ccccttggtc tagactgtct aacttctgga gccttactcc tagaaaagcg tcatgcccaa    134700
atgtaatgat caataaagac ttgttattgg attaaatgtg cttgcacatg tgattgcata    134760
cactggacat acatgtgcat gtgcataggg caccagccag tgtgagagcc agaacagacg    134820
tgcgtgtgag atgcacacta atagcagagt ggtagctaag taatatctgt ctgcacacat    134880
ctgcctgggg ggccacacaa aagggcctga gttcatttag ctgtggactc actccctttt    134940
ccagaaccct tgcacatcctg gaatggagct ggaaacatct tagcccttgg aggcaggag    135000 gaagcttcca gaaccataga cagcagtaaa cccaatgctg tataactgac cacacttttct   135060 ctcccccttca aactccttca gccttcttaa gatggagcac aacattacct ttgtggctat    135120
agagcttaat tcatctcctg agaaaagtac tagaaagggt cccaagtcct tcgtggtctc    135180
ggctgtccag tgctgaggga gtctaaaaag agataataac cagtaaagtg aaaaacatg     135240 ctgtggtgga catctgttgc cttttccccc agcaccctttt ctttcagga atagattgtc    135300 ttatactcat gtcaatcaca tggtcccact tccttgacca agaaaattgg catgtgatgc    135360
aggctgacca atcagagtca tccctgggag ttttgatgga actatcagag aagctctcct    135420
ttctctggta tctctggcag tagggagga tattggagga cattcatatt accaagtgga    135480
aaaagtaaag accacaccaa ggaacacaga gctgagggat gggaggaaca tattcctgaa    135540
gatatcattt gagacacggg attcagccat gcctgaagac caccagtgga gtttcccgtt    135600
acattccatt cctgaattca atacattccc gttctcttta gtttgaatta aattattgaa    135660
tttctgccat ttcatcaca gtgtgtcctt cttctccctc ctcaatagaa gagtaattat    135720
atatttcttc cttttacttt accataacag tcttctctta gaataagaaa aaacctttct    135780
```

```
cttgaacttg gcaggataaa ataaaggcac tgacccagaa tccactgtta ttcttgtata   135840
gatcataaat gcctacagtg aagagcatta cactatcttt ggcgacatct ctaaaggagg   135900
tctgcccaat tagcagtgac agctggtggg aatgcaaaat catacagcca ctttggaaga   135960
cattttgttg gtttcttaca aaagcaaaca tgttttgcc atataaccca gcaaacacac    136020
tctttggtat ttacacaaag gagttgaaaa cttacgtcta catgaaaacc tgtatatgga   136080
tgttgatagc agctttatcc ataattgcca aaacttggaa gcaaccaaat gtccttctgt   136140
aggtgaatgg ctaaataaac tgtggttcat taagacaatg aaatatgatt cagcactaaa   136200
aagaaatgag ctatcaagcc aaaaaaagac ctggagaaaa cttaagtgca tattactaag   136260
tgaaagaagt ctatctgaaa aggctatcta ctgtatgatt ccaaatatat gatattctag   136320
aaaaggcaaa agtatcagtg gttgccagga attaggagtg agagaggaat gaacaggcaa   136380
agcccggaag gattttttagg gcagtgaaaa tactccgtat gatactataa tggtgaatac   136440
atgttattat atacttgtct gaacccatag aatgtaaagc accaagagtg aatcctaatg   136500
taaaatatgg actatggatg ataatgagaa tccaatgacg ataatgtcaa cataggttca   136560
tcagttctaa caaatgtaca actttggtgg gggatattga tcatggggag cttatgcgtg   136620
tacggggtca gagagatatg ggaaatctct atcttctcca tttttctgag aacctaaaac   136680
tagtattaaa aatagtctct agggtcaggc atggtggccc atacctataa tcccaacact   136740
gtgggaggct taggtgggtg aatcccttga gcccaggagt tcaagaccca cctaggcaac   136800
atggtgaaat tccatccctt aaaaaaaaat acaaaaatta gctgggtaca gtgatgtgca   136860
cctgtggtcc cagctacttg ggaggctcag gtgggaggat cacctgagcc cagggaggtt   136920
gaggctgcag tgagccatta ctgtgccaca gcactccagc ctgggtgaca gagcgagacc   136980
ccatttaaaa aaaaaatagt cttaaaacta ataataatac cactaccttg catctgtaaa   137040
gggccacctt ttccaaattt ccccttcata tgccaagctg tgtaagaaac aactctttga   137100 gattttagg gcagctacta ttgattccac tttacagcaa atctgaagcc aaggccaggc    137160
gcggtgactc acgcctgtaa tcccagaact ttgggaggcc gaggtgggtg gattacgagg   137220
tcaggagatc aagaccatcc tggccaacat ggtgaaaccc agtctctact aaaaatgcaa   137280
aaaatagctg ggcgtggtgg cacatgcctg taatcccagc tactcgggag gctgaggcag   137340
gagaatcgct tgaaccaggg agtcagaagt tgcagtgagc caaggtcgtg ccactgtact   137400
ccagcctggc cacagagcga gactccgtct aagaaaaaaa aaaaaatct gaagccaaaa    137460 gaagaaaggt cacatttcca aaataagcat aagaattta tctcatccta agccagagac    137520
tctgtttgca gggcaggaga gccaaggttg agtgtccctc cacagagcat accacaccac   137580
caaaagccaa acccagccgc tcctcaccca tactgtccca ggagcttgag cctcactgca   137640
gccttttgct cagggttgag gtctgggcag tctctgaggc cgtgtagagc agtcgcccaa   137700
gccctggggg agatccccct gtcgatgatg gctgccggca agtgacacag caggttcccc   137760
atgatgtcca cagtgtactc atcagcaatg gagtcgtcct gaacccaaaa agtggagcca   137820
atgggcagtt ccaacagagc ataagatcgt gagccattag aaacacatcc tgtggggtgg   137880
gcactgtggc ttatgcctat aatcccagca ctctgggagg ccgaggcaga cagatcattt   137940
gaggccagga gttcgaaatc agcctggcca acatggtgaa accccatcta tactaaaaat   138000
acaaaaatta gccaggcatt gtggcacatg cctgtagtcc cagctactcg agaggctgag   138060
gcacaagaat tgcttgaacc cgggaggcag aggtcgcagt gagcctagat gatcatgcca   138120
```

-continued

```
ttgcactcca gcctgggtga cagaggaaaa ctctgtctca aaaaaaaaaa aaaaaaagtt   138180
ccgatcccaa acttcttaaa gattccagga tcttaactgc ctaccctgcc atggattcct   138240
agagatggaa caggacctga tcttccccag ggatgcaggc ctcagaaatc tggaaaaccc   138300
tggcttggca caccaggagc actcagtaat tgagcgctgc tgtcactgtt attgctctga   138360
gaatattcca gacttcaacc accattatac tattggcacc acaacaatga aacagcact   138420
tcaaagtttg tatgccactt gaaagccttc aaagctcttt tgcactttca caaaatgaca   138480
aaaatagttc acatttattg tgtgtttcct atgtgcgggc accgtcctga gtatctgtgg   138540
gtctcaatct agtcatcttc aaagtaactg taagaagtaa gtactactat tatccatttt   138600
ttaaagaaaa agaaactgcc agctagtggc aaggctagga ttcacaccca gacaatctgg   138660
cctttgagcc tttacattaa ataatacatt gcccatgtca tgttttcaat actctatgag   138720
gagactaggt atggtggctc atgtctgtaa tcccaacact tgggaggcc gaggtggatg   138780
gatcacctga tgtcaggagt ttgagaccat cctggccaac atggtgaaac cctgtctcta   138840
ctaaaaatac aaaaaataac cgggtgtagt ggtacacacc tgtagtccca gctacttggg   138900
aggctgaggc aggagaatca gttgaacctg ggaggcagag gttgcagtga gctgagatcg   138960
tgctactgca ctccagcctg ggtgacagag tgagactctg tcccaaaaaa aaaaaaaaa   139020
aaaaaactct aaggggatg tgctactccc cccaccttac agatgagaag actgaggctc   139080
agggaggaaa ggtgattcac ccaaagccac ataaccaatc actggcaccc agtctctggg   139140
tactgtgctc tttccattcc tccagagtag cctcccctcc tttgggccgt ggggcagaag   139200
tctccagaac caatgaaaaa gattgttcca accagcaact ttagagtaag cttcaagacc   139260
caccagtcag acttctggcc atcacagcag gctcaagatc ctagccagat ccctcacagg   139320
gctccccaag atggccacag atacccagag ggaggggaca cccaggaaga gttttcttac   139380
caggcactgc tgcactttcc tgaggactga agtcttttg tgggaatcta aaaccaagga   139440
gtccaaccag ctcttcccca ggctgatcag aaagggcaca cactgggagg ctgggacaga   139500
agccaggtag cgggccctgg agagagatgg ggagaacaag aggaggaaca catggctgct   139560
cctgttggcc cctaaaatca gggttcgcct gcccaagagc tcatcccaaa gacattcttt   139620
aaatgtttgt tcttcccagt gatgctttgg ctccctgcag caggtagcaa gcttcccacc   139680
catcatgctc ctcttctatg ggtgggaaca aacttcccat catgctcctc ttccatgaat   139740
gggcaacaaa cttcccatca tgctctcttc tatgggtggg aacaaacttc ccatcatgac   139800
cctcttctgt gggtgggaac aaacttccca tcatgctcct cttctatgcc ccagagcatt   139860
gatcagagaa tgggttctcg taaatagaca tgttgattga tggactggtt gagggagat   139920
gaaaagaaa ggaaaagta gatgaaaaaa gagacaacga ggagagaa taactagaaa   139980
gtgagaaaga aagataagaa aaagagtgga aagagaaatt ctgtcatctc cagtccagaa   140040
ctctgccttc cactcttgat ccttcagctc ttgacaatgt attctcaaca gggtcaaagt   140100
caccctcaag aaggagaaac tggtttggat ggagataaaa aagactgtta tgacaacgat   140160
ctgtaaccca ctgaagctca ttcctactca aaatattttt cctcagtgta aatttctttt   140220
cattcaggag aaattaaaat tttctccttt ggaaggcatt aacaaaagtt gagaaagtct   140280
gcatgaaacc catccggcct actcaacccc accacttcac tgttccaaaa ccagatacaa   140340
cgtcttcccc caaacatgtt cttccgcctc tatgctatcc cacactcctt tttttcttta   140400
tcccaagcct gtcattgcta tctccttagc attatcccaa tctgttctta cttctggcca   140460
ggtgtggtgg ctcacagcta taatcccagc actttgggag gccaaggtgg gtcacctgag   140520
```

```
atcaggagtt tgagaccagc ctgagcgaca tggtgaaatc ccatctctac caaaaattca  140580
aaaaattagc tgggcatggt ggcatgcaca cctggggttt caactactct agaggctgaa  140640
gtggaagaat cacttgaacc tgggagacag aggttgcagt gagctgagat cgcaccactg  140700
cactccaacc tgggtgacag aatgggaccc cgtctcaaaa caacaacaac aaaaaaatct  140760
attctaactt ctccattccc agtaccactg tcttatttat ttcttcattc atccagcaaa  140820
tatctacaaa gcaactacag taagccaggc actgttctag gcaccaaata taacaatgaa  140880
caagacacaa gtggtcctta attctagcag agagaagaaa cacagaaacc agtgaacaaa  140940
acaagacatt tgagctatta atagctggca tggtggctca cgcctgtaat cccagcactt  141000
tgggaggccg aggcaagcag atcatctgag gtcaggagtt tgagaccagc ctggccatca  141060
cggtgaaacc ctgtctctac caaaaatac aaaaattagc caggcgtggt ggcgcacacc  141120
tgtaatccca gctactgggg aggctgaggt aggagaatct cttgaaccca ggtggcggag  141180
gttgcaatga gccaagatta caccactgca ctccagcctg ggtgacagag ggagactctg  141240
tctcaaaaat aaataaatta attaattaat taattaatgt aaggaagaaa ataaaatggc  141300
tctgtaaaag agaatgacaa tggggataat caaacgagcc ccttctaagg cagttccatt  141360
tgagctgaga catgaatgag tggtagaagt gccatgccaa gatctgggtt actgaaataa  141420
tcttcagctg tctcccttct ttccattcag cctccctgca ttctatcctc tatgtgggta  141480
gtggctatga tctttctgaa atataaatct gatggctgca cacagaatat gtgtgaaaca  141540
cctcacttta caaagccccc atgatctgat gtcccttaac tctctggcct tctctcccct  141600
atctactctg cagatatacc cccatgtgtt cccagagtga ttggcttttc ttacccactg  141660
ctgaaccgga catccccatt ccactgcctg gaatgtccat cttaaactct ctatccagca  141720
ttagttcggt ctcccctgtc tctccagtct atgggtgata ttccctcctc tatgtccagt  141780
cctcattatc cctcccctt gcctctcctt tggaaggcaa taaaaagtt gagaaaggct  141840 gcatgaaacc catctggcct agtcaaaccc accacttgac tgttcaagaa ccagattcaa  141900
catcttcccc caaacatgtt cttccacctc tgtcctaaca gaggtgtgta acagcacctg  141960
gctttcttgg aaagcaccta gttttcttg gagaaccatc tccctcactc taagtccttg  142020
tggtttctct ccagctccag gggtgcaata cagattgaag tcagtcaaag ttacccatcc  142080
tcccaacctc actgattggt tcaaggaaaa caaattcgcc caattaaggt caatgagagt  142140
caaacccaag atgtgtattg agaatgatgg gaagagaaca ttttctatt ttccctgaat  142200 atgaaactgg gaaaatttaa ccttagatct tccagggttc ccacagagga caacttgcc  142260 tgatagtgaa gccaacagag aaaagctggg acaagagaca aatgacatca tttgcacccc  142320
tagatcgagc catgcctgaa gtccctctct gaactttcca gttacctgaa caaaaaattc  142380 cctttattg cataagccag tttcagtttc agttctgttg ctttcaacca aatatcaacc  142440
tgatataatt ggcttcatgt ttgtctattc cctctcccac catgagatta taaggtctta  142500
taaattaata ggaatttcta atcttcaga tagaaaattt agctatctga gaactagcac  142560
acagcaagta ctcaatgaac tttttttttt ttttgaatga acgaagacaa taagagcaaa  142620 aaaggtaga gggaaataaa gaaggagaga aggagagaaa caatgtccag atcatgtttg  142680
aaaagcaggg ccaccctgca ggcccaaaag ctcacacatg ccaggagaaa cgcctactgc  142740 tccccctcaac tctgattccc ctggagcctg gcacagccgc aaagccaggc cagatgggac  142800
ctgcctcact gacactcatt caggcttggg ttgctttggc ttggttttta gataacagga  142860
```

```
aaagcaagaa ggtctgtctc aaatgtctgt gtgatactca gaattgaaat cctggatctc    142920
aagggcttaa ctctctaagg catcctccac tctgcctctg gttcctgaag aaaacccagt    142980
ggggagagaa tcattttgac ttcagtgatt cccaccgatc tcactgatga gccagaaggt    143040
gggggctgat gttcacttac gggagtgcag ccaagaggaa aggtggcata gacaatctgg    143100
aaacttccca gtatttccac gccaaacaat taacctgaaa gattaagcag ttctggggat    143160
ttaatgcagt aagaagaaga acaaacacag tgctttccat gtgccaggta ctattctaag    143220
tgcttcatac gtgttcattt atgcaataga gcaccctatg atgtgagtac cactactgtg    143280
cccagtttat ggatgagaac gctgaggtaa taacaaacat gaacacggac atttaagtgt    143340
gagaatgctc atcgcaattt tgcttatatc tgcaagaaag ggagatataa ttttaatgtt    143400
cctcagcagg ggattggtta agtaaattat ggtatataca tacaatggaa tagtgcacct    143460
actttgtttt aataaggtag atttatatat atattaacac taaatgatgt ctgtgctatt    143520
ttatgcatgt gcatatatat agttatatta tatataatgt aaaaaccaca aatgggctca    143580
tattgtacac acaattctgt taaactatat atatagctta actatacata tagttatata    143640
tagcttaact atacatatag ttatatatag cttaactata tatatagttt tacacatata    143700
tatatcttag ctatatatat aaacagaaca gcatgtatag tatgagctca cttgtgtttt    143760 tttttttgt ttttttttg agacagtctc actctgtcac ctaggctgta gtacagtggt    143820
gtaatctcag ctcactgcaa cctccgcctt ccaggttcaa gcagttctcc tgcgtcagcc    143880
tcccgagtag ctaggattac aggcaccccc caccatgcac ggctaatttt tttttttttt    143940 tgtatttta gtgggttttt ttggggtttt ttttttgtat ttttaaaaa ttttttagg     144000 ttggccaggc tggtttcgaa ctcctaacct caagtaatcc acccatctcg gcctcctaaa    144060
gtgctaagat tactggcgtg agcactgtgc ccggcccact tgtggttttt atattacata    144120
tagatacttt tttaaaattt ggtttagaga tagagtctca ctctgtcacc caggctgaaa    144180
tgcagtgact ccatcataac tcactgccac cttgaactcc caggttcaag tgatcctcct    144240
gcctcagttt cccaagtagc taggactaca ggcatgtgcc accatatttg ctaatttttt    144300 gtatttttt gtagagttag agtcttgctg tatgttccc aggttggttt caaagtccta     144360
tcctcaaatg aacctcccac ttcagcctcc caaagtgcta gaattacagg catgagtcat    144420
tgtgaccggc ctatatttta tatataaaag aaaactctca aaagtaatag caaactgttc    144480
tttatagtta cctctgaaac acagttgctc acctcagtat tattgacatt ttcgaccagg    144540
tacctctgtg tagtggtgct gtcctacgca ttgtaggatg ttgagctcca cccctggcct    144600
ctacccacta gaggccagta gctctgctcc ggttgtgaca accaaaaatg tttgcagaca    144660
tggccaaaag tcccctaaga gggcaaaaca gtactctgtt gagaacaact gctctgggga    144720
aaatttgggg aaattttact ttctctgtat tggttgtttg tgtgtgtgtg tgtgtgtgtg    144780
tgtgtgtgtg tgtgtgtgtg tgtaataatt atgtgttttc agaatgggcg tggtggctca    144840
tgcctgtaat cccagcactt taggaggctg aggctggtgg atcactggag gtcaggagtt    144900
caagaccagc ctggccaaca tgatgaaacc ccgtccctac taaaaataca aaaattagcc    144960
aggtgtggtg gtgcgcacct agaatcccag ttagacagga gactgaggca ggagaatcac    145020
ttgaacccag gggcggaggt tgcagtgaga ttgaaccact gcattccagc ctgggcaaca    145080
gagcaaggtc ctgtctcaat aataataata atgataataa taataataat aataataatg    145140
tgttttagta aaaatataaa cgagaaaggc aaatttccta attaactggt atttgaaggc    145200
tctgagagct ggaagcctag gaaagcacct tcactggggc aactcttcct gctcgaacat    145260
```

```
gtaggtcttc ctcaaagcag gtctagcttc catccatttg ctcagttatt ggcttgccca  145320
cctgggcagg tcttttaata tagttcagtg gtttgtacca gcaaactgat tagaaatgca  145380
aagtattagg cctcacccct tacctactat atgtaaaact ctgggagtgg ggcccccaat  145440
ttgtgttttt acagccttcc acacaatgct gatgcaagct caactttgag aatcactaac  145500
agaattaaca gtccaaggga atgagagagc ttcattaaaa ctttgcatat tcctgtaatg  145560
atcttgaagg attatacacc aagcactcta tgcttcctgg ttttctggga gataatttac  145620
tctttggaaa ttcttcattc tggtctgaaa cacaaggcca gagttgagaa ggtgcttttt  145680
aatatccatt acaggagtct gtaagccagc ggttcacacc aaaagttcaa atgctgtaag  145740
gcctgtgttt actagcttag acactgaaaa atcagtcact ggctgggtga agtggctcat  145800
gcctgtcatc ccagcacttt gagaggctga ggcaggagga tcacttgagc ccaggaattt  145860
gagaccagcc tgggcaacat atcaagaccc tatctctgca aaaataaat  aaattagcca  145920 ggcatggtgg tgtgtgcctt tagttccagc tactcaagaa gttgagacgg aaggatctct  145980
tgagcccagg aggttgaggc tgcaatgaac catgattatg ccactgtact ccagcctggg  146040
tgacagggca agactgtgtc tcaaaaaaaa aaaaaaaga aatcagttac tgcttctagt  146100
ctccccaaag gttaaatagc ctccataacc ttttagaaaa tgaagtttta agtgagaaag  146160
aaaatgttct cagagtactg tttgcattca cagctactcc tggaaagtgt tggaatatta  146220
gctgaaggag taccttccat cccacgggaa cataattatg aacacacaaa atactgtccc  146280
ttatgaatat attttaaggc ttaaatttga gtatggaata accatctgt  tgattctttg  146340 gctgtagtga tgtgggtatt tggagctgtt taaaagaaa ctggaaaaaa cctggctcaa  146400
tctttggccc taagtcatca cttgcgtctg aatgattctg gcataaagat ctttagatgc  146460
cacagccaat ccaggcccag tgactggggt agggagagag aattagaagc tggaaaatgc  146520
tttaacggta cctgataggg tgaaagcagg gcgaagttgt tctgaaaatc ctggaaatgg  146580
gccagaaaga agtcagtgct catggcatca atgtgtgagc aggtcacgcc tttgaccagc  146640
tgcccagcac tagaaaacaa acaaggcac  tcgggagagg aaggaagtga ggaggagagg  146700
aaagaaagag cgagagaagg cagatatgat cagatacaag ctacagatgt gactgcctaa  146760
ctctcccacc tggaaaagta ggctgctctg gcagaaggct ctgaaaggcc tgttcagcac  146820
ccaggccgag ttcattttc ctacctcaaa agctcctcag gccttctggt ggtctttaac  146880
agaagctcat acaggaacag agcctgcaag aagagaatga tcgttagcac tgatggcaca  146940
ctcagcgtgt gcccaacact gtgaggccct atcaggaagg cattccacaa tcccatttta  147000
cagatgggga aatggaggct taacaggcta tgtgagttac ctaggactag accattgcta  147060
agtggcagtg cctggatttg aaccagtgtc aaggtaattc cagagcccca ctctcacact  147120
ccagatgatt ctctacaccc catgaggcag atgagaggca aagacattgg tggcagggct  147180
ggagttttac ttcctgtgct ttaggaagct gctgaccagt tgagaactcc ctgtgtctcc  147240
tattcacatg tgcacctgcc aggttctgaa caccaggcat cccagaataa accaggatgg  147300
gctagaaagc accagcaata aagtacctgc agctagcagc atgcactgtc ttcaaaccac  147360
cccccaatga gcactctaga acaatgccta gtagacaggg gagtcatttg ttttaaggaa  147420
cataatttta cagaatccct aacttgcaga cgcaatcaag tactacattt gtctatttta  147480
tagactctga aactttgagt atcattcccc agacagaata aattatgagc tagcattaga  147540
catggtagct gagagccaaa aagcagcaca aaagcccagg caaaaggaat ggacgatgga  147600
```

```
ggaaagttct ggacactgtt tgtggcccca gagattttcc tgggctcagg gtcaaattct    147660
gggaccctcc catggtcttc cccatctcag gaaacagcaa tcccatcagc tcaatggccg    147720
agacaaaagt atcttgaagt cttcggtggc agaatgtatt ttccaaaata aaactattgg    147780
ctgggtgccc tggttcacgc ctgtaatccc aggactttgg gaggccaagg cgggcagatc    147840
acttgaggtc aagagttcga caccagcctg gccaacatgg tgaaaccctg tctctataaa    147900
aaatacaaaa attagccggg catgatggtg tgtgcctgta atcccagcta cttcaggagg    147960
tggagccatg aggattgctt gaactcagga ggaggaggtt acagtgagcc aagattgtgc    148020
cactgcaccc cagcctgggt gaccgagaga gactctgtct caaaaaataa aacagaataa    148080
aataaaacgg ttgccactgt cactaaattt agaggtggtt tgtgacacag caatagatca    148140
gcaggacatc atccagcctc atgagagacc ctgagcaaga gcgcctggaa cagacaggga    148200
tttgtgtcgt ttcattcact tttgcacact cagcactgtg agcagtgcct ggcgcactgt    148260
tgggctgtgc ttgataaaca tttgctgggt gcatgtaatg aagactgact gaatacaaag    148320
gtagtcaacg atggtactaa ggcagagcat ccacttcaac agcaccatcc ccccaagcgg    148380
cctcaatgct cacagcattt aataatacac ataatagccg cgaatactta cagtacacag    148440
cccaggtggc atgtatcagt gaccctcatt ttattatcaa aattatcccc atttcgcaca    148500
tgagaaaact gaggccatat aaggaacttc tccaaagcta ataaataagt gggagccaga    148560
attcatgctc aggtcttgtc taacttttt tttaagagac agggtctcgc tctgtcgccc    148620
agactggagt ggagtagcat gaccataact cactgcattg cggaactccc atgctcatgt    148680
gatcctcctg tctcagcctc ctgagtagct gggaccacag acatgcatca ccatgcctgg    148740
ctaatttttt aactttttgt agagacagga tcttgcttgc tatgttgccc aggctggtct    148800
cgaactcctg gcgtcaagcg atcctcctgc ctcagcctgt ccaaattctt aacactatac    148860
tattctgcct cctatactaa tcccacagaa ataaatttct tttatcaaat taaccttaaa    148920
acagaccatt cattctcaca agacagatag tcagaaatac aggatcgatc tgtgtttcat    148980
ggtaatacct ggctccttcc aagttcctta tccttcagga ctgtagagtt gaatccaggt    149040
tgcctcctta aatcaaagag agacacttcc ttaaagaaag cccccttgtat ctccacgatg    149100
cctggggcag tgtcttccgc ttggaccatc tgccagaagc gagaagcaac aaaacaacat    149160
tgtaaaaaat gcattgagct ttgaggaagg gccaggcact acatcacagg caataaaatc    149220
catcagaacc gctcagcaac cctaggaagt ggagagtagc atcatcccca tttcacaggt    149280
gaggaaacag agacttaaag tgtgatgagt tgaaagtcag taagtgacat tcaagcccaa    149340
gtctgtctga ttccaaaacc cgtgctcctt atttctttat tttaactgta tgggctactt    149400
gctatctgca aggtattggt gttttaggcc aaacccctta ggttttaggg ttttttttctt    149460
tttttgagat gggaatctcc ctctgtcgcc aggctggaat tcagtggcat gatattggct    149520
cgctgcagtc tccgcctcct gggttcaagc aatttccctg cctcagcctc ccgagtagct    149580
gggactacag aagtgcacta ccacacccgg ctaattttc gtattttag tagagacggg    149640
gtttcaccat gttggccagg ctggtctcaa tctcctaacc tcatgatccg cccaccttgg    149700
cctaccaaag tgctgggatt acaggcgtga gccacctcac ctggccaagt tttggtttct    149760
taacagattt tgccattgga cagaacggac ctgatagagc aagatgtcaa aagactccct    149820
gacaagtaaa aaaggggcca ggcatggtgg ctcacacctg taatcccagc actgtaggag    149880
gccggggcag gtagatcact tgagcccagg agtttgagac cagcctgggc aacatggcaa    149940
gaccccatct ctagaaaaac aaaaattagt gagcagcaca ggcctgtagt cccagctact    150000
```

```
tgggaggctg aggtgggagg atcccttgag ccccagaggt ggaggctgca gtgaaccaag  150060
atcacgccac tgcatgctgg ctggggtaat agagcaagac cctatctaaa caaacaaaca  150120
aaaaaacaga atacggacat ggctgtggac catgaaaagg gctttcagat gcaccctagg  150180
actttgggtt tatttttaga tttgaaaaac aaattttagg ccaggcacag tggctcacac  150240
ctataatccc agcactttgg gaggccgaag cagaaggatt atttgaggcc aggagttgga  150300
gaccagcctg gcaacatag caatactcca tctctacaaa aaattaataa attagccaga  150360
catggtggct tgaggccagg agtttgagac tagcctgcgc aacatagcaa gaccatgtct  150420
ctacaaaaag ttaaaaaaat tagccaggca tggtgatgta tgcctgtggt cccagctact  150480
caggaggttg aggcaggagg attgcttgag cccaggagac tgtggtgagc tatgatcata  150540
ccactgtact ccagcctggg caacacagaa agactgtctc aaaaaaaaaa aaaaaacttg  150600
aacctgaagt gttataagat caggaaacct gatttaagaa aagtcttcca gattagactg  150660
tctggcagaa caaaggggtc tggaagaat gacagcatga ctgaagggct ccgtctggaa  150720
aggaaggaag gtgtgccacc aggagaaggc agagccaccc cagacaccaa cagctgagac  150780
aatcccagcc ctgggttcat ggcccaaagt cacagcccac tcaccaaccc caaaaacata  150840 cccccctgtga catgtggctg agcaccagac atcttcctct caccttgctg aggatacctt  150900
gctgctgggc aggtgacaag tcggatacat actgggagac ggcacttctc aggacctgcg  150960
agatgtcctt gcgtttcatg ctgcagaagg cctgggtgct gaccccagcc agcagtgcgc  151020
ccatctggct gacattgtag aaagacagca cctggaagag gagcggctgc gcagtcaggc  151080
tctgctcccg cctttcacct ctccaacgtg cactcagccc atctatgtgc caagtatagg  151140
gatgggtgac accttagggg cacagcagtg agccagacag atgctgcctc cacaggcctt  151200
ccttccttct atcaagaaag agagttggcc aggcatggtg gctcacgcct gtaatcccag  151260
cactttgaga ggccaggcgg gtggatcacc tgaggtcaag agttcgagac cacctggcca  151320
acatggtgca accccatctc tactaaaaat acaaaaatta gccaggcatg gtagcaggtt  151380
cctgtaatcc cagctacttg ggaggctgag gcaggagaat tgcttgaacc caggaggcag  151440
aggttgcagt gagctgagat tgtaccattg cactccagac tgggcaacaa gagcaaaact  151500
ctgtcagaaa gaaagaaag aaagaaagaa agaaagaaag agagagagag ggagaggaaa  151560
gaaagaaaga agaaagaag agagagagag agaaagaaag aaagagagaa agaaaggaaa  151620
gaaagaaaga gaaagaaaga gagaaagaga gaaagagaga gagaaagaga gaaggaaaga  151680
aagaaagaaa gaaaggaagg aaggaaggaa ggaaggaagg aaggaaggaa ggaaggaaga  151740
aaggaaaaga aagaaaggaa ggaggaaaga aagaaagaaa gaaaaagaa agaaaggaaa  151800 gaaagaaaga gagagagaga aagaaagaga aagaaagaaa gaaattatac ttgggttttt  151860
tttccttcct ttagagtgaa gatgctagat agttttccat ataatcaagg acatgctttg  151920
gttctatgaa aagacagctg agtgggttcc tttagttatt ctgtgtataa tgggtgatct  151980
catgctgtct tcaaagaagg caagaccttt tgacctcttg ccttctgagt aaaagtggcc  152040
tcacccctca gtaggaagag ttgggtatta ggaaagagac aaaccacttt gtcctgggct  152100
gggagggaac aaaaccgtct ccctcaactc cctaaaatca aattcagaga ggactgtcaa  152160
ggtggaccca tggagcccca gtcaaggtcc agaaacaagg attcaaagcc ttcaacataa  152220
agtcaccacg aggctagaag agaccagatg aatgggctgg cctggtacct gagtcagaaa  152280
gtgggagtgc gtgggcattg gtcatggtgc cataatggag acagtgagca caggagttaa  152340
```

-continued

```
acaagatggc tctgaggcca ggtgccctgg gttcaatccc agctgcgtaa ctttcacgtg 152400
gccttttcca gttcccttac acactctgta cctcacatga atgaactgga aaatgaagac 152460
tacagcacta ctgacttcag aggattgttg gattaagtta ttaattcact tagaacacaa 152520
cctggcacat agtaagtgtt cagtaaatgt ttgttattcc acaccctccc tcccttggcc 152580
ccgcgatgga ggaagcaggc taggaccagc cctcggagct gcagctgccc ttcatccctc 152640
cctcgccctc tctaccgaca tcctgctcca gttcccactt ggatttactt tggggaatgt 152700
ggttggaata tatctggctc agaaccatga cataccaaac ccagctttaa aaacttgaag 152760
aaatttaaaa agacttggat gccaagaaga aattccctac tccttctctt tgggaggcca 152820
aggcgagtag attgcttgag cccaggagtt tgagatctgc ctgggcaaca ttgcaaaatc 152880
ccatctctac aaaaaaatac aaaaatcagc ccggcgtagt ggcatgtgcc tgtggtccca 152940
gctactcagg aggctgaggt gggaggatca cctgagcctg gggggtcaag gctgaagtga 153000
gccaagatca gatcacttca ctccagcctg ggcaacatag tgagaacctg tctcaaaaaa 153060
caaaaaaga agaagaaacc ccccagttcc tgaggccaac tccagcactg ccttctggat 153120
gcatggattc tactctataa ctcttaaacc ccttttaccgc ctgaatcaaa agcttttgtt 153180
ttcattttac cacctgaatc aaaagctttt gttttcattt ccaacctcag tgatgcgatc 153240
tcggctcact gcaagcaccg cctcccaggt tcacgccatt ctcctgcctc agcctcccga 153300
gtagctggga ctacaggcac ccgccaccat gcccagctaa ttttttttttt ttttatttt 153360
agtagagaca tggtttcacc gtgttagcca ggatggtctt gatctcctga cctcgtgatc 153420
tgcctgtctc ggcctcccaa agtgctggga ttacaggcgt gagccatcgt gcctggccta 153480
gtgattttct tccttgtgag acactgtggt attttgcttt agaacaagca aatggggcc 153540
ccttacattt tcaacatctt cacctcttcc catatcctcc ttcaagctgc atgggaggta 153600
ctaacactag aattacggtg ctaggttagt aaacatgacc tttaaggagt agtctctcct 153660
ttattctttg ggattcctac tactttttc tttttttttt ttaagacaga gtcttgctct 153720
gtagctcagc ccagtctgga gtacagtggc atgatctcgg ctcactgcaa cctcctctgc 153780
ctcctgggtt caagtaattc ttctgcttcg gccttccaag tagctgaaat tacgggtgtg 153840
caccatcatg gccagctaat ttttctattt ttagtagaga cagggtttca ccatgttgtc 153900
cagctggtct caaacccta gcctcaagtg atccattcat cttggcctcc caaagtgctg 153960
ggattacagg cataagccac catgcccagc ctactacctt ttgtcaaaat aaaaattgat 154020
gagttttgta tagttggtca gacacagtta aaactaaatt cacagtttag caattataat 154080
gggtgcttgt taaacatctg gtagtaaatt atgttgtttc aaagtaatta aaattaatat 154140
ccagaagcca aaaataaaca aatgtttgtt attattattt gattggaatg ggtcctaatc 154200
caatccttgt gagccagttt gcatcctggg aagtggccag gagtgtggac taaacgagaa 154260
ggacaccaaa agccaggcac ggtggctaat gcctgtaatc ccagcacttt gggaggctga 154320
ggcaggcgga ttcaaggtc tggagttcga gaccagcctg ccaacatgg cgaaacctcg 154380
tctctactaa aaacacaaaa attcgctggg tgtggtggtg ggtgcctata atcccagcta 154440
ctcggaaggc tgaggcagga gaattgcttg aacccggagg cggaggttgc aatgagctga 154500
ggttgtgcca ttgcattcca gcatgggcga caagggcaag actccgtatc aaaaaaaaaa 154560
ttagatgaca ccaaaatgct tagaactcaa gtctcccaga tttggagccc tctggactgg 154620
acccaaccca gggacattaa ttgtccccaa aagaatgtcc attttccacc ccaggagcag 154680
caagaacaca gattaagact cctgtcccca ccaaagagga ctgtctgcct gacagttccc 154740
```

```
tctctgcagc ccaagattgg aataaaatag catcatccct aatcccaaag taatggcaaa  154800
aaccgcaatt acttttttgca tcaacctaat agcagcttaa cagcaggcag gaaaatcctg  154860
ggatgagtcc cacacgttga tcccactcag ggatggctaa tgccccttga gctcctactc  154920
tgtggtgtca cctggtggtc tagcttcttc atgtgtacca actcacataa tattcgcagc  154980
aatgctacag gataagtgct actgatttgt tgttgttgtt gtttaatttt ttttgaaatg  155040
gagtcttgct ctgtcgccca ggctggagtg tggtggcaca atctctgctc actgcaacct  155100
ctgcctccca ggttcaagcc atcctcctgc ctcagcctcc caagtagctg gaagtacagg  155160
catgcaccac cacgcccagc taattttttgt attttttagta gagacgggat ttcaccatgt  155220
tgatcaggct ggtcccaaac tcctggcgtc aggtgatcct cccacctcag ccttccaaag  155280
tgctgggatt gcaggtgtga gccaccttgc ccggcagtaa gtgctattgt tgtccacata  155340
ttacaaatag agaaactgag tcaaagtgaa aatagcaaat tgcctagtgt cacacagcta  155400
gtaaatggca gagcaaggat ttgaacccag gcagtcctcc tcagcatcat cttcttactg  155460
attggttgcc ccctgctgtg tgtgtataac tgattgttat ggattaaata tttgtgtctc  155520
ccaagaattc atatgtcaaa gtcctaaccc ctaatgtgat ggcattggga ggtgagacct  155580
ttaagaggcc tttaagggtt agatgaggtc atgagataat gagggtcagg tggggccctg  155640
atccaatggg attagtttcc ttgtaagacg caacaccaga gagcttgctc tcatgtggtc  155700
aggtgagcac acagcaagat ggcggccacc tacaggccaa gagaagaggc ctcagaatga  155760
aacctacctt tctgacacct cgatgttgga cttcccagtc tccagaactg tgagaaataa  155820
atttatgttg tttacgtcac tcaatctaca gtatattttt atggcagcct ggcaggtcta  155880
atacacttag gtcatcttag gggaataaaa aagagtttaa aactccagct gaccttctca  155940
tgggccaagt atttggcaga caagatgatg acctggctct tggcccaacc tgagacctgg  156000
ttgagggtgg agatggctcc gtgcacagcc tcggggaga gggattccag ttggctgtag  156060
gtcaaaccta caactgcatc cgacaaagaa cccagggtct cattgagggt ctggttctcc  156120
atggcaatgt ccaggagttc tgctttgagc tggaaggaga gcaaactgga atgagtgttg  156180
acaggaagca gggcggtggc tccctctgac catatccagg gctattagga ctccacagca  156240
cctcccttga ccctgttcca tcaaagcttt tgggctcaga aacgatgaag gaaagggact  156300
cctgccatgc ccagacagtg agacaccaca cggaggacac ctcttctggc cttagctttc  156360
atgtgccaaa aattcccttt gtacttcatt taaatattaa tttgttatta aatcaacctt  156420
aatccatgtc agaaagaaat gttccttta taactcacacc acactcttat agcatctgtt  156480
gtcctctggt gaccttgaac tctatatcca tatatacagg ctgttttcct ttcattaaat  156540
agccaggggc cttttcacga taatttataa tctgtgtaaa aataactttt tttttttct  156600 taagacagag ttttgctctt gtcacccagg ctggagtata atggtgtggt cttggctcac  156660
tgcaacactg caacctccac cttccgggtt caagcgattc tcctgcctca gtcttctgag  156720
tagctgggat tacaggcacc caccaccaca ctaatgtttg tattttttagt agagacaggg  156780 tttcaccatg ttggccaggc tggtctcaaa ctcctgacct aatgtaatcc acatgcctca  156840
gcctcccaaa gtgctgggat tagaggcatg agccaccaca tccagccaaa ataactctt  156900 cacagtacaa gaaagtaaaa gtctcctgaa catcctacca cataaaaata accatgatta  156960
gcaattgggt gtatatgctt ccaagatttc ttatacctttt ataaatatag agacactaca  157020
tagtttttac agagttgtaa tatgaacaga agcacaattt actcttctta aaattatctc  157080
```

```
ttgcacctct tgcacatttt ctatgatcat tttaataatt attttattgc aatatgcctg   157140
cctaatgata gtaaagtgtg cgttacagct gctttcggta aggaatgtga taaagtcacc   157200
tactatacaa tgagctctgt aacaaaaaac aagaatggtt catattttaa cacccgaatt   157260
tacgtaataa cgtagtcatt tcaggcaggt gcacaaaacg ggtttctggc aatattgaaa   157320
tagccactgg ggggcagcag agtgaagtag aagaaacaac tgtcaaagcg cctgggttct   157380
ctaagttcgg caactgcctt acctagaaat cagtttccac atctgtaaaa cgaaggggtg   157440
gactacagtg gcagctccca aagtgtggag cacacccagc ggcatctgca cacctggga    157500 acttgttaga aacgcagatt gccaggctgc tcccggacct cctgaatcag agactgggtg   157560
gggctccgaa atccagggat ccccagactc cgggtcacag atggggacca ccgggaccct   157620
ggcctgttag gaaccagcca cagcaggagg tgagcagcag gccagtgagc attaccgcct   157680
gagctctgcc tcctgccaga tcagaagcgg cattagattc tcctaagagc aaaccctatt   157740
gtgcactgtg catgcaaggg acctagtctg tgcgctcttt atgagaatct aatgcctgat   157800
gatctgtcac tgtctctcat cacccccaga tgggaccgtc tagttgcagg aaaacaagct   157860
cagagctccc actgatttca cattatggtg agttctatag ttatttcatt atatattaca   157920
atgtaataat agaaataaag tgcacagacc gggcgtggtg gctcacgcct gtagtcccag   157980
tactttaaga ggccatggca ggcggatcac gaggttaaga aatgagatc atcctggcca    158040 catggtgaaa ccccgtctct actacaaata caataaatag ctgggcgtgg tggcgtgcac   158100
ctgtagtccc agctactcag gaggctgagg cagagaattg cttgaacctg ggaggcagag   158160
gttgcagtga gccaagatcg tgctaccgca ctccagcctg gcaacagagc gacactccat   158220
caagaaagga gaggagagggg gaaggggaaa gggatggggg gggagggggg agggagggag   158280
ggaaggagga aagaaagaaa gagagagagt gagaaagaga agaagaaag gaaggaagga    158340 gggaagaaag aaagagagag acagaaagag aaagaaagaa gaaagaaag aaagaaagaa    158400 agaaagaaag aaagaaagaa agaaagaaag aaaggaagg agaaggaagg tagggaggga    158460
gggagggagg gaggaaggga gggaaggaag gaagagcaca ataaatgtca tgcacttgaa   158520
tcatcctgaa acaatccccc ggccccagtc cacggaaaaa aattgtcttc cacaaaaccg   158580
gtccctgatg ccaaaaaatt gtcttccaca aaactggagc gctgccacaa gctgtatttg   158640
aacaggccct ccctgtgatt tagatgcacc ctccagtttg agaacaactg agctagatga   158700
tcccaagggg ctccctcgta tctaattgca tgccaccttc tccttggtca gggctgccac   158760
atgttgagac ccctgggcct taaaatacat ttatcttctt attttttgctt gagcttgctt   158820 aggacggatt cttttccttg gaaacaaaaa tatgcattca caggctaggc tcggtggctg   158880
acgcctgtaa tcccagtact ttgggaggcc aaggcaggtg gatcacttga ggtcaggagt   158940
tcaagaccag cctagtcaac atggtaaaac cccatctcta ctaaaacac aaaaaattag    159000 ccgggcatgg tggcatgcac ctgtagtccc agctactcca gaggctgagg caaggcgaag   159060
gttgcaatga gctgaaattg tgccacttga acccggaagg tggaggttgc agtgagctga   159120
gattatgcca ctgcattcca gcctgggtga cagaatgaaa ctcaaaaaaa aaaaaaaat    159180 gaatcttata aaaaaaaaaa aaaagatgcg ctgaccaaaa tagatgacca cactctcaaa   159240
tgtcaaatgt gtttggggac tttatggtga tgtgtgggaa actgctgtga aattattgat   159300
ggctttatca aaatttcatt taatattatt ttcatgtcat cgtttcgatt ttaagcaaat   159360 tgaaagggc cacaaaagt ggaatggaag ggggtagaat tgagacttga ctggaaggaa     159420
gaagagagag atggagagga aggaaaatga gagagagcgt gtttgctcat ctggtcttgg   159480
```

```
gaactcataa ccaccctgca atccagtgtt ctcaatcctg ctgcattga aatcacctga   159540 gaagcattaa aatcaggcca tacctcaggc cacaccccag aacaataaca tcagattctc   159600
tgagggtggc acctggcagg gatgttacta atctagaggc aggtttgaga accactgctt   159660
tatctcctgc cgctccaggt gtgctcacca gagcagcggg tccagaatca cctggaagct   159720
tgttggaagt gcagcgtcag ctgggcgcaa tggctcacac ctgtaatcca aacactttgg   159780
gaggccaagg gaagaaggag gaagaagagg aagatgggag tcctgggcct caaccaagag   159840
ctcctgaatc agaatctgca tttaagatcc ccaggtgatc tgtatgcata tttaagttcg   159900
aagtagctgt ccctttctttt tcttttctgt tctttttttt agatagggtc ttgctctgtc   159960
atccaactag agtgcaaagt cactatcata gctcactgca ggctggcact cctgggctca   160020
agcgatcctc ctacctcagc ctcccaagta gctggcacta taggcacatg gcttttttt    160080 ttttcttttg agacagagtc tcactctgtc acccaggctg gagtgcagtg gcacgatctc   160140
agctcgccac aacctctgcc tcccaggctc aagcaattct cctgcctcag cctcctgagt   160200
agctgggatt acaggcgcat gccaccacgc ctgttttttg attttttagta gagacagggt   160260 tttaccatgt tggccatgct ggtctcaaac tgacctcagg tgatctgcct gccttggcct   160320
cccaaagtgc tgggattaca ggtgtgaacc accgtgccca gccattttt tgtattttt    160380 gcagagacaa gggtctcatg atgttgacca ggctggtatc aaactcctgg cctcaaatga   160440
tcctcccatc ttggcctccc aaagtgctgg gattacaggc atgagccacc gcgcctggct   160500
gagacagctt tctgattaaa ttttgatctc cccagggtct gttcctttgc tattttctgt   160560
ctgggcttcg atgttacact tacctcagta tttgagatgc catctgctgt gactggactt   160620
aaatcccgac taatgctgtg tgttttctcc caaaggctaa gctaggctgt tctccccatt   160680
tctctggcta gtgacactga ggcagaggcc tcagggcctt gcaccccagc tgtaccttct   160740
ggacgccagc ctgaagccc ctcaggtggc tgcacttgat catctggtaa agcaggactt    160800
gagccacagt ggcatccagc aattccaggt cattgtagaa acaaaccagc agccccagcc   160860
tgtgtgagaa gaggagggat ggtggtggag gtgtaaccgc agaaccagcc cattctggtt   160920
caattttgtg taataaaatg gtgagttgtt tttcagttgc cacggactcc caggttgaag   160980
gtcacataac ctgaacatcc tcagatgaac caaatgtgca accacaggcg gaacctaact   161040
gctcagacga gaccaaggaa tgggggctga attatgaagt ggacaccaca tggcatggtc   161100
cacgatccaa tcagaatgag tcctggcatc acctcatggc atgatccaat cagatcacac   161160
ctcccagcat caccttgtag caagacccaa tcagatcaag tctcattacc ctccgcctat   161220
aaaacctgcc ccagtcccca gctcagagac acagatttga gcactgtctt ctgtctcctt   161280
ggcagttgat tcacagtaac cgtttctctc tacaaaaacc tagtgcttca gtgtttggtt   161340
ttccattgcg catgggcaaa cagacccagt ttggttccat aacagagcgc tgagagctgg   161400
tggacacgac acccctccc cagtccaaac caatggggtc ttgattatat taatagcagc    161460
taccacttat caggtcttgc actgagccgt ttacctgcat tatctcatta cagcaaccct   161520
acaaggcagg tgctctcatt agccccattt cacagatggg gaaactgaga tttgatttgt   161580
ccaaggcaag tcggtggagc tgggacttaa atgtagatcc atccacctat gccatctctc   161640
cacctgggat gaataaaggg aataaggaaa gaaggtgcc ggtagccaca gaaaactccc    161700
cattttccac attacaatca ctaaattcta gagctgatct caccctgagg gattctctga   161760
ggcagagatc tgtttctagg atgccttctg gtacccaccc agatgatgca aagatttcag   161820
```

```
aaggaaaaca aaaaagactg gaggaaaaca atggaagggc agaagtgaga ttggaaccct   161880
ggtataactg agagcaatgt ttctaatcat taagagcatt gattcaggcc tactgcagtt   161940
tgaagcccag ctctgtgaga tgtttgctct ccaccaagtt acttaacttc tctgtgaggc   162000
cgctatacac agttctgcag tgcacactct gtactcccat actgtacaga dacagggtgc   162060
ctctccctct ctgagcctct aataaatggg aggttttctt tgttcatcgt agcacatcat   162120
aataaacatg agtgaaagaa agaggatgat tgtgaaagtt aaatgagaag tggtatacca   162180
actgatttgc atacatcctg gtggaaacca agcactcatt cattaatgaa tgctcttaga   162240
gttagaatga agactaccta gttgaccaca gtcagcctgg ctccaccctc tcagagcgat   162300
attgacatat tcagacatgc ccacaggaga gctgccaggt ccagggaaaa gatttgaaag   162360
tgtgtctcat gaggaaaaga gatctgctta acttcgagta aagaagactc agggggaagtg  162420 agggctgaac gttaataacc acgttgagaa taactattca caacagccaa gacatggaat   162480
catcctaagt gtccaacacg tcagtggatg aatggatttt tttttttaatt tggtggatac   162540 acaatggaat gctcttcagc tttgaaaaag aaggaaattc tatcatatgg gaccccatgg   162600
atgaacttgg aggatcttat gctaagtgca ataagctagg cacagaaaga caaatactgt   162660
atgacctcat ttatattatg aatctgaaaa acaaataaac aaacgtcata ctcatggaag   162720
cagagcctta gaatggttgg taccaggggc tggaggtggg aagggagttg gagagacttg   162780
gacaaaggac acaatgtttc agttaaatag gaaaataggt tctggagatc tattgtacat   162840
gctgactaca gttaataaca atgtatcata tactcaaaaa ttgctaagag tagattttaa   162900
gtgttctcac cgcaaaaaaa gtatgtgagg taatgataac ttaattagct tgatttagcc   162960
attccacaat gaatatatat ctcaaaacat gttgcacacc atagatataa tttttattta   163020
tcaatttaaa aaaataaatt ataaagaaaa aataggcttg gcgtggtagt tcatgcctct   163080
aatcccagca ctttgggagg ccgaggcggg cggatcacaa ggtcaagaga tcaagaccat   163140
cctggccaac atggtgaaac cccgtctcta ctaaaaatac agaaattagc tgggcgtggt   163200
ggcgtgtgcc tgtagtccca gctacttggg aggctgaggc aggagaatca cttgaaccca   163260
ggaggcagag gttgcagtaa gccgagattg tgctactgca ctccagcctg gcgacagagt   163320
gagactccgt ctcaataaat aaataaataa aagaaaaaa tattattcat tgagcactta   163380
ctatgtgtca agtgtgcaaa tccctacaaa gaccttaatg cagtaggcat atttttatct   163440 cccatttac agatggggaa gcggaagtat agagaggtga tgtaaaaata gcaaagatca   163500
caccattagt aagcagcagg gaaggattaa gccacgaagt ctggctcgag gtcccatgtt   163560
cttaatcatg aggctatttt tgtgtgtgtg aaaccataga aaaatgagac acatgctaat   163620
aagtgaaaat tactaaaggt aggtgaaaca gatgtaattg tttcctatga gtacattccc   163680
taagagtggc tcatttgaaa aaccttaagg taatatggga tgggagcagt gtggcaataa   163740
taagaccttg agagacggac acaagaggat tgaatgatgg cccagcacag tggctcacgc   163800
ctgtaatctc agcactttgg aagtccaaga tgggtggatc acttgaggtc aggagtttga   163860
gaccagcctg gccaacatgg cgaaacccag tctccactaa aaatacaaaa attagctggg   163920
tgtggtggca cacgcctgta atcccagcta cttgggaggc tgaggcagga ggatctcttg   163980
aatctggagg tggaggttgt agtgagctgg tattgcacca ctgccctcca gcctggacaa   164040
caaagtgaga ctctgtctca aaaaaaaaa aaaaaacag gattgaatgg gccaggcgtg   164100
gtggctcatg cctgtaatcc cagcagtttg ggaggccaag gcaggcagac cacctgaggt   164160
cagcagttca agaggtcagg agtttgagac cagcctgacc aacatggcaa accccatct   164220
```

```
ctactgaaaa tacaaaaaat ttagctgggc atggtggcac acatctgtag tcccagctac 164280
tctggaggct gaggcatgag gattgcttga acccaggagg tggaggttgc agtgagccaa 164340
ggtcacatca ctgcactcca gcctgggtga caggacaaga ctctgtctca aaaaaataaa 164400
taaataaaag gaaaaggagg gagtattgag ctgtactcac cacctccttc ccattgccca 164460
ctcccttcct gacacccctg gaatgtagag ttcctgtccc tcctcccctg ctgggaatgg 164520
ttttagggag gatcacatta cagtcactaa attctagagc tgatctcatc caggggctcc 164580
ccagctaaga gtctgataac aagtggttct catatatggg gacccatgag ttatttccaa 164640
cacttgactc aacttaaacg gaaatcacac attcactttg gaacaggacc cagtcctgag 164700
tatttaaaat gtttcatttc tgtgctgaga gacagaatta gcacttgata aggttgcata 164760
aaatgcctgg cacacaggag atgctcagaa agcatttatc ctttcaccca gcttcataac 164820
ctcttcataa aaaagttgc agacacctct cctcacatgc acagagaaat atgggactat 164880
tcaaagagat ggaccagcca cctcccttcc ctccctgggt gttttgctgc tcagagaatt 164940
ctgatgctta gatcacatct tgggaaaggg ctccaaggcc cagagctcat gcgcttgcct 165000
gtggatggtg gaggtattcc tcatgttaaa gttggaggag ctgatcctct ccagaaacgc 165060
ctgggccagc tcaggtgtga tgtcatagac catgtccagc tgcttggtgg cgttgtcata 165120
gctgataaac agcccaatct agttggtgga caaggacgag aatatcagtg aggagggtgg 165180
aagtggccca gtgtggcccc accctggtgg tctgcactgt gccccatcat ggacacttgg 165240
atacacctcc tggttctcat tgtcattgat gtcttttttt cttttctttt tttttttttt 165300
tttgagatgg agtctcactc tgtcgcccag gctggagtgc agtgacatga tctcagttca 165360
ctgcaacctc cacctcctga gttcaagcaa ttctcctgcc tcagcctccg gagtagctgg 165420
gactacaggt gcccaccacc acgcttggct aatatttgta ttttttagtag atatggggat 165480 tcaccatgtt gtccagggtg gtctcgaact cccagcatca agtgatccac ccgcctcggc 165540
ctcccaaagt gctgggatta caggcgtaag ccaccatgcc tggcctcatt gtcattgatt 165600
tcttagtggt ctgtaactgc tactttagtt tcctcctcaa cctaactatt ctttaggaaa 165660
gaattatttt ttaatatctg agaaactggg cttttttaaaa gctaatcttt gcacatttat 165720
ttctagattt gttatatgga ggtcagagaa tgtggtccac aaactttctg ctttgaagaa 165780
tcagaatttt tttaatagat gaatgagttt ataaatggcc cttgggtgat ggaaaagagt 165840
atgtgttctc tttgtaagac acaaagtttg gtgcatatat attcaactta ttaaatatac 165900
tattcagatt cccaacattc ttgttccttt ttggcccaca tgtccaaggg tgccacgtgc 165960
aagtcttcta ctactacagg actcatatct atctattctt ccttgtattt ctagcagatt 166020
ataaattata tatataattt tgggggggaca ctgactcact cttttttattt tattttttgtt 166080 tttattttta ttttttatttt tatttttttg agatggagtc tcgctctgtc acccaggctg 166140
gagtgcagtg gcacaatctc agctcactgc aacttcagcc tccgggttc aagtgatact 166200 cctgcctcag cctcctgagt agctgggatt acaggcatgt gcaaacatgc ccagctaatt 166260
attgtatttt tagtagagac ggggtttcgc catgttggcc aggctggtct tgaacacctg 166320
acctcacatg atccacccgc tcagcctcc caaagtgctg ggagtagagg cgtgagccac 166380
tgcgcccggc caagacacag tctcactctt ttacccaggc ttgggtgcag tggtgtgatc 166440
atggcttatt gcagcctcga cctcctgggc tcaagtgatc ctcccacctc agcctcccaa 166500
gtagctgaga cctcaggcac acaccactac acctggctaa ttttttaaatt tttttgtaga 166560
```

```
gatgaggttt cactatgttg cccaggctgg tcttgcactt ctgggctcaa gtgatcctcc   166620
cgccttggcc tcccaaagtg ctgggattac tggcatgggc cacggcagcc ggcacattct   166680
atattttgag acagtattat gctgtgctca aaggggctca taaagttgtc tctcctttgt   166740
ggatcgtact ctttgtccat ataaaattcc tttttaggct gggtgcggtg tctcacacct   166800
gtaataccag cactttggga ggctgaggca aggcagatca cctgaggtca agagttcaag   166860
accagcctgg ccaacatggt gaaacctcgt ctctgctaaa aatataaaaa ttagccaggc   166920
atggtggcat gtgcctgtaa tcccagctac tcaagaggct gaggcaggag aatcaattga   166980
atctgggaga aggaggttgc agtgagctga gatcacgcca ctgcacttta gcctggacga   167040
cagaacgaga ctccatttca taaataaaca aataaaataa aataaaattc ccttttagca   167100
gtgttattct tgacttctcc cttctctaca tttttagcga ataaaaagtt gcaaatgagt   167160
gcttgacctt agaaatttcc tctagggggc tcagctttct aagaatttaa gctgttacct   167220
actcaaagca actctacatt gagagagtaa atggcagtgg ggtgcgggt taattctagg    167280 actgcgggtt ataaaaatcg gaagacactt gaaatactcc cagcccccta ggtaaaagag   167340
agaaagctcg ttctgcctct ggtttcataa taaccacaca ttgctgggtc aatgggtcct   167400
tgaacaggcc agtcatttga tgcaaacact tctctcactg gccagaagag tcagggcaca   167460
tatgacttaa aaagaagaa gaagaagaag aaaaattgga agcaaggccc acagtctctt    167520
catgaatccc tttgtgttgg cagcattctt tggagaccgc attcaagaat catgatgccc   167580
aagggatttt agtgtcattg ggtcaacatc aaaaggagag ggacaggttg actagtgagt   167640
taagtaatcc tagaatgtgt gtatttctcc actgtaaact ctagaattaa aatctaacca   167700
ttgctcatgc tcaagtagct attaacagaa gtagctataa atagaagtag ctattaatcc   167760
attttgcttt tgctttgagt tcatgatccc aaggatggga aactttatat cttttgtcct   167820
tggccttctc cagtacaaaa ataccttaa atgattttg gttcatagcc aacaatccct     167880
ttaaatcatg tttgctcaca tcagagatgt gatcttagtt gtccacaatt cttttctctt   167940
tcttagccct tccacactaa aacaatccca tgactgccca cttgaaactt tcttccaata   168000
gttttcttca gaggcccaag gtctattggg ctgaggaggg tacacaattt ccaaggcacc   168060
ttgactggct ggatgaacat tagagtttga gaatacacct taccccaagt gtattagtaa   168120
tggtgacata taaatgtact tttccaactt acttctatag gactaatttt cgtaatttct   168180
tcaaacgata ggtgaaccat gtatctgccc aaaacccata agtgttccgc actgacccat   168240
gaagcagagt catctacaaa aaataaagaa atgaataaat gagtacatac ataaataaaa   168300
gcctttacac tggtatgtga tagtcaacag catctttgct gtcaagacct acttcttgca   168360
ttcattaatt cgttatttg ttttttcgggg ttttttgaga cagaatctca ctctgttgcc    168420
taggttggag tgcagtggtg tgatctcagc tcatctcaac ctccgcctgc cggttcaagc   168480
gattctcctg cctcagtctc ccaagtagct gggattacag gcaccacca ccatgcccag    168540 ctaattttg tattttagt agagacagag tttcaccatg ttggtcaggc tggtctcaaa     168600
ctcctgacct caggtgatct gcccgcctct gcctcccca agtgctggga ttacaggcat    168660
gagccaccat gcccagccac attaatttgt tattaactca ttcaacaatc atatacgtag   168720
ggcctacctg tgagatcaca cgtaggatgt gaacacagat tcgcaccacc tcagaccttg   168780
ttactcaata gtgtggtctt tggaattgca acatctgtgt cacctggcca cttgttagaa   168840
atacagatta ttctttctgg ccaggcacct gtaatctcag cattttggga ggctgaggca   168900
ggaggattgc ttgaggccag gagtttgaga ccagcctgag caatatatca agaccctcat   168960
```

```
cgctacaaaa aaaaaaaaaa aaaaaaaaaa agccagctgt agtcccagct actcaggaaa   169020
ctgagaaggg aggattgctt gaaaccagga atttgaggct acagtgagct atgtgctcac   169080
tctactgcac tccagcctgg gcaacagagt gagaccctgt ctctttaaaa agtaataat    169140 aattaaaaat aaataaataa ataagaaatg caggttattt ttaatactta aacccacaa    169200 aatgtagttt tattttttca ttcgattggt tactaaataa tctggaaaca tgaggccaga   169260
tgtggtggct cacacctgta atcacgaaat cccgtctcta ctaaaaatac aaagaaaaat   169320
tagccaggtg taatcccagc tacttgggag gctgaggcag gagaatctct tgagcccggg   169380
aggtggaggt ggcagtgagc cgggatcaca tcactgcatt ccagcctagg tgacagagcg   169440
agactctgtc taataataat aataatgata ataatctggc aacatgaaat atgtttgact   169500
gtcttgcatc actaccacta gtaaggatca tcctcactga ttatcaccat gttactatac   169560
ttgaaccaaa gcaaactact tgtacctccc caaaacattc tccaaatctt ggctggcctt   169620
ggccctgctc accacctaca atgcttttcc ttaccccttc tgcatccaaa tcctacttta   169680
agatcaagct caaattttcc tctcccttaa agccttctct tatctccttc acgagaagta   169740
ctttctccct ccactgaatt cccagaggac tctctctgac ccccgttct ggcttttgaa    169800 attccccatc actgagatgt cagtggaatt ttaaaaacca tcaagtcagc caggtgcggt   169860
ggctcaagcc tgtaatccca gaactttggg aggccgaggc aggtggatca caaggtcagg   169920
agatcgagag catactggtc aacatggcga accccatct ctaataaaac tacaaaaatt    169980
agccaggcgt ggtagcgcac gcctgtagtc ccagctactc aggaagctga ggcaggaaa    170040 tcacttgaac ccgggaggca gaagttgcag tgagctgaga tcataccact gcactccagc   170100
ctgagtgaca gagccagact ccatctcaga aaaaaaaaaa aaaaaaaaa aaaatatata    170160 tatatatata tatatctcaa gtctaggatc agacttcaag tttcactgag ctggaagtgg   170220
ctgccaatgc tccccagctc tttagcaaaa gacatttaca cacgatattg tattggaggc   170280
atttggggaa aatgaaggaa gtggggagca tttacagggt gcagtgactc taacatcaag   170340
agctatttgc agaagccgtg ggcaatgaca gatgccaaaa caagatggag aaatcaactt   170400
ttatatagac tgattcacaa gaaaatatgg agtgcctctc ccaaaccagg aatcaaagat   170460
gttggggtga cacaggcaga ctcctacgat cctctagatg gggaccctgg acatttgcct   170520
tgcctatata gagggctgga aacttttgag gctagaacca cacattcaca agaaccaag    170580 cttagttgtt tatttttaa  cttattacta agcataaact gtatttctgt agatcaatca    170640
tccccaagct tgggattttt ttttttcttc ctctgttgtc caggctggag tgcagttgga   170700
tgatcatagc tcactgaagc ctcaaactcc tgcctcagcc tccctagtag ctaggactac   170760
aggcacacat caccacatca ggctaatctt ttaatttttt tgtatggggg gggggtctc    170820 actacattgc ccaggctggc cttgaactcc tggcctcaag caatcctcct tcctcagcct   170880
tccaaaatgc taggattaga ggtgtaagcg accacacctg gccagcaagg ttgggatatt   170940
tttaacagcc aaagtatttc cagttccctc aagggccttc atgaaaaaac aatttaagtc   171000
caaacagaat taattttaac tcactgtagt ttaataatga agcgcaccgt ataagaattt   171060
tagaaggaaa gtctgtgcct aattaaactc tggcaataaa gacagagaag tctgaaggta   171120
gagaggcttt tcatggttta cccagtgtga gactctgatt cctggagacc acaattatgc   171180
accaggcaga gggaattcta ctatgcattt gagactttga ttatgatgtt gtttaatgtt   171240
cattatgcac aaatctcaga gctgaattcc aggaaaagat tgattggcat tccccatcct   171300
```

```
ccagccccat ctgctttcct tatgttttcc ccacaccgag ctcattcccg tctcagggcc    171360
tttgtatttc ctgggatttc tctctgggat gcccttcctc cagagcctta cgtgactggt    171420
tccatctcct cattttggtc ttgattcaaa tgtcacccac ttgagaggtc ttccctgatt    171480
ccttagtcca agagttggca aactacaatc catgggcaa actctgccca tcacctgttt     171540
ttatacagcc catgagccaa aagtggtttt tacatttatt attttggact ttttttttaga   171600 gacaaggtct cgctctgtca cccaggctgg agtccagtgg ctccatcacg gctcactgca    171660
gtctcaaact cctaggttca aggatcctc cccccctcag cctccagggt agctgggact      171720
acaggcatgt accaggacac cggctatttt ttaaaaaatt ttttaagaaa tggggtcttg    171780
ctatgttgcc caggctggtc ttgaactttt ggcttcaagt aatcctcctg cctgggcctc    171840
ccaaagtgct gggattacaa gcatgagcca ctgcaccctg cctgcttttt acctttttta    171900
atagctgaaa ggaaaatcaa aagaagaatc ctatttggtg acacatgaaa attatgcaaa   171960
tttcagcatc cattagtaaa gctttactgg gacacaggca tgctcattca tctattgtct    172020
acagctgtct tcaagctgca gcgtcagagc tgaatagttg aggcagagat ggtaggctta    172080
caaagcctaa aatatttacc tggtccttta cagaaaacat ttgccaagcg ctcttctagt    172140
ctaaagtacc tgtaatatcc tttctgcctg ggtgcagtgg tttatgcctg taatcccagc    172200
actttgggag gccaagccag gtggatctgt tgaggtcagg agtttgagac cagcctggcc    172260
aacatggagg aatcacatct ctactaaaaa tacaaaaatc agctggacat ggtggcaggc    172320
acctatactc tcagctattc aggagctgag agaatcactt gaactctgga ggcagaggtt    172380
gcagtgagcc gagattgtgc cactgcactc cagcctgggt gacagagtaa gactccgtct    172440
caacaaacta ttttatttt ttcatagccg ctaccagtat ctaaatttct aagttctctc     172500
tctctcttta tttacttaca tgtttaaaaa aattgtctcc accaacactc ccacaataaa    172560
acaatagggc cgtaagagca gagactttgt tttgtttcct tctctatctt cagctattga    172620
tacataatgg gcttttaaaa agtttattct gtttacatta ctgacattaa aggtttaaca    172680
aattgaagct atctgagaaa ttgtttgtat tgctaatcta tatagccatt cttttctatc    172740
gctgttttgt ttgtttgttt gttgtttgc ttgtttgcg acaaggtctc actacatcac     172800
tcaggctgga atgcagtggc acaatcccag ctcactgcaa gttctgcctc ccgggctcaa    172860
gtgattctcc cacctcagcc tcctgagtag ctgggaccac aggcgcacgc caccacacct    172920
ggcttttgtt tttttgtttg tttgttttgg taaagacaga gttttgccat gttggccagg    172980
ctggtctcaa actcctaacc tcaagtgatc tgcccgtctc agcctcccaa agtgctggga    173040
ttacaggtgt aagccaccgc acttggcccc aattttcttt tctttctttt ctttcttttt    173100
tttttttttt ttttgagaca gagtctcact ctgtcaccca ggatgcagtg caattgcatg    173160
atctcagttc actgtaacct ccacctcctg ggttcaagtg attctcctgc ctctgcctcc    173220
caaatagctg ggattacaga catgaaccac cacgccaggc taattttttg tatttttagt    173280
agagaagggg gttcaccatg ttggccaggc tggtctcgaa ctcctgacct cagttgatct    173340
gcctgactca gcctcccaaa gtgctggatt gtaggcatga gccaccatgc ccggcccacc    173400
tggccccatt tttaagtgta gagttgagcg ggagtaagta cattcacatc cacactattg    173460
tgcaaccgtc actaccagcc atatccagaa tattttgaac cttgcaaaat cgaaactgta    173520
ccaccattct aatttctgtc tctatgaatt tgactgctct aggacacaag gaggctttaa    173580
gcaacatcca tcaaataaat aaatcctgac ctacctgctt tggtagccag gacgctcaga    173640
gttaaatttc tgtgttttat tgcctagatt tcctaataaa attctcttct gtctctctct    173700
```

```
cttttttttt ttttcgagac ggagtctcgc tctgtcaccc aggccggagt gcagtggtgc    173760
aatctcagct cactgcaatc tctgcctccc cggttgaagc gattctcctg cctcaacctc    173820
ctgagtagct gggattacag gtgcccgcca ccacgctcgg ttaatctttg tattttagt    173880
agagatgtgg tttcaccatg tcggtcaggc tggtctcaaa ctcctgacct ccggcaatcc    173940
tcctgccttg gcctcccaaa gtgctgggat tacaggcgtg agccaccacg cccagcctct    174000
tctctcattt taatatagat ttttttatac agattttgaa cttgtacccc tactcaaggt    174060
tcacattgaa tctaagttac catcattatt tatattccac tgaaaaacta ggacacaaca    174120
tagattatga aatacaaaca catcattatt tcagacttcc acatgtgcga attgcattga    174180
cgaaatggag tatgtgtttt actccataag ccacatcaaa ctgtttttcg aagcagtggg    174240
aggtggtaaa aatcagaaga gaacaacatc aaatccatgt tttcagagat gaaacacctc    174300
ttctgaagat attcttcccc caaaagtga ccccacctcc aagtacaggc tcaccagtgg    174360
cattggagga tgtctgcagt attccagtca tccaggaata gagagctctc tgggaatgag    174420
ccgaggtttt gtcgtagaga tctttgaaca ctgcagatct aaatgacaca aacacaggca    174480
tcagctaata acaagcaggt gggggctgca ttaaaaaggg agtcacaaca gcaaatgtga    174540
cccaaagctg tcttgtgtta aaacccttcc ctctcctgga tgtggagaaa tagaaacgct    174600
tttacactgt tggttggaat gtaaattgat tcaaccattg tggaagacag cgtggtgatt    174660
cctcaagaat ctaggactag aattaccatt tgacccagca atcccatttc tgggtatgta    174720
cccaaaggat tataaatcat gctactataa agacacatgc acacgtatgt ttattgtggc    174780
actattcaca atagcaaaga cttggaacca acccaaatgt cctccaatga tggactggat    174840
taagaaaatg tgacacatat acaccatgga atactatgca gccctaaaaa aggatgagtt    174900
cgtgtccttt gcagggacat ggatgaagct ggaaaccacc attctcagca aactatcaca    174960
aggacagaaa accaaacacc gcatgttctc actcataggt gggaattgaa caatgagatc    175020
acttgggcac agcaagggga acatcacaca ccggggcctg ttgggggtg ggggagggg    175080
gtggggatag cattaggaga tatacctaat gtaaatgatg agttgatggg tgcagcaaac    175140
caacatggca catgtatacc tatgtatcaa acctgcacgt tgtgcacatg taccctagaa    175200
cttaaagtat atttaaaaaa aaaaaacctt ccctttcttg aatgtaaatt ggttcaacca    175260
ttgtggaaga cagtgtagcg attcctcaga gatctagaac tagaaatacc atttgaccca    175320
gcaatcccat tatcgggtat atacccaaaa atatataaat cattctgtca caaagataaa    175380
tgcacacatg atcattgcag cactaatcac aatagtaaag acatgtagtc aacccaaatg    175440
cccatcaata atagactgga taaagaaaat gtggtacata taccatgg aatactatgc    175500
agccataaaa atgaacaaga ttatgtcttt tgcagggaca tgaatggacc tggaagccat    175560
tatcctcagc aaactaacgc aggaacagaa aatgaaacac cccatgttct cacttgtaag    175620
tggaagctga acgatgagat cacatggaca cagggagggg aacaacacac actgggtcct    175680
attgtggggg tggggtgggg gagggagagc attaggaaaa atatctaatg catgctgggc    175740
ttgataccta ggtggtgggt tgataggtac agcaaaccac catggtacac gtttacctat    175800
gtaacaaacc tgcacatcct gcacgtgtac cccagaactt aaaaataaaa aatacccca    175860
aacacactcc ttaggtatat gtaactattt ttcccatttt cctcttcccc ttcacagcta    175920
aacaccttcc aaagaatatt ccatacatat tgtctccact tcctcacctc ttggtccttt    175980
tttggggaag tgggggcagc tctgttgaga tataattccc acaccttaca attcacccat    176040
```

```
ttaaagtaca caattgggcc gggtgcagtg gctcacacct gtaatcccag cactttggga    176100
agccaaggca ggcggatcac ctgaggtcag gagtttgaga ccagcctgac caatatgatg    176160
aaactctgtc tctactaaaa atacaaaaag tagccaggcg tggtggcatg cacctgtaat    176220
cccagctact tgggaggctg agacaggaga atcacttgaa cctgggaggt ggaggttgca    176280
gtgagccgag atggggccat tgcactccag cctgggcaac aagagtgaaa ctctgtctca    176340
aaaaaaaaaa aattacataa ataaagtgca caattcagtg gttttcagca tataagacaa    176400
agagccaaag atgtttctga tggcatcatt tgagtctctg gatccagctg cgtctgaagt    176460 cagcccctaca cctaaaacta ttcaattaca tgttccaata attcccttt tgcttcaagc    176520 cagtttgaat gggttttct gccacttggg cttactgctt actcaggtga gcagtaacca    176580
ataaactctc tctcccaatg atgttctctt ccacaatctg catgaacgga ggagggaaga    176640
gatgctgaat ttaaaaggaa tagtataata gcctgcagag caaaagggtt tcatttatat    176700
acatcttagt gaaaaaaact ggcaacctag agaaacgatg aggtcagcat actgtctgtt    176760
ttccttactg tcatttggct acaaaagata aaggaatct cccacattgt tatcatcata    176820
ttggtctttt ccttcttcta aatcattttt agatttagaa agagtgcttt atggccataa    176880
agcactacga ttagtaaaag gagggagttg gcggtggttg caatgcctat ggcccttcaa    176940
gtcctagaca caatcctcga atttggttta catcaaagcg caatttcatg cagggctagg    177000
tgtaaccaat ctaagctggc atggcatctc aaaaggagaa gtcctccttt ttcagtgctc    177060
tgtcactcct tctgttgtcc ctcaagaaca aagtctcagt ttagtgccag tgaatcttta    177120
aaacacactc agattgtttt taaatcaatg gaacaagacc caggctcaga gcctttgtgc    177180
tgtggactga atgtttgcgt ttccccaaat tcatgtgtt gaaatcctaa ttcccaacat    177240
gaaggtatta agaggtggag ttttgaggag gtgattaggt catgaggctg gatacctcat    177300
gaatgggatt agtgccctta taaagagat cccagagggc ttgcccaccc cttccaccac    177360
aaggggacac agcgagaagg tgccacctat aaaccagaaa gcgagccctc accagacacc    177420
aagtctgtca gcaccttgat cttggacttc ccagcctcca gaaccatgag aaataaatgc    177480
ttcttgttta ctagccacac agtctatggt atttttgtta cagcagccca atctgactaa    177540
cacacttaag caagcaacat atctagctag gatttagtaa cactttttt cccactgtat    177600 ttatttatgt gggtttttt gttttttgttt tttgtttgtt tgtttttgtt tttgagatgg    177660
agtctcactc tgtcgcccag gttggagtgc agtggcatga tcccagctca ctgcaacctc    177720
cacctcccag gttcaagcaa ttctcctgcc tcaagcctcc caagtagctg agattacagg    177780
cgcccaccac catgcccaac taatttttgt attttagta gagacgtggt ttcattatgt    177840
tggccaggct ggtctcgaac tgctgacatc atgatccacc cacctctgct tcccaaagtg    177900
ctgggatcac aggtgtgagc taccacaccc agcctaactc tacagatgtt aagcttttgc    177960
tccaaaacgt gcatatcaac ctgtccccac ttgtcttctc cctgctgcca ggtgagatct    178020
ctttgcattc tcacggcagc ccctgaagga tactgtgatg agttaagaag gtgggagtgg    178080
ctgggtgcag tggctcatgc ccgtaatcca agcactttgg gaggccaagg caggtggatc    178140
acttgatgtc aggagttcga aaccagcctg gccaacatgg tgaaactcca tctgtacaaa    178200
aatacaaaaa ttagtcgggt gtggtaggcg cccctgtagt cccagctact ggaattgag    178260 gcaggagaat cacttgaacc tgggaggcag aggttgcagt gagccgagac tgcaccactg    178320
cactccaacc tgggcgacag agtgaaactc catctcaaaa aaaaaaaaa aaagttcgg    178380 aggaaccact cacaggttct taaaggcatc ctcgcgcagg tcccgaggga gccgctctgt    178440
```

```
gatgtctggc tggagaaagc tccctgagga cccctcagc accttgccca ggatctccac 178500
acactccagg gagttcagca tctggaaaca cctctccagt gtgatgagaa acaggctgcg 178560
gttcacgcca gggctctgca aggctcgttc tcgaatctct cctaagtcga tgatgatgtc 178620
tttcaggtcc taaagcaatg acagaagcca gggtcagttt gagagctgcc tctcaatttg 178680
gaagccctgg gagggaccac acattgcaac agtggggaaa gtcaggatca ctgtttaaca 178740
ccatgctgct atgttgaaac ttctagaact ttccattccc tgcagaacaa agtcaaggcc 178800
tttacctgct ccactcactg tggagcctcc ccactctcca gatacacctg accagcatac 178860
atcaggccct tggtctacct ggaattctgc atctttcctt tttctggtga aatctagctc 178920
atcctttaag tctgggctcc attgccatca ccttcgtgaa gtctctgatc cctccaactt 178980
cctacttcag atcagatttc cctcccttat gtggccccag gcatcttga accaaactct 179040 ataatgcatt aaagggactc atgcgtcttt cctccaagcc cgtggttctc atctctgggt 179100
gcacatcaga atcacctggg gagctttttt aaagttttat tttatttttg agacagggtc 179160
tcgctctgtc acccagtccg cagtgcagtg gtgtgattat agctcactgc agcctcaacc 179220
tcctgggatt gagcgatcct cccacctcag cctcccaagt agctgggact acaggcacac 179280
accaccatgc tcagctgttt tttgtagaga tggagttttg ccatgttgtc caggctggtc 179340
tcaaactact gggctcaagc aatctgccca caacctccca aagtgctagg gttacagta 179400 tgagccacca tgcccagccc atctggggag attttgaaaa ggactgattg gcctggaaca 179460
gtggctcaca tctataaccc cagcatgttg ggaggctgag gcaggttgat cgcttgagcc 179520
taggagtttg agaccagcct aggcaacaca gggagacccc gtccctaaaa aataaatttt 179580
ttaaaattag ctgggtgtgc taatgcgcac ctgtagtcct agctgcttga gaggctgagg 179640
tgggaggatc acttgggctc aggatatcaa ggctgcagtg agctataatt ataccactgc 179700
actccagcct ggatgacaga gcaagcccct gtctctaaga aaaaaaaaa aagcctccat 179760 tttactgagc attgactcta ctgtgccaag cttggagcaa acgcatcatc tgattaattc 179820
tcatgacaat cctaccggtt aagccccatg ggtactaggg tcaggcattc ccaggttcca 179880
gtcccagggc ctccattatc tgtgtgtcct gagcaaatga cttaccttt ttaagtccca 179940 gtttttaagg tctcagaggc cttgctttgt gatattcttg gatcactaaa ctcattttgt 180000
ggaaattaac tgttcctgtt ttttgtctcc cctccagacc gtgagctcct tgagtgcagg 180060
aggatctctg tgtccactgg tgcatagtaa ttttactag tggatgttta ttgacccaaa 180120
caaccaggag attctcagat ccttaattag gacccgtcat ttcttagtac tgacaaaaat 180180
atgaattagg ccaggcatgg tggctcacac ctgtaatccc agcactttgg gatgccgagg 180240
caggcaaatc acttgaggcc aggagtttga gccagcctg gcaaaatctc gtctctacta 180300
aaaatacaaa aattagccag gcatggtggt gcacacttgt aatcccagct acttgggagg 180360
ctgaggcaca agaatcactt aaacccagga ggcagaagtt acagtgagct gagattgtgc 180420
cactgcactc cagcctgagt gacagagtga gactctaaaa caaaaataaa ataaaaatt 180480 gtaaggctct tcattttaac tttggagaaa gtaagtgaga aaacttaggt cctaaagccc 180540 ccaggggtt ggaggaggca gaaggagaga ggaagagaca atgaagtgcc aaggcctaag 180600
tcaggctcca tttattcaat tcaacaaaca ccacgtggtg ctggacttcc tctatccccg 180660
ggatgccaag ggctcctcac caagccgtcc ttcttgtctt ctaagaggca tttcatggca 180720
gtgcggaact gctgggcgtc tgtcttcctc aggtcctcca gcagcttctg gggctggtgc 180780
```

```
agacgctgct ccaggtggtt ttccacggct gcctgtattt ggggtgttgg gagagtcggt    180840
gagaacagaa agagcaggag cacatggtca gcaccatggc cagcggccca gcccggcccc    180900
ctcattccct gcagagacca caactagtgg ccagcagtct ggtttggcca cctccaaatt    180960
tcctcattag ccgccaacat ttaaaaatga ggggccgggc gcggtggctc atgcctgtaa    181020
tcccagcact ttgggaggcc gaggcgggtg gatcacgagg tgaagagatc aagaccatcc    181080
tggccaacat ggtgaaaccc cgtctctact aaaaatacaa aaattagctg ggtgtggtgg    181140
cgcacgcctg tagtcccagc tacttgggag gctgaggcag gagaatcgct taaacccggg    181200
aggcggaggt tgcagtgagc cgagatcacg ccactgcact ccagcctggt gacagagcga    181260
gactccacct aaataataat aataataata ataataataa taataagggg attcctcaca    181320
agatcaagat ttccaacttc tcttgaaaaa gtaaaggttt ggcaacaccg ggcgcacatc    181380
cccttttagg caataattgg caagccaagg gacagctgct tgttgaagta actctcaggc    181440
ccagccagcc cgattccccc attccatggc ctgcctggtc cctgtaggtg attgagtttc    181500
ccatcagcag cagctggcct ttgtccagga agtttagaac cccagatggc actgtgccca    181560
aacccaagct accagcgcag gagcaaaata caggcgaaat gaacatactc tgtggcgccc    181620
cctacagggc aaggagcaga agccatcagc ctctcctgaa agagatttcc tctgctgtct    181680
ggggaattgt tctctaaatc tccgttaaac agacatgccc agtgtgatgt catgggcaaa    181740
aggtgaactc tagacccaga caagccacat gcaaatcccc accttgacac ttactagctg    181800
tgtggcttgg acgagttact taactagggt tgctgggtaa aatacaggat gctcagttaa    181860
atttgaattt cgggaaaaac tacacatttt tttttttta gtataagtat gtctcaaatg    181920
ttgcatagga catacttaac ttaaaaaatc actcattgtt tgccaggcaa ggtggcccac    181980
acctgtaatc ccagcacttt gggaggccaa gacaggcgga tcatgaggtc aggagtttga    182040
gaccagcctg gccaacatag tgaaacccca tctctactaa aaatacacaa attagccagg    182100
catgatggca tgcacctgta gtcccagcta ctcaggaggc tgaggcagga gaattgcttg    182160
aacctgggag gaggaggttg tggtgagctg aggtggcacc actgcactcc agcctgggca    182220
acagagcaag actctgtctc aaaaaaaaaa aaatcactca ttatttatct gaaattcaaa    182280
cgaaattgga catctgtttt ttgtttttgt ttttgtttta gagacggggt cttgctctgt    182340
tgcccaggct gaaatgcagt ggtatgatca tagctcaccg taacctcaaa ctcctgggct    182400
caagcaatcc tcctgcctca gccttccaag tagctgggac tacaggccac accaccacac    182460
tcagctaatt ttttgtttgt ttgtttgttt gttttttgtag agacaaggtc tcgctatgtt    182520
ggcaaggctt gtctccaact cctggtatca agcaatcctc ccacctatgc ctctcaaagt    182580
gctgggatta caggcatgag ccaccacgca gagtcacatc tgtattttta tttgctaaat    182640
cagcaacatt tcttctgggc tcagtttttc ttatctgcaa aatggaggca ataaaaggac    182700
ttaccacata gagttattac gaggattcag tgtgtaaagt gttttcaata gttgctagca    182760
cacagtaagt gctcaatagt gccagctatt attctctatc ttgaccaagg tgaataatgg    182820
cttaattaaa gcctcacccc taaaatgaaa ggtccttgtg ggtagtatca tgactgcctt    182880
gttccctact gagtcctcag tgtctagagc tatgcctggc agaaagcaga tgttaactca    182940
gtagatatta aatgaataaa taaatatggt atatacacag gaagaaacgt atcagattaa    183000
agtggataca tctcatgagt atccattact gctagagaga aaagtggcaa gcattgcttc    183060
tctttcagtt tccctgactg atgaagaaga aagaaaagc agatgccatg tggggccaac    183120
agccacctcc agctagtggc tgtcctggga cctggcagac aacaagctct ctgagtatat    183180
```

```
ttgtgatatc aatgttggtt gatgtttcca ttttcattca aacataagta aaaatggaaa  183240
caatgaagac atatgtcaga actttattca ttaattaatg acataaatgg tcttttgcta  183300
aactgaataa ctttctcaat actgaaagaa tttttctcca attttctgtg ttatccacag  183360
tgtgatgata aagacacaac atgccacact aggctaacag tcaggcaggt gctgtgcagt  183420
tcaccgcagt caccaccaca ggcacgagcc ctattgcccc ttaaggcaaa tatcctttgc  183480
cacctatcaa cacgcttgtg ctattgtttt cattacagta gtacatttct tggacccatg  183540
gtagaaagac tgatcactat atccaaatat ccactctctc actgctcttt atcaattgaa  183600
cccttcaact tttagttggg tacatggctc ctttgcagta agatgtgact atggtgtgtg  183660
agccaatcta atgtgtgcag agggaattgt gtaacttgcg tcatatcctc agaagagaag  183720
atgctaccct tgtcttcttc ttcccaccca tccctggat tggagaaagg aagaggtgtt  183780
tccaccacat gggcaataac tccccaggag atgacaaagc aaaagataa aaggaacctg  183840 ggtccttgga taacctcatg gaatagagct gccttttctc tgtggctttc ccacttagct  183900
ctggactatt gtacgagaaa gaaataaact aaattgtttg agctgctgtc atctggggt  183960 cttttttgtta tagcagctca gcctatatcc taatatacca tgtctccatc aaaggtggga  184020
aaatgaaaga aagacaaaat agcttatatc atgtttcaag aaaaactgga cagaacccttt  184080 ttccttgcag aagcaaagac tatctctaca tccagcccac ttctccaact tacctggccc  184140
ctgagtttgc aatccctgag cactgagatg gaacatata gatgggtctc aggtacacac  184200
ctgcaggctg gggatggtga aggcaacatt ccgggaattc agataggcca ggactctgtg  184260
ggacaggtca tccgtccaca cgtgggagct tcagttgaag acagacagga aaagatcaca  184320
atgacagatt ctcctacaag cactactgta ctagctaagt gcccagggga caggtaggga  184380
tggaccaggg gtgttaggac tttgtacttg gaagtgggag gtttctcttt tcttttcttt  184440
ccttttttct tttctctttt tttgaaacag ggtcttgctc tgttgcgcga tcacggctca  184500
ctgcagcctc aatctcccca gcccaagtga tcttccaacc tcagccaccc aagcagctgg  184560
gatcacaggt gcatgccaca acacccagct aatttttttgt agagatgggg tctcactatg  184620
ttgcccaggc tggtctcaaa ctcctgggct caagcaatcc tcccacctct gcctcccaaa  184680
gtgctgggat tacaggagtg agctgctgca cccagcctga agtaaaaaat ttcttaacca  184740
ggcacagtga taggatagtt tccaattcta ggaatctgcc tggatcccat tctctcaaag  184800
ccaattccca aatttctaag ctgtatgcaa tattctaatt cccgtaacaa tctgcttaga  184860
ttgactacaa tccaaactga ttgtgttaga aagatgtaca tttaaaagca gacgctaggt  184920
acaccatgag aggctggaat agcatagtta ggagtgtggg ctccaaactg gatttgaatc  184980
ctagttccat cacttagttg tgtggcttga gacaatttga taaattttct tgtgcctcag  185040
tttcccttta tatgaaatat ggttaacaac tgtgagatta aaatttgttc acacatgaaa  185100
attgcgtaag actgtgccca acacacagta aatgcccatg aatagccttt tctcatttt  185160 tttttttttt ttggagacag agtctcactc tgttacccag gctggagtgc agtggtgcaa  185220
tctcagctca ctgcaacctc cgcctcccag gttcaagcga ttctcctgcc tcagccttcc  185280
aagtagctgg aattacaggc gtgcaccacc acatccagct cattttttcta tttttagtag  185340 atactgagtt ttgccatgtt ggccgggctg ggctggaact cctggcctta gcgatcctc  185400 ctaccttggc ctcccaaagt gctgggatta caggataagc caccatgccc agcctatgaa  185460
aagccttttg taatcttacg tttgcttctt tgtttgtttg tttgtttgtt ttgcgatgga  185520
```

```
gtctcactct gttgcccagg ctggagtgca gtggctcaat cttggcttat cacaacctca   185580
gcctcccgcg ttcaagtgat cctcctgcct cagcctcctg agtagctggg actacaggta   185640
tgcaccacca tgcctagcta attcttttgt acttttagta gggacagggt ttcactatgt   185700
tggccaggct ggtcccgaac tcctgacttc atgatccgcc cccttggcc tctcaaagtc    185760 ctggaattat aggcatgagc caccgcgccc ggcctgtaat cttataaaga gatggatgga   185820
tggatggatg gatggatgga tggataaatt aataaacaaa taaaatactt agactgaaag   185880
aatatatcca aaagtaccca ttggtgttat cttagggaaa ggagtggtta tgggagtctt   185940
tcactttaac ataactgggt atccctgata tgaggcccca agaccccat ttcttatcga    186000 tcatagtact catcatatta gaattgttta ttaatattgg cgtttccaca ctacctagtt   186060
ccctgcccca tgtccctggt atctgtctgt atgcagctta taatgcaaca gtaaagggaa   186120
tgggtcctgg agccaggcca ctggttcaca tcccagttgt gtgtccttga tttacccttc   186180
ctggacctca gtttcaccat tgtgtgcaat gggataacaa tgggaactac attgtgtggc   186240
acttgtgagg attagattgt ttctatacca agcgcttagt agaatacccca ctacatgaa   186300 agcactcaat aaatttcagc tcttaggccg gttgcggtgg ctcacacctg taatcccagc   186360
actttgggag gctgaggccg gcagatcacc tgaggtcagg agtttgagac cagcctggcc   186420
aacatggtga aaacccatct ctactaaaaa tacaaaaatt agccgggcat ggtgacaggt   186480
acctgttacc ccagctactc aggaggctga ggcaggaaaa ttgcttgaac cccgaggca    186540 gaggttgcag tagtgagcca agatagcacc actgcactcc atcctgggca acaagagcga   186600
aactccattc aaaaaagaa aaaaattgg cccttatgct agagtgagga ggaatgatgc    186660
ccgtggagca agggtgtttg ttgactttta acacattgtg cattgattga cattttttgt   186720
aatgagcaca tattacttt tacaattaag agacttccat taagaatttt tattaaaat    186780 ctataccatc ccttccccctc tcctctaggg cattttacct ttgaaactgt atgagatcca   186840
gcagtgctac aatgggagta aaatgaaaag acatcttttaa aaggaatcat tccagagaga   186900
tcacagctac attctgtttg aaattcttag aagaagcaag tggagatcaa ggggcacat    186960 taccattcag atagcttcca tctattattt cttcctaaaa ggcaaagaga taacatcaag   187020
tataacaacc aaaagttggc aattccagta gaggggactc tgattaacag aaaatagaat   187080
actcaccgcc atgttttgca acaatggatg caaatctgta agaaagccat tgaatgtata   187140
actagaattg aattgtgtga ccttcaaaac tacaaatatg ggttagagga aaagcccag    187200 aaagccactc atgaaggaaa ttttagtga atttaatta taactgtcca ctctgagaaa    187260
accgtggctt gaaaaatcct cttagaataa tcctgaaaaa tcatacatgc acacacacac   187320
agcccaaaaa caacttacag catcatgtac ctaatgtatc tatcccacct cattccctaa   187380
actgtgtgga aaccacaaag ggtgattctt ccctcaggac ttaccctgcc tggaatttgg   187440
cactgtataa ctcgacactc catggctcag aaaaaggaat aggaaaaggg agtatgtcgt   187500
aggttcctga gacattctcc tgtagttaat ttaagcatag aagtgattca tgtttttttt   187560
atatatatat atatacacac acacacatat atatacatgt atataaacat atatatatat   187620
atggacattc agaagacaaa aggaaaaacc aagtacaccc agaatccctt gaagtctttt   187680
ttaaaaataa ttttaaaact cacctacttt cctccatcta aaccccccatt cttgtctaag   187740 acactatcat ctctctcctt ggtgactaca atggcctgtt tatcttacca ctacccccaa   187800
ctcctctcaa tccagcaaaa aggtatagtc aaaagtagac tctgggccaa gcatggtggc   187860
tcacacctgt aatcccagca ctttgcatgg ccaaggtggg tggatctctt gaggtcagga   187920
```

```
gttcgagacc agcctggcca acatagtgaa accctgtctc tactaaaaat aaaaaattaa  187980
ctgggtatgg tggtgcatgt ctgtagtccc agctacttgg gaggctaaga caggagaagt  188040
gcctgaatct gtgaggtaga ggttgcagtg agccaagatt gtgccactgc actccagcct  188100
gggcaacaga gcgagactct ggaaaaaaaa aagtatagac tctattttat ctgcaagaaa  188160
tttatatcca gaatacaaaa actactctta taattcaata agaagataga caagccaagg  188220
ggaaaaaatg ttaaaaagat atgaagttgg ccaggcgcag tggctcacgc ctgtaatccc  188280
agcactttgg gaggctgagg tgggcggatc atgaggtcag gagatccaga ccatcctggc  188340
taacacggtg aaaccccgtc tctaataaaa atacaaaaaa attagacggg cgtggtggcg  188400
ggcgcctgta gtcccagcta ctcaggaggc tgaggaagaa gaatggcgtg aaccctggat  188460
gcggagcttg cagtgagccg agatcacgcc actgcactcc agcctgggcg acagagcaag  188520
actccgtctc aaaaaaaaaa aaaaaaaaaa gatatgaagc taaacttcat aaaaacagat  188580
gtaaaaatgg ccaataagca cacaaatgat tatcacatta gctaacaaga actagcaaat  188640
taaactcaca acgagaccac tacaaagtca ctagaatggg caaaaatttc aaagactgac  188700
tatcaaatgt tggtgatgat atggaacaac aggaactctg atacagctgc ttggaaaaac  188760
tgtttgacag tgtcttacag agttaaatat acaatacctt atgatcaaga aatgccaccc  188820
ctaggtattt aagcaagaga aatgaaaaca tgtctacaca aagatttata tagcttcatt  188880
catagtagcc agatattgga aacaatcaca tatccaataa caggtgaaag gttaaacatg  188940
gatctccatt cagtgggata ccattcagta ataacaataa aaagaaattc atcataattt  189000
tattctagct atgatggagt aattggcaat ggataaaccg tcctgcctta aacaattaaa  189060
aagctggctg aaatatgtgc atccaaaggt ttttcagaca ttgggcagca ggtagcacaa  189120
gactgagatc cctgagcaag gaaggcaaac aagctgagct ctataattgc tcctgctcac  189180
tgcctggagt ctccatccaa cagcacaagg agggagaatc caaacagagc ctacaggtct  189240
cactgagcag aagagacgga gtggaacttc agggaaatca aggcagctag aatccataag  189300
aagaatactt ggagaggagg aagttgcaca gagagaaagt tctggagatc tgaagaaggg  189360
tcttttgaga ctttggctga atatttatct acctttgcat gtaagaaacc tcctgaggct  189420
ggagaatgaa ccaccagtag gcagaacaat ccttggacct cacagggaa tgagaatagc  189480 tcctgcaagc tgcaatggaa aaacctccaa acacattggg catcagggtc aatcatcaaa  189540
gaacaattgc ctccatgata ggccaaatta gccctaggct aaagtttatt ccagatctgc  189600
cctaacaaat ctcaaaagca agttctggaa ggatctaatt gattccaagt aactgaattg  189660
cattccagaa caaacccaa caatatttaa agcagtatca taaaacccag aaacttcaga  189720
aaaccagaag atggagaaag aaaaaaaaga aaaaaaaat ccagcaatgt aaaatccgaa  189780
gtgtccagat ctaatcaaaa attatcaggc aggccaagca cagtggctca tgcctataat  189840
cccagccctt tgggaggcca aggaaggtga attgtctgag ctcaggagtt tgtgaccagc  189900
ctgggcaaca tggtgaaact ctgtctttac caaaaatgca aaactttgcc agggatgtgg  189960
caggtgccca actactcagg aggctgaggt gggagggtca ctgaagcctg gaaagttgag  190020
gctgcaatga gccatgatta tgccactgca ctccagccag ggtgacagag cgagaacctg  190080
tctcaaagaa atttttttaat aaataaataa aaattaccag gcatactagg aagcaggaaa  190140
atatggctga ttatcaggag aaaaatccaa tcaatagaac agatccagaa atgcacagaa  190200
agatccaatt aatggacaag gatgtttatt ataaatacac tctggaagtt caagaaagta  190260
```

```
gggaaaactg cgagcatgtt aaagggagag acatggtagg tgcgaaaaaa accccaagag   190320
gaacttctag agataaaaat acaatatctg aaatggaaaa tacacgggat agagttaaca   190380
gcatattaga cactgcagaa gaaaaattag tgaacttgaa gtcatagcaa aataaattat   190440
ccaaagtaaa atgcaggggg aaaaagactg aaaaaattaa gagggctctg gagcaatatg   190500
aaactatttg aaatatgtgt aactggagtc ccaggaaagg aggggtggc acaaaaatat    190560 ctgaataaat cattagcagg gcacagtggc tcacgcctgt aatcccacat tttggaaggt   190620
tgaggtgggc aaatcacttg aggccaagag ttcaaaacca gcctggccaa catggtgaag   190680
ccccatctct ataaaaaaaa aaaaaaaaa aaaaaaaaa atagccaggt gtggtggctg      190740
taatcccagc tactcaggag gctgggcaca aaatcactt gaacctggga ggcggaagtt     190800
gtagtgagcc aagattgcac cactgcactc cagcctaggt gacagaatga gactgaaaaa   190860 aaaagagag agagagaaag aaaaagaaag aaggaaagaa agagagaaag aaaaagaaag     190920
aaagaaagaa agaagaaag aaagaaagaa agacagaaag aaaacatgac ctcatgacca    190980
aatttgtgta aagtttgata gaactacaga tccacagatc caagaagctc aaccaacccc   191040
aagcagagga atcatgaata aagccacgcc aaggcatata ataatcaaat tgctaaaaaa    191100
aaaaaaaaaa aaaaaaaaa gattttaaa aaaatccag caaaaggag ttgcatctag       191160 actatattga aaaactctta aaactaaaaa ataaataagc aatccaatca gaaacgagc    191220 agaagatatg tgcagatata tcatcaaagt atatatacag atagcaaata aacacatggg   191280
aagatactca gcactgttag ccattaggaa aatgaccact gaaaccacag tataattata    191340
ggcctatcag atggctaaaa taaaaaaaaa aaaccataa tgaagccagg cgcagtgaat    191400
catgcctgta atcccagcac tttggaaggc cgaggtgggt gaatcacctg agatcaggag   191460
tttgagacca gcctggccaa catggtgaaa ccccatctct actaaaaata caaatattag   191520
ccgggcatgg tggctcatgc ctgtagtccc agctactcag gaggctgagg caggagaatt    191580
gcttgaaccg aggaggcgga ggttgcagtg actgggaggc agaggttgca gtgagccaag    191640
attgcaccac tgcactccag cctgggcaac agagtgagac ttcaactcaa aaataaataa   191700
ataaatgtaa ccataatgcc attaactaga aagaatgagg agaaactgga tcactcacac    191760
attgctgatg agaatataag gtggtacagc tattctggaa aatagttttg ttgtttctta   191820
taaaattaaa tgtgtactta acgtacagcc caacaattac actcttgggc atttatccca    191880 gaaaatgaa aatttatgtt cacataaaaa cctgtacaca ggctgggcat ggtggctcac     191940
gcctataatc ccagcacttt gggaggctga ggcgggtgga tcacgaggtc aggagatcaa   192000
gaccatcctg gctaacatgg tgaaacccca tctctactaa aaatacaaaa aattagctag    192060
gcgtggtggt gggcgcctgt agtcccagct acttgggagg ctgaggcagg agaatggcat    192120
gaacccagga gacagagctt gcagtgatgc agtgagccaa gatcacgcca ctgcattcca   192180
gcctgggtga cagtgtgaga ctccaactca aaaacaaac aaacaaacaa acaaaacctg    192240
tacacaaatg ttcatagcat ctttattcat agtagctgaa aaattgaacc aatctaaatg    192300
tcattccgta ggtgaatggt taaactcact gtgtgtggta tgtccacgcc attgaatact    192360
actcagcaat gaaaaggaat gaactattga tacaggcaac aactttgatg cacctaaagg   192420
gaattatgca gagggaagaa agccaatcac tgaaagttat atactaatga ttccaattat   192480
aaagcattct tgaaataaaa ttatagaaat gcagactaga ttggtatttg ccatggggag    192540
agggagataa ggctgtcaag ggatgcatga aagaggcttg tgatcaccag gagagttctg    192600
ggtcctgatt agggtagctg atacattagt ctacacatgt cacaaaattg aagaaaacga   192660
```

```
tataaaatat acacacaaag gagtgcatgt aaaactagtg aaatctgaat aagccctgaa 192720
tttgtaccat gatttcctga attttatatg gtactattgt tacataacat gtaaccaatg 192780
ggggaaactg ggtgaagagt acacaggata tttcttttgc aacttcctat gaatctgtag 192840
ttatttcaaa ttcttttta ttttcttgag agacagagtc tttctctgtc acccagcctg 192900
cagtgcagtg gcatgatcat ggctcactgc agccttgaac tcctgtgttc aagtgatcct 192960
ctggtctcag cctcctgaga agctgagact acaggcatgc actaccatgc ccagctaatt 193020
cttttagttc ttgtagaaat gggttcttgc tatgtttccc aggctgatct caaactcctg 193080
gcctcaagca atcctcccat ctcggcctcc caaagtgcta ggaatacagg catgggccac 193140
catccctggc cacacaattg ttttttaatt tagttatagt agtctgtacc actgtaggat 193200
gacaatagtt aacaataata tatagtttca aatagctaga aggaagatac tgaacagaaa 193260
gaaatgagaa atgtttgaga tggtagacat gctaattacc ctgactgatc accatacatt 193320
atacacatca aaacatcttt atgtacccca taaatatgta caattattat atgtcaattt 193380
tttttttttt ttttgagatg gagtctcact ctgtcaccca ggctggagtg tagtggcgca 193440
atctcggctc actgcaacct ccgcctccca ggtgcaagcg attctcctgc ctcagcctcc 193500
tgagtagctg ggataacagg catgcgccac cacacccagc taattttgt attttagta 193560 gagatggggt ttcgccatgt tggtcaggct ggtctggaac tcctgacctc tggtgatcag 193620
cccacttcag cctcccaaag tgctgggatt gctggcgtga gccaccgtgc ccggcgtata 193680
tgtcaatttt ttaaataaat aaaataataa atttttaagc acccaagggg aaaaaaccca 193740
tattatatgc ataggaaaag gaatacacta ctgatatagg caacaacaca gatgaacctc 193800
agaaacatta tgcttatgct gagcaaaaga agccagtcaa aaaagaccac ataacatatg 193860
attccatttc tgtgaaactc taagttatct agaatatcta gattctaggt tatctaggtt 193920
acctagaata atcttcagtg acaggaaaca aattaggatt ggtctggggc attattaggg 193980
tacaatggga aaagtttatt gcaacagggc acaagggaac ttcttggagt gatggaaaaa 194040
ttttttttgt agatataggg tctcactata gtgcccaagc tggtctcaaa ctcctggttt 194100
caagcaatcc tcccttcgag cttcccaaag tactgggatt acaggtggat gccattgcac 194160
ccagccccca ttttttgtat cttgattgtg gtggttgtca cacagataca tacatttatc 194220
agatctcact gaactgtaca cttagtgtgc attgtattgc ctgtaaattt atacctcaca 194280
aaagtcagta tcaaacagaa atggaaaagc atggactgtg gagccagtca cctgttctga 194340
atcacgtctc cgccacttac tagctgtgca atgttggaca tatttctttc tttttttttt 194400 tctttttct ttttttcttt ttttttttt gatatggagt cttactctct tgcccaggct 194460
ggagtgcagt ggtgcaatgt aggctcactg caacctctgc ttcccaggtt caagcgattc 194520
ttctgcctca gcctcctgag tagctaggat tacaggtacc caccaccaca ccaggctaag 194580
ttttgtattt ttagtagaga caggctccca ccatgttggc caggctgatc tcgaactcct 194640
gacctcaagt gatccaccca ctttggcctc ccaaagtgct gagattacag gtgtgagcca 194700
ctgagcccgg ccttggacga gtttcttaat ctctctgcac tccaattttc tcgtctgtaa 194760
aatgagatta atgatggtac cagcatcact gtgtcgtatg agggtaaaat gagttgttaa 194820
tagtgaatca cttcaaacag ggcttgacac aaagtcagct ctgtatacaa gtttattaaa 194880
taagcaaaga aaccagattg ctgttttcaa acagatgctg ttttgaaaaa caccatctca 194940
ataaactcat gtcaccctcc gcctctcccc attaccctca agataaagcc caaagctttt 195000
```

```
ccagtggctg tatcaccctc ctctttgccc ctcattcccc aaggttcctg cccgggccat   195060
ctgtctgtcc ctccaaggtg ctatcctccc cagattaaga ccctctcaca ggctgttcct   195120
cggcccagag gattcttccc cttcctcttt gcccggctaa gatcaattca ttgtaaattt   195180
caagtcttca atgaagcctt ccctgaattc tctgaccagg ccaaagcaat tagccagaag   195240
aaaaggccaa tacttctctt ttatagcacc aagcacagct ataatacata tttatgtttg   195300
tgtaattatt tcatgctttc attcttcaaa tatttgttga gtagtgctgt gagccaggca   195360
ttattctatg ctctgagaat acagcagttt acaaaactaa ctccctgctg gtgtgttgga   195420
atgaaccagg cagaaaatag ataatcaaat aactatatta tgtcaggag tgatgagtgc    195480
catggagaaa aatacaacag ggtaggaaaa aggagccaaa gaaggagcag gtactattat   195540
agacagtttg gtcagggaag acctgaggag gtgacattta agcagagacc tcaggaagtg   195600
aaggaatgaa ccacgggaat atctggagaa agaaagttcc agaaagaaaa gaaaatgaca   195660
gtgcaaaggc tttgatatta ggagcataat ttgcatgttc ttcagtaaat tgcacgaaga   195720
ggatataaca gtaggacatg gggttggaga ggtatcaggg ccagagtgag tagggtcttt   195780
caggccattg tgagcgctct gactttact tggaggagg tgggagccac tgaagggata      195840
ttagccagga tggatgctct gacttgtttt tgttttgtt ttgttttgtt tgagatggtg     195900
tctcactctg tcgcccaggc tagagtgcag tggcacaatc tcagctcact gcaacctctg   195960
cctccccggc tcaagtgatt ctcctgcctc agcctctcaa gtagctggga ttataggtgc   196020
ccaccaccac acccagctaa ttttatatt tttggtagag acgagatttc accctgttgg     196080
ccaggctggt ctcgaactcc taagctcaag tgatccaccc acctcagcct cccaaagctc   196140
tgggatgaca ggtgtgagcc actgtgcctg gccctgactt ttattttaac tggatcaagc   196200
acattgattg ctgtgttgag aatacccctgg agtggaacaa tggctgtagc aggcagacca   196260
atctaggaaa gagatgacaa taacttggtc attgatagca gtgaaggtgg tgagaagtgg   196320
ttggattttg gaggtatttg gaaggcggaa ccaaaagatc gaatgtaggg aataaaagaa   196380
atagacaggt caaagacaac gccaaggatt tggcctgagc atgtagagag ggagatggga   196440
aaaccatagg agttccaagt ttagggaagg atccctggag ctcagttttg gacatactaa   196500
gcttgagaag ccttttagag tgcagatagc atagcaagta ggcagtttga tgtttgagcc   196560
tgcaggttag gggagaggtg ctgtcagaag cagctatcta aacagagata gtcagtggtt   196620
ttttgtgttt gctttttgt ttgttcttct gttttggggg ttttttggg gtggggaca      196680
gagtctcact ctgtcacgca cgctggagtg cagtggcacg atctcagctc actgcaacct   196740
ctgcctccca ggttcaagtg attcttgtgt ctcaacctcc cgagtagctg ggattacagg   196800
cttgtgccac cgcaccggct aattttttgta ttttagtag agacggggtt tcaccatgtt   196860
ggccaggctg gtctcaaact catgacctca agggatccac ctgacacagg ctcccaaagt   196920
gctgggatta caggcatgta atcccactgc acccggcccc agatagtcag catgtattta   196980
aaccctgaat gatatcacca agaaagtaaa tttacggaga aattaggtga gttttaagga   197040
ctgagaccca tggcaccccc attgccaaga cgttgagtag actaggtgca gccagagaaa   197100
tcaagactgt ggaaaactcc ccaaaacaaa caacctagtt tctttagcca atatattaca   197160
gagagagaga gaaagagaac ctattaactc aaaaacaaaa gattgatcac ttgtagaatc   197220
tagactttat ttggatcctg attcaaacac gtcatgtctg ggcacggtgg ctcacacctg   197280
taatcccagc actttgggag gccgaggcgg gcagatcact tgaggtcagg agtttgagac   197340
cagcctggcc aacatggtga aaacccatct ctactaaaga tacaaaaact agctgggca    197400
```

```
tggtggcgca tgctaataat cccagctact cgggaggctg aggcaggaga atctcttgaa  197460
cccgggaggc agaggttgca gtgacccgag atcatcccat tgcactccaa cctggatgac  197520
aagagtgaaa ctctgtctcc aaaaaaaaaa aaaaaagaa agaaacaaag caaacaaaca    197580
aaaaatacca taaaataaaa taaaaaatta ggccaggcac agtggctcac acctaatccc  197640
agtgttttgg gaggccaagg cggaggattg tttgaggcca ggagtttgag accagcctgg  197700
gcaacacagc atgactccat ctctataaaa acatttaaaa tttagcctgg cgtggtgatg  197760
cacacctgta gtcctagcca ctcaggaggc tgagatggga ggatctcttg agctccagaa  197820
ttcaaggctg cagtgagcta tgatcatgcc acagcactcc agcctgagtg acagaacaag  197880
atcctgtctc aaaaaaaccc aaaaaattgt gagacaattg aggaaatttg aacccctgat  197940
tagatatttg aagattttaa agaattattg ttaatagttt taagtttgat aatgaaactg  198000
tggttatatt tttaaaggag tccttattgt ttcaaggagg ggttagtaaa gtaccaccca  198060
cggaccaaat ggaaatggcc acctgatttt gcgtggctca tgagcttaaa atgattttt  198120
aggttgttta aatagttttt taaaaccaaa agaataatat ttattgacat atgaaaattt  198180
cctgtgtgaa atttaaattt aagtgtctat aaataaagtt ttattggcac atgtccatgc  198240
ccattcattg gcctattgtc catggcagct tcctgctacc atagcagagt tgagtacttg  198300
ggacagggac cacacggcct ccaaagctca aaatatgtat tccatgttcc cttactgaaa  198360
aagcttgcca gcccttcttt tattttatgt atttatttaa ttgtttttt ttttttaaga  198420
cagagtctct ctctgttacc cacgctgggg ttaccatgcc tcagcctccc aagtagctgg  198480
gactacaggc gcccgccact acgcccggct aatttttttgt attttttagta gagacagggt  198540
ttcgccgtgt tggccaggat ggtctcgatc tcctgatctt gtgatctgcc cgcctcggcc  198600
tcccaaagtg ctgggattac aggcgtgagc caccgcgccc agccgccatc ccagcattct  198660
ttaatacaga tttccctcgt attgtctaac ttgttatgca aatgattat tttccccca  198720
aggggacctc cacaaccagc tttgaaaaca attatgctta ctttactgcc caggacaaaa  198780
acagtaaaac ttttgaagtt cccagacacc aaaagccctg cattctaaca ggttttgagc  198840
aaacctgatc ccaaagcact ttgtaggtgt gttggcccac catcaccatc ctgtaactgg  198900
aatgctcaac tccaattaga agtcttcctg gtttgggtca tttggggctt tggggaacct  198960
ttgacccttt tttctcccctt ccctttgggc agctgccctg ggacattggc cccattcaca  199020
attctccagt ttcccagaca atgtggcttc ttgtgctctt tgctcgggcc cctctattaa  199080
ccctacagag aggtttcagg ttactgaaac agacgccttg ctttctgctg tgcataatgt  199140
cctttttcca gcgagaaact gcagcccatc aggatctggt tttcattaaa ggcactttgg  199200
gtcactttt tagcagattg gtcaaaagga ctgaaaggac tgggcaggggc gatgatgatt  199260
tggaggtcaa tagctttctc tatgggccat accccttccc cactgaaaga ttcccccact  199320
gcagactgga ggaaatcagt caggcaagga tccctgtggt gaaaactact cgaaaacagc  199380
aacaataacc acaaacctga aatgaagaca atttcctgag aaactatgaa tgtttggatg  199440
tgcaaggtga tcaactttcc cagttgcccg ggaccaaaag gtttcccagg actcaaaact  199500
ttccattttg aaaccagaaa gtcacaggca aacccggagg agttggtcaa cccatggatc  199560
agagtcactt catcttctgt gaaatttgca aagatgctag gaggttcccc tcctgctggg  199620
acacccccagc ccagacacaa accattaatt cacaattaca tggagtttca ctgtctgcaa  199680
ggctgctcca tttaagctct gggtcatgaa cacataactc taggcatact gacactagct  199740
```

-continued

```
gggagattttt ccaccaaaaa aaaaaaaaaa aaatgccatt tcatgactat taatccaaaa   199800
taggtaaatg tgtctggctt atagaatacc agcctgatta caaatgcttg gtgttggaat   199860
ggcccagctc acagtggttg tagaagtcca gtaggcccag gctttgtggc tcactcctgt   199920
aaccccagca ctttgggagg ccaaggtggg aggatcactt gagtccagaa gttcaaaacc   199980
agcctgggca acatagggag actccatttc tacaaataat ttaaaaatta gctgggtgca   200040
tgcttgtagc cctagctact caggaggttg aggcaggaga attgcctgag cctgggaggt   200100
cgaggccaca gtgagccgcg atcacatgtc actacattcc agcctgggtg acagagcaaa   200160
accctggctg gaaaaaaaaa aaattcaagc agtcaagggg atgggagctt ggtggactag   200220
agatgcccag acttgagttc ctgtcccagc cctgccacta atagtgagat tttaggcaca   200280
gctattcccc ttcttctctc ctaagtctcc ggagaacaaa tggctttgga ttcaatgagg   200340
aaaagaagga aagaaaggaa gaaactggtc tcactgagca tcctctatga gccgggcatc   200400
acaccaaacc ctcctccctg ccatttactc tttccaccag ccttgaaggg ttaccgtact   200460
cagtttcaca gatgagttca gtgcacatga acgatcacac agcaagcgaa tggcagggag   200520
ggggttatga tgcagggctg tggggctccc tagtaacctt aatcccagca gtcatttaat   200580
gagacagaac taagtacacg cctctctaac atacattgtc tcgcttaatt cttgtagaat   200640
ctttgaggca agcattacca ttatctctac ttcacagatg agcaaatggg ttctgagagg   200700
tcaagtgacc tgcccaaggt cacacagcta tgcatgcaca gccaggtggc aaacccgag   200760 ctaaatgatt ccaacgctca ctggctttgc tctccagtgt cagctcagca gccctgaacc   200820
taaaactcca ggtggcaggt gccacccccag ggataagacc ccagctttaa cctgaaccaa   200880
accttaacca gctgtgtgct attgggcaaa ttccttaacc tctataggct tgcatttcct   200940
cctctgcata gtaggcatgg cactcatacc tccctggcaa aaaactatca actttatttg   201000
tttatttatt tatttattta tttatttatt tattattca ttcatgagac agagtctccc   201060
tgtgtcgccc agaatggagg gcagtggcct gatctcggct cactgcaacc tccacctgcc   201120
ggattgatgc gattctcctg cctcagcctc cggagtagct gagattacag gcgcccgcca   201180
ccacacctgg ctaatatttg tattttagt agagatggaa tttcaccact ttggccaggc   201240
tggtctcgaa ctcctggcct caagtgattc tcctgcctca gcctcccaaa gtgctgggat   201300
tacaggtgtg agccccggcc tttacctgca tttttccatt tcttccacac aactgttatg   201360
aggtaggcat tactttatac ataaaatacca taaagaacta agcccagcac tggcacatat   201420
aagaatgcaa tgaatcgtag ctattattac taatgctatt gttttactg ctgctatatt   201480 attataacaa ataatcattg tgatagttat tgcaacagtt gtcatcgctg ttattatatt   201540
actaagtagt tttggatccc ttttctcgaa gtttcatcgt ccccccctc caagtgccct   201600 ccaatcccag gagcccttaa agccgctgca cccacacttt gcccacccctc tttctctcgg   201660 tctgtccccc acgccatcca tcacctgcac cccttcccta gggaggccca gcggtgggcg   201720
cccacccgct cccccagcgc tttgccccgt gagtcctccg cccaggcccc cgcgcgcgcc   201780
tcacctgcgg agcccggctt ggccgcactg agtcccacgg gcgggcgggt ggcgcagggc   201840
ggggccgcgg ggctcatgcg gggagcgggc aggcaggaga gcgcgcgggc ggcgccagcc   201900
ggcagctctg cgacctcctc cctgcagcgg cccaggtggg aactcagcca gggcagcggc   201960
gggggtcaca gtccccgcct gggacttcct atctgtcgaa gctt                     202004
```

<210> SEQ ID NO 19
<211> LENGTH: 3796

<212> TYPE: DNA
<213> ORGANISM: Homo sapiens

<400> SEQUENCE: 19

```
gctgaaggtt gcgctggcac gcgcaacttc cgggacagag gctgtggctg gaaggagctg      60
ggcatccggc ctgaggcgca gcggtcgcgt tagttcggcc caatggcggc accgctgctt     120
cacacgcgtt tgccgggaga tgcggccgct tcgtcctctg cagttaagaa gctgggcgcg     180
tcgaggactg ggatttcaaa tatgcgtgca ttagagaatg acttttcaa ttctccccca      240
agaaaaactg ttcggtttgg tggaactgtg acagaagtct tgctgaagta caaaagggt      300
gaaacaaatg actttgagtt gttgaagaac cagctgttag atccagacat aaaggatgac     360
cagatcatca actggctgct agaattccgt tcttctatca tgtacttgac aaaagacttt     420
gagcaactta tcagtattat attaagattg ccttggttga atagaagtca aacagtagtg     480
gaagagtatt tggcttttct tggtaatctt gtatcagcac agactgtttt cctcagaccg     540
tgtctcagca tgattgcttc ccattttgtg cctccccgag tgatcattaa ggaaggcgat     600
gtagatgttt cagattctga tgatgaagat gataatcttc ctgcaaattt tgacacatgt     660
cacagagcct tgcaaataat agcaagatat gtaccatcga caccgtggtt tctcatgcca     720
atactggtgg aaaaatttcc atttgttcga aaatcagaga gaacactgga atgttacgtt     780
cataacttac taaggattag tgtatatttt ccaaccttga ggcatgaaat tctggagctt     840
attattgaaa aactactcaa gttggatgtg aatgcatccc ggcagggtat tgaagatgct     900
gaagaaacag caactcaaac ttgtggtggg acagattcca cggaaggatt gtttaatatg     960
gatgaagatg aagaaactga acatgaaaca aaggctggtc ctgaacggct cgaccagatg    1020
gtgcatcctg tagccgagcg cctggacatc ctgatgtctt ggttttgtc ctacatgaag     1080
gatgtctgct atgtagatgg taaggttgat aacggcaaaa caaggatct atatcgcgac     1140
ctgataaaca tctttgacaa actcctgttg cccacccatg cctcctgcca tgtacagttt    1200
ttcatgtttt acctctgtag tttcaaattg ggattcgcag aggcattttt ggaacatctc    1260
tggaaaaaat tgcaggaccc aagtaatcct gccatcatca ggcaggctgc tggaaattat    1320
attggaagct ttttggcaag agctaaattt attcctctta ttactgtaaa atcatgccta    1380
gatcttttgg ttaactggct gcacatatac cttaataacc aggattcggg aacaaaggca    1440
ttctgcgatg ttgctctcca tggaccattt tactcagcct gccaagctgt gttctacacc    1500
tttgttttta gacacaagca gcttttgagc ggaaacctga agaaggtttt gcagtatctt    1560
cagagtctga atttgagcg gatagtgatg agccagctaa atcccctgaa gatttgcctg    1620
ccctcagtgg ttaactttt tgctgcaatc acaataagt accagctcgt cttctgctac     1680
accatcattg agaggaacaa tcgccagatg ctgccagtca ttaggagtac cgctggagga    1740
gactcagtgc agatctgcac aaacccgctg gacaccttct tccccttga tccctgtgtg    1800
ctgaagaggt caaagaaatt cattgatcct atttatcagg tgtgggaaga catgagtgct    1860
gaagagctac aggagttcaa gaaacccatg aaaaaggaca tagtggaaga tgaagatgat    1920
gactttctga aaggcgaagt gccccagaat gataccgtga ttgggatcac accaagctcc    1980
tttgacacgc atttccgaag tccttcaagt agtgtgggct ccccacccgt gttgtacatg    2040
caacccagtc ccctctgacg gcagaaattt gtgactgaga tgtgacattt gggattcccc    2100
atcacttgtc atgccctcag cacccagctt gtgccattgg cattgatgg cattgaacta    2160
gagcgagtgc ctgcctcggc tgtggcactt ccaggttcga ctgaatcaag catctgaaga    2220
```

-continued

```
ctgggttttt ttgttgttgt tgttcccctt acagacaaaa tgaagactat catgtgcaat   2280
cttttacagt ggggttgatg atacatttgg aaggatttgc ttgtttaata tgtacatttt   2340
ttgtgttaac agctttttga cacaattact gggtaatttc taatataggc agcagactgt   2400
tttacgggtt gctgttttaa catgggtttt tgtcagatcc atggtcttag gacttgactg   2460
atgagctttc agtgaagaat cctctaagat aaaacttcta tttaaagact ttaactagaa   2520
agtgtttatt ttggctacat tgttcacctt ctgctgtatt ggtatttgtc tgttgggatt   2580
tcaagggagt gtagagaaga cagaaggaaa gctgagagct ggcccgacat ggtctgggac   2640
acagagttgg agctggcact gaagatctcc agggacttca gagaccaata aaagcccata   2700
gggaagagag agaggatata gggaaacaga atcagatgtg taatatactt ggcacagcga   2760
aaaaatggat ttaaaagaca aaaatggagg tccaggtaga tgtaattcac acagactgaa   2820
agtgagttcg ggcttgtgta aaacacatga gattggattt gaccccttgg ctctcaagtg   2880
tccccttaga tctagaactg ctccttggtg gccattagat cgagtcagtt ttgatctgca   2940
tcacttagtt attgggaatt tctttgttgg aaacaggaaa attttttag attatttggt   3000 gtacggtttt gctcacaaca ataggtggaa gttgctagtg cagtcttggt ctgatggctg   3060
tgtgcatcgc acattcggct tggtgaaatc cttctctaaa gcctcttttt gtatttttat   3120
aactaaacag aggaagtctt cagaagacct cgctttaaaa caaatttgtg caaacactgc   3180
tagagtcatt ttgaagctca agcattttca ctttgtttct tacatgtgta ctttttttgtt   3240 tacttgtgaa aatggccatc tttaagcata tttattttct gccactttat ttaaaggcaa   3300
gcaatatttt cttgatcata aatattttgt aatgaaatac ttcctctttt ccagggcttt   3360
gtatgcactt gtataattac attgatggca atgtagagtt tgaatttcag tctgtaaata   3420 ctttttgga aaatagaaat ttttattgct ttaaagtttt ggatatgggt ggttttcttt   3480
tccgggtttg gtggaaagta atttgagaac tttaaggttg tctttttaac tgctggcaaa   3540
atgttgattt tttaatatta gataaaacga gtaaacgaaa ttccccagaa attagtagta   3600
agtggggtct ttgtgggttg ggaagtagtt ttaatgtaga aagacattta catataagtc   3660
tgtttaattt caaaggagtt tgtgaaaaaa aatccatggt gaaaatgaaa caatgacatg   3720
gttaatctgg aacttacgtt cttataccaa taaaaggtac ctcaatacat gttctttcaa   3780
aaaaaaaaaa aaaaaa                                                  3796
```

<210> SEQ ID NO 20
<211> LENGTH: 719
<212> TYPE: DNA
<213> ORGANISM: Homo sapiens
<220> FEATURE:
<221> NAME/KEY: misc_feature
<222> LOCATION: (520)..(520)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t

<400> SEQUENCE: 20

```
acataaagaa aattttcatt tatttttccc tcagatatac ttcaaaataa catgtagaca     60
cagaatcaca aatatataca aaacaaagta tcgcctggtt atttcaagaa gagttttccc    120
tcaattttct tagctgctgt gcataaaatt caaagctttc agggggttca atgaaaggga    180
```

```
caggctctcc agcatacttc agcaaagatg cgtaacgctt tagaaacaga tcatccaatt      240
ttgtattctt tgcagtcaaa tgttcataca gtgctttagc agatgtgaca tctttctctg      300
agacatagct tttcatgagg gaattgtatg cttcttcctt ttcatttaat tcaggaatca      360
attctaacac agatttcaca gttgatgcct tccttgttt cctagaattc ctaaggagga       420
acaacaacaa aatcggggtt tgttcagcaa ttgcaccaca tctctgtagg agagctctgg      480
catcatccac cttgcctgca tccacaagtt gaaggaaaan atcagtgaca ggtttataaa      540
ttgcaaactg attggccaat ctctccgcca tgatggctta tctttcaaac tgctggtcca      600
actgctcctc tattactttc tggataagat gccaaggccg agtantcggg tcaatgactt      660
tatcctctga agtaagctat tntcatggtt tctattgcgg catctatgta atcattctt       719

<210> SEQ ID NO 21
<211> LENGTH: 6637
<212> TYPE: DNA
<213> ORGANISM: Homo sapiens

<400> SEQUENCE: 21
acatgctcct cctgtccttc tggcggagcg tgcttcccgc tgcggggacg ttcgagcaat       60
ggcagccctg ctgagatccg cgcgttggtt gctgcgtgcc ggggcggccc cgcgcctccc      120
gctctccctg cgcctcctcc ctggcggccc gggccggctg catgccgcct cctatctgcc      180
cgccgctcgc gccgggcccg tggccggagg actactgagc ccagccaggc tgtatgccat      240
tgctgccaaa gaaaaagata ttcaaggaga gtccactttt tcttctagga agatttccaa      300
tcagtttgat tgggctctaa tgagactaga tctttctgtt cgaagaactg gccgcattcc      360
aaagaagctt ctacaaaaag ttttttaatga tacctgccgc tcaggtggcc taggtggtag      420
tcatgccttg cttctactac gtagttgtgg ttctctcttg cctgaactaa agcttgaaga      480
gagaacagaa tttgctcata ggatatggga cacacttcag aaattaggtg ctgtgtatga      540
tgtgagtcac tataatgctt tacttaaagt ctatcttcaa aatgaatata aattctcacc      600
aactgatttc ctggcaaaaa tggaggaagc aaacattcaa ccaaatcgag tgacatacca      660
gagattgatt gcttcttatt gtaatgtagg agatattgaa ggtgccagca agattcttgg      720
atttatgaaa actaaggatc tcccagttac agaggcagta ttcagtgccc ttgtgacagg      780
gcatgccaga gctggtgata tggagaatgc agaaaacatt tcacagtga tgagagatgc      840 cggaattgag cctggtccag acacatacct cgcattattg aatgcatatg ctgagaaggg      900
cgacattgac catgttaagc agactctgga aaggtggag aagtccgagc ttcaccttat       960
ggaccgtgat ttactgcaaa ttatttttag cttcagtaaa gctgggtatc ctcagtatgt     1020
ctcagaaatt ttgaaaaag ttacatgtga aagaagatat attccagatg caatgaacct      1080 catttactt ttagtcactg aaaaattgga agatgtagcg ttgcaaattt tactagcatg      1140
ccccgtatca aaggaagatg gcccaagtgt cttttggcagt ttcttttttac aacactgtgt     1200 gactatgaat acgcctgtgg agaagctaac agactactgt aagaagttaa aggaagtcca     1260
gatgcactcc tttcctctgc agttcaccct ccattgtgct ttactcgcca ataaaactga     1320
tttggcaaaa gccttaatga aggctgtgaa ggaggaaggt tttcctatca gacctcacta     1380
tttctggcca ttgctagttg gacgtcggaa ggaaaaaaat gttcaaggta taattgaaat     1440
cctcaaagga atgcaagaat tgggagtaca tcctgatcag gaaacatata cagattatgt     1500
gattccatgc tttgatagtg taaactcagc acgagccatt ttgcaggaaa atggatgtct     1560
```

```
gtctgatagt gatatgtttt ctcaagctgg attgagaagt gaagcagcaa atgggaactt    1620
agactttgta ttatcatttt tgaaatcaaa tacattgccc atctcgctgc agtctataag    1680
aagtagccta ctgctaggct tcaggaggtc tatgaatata atctttgga gcgagataac    1740 agaattgttg tacaaggatg gacgttattg ccaggagcct cgaggaccga cggaagctgt    1800
tggctatttt ctttataact tgattgacag catgagtgac tcagaggtac aggccaagga    1860
ggagcatttg agacaatact tccatcagct ggagaagatg aatgtaaaaa ttcctgaaaa    1920
tatctacaga ggcattcgta atctcctgga aagctaccat gttcctgaat tgattaagga    1980
tgctcacttg ttggttgaga gtaagaattt agactttcaa aaaactgtgc aacttacatc    2040
atctgaattg gagtccacac ttgaaacact aaaagctgaa atcaaccta aagagatgt     2100 cctaaagcaa ctcatattag tgctttgttc agaagagaat atgcaaaaag cccttgaatt    2160
gaaagcaaaa tatgaatccg acatggttac tggtggctat gcagctttaa taaatttatg    2220
ctgtcgacat gataaagtag aagatgcctt gaacttgaaa gaagaatttg accgcttaga    2280
ttcatctgct gtccttgaca ccggcaagta tgtaggcctt gtaagagtat ggcaaagca    2340 tggcaagctc caagatgcta ttaacattct gaaggagatg aaagagaagg atgttcttat    2400
caaagataca acagccttgt ccttttttcca catgctaaat ggcgcagctt taagaggtga    2460
aattgaaaca gtaaacagt tgcatgaagc catcgtgact ctagggttag cagaaccatc    2520
caccaacata agtttcccat tggtcactgt acacttggaa aagggcgacc tatctactgc    2580
tcttgaggtc gccattgact gctatgaaaa gtataagta ttaccaagga ttcatgatgt    2640
cttgtgtaaa ctggtagaga aaggcgagac tgatctaatt cagaaagcaa tggactttgt    2700
gagccaagaa caaggtgaaa tggtgatgct ctatgatctc ttctttgcct tcctacaaac    2760
aggaaattac aaagaggcca agaagatcat tgagactcca gggattagag ctcgatctgc    2820
aaggcttcag tggttttgtg acagatgtgt tgcaaataat caggttgaaa ctctggaaaa    2880
attagtggag ctgacacaga agctatttga atgtgataga gaccagatgt actacaatct    2940
gctaaaactg tataaaataa acggtgactg gcaaagagct gatgcagtct ggaataaaat    3000
ccaagaagaa aatgttattc ctcgtgaaaa gacattaaga ttattagcag aaatccttag    3060
agagggtaac caggaagttc cgtttgacgt acctgagttg tggtatgaag atgaaaaaca    3120
ttccctgaat tcttcgtcag cctcaaccac agaacctgat ttccagaaag atatattgat    3180
tgcctgccga ttgaaccaaa aaaagggc atatgatatt ttcctgaatg caaagagca    3240 aaacattgtg tttaatgctg aaacctacag caatctcatt aaattactga tgtcagaaga    3300
ttattttaca caagcaatgg aagtgaaagc attcgcggag acccacatca agggcttcac    3360
actgaacgat gctgccaaca gccgcctcat cataacgcaa gttaggcggg attattgaa    3420 agaggctgtg acaacactga aacagtatt ggatcagcag cagaccccctt ctaggttagc    3480 agtgacccgt gtcatccagg cattggccat gaagggtgat gttgaaaaca tagaagtagt    3540
tcagaagatg ttaaatggac tcgaagactc cattggactt tcaaaaatgg ttttcatcaa    3600
taacattgct ttggctcaaa taaagaataa taacatagat gccgcaatag aaaacattga    3660
aaatatgctt acttcagaga ataaagtcat tgaaccccaa tacttcggct tggcatactt    3720
attcagaaaa gtaatagagg agcagttgga accagcagtt gaaaagataa gcatcatggc    3780
ggagagattg gccaatcagt ttgcaattta taaacctgtc actgattttt tccttcaact    3840
tgtggatgca ggcaaggtgg atgatgccag agctctccta cagagatgtg gtgcaattgc    3900
tgaacaaacc ccgattttgt tgttgttcct ccttaggaat tctaggaaac aaggaaaggc    3960
```

```
atcaactgtg aaatctgtgt tagaattgat tcctgaatta aatgaaaagg aagaagcata    4020
caattccctc atgaaaagct atgtctcaga gaaagatgtc acatctgcta aagcactgta    4080
tgaacatttg actgcaaaga atacaaaatt ggatgatctg tttctaaagc gttacgcatc    4140
tttgctgaag tatgctggag agcctgtccc tttcattgaa cccctgaaa gctttgaatt     4200 ttatgcacag cagctaagaa aattgaggga aaactcttct tgaaataacc aggcgatact    4260
ttgttttgta tatatttgtg attctgtgtc tacatgttat tttgaagtat atctgaggga    4320
aaaataaatg aaaattttct ttatgtactt atgtatgtgt gatgcatgtt caaagtctta    4380
ttgaccataa ctctgtgcac ttggttattg dacattttg gagttttttt ctctgggaaa    4440
aatcgatagt gttttcttca atgctgctgc tgtgtgaagc cataatttt caggattctt     4500 cccctaattg gctctttggt ttccctgctc tgtttcattt atttcattaa aatgttattc    4560
ctttatttaa gattcactta ttagtctgct gtttctctga aaaattttag agctaggtat    4620
agtgaccgtg aactttctaa cgcataatat tctgtgatac agccattccg tacatgtgtg    4680
aagtcctgca taactttcga actttgttaa atgttggcac taggagtcat cagatctagg    4740
cttcatcatt ttccagtgag aagcagagac ccaaagggcc tgttacttgt gcttggtcag    4800
gggactgtct gtcatgcctg gaggctcttc ggcacacttc cccatctttc ccttctgcca    4860
ctgtggcttc aagcacctct gttcatagag cgtctctgaa attgagtctc ggtcatgact    4920
tatcccgaag tagagcaatg tgtttcctct cattgtagtt tcaggacttt gtcagtacaa    4980
gctctgccct aggcttgtta ctttatactc atatcctgaa aagatgtgat ttcatctatg    5040
aaggggtaaa atattggttt gtatttaatt gtttgaaata aaagtgatcc ctatattgaa    5100
tctcatgcct gttaatatct acactgtaag tagtgacttc aaaaaaattc taagataggt    5160
agtcaggaga gtttgccatt ataaaaggtg tcttaataat atggaatatt gacctaactg    5220
gagatgaggt aattaattac cgaaatgttg aaaatgtttt gagaactctc cccattttgg    5280
ggtattcctt gttcatttga atttggtgac tccctactgt tccagtttca gtgccaactt    5340
gggtcacact gttcacatca ggggagacct tgccttgggg acgtaggcgg gcctcttgca    5400
acttgtgctg ttgaccttct gtcttgtgga actctctctc ctgcatctgc tacctgcccg    5460
cagatggtgt gagggagggt tgatggcggg aagccaggaa gtagatgtca tcatggtatt    5520
ggccaggctt ttacttcaac tcttttttgtg gcgttagatt taaggaagca gggggcatgg    5580
ccaacgttga gtcttggccc agtggacata tgcggctttc ccttgagca ctgcccagat     5640 gcaggacctg cacatgttac aggtttgcca aaagcatctt tttttttttt tttttttttg    5700
agatagtctt gctctgttgc ttaagccaga gtgcagtggc gcaatctcag ctcactgcaa    5760
cctccgcctc ctgggttcaa gtgattcttg tgcctcagcc tcccacgtag ctgagattac    5820
aggcttgcac caccatgttc agctaatttt tgtatggtaa agacggagtt tcaccatgtt    5880
ggccaggttg gtctcgaact cctggcccca agtgatcctc cccctgcgct cgcttcagcc    5940
tcccaaagtg ctgggattac aggtgtgagc caccgcct ggccaagagc ctcactcctg      6000
tctttagtga ttgcactgaa gcaggcctca tttttttgca gtcatgctaa ccacaagtta    6060
gtcaacattc actaattgac attcattaga ataggtctcc aaggtgaggc ataacgttgg    6120
ggtgtaatct ggatttcgca gtcatctttt tggggaaact gaaagtacca tctcatttgc    6180
atgaagtgac tccacactgg ccctgtatat ggactctggt aaaatgtgag tgtggtacag    6240
aggaaatagg taagacccccc ttatctagcc ctctcggcag cagcgggggg gtgttacaaa   6300
```

```
ggactagctg ttcaaatatc ttttgtattg tattgattcc cctattgaat ataaatattt   6360
aaagtataat aactatactg taggtgggct tatgagtgtt ctaaatatct aatagctaaa   6420
ttgaaataag tagaaatata acaatttag cagctttctg taatacattt acactcaaat    6480
tataagcagc taattctaaa aaagatgtca ctgtaaacta ttgagaacta tagtattta    6540 tatataatta tatgttcatg tatttgaacc caaaataatt ttaactgaaa tgctttgaat   6600
aaagtatact gtaaatatca aaaaaaaaaa aaaaaa                            6637
```

<210> SEQ ID NO 22
<211> LENGTH: 5427
<212> TYPE: DNA
<213> ORGANISM: Homo sapiens

<400> SEQUENCE: 22

```
agatgcgacg aggttagcgg ggcccgacca ctccttggct tcccaggggt gagcctcgcg     60
agttaggagt tgggtagaga gtcagcccgg ggcccggcat ccgcttttc gttgaagcaa     120 cgactttggc cggatgactc cccagggtcg gcatcagcgt gggactggga acaggtgaag    180
ggaaacagaa gagagcctga gaagaccgct ctcctccgat cctaattgac tgagccaatg    240
agagccaaag aggtcacatg ctcaactggg cggggagcgg gtttccacct gcggcatctt    300
tcgcgagcgg ggagatgagt ggggcggaat atgggagaaa gggagggccc gccacgctct    360
ggctggacac ggccttaatc ggcccgttca ctcgacgttt tggttctac gttgaccccg     420 agaaaccgaa accgcagggc ctagggcggg tggaacgaga gggaactaca tttcccagca    480
ggctgcggaa acgggactgc ggccactact tccggcgtgt accgagagac tggcgtccgg    540
cgtgtaccga gagactggcg tccggtgtgc aggtggccac atggatcctg cagccggtg     600 gcggaacctg cccagcgggc ctagcctaaa gcacttgact gacccctctt atggaatccc    660
gcgggaacag caaaaggcag cgttgcagga gctgacgcgg gcgcacgtgg agtccttcaa    720
ctacgctgtg cacgagggtc tcggcctcgc ggtgcaggct ataccctccct ttgaatttgc   780 tttcaaagat gagcgtatct cttttactat tctggatgct gttatcagtc cacctacagt    840
tccaaaaggg accatctgca agaggccaa tgtttatcca gcagaatgcc ggggccgaag    900
gagtacctac cgtgggaagt tgacagctga tatcaactgg gcagtgaatg gaatctcaaa    960
aggaatcatt aagcagtttc ttggctatgt tcccatcatg gtgaaatcca gctttgcaa   1020 cttacgtaac cttccccca aagccctcat tgagcaccat gaggaggcag aggaaatggg    1080
gggctatttt ataatcaatg gcattgaaaa agtcatccga atgttgatta tgcctcggag    1140 aaatttccc attgcaatga taagaccaaa atggaaaacc agagggcctg ttatactca    1200 gtatggagtt tcaatgcact gtgtgaggga agaacattcc gctgtcaata tgaacctcca    1260
ctacttggaa aatggcactg ttatgttgaa ctttatttac cgaaaagaac tgttctttct    1320
tcctttggga tttgcactta aggcacttgt cagcttttct gattatcaga tctttcagga    1380
gctcatcaaa ggaaaagagg atgattcttt ccttaggaac tctgtttctc agatgttaag    1440
gattgtaatg gaagagggtt gttcgacaca aaaacaggtc cttaactacc taggtgaatg    1500
cttcagagta aaactcaatg ttcctgactg gtacccaaat gagcaagctg cggagttcct    1560
gtttaaccag tgcatctgta tccacttgaa atccaatact gaaaagtttt atatgctttg    1620
tctcatgacg cgaaagctct ttgctttagc caaaggagag tgcatggagg acaatcctga    1680
tagtttggtg aaccaggaag tcctcacacc gggtcagctc ttccttatgt tcctgaagga    1740
aaaactggaa ggttggttag tgtctattaa aatagctttt gataagaagg ctcagaagac    1800
```

```
cagtgtttcc atgaacactg acaatttgat gaggattttt acaatgggca tagaccttac    1860
aaaaccattt gaatacccttt ttgctactgg gaatctgcgt tctaaaacag gtcttggcct   1920
```



```
cagtgtttcc atgaacactg acaatttgat gaggattttt acaatgggca tagaccttac    1860
aaaaccattt gaatacctttt ttgctactgg gaatctgcgt tctaaaacag gtcttggcct   1920
cctacaagat tctggacttt gtgttgtggc tgacaagctg aacttcatac gctacctctc    1980
ccatttccgc tgcgtgcaca gagggctga ttttgccaag atgaggacca ccacagtacg     2040
caggctgctg ccagagtcct ggggcttcct ttgtcccgtg cataccccag acggggagcc    2100
ctgtggcctg atgaaccacc taactgccgt atgtgaggtt gtcacacagt ttgtgtatac    2160
ggcatctatt ccagctttac tgtgcaactt gggggtcact cccattgatg agctcccca    2220
ccgatcatac agtgagtgct accctgtcct gctggacggt gtcatggttg ctgggtgga    2280
taaggatctt gctccaggca tcgcagattc tcttcgtcat tttaaggtgt tgagagagaa    2340
aagaattcct ccctggatgg aagtggtcct tatacccatg acaggaaaac caagtctgta   2400
cccaggattg ttcctttta ccactccttg tagactggta cggcctgtgc agaacttagc    2460
attgggcaaa gaagagctaa ttggaactat ggaacagatc ttcatgaatg tcgctatctt   2520
tgaggatgaa gttttttgctg agttaccac acaccaggaa ctctttccac acagcctgct   2580
gagtgtgatt gccaacttca tccctttctc tgatcacaac cagagtccac ggaacatgta   2640
ccaatgccag atgggtaagc aaactatggg ctttccactt ctcacttatc aagaccgatc   2700
ggataacaaa ctgtatcgtc ttcagactcc tcagagtccc ttggtgagac cctccatgta   2760
tgattattat gacatggata actatccaat tgggaccaat gccatcgttg ctgtgatttc   2820
ttacactggc tatgatatgg aagatgccat gattgtgaat aaggcctctt gggaacgagg   2880
cttttgcccat ggaagtgtct acaagtctga gttcatagac ctctctgaaa aaattaaaca  2940
aggagatagt agcctggtgt ttggcatcaa acctggtgac ccacgcgttc tgcagaagtt   3000
agatgacgat ggattgccgt ttataggagc aaaactgcag tacggagatc cgtattacag   3060
ctacctcaac ctcaacaccg gggaaagttt tgtgatgtac tataagagta agaaaattg    3120
tgttgtggat aacatcaaag tgtgcagtaa tgacactggg agtggaaaat tcaagtgtgt   3180
ttgcatcact atgagagtgc ctcggaaccc aactatcgga gataaattg ccagtcgcca    3240
tgggcagaag ggcatttaa gcagattgtg gccggctgag gacatgcctt ttactgagag    3300
tgggatggtc ccagacattc tgttcaatcc ccatggtttt ccatcccgca tgaccattgg   3360
gatgttaatt gagagtatgg ccgggaagtc tgcagctttg catggtctct gccatgatgc   3420
tacacccttc atcttctcag aggagaactc ggccttagaa tactttggtg agatgttaaa    3480
ggctgctggc tacaattcct atggcaccga gaggttatat agtggcatca gtgggctaga   3540
actggaagca gacatcttca taggagtggt ttattatcag cgcttacgcc atatggtctc   3600
agacaaattt caagtaagga caactggagc ccgagacaga gtcaccaacc agcctattgg   3660
gggaagaaat gtccagggtg gaatccgttt tggggagatg gaacgggatg cgcttttagc   3720
tcatggtaca tcttttctcc ttcatgaccg cctcttcaac tgctcagatc ggtcggtagc   3780
ccatgtgtgt gtgaagtgtg gcagtttact ctctccactg ttggagaagc cacccccttc   3840
ttggtctgcc atgcgcaaca gaaaatacaa ctgtactctg tgtagtcgca gtgacactat   3900
cgatactgtt tctgtgcctt atgttttttcg gtattttgta gctgaactgg cagctatgaa   3960
catcaaagtg aaactggatg ttgtttaact tgatgttgac cttttggatt aagaggacta   4020
tcagattaaa gcaaaatgta attttaattc aatgaagata tcattaccag gttactcttg   4080
agatttttca acggtgttag aactctcaac caagacctga aaaccaagta tgcaaggttt   4140
```

```
ctgaatctct ctggtagatt aactattgac aatgattttc tgttatcttt gttcaaaaag    4200
ttcatgtctt ctcaaaatat gaaatattga taaatggaag agcatacggt gacaagtctc    4260
ctttccaacc ccaggttccc tacaccctgc tctcagcagg cagtgagtgt cacacacctg    4320
ttaatccatc ttgagcagga cagtactata caaatagaat gcaagctgta atgtaattt     4380 atattttctt atagccacgt tgaagtaaaa acaaacaggt acagtgtttt ttaccagctt    4440
tatagaagta cagttgttac atatttaatg aatacaattt gatgggtctg actatatgca    4500
cacacctttg ataccatcac cacaatcagg gtaataaaca tacctgtcat ctccacaagt    4560
ttcctcctgc cccttttgttt tttgcttttt ggttgctgtt gagttttgt tttgtcttct    4620 gtggtaagaa cacttaactc aagacctacc ctcttaacaa atctttaagt gcacgatata    4680
gtattgttaa ttccaggcac catgttgtac aacagatctt tagaccttac ttgtcttgca    4740
taactgaagc tttatacctg ttgaacaact ctccatttcc ctggcccta gcaaccaccc     4800 ttctaccctg tttctatgag tttgactatt acagatatct catatagtgg gatcatgcaa    4860
tatttgtcct gtgactggct tatttcactt agcatagtga aataagattc atccattttg    4920
gaagccaggc atggtgctgt gcatctatag tccctgctat ttgagaggct gaggtgggag    4980
gatcatttga gtgcaggagt tcaaggacag cctgggtaat ataggaagac cctgtcttga    5040
agaccctgac ctcaagtgat ccacccacct cggcctccga aagtgctagg attacaggtg    5100
tgagccactg tgcctggcct ccggtgagta ttttatattt agtctacact tccatacttg    5160
gcttttttct gcttttatat tgatctgctt tcatagcagt gtgtagagtg ccacttatgt    5220
tttctttctt gtgtacagta ttttattgta tggatttacc atcccctgtg tatttaagtt    5280
gttccattct ttggccatta taactttttt ctgcaaatat tctggtgact tatctttggc    5340
cattataaac tgttgataat agatcatctt gtatatactt ctgcaattat aagatgtttt    5400
ttgatgatga aaaaaaaaaa aaaaaaa                                         5427

<210> SEQ ID NO 23
<211> LENGTH: 1138
<212> TYPE: DNA
<213> ORGANISM: Homo sapiens

<400> SEQUENCE: 23
agggctacta ggacgcacgc gcgagataga acctctagtc tcgtggagag attgaagatg      60
gcggcttctc aggcggtgga ggaaatgcgg agccgcgtgg ttctggggga gtttggggtt    120
cgcaatgtcc atactactga ctttcccggt aactattccg gttatgatga tgcctgggac    180
caggaccgct tcgagaagaa tttccgtgtg gatgtagtac acatggatga aaactcactg    240
gagtttgaca tggtgggaat tgacgcagcc attgccaatg cttttcgacg aattctgcta    300
gctgaggtgc caactatggc tgtggagaag gtcctggtgt acaataatac atccattgtt    360
caggatgaga ttcttgctca ccgtctgggg ctcattccca ttcatgctga tcccgtctt    420 tttgagtatc ggaaccaagg agatgaagaa ggcacagaga tagatactct acagtttcgt    480
ctccaggtca gatgcactcg gaaccccat gctgctaaag attcctctga ccccaacgaa    540
ctgtacgtga accacaaagt gtataccagg catatgacat ggatccccct ggggaaccag    600
gctgatctct ttccagaggg cactatccga ccagtgcatg atgatatcct catcgctcag    660
ctgcggcctg gccaagaaat tgacctgctc atgcactgtg tcaagggcat tggcaaagat    720
catgccaagt tttcaccagt ggcaacagcc agttacaggc cctgccagca catcccctg     780 cttgagcccg tggaagggga ggcagctgag gagttgagca ggtgcttctc acctggtgtt    840
```

| | |
|---|---|
| attgaggtgc aggaagtcca aggtaaaaag gtggccagag ttgccaaccc ccggctggat | 900 |
| accttcagca gagaaatctt ccggaatgag aagctaaaga aggttgtgag gcttgcccgg | 960 |
| gttcgagatc attatatctg taagaaagat ttgctggctg cggtggctca cacctgtaat | 1020 |
| cccagcactt tgggaggcca aggcgagtgg atcacgggt caagagagcg agaccatcct | 1080 |
| ggctaacatg gtgaaacccc gtctctataa aaaaaaaaa aaaaaaaaaa aaaaaaa | 1138 |

<210> SEQ ID NO 24
<211> LENGTH: 817
<212> TYPE: DNA
<213> ORGANISM: Homo sapiens

<400> SEQUENCE: 24

| | |
|---|---|
| gtcggggcgg gggctggggg tggagcctca tgccccgccc cgcggctggg ccctgccgcg | 60 |
| ccgctgcggc tcctcctccc tccttccgtc ctccgcgcct tccgtcggtc ggtccttgct | 120 |
| tcctgcttcg cctccgcgcc tcgcgctatg ggacagagcc cccgatccgc cagcaccacc | 180 |
| tgaggatcca gaaaccgccc cagcgatgga agaggatcag gagctggaga gaaaaatatc | 240 |
| tggattgaag acctcaatgg ctgaaggcga gaggaagaca gccctggaaa tggtccaggc | 300 |
| agctggaaca gatagacact gtgtgacatt tgtattgcac gaggaagacc atacccctagg | 360 |
| aaattctcta cgttacatga tcatgaagaa cccggaagtg gaattttgtg gttacactac | 420 |
| gacccatcct tcagagagca aaattaattt acgcattcag actcgaggta cccttccagc | 480 |
| tgttgagcca tttcagagag gcctgaatga gctcatgaat gtctgccaac atgtgcttga | 540 |
| caagtttgag gccagcataa aggactataa ggatcaaaaa gcaagcagaa atgaatccac | 600 |
| attctagtcc tttatgcagt atacaaggag aactgtcctg taggatattc tcttcctgat | 660 |
| ggtgcagaac ccagaattag aagtttgtgg ttacagcata ctctgtcctt cagaaaggcg | 720 |
| tgattctagc tgttgacccc ttgcagctgt tggaatctct gcaagaacct ctgtattctt | 780 |
| ctaataaatt ccctctttta tttaaactag aaaaaaa | 817 |

<210> SEQ ID NO 25
<211> LENGTH: 2732
<212> TYPE: DNA
<213> ORGANISM: Homo sapiens

<400> SEQUENCE: 25

| | |
|---|---|
| ctttcgcctc agtctcgagc tctcgctggc cttcgggtgt acgtgctccg ggatcttcag | 60 |
| cacccgcggc cgccatcgcc gtcgcttggc ttcttctgga ctcatctgcg ccacttgtcc | 120 |
| gcttcacact ccgccgccat catggtgaag ctcgcgaagg caggtaaaaa tcaaggtgac | 180 |
| cccaagaaaa tggctcctcc tccaaaggag gtagaagaag atagtgaaga tgaggaaatg | 240 |
| tcagaagatg aagaagatga tagcagtgga gaagaggtcg tcatacctca gaagaaaggc | 300 |
| aagaaggctg ctgcaacctc agcaaagaag gtggtcgttt ccccaacaaa aaaggttgca | 360 |
| gttgccacac cagccaagaa agcagctgtc actccaggca aaaaggcagc agcaacacct | 420 |
| gccaagaaga cagttacacc agccaaagca gttaccacac ctggcaagaa gggagccaca | 480 |
| ccaggcaaag cattggtagc aactcctggt aagaagggtg ctgccatccc agccaagggg | 540 |
| gcaaagaatg gcaagaatgc caagaaggaa gacagtgatg aagaggagga tgatgacagt | 600 |
| gaggaggatg aggaggatga cgaggacgag gatgaggatg aagatgaaat tgaaccagca | 660 |
| gcgatgaaag cagcagctgc tgcccctgcc tcagaggatg aggacgatga ggatgacgaa | 720 |

```
gatgatgagg atgacgatga cgatgaggaa gatgactctg aagaagaagc tatggagact    780
acaccagcca aaggaaagaa agctgcaaaa gttgttcctg tgaaagccaa gaacgtggct    840
gaggatgaag atgaagaaga ggatgatgag gacgaggatg acgacgacga cgaagatgat    900
gaagatgatg atgatgaaga tgatgaggag gaggaagaag aggaggagga agagcctgtc    960
aaagaagcac ctggaaaacg aaagaaggaa atggccaaac agaaagcagc tcctgaagcc   1020
aagaaacaga aagtgaagg cacagaaccg actacggctt tcaatctctt tgttggaaac   1080
ctaaacttta caaatctgc tcctgaatta aaaactggta tcagcgatgt ttttgctaaa    1140
aatgatcttg ctgttgtgga tgtcagaatt ggtatgacta ggaaatttgg ttatgtggat   1200
tttgaatctg ctgaagacct ggagaaagcg ttgaactca ctggtttgaa agtctttggc    1260
aatgaaatta actagagaa accaaaagga aagacagta agaagagcg agatgcgaga     1320 acactttggg ctaaaaatct cccttacaaa gtcactcagg atgaattgaa agaagtgttt   1380
gaagatgctg cggagatcag attagtcagc aaggatggga aaagtaaagg gattgcttat   1440
attgaattta agacagaagc tgatgcagag aaaaccttg aagaaaagca gggaacagag    1500
atcgatgggc gatctatttc cctgtactat actggagaga aggtcaaaa tcaagactat    1560 agaggtggaa agaatagcac ttggagtggt gaatcaaaaa ctctggtttt aagcaacctc   1620
tcctacagtg caacgaaga aactcttcag gaagtatttg agaaagcaac ttttatcaaa   1680
gtaccccaga accaaaatgg caaatctaaa gggtatgcat ttatagagtt tgcttcattc   1740
gaagacgcta agaagctttt aaattcctgt aataaaaggg aaattgaggg cagagcaatc   1800
aggctggagt tgcaaggacc caggggatca cctaatgcca gaagccagcc atccaaaact   1860
ctgtttgtca aaggcctgtc tgaggatacc actgaagaga cattaaagga gtcatttgac   1920
ggctccgttc gggcaaggat agttactgac cgggaaactg gtcctccaa aggtttggt    1980 tttgtagact tcaacagtga ggaggatgcc aaagctgcca aggaggccat ggaagacggt   2040
gaaattgatg gaaataaagt taccttggac tgggccaaac ctaagggtga aggtggcttc   2100
gggggtcgtg gtggaggcag aggcggcttt ggaggacgag gtggtggtag aggaggccga   2160
ggaggatttg gtgcagagg ccggggaggc tttggagggc gaggaggctt ccgaggaggc    2220
agaggaggag gaggtgacca aagccacaa ggaaagaaga cgaagtttga atagcttctg    2280
tccctctgct ttccctttc catttgaaag aaaggactct ggggttttta ctgttacctg    2340
atcaatgaca gagccttctg aggacattcc aagacagtat acagtcctgt ggtctccttg   2400
gaaatccgtc tagttaacat ttcaagggca ataccgtgtt ggttttgact ggatattcat   2460
ataaactttt taagagttg agtgatagag ctaaccctta tctgtaagtt ttgaatttat    2520
attgtttcat cccatgtaca aaaccatttt ttcctacaaa tagtttgggt tttgttgttg   2580 tttcttttt ttgttttgtt tttgttttt tttttttgc gttcgtgggg ttgtaaaaga     2640
aaagaaagca gaatgtttta tcatggtttt tgcttcagcg gctttaggac aaattaaaag   2700
tcaactctgg tgccagaaaa aaaaaaaaaa aa                                 2732
```

<210> SEQ ID NO 26
<211> LENGTH: 583
<212> TYPE: DNA
<213> ORGANISM: Homo sapiens
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature

```
<222> LOCATION: (406)..(406)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t

<400> SEQUENCE: 26
ttttgttgta aaaaaaacca agtttttttt ctttcctaat agctagttcc aatgatgtta      60
attacccgcc ctgagctgaa ataacagtag acaaagatag aagctagcct ctggttttac     120
aaagcctttg tacaagtcct ctctgtcttt tctgtccatn gccagggaaa tgtattgctg     180
gtgctagagg gagaggaaac gtggacggcc aagaacaggg cggcacagtc ctctgggctg     240
gaggctcgtg ttccttccca taagcagggc ctgtggggtg tatggggcag aacataggcc     300
tccacaccaa actgacagca gagaaaagcc aggcaacctg ttcaatcgcc ccagcagttg     360
acctgggttc tatgtgtggg agtgaactgc tgcggcnctg ggagcnactg tccccagcct     420
tggggctgat gtggtctana aggacacctc ggccacacag tggaagggggc cagggancct    480 ggccaggcaa anaagttngg ttgggtggag gactatgcta cgctgtactt gactcnggga    540
agaagtcttg attggggncc tttnttggat ntggcccncng ggg                     583

<210> SEQ ID NO 27
<211> LENGTH: 1884
<212> TYPE: DNA
<213> ORGANISM: Homo sapiens

<400> SEQUENCE: 27
ggcggggcca cgccttttcc ggcccgcagc gcggcctggg ctcccgcgtg tttaaaagtg      60
cgcttgtggc tgctgctgtc ttaactcctg tgcttggcgg acagacaggc gagatggcgg    120
cggaggtgtt gccgagtgcg aggtggcagt attgtgggggc gcccgacggg agccagagag   180
ctgtactggt ccagttctcc aacgggaagc tacagagtcc aggcaacatg cgctttacct   240
tgtatgagaa caaagattcc accaacccca ggaagaggaa tcaacggatc ctggcagctg   300
```

| | |
|---|---:|
| aaacagatag gctctcctat gtgggaaaca attttgggac tggagccctc aaatgcaaca | 360 |
| ctttgtgcag gcactttgtg ggaattttga acaagacctc tggccaaatg aagtatatg | 420 |
| atgctgaatt gttcaacatg cagccactat tttcagatgt atcagttgag agtgaactgg | 480 |
| cgctagagag tcagaccaaa acttacagag aaaagatgga ttcttgtatt gaagcctttg | 540 |
| gtaccaccaa acagaagcga gctctgaaca ccaggagaat gaacagagtt ggcaatgaat | 600 |
| ctttgaatcg tgcagtggct aaagctgcag agactatcat tgatacgaag ggtgtgactg | 660 |
| ctctggtcag cgatgctatc cacaatgact tgcaagatga ctccctctac cttcctccct | 720 |
| gctatgatga tgcagccaag cctgaagacg tgtataaatt tgaagatctt ctttcccctg | 780 |
| cggagtatga agctcttcag agcccatctg aagctttcag gaacgtcacg tcagaagaaa | 840 |
| tactgaagat gattgaggag aacagccatt gcacctttgt catagaagcg ttgaagtctt | 900 |
| tgccatcaga tgtggagagc cgagaccgcc aggcccgatg catatggttt ctggatacccc | 960 |
| tcatcaaatt tcgagctcat agggtagtta agcggaaaag tgctctggga cctggagttc | 1020 |
| cccacatcat caacaccaaa ctgctgaagc actttacttg cttgacctac aacaatggca | 1080 |
| gattacggaa cttaatttcg gattctatga aggcgaagat tactgcatat gtgatcatac | 1140 |
| ttgccttgca catacatgac ttccaaattg acctgacagt gttacagagg gacttgaagc | 1200 |
| tcagtgagaa aaggatgatg gagatagcca agccatgag gctgaagatc tccaaaagaa | 1260 |
| gggtgtctgt ggccgccggc agtgaagaag atcacaaact gggcaccctg tccctcccgc | 1320 |
| tgcctccagc ccagacctca gaccgcctgg caaagcggag gaagattacc tagacgcatg | 1380 |
| cttttccagac agggcgtttt ggctgcatca cagccactgg ctggtcctat tcatttccat | 1440 |
| ttttatgtat gttttgaaaa gaaaaggtcc ggggatggtg gctcacacct gaaatcccag | 1500 |
| cactttggga ggccgaggca ggaagatcat tgagctcagg agtttgaaac cagtctggac | 1560 |
| aacataggga gacccatct ctaccggagg aaaaaaaaaa gagtcaggcc tggtggtgtg | 1620 |
| cgcctgtaat cccagctact cgggaggctg aggcaggacg attacttgag cttgggaaat | 1680 |
| caaggttgca gtgagctatg attgtgtggc cacactccat cctgggtcac agagtgagac | 1740 |
| cttgtctcaa aaaagtaaca taaggaaaaa agaagccttg cttagcaca ggtatgaagc | 1800 |
| cagaagccag catctcaact gtgcttgtct tatgcagaaa tataaagcga tggccaggtt | 1860 |
| ggacttcaaa aaaaaaaaaa aaaa | 1884 |

<210> SEQ ID NO 28
<211> LENGTH: 3216
<212> TYPE: DNA
<213> ORGANISM: Homo sapiens

<400> SEQUENCE: 28

| | |
|---|---:|
| gcggacggtg agtggggatg gactggagtt gaagagctcg agatgaaggg cttgagggcg | 60 |
| tgtgttattt gttttcttca agcatttggt cgagattaag aattaaaaat gtcatccaaa | 120 |
| caagaaataa tgagtgacca gcggtttaga cgggttgcaa aggacccgag attttgggaa | 180 |
| atgccagaaa aggatcgaaa agtcaaaatt gacaagagat ttcgagccat gtttcatgac | 240 |
| aagaagttca gttgaactac tgccgtggat aaaagagggc gccccattag ccatagcact | 300 |
| acagaggatt tgaagcgttt ttacgacctt tcagattctg attccaatct ctctggtgaa | 360 |
| gatagcaaag cattgagtca aagaaaata aagaagaaaa aaacccagac taaaaaagaa | 420 |
| atcgattcaa aaaatctagt tgagaaaaag aagaaacca agaaggctaa tcacaagggt | 480 |
| tctgaaaata aaactgattt agataattct ataggaatta aaaaaatgaa aacctcatgt | 540 |

```
aaatttaaga tagattcaaa cataagtccg aagaaggata gcaaagaatt tacacaaaaa    600
aataagaaag agaaaaaaaa cattgttcaa catactacag actcttctct cgaagaaaaa    660
caaaggacat tagactcagg cacctctgaa attgtgaaat ctcccagaat cgagtgttct    720
aagacaagaa gagaaatgca atcagtggtt caactcataa tgacaagaga cagtgatggt    780
tatgaaaact caacagatgg tgaaatgtgt gacaaagatg ctctggagga agattcagaa    840
agcgttagtg aaataggaag tgatgaggaa tctgaaaatg aaattacaag tgttggtaga    900
gcttcaggtg atgacgatgg aagtgaagat gatgaagagg aggatgaaga tgaagaggag    960
gatgaagatg aggatagtga ggatgatgat aaaagtgaca gtggccctga tcttgcaagg   1020
ggtaaaggaa atatagaaac tagttctgaa gatgaagatg atacggcaga tttgtttcca   1080
gaagaatctg gttttgagca tgcttggaga gaattagata aagatgctcc tcgtgctgat   1140
gagattacac gtcgattagc agtttgtaac atggactggg atagattaaa ggcaaaagat   1200
ttgctggctc tgttcaattc atttaaaccc aaaggaggtg taatattttc cgtcaagata   1260
tatccttcag aatttggaaa ggagaggatg aaggaagagc aagttcaagg accagtagag   1320
ctattaagta ttcctgaaga tgccccagaa aaagactgga cgtctagaga aaaattgaga   1380
gattatcaat tcaaacgact gaagtactat tatgcagtag tagactgtga ttctccggaa   1440
acagctagta aaatttatga ggattgtgat ggcctggaat ttgaaagtag ttgttctttc   1500
atagatctaa ggtttatacc agatgatatt acttttgatg atgagcctaa ggatgtagcc   1560
tcagaagtga atttaacagc atataaacca aaatatttca cttctgctgc aatgggaaca   1620
tcaacggtgg aaatcacttg ggatgagact gatcatgaaa gaattacaat gctcaacagg   1680
aagtttaaaa aggaagagct tttggacatg gattttcaag cctacttagc ttcctctagt   1740
gaagatgaag aggagataga agaggagcta caaggtgatg atggagtcaa tgtagaagaa   1800
gatgggaaaa caaagaaaag tcagaaggat gatgaagaac aaattgctaa atacaggcag   1860
ctcttgcagg ttattcaaga aaaagaaaag aaaggcaaag aaaatgatat ggaaatggaa   1920
attaaatggg ttccaggtct taagaaagt gcagaagaga tggtcaaaaa caaattggaa   1980
ggaaaggata aactgacccc ttgggaacaa tttttagaga agaagaaaga gaaaaaaga   2040
ctgaaaagga aacagaaggc tcttgctgaa gaggccagtg aagaggaact tccctctgat   2100
gttgatttga atgacccata cttttgctgaa gaagttaaac aaataggtat aaataaaaaa   2160
tcggtaaaat ctgcaaaaga tggcacatct ccagaagaag aaattgaaat agaaagacaa   2220
aaggctgaaa tggcttttgct tatgatggat gaggacgagg acagtaagaa acacttcaat   2280
tacaacaaga ttgtggagca ccagaatctg agcaaaaaga agaaaaagca gctcatgaaa   2340
aagaaggaat taatagagga tgactttgag gtaaatgtta acgatgcacg gtttcaggca   2400
atgtacactt cccacttgtt caatttggac ccctcagatc ccaatttcaa gaaaacaaaa   2460
gctatggaaa aaatccttga ggagaaggcc cggcaaagag aacggaaaga acaagaactt   2520
actcaggcaa taaagaaaaa agagagtgag attgaaaagg aatcacaaag gaagtccatt   2580
gatcctgctt tgtcaatgtt gattaaatct ataaaaacca aaacagagca gtttcaagca   2640
agaaaaaagc aaaaagtcaa ataactggat gttacttatt tttgaactga atacatcttt   2700
tcctaaaatg tacaaaaata ataggaggga atatttattg ggaacaaagc tatcttttcaa   2760
gaacatgaat aaaaatcttt tctggacata gtaaaatttt tctccataaa taattgtact   2820
taattgtgga tgactgacaa attttttattg tatattccta cagatcagtc ataattaaat   2880
```

| | |
|---|---|
| tacctgcatt atagggttta taaaattttt atattttaca atgttcagtt ctaactagtg | 2940 |
| gaaagttact ctagcttttt aaaaggctgt ttacaattct gtgtaaaaat agagcagtat | 3000 |
| ctactcaagt ttgtgtaaat gttagggata atttgaaaaa tatatatatt taatacatta | 3060 |
| atttctctgg aagcaggagg catgtttaaa taactattaa aataatttat ttttctagcc | 3120 |
| ataaaggatg gaagtcaaga acttttttgtt gtttagtcat gttaagtata gtttatgaaa | 3180 |
| ttaacttgta aataaaagtg taaaatattt tcatta | 3216 |

<210> SEQ ID NO 29
<211> LENGTH: 1931
<212> TYPE: DNA
<213> ORGANISM: Homo sapiens

<400> SEQUENCE: 29

| | |
|---|---|
| acttccgggg tcgaggcgag gccaacgata cgcctgctgc agcaggagga gttacgagcc | 60 |
| gggccgcgcg ctgcctaaat acctaaacca ggtttagcgc ctgctcatat aaagctctcc | 120 |
| taactcgtct tccggtggga atttcttcac gtgggccgga gtcggagact gagtttagct | 180 |
| ttactgagga gctctaaatt taggcgggta tgagtgattt cagtgaagaa ttaaaagggc | 240 |
| ctgtgacaga tgatgaagaa gtggaaacat ctgtgctcag tggtgcagga atgcattttc | 300 |
| cttggcttca aacatacgta gaaactgtgc ccattggagg gaaaggagg aaggattttg | 360 |
| ctcagacaac aagtgcttgt ttaagtttta tccaagaagc tctgctgaag caccaatggc | 420 |
| agcaagctgc agaatacatg tacagttatt ttcagacctt ggaagattca gatagctaca | 480 |
| aaaggcaggc tgcacctgag attatttgga agctcggaag tgaaattcta ttttatcatc | 540 |
| ccaaaagcaa catggagagt ttcaatactt ttgctaaccg gatgaaaaat attggcgtca | 600 |
| tgaattattt aaagatctcc ttacaacatg cattatacct tctgcatcat ggaatgctta | 660 |
| aagatgctaa gagaaatctg agtgaggcag agacatggag acatggtgaa aatacgtctt | 720 |
| cccgggaaat attaatcaac cttattcagg cctataaagg gcttttacag tattatacct | 780 |
| ggtctgaaaa aagatggaa ttgtcaaagc ttgataagga tgattatgct tacaatgcag | 840 |
| tagcccagga tgtgttcaac cacagctgga agacatctgc aaatatttct gcattgatta | 900 |
| aaattcctgg agtttgggac cctttttgtga agagttatgt agaaatgctg gaattctatg | 960 |
| gggatcgaga tggagcccaa gaggtactca ccaattatgc atatgatgaa aagtttccat | 1020 |
| caaatccaaa tgcccatatc tacttataca actttctaaa gagacagaag gcaccaagat | 1080 |
| caaaattgat aagtgtgctt aagattttgt atcagattgt accatctcat aaaattgatgt | 1140 |
| tggaattcca tacattactt agaaaatcag aaaaagaaga acaccgtaaa ctggggttgg | 1200 |
| aggtattatt tggagtctta gattttgccg gatgcactaa gaatataact gcttggaaat | 1260 |
| acttggcaaa atatctgaaa aatatcttaa tgggaaacca ccttgcgtgg gttcaagaag | 1320 |
| agtggaactc caggaaaaac tggtggccag gctttcattt cagctacttt tgggcaaaaa | 1380 |
| gtgattggaa ggaagataca gctttggcct gtgagaaagc ttttgtggct ggtttactgt | 1440 |
| taggaaaagg ttgtagatat ttccggtata tttaaagca agatcaccaa atcttaggga | 1500 |
| agaaaattaa gcggatgaag agatctgtga aaaaatacag tattgtaaat ccaagactct | 1560 |
| gatactgaat tttagttatt tcacagttgt agctacacag taagtagctt ggtagatagt | 1620 |
| tattgaatgt atttatgtag tgtattaaga agcttatatt actacaaaaa acttatttt | 1680 |
| atatattttt atattttgt attatttata gctagagaaa caatattact gcctttgctc | 1740 |
| tttgtaacta tgtctgtttt cttttttgta atgttaaatg ttacatttgt taaggaataa | 1800 | ttcttcaaat gacaaactaa ttacagaata tagctctaca gcagttattg tttgcaaata     1860 ctttgcctct tgctattgtg taataaactg taacttgtag tgctgtgaaa tgtaaaaaaa     1920 aaaaaaaaaa a     1931

<210> SEQ ID NO 30
<211> LENGTH: 409
<212> TYPE: DNA
<213> ORGANISM: Homo sapiens
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (200)..(201)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t

<400> SEQUENCE: 30
aacattcttg agaaagttaa aacaatagca aattgtataa ttgtatccag aaatgtatac       60
tcatcgtatt ttaaagctaa atttattttt taaactagat cccttcatta ttctttatgc      120
cccagagtaa atcccagatg gatcaaagat ctaaacataa tctttcatat gtaaaaatat      180
aaaagtattn gtagaaaacn natatgaatg ctttgatgat cttggaatgg caangtcaat      240
ttttgcagca tatggtggac aaaggagata atttctttaa tgtatcaata gctcttgcaa      300
agcaaacagg anaaaagcaa actgagtang ggatatgana attagtnttc tgagccaccg      360
tgcccagcct aattttgta actntgtata ntggagactt acacagtgg      409

<210> SEQ ID NO 31
<211> LENGTH: 229
<212> TYPE: DNA
<213> ORGANISM: Homo sapiens

<400> SEQUENCE: 31
tttttttttt tttttttaca aaagaaacta ctactgtatt tgttgccct gtcccttcaa       60 cttggctcca aattgcttgg ctcatcatca cagtggcctc cagaaggtgg cgagctctgc      120
ttctcaagtt tcaactgtgg aaggcacatc tggtcccaga ggaaggatga ggggctctct      180

| ggggcttgag ggcagcccac cttgtgtcct cagaagcccc ctcgtgccg | 229 |

<210> SEQ ID NO 32
<211> LENGTH: 1323
<212> TYPE: DNA
<213> ORGANISM: Homo sapiens

<400> SEQUENCE: 32

| gatttcggcc tgactattac ttgggccacg gaaatagcca acccttttct tccgcacggt | 60 |
| tggaggaggt cggctggtta tcgggagttg gagggctgag gtcgggaggg tggtgtgtac | 120 |
| agagctctag gacaccaggc cagtcgcggg ttttgggccg aggcctgggt tacaagcagc | 180 |
| aagtgcgcgg ttggggccac tgcgaggccg ttttagaaaa ctgtttaaaa caaagagcaa | 240 |
| ttgatggata aatcaggaat agattctctt gaccatgtga catctgatgc tgtggaactt | 300 |
| gcaaatcgaa gtgataactc ttctgatagc agcttattta aaactcagtg tatcccttac | 360 |
| tcacctaaag gggagaaaag aaacccccatt cgaaaatttg ttcgtacacc tgaaagtgtt | 420 |
| cacgcaagtg attcatcaag tgactcatct tttgaaccaa taccattgac tataaaagct | 480 |
| attttgaaa gattcaagaa caggaaaaag agatataaaa aaagaaaaa gaggaggtac | 540 |
| cagccaacag gaagaccacg gggaagacca gaaggaagga gaaatcctat atactcacta | 600 |
| atagataaga agaaacaatt tagaagcaga ggatctggct tcccattttt agaatcagag | 660 |
| aatgaaaaaa acgcaccttg gagaaaaatt ttaacgtttg agcaagctgt tgcaagagga | 720 |
| ttttttaact atattgaaaa actgaagtat gaacaccacc tgaaagaatc attgaagcaa | 780 |
| atgaatgttg gtgaagattt agaaaatgaa gattttgaca gtcgtagata caaatttttg | 840 |
| gatgatgatg gatccattc tcctattgag gagtcaacag cagaggatga ggatgcaaca | 900 |
| catcttgaag ataacgaatg tgatatcaaa ttggcagggg atagtttcat agtaagttct | 960 |
| gaattccctg taagactgag tgtatactta gaagaagagg atattactga gaagctgct | 1020 |
| ttgtctaaaa agagagctac aaaagccaaa atactggac agagaggcct gaaaatgtga | 1080 |
| caggatcatg aatgtcaaag gtgaagcata tagaaaaac gacttcatag aaatgaataa | 1140 |
| agataaatgt ggatatatgt accagtctgg tggtgaagaa attctgaaac ccagaacttt | 1200 |
| ataacaagaa aaaaattttt taaccctgtg aagaagtttg tgaaagaaac ttgtgaagta | 1260 |
| gtaataatta gaaaaaaaac cattaaaaca ccagagaaaa tacatagaaa aaaaaaaaaa | 1320 |
| aaa | 1323 |

<210> SEQ ID NO 33
<211> LENGTH: 2489
<212> TYPE: DNA
<213> ORGANISM: Homo sapiens

<400> SEQUENCE: 33

| ctccgccgcg ggagggagct gcggctgtgc cggccgagcg ggggagggcg ccgccactca | 60 |
| gagccaggga gggagccgct ggagcggaag cccgagggcc gcgctgcgcc gggtgaggt | 120 |
| ggctttgacc ccgggttgcc cggccagcac gaccgaggag gtggctggac agctggagga | 180 |
| tgaacggaga agccgactgc cccacagacc tggaaatggc cgcccccaaa ggccaagacc | 240 |
| gttggtccca ggaagacatg ctgactttgc tggaatgcat gaagaacaac cttccatcca | 300 |
| atgacagctc caagttcaaa accaccgaat cacacatgga ctgggaaaaa gtagcattta | 360 |
| aagactttc tggagacatg tgcaagctca atgggtggga gatttctaat gaggtgagga | 420 |
| agttccgtac attgacagaa ttgatcctcg atgctcagga acatgttaaa aatccttaca | 480 |

| | |
|---|---|
| aaggcaaaaa actcaagaaa cacccagact tcccaaagaa gcccctgacc ccttatttcc | 540 |
| gcttcttcat ggagaagcgg gccaagtatg cgaaactcca ccctgagatg agcaacctgg | 600 |
| acctaaccaa gattctgtcc aagaaataca aggagcttcc ggagaagaag aagatgaaat | 660 |
| atattcagga cttccagaga gagaaacagg agttcgagcg aaacctggcc cgattcaggg | 720 |
| aggatcaccc cgacctaatc cagaatgcca agaaatcgga catcccagag aagcccaaaa | 780 |
| ccccccagca gctgtggtac acccacgaga gaaggtgta tctcaaagtg cggccagatg | 840 |
| agatcatgag agactatatc cagaagcacc cagagctgaa catcagtgag gagggtatca | 900 |
| ccaagtccac cctcaccaag gccgaacgcc agctcaagga caagtttgac gggcgaccca | 960 |
| ccaagccacc tccgaacagc tactcgctgt actgcgcaga gctcatggcc aacatgaagg | 1020 |
| acgtgcccag cacagagcgc atggtgctgt gcagccagca gtggaagctg ctgtcccaga | 1080 |
| aggagaagga cgcctatcac aagaagtgtg atcagaaaaa gaaagattac gaggtggagc | 1140 |
| tgctccgttt cctcgagagc ctgcctgagg aggagcagca gcgggtcttg ggggaagaga | 1200 |
| agatgctgaa catcaacaag aagcaggcca ccagcccgc ctccaagaag ccagcccagg | 1260 |
| aaggggcaa gggcggctcc gagaagccca agcggcccgt gtcggccatg ttcatcttct | 1320 |
| cggaggagaa acggcggcag ctgcaggagg agcggcctga gctctccgag agcgagctga | 1380 |
| cccgcctgct ggcccgaatg tggaacgacc tgtctgagaa gaagaaggcc aagtacaagg | 1440 |
| cccgagaggc ggcgctcaag gctcagtcgg agaggaagcc cggcggggag cgcgaggaac | 1500 |
| ggggcaagct gcccgagtcc cccaaaagag ctgaggagat ctggcaacag agcgttatcg | 1560 |
| gcgactacct ggcccgcttc aagaatgacc gggtgaaggc cttgaaagcc atggaaatga | 1620 |
| cctggaataa catggaaaag aaggagaaac tgatgtggat taagaaggca gccgaagacc | 1680 |
| aaaagcgata tgagagagag ctgagtgaga tgcgggcacc tccagctgct acaaattctt | 1740 |
| ccaagaagat gaaattccag ggagaaccca agaagcctcc catgaacggt taccagaagt | 1800 |
| ctctcccagga gctgctgtcc aatggggagc tgaaccacct gccgctgaag gagcgcatgg | 1860 |
| tggagatcgg cagtcgctgg cagcgcatct cccagagcca gaaggagcac tacaaaaagc | 1920 |
| tggccgagga gcagcaaaag cagtacaagg tgcacctgga cctctgggtt aagagcctgt | 1980 |
| ctccccagga ccgtgcagca tataaagagt acatctccaa taaacgtaag agcatgacca | 2040 |
| agctgcgagg cccaaacccc aaatccagcc ggactactct gcagtccaag tcggagtccg | 2100 |
| aggaggatga tgaagaggat gaggatgacg aggacgagga tgaagaagag gaagatgatg | 2160 |
| agaatgggga ctcctctgaa gatggcggcg actcctctga gtccagcagc gaggacgaga | 2220 |
| gcgaggatgg ggatgagaat gaagaggatg acgaggacga agacgacgac gaggatgacg | 2280 |
| atgaggatga agataatgag tccgagggca gcagctccag ctcctcctcc tcagggggact | 2340 |
| cctcagactc tgactccaac tgaggctcag ccccaccccca gggcagccag ggagagccca | 2400 |
| ggagctcccc tccccaactg accacctttg tttctccccc atgttctgtc ccttgccccc | 2460 |
| ctggcctccc ccactttctt tctttcttt | 2489 |

<210> SEQ ID NO 34
<211> LENGTH: 3154
<212> TYPE: DNA
<213> ORGANISM: Homo sapiens

<400> SEQUENCE: 34

| | |
|---|---|
| acttccgctt cctcaacagc agcacttccg ggttgggaga aaggtggcgg cgctttcgga | 60 |

```
gggaataaaa tggaaggaga atcaagcaga tttgaaatcc acactccagt ttctgacaag    120
aaaaagaaaa agtgttctat acataaggaa agacctcaga acattccca cgaaattttc    180 agagactcct ccctggtgaa tgaacagtct caaataacta ggaggaaaaa gaggaaaaaa    240
gatttccagc atctcatttc ttctcctttg aaaaaatcca gaatctgtga tgagactgca    300
aatgccactt ccacactcaa aaagagaaaa aagagaagat atagtgcttt ggaggtggac    360
gaggaagcag gtgttacagt tgtccttgtg gataaagaaa atattaacaa cacaccaaag    420
cattttagaa aggatgttga tgttgtttgt gttgatatga gcatagaaca gaagttacca    480
agaaagccta aaacagacaa atttcaggta cttgctaagt cacatgcaca taaatcagaa    540
gccctgcaca gtaaagttag ggagaaaaag aataaaaagc atcagaggaa agctgcatcc    600
tgggagagcc agcgggcaag ggacaccctg cctcagtcag aatcccacca ggaggagtcc    660
tggctttctg tgggtccagg gggtgaaatt acagaactac cagcatctgc tcataaaaac    720
aagtctaaga aaaaaagaa aaagtccagt aaccgggaat atgagacact ggccatgcct    780
gaaggatcgc aagcaggcag agaggccggg actgatatgc aggaatccca gcctactgtg    840
ggcttggatg atgaaactcc acaactacta ggacctactc acaaaaaaaa gtctaagaaa    900
aaaaagaaga aaaagtccaa tcaccaggaa tttgaggcat tggccatgcc tgaaggatca    960
caagtgggca gtgaggttgg ggctgatatg caggaatccc ggcctgctgt gggcctgcat   1020
ggtgaaactg caggaatacc agcacctgct tataaaaaca gtctaagaa aaaaagaaa   1080 aagtccaatc accaggaatt tgaggcagtg gccatgcctg agagcctcga gagtgcatac   1140
cctgaaggat cacaggtggg cagtgaggtt gggactgtgg aaggcagtac agctcttaaa   1200
gggttcaagg aatccaacag tacaaagaag aagtctaaga aaaggaagct tacgtctgtc   1260
aaaagggcac gagtgtctgg tgatgatttt tcagtgccca gtaagaactc tgagagcaca   1320
ctctttgatt cagtagaagg tgatggcgcc atgatggaag aaggtgtgaa atctaggccc   1380
cgacaaaaga aaacccaggc ctgtttggca agcaagcacg tgcaagaggc gccaaggtta   1440
gaacctgcaa atgaagaaca caatgtggaa acagctgaag attccgaaat aagatactta   1500
tctgcagatt caggagatgc cgatgattca gatgcggatt tgggttctgc cgtgaaacag   1560
cttcaggagt tcattcctaa catcaaggac agggccacca gcacaatcaa gcggatgtac   1620
cgggacgact tggaacggtt taaggaattt aaagcacaag tgtcgctat taaatttggc   1680 aagttttctg taaaggaaaa taagcagtta gagaaaaatg tggaagactt tctagccctg   1740
acaggcattg agagtgcaga caagctgctg tacacggaca gatatcctga ggaaaaatct   1800
gtgatcacca acttaaaaag gagatactcg tttagattac acattggtag gaacattgcc   1860
cggccctgga aacttatata ctatcgagca agaagatgt tcgatgtcaa caattacaaa   1920
ggcaggtata gcgaaggaga tactgagaag ttaaagatgt accattctct ccttgggaat   1980
gactggaaga cgattggtga gatggtggcc cgaagtagcc tctccgtggc cctcaagttc   2040
tcacagatca gcagtcaaag aaatcgtggt gcttggagta agtctgaaac ccggaaacta   2100
atcaaggctg tcgaagaagt gattctgaag aagatgtctc cccaggagtt aaaagaggtg   2160
gattccaaac tccaagaaaa tcctgaaagt tgcctatcaa ttgttcggga aaaactctac   2220
aagggcatat cttgggtaga agtagaagct aaagtgcaaa ccagaaattg gatgcagtgt   2280
aaaagtaagt ggacagaaat tctaaccaag aggatgacta atggtcggcg tatctactat   2340
ggcatgaatg ccctgcgggc caaggtcagc cttattgaaa ggttgtatga aataaatgtg   2400
gaagatacta atgaaataga ctgggaagat cttgctagtg ccataggtga tgttcctcca   2460
```

```
tcttacgttc aaactaaatt ttctaggctg aaagctgtct atgttccatt ttggcagaaa    2520 aagactttc cagagatcat cgactacctt tatgagacga ctctaccttt gctgaaggaa    2580
aagttagaaa aaatgatgga gaaaaaaggc actaaaatcc agactcctgc agcacccaag   2640
caagttttcc catttcgaga catcttttat tatgaagacg atagtgaagg agaggacata   2700 gaaaagaaa gcgaaggcca ggcgccatgc atggctcacg cctgtaattc cagtactttg    2760
ggaggccaag gccggtggat catctgaggt caggagttcg agaccggcct gaccaacatg   2820
gtgaagacct gtcactatta aaaatgcaaa aattagccgg gtgtggtagt gcacacctgt   2880
aatttcaact acttgggagg ctgaggcagg agaattgctt gaacccagga ggtggaggtt   2940
gcagtgagcc aagatcgcac accgcatga gagagagaga ttactatttc ttgtcccttt    3000
ttctcagttt gattatattt atatacatat gtcagtaaat ctgttttcag tattgatgtt   3060
taataaagaa tgtacaatgg ccagagttct actctttcct ctggagcatt aaaatatatt   3120
gccattccta ttaaaacgta tttgaatgtg aaaa                               3154
```

<210> SEQ ID NO 35
<211> LENGTH: 2362
<212> TYPE: DNA
<213> ORGANISM: Homo sapiens

<400> SEQUENCE: 35

```
acctgattcc gttcctcagc tcgcattcct ccgcccgtcc cgctcccgcc gccagcggag    60
gccctagtct cccgctccaa ctattccaac catcccggga agggtggggc gctcggctct   120
tgggtccccc tccgccgccc cgcctcgtcg atctcccctt ctaccccggt ccctcccttt   180
ctggggtggg gccagccaat cagcgatcag actccggagt ttggcccggg agctggggag   240
ctcaccgatc ccccgcccag cagttctggc cgctgtcccg gtgcgcacgg acgtggctcg   300
agtttcctct gctctccgct ctcgcccgct agctctcctc ccttccgctc ctgcttctct   360
ccgggtctcc cgctccagct ccagcccac ccggccggtc ccgcacggct ccgggtagcc    420
atggaggacc ccacgctcta tattgtcgag cggccgcttc ccgggtaccc cgacgccgag   480
gccccggagc cttcctccgc tggggctcag gcagcggagg agccgtcggg ggccggctca   540
gaagagctga tcaagtcgga ccaggtgaac ggcgtgctgg tgctgagcct cctggacaaa   600
atcatcgggg ccgtagacca gatccagctg actcaagcac agctggagga gcggcaggcg   660
gagatggagg gcgcagtgca gagcatccag ggcgagctga gcaagctggg caaggcgcac   720
gccaccacga gcaatacggt gagcaagctg ctggagaagg tgcgcaaggt cagcgtcaac   780
gtgaagaccg tgcgcggcag cctggagcgc caggcggggc agatcaagaa gctggaggtc   840
aacgaggcca gctgctgcg gcgccgcaac tttaaagtca tgatctacca ggatgaagtg   900
aagctgccgg ccaaactgag catcagcaaa tcgctgaaag agtcggaggc gctgccagag   960
aaggagggcg aggagctggg cgagggcgag cggcccgagg aggacgcagc ggcgctggag   1020
ctttcgtcgg acgaagcggt ggaggttgag gaggttattg aggagtcccg cgcaaagcgt   1080
atcaagcgca gcggcctgcg gcgcgtggac gacttcaaga aggccttctc caaggagaag   1140
atggagaaga ccaaggtgcg tacccgcgag aacctggaga gacgcgcct caagaccaag   1200 gaaaacctgg agaagacgcg gcacaccctg agaagcgca tgaacaagct gggcacgcgc   1260
ctggtgcccg ccgagcggcg cgagaaactg aagacgtcgc gggacaagtt gcgcaaatcc   1320
ttcacgcccg accacgtggt gtacgcgcgc tccaagaccg cggtctacaa ggtgccaccc   1380
```

| | |
|---|---|
| ttcaccttcc acgtcaagaa gatccgcgag ggccaggtgg aagtgctcaa ggccaccgag | 1440 |
| atggtggagg tgggcgccga cgacgacgag ggcggcgcgg agcgcgggga ggccggcgac | 1500 |
| ctgcggcgcg ggagcagccc cgacgtgcac gcgctgctgg agatcaccga ggagtcggac | 1560 |
| gccgtgctgg tggacaagag cgacagcgac tgagccgccc ccgctgccac ccaccccatt | 1620 |
| cctcgctcct tccgaacttc ctctttcgca ttctctctcg gctcgagctg gctgagattt | 1680 |
| ttctaaattg aaaacacgcc ccctcccca cacctccagg aactccactc ccagtcttag | 1740 |
| agctgttagg acccgatggg gaggcagccc ccgcagtgga cagcccccgc ttggacacag | 1800 |
| tccgagtgga atgggaaggg aatggtcaat ccctgtcctg gttgtccaag tcgggatctc | 1860 |
| agaggaaatt gcagtgattc cacggttagg ccccctggg ggggctgcct tcccctcagc | 1920 |
| ctctccccac accacccacc cagctgctgt cattccgctc actgagctct tcttcattct | 1980 |
| caccctgatc cctgggggac tcaaagccaa aactgcccaa agaggaaaga ttgaatccta | 2040 |
| aaggggatcc ttgcccccat ggaggcccc ctactagaag gacgtgaaag cagcttttgg | 2100 |
| gggaaactga ggcagtgggg aagacagagc agaatgagcc ctcaccctgg ctgggggtcc | 2160 |
| agcacaggct gtatctgcag agggtcccag aggaacgctg gagccaagag aagccctggg | 2220 |
| aaggaggggt ggggaacgac atgcatgtga gggatggcac actgatgtgt ttatgcacct | 2280 |
| gtacacagga gcgcatggcc atggctttgg aaaggagaat ggaaaaatag aagaaggtcg | 2340 |
| gccgggcttg gtggcttatg cc | 2362 |

<210> SEQ ID NO 36
<211> LENGTH: 2328
<212> TYPE: DNA
<213> ORGANISM: Homo sapiens

<400> SEQUENCE: 36

| | |
|---|---|
| gtggccgtgg ctaccgatgg gatagtcgcc gcggtcgcca tcttcccagc aacaacgtca | 60 |
| cttcccttcc ggaccacaag gggcgctgac tccgaactta ggacaggaag aaacaggcac | 120 |
| atttccggtc tctatgcttt ctcatccggc cggcttgctt tccctgcgg tcgtccagac | 180 |
| tattgggcgc tagcgagacg aactattggt acgggctag agaggaaggc tttgggattg | 240 |
| ccggggagca gcgagcgacc gacttccgtt tccagttacc aaggcacgag gatccggtgt | 300 |
| tccaacccag ggggaaaaat gcggcctttg actgaagagg agaccgtgt catgtttgag | 360 |
| aagatagcga aatacattgg ggagaatctt caactgctgg tggaccggcc cgatggcacc | 420 |
| tactgtttcc gtctgcacaa cgaccgggtg tactatgtga gtgagaagat tatgaagctg | 480 |
| gccgccaata tttccgggga caagctggtg tcgctgggga cctgctttgg aaaattcact | 540 |
| aaaacccaca agtttcggtt gcacgtcaca gctctggatt accttgcacc ttatgccaag | 600 |
| tataaagttt ggataaagcc tggtgcagag cagtccttcc tgtatgggaa ccatgtgttg | 660 |
| aaatctggtc tgggtcgaat cactgaaaat acttctcagt accagggcgt ggtggtgtac | 720 |
| tccatggcag acatcccttt gggttttggg gtggcagcca atctacaca agactgcaga | 780 |
| aaagtagacc ccatggcgat tgtggtattt catcaagcag acattgggga atatgtgcgg | 840 |
| catgaagaga cgttgactta aaacgaagcc attccaagga cagacggctg tatggaaagg | 900 |
| ccgagctttg tttcctgtgt tgtgtggac tccaccatca tgttgaattt tgtcaacact | 960 |
| ctggcctctt cagggacttc ttatttactg tactctctat cactgacaaa tgcaggctgg | 1020 |
| attcttatta tatacagaga tggctcaaaa atggggtttc agatctttgt gacgaaatag | 1080 |
| aatactgttt catatttgaa tcagagggct tcttgttctg agaaataggt tcaaaatcat | 1140 |

```
tggaaccagg aacaagaata gcttattgtt atctgtgata acactgtttt ctaaacacaa    1200
ggattttctt ttttattaat atgcaacata gacattgcca taacagaata ataaaccaca    1260
tgtggggttt taaaaatgaa atttggctaa taggagcaat tcagctattt ttctatacag    1320
taattggtgt gtggtataga agaaaaacgg gttcaaaccc cacttctgcc acctaccagc    1380
tatatggcct tgaatgagtc attcagcttt aataaggttc attttcttct gtttaaaaag    1440
acacaaaact tgaaaatcag ctttggccat ctacctgaga attagaaagt ctgattttg     1500 gaattagaaa tcatgattgt aggctgggca cagtggctcg cgcctgtaat cccagcactt    1560
tgggaggcca aggcggacgg atcacttgag gttaggagtt tgagaccagc ctggccaaca    1620
tggtgaaacc ccatctctac taaaaaaaaa aaaaaaatta ggtgtggtga cacatggctg    1680
tggtcctagt tacttgggag gctgaggcag gagaatggct tgaactgggg aagcagagct    1740
tgcagtgagc caagatggtg ccattgcact ccagcctggg cgtgacagag tgagactcca    1800
tctgattgta aagcatctag tacagtgtac agtgccttgg aaatgatagg tatggaataa    1860
atggtaatta ttttatatt atatatatta tgtattcctg ttattaagtg tagagtttta    1920
tgagtataat ttgattttat taccttcttt tttacaagct gttttctcag tattttctt     1980 ggatgggatg acgctaggct ggaaagtttt tttcatcact atgattttat aaaacaattt    2040
tttctatgaa cctttactta cttgactgga ttggactaaa agcactgatc agaggccacg    2100
acataaaaat tcagtccctt tgtccttccc cgtgcctccc aaagttactt taagatcctt    2160
agaatatttc tttaaatatt ttatagacaa aaaatttaaa gactatctgt attgcaaaat    2220
taaactattt ctttaatgaa tatattgctt attttaagtt ccaaaggtga agtctttaag    2280
aataaaacat taccaactcc tgcttttata tgtaagcaaa aaaaaaaa                 2328

<210> SEQ ID NO 37
<211> LENGTH: 13357
<212> TYPE: DNA
<213> ORGANISM: Homo sapiens

<400> SEQUENCE: 37
gctgacacgc tgtcctctgg cgacctgtcg ctggagaggt tgggcctccg gatgcgcgcg      60
gggctctggc ctaccggtga cccggctagc cggccgcgct cctgcttgag ccgcctgccg     120
gggcccgcgg gcctgctgtt ctctcgcgcg tccgagcgtc ccgactcccg gtgccggccc     180
gggtccgggt ctctgaccca cccggggggcg gcggggaagg cggcgagggc caccgtgccc     240
ccgtgcgctc tccgctgcgg gcgcccgggg cggccgcgac aacccaccc cgctggctcc      300 gtgccgtgcg tgtcaggcgt tctcgtctcc gcggggttgt ccgccgcccc ttccccggag     360
tggggggttg gccggagccg atcggctcgc tggccggccg gccggcctcc gctcccgggg     420
ggctcttcgt gatcgatgtg gtgacgtcgt gctctcccgg gccgggtccg agccgcgacg     480
ggcgaggggc ggacgttcgt ggcgaacggg accgtcctcc tcgctccgcc ccgcgggggt     540
cccctcgtct ctcctctccc cgcccgccgg cggtgcgtgt gggaaggcgt ggggtgcgga     600
ccccggcccg acctcgccgt cccgcccgcc gccttctgcg tcgcggggcg ggccggcggg     660
gtcctctgac gcggcagaca gccctcgctg tcgcctccag tggttgtcga cttgcgggcg     720 gccccctcc gcggcggtgg gggtgccgtc ccgccggccc gtcgtgctgc cctctcgggg      780
ggtttgcgcg agcgtcggct ccgcctgggc ccttgcggtg ctcctggagc gctccgggtt     840
gtccctcagg tgcccgaggc cgaacggtgg tgtgtcgttc ccgcccccgg cgccccctcc     900
```

```
tccggtcgcc gccgcggtgt ccgcgcgtgg gtcctgaggg agctcgtcgg tgtggggttc    960
gaggcggttt gagtgagacg agacgagacg cgcccctccc acgcggggaa gggcgcccgc   1020
ctgctctcgg tgagcgcacg tcccgtgctc ccctctggcg ggtgcgcgcg ggccgtgtga   1080
gcgatcgcgg tgggttcggg ccggtgtgac gcgtgcgccg gccggccgcc gaggggctgc   1140
cgttctgcct ccgaccggtc gtgtgtgggt tgacttcgga ggcgctctgc ctcggaagga   1200
aggaggtggg tggacggggg ggcctggtgg ggttgcgcgc acgcgcgcac cggccgggcc   1260
cccgccctga acgcgaacgc tcgaggtggc cgcgcgcagg tgtttcctcg taccgcaggg   1320
ccccctccct tccccaggcg tccctcggcg cctctgcggg cccgaggagg agcggctggc   1380
gggtgggggg agtgtgaccc accctcggtg agaaaagcct tctctagcga tctgagaggc   1440
gtgccttggg ggtaccggat ccccccggcc gccgcctctg tctctgcctc cgttatggta   1500
gcgctgccgt agcgacccgc tcgcagagga ccctcctccg cttccccctc gacggggttg   1560
ggggggagaa gcgagggttc cgccggccac cgcggtggtg gccgagtgcg gctcgtcgcc   1620
tactgtggcc cgcgcctccc ccttccgagt cggggggagga tccgccgggg ccgggcccgg   1680
cgttcccagc gggttgggac cggcggccg gcggcggtg ggtgtgcgcg cccggcgctc   1740
tgtccggcgc gtgacccect ccgccgcgag tcggctctcc gcccgctccc gtgccgagtc   1800
gtgaccggtg ccgacgaccg cgtttgcgtg gcacggggtc gggcccgcct ggccctggga   1860
aagcgtccca cggtggggc gcgccggtct cccgagcgg gaccgggtcg gaggatggac   1920
gagaatcacg agcgacggtg gtgcgggcgt gtcgggttcg tggctgcggt cgctccgggg   1980
cccccggtgg cggggcccg gggctcgcga ggcggttctc ggtgggggcc gagggccgtc   2040
cggcgtccca gcggggcgc cgcgggaccg ccctcgtgtc tgtggcggtg ggatcccgcg   2100
gccgtgtttt cctggtggcc cggccgtgcc tgaggtttct ccccgagccg ccgcctctgc   2160
gggctcccgg gtgcccttgc cctcgcggtc cccggccctc gccgtctgt gccctcttcc   2220
ccgcccgccg cccgccgatc ctcttcttcc cccgagcgg ctcaccggct tcacgtccgt   2280
tggtggcccc gcctgggacc gaacccggca ccgcctcgtg gggcgccgcc gccggccact   2340
gatcggcccg gcgtccgcgt ccccggcgc gcgccttggg gaccgggtcg gtggcgcccc   2400
gcgtggggcc cggtgggctt cccggagggt tccggggtc ggcctgcggc gcgtgcgggg   2460
gaggagacgg ttccggggga ccggccgcga ctgcggcggc ggtggtgggg gcagccgcgg   2520
ggatcgccga gggccggtcg gccgcccgg gtgccgcgcg gtgccgccgg cggcggtgag   2580
gccccgcgcg tgtgtcccgg ccggtcgg ccgcgctcga ggggtccccg tggcgtcccc   2640
ttccccgccg gccgcctttc tcgcgccttc cccgtcgccc cggcctcgcc cgtggtctct   2700
cgtcttctcc cggcccgctc ttccgaaccg ggtcggcgcg tccccgggt gcgcctcgct   2760
tcccgggcct gccgcggccc ttcccgagg cgtccgtccc gggcgtcggc gtcggggaga   2820
gcccgtcctc cccgcgtggc gtcgcccgt tcggcgcgcg cgtgcgcccg agcgcggccc   2880
ggtggtccct gccggacagg cgttcgtgcg acgtgtggcg tgggtcgacc tccgccttgc   2940
cggtcgctcg ccctttcccc gggtcggggg gtggggcccg ggcggggcc tcggccccgg   3000
tcgcggtccc ccgtcccggg cggggcggg cgcgccggcc ggcctcggtc ggccctccct   3060
tggccgtcgt gtggcgtgtg ccaccctgc gccgcgccc gcggcgggg ctcggagccg   3120
ggcttcggcc gggcccccggg ccctcgaccg gaccggtgcg cggcgctgc ggccgcacgg   3180
cgcgactgtc cccgggccgg gcaccgcggt ccgcctctcg ctcgccgccc ggacgtcggg   3240
gccgccccgc ggggcgggcg gagcgccgtc cccgcctcgc cgccgcccgc gggcgccggc   3300
```

```
cgcgcgcgcg cgcgcgtggc cgccggtccc tcccggccgc cgggcgcggg tcgggccgtc    3360
cgcctcctcg cgggcgggcg cgacgaagaa gcgtcgcggg tctgtggcgc ggggcccgg     3420 tggtcgtgtc gcgtgggggg cgggtggttg gggcgtccgg ttcgccgcgc ccgccccgg     3480 ccccaccggt cccggccgcc gccccgcgc ccgctcgctc cctcccgtcc gcccgtccgc     3540
ggcccgtccg tccgtccgtc gtcctcctcg cttgcggggc gccgggcccg tcctcgcgag    3600
gccccccggc cggccgtccg gccgcgtcgg ggcctcgccg cgctctacct tacctacctg    3660
gttgatcctg ccagtagcat atgcttgtct caaagattaa gccatgcatg tctgagtacg    3720 cacgccggt acagtgaaac tgcgaatggc tcattaaatc agttatggtt cctttggtcg    3780
ctcgctcctc tcctacttgg ataactgtgg taattctaga gctaatacat gccgacgggc    3840 gctgacccc ttcgcggggg ggatgcgtgc atttatcaga tcaaaaccaa cccggtcagc     3900
ccctctccgg ccccggccgg ggggcgggcg ccggcggctt tggtgactct agataaccttc   3960 gggccgatcg cacgccccc gtggcggcga cgacccattc gaacgtctgc cctatcaact     4020
ttcgatggta gtcgccgtgc ctaccatggt gaccacgggt gacggggaat cagggttcga    4080
ttccggagag ggagcctgag aaacggctac cacatccaag gaaggcagca ggcgcgcaaa    4140
ttacccactc ccgacccggg gaggtagtga cgaaaaataa caatacagga ctctttcgag    4200
gccctgtaat tggaatgagt ccactttaaa tcctttaacg aggatccatt ggagggcaag    4260
tctggtgcca gcagccgcgg taattccagc tccaatagcg tatattaaag ttgctgcagt    4320
taaaaagctc gtagttggat cttgggagcg ggcgggcggt ccgccgcgag gcgagccacc    4380
gcccgtcccc gccccttgcc tctcggcgcc ccctcgatgc tcttagctga gtgtcccgcg    4440
gggcccgaag cgtttactttt gaaaaaatta gagtgttcaa agcaggcccg agccgcctgg    4500
ataccgcagc taggaataat ggaataggac gcgcggttcta tttttgttggt ttcggaact   4560 gaggccatga ttaagaggga cggccggggg cattcgtatt gcgccgctag aggtgaaatt    4620
cttggaccgg cgcaagacgg accagagcga aagcatttgc caagaatgtt ttcattaatc    4680
aagaacgaaa gtcggaggtt cgaagacgat cagataccgt cgtagttccg accataaacg    4740
atgccgaccg gcgatgcggc ggcgttattc ccatgacccg ccgggcagct tccgggaaac    4800 caaagtctttt gggttccggg gggagtatgg ttgcaaagct gaaacttaaa ggaattgacg    4860
gaagggcacc accaggagtg gagcctgcgg cttaatttga ctcaacacgg gaaacctcac    4920
ccggcccgga cacggacagg attgacagat tgatagctct ttctcgattc cgtgggtggt    4980
ggtgcatggc cgttcttagt tggtggagcg atttgtctgg ttaattccga taacgaacga    5040
gactctggca tgctaactag ttacgcgacc cccgagcggt cggcgtcccc caacttctta    5100
gagggacaag tggcgttcag ccacccgaga ttgagcaata acaggtctgt gatgccctta    5160
gatgtccggg gctgcacgcg cgctacactg actggctcag cgtgtgccta ccctacgccg    5220
gcaggcgcgg gtaacccgtt gaaccccatt cgtgatgggg atcggggatt gcaattattc    5280
cccatgaacg aggaattccc agtaagtgcg ggtcataagc ttgcgttgat taagtccctg    5340 cccttttgtac acaccgcccg tcgctactac cgattggatg gtttagtgag gccctcggat    5400
cggccccgcc ggggtcggcc cacggccctg gcggagcgct gagaagacgg tcgaacttga    5460
ctatctagag gaagtaaaag tcgtaacaag gtttccgtag gtgaacctgc ggaaggatca    5520
ttaacggagc ccggagggcg aggcccgcgg cggcgccgcc gccgccgcgc gcttccctcc    5580
gcacacccac ccccccaccg cgacgcggcg cgtgcgcggg cggggcccgc gtgcccgttc    5640
```

-continued

```
gttcgctcgc tcgttcgttc gccgcccggc cccgccggcc gcgagagccg gagaactcgg   5700
gagggagacg ggggagagag agagagagag agaaagagaa agaagggcgt gtcgttggtg   5760
tgcgcgtgtc gtggggccgg cgggcggcgg ggagcggtcc ccggccgcgg ccccgacgac   5820
gtgggtgtcg gcgggcgcgg gggcggttct cggcggcgtc gcggcgggtc tgggggggtc   5880
tcggtgccct cctccccgcc ggggcccgtc gtccggcccc gccgcgccgg ctccccgtct   5940
tcggggccgg ccggattccc gtcgcctccg ccgcgccgct ccgcgccgcc gggcacggcc   6000
ccgctcgctc tccccggcct tcccgctagg gcgtctcgag ggtcggggc cggacgccgg   6060
tccctccccc cgcctcctcg tccgcccccc cgccgtccag gtacctagcg cgttccggcg   6120
cggaggttta aagaccccctt gggggatcg cccgtccgcc cgtgggtcgg gggcggtggt   6180
gggcccgcgg gggagtcccg tcgggagggg cccggcccct cccgcgcctc caccgcggac   6240
tccgctcccc ggccggggcc gcgccgccgc cgccgccgcg cggccgtcg ggtggggct    6300
ttacccggcg gccgtcgcgc gcctgccgcg cgtgtggcgt gcgccccgcg ccgtgggggc   6360
gggaaccccc gggcgcctgt ggggtggtgt ccgcgctcgc ccccgcgtgg gcggcgcgcg   6420
cctccccgtg gtgtgaaacc ttccgacccc tctccggagt ccggtcccgt ttgctgtctc   6480
gtctggccgg cctgaggcaa cccccctctcc tcttgggcgg ggggggggg gacgtgccgc   6540
gccaggaagg gcctcctccc ggtgcgtcgt cgggagcgcc ctcgccaaat cgacctcgta   6600
cgactcttag cggtggatca tcggctcgt gcgtcgatga agaacgcagc tagctgcgag   6660
aattaatgtg aattgcagga cacattgatc atcgacactt cgaacgcact tgcggccccg   6720
ggttcctccc ggggctacgc ctgtctgagc gtcgcttgcc gatcaatcgc ccccgggggt   6780
gcctccgggc tcctcggggt gcgcggctgg gggttccctc gcagggcccg ccggggggccc   6840
tccgtccccc taagcgcaga cccggcggcg tccgccctcc tcttgccgcc gcgcccgccc   6900
cttccccctc ccccgcggg ccctgcgtgg tcacgcgtcg ggtggcgggg gggagagggg    6960
ggcgcgcccg gctgagagag acggggaggg cggcgccgcc gccgcccgcg aagacggaga   7020
gggaaagaga gagccggctc gggccgagtt cccgtggccg ccgcctgcgg tccgggttcc   7080
tccctcgggg ggctccctcg cgccgcgcgc ggctcggggt tcggggttcg tcggcccgg    7140
ccgggtggaa ggtcccgtgc ccgtcgtcgt cgtcgtcgtc gcgcgtcgtc ggcggtgggg   7200
gcgtgttgcg tgcggtgtgg tggtggggga ggaggaaggc gggtccggaa ggggaagggt   7260
gccggcgggg agagagggtc gggggagcgc gtccggtcg ccgcggttcg ccgcccgccc    7320
ccggtggcgg cccggcgtcc ggccgaccgc cgctcccgcg ccctcctcc tccccgccgc    7380
ccctcctccg aggccccgcc cgtcctcctc gccctcccccg cgcgtacgcg cgcccgcccg   7440
cccggctcgc ctcgcggcgc gtcggccggg gccgggagcc cgccccgcgg cccgccggc    7500
cgcgcccgtg gccgcggcgc cggggttcgc gtgtccccgg cggcgacccg cgggacgccg   7560
cggtgtcgtc cgccgtcgcg cgccccgcctc cggctcgcgg ccgcgccgcg ccgcgccggg   7620
gccccgtccc gagcttccgc gtcggggcgg ggcggctccg ccgccgcgtc ctcggacccg   7680
tcccccgac ctccgcgggg gagacgggtc ggggcgtgcg gcgcccgtcc cgccccggc    7740
ccgtgccccct ccctccggtc gtcccgctcc gcgggcgcg cgcggggtg ccgccggccg    7800
cgcgctctct ctcccgtcgc ctctccccct cgccgggccc gtctcccgac ggagcgtcgg   7860
gcgggcggtc gggccggcgc gattccgtcc gtccgtccgc cgagcggccc gtccccctcc   7920
gagacgcgac ctcagatcag acgtggcgac ccgctgaatt taagcatatt agtcagcgga   7980
ggagaagaaa ctaaccagga ttccctcagt aacggcgagt gaacagggaa gagcccagcg   8040
```

```
ccgaatcccc gccccgcggc ggggcgcggg acatgtggcg tacgaagac  ccgctccccg    8100 gcgccgctcg tgggggggccc aagtccttct gatcgaggcc cagcccgtgg acggtgtgag    8160
gccggtagcg gccccggcg cgccgggccc gggtcttccc ggagtcgggt tgcttgggaa     8220
tgcagcccaa agcgggtggt aaactccatc taaggctaaa taccggcacg agaccgatag    8280
tcaacaagta ccgtaaggga aagttgaaaa gaactttgaa gagagagttc aagagggcgt    8340
gaaaccgtta agaggtaaac gggtgggggtc cgcgcagtcc gcccggagga ttcaacccgg   8400
cggcgggtcc ggccgtgtcg gcggcccggc ggatcttttcc cgcccccccgt tcctcccgac  8460 ccctccaccc gccctccctt ccccgccgc ccctcctcct cctccccgga ggggcgggc     8520 tccggcgggt gcggggggtgg gcgggcgggg ccggggggtgg ggtcggcggg ggaccgtccc  8580
ccgaccggcg accggccgcc gccgggcgca tttccaccgc ggcggtgcgc cgcgaccggc    8640
tccgggacgg ctgggaaggc ccggcggggga aggtggctcg ggggggccccg tccgtccgtc  8700 cgtccgtcct cctcctcccc cgtctccgcc ccccggcccc gcgtcctccc tcgggagggc    8760
gcgcgggtcg gggcggcggc ggcggcggcg gtggcggcgg cggcggcggc ggcgggaccg    8820 aaacccccccc cgagtgttac agccccccccg gcagcagcac tcgccgaatc ccgggggccga 8880 gggagcgaga cccgtcgccg cgctctcccc cctccggcg cccaccccccg cggggaatcc    8940 cccgcgaggg gggtctcccc cgcggggggcg cgccggcgtc tcctcgtggg ggggccgggc   9000 caccccctccc acggcgcgac cgctctccca ccctcctcc ccgcgccccc gccccggcga    9060 cggggggggggt gccgcgcgcg ggtcgggggg cggggcggac tgtccccagt gcgccccggg 9120
cgggtcgcgc cgtcgggccc ggggggaggtt ctctcggggc cacgcgcgcg tccccccgaag 9180 aggggggacgg cggagcgagc gcacgggggtc ggcggcgacg tcggctaccc acccgacccg  9240
tcttgaaaca cggaccaagg agtctaacac gtgcgcgagt cgggggctcg cacgaaagcc    9300
gccgtggcgc aatgaaggtg aaggccggcg cgctcgccgg ccgaggtggg atcccgaggc    9360
ctctccagtc cgccgagggc gcaccaccgg cccgtctcgc ccgccgcgcc gggggaggtgg   9420 agcacgagcg cacgtgttag gacccgaaag atggtgaact atgcctgggc agggcgaagc    9480
cagaggaaac tctggtggag gtccgtagcg gtcctgacgt gcaaatcggt cgtccgacct    9540
gggtataggg gcgaaagact aatcgaacca tctagtagct ggttccctcc gaagtttccc    9600
tcaggatagc tggcgctctc gcagacccga cgcaccccg ccacgcagtt ttatccggta    9660
aagcgaatga ttagaggtct tggggccgaa acgatctcaa cctattctca aactttaaat    9720
gggtaagaag cccggctcgc tggcgtggag ccgggcgtgg aatgcgagtg cctagtgggc    9780 cactttttggt aagcagaact ggcgctgcgg gatgaaccga acgccgggtt aaggcgcccg    9840
atgccgacgc tcatcagacc ccagaaaagg tgttggttga tatagacagc aggacggtgg    9900
ccatggaagt cggaatccgc taaggagtgt gtaacaactc acctgccgaa tcaactagcc    9960
ctgaaaatgg atggcgctgg agcgtcgggc ccatacccgg ccgtcgccgg cagtcgagag  10020
tggacgggag cggcgggggc ggcgcgcgcg cgcgcgcgtg tggtgtgcgt cggagggcgg  10080
cggcggcggc ggcggcgggg gtgtgggggtc cttccccgc cccccccccc acgcctcctc  10140
ccctcctccc gcccacgccc cgctcccccgc ccccggagcc ccgcggacgc tacgccgcga  10200
cgagtaggag ggccgctgcg gtgagccttg aagcctaggg cgcgggcccg ggtggagccg  10260
ccgcaggtgc agatcttggt ggtagtagca aatattcaaa cgagaactttt gaaggccgaa  10320 gtggagaagg gttccatgtg aacagcagtt gaacatgggt cagtcggtcc tgagagatgg  10380
```

```
gcgagcgccg ttccgaaggg acgggcgatg gcctccgttg ccctcggccg atcgaaaggg   10440
agtcgggttc agatccccga atccggagtg gcggagatgg gcgccgcgag gcgtccagtg   10500
cggtaacgcg accgatcccg gagaagccgg cgggagcccc ggggagagtt ctcttttctt   10560
tgtgaagggc agggcgccct ggaatgggtt cgcccgaga gaggggcccg tgccttggaa    10620
agcgtcgcgg ttccggcggc gtccggtgag ctctcgctgg cccttgaaaa tccgggggag   10680
agggtgtaaa tctcgcgccg ggccgtaccc atatccgcag caggtctcca aggtgaacag   10740
cctctggcat gttggaacaa tgtaggtaag ggaagtcggc aagccggatc cgtaacttcg   10800
ggataaggat tggctctaag ggctgggtcg gtcgggctgg ggcgcgaagc ggggctgggc   10860
gcgcgccgcg gctggacgag gcgccgccgc ccccccacg  cccggggcac cccctcgcg    10920
gccctccccc gccccacccc gcgcgcgccg ctcgctccct ccccgccccg cgccctctct   10980
ctctctctct ccccgctcc  ccgtcctccc ccctccccgg gggagcgccg cgtgggggcg   11040
gcggcggggg gagaagggtc ggggcggcag gggccggcgg cggcccgccg cggggccccg   11100
gcggcggggg cacggtcccc cgcgaggggg gcccgggcac ccggggggcc ggcggcgcg    11160
gcgactctgg acgcgagccg ggcccttccc gtggatcgcc ccagctgcgg cgggcgtcgc   11220
ggccgccccc ggggagcccg gcgggcgccg gcgcgccccc ccccccaccc cacgtctcgt   11280
cgcgcgcgcg tccgctgggg gcggggagcg gtcgggcggc ggcggtcggc gggcggcggg   11340
gcggggcggt tcgtccccc  gccctacccc cccggccccg tccgcccccc gttccccct    11400
cctcctcggc gcgcggcggc ggcggcggca ggcggcggag gggccgcggg ccggtccccc   11460
ccgccgggtc cgccccgggg gccgcggttc cgcgcggcgc ctcgcctcgg ccggcgccta   11520
gcagccgact tagaactggt gcggaccagg ggaatccgac tgtttaatta aaacaaagca   11580
tcgcgaaggc ccgcggcggg tgttgacgcg atgtgatttc tgcccagtgc tctgaatgtc   11640
aaagtgaaga aattcaatga agcgcgggta aacggcggga gtaactatga ctctcttaag   11700
gtagccaaat gcctcgtcat ctaattagtg acgcgcatga atggatgaac gagattccca   11760
ctgtccctac ctactatcca gcgaaaccac agccaaggga acgggcttgg cggaatcagc   11820
ggggaaagaa gaccctgttg agcttgactc tagtctggca cggtgaagag acatgagagg   11880
tgtagaataa gtgggaggcc cccggcgccc ccccggtgtc cccgcgaggg gcccggggcg   11940
gggtccgccg gccctgcggg ccgccggtga aataccacta ctctgatcgt ttttcactg    12000
acccggtgag gcgggggggc gagccccgag gggctctcgc ttctggcgcc aagcgcccgg   12060
ccgcgcgccg gccgggcgcg acccgctccg gggacagtgc caggtgggga gtttgactgg   12120
ggcggtacac ctgtcaaacg gtaacgcagg tgtcctaagg cgagctcagg gaggacagaa   12180
acctcccgtg gagcagaagg gcaaaagctc gcttgatctt gattttcagt acgaatacag   12240
accgtgaaag cggggcctca cgatccttct gacctttgg  gttttaagca ggaggtgtca   12300
gaaaagttac cacagggata actggcttgt ggcggccaag cgttcatagc gacgtcgctt   12360
tttgatcctt cgatgtcggc tcttcctatc attgtgaagc agaattcacc aagcgttgga   12420
ttgttcaccc actaataggg aacgtgagct gggtttagac cgtcgtgaga caggttagtt   12480
ttaccctact gatgatgtgt tgttgccatg gtaatcctgc tcagtacgag aggaaccgca   12540
ggttcagaca tttggtgtat gtgcttggct gaggagccaa tggggcgaag ctaccatctg   12600
tgggattatg actgaacgcc tctaagtcag aatcccgccc aggcggaacg atacggcagc   12660
gccgcgggagc ctcggttggc ctcggatagc cggtcccccg cctgtccccg ccggcgggcc   12720
gccccccccc tccacgcgcc ccgcgcgcgc gggagggcgc gtgccccgcc gcgcgccggg   12780
```

```
accgggtcc ggtgcggagt gcccttcgtc ctgggaaacg gggcgcggcc ggagaggcgg    12840 ccgcccctc gcccgtcacg caccgcacgt tcgtggggaa cctggcgcta aaccattcgt    12900
agacgacctg cttctgggtc ggggtttcgt acgtagcaga gcagctccct cgctgcgatc    12960
tattgaaagt cagccctcga cacaagggtt tgtccgcgcg cgcgcgcgcg cgcgcgtgcg    13020 ggggcccgg cggggcgtgc gcgtccggcg ccgtccgtcc ttccgttcgt cttcctccct    13080 cccgcctct cccgccgacc gcgggcgtgg tggtgggggt gtgggggga gggcgcgcga    13140 ccccggtcgg cgcgccccgc ttcttcggtt cccgcctcct ccccgttcac cgccggggcg    13200
gctcgtccgc tccgggccgg gacgggtcc ggggagcgtg gtttgggagc gcggaggcg    13260 gccgcgccga gccgggcccg tgcccgccg gtccccgtcc cggggttgg ccgcgcgggc    13320 cccggtgggg cggccacccg ggtcccggc cctcgcg                             13357
```

<210> SEQ ID NO 38
<211> LENGTH: 651
<212> TYPE: PRT
<213> ORGANISM: Homo sapiens

<400> SEQUENCE: 38

```
Met Ala Ala Pro Leu His Thr Arg Leu Pro Gly Asp Ala Ala Ala
1               5                   10                  15

Ser Ser Ser Ala Val Lys Lys Leu Gly Ala Ser Arg Thr Gly Ile Ser
                20                  25                  30

Asn Met Arg Ala Leu Glu Asn Asp Phe Phe Asn Ser Pro Pro Arg Lys
            35                  40                  45

Thr Val Arg Phe Gly Gly Thr Val Thr Glu Val Leu Leu Lys Tyr Lys
        50                  55                  60

Lys Gly Glu Thr Asn Asp Phe Glu Leu Leu Lys Asn Gln Leu Leu Asp
65                  70                  75                  80

Pro Asp Ile Lys Asp Asp Gln Ile Ile Asn Trp Leu Leu Glu Phe Arg
                85                  90                  95

Ser Ser Ile Met Tyr Leu Thr Lys Asp Phe Glu Gln Leu Ile Ser Ile
            100                 105                 110

Ile Leu Arg Leu Pro Trp Leu Asn Arg Ser Gln Thr Val Val Glu Glu
        115                 120                 125

Tyr Leu Ala Phe Leu Gly Asn Leu Val Ser Ala Gln Thr Val Phe Leu
    130                 135                 140

Arg Pro Cys Leu Ser Met Ile Ala Ser His Phe Val Pro Pro Arg Val
145                 150                 155                 160

Ile Ile Lys Glu Gly Asp Val Asp Val Ser Asp Ser Asp Glu Asp
                165                 170                 175

Asp Asn Leu Pro Ala Asn Phe Asp Thr Cys His Arg Ala Leu Gln Ile
            180                 185                 190

Ile Ala Arg Tyr Val Pro Ser Thr Pro Trp Phe Leu Met Pro Ile Leu
        195                 200                 205

Val Glu Lys Phe Pro Phe Val Arg Lys Ser Glu Arg Thr Leu Glu Cys
    210                 215                 220

Tyr Val His Asn Leu Leu Arg Ile Ser Val Tyr Phe Pro Thr Leu Arg
225                 230                 235                 240

His Glu Ile Leu Glu Leu Ile Ile Glu Lys Leu Leu Lys Leu Asp Val
                245                 250                 255

Asn Ala Ser Arg Gln Gly Ile Glu Asp Ala Glu Glu Thr Ala Thr Gln
            260                 265                 270
```

Thr Cys Gly Gly Thr Asp Ser Thr Glu Gly Leu Phe Asn Met Asp Glu
            275                 280                 285

Asp Glu Glu Thr Glu His Glu Thr Lys Ala Gly Pro Glu Arg Leu Asp
290                 295                 300

Gln Met Val His Pro Val Ala Glu Arg Leu Asp Ile Leu Met Ser Leu
305                 310                 315                 320

Val Leu Ser Tyr Met Lys Asp Val Cys Tyr Val Asp Gly Lys Val Asp
            325                 330                 335

Asn Gly Lys Thr Lys Asp Leu Tyr Arg Asp Leu Ile Asn Ile Phe Asp
            340                 345                 350

Lys Leu Leu Pro Thr His Ala Ser Cys His Val Gln Phe Phe Met
            355                 360                 365

Phe Tyr Leu Cys Ser Phe Lys Leu Gly Phe Ala Glu Ala Phe Leu Glu
            370                 375                 380

His Leu Trp Lys Lys Leu Gln Asp Pro Ser Asn Pro Ala Ile Ile Arg
385                 390                 395                 400

Gln Ala Ala Gly Asn Tyr Ile Gly Ser Phe Leu Ala Arg Ala Lys Phe
            405                 410                 415

Ile Pro Leu Ile Thr Val Lys Ser Cys Leu Asp Leu Leu Val Asn Trp
            420                 425                 430

Leu His Ile Tyr Leu Asn Asn Gln Asp Ser Gly Thr Lys Ala Phe Cys
            435                 440                 445

Asp Val Ala Leu His Gly Pro Phe Tyr Ser Ala Cys Gln Ala Val Phe
            450                 455                 460

Tyr Thr Phe Val Phe Arg His Lys Gln Leu Leu Ser Gly Asn Leu Lys
465                 470                 475                 480

Glu Gly Leu Gln Tyr Leu Gln Ser Leu Asn Phe Glu Arg Ile Val Met
            485                 490                 495

Ser Gln Leu Asn Pro Leu Lys Ile Cys Leu Pro Ser Val Val Asn Phe
            500                 505                 510

Phe Ala Ala Ile Thr Asn Lys Tyr Gln Leu Val Phe Cys Tyr Thr Ile
            515                 520                 525

Ile Glu Arg Asn Asn Arg Gln Met Leu Pro Val Ile Arg Ser Thr Ala
            530                 535                 540

Gly Gly Asp Ser Val Gln Ile Cys Thr Asn Pro Leu Asp Thr Phe Phe
545                 550                 555                 560

Pro Phe Asp Pro Cys Val Leu Lys Arg Ser Lys Lys Phe Ile Asp Pro
            565                 570                 575

Ile Tyr Gln Val Trp Glu Asp Met Ser Ala Glu Glu Leu Gln Glu Phe
            580                 585                 590

Lys Lys Pro Met Lys Lys Asp Ile Val Glu Asp Glu Asp Asp Phe
            595                 600                 605

Leu Lys Gly Glu Val Pro Gln Asn Asp Thr Val Ile Gly Ile Thr Pro
            610                 615                 620

Ser Ser Phe Asp Thr His Phe Arg Ser Pro Ser Ser Val Gly Ser
625                 630                 635                 640

Pro Pro Val Leu Tyr Met Gln Pro Ser Pro Leu
            645                 650

<210> SEQ ID NO 39
<211> LENGTH: 1394
<212> TYPE: PRT
<213> ORGANISM: Homo sapiens

<400> SEQUENCE: 39

Met Ala Ala Leu Leu Arg Ser Ala Arg Trp Leu Leu Arg Ala Gly Ala
1               5                   10                  15

Ala Pro Arg Leu Pro Leu Ser Leu Arg Leu Leu Pro Gly Gly Pro Gly
            20                  25                  30

Arg Leu His Ala Ala Ser Tyr Leu Pro Ala Ala Arg Ala Gly Pro Val
        35                  40                  45

Ala Gly Gly Leu Leu Ser Pro Ala Arg Leu Tyr Ala Ile Ala Ala Lys
    50                  55                  60

Glu Lys Asp Ile Gln Glu Glu Ser Thr Phe Ser Ser Arg Lys Ile Ser
65              70                  75                  80

Asn Gln Phe Asp Trp Ala Leu Met Arg Leu Asp Leu Ser Val Arg Arg
                85                  90                  95

Thr Gly Arg Ile Pro Lys Lys Leu Leu Gln Lys Val Phe Asn Asp Thr
            100                 105                 110

Cys Arg Ser Gly Gly Leu Gly Gly Ser His Ala Leu Leu Leu Leu Arg
        115                 120                 125

Ser Cys Gly Ser Leu Leu Pro Glu Leu Lys Leu Glu Glu Arg Thr Glu
    130                 135                 140

Phe Ala His Arg Ile Trp Asp Thr Leu Gln Lys Leu Gly Ala Val Tyr
145                 150                 155                 160

Asp Val Ser His Tyr Asn Ala Leu Leu Lys Val Tyr Leu Gln Asn Glu
                165                 170                 175

Tyr Lys Phe Ser Pro Thr Asp Phe Leu Ala Lys Met Glu Glu Ala Asn
            180                 185                 190

Ile Gln Pro Asn Arg Val Thr Tyr Gln Arg Leu Ile Ala Ser Tyr Cys
        195                 200                 205

Asn Val Gly Asp Ile Glu Gly Ala Ser Lys Ile Leu Gly Phe Met Lys
    210                 215                 220

Thr Lys Asp Leu Pro Val Thr Glu Ala Val Phe Ser Ala Leu Val Thr
225                 230                 235                 240

Gly His Ala Arg Ala Gly Asp Met Glu Asn Ala Glu Asn Ile Leu Thr
                245                 250                 255

Val Met Arg Asp Ala Gly Ile Glu Pro Gly Pro Asp Thr Tyr Leu Ala
            260                 265                 270

Leu Leu Asn Ala Tyr Ala Glu Lys Gly Asp Ile Asp His Val Lys Gln
        275                 280                 285

Thr Leu Glu Lys Val Glu Lys Ser Glu Leu His Leu Met Asp Arg Asp
    290                 295                 300

Leu Leu Gln Ile Ile Phe Ser Phe Ser Lys Ala Gly Tyr Pro Gln Tyr
305                 310                 315                 320

Val Ser Glu Ile Leu Glu Lys Val Thr Cys Glu Arg Arg Tyr Ile Pro
                325                 330                 335

Asp Ala Met Asn Leu Ile Leu Leu Val Thr Glu Lys Leu Glu Asp
            340                 345                 350

Val Ala Leu Gln Ile Leu Leu Ala Cys Pro Val Ser Lys Glu Asp Gly
        355                 360                 365

Pro Ser Val Phe Gly Ser Phe Leu Gln His Cys Val Thr Met Asn
    370                 375                 380

Thr Pro Val Glu Lys Leu Thr Asp Tyr Cys Lys Lys Leu Lys Glu Val
385                 390                 395                 400

Gln Met His Ser Phe Pro Leu Gln Phe Thr Leu His Cys Ala Leu Leu
                405                 410                 415

```
Ala Asn Lys Thr Asp Leu Ala Lys Ala Leu Met Lys Ala Val Lys Glu
            420                 425                 430

Glu Gly Phe Pro Ile Arg Pro His Tyr Phe Trp Pro Leu Leu Val Gly
            435                 440                 445

Arg Arg Lys Glu Lys Asn Val Gln Gly Ile Ile Glu Ile Leu Lys Gly
            450                 455                 460

Met Gln Glu Leu Gly Val His Pro Asp Gln Glu Thr Tyr Thr Asp Tyr
465                 470                 475                 480

Val Ile Pro Cys Phe Asp Ser Val Asn Ser Ala Arg Ala Ile Leu Gln
                485                 490                 495

Glu Asn Gly Cys Leu Ser Asp Ser Asp Met Phe Ser Gln Ala Gly Leu
            500                 505                 510

Arg Ser Glu Ala Ala Asn Gly Asn Leu Asp Phe Val Leu Ser Phe Leu
            515                 520                 525

Lys Ser Asn Thr Leu Pro Ile Ser Leu Gln Ser Ile Arg Ser Ser Leu
530                 535                 540

Leu Leu Gly Phe Arg Arg Ser Met Asn Ile Asn Leu Trp Ser Glu Ile
545                 550                 555                 560

Thr Glu Leu Leu Tyr Lys Asp Gly Arg Tyr Cys Gln Glu Pro Arg Gly
                565                 570                 575

Pro Thr Glu Ala Val Gly Tyr Phe Leu Tyr Asn Leu Ile Asp Ser Met
            580                 585                 590

Ser Asp Ser Glu Val Gln Ala Lys Glu Glu His Leu Arg Gln Tyr Phe
            595                 600                 605

His Gln Leu Glu Lys Met Asn Val Lys Ile Pro Glu Asn Ile Tyr Arg
            610                 615                 620

Gly Ile Arg Asn Leu Leu Glu Ser Tyr His Val Pro Glu Leu Ile Lys
625                 630                 635                 640

Asp Ala His Leu Leu Val Glu Ser Lys Asn Leu Asp Phe Gln Lys Thr
                645                 650                 655

Val Gln Leu Thr Ser Ser Glu Leu Glu Ser Thr Leu Glu Thr Leu Lys
            660                 665                 670

Ala Glu Asn Gln Pro Ile Arg Asp Val Leu Lys Gln Leu Ile Leu Val
            675                 680                 685

Leu Cys Ser Glu Glu Asn Met Gln Lys Ala Leu Glu Leu Lys Ala Lys
            690                 695                 700

Tyr Glu Ser Asp Met Val Thr Gly Gly Tyr Ala Ala Leu Ile Asn Leu
705                 710                 715                 720

Cys Cys Arg His Asp Lys Val Glu Asp Ala Leu Asn Leu Lys Glu Glu
                725                 730                 735

Phe Asp Arg Leu Asp Ser Ser Ala Val Leu Asp Thr Gly Lys Tyr Val
            740                 745                 750

Gly Leu Val Arg Val Leu Ala Lys His Gly Lys Leu Gln Asp Ala Ile
            755                 760                 765

Asn Ile Leu Lys Glu Met Lys Glu Lys Asp Val Leu Ile Lys Asp Thr
            770                 775                 780

Thr Ala Leu Ser Phe Phe His Met Leu Asn Gly Ala Ala Leu Arg Gly
785                 790                 795                 800

Glu Ile Glu Thr Val Lys Gln Leu His Glu Ala Ile Val Thr Leu Gly
                805                 810                 815

Leu Ala Glu Pro Ser Thr Asn Ile Ser Phe Pro Leu Val Thr Val His
            820                 825                 830
```

-continued

Leu Glu Lys Gly Asp Leu Ser Thr Ala Leu Glu Val Ala Ile Asp Cys
835                 840                 845

Tyr Glu Lys Tyr Lys Val Leu Pro Arg Ile His Asp Val Leu Cys Lys
850                 855                 860

Leu Val Glu Lys Gly Glu Thr Asp Leu Ile Gln Lys Ala Met Asp Phe
865                 870                 875                 880

Val Ser Gln Glu Gln Gly Glu Met Val Met Leu Tyr Asp Leu Phe Phe
                885                 890                 895

Ala Phe Leu Gln Thr Gly Asn Tyr Lys Glu Ala Lys Lys Ile Ile Glu
            900                 905                 910

Thr Pro Gly Ile Arg Ala Arg Ser Ala Arg Leu Gln Trp Phe Cys Asp
            915                 920                 925

Arg Cys Val Ala Asn Asn Gln Val Glu Thr Leu Glu Lys Leu Val Glu
            930                 935                 940

Leu Thr Gln Lys Leu Phe Glu Cys Asp Arg Asp Gln Met Tyr Tyr Asn
945                 950                 955                 960

Leu Leu Lys Leu Tyr Lys Ile Asn Gly Asp Trp Gln Arg Ala Asp Ala
                965                 970                 975

Val Trp Asn Lys Ile Gln Glu Glu Asn Val Ile Pro Arg Glu Lys Thr
            980                 985                 990

Leu Arg Leu Leu Ala Glu Ile Leu Arg Glu Gly Asn Gln Glu Val Pro
            995                 1000                1005

Phe Asp Val Pro Glu Leu Trp Tyr Glu Asp Glu Lys His Ser Leu
    1010                1015                1020

Asn Ser Ser Ser Ala Ser Thr Thr Glu Pro Asp Phe Gln Lys Asp
    1025                1030                1035

Ile Leu Ile Ala Cys Arg Leu Asn Gln Lys Lys Gly Ala Tyr Asp
    1040                1045                1050

Ile Phe Leu Asn Ala Lys Glu Gln Asn Ile Val Phe Asn Ala Glu
    1055                1060                1065

Thr Tyr Ser Asn Leu Ile Lys Leu Leu Met Ser Glu Asp Tyr Phe
    1070                1075                1080

Thr Gln Ala Met Glu Val Lys Ala Phe Ala Glu Thr His Ile Lys
    1085                1090                1095

Gly Phe Thr Leu Asn Asp Ala Ala Asn Ser Arg Leu Ile Ile Thr
    1100                1105                1110

Gln Val Arg Arg Asp Tyr Leu Lys Glu Ala Val Thr Thr Leu Lys
    1115                1120                1125

Thr Val Leu Asp Gln Gln Gln Thr Pro Ser Arg Leu Ala Val Thr
    1130                1135                1140

Arg Val Ile Gln Ala Leu Ala Met Lys Gly Asp Val Glu Asn Ile
    1145                1150                1155

Glu Val Val Gln Lys Met Leu Asn Gly Leu Glu Asp Ser Ile Gly
    1160                1165                1170

Leu Ser Lys Met Val Phe Ile Asn Asn Ile Ala Leu Ala Gln Ile
    1175                1180                1185

Lys Asn Asn Asn Ile Asp Ala Ile Glu Asn Ile Glu Asn Met
    1190                1195                1200

Leu Thr Ser Glu Asn Lys Val Ile Glu Pro Gln Tyr Phe Gly Leu
    1205                1210                1215

Ala Tyr Leu Phe Arg Lys Val Ile Glu Glu Gln Leu Glu Pro Ala
    1220                1225                1230

Val Glu Lys Ile Ser Ile Met Ala Glu Arg Leu Ala Asn Gln Phe

```
                    1235                1240                1245

Ala Ile Tyr Lys Pro Val Thr Asp Phe Phe Leu Gln Leu Val Asp
            1250                1255                1260

Ala Gly Lys Val Asp Asp Ala Arg Ala Leu Leu Gln Arg Cys Gly
        1265                1270                1275

Ala Ile Ala Glu Gln Thr Pro Ile Leu Leu Leu Phe Leu Leu Arg
    1280                1285                1290

Asn Ser Arg Lys Gln Gly Lys Ala Ser Thr Val Lys Ser Val Leu
1295                1300                1305

Glu Leu Ile Pro Glu Leu Asn Glu Lys Glu Ala Tyr Asn Ser
        1310                1315                1320

Leu Met Lys Ser Tyr Val Ser Glu Lys Asp Val Thr Ser Ala Lys
    1325                1330                1335

Ala Leu Tyr Glu His Leu Thr Ala Lys Asn Thr Lys Leu Asp Asp
1340                1345                1350

Leu Phe Leu Lys Arg Tyr Ala Ser Leu Leu Lys Tyr Ala Gly Glu
        1355                1360                1365

Pro Val Pro Phe Ile Glu Pro Pro Glu Ser Phe Glu Phe Tyr Ala
    1370                1375                1380

Gln Gln Leu Arg Lys Leu Arg Glu Asn Ser Ser
1385                1390

<210> SEQ ID NO 40
<211> LENGTH: 1079
<212> TYPE: PRT
<213> ORGANISM: Homo sapiens

<400> SEQUENCE: 40

Met Asp Pro Gly Ser Arg Trp Arg Asn Leu Pro Ser Gly Pro Ser Leu
1               5                   10                  15

Lys His Leu Thr Asp Pro Ser Tyr Gly Ile Pro Arg Glu Gln Gln Lys
            20                  25                  30

Ala Ala Leu Gln Glu Leu Thr Arg Ala His Val Glu Ser Phe Asn Tyr
        35                  40                  45

Ala Val His Glu Gly Leu Gly Leu Ala Val Gln Ala Asp Ile Asn Trp
    50                  55                  60

Ala Val Asn Gly Ile Ser Lys Gly Ile Ile Lys Gln Phe Leu Gly Tyr
65                  70                  75                  80

Val Pro Ile Met Val Lys Ser Lys Leu Cys Asn Leu Arg Asn Leu Pro
                85                  90                  95

Pro Gln Ala Leu Ile Glu His His Glu Ala Glu Glu Met Gly Gly
            100                 105                 110

Tyr Phe Ile Ile Asn Gly Ile Glu Lys Val Ile Arg Met Leu Ile Met
        115                 120                 125

Pro Arg Arg Asn Phe Pro Ile Ala Met Ile Arg Pro Lys Trp Lys Thr
    130                 135                 140

Arg Gly Pro Gly Tyr Thr Gln Tyr Gly Val Ser Met His Cys Val Arg
145                 150                 155                 160

Glu Glu His Ser Ala Val Asn Met Asn Leu His Tyr Leu Glu Asn Gly
                165                 170                 175

Thr Val Met Leu Asn Phe Ile Tyr Arg Lys Glu Leu Phe Phe Leu Pro
            180                 185                 190

Leu Gly Phe Ala Leu Lys Ala Leu Val Ser Phe Ser Asp Tyr Gln Ile
        195                 200                 205
```

-continued

Phe Gln Glu Leu Ile Lys Gly Lys Glu Asp Asp Ser Phe Leu Arg Asn
210                 215                 220

Ser Val Ser Gln Met Leu Arg Ile Val Met Glu Glu Gly Cys Ser Thr
225                 230                 235                 240

Gln Lys Gln Val Leu Asn Tyr Leu Gly Glu Cys Phe Arg Val Lys Leu
            245                 250                 255

Asn Val Pro Asp Trp Tyr Pro Asn Glu Gln Ala Ala Glu Phe Leu Phe
            260                 265                 270

Asn Gln Cys Ile Cys Ile His Leu Lys Ser Asn Thr Glu Lys Phe Tyr
            275                 280                 285

Met Leu Cys Leu Met Thr Arg Lys Leu Phe Ala Leu Ala Lys Gly Glu
290                 295                 300

Cys Met Glu Asp Asn Pro Asp Ser Leu Val Asn Gln Glu Val Leu Thr
305                 310                 315                 320

Pro Gly Gln Leu Phe Leu Met Phe Leu Lys Glu Lys Leu Glu Gly Trp
            325                 330                 335

Leu Val Ser Ile Lys Ile Ala Phe Asp Lys Lys Ala Gln Lys Thr Ser
            340                 345                 350

Val Ser Met Asn Thr Asp Asn Leu Met Arg Ile Phe Thr Met Gly Ile
            355                 360                 365

Asp Leu Thr Lys Pro Phe Glu Tyr Leu Phe Ala Thr Gly Asn Leu Arg
370                 375                 380

Ser Lys Thr Gly Leu Gly Leu Leu Gln Asp Ser Gly Leu Cys Val Val
385                 390                 395                 400

Ala Asp Lys Leu Asn Phe Ile Arg Tyr Leu Ser His Phe Arg Cys Val
            405                 410                 415

His Arg Gly Ala Asp Phe Ala Lys Met Arg Thr Thr Val Arg Arg
            420                 425                 430

Leu Leu Pro Glu Ser Trp Gly Phe Leu Cys Pro Val His Thr Pro Asp
            435                 440                 445

Gly Glu Pro Cys Gly Leu Met Asn His Leu Thr Ala Val Cys Glu Val
            450                 455                 460

Val Thr Gln Phe Val Tyr Thr Ala Ser Ile Pro Ala Leu Leu Cys Asn
465                 470                 475                 480

Leu Gly Val Thr Pro Ile Asp Gly Ala Pro His Arg Ser Tyr Ser Glu
            485                 490                 495

Cys Tyr Pro Val Leu Leu Asp Gly Val Met Val Gly Trp Val Asp Lys
            500                 505                 510

Asp Leu Ala Pro Gly Ile Ala Asp Ser Leu Arg His Phe Lys Val Leu
            515                 520                 525

Arg Glu Lys Arg Ile Pro Pro Trp Met Glu Val Val Leu Ile Pro Met
530                 535                 540

Thr Gly Lys Pro Ser Leu Tyr Pro Gly Leu Phe Leu Phe Thr Thr Pro
545                 550                 555                 560

Cys Arg Leu Val Arg Pro Val Gln Asn Leu Ala Leu Gly Lys Glu Glu
            565                 570                 575

Leu Ile Gly Thr Met Glu Gln Ile Phe Met Asn Val Ala Ile Phe Glu
            580                 585                 590

Asp Glu Val Phe Ala Gly Val Thr Thr His Gln Glu Leu Phe Pro His
            595                 600                 605

Ser Leu Leu Ser Val Ile Ala Asn Phe Ile Pro Phe Ser Asp His Asn
610                 615                 620

Gln Ser Pro Arg Asn Met Tyr Gln Cys Gln Met Gly Lys Gln Thr Met

-continued

```
            625                 630                 635                 640
        Gly Phe Pro Leu Leu Thr Tyr Gln Asp Arg Ser Asp Asn Lys Leu Tyr
                        645                 650                 655

Arg Leu Gln Thr Pro Gln Ser Pro Leu Val Arg Pro Ser Met Tyr Asp
                        660                 665                 670

Tyr Tyr Asp Met Asp Asn Tyr Pro Ile Gly Thr Asn Ala Ile Val Ala
                        675                 680                 685

Val Ile Ser Tyr Thr Gly Tyr Asp Met Glu Asp Ala Met Ile Val Asn
                        690                 695                 700

Lys Ala Ser Trp Glu Arg Gly Phe Ala His Gly Ser Val Tyr Lys Ser
        705                 710                 715                 720

Glu Phe Ile Asp Leu Ser Glu Lys Ile Lys Gln Gly Asp Ser Ser Leu
                        725                 730                 735

Val Phe Gly Ile Lys Pro Gly Asp Pro Arg Val Leu Gln Lys Leu Asp
                        740                 745                 750

Asp Asp Gly Leu Pro Phe Ile Gly Ala Lys Leu Gln Tyr Gly Asp Pro
                        755                 760                 765

Tyr Tyr Ser Tyr Leu Asn Leu Asn Thr Gly Glu Ser Phe Val Met Tyr
                        770                 775                 780

Tyr Lys Ser Lys Glu Asn Cys Val Val Asp Asn Ile Lys Val Cys Ser
        785                 790                 795                 800

Asn Asp Thr Gly Ser Gly Lys Phe Lys Cys Val Cys Ile Thr Met Arg
                        805                 810                 815

Val Pro Arg Asn Pro Thr Ile Gly Asp Lys Phe Ala Ser Arg His Gly
                        820                 825                 830

Gln Lys Gly Ile Leu Ser Arg Leu Trp Pro Ala Glu Asp Met Pro Phe
                        835                 840                 845

Thr Glu Ser Gly Met Val Pro Asp Ile Leu Phe Asn Pro His Gly Phe
                        850                 855                 860

Pro Ser Arg Met Thr Ile Gly Met Leu Ile Glu Ser Met Ala Gly Lys
        865                 870                 875                 880

Ser Ala Ala Leu His Gly Leu Cys His Asp Ala Thr Pro Phe Ile Phe
                        885                 890                 895

Ser Glu Glu Asn Ser Ala Leu Glu Tyr Phe Gly Glu Met Leu Lys Ala
                        900                 905                 910

Ala Gly Tyr Asn Phe Tyr Gly Thr Glu Arg Leu Tyr Ser Gly Ile Ser
                        915                 920                 925

Gly Leu Glu Leu Glu Ala Asp Ile Phe Ile Gly Val Val Tyr Tyr Gln
                        930                 935                 940

Arg Leu Arg His Met Val Ser Asp Lys Phe Gln Val Arg Thr Thr Gly
        945                 950                 955                 960

Ala Arg Asp Arg Val Thr Asn Gln Pro Ile Gly Arg Asn Val Gln
                        965                 970                 975

Gly Gly Ile Arg Phe Gly Glu Met Glu Arg Asp Ala Leu Leu Ala His
                        980                 985                 990

Gly Thr Ser Phe Leu Leu His Asp Arg Leu Phe Asn Cys Ser Asp Arg
                        995                 1000                1005

Ser Val Ala His Val Cys Val Lys Cys Gly Ser Leu Leu Ser Pro
                    1010                1015                1020

Leu Leu Glu Lys Pro Pro Pro Ser Trp Ser Ala Met Arg Asn Arg
                    1025                1030                1035

Lys Tyr Asn Cys Thr Leu Cys Ser Arg Ser Asp Thr Ile Asp Thr
                    1040                1045                1050
```

```
Val Ser Val Pro Tyr Val Phe Arg Tyr Phe Val Ala Glu Leu Ala
    1055                1060                1065

Ala Met Asn Ile Lys Val Lys Leu Asp Val Val
    1070                1075
```

<210> SEQ ID NO 41
<211> LENGTH: 1135
<212> TYPE: PRT
<213> ORGANISM: Homo sapiens

<400> SEQUENCE: 41

```
Met Asp Pro Gly Ser Arg Trp Arg Asn Leu Pro Ser Gly Pro Ser Leu
1               5                   10                  15

Lys His Leu Thr Asp Pro Ser Tyr Gly Ile Pro Arg Glu Gln Gln Lys
                20                  25                  30

Ala Ala Leu Gln Glu Leu Thr Arg Ala His Val Glu Ser Phe Asn Tyr
            35                  40                  45

Ala Val His Glu Gly Leu Gly Leu Ala Val Gln Ala Ile Pro Pro Phe
        50                  55                  60

Glu Phe Ala Phe Lys Asp Glu Arg Ile Ser Phe Thr Ile Leu Asp Ala
65                  70                  75                  80

Val Ile Ser Pro Pro Thr Val Pro Lys Gly Thr Ile Cys Lys Glu Ala
                85                  90                  95

Asn Val Tyr Pro Ala Glu Cys Arg Gly Arg Arg Ser Thr Tyr Arg Gly
            100                 105                 110

Lys Leu Thr Ala Asp Ile Asn Trp Ala Val Asn Gly Ile Ser Lys Gly
        115                 120                 125

Ile Ile Lys Gln Phe Leu Gly Tyr Val Pro Ile Met Val Lys Ser Lys
130                 135                 140

Leu Cys Asn Leu Arg Asn Leu Pro Pro Gln Ala Leu Ile Glu His His
145                 150                 155                 160

Glu Glu Ala Glu Glu Met Gly Gly Tyr Phe Ile Ile Asn Gly Ile Glu
                165                 170                 175

Lys Val Ile Arg Met Leu Ile Met Pro Arg Arg Asn Phe Pro Ile Ala
            180                 185                 190

Met Ile Arg Pro Lys Trp Lys Thr Arg Gly Pro Gly Tyr Thr Gln Tyr
        195                 200                 205

Gly Val Ser Met His Cys Val Arg Glu Glu His Ser Ala Val Asn Met
    210                 215                 220

Asn Leu His Tyr Leu Glu Asn Gly Thr Val Met Leu Asn Phe Ile Tyr
225                 230                 235                 240

Arg Lys Glu Leu Phe Phe Leu Pro Leu Gly Phe Ala Leu Lys Ala Leu
                245                 250                 255

Val Ser Phe Ser Asp Tyr Gln Ile Phe Gln Glu Leu Ile Lys Gly Lys
            260                 265                 270

Glu Asp Asp Ser Phe Leu Arg Asn Ser Val Ser Gln Met Leu Arg Ile
        275                 280                 285

Val Met Glu Glu Gly Cys Ser Thr Gln Lys Gln Val Leu Asn Tyr Leu
    290                 295                 300

Gly Glu Cys Phe Arg Val Lys Leu Asn Val Pro Asp Trp Tyr Pro Asn
305                 310                 315                 320

Glu Gln Ala Ala Glu Phe Leu Phe Asn Gln Cys Ile Cys Ile His Leu
                325                 330                 335

Lys Ser Asn Thr Glu Lys Phe Tyr Met Leu Cys Leu Met Thr Arg Lys
```

```
              340                 345                 350
Leu Phe Ala Leu Ala Lys Gly Glu Cys Met Glu Asp Asn Pro Asp Ser
            355                 360                 365

Leu Val Asn Gln Glu Val Leu Thr Pro Gly Gln Leu Phe Leu Met Phe
        370                 375                 380

Leu Lys Glu Lys Leu Glu Gly Trp Leu Val Ser Ile Lys Ile Ala Phe
385                 390                 395                 400

Asp Lys Lys Ala Gln Lys Thr Ser Val Ser Met Asn Thr Asp Asn Leu
                405                 410                 415

Met Arg Ile Phe Thr Met Gly Ile Asp Leu Thr Lys Pro Phe Glu Tyr
            420                 425                 430

Leu Phe Ala Thr Gly Asn Leu Arg Ser Lys Thr Gly Leu Gly Leu Leu
        435                 440                 445

Gln Asp Ser Gly Leu Cys Val Val Ala Asp Lys Leu Asn Phe Ile Arg
    450                 455                 460

Tyr Leu Ser His Phe Arg Cys Val His Arg Gly Ala Asp Phe Ala Lys
465                 470                 475                 480

Met Arg Thr Thr Thr Val Arg Arg Leu Leu Pro Glu Ser Trp Gly Phe
                485                 490                 495

Leu Cys Pro Val His Thr Pro Asp Gly Glu Pro Cys Gly Leu Met Asn
            500                 505                 510

His Leu Thr Ala Val Cys Glu Val Val Thr Gln Phe Val Tyr Thr Ala
        515                 520                 525

Ser Ile Pro Ala Leu Leu Cys Asn Leu Gly Val Thr Pro Ile Asp Gly
    530                 535                 540

Ala Pro His Arg Ser Tyr Ser Glu Cys Tyr Pro Val Leu Leu Asp Gly
545                 550                 555                 560

Val Met Val Gly Trp Val Asp Lys Asp Leu Ala Pro Gly Ile Ala Asp
                565                 570                 575

Ser Leu Arg His Phe Lys Val Leu Arg Glu Lys Arg Ile Pro Pro Trp
            580                 585                 590

Met Glu Val Val Leu Ile Pro Met Thr Gly Lys Pro Ser Leu Tyr Pro
        595                 600                 605

Gly Leu Phe Leu Phe Thr Thr Pro Cys Arg Leu Val Arg Pro Val Gln
    610                 615                 620

Asn Leu Ala Leu Gly Lys Glu Glu Leu Ile Gly Thr Met Glu Gln Ile
625                 630                 635                 640

Phe Met Asn Val Ala Ile Phe Glu Asp Glu Val Phe Ala Gly Val Thr
                645                 650                 655

Thr His Gln Glu Leu Phe Pro His Ser Leu Leu Ser Val Ile Ala Asn
            660                 665                 670

Phe Ile Pro Phe Ser Asp His Asn Gln Ser Pro Arg Asn Met Tyr Gln
        675                 680                 685

Cys Gln Met Gly Lys Gln Thr Met Gly Phe Pro Leu Leu Thr Tyr Gln
    690                 695                 700

Asp Arg Ser Asp Asn Lys Leu Tyr Arg Leu Gln Thr Pro Gln Ser Pro
705                 710                 715                 720

Leu Val Arg Pro Ser Met Tyr Asp Tyr Tyr Asp Met Asp Asn Tyr Pro
                725                 730                 735

Ile Gly Thr Asn Ala Ile Val Ala Val Ile Ser Tyr Thr Gly Tyr Asp
            740                 745                 750

Met Glu Asp Ala Met Ile Val Asn Lys Ala Ser Trp Glu Arg Gly Phe
        755                 760                 765
```

Ala His Gly Ser Val Tyr Lys Ser Glu Phe Ile Asp Leu Ser Glu Lys
        770                 775                 780

Ile Lys Gln Gly Asp Ser Ser Leu Val Phe Gly Ile Lys Pro Gly Asp
785                 790                 795                 800

Pro Arg Val Leu Gln Lys Leu Asp Asp Gly Leu Pro Phe Ile Gly
                805                 810                 815

Ala Lys Leu Gln Tyr Gly Asp Pro Tyr Tyr Ser Tyr Leu Asn Leu Asn
            820                 825                 830

Thr Gly Glu Ser Phe Val Met Tyr Tyr Lys Ser Lys Glu Asn Cys Val
        835                 840                 845

Val Asp Asn Ile Lys Val Cys Ser Asn Asp Thr Gly Ser Gly Lys Phe
850                 855                 860

Lys Cys Val Cys Ile Thr Met Arg Val Pro Arg Asn Pro Thr Ile Gly
865                 870                 875                 880

Asp Lys Phe Ala Ser Arg His Gly Gln Lys Gly Ile Leu Ser Arg Leu
                885                 890                 895

Trp Pro Ala Glu Asp Met Pro Phe Thr Glu Ser Gly Met Val Pro Asp
            900                 905                 910

Ile Leu Phe Asn Pro His Gly Phe Pro Ser Arg Met Thr Ile Gly Met
        915                 920                 925

Leu Ile Glu Ser Met Ala Gly Lys Ser Ala Ala Leu His Gly Leu Cys
930                 935                 940

His Asp Ala Thr Pro Phe Ile Phe Ser Glu Glu Asn Ser Ala Leu Glu
945                 950                 955                 960

Tyr Phe Gly Glu Met Leu Lys Ala Ala Gly Tyr Asn Phe Tyr Gly Thr
                965                 970                 975

Glu Arg Leu Tyr Ser Gly Ile Ser Gly Leu Glu Leu Glu Ala Asp Ile
            980                 985                 990

Phe Ile Gly Val Val Tyr Tyr Gln Arg Leu Arg His Met Val Ser Asp
        995                 1000                1005

Lys Phe Gln Val Arg Thr Thr Gly Ala Arg Asp Arg Val Thr Asn
    1010                1015                1020

Gln Pro Ile Gly Gly Arg Asn Val Gln Gly Gly Ile Arg Phe Gly
    1025                1030                1035

Glu Met Glu Arg Asp Ala Leu Leu Ala His Gly Thr Ser Phe Leu
    1040                1045                1050

Leu His Asp Arg Leu Phe Asn Cys Ser Asp Arg Ser Val Ala His
    1055                1060                1065

Val Cys Val Lys Cys Gly Ser Leu Leu Ser Pro Leu Leu Glu Lys
    1070                1075                1080

Pro Pro Pro Ser Trp Ser Ala Met Arg Asn Arg Lys Tyr Asn Cys
    1085                1090                1095

Thr Leu Cys Ser Arg Ser Asp Thr Ile Asp Thr Val Ser Val Pro
    1100                1105                1110

Tyr Val Phe Arg Tyr Phe Val Ala Glu Leu Ala Ala Met Asn Ile
    1115                1120                1125

Lys Val Lys Leu Asp Val Val
    1130                1135

<210> SEQ ID NO 42
<211> LENGTH: 346
<212> TYPE: PRT
<213> ORGANISM: Homo sapiens

<400> SEQUENCE: 42

Met Ala Ala Ser Gln Ala Val Glu Glu Met Arg Ser Arg Val Val Leu
1               5                   10                  15

Gly Glu Phe Gly Val Arg Asn Val His Thr Thr Asp Phe Pro Gly Asn
            20                  25                  30

Tyr Ser Gly Tyr Asp Asp Ala Trp Asp Gln Asp Arg Phe Glu Lys Asn
        35                  40                  45

Phe Arg Val Asp Val Val His Met Asp Glu Asn Ser Leu Glu Phe Asp
    50                  55                  60

Met Val Gly Ile Asp Ala Ala Ile Ala Asn Ala Phe Arg Arg Ile Leu
65                  70                  75                  80

Leu Ala Glu Val Pro Thr Met Ala Val Glu Lys Val Leu Val Tyr Asn
                85                  90                  95

Asn Thr Ser Ile Val Gln Asp Glu Ile Leu Ala His Arg Leu Gly Leu
            100                 105                 110

Ile Pro Ile His Ala Asp Pro Arg Leu Phe Glu Tyr Arg Asn Gln Gly
        115                 120                 125

Asp Glu Glu Gly Thr Glu Ile Asp Thr Leu Gln Phe Arg Leu Gln Val
    130                 135                 140

Arg Cys Thr Arg Asn Pro His Ala Ala Lys Asp Ser Ser Asp Pro Asn
145                 150                 155                 160

Glu Leu Tyr Val Asn His Lys Val Tyr Thr Arg His Met Thr Trp Ile
                165                 170                 175

Pro Leu Gly Asn Gln Ala Asp Leu Phe Pro Glu Gly Thr Ile Arg Pro
            180                 185                 190

Val His Asp Asp Ile Leu Ile Ala Gln Leu Arg Pro Gly Gln Glu Ile
        195                 200                 205

Asp Leu Leu Met His Cys Val Lys Gly Ile Gly Lys Asp His Ala Lys
    210                 215                 220

Phe Ser Pro Val Ala Thr Ala Ser Tyr Arg Leu Leu Pro Asp Ile Thr
225                 230                 235                 240

Leu Leu Glu Pro Val Glu Gly Glu Ala Ala Glu Glu Leu Ser Arg Cys
                245                 250                 255

Phe Ser Pro Gly Val Ile Glu Val Gln Glu Val Gln Gly Lys Lys Val
            260                 265                 270

Ala Arg Val Ala Asn Pro Arg Leu Asp Thr Phe Ser Arg Glu Ile Phe
        275                 280                 285

Arg Asn Glu Lys Leu Lys Lys Val Val Arg Leu Ala Arg Val Arg Asp
    290                 295                 300

His Tyr Ile Phe Ser Val Glu Ser Thr Gly Val Leu Pro Pro Asp Val
305                 310                 315                 320

Leu Val Ser Glu Ala Ile Lys Val Leu Met Gly Lys Cys Arg Arg Phe
                325                 330                 335

Leu Asp Glu Leu Asp Ala Val Gln Met Asp
            340                 345

<210> SEQ ID NO 43
<211> LENGTH: 133
<212> TYPE: PRT
<213> ORGANISM: Homo sapiens

<400> SEQUENCE: 43

Met Glu Glu Asp Gln Glu Leu Glu Arg Lys Ile Ser Gly Leu Lys Thr
1               5                   10                  15

Ser Met Ala Glu Gly Glu Arg Lys Thr Ala Leu Glu Met Val Gln Ala
          20                  25                  30

Ala Gly Thr Asp Arg His Cys Val Thr Phe Val Leu His Glu Glu Asp
              35                  40                  45

His Thr Leu Gly Asn Ser Leu Arg Tyr Met Ile Met Lys Asn Pro Glu
 50                  55                  60

Val Glu Phe Cys Gly Tyr Thr Thr Thr His Pro Ser Glu Ser Lys Ile
 65                  70                  75                  80

Asn Leu Arg Ile Gln Thr Arg Gly Thr Leu Pro Ala Val Glu Pro Phe
                 85                  90                  95

Gln Arg Gly Leu Asn Glu Leu Met Asn Val Cys Gln His Val Leu Asp
            100                 105                 110

Lys Phe Glu Ala Ser Ile Lys Asp Tyr Lys Asp Gln Lys Ala Ser Arg
        115                 120                 125

Asn Glu Ser Thr Phe
        130

<210> SEQ ID NO 44
<211> LENGTH: 122
<212> TYPE: PRT
<213> ORGANISM: Homo sapiens

<400> SEQUENCE: 44

Met Glu Glu Asp Gln Glu Leu Glu Arg Lys Ala Ile Glu Glu Leu Leu
 1               5                  10                  15

Lys Glu Ala Lys Arg Gly Lys Thr Arg Ala Glu Thr Met Gly Pro Met
            20                  25                  30

Gly Trp Met Lys Cys Pro Leu Ala Ser Thr Asn Lys Arg Phe Leu Ile
        35                  40                  45

Asn Thr Ile Lys Asn Thr Leu Pro Ser His Lys Glu Gln Asp His Glu
 50                  55                  60

Gln Lys Glu Gly Asp Lys Glu Pro Ala Lys Ser Gln Ala Gln Lys Glu
 65                  70                  75                  80

Glu Asn Pro Lys Lys His Arg Ser His Pro Tyr Lys His Ser Phe Arg
                 85                  90                  95

Ala Arg Gly Ser Ala Ser Tyr Ser Pro Pro Arg Lys Arg Ser Ser Gln
            100                 105                 110

Asp Lys Tyr Glu Lys Arg Ser Asn Arg Arg
        115                 120

<210> SEQ ID NO 45
<211> LENGTH: 710
<212> TYPE: PRT
<213> ORGANISM: Homo sapiens

<400> SEQUENCE: 45

Met Val Lys Leu Ala Lys Ala Gly Lys Asn Gln Gly Asp Pro Lys Lys
 1               5                  10                  15

Met Ala Pro Pro Lys Glu Val Glu Asp Ser Glu Asp Glu Glu
            20                  25                  30

Met Ser Glu Asp Glu Asp Asp Ser Ser Gly Glu Glu Val Val Ile
        35                  40                  45

Pro Gln Lys Lys Gly Lys Lys Ala Ala Thr Ser Ala Lys Lys Val
     50                  55                  60

Val Val Ser Pro Thr Lys Lys Val Ala Val Ala Thr Pro Ala Lys Lys
 65                  70                  75                  80

```
Ala Ala Val Thr Pro Gly Lys Lys Ala Ala Thr Pro Ala Lys Lys
            85                  90                  95

Thr Val Thr Pro Ala Lys Ala Val Thr Thr Pro Gly Lys Lys Gly Ala
        100                 105                 110

Thr Pro Gly Lys Ala Leu Val Ala Thr Pro Gly Lys Lys Gly Ala Ala
        115                 120                 125

Ile Pro Ala Lys Gly Ala Lys Asn Gly Lys Asn Ala Lys Lys Glu Asp
        130                 135                 140

Ser Asp Glu Glu Glu Asp Asp Ser Glu Asp Glu Glu Asp Asp
145                 150                 155                 160

Glu Asp Glu Asp Glu Asp Glu Asp Ile Glu Pro Ala Ala Met Lys
            165                 170                 175

Ala Ala Ala Ala Ala Pro Ala Ser Glu Asp Glu Asp Asp Glu Asp Asp
            180                 185                 190

Glu Asp Asp Glu Asp Asp Asp Asp Glu Glu Asp Asp Ser Glu Glu
            195                 200                 205

Glu Ala Met Glu Thr Thr Pro Ala Lys Gly Lys Lys Ala Ala Lys Val
            210                 215                 220

Val Pro Val Lys Ala Lys Asn Val Ala Glu Asp Glu Asp Glu Glu
225                 230                 235                 240

Asp Asp Glu Asp Glu Asp Asp Asp Glu Asp Asp Glu Asp Asp
            245                 250                 255

Asp Asp Glu Asp Asp Glu Glu Glu Glu Glu Glu Glu Glu Glu Pro
            260                 265                 270

Val Lys Glu Ala Pro Gly Lys Arg Lys Lys Glu Met Ala Lys Gln Lys
            275                 280                 285

Ala Ala Pro Glu Ala Lys Lys Gln Lys Val Glu Gly Thr Glu Pro Thr
            290                 295                 300

Thr Ala Phe Asn Leu Phe Val Gly Asn Leu Asn Phe Asn Lys Ser Ala
305                 310                 315                 320

Pro Glu Leu Lys Thr Gly Ile Ser Asp Val Phe Ala Lys Asn Asp Leu
                325                 330                 335

Ala Val Val Asp Val Arg Ile Gly Met Thr Arg Lys Phe Gly Tyr Val
                340                 345                 350

Asp Phe Glu Ser Ala Glu Asp Leu Glu Lys Ala Leu Glu Leu Thr Gly
            355                 360                 365

Leu Lys Val Phe Gly Asn Glu Ile Lys Leu Glu Lys Pro Lys Gly Lys
        370                 375                 380

Asp Ser Lys Lys Glu Arg Asp Ala Arg Thr Leu Leu Ala Lys Asn Leu
385                 390                 395                 400

Pro Tyr Lys Val Thr Gln Asp Glu Leu Lys Glu Val Phe Glu Asp Ala
        405                 410                 415

Ala Glu Ile Arg Leu Val Ser Lys Asp Gly Lys Ser Lys Gly Ile Ala
            420                 425                 430

Tyr Ile Glu Phe Lys Thr Glu Ala Asp Ala Glu Lys Thr Phe Glu Glu
            435                 440                 445

Lys Gln Gly Thr Glu Ile Asp Gly Arg Ser Ile Ser Leu Tyr Tyr Thr
        450                 455                 460

Gly Glu Lys Gly Gln Asn Gln Asp Tyr Arg Gly Gly Lys Asn Ser Thr
465                 470                 475                 480

Trp Ser Gly Glu Ser Lys Thr Leu Val Leu Ser Asn Leu Ser Tyr Ser
                485                 490                 495

Ala Thr Glu Glu Thr Leu Gln Glu Val Phe Glu Lys Ala Thr Phe Ile
```

```
                500                 505                 510
Lys Val Pro Gln Asn Gln Asn Gly Lys Ser Lys Gly Tyr Ala Phe Ile
            515                 520                 525

Glu Phe Ala Ser Phe Glu Asp Ala Lys Glu Ala Leu Asn Ser Cys Asn
        530                 535                 540

Lys Arg Glu Ile Glu Gly Arg Ala Ile Arg Leu Glu Leu Gln Gly Pro
545                 550                 555                 560

Arg Gly Ser Pro Asn Ala Arg Ser Gln Pro Ser Lys Thr Leu Phe Val
                565                 570                 575

Lys Gly Leu Ser Glu Asp Thr Thr Glu Glu Thr Leu Lys Glu Ser Phe
            580                 585                 590

Asp Gly Ser Val Arg Ala Arg Ile Val Thr Asp Arg Glu Thr Gly Ser
        595                 600                 605

Ser Lys Gly Phe Gly Phe Val Asp Phe Asn Ser Glu Glu Asp Ala Lys
            610                 615                 620

Ala Ala Lys Glu Ala Met Glu Asp Gly Glu Ile Asp Gly Asn Lys Val
625                 630                 635                 640

Thr Leu Asp Trp Ala Lys Pro Lys Gly Glu Gly Gly Phe Gly Gly Arg
                645                 650                 655

Gly Gly Gly Arg Gly Gly Phe Gly Gly Arg Gly Gly Arg Gly Arg Gly
            660                 665                 670

Arg Gly Gly Phe Gly Gly Arg Gly Arg Gly Phe Gly Gly Arg Gly
        675                 680                 685

Gly Phe Arg Gly Gly Arg Gly Gly Gly Asp His Lys Pro Gln Gly
            690                 695                 700

Lys Lys Thr Lys Phe Glu
705                 710

<210> SEQ ID NO 46
<211> LENGTH: 6637
<212> TYPE: PRT
<213> ORGANISM: Homo sapiens

<400> SEQUENCE: 46

Ala Thr Thr Gly Gly Cys Thr Gly Ala Ala Gly Cys Gly Gly Ala Ala
1               5                   10                  15

Gly Ala Ala Gly Ala Cys Gly Ala Ala Ala Gly Cys Ala Ala Thr Cys
            20                  25                  30

Ala Thr Ala Ala Ala Thr Gly Gly Gly Ala Gly Gly Thr Thr Gly
        35                  40                  45

Cys Ala Ala Gly Cys Thr Cys Ala Thr Gly Gly Thr Thr Gly Ala
            50                  55                  60

Ala Ala Gly Ala Cys Thr Thr Cys Gly Thr Cys Ala Cys Gly Gly Ala
65                  70                  75                  80

Ala Gly Cys Thr Ala Ala Ala Gly Cys Thr Cys Ala Thr Ala
        85                  90                  95

Cys Ala Cys Cys Cys Gly Ala Thr Thr Thr Gly Cys Cys Thr Cys Gly
            100                 105                 110

Gly Ala Gly Gly Ala Ala Thr Thr Thr Thr Cys Cys Thr Ala Ala Ala
            115                 120                 125

Thr Gly Ala Thr Thr Ala Thr Thr Thr Thr Gly Ala Thr Gly Thr Cys
        130                 135                 140

Thr Thr Ala Thr Ala Thr Ala Cys Thr Thr Thr Gly Ala Thr Thr
145                 150                 155                 160
```

-continued

```
Gly Thr Thr Thr Thr Cys Ala Ala Ala Ala Cys Ala Ala Ala Ala Gly
                165                 170                 175

Ala Gly Cys Gly Ala Gly Cys Ala Gly Ala Gly Ala Gly Thr Cys Gly
            180                 185                 190

Thr Ala Cys Ala Ala Cys Thr Ala Thr Thr Thr Gly Thr Thr Cys Cys
        195                 200                 205

Cys Cys Cys Cys Cys Cys Ala Thr Gly Thr Ala Gly Ala Ala Gly Thr
    210                 215                 220

Gly Ala Thr Cys Thr Cys Ala Thr Cys Cys Ala Cys Gly Thr Ala Ala
225                 230                 235                 240

Ala Thr Gly Thr Cys Gly Thr Thr Cys Cys Thr Gly Cys Gly Ala Cys
                245                 250                 255

Cys Gly Cys Thr Thr Cys Cys Gly Cys Gly Cys Gly Cys Ala Ala Gly
            260                 265                 270

Cys Gly Cys Ala Cys Gly Thr Thr Gly Ala Ala Thr Cys Gly Cys Gly
        275                 280                 285

Thr Gly Gly Thr Gly Ala Cys Thr Cys Cys Gly Gly Gly Cys Thr Thr
    290                 295                 300

Gly Ala Gly Gly Thr Thr Gly Ala Ala Thr Thr Ala Ala Gly Ala Ala
305                 310                 315                 320

Thr Ala Gly Thr Cys Ala Gly Gly Thr Gly Gly Thr Gly Ala Gly Thr
                325                 330                 335

Gly Gly Ala Ala Cys Gly Thr Cys Thr Cys Thr Thr Gly Gly Gly Gly
            340                 345                 350

Thr Gly Thr Cys Gly Gly Ala Ala Thr Thr Cys Ala Ala Ala Ala Cys
        355                 360                 365

Gly Gly Ala Cys Cys Thr Gly Gly Ala Gly Gly Ala Thr Gly Thr Thr
    370                 375                 380

Gly Ala Thr Cys Thr Cys Cys Ala Ala Gly Ala Ala Cys Ala Thr Gly
385                 390                 395                 400

Cys Cys Cys Thr Gly Gly Cys Gly Gly Cys Gly Gly Cys Thr Gly Cys
                405                 410                 415

Ala Gly Gly Gly Cys Ala Thr Thr Thr Cys Cys Thr Thr Cys Gly Gly
            420                 425                 430

Gly Ala Thr Gly Thr Ala Thr Thr Cys Gly Gly Cys Thr Gly Ala Ala
        435                 440                 445

Gly Ala Gly Cys Thr Cys Ala Ala Gly Ala Ala Ala Thr Thr Ala Ala
    450                 455                 460

Gly Thr Gly Thr Thr Ala Ala Ala Thr Cys Cys Ala Thr Thr Ala Cys
465                 470                 475                 480

Gly Ala Ala Cys Cys Cys Thr Cys Gly Ala Thr Ala Cys Cys Thr Gly
                485                 490                 495

Gly Ala Cys Ala Gly Cys Cys Thr Gly Gly Gly Ala Ala Cys Cys
            500                 505                 510

Cys Ala Thr Cys Gly Gly Cys Ala Ala Ala Cys Gly Gly Cys Cys Thr
        515                 520                 525

Gly Thr Ala Cys Gly Ala Thr Thr Thr Ala Gly Cys Thr Thr Thr Gly
    530                 535                 540

Gly Gly Cys Cys Cys Thr Gly Cys Ala Gly Ala Thr Thr Cys Cys Ala
545                 550                 555                 560

Ala Ala Gly Ala Gly Gly Thr Gly Thr Gly Cys Thr Cys Cys Ala Cys
                565                 570                 575

Cys Thr Gly Cys Gly Thr Gly Cys Ala Gly Gly Ala Cys Thr Thr Cys
```

```
                580             585             590
Ala Gly Cys Ala Ala Cys Thr Gly Thr Thr Cys Thr Gly Gly Cys
            595             600             605
Ala Cys Cys Thr Gly Gly Cys Cys Ala Cys Ala Thr Gly Ala
    610             615             620
Gly Cys Thr Cys Cys Ala Cys Thr Cys Ala Cys Ala Gly Thr Gly
625             630             635             640
Thr Ala Thr Ala Ala Cys Cys Thr Cys Thr Cys Cys Thr Cys Thr
                645             650             655
Thr Cys Gly Ala Thr Ala Ala Gly Cys Thr Gly Thr Ala Cys Cys Thr
            660             665             670
Gly Cys Thr Gly Cys Thr Thr Cys Gly Gly Gly Cys Thr Cys Thr
    675             680             685
Thr Gly Thr Thr Thr Ala Ala Ala Cys Thr Gly Cys Cys Ala Cys Ala
            690             695             700
Thr Gly Cys Thr Gly Ala Cys Thr Thr Gly Thr Cys Cys Cys Gly
705             710             715             720
Gly Gly Cys Cys Gly Thr Gly Ala Thr Thr Cys Ala Cys Cys Thr Cys
                725             730             735
Thr Thr Ala Cys Thr Cys Thr Gly Cys Cys Ala Gly Cys Thr Gly Ala
            740             745             750
Gly Gly Gly Thr Thr Cys Thr Gly Gly Ala Ala Gly Thr Cys Gly Gly
            755             760             765
Gly Gly Cys Cys Thr Ala Cys Ala Ala Gly Cys Ala Gly Thr Cys
    770             775             780
Thr Ala Cys Gly Ala Gly Cys Thr Gly Ala Gly Ala Gly Ala Ala
785             790             795             800
Thr Thr Cys Thr Gly Ala Ala Cys Ala Gly Gly Thr Thr Thr Cys Thr
            805             810             815
Gly Gly Ala Ala Gly Ala Ala Ala Ala Thr Cys Cys Cys Gly Ala Thr
            820             825             830
Cys Cys Cys Thr Cys Thr Gly Cys Cys Thr Cys Thr Gly Ala Ala Ala
            835             840             845
Thr Thr Cys Gly Gly Gly Ala Gly Gly Ala Ala Thr Thr Ala Gly Ala
    850             855             860
Ala Cys Ala Ala Thr Ala Cys Ala Cys Ala Ala Cys Thr Gly Ala Ala
865             870             875             880
Ala Thr Thr Gly Thr Gly Cys Ala Gly Ala Ala Cys Ala Ala Cys Cys
            885             890             895
Thr Cys Cys Thr Gly Gly Gly Gly Thr Cys Cys Cys Ala Gly Gly Gly
            900             905             910
Cys Gly Cys Ala Cys Ala Thr Gly Thr Ala Ala Gly Ala Ala Cys
    915             920             925
Gly Thr Gly Thr Gly Thr Gly Ala Gly Ala Cys Ala Ala Gly Ala
    930             935             940
Gly Cys Ala Ala Gly Cys Thr Cys Ala Thr Thr Gly Cys Thr Cys Thr
945             950             955             960
Cys Thr Thr Cys Thr Gly Gly Ala Ala Gly Gly Cys Ala Cys Ala
                965             970             975
Ala Thr Gly Ala Ala Thr Gly Cys Thr Ala Ala Gly Cys Gly Cys Thr
            980             985             990
Gly Thr Cys Cys Cys Cys Ala Cys Thr Gly Cys Ala Ala Gly Ala Cys
            995             1000            1005
```

-continued

Cys Gly Gly Gly Cys Gly Ala Thr Cys Gly Thr Thr Gly Thr
1010              1015                1020

Cys Cys Gly Ala Ala Gly Gly Ala Cys Ala Cys Ala Ala
1025              1030                1035

Cys Ala Gly Cys Ala Ala Gly Thr Thr Gly Ala Cys Thr Ala Thr
1040              1045                1050

Cys Ala Cys Gly Thr Thr Thr Cys Cys Ala Gly Cys Cys Ala Thr
1055              1060                1065

Gly Gly Thr Gly Cys Ala Cys Ala Gly Gly Ala Cys Ala Gly Cys
1070              1075                1080

Thr Gly Gly Cys Cys Ala Gly Ala Ala Gly Gly Ala Cys Thr Cys
1085              1090                1095

Thr Gly Ala Gly Cys Cys Cys Thr Gly Gly Ala Ala Thr
1100              1105                1110

Thr Gly Ala Gly Gly Ala Ala Gly Cys Thr Cys Ala Gly Ala Thr
1115              1120                1125

Ala Gly Gly Ala Ala Ala Cys Gly Ala Gly Gly Ala Thr Ala
1130              1135                1140

Cys Thr Thr Ala Ala Cys Ala Cys Cys Cys Ala Cys Cys Ala Gly
1145              1150                1155

Thr Gly Cys Cys Cys Gly Cys Gly Ala Ala Cys Ala Cys Cys Thr
1160              1165                1170

Thr Thr Cys Thr Gly Cys Cys Cys Thr Gly Thr Gly Gly Ala Ala
1175              1180                1185

Gly Ala Ala Thr Gly Ala Ala Gly Gly Ala Thr Thr Cys Thr Thr
1190              1195                1200

Thr Cys Thr Gly Ala Ala Cys Thr Ala Cys Cys Thr Thr Thr Thr
1205              1210                1215

Thr Thr Cys Gly Gly Gly Ala Ala Thr Gly Gly Ala Thr Gly Ala
1220              1225                1230

Thr Gly Ala Thr Gly Gly Thr Ala Thr Gly Gly Ala Ala Thr Cys
1235              1240                1245

Cys Ala Gly Ala Thr Thr Cys Ala Ala Thr Cys Cys Ala Gly
1250              1255                1260

Thr Gly Thr Gly Thr Thr Cys Thr Thr Thr Cys Thr Ala Gly Ala
1265              1270                1275

Thr Thr Thr Cys Thr Thr Gly Gly Thr Gly Thr Gly Cys Cys
1280              1285                1290

Gly Cys Cys Cys Thr Cys Ala Ala Gly Gly Thr Ala Thr Cys Gly
1295              1300                1305

Cys Cys Cys Ala Gly Thr Cys Ala Gly Thr Cys Gly Cys Cys Thr
1310              1315                1320

Ala Gly Gly Ala Gly Ala Cys Cys Ala Gly Ala Thr Gly Thr Thr
1325              1330                1335

Thr Ala Cys Thr Ala Ala Thr Gly Gly Cys Cys Ala Gly Ala Cys
1340              1345                1350

Gly Gly Thr Gly Ala Ala Cys Thr Thr Gly Cys Ala Gly Gly Cys
1355              1360                1365

Thr Gly Thr Cys Ala Thr Gly Ala Ala Gly Gly Ala Thr Gly Thr
1370              1375                1380

Ala Gly Thr Thr Cys Thr Gly Ala Thr Thr Cys Gly Ala Ala Ala
1385              1390                1395

-continued

```
Ala Cys Thr Thr Cys Thr Gly Gly Cys Ala Thr Thr Gly Ala Thr
    1400                1405                1410
Gly Gly Cys Cys Cys Ala Ala Gly Ala Ala Cys Ala Gly Ala Ala
    1415                1420                1425
Gly Thr Thr Gly Cys Ala Gly Ala Gly Ala Ala Gly Thr
    1430                1435                1440
Gly Gly Cys Cys Ala Cys Ala Cys Cys Cys Ala Cys Thr Ala Cys
    1445                1450                1455
Ala Gly Ala Thr Gly Ala Gly Gly Ala Ala Ala Ala Gly Ala
    1460                1465                1470
Cys Thr Cys Thr Thr Thr Gly Ala Thr Gly Cys Thr Ala Thr
    1475                1480                1485
Thr Gly Ala Cys Cys Gly Ala Thr Cys Cys Thr Thr Thr Thr
    1490                1495                1500
Gly Ala Gly Thr Ala Cys Ala Cys Thr Thr Cys Cys Ala Gly Gly
    1505                1510                1515
Cys Cys Ala Gly Thr Cys Cys Cys Thr Cys Ala Thr Ala Gly Ala
    1520                1525                1530
Cys Ala Ala Ala Cys Thr Thr Thr Ala Cys Ala Ala Cys Ala Thr
    1535                1540                1545
Thr Thr Gly Gly Ala Thr Thr Cys Gly Cys Cys Thr Thr Cys Ala
    1550                1555                1560
Gly Ala Gly Cys Cys Ala Cys Gly Thr Cys Ala Ala Thr Ala Thr
    1565                1570                1575
Thr Gly Thr Gly Thr Thr Thr Gly Ala Thr Ala Gly Cys Gly Ala
    1580                1585                1590
Gly Ala Thr Gly Gly Ala Cys Ala Ala Ala Cys Thr Ala Ala Thr
    1595                1600                1605
Gly Ala Thr Gly Gly Ala Cys Ala Ala Gly Thr Ala Cys Cys Cys
    1610                1615                1620
Ala Gly Gly Cys Ala Thr Thr Ala Gly Gly Cys Ala Gly Ala Thr
    1625                1630                1635
Cys Cys Thr Gly Gly Ala Gly Ala Ala Gly Ala Ala Ala Gly Ala
    1640                1645                1650
Ala Gly Gly Cys Cys Thr Gly Thr Thr Cys Cys Gly Ala Ala Ala
    1655                1660                1665
Ala Cys Ala Cys Ala Thr Gly Ala Thr Gly Gly Gly Ala Ala Ala
    1670                1675                1680
Gly Cys Gly Ala Gly Thr Gly Gly Ala Cys Thr Ala Cys Gly Cys
    1685                1690                1695
Thr Gly Cys Gly Cys Gly Cys Thr Cys Ala Gly Thr Cys Ala Thr
    1700                1705                1710
Cys Thr Gly Cys Cys Cys Ala Gly Ala Cys Ala Thr Gly Thr Ala
    1715                1720                1725
Cys Ala Thr Cys Ala Ala Cys Ala Cys Cys Ala Ala Cys Gly Ala
    1730                1735                1740
Ala Ala Thr Thr Gly Gly Ala Ala Thr Thr Cys Cys Cys Ala Thr
    1745                1750                1755
Gly Gly Thr Gly Thr Thr Thr Gly Cys Cys Ala Cys Ala Ala Ala
    1760                1765                1770
Ala Cys Thr Gly Ala Cys Thr Ala Cys Cys Ala Cys Ala
    1775                1780                1785
Gly Cys Cys Ala Gly Thr Thr Ala Cys Cys Cys Cys Ala Thr Gly
```

-continued

```
                1790                1795                1800

Gly Ala Ala Thr Gly Thr Thr Cys Ala Gly Ala Ala Cys Thr
        1805                1810                1815

Thr Ala Gly Gly Cys Ala Ala Gly Cys Gly Gly Thr Cys Ala Thr
        1820                1825                1830

Cys Ala Ala Cys Gly Gly Cys Cys Cys Thr Ala Ala Thr Gly Thr
        1835                1840                1845

Gly Cys Ala Cys Cys Cys Ala Gly Gly Ala Gly Cys Cys Thr Cys
        1850                1855                1860

Cys Ala Thr Gly Gly Thr Cys Ala Thr Cys Ala Ala Thr Gly Ala
        1865                1870                1875

Gly Gly Ala Cys Gly Gly Cys Ala Gly Cys Cys Gly Cys Ala Cys
        1880                1885                1890

Ala Gly Cys Cys Cys Thr Gly Ala Gly Cys Gly Cys Thr Gly Thr
        1895                1900                1905

Gly Gly Ala Cys Ala Thr Gly Ala Cys Cys Cys Ala Gly Cys Gly
        1910                1915                1920

Ala Gly Ala Gly Gly Cys Cys Gly Thr Gly Gly Cys Cys Ala Ala
        1925                1930                1935

Gly Cys Ala Gly Cys Thr Thr Cys Thr Gly Ala Cys Cys Cys Cys
        1940                1945                1950

Ala Gly Cys Cys Ala Cys Gly Gly Gly Gly Gly Cys Ala Cys Cys
        1955                1960                1965

Thr Ala Ala Gly Cys Cys Cys Ala Gly Gly Gly Gly Ala Cys
        1970                1975                1980

Ala Ala Ala Ala Thr Thr Gly Thr Gly Thr Gly Cys Cys Gly
        1985                1990                1995

Gly Cys Ala Thr Gly Thr Gly Ala Ala Gly Ala Ala Thr Gly Gly
        2000                2005                2010

Gly Gly Ala Cys Ala Thr Thr Cys Thr Gly Cys Thr Ala Cys Thr
        2015                2020                2025

Gly Ala Ala Cys Cys Gly Ala Cys Ala Gly Cys Cys Cys Ala Cys
        2030                2035                2040

Ala Cys Thr Gly Cys Ala Cys Ala Gly Ala Cys Cys Cys Thr Cys
        2045                2050                2055

Cys Ala Thr Cys Cys Ala Gly Gly Cys Cys Cys Ala Cys Cys Gly
        2060                2065                2070

Thr Gly Cys Cys Cys Gly Cys Ala Thr Cys Cys Thr Gly Cys Cys
        2075                2080                2085

Thr Gly Ala Ala Gly Ala Gly Ala Ala Ala Gly Thr Gly Cys Thr
        2090                2095                2100

Gly Cys Gly Gly Cys Thr Cys Cys Ala Cys Thr Ala Thr Gly Cys
        2105                2110                2115

Cys Ala Ala Cys Thr Gly Cys Ala Ala Gly Gly Cys Cys Thr Ala
        2120                2125                2130

Thr Ala Ala Thr Gly Cys Cys Gly Ala Cys Thr Thr Thr Gly Ala
        2135                2140                2145

Thr Gly Gly Ala Gly Ala Cys Gly Ala Gly Ala Thr Gly Ala Ala
        2150                2155                2160

Thr Gly Cys Cys Cys Ala Thr Thr Cys Cys Cys Cys Ala
        2165                2170                2175

Gly Ala Gly Thr Gly Ala Gly Cys Thr Gly Gly Cys Cys Gly
        2180                2185                2190
```

```
Gly Gly Cys Cys Gly Ala Gly Gly Cys Thr Ala Cys Gly Thr
    2195                2200                2205

Cys Cys Thr Gly Gly Cys Cys Thr Gly Cys Ala Cys Thr Gly Ala
    2210                2215                2220

Thr Cys Ala Gly Cys Ala Gly Thr Ala Cys Cys Thr Thr Gly Thr
    2225                2230                2235

Thr Cys Cys Cys Ala Ala Gly Gly Ala Thr Gly Gly Cys Cys Ala
    2240                2245                2250

Ala Cys Cys Ala Thr Thr Gly Gly Cys Gly Gly Ala Cys Thr
    2255                2260                2265

Gly Ala Thr Cys Cys Ala Gly Gly Ala Thr Cys Ala Cys Ala Thr
    2270                2275                2280

Gly Gly Thr Thr Thr Cys Ala Gly Gly Gly Gly Cys Ala Ala Gly
    2285                2290                2295

Cys Ala Thr Gly Ala Cys Thr Ala Cys Thr Cys Gly Gly Gly Gly
    2300                2305                2310

Thr Thr Gly Cys Thr Thr Thr Thr Thr Cys Ala Cys Cys Cys Gly
    2315                2320                2325

Gly Gly Ala Gly Cys Ala Cys Thr Ala Thr Ala Thr Gly Gly Ala
    2330                2335                2340

Gly Cys Thr Gly Gly Thr Gly Thr Ala Cys Cys Gly Ala Gly Gly
    2345                2350                2355

Ala Cys Thr Cys Ala Cys Gly Gly Ala Cys Ala Ala Ala Gly Thr
    2360                2365                2370

Gly Gly Gly Gly Cys Gly Cys Gly Thr Gly Ala Ala Gly Cys Thr
    2375                2380                2385

Cys Cys Thr Thr Thr Cys Thr Cys Cys Thr Thr Cys Cys Ala Thr
    2390                2395                2400

Cys Cys Thr Gly Ala Ala Gly Cys Cys Cys Thr Thr Thr Cys Cys
    2405                2410                2415

Gly Cys Thr Gly Thr Gly Gly Ala Cys Ala Gly Gly Ala Ala Ala
    2420                2425                2430

Ala Cys Ala Gly Gly Thr Thr Gly Thr Gly Thr Cys Ala Ala Cys
    2435                2440                2445

Gly Cys Thr Gly Cys Thr Cys Ala Thr Ala Ala Ala Thr Ala Thr
    2450                2455                2460

Ala Ala Thr Cys Cys Cys Ala Gly Ala Gly Gly Ala Cys Cys Ala
    2465                2470                2475

Cys Ala Thr Cys Cys Cys Ala Cys Thr Gly Ala Ala Cys Thr Thr
    2480                2485                2490

Ala Thr Cys Thr Gly Gly Ala Ala Ala Gly Gly Cys Gly Ala Ala
    2495                2500                2505

Ala Ala Thr Cys Ala Cys Thr Gly Gly Gly Ala Ala Ala Gly Cys
    2510                2515                2520

Cys Thr Gly Gly Gly Thr Gly Ala Ala Gly Gly Ala Ala Ala Cys
    2525                2530                2535

Thr Cys Cys Thr Cys Gly Ala Thr Cys Cys Gly Thr Thr Cys Cys
    2540                2545                2550

Thr Gly Gly Cys Thr Thr Thr Ala Ala Cys Cys Thr Gly Ala
    2555                2560                2565

Cys Thr Cys Gly Ala Thr Gly Thr Gly Cys Gly Ala Gly Thr Cys
    2570                2575                2580
```

-continued

Cys Cys Ala Gly Gly Thr Gly Ala Thr Cys Ala Thr Cys Ala Gly
2585                2590                2595

Gly Gly Ala Ala Gly Gly Gly Ala Gly Cys Thr Gly Cys Thr
2600                2605                2610

Cys Thr Gly Cys Gly Gly Ala Gly Thr Gly Cys Thr Gly Gly Ala
2615                2620                2625

Cys Ala Ala Gly Gly Cys Gly Cys Ala Cys Thr Ala Thr Gly Gly
2630                2635                2640

Gly Ala Gly Cys Thr Cys Cys Gly Cys Cys Thr Ala Cys Gly Gly
2645                2650                2655

Cys Cys Thr Gly Gly Thr Cys Cys Ala Cys Thr Gly Cys Thr Gly
2660                2665                2670

Cys Thr Ala Thr Gly Ala Gly Ala Thr Cys Thr Ala Thr Gly Gly
2675                2680                2685

Ala Gly Gly Cys Gly Ala Gly Ala Cys Cys Ala Gly Cys Gly Gly
2690                2695                2700

Cys Ala Ala Gly Gly Thr Thr Cys Thr Ala Ala Cys Cys Thr Gly
2705                2710                2715

Cys Cys Thr Gly Gly Cys Cys Cys Gly Cys Cys Thr Cys Thr Thr
2720                2725                2730

Cys Ala Cys Cys Gly Cys Cys Thr Ala Cys Cys Thr Gly Cys Ala
2735                2740                2745

Gly Cys Thr Cys Thr Ala Cys Ala Gly Ala Gly Gly Cys Thr Thr
2750                2755                2760

Cys Ala Cys Cys Thr Thr Gly Gly Gly Cys Gly Thr Gly Gly Ala
2765                2770                2775

Ala Gly Ala Cys Ala Thr Thr Thr Thr Gly Gly Thr Gly Ala Ala
2780                2785                2790

Gly Cys Cys Ala Ala Ala Gly Gly Cys Ala Gly Ala Thr Gly Thr
2795                2800                2805

Cys Ala Ala Gly Ala Gly Gly Cys Ala Ala Cys Gly Thr Ala Thr
2810                2815                2820

Cys Ala Thr Thr Gly Ala Ala Gly Ala Ala Thr Cys Cys Ala Cys
2825                2830                2835

Cys Cys Ala Cys Thr Gly Cys Gly Gly Gly Cys Cys Cys Cys Ala
2840                2845                2850

Gly Gly Cys Thr Gly Thr Cys Ala Gly Gly Gly Cys Thr Gly Cys
2855                2860                2865

Ala Thr Thr Ala Ala Ala Cys Cys Thr Gly Cys Cys Ala Gly Ala
2870                2875                2880

Ala Gly Cys Cys Gly Cys Ala Thr Cys Ala Thr Ala Thr Gly Ala
2885                2890                2895

Thr Gly Ala Gly Gly Thr Cys Cys Gly Ala Gly Gly Ala Ala Ala
2900                2905                2910

Ala Thr Gly Gly Cys Ala Gly Gly Ala Thr Gly Cys Cys Cys Ala
2915                2920                2925

Thr Cys Thr Gly Gly Gly Cys Ala Ala Gly Gly Ala Cys Cys Ala
2930                2935                2940

Gly Ala Gly Gly Gly Ala Thr Thr Thr Ala Ala Cys Ala Thr
2945                2950                2955

Gly Ala Thr Thr Gly Ala Thr Cys Thr Gly Ala Ala Gly Thr Thr
2960                2965                2970

Cys Ala Ala Gly Gly Ala Gly Gly Ala Ala Gly Thr Gly Ala Ala

```
                  2975              2980              2985

Cys Cys Ala Thr Thr Ala Cys Ala Gly Cys Ala Ala  Thr Gly Ala
            2990              2995              3000

Gly Ala Thr Thr Ala Ala Cys Ala Ala Gly Gly Cys  Ala Thr Gly
            3005              3010              3015

Cys Ala Thr Gly Cys Cys Thr Thr Thr Thr Gly Cys  Cys Cys Thr
            3020              3025              3030

Ala Cys Ala Cys Ala Gly Ala Cys Ala Gly Thr Thr  Cys Cys Cys
            3035              3040              3045

Ala Gly Ala Gly Ala Ala Cys Ala Gly Cys Cys Thr  Gly Cys Ala
            3050              3055              3060

Gly Ala Thr Gly Ala Thr Gly Gly Thr Gly Cys Ala  Gly Thr Cys
            3065              3070              3075

Gly Gly Gly Ala Gly Cys Cys Ala Ala Ala Gly Gly  Thr Thr Cys
            3080              3085              3090

Ala Ala Cys Thr Gly Thr Gly Ala Ala Cys Ala Cys  Gly Ala Thr
            3095              3100              3105

Gly Cys Ala Gly Ala Thr Cys Thr Cys Gly Thr Gly  Cys Cys Thr
            3110              3115              3120

Gly Cys Thr Gly Gly Gly Cys Cys Ala Gly Ala Thr  Thr Gly Ala
            3125              3130              3135

Ala Cys Thr Gly Gly Ala Ala Gly Gly Thr Cys Gly  Gly Ala Gly
            3140              3145              3150

Ala Cys Cys Cys Cys Cys Gly Cys Thr Gly Ala Thr  Gly Gly Cys
            3155              3160              3165

Gly Thr Cys Thr Gly Gly Cys Ala Ala Gly Thr Cys  Ala Cys Thr
            3170              3175              3180

Gly Cys Cys Cys Thr Gly Cys Thr Thr Thr Gly Ala  Gly Cys Cys
            3185              3190              3195

Thr Thr Ala Thr Gly Ala Gly Thr Thr Cys Ala Cys  Cys Cys Cys
            3200              3205              3210

Cys Ala Gly Gly Gly Cys Thr Gly Gly Thr Gly Gly  Cys Thr Thr
            3215              3220              3225

Thr Gly Thr Cys Ala Cys Thr Gly Gly Cys Ala Gly  Gly Thr Thr
            3230              3235              3240

Cys Cys Thr Cys Ala Cys Cys Gly Gly Cys Ala Thr  Cys Ala Ala
            3245              3250              3255

Ala Cys Cys Thr Cys Cys Thr Gly Ala Gly Thr Thr  Cys Thr Thr
            3260              3265              3270

Cys Thr Thr Cys Cys Ala Cys Thr Gly Cys Ala Thr  Gly Gly Cys
            3275              3280              3285

Ala Gly Gly Ala Cys Gly Ala Gly Ala Gly Gly Cys  Cys Cys Thr
            3290              3295              3300

Gly Gly Thr Gly Gly Ala Cys Ala Cys Thr Gly Cys  Thr Gly Thr
            3305              3310              3315

Gly Ala Ala Ala Cys Cys Ala Gly Cys Cys Gly Cys  Thr Cys
            3320              3325              3330

Ala Gly Gly Cys Thr Ala Thr Cys Thr Cys Ala Ala  Ala Gly
            3335              3340              3345

Gly Thr Gly Cys Ala Thr Cys Ala Thr Cys Ala Ala  Gly Cys Ala
            3350              3355              3360

Cys Cys Thr Ala Gly Ala Gly Gly Gly Gly Cys Thr  Gly Gly Thr
            3365              3370              3375
```

-continued

Cys Gly Thr Gly Cys Ala Gly Thr Ala Thr Gly Ala Thr Cys Thr
            3380                3385                3390

Cys Ala Cys Gly Gly Thr Cys Cys Gly Thr Gly Ala Cys Ala Gly
            3395                3400                3405

Thr Gly Ala Cys Gly Gly Cys Ala Gly Thr Gly Thr Gly Gly Thr
            3410                3415                3420

Gly Cys Ala Gly Thr Thr Cys Cys Thr Gly Thr Ala Thr Gly Gly
            3425                3430                3435

Gly Gly Ala Gly Gly Ala Thr Gly Gly Cys Cys Thr Gly Gly Ala
            3440                3445                3450

Cys Ala Thr Cys Cys Cys Ala Ala Gly Ala Cys Ala Cys Ala
            3455                3460                3465

Gly Thr Thr Cys Cys Thr Gly Cys Ala Gly Cys Cys Cys Ala Ala
            3470                3475                3480

Gly Cys Ala Gly Thr Thr Cys Cys Cys Thr Thr Cys Cys Thr
            3485                3490                3495

Gly Gly Cys Cys Ala Gly Cys Ala Ala Cys Thr Ala Cys Gly Ala
            3500                3505                3510

Gly Gly Thr Gly Ala Thr Ala Ala Thr Gly Ala Ala Ala Thr Cys
            3515                3520                3525

Ala Cys Ala Gly Cys Ala Thr Cys Thr Cys Cys Ala Thr Gly Ala
            3530                3535                3540

Ala Gly Thr Thr Thr Thr Ala Thr Cys Cys Ala Gly Ala Gly Cys
            3545                3550                3555

Ala Gly Ala Thr Cys Cys Cys Ala Ala Ala Ala Ala Ala Gly Cys
            3560                3565                3570

Thr Cys Thr Cys Cys Ala Cys Cys Ala Cys Thr Thr Cys Ala Gly
            3575                3580                3585

Ala Gly Cys Thr Ala Thr Cys Ala Ala Ala Ala Ala Thr Gly
            3590                3595                3600

Gly Cys Ala Ala Ala Gly Cys Ala Ala Gly Cys Ala Cys Cys Cys
            3605                3610                3615

Cys Ala Ala Cys Ala Cys Cys Cys Thr Gly Cys Thr Gly Ala Gly
            3620                3625                3630

Ala Ala Gly Ala Gly Gly Cys Gly Cys Cys Thr Thr Cys Thr Thr
            3635                3640                3645

Gly Ala Gly Thr Thr Ala Thr Thr Cys Cys Ala Gly Ala Ala
            3650                3655                3660

Ala Ala Thr Thr Cys Ala Gly Gly Ala Ala Gly Cys Thr Gly Thr
            3665                3670                3675

Gly Ala Ala Ala Gly Cys Cys Cys Thr Gly Ala Ala Ala Cys Thr
            3680                3685                3690

Thr Gly Ala Gly Ala Gly Thr Gly Ala Ala Ala Cys Cys Gly
            3695                3700                3705

Cys Ala Ala Thr Gly Gly Cys Cys Gly Cys Ala Gly Cys Cys Cys
            3710                3715                3720

Thr Gly Gly Gly Ala Cys Thr Cys Ala Gly Gly Ala Gly Ala Thr
            3725                3730                3735

Gly Cys Thr Gly Ala Gly Gly Ala Thr Gly Thr Gly Gly Thr Ala
            3740                3745                3750

Thr Gly Ala Gly Thr Thr Gly Gly Ala Thr Gly Ala Gly Gly Ala
            3755                3760                3765

-continued

Ala Ala Gly Cys Cys Gly Ala Ala Gly Gly Ala Ala Thr Ala
3770            3775            3780

Cys Cys Ala Gly Ala Ala Gly Ala Ala Gly Gly Cys Gly Gly Cys
3785            3790            3795

Cys Gly Cys Thr Thr Gly Thr Cys Cys Thr Gly Ala Cys Cys Cys
3800            3805            3810

Cys Ala Gly Thr Cys Thr Gly Thr Cys Thr Gly Thr Cys Thr Gly
3815            3820            3825

Gly Cys Gly Thr Cys Cys Thr Gly Ala Cys Ala Thr Cys Thr Ala
3830            3835            3840

Cys Thr Thr Thr Gly Cys Ala Thr Cys Ala Gly Thr Gly Thr Cys
3845            3850            3855

Ala Gly Ala Ala Ala Cys Ala Thr Thr Gly Ala Ala Ala Cys
3860            3865            3870

Ala Ala Ala Gly Gly Thr Thr Gly Ala Thr Gly Ala Cys Thr Ala
3875            3880            3885

Cys Ala Gly Thr Cys Ala Ala Gly Ala Gly Thr Gly Gly Gly Cys
3890            3895            3900

Ala Gly Cys Thr Cys Ala Ala Ala Cys Ala Gly Ala Gly Ala Ala
3905            3910            3915

Gly Ala Gly Thr Thr Ala Thr Gly Ala Gly Ala Ala Ala Thr Cys
3920            3925            3930

Ala Gly Ala Gly Cys Thr Thr Thr Cys Thr Cys Thr Cys Gly Ala
3935            3940            3945

Cys Ala Gly Gly Thr Thr Gly Ala Gly Gly Ala Cys Cys Thr Thr
3950            3955            3960

Gly Cys Thr Gly Cys Ala Gly Cys Thr Gly Ala Ala Gly Thr Gly
3965            3970            3975

Gly Cys Ala Gly Cys Gly Cys Thr Cys Ala Cys Thr Gly Thr Gly
3980            3985            3990

Thr Gly Ala Gly Cys Cys Gly Gly Gly Cys Gly Ala Gly Gly Cys
3995            4000            4005

Thr Gly Thr Gly Gly Gly Cys Cys Thr Gly Cys Thr Gly Gly Cys
4010            4015            4020

Thr Gly Cys Cys Cys Ala Gly Ala Gly Cys Ala Thr Cys Gly Gly
4025            4030            4035

Ala Gly Ala Gly Cys Cys Cys Thr Cys Cys Ala Cys Cys Cys Ala
4040            4045            4050

Gly Ala Thr Gly Ala Cys Cys Cys Thr Cys Ala Ala Cys Ala Cys
4055            4060            4065

Cys Thr Thr Cys Cys Ala Cys Thr Thr Gly Cys Ala Gly Gly
4070            4075            4080

Cys Ala Gly Ala Gly Gly Cys Gly Ala Gly Ala Thr Gly Ala Ala
4085            4090            4095

Cys Gly Thr Cys Ala Cys Cys Cys Thr Gly Gly Gly Cys Ala Thr
4100            4105            4110

Thr Cys Cys Ala Ala Gly Gly Thr Thr Gly Cys Gly Gly Gly Ala
4115            4120            4125

Gly Ala Thr Thr Cys Thr Cys Ala Thr Gly Thr Gly Gly Cys
4130            4135            4140

Cys Ala Gly Cys Gly Cys Ala Ala Cys Ala Thr Cys Ala Ala
4145            4150            4155

Gly Ala Cys Ala Cys Cys Cys Ala Thr Gly Ala Thr Gly Ala Gly

```
                4160                4165                4170
Cys Gly Thr Gly Cys Cys Cys Gly Thr Gly Cys Thr Cys Ala Ala
        4175                4180                4185
Cys Ala Cys Cys Ala Ala Gly Ala Ala Gly Cys Cys Cys Thr
        4190                4195                4200
Gly Ala Ala Gly Ala Gly Ala Gly Thr Gly Ala Ala Ala Ala Gly
        4205                4210                4215
Cys Cys Thr Gly Ala Ala Gly Ala Ala Gly Cys Ala Ala Cys Thr
        4220                4225                4230
Cys Ala Cys Cys Ala Gly Gly Thr Gly Thr Gly Cys Thr Thr
        4235                4240                4245
Gly Gly Gly Gly Gly Ala Gly Gly Thr Gly Thr Gly Cys Ala
        4250                4255                4260
Gly Ala Ala Ala Ala Thr Thr Gly Ala Cys Gly Thr Cys Cys Ala
        4265                4270                4275
Gly Gly Ala Gly Thr Cys Cys Thr Thr Cys Thr Gly Thr Ala Thr
        4280                4285                4290
Gly Gly Ala Ala Gly Ala Ala Ala Ala Cys Ala Gly Ala Ala
        4295                4300                4305
Cys Ala Ala Ala Thr Thr Cys Cys Ala Gly Gly Thr Gly Thr Ala
        4310                4315                4320
Cys Cys Ala Gly Cys Thr Gly Cys Gly Gly Thr Thr Thr Cys Ala
        4325                4330                4335
Gly Thr Thr Cys Cys Thr Gly Cys Cys Ala Cys Ala Thr Gly Cys
        4340                4345                4350
Ala Thr Ala Thr Thr Ala Cys Cys Ala Gly Cys Ala Gly Gly Ala
        4355                4360                4365
Gly Ala Ala Gly Thr Gly Cys Cys Thr Gly Ala Gly Ala Cys Cys
        4370                4375                4380
Cys Gly Ala Gly Gly Ala Cys Ala Thr Cys Cys Thr Gly Cys Gly
        4385                4390                4395
Cys Thr Thr Cys Ala Thr Gly Gly Ala Ala Ala Cys Ala Ala Gly
        4400                4405                4410
Ala Thr Thr Cys Thr Thr Thr Ala Ala Ala Cys Thr Thr Cys Thr
        4415                4420                4425
Gly Ala Thr Gly Gly Ala Ala Thr Cys Cys Ala Thr Cys Ala Ala
        4430                4435                4440
Ala Ala Ala Gly Ala Ala Gly Ala Ala Thr Ala Ala Thr Ala Ala
        4445                4450                4455
Ala Gly Cys Ala Thr Cys Ala Gly Cys Thr Thr Cys Ala Gly
        4460                4465                4470
Gly Ala Ala Cys Gly Thr Ala Ala Ala Cys Ala Cys Thr Cys Gly
        4475                4480                4485
Ala Ala Gly Ala Gly Cys Thr Ala Cys Ala Cys Ala Gly Cys Gly
        4490                4495                4500
Gly Gly Ala Thr Cys Thr Gly Gly Ala Cys Ala Ala Cys Gly Cys
        4505                4510                4515
Thr Gly Gly Gly Gly Ala Gly Thr Thr Gly Gly Gly Ala Gly
        4520                4525                4530
Gly Ala Gly Thr Cys Gly Gly Gly Gly Ala Gly Ala Gly Cys Ala
        4535                4540                4545
Gly Gly Ala Gly Gly Gly Thr Gly Ala Thr Gly Ala Gly Gly Ala
        4550                4555                4560
```

```
Ala Gly Ala Gly Gly Ala Gly Gly Gly Gly Cys Ala Cys Ala Thr
    4565            4570                4575

Thr Gly Thr Gly Gly Ala Thr Gly Cys Thr Gly Ala Ala Gly Cys
    4580            4585                4590

Thr Gly Ala Gly Gly Ala Gly Gly Gly Gly Gly Ala Cys Gly Cys
    4595            4600                4605

Cys Gly Ala Thr Gly Cys Cys Thr Cys Thr Gly Ala Thr Gly Cys
    4610            4615                4620

Cys Ala Ala Ala Cys Gly Cys Ala Ala Gly Gly Ala Gly Ala Ala
    4625            4630                4635

Gly Cys Ala Gly Gly Ala Gly Gly Ala Gly Gly Ala Gly Gly Thr
    4640            4645                4650

Thr Gly Ala Thr Thr Ala Thr Gly Ala Gly Ala Gly Thr Gly Ala
    4655            4660                4665

Gly Gly Ala Ala Gly Ala Gly Gly Ala Gly Gly Ala Gly Ala Gly
    4670            4675                4680

Gly Gly Ala Gly Gly Gly Cys Gly Ala Gly Gly Ala Gly Ala Ala
    4685            4690                4695

Cys Gly Ala Cys Gly Ala Thr Gly Ala Ala Gly Ala Cys Ala Thr
    4700            4705                4710

Gly Cys Ala Gly Gly Ala Gly Gly Ala Ala Cys Gly Ala Ala Ala
    4715            4720                4725

Thr Cys Cys Cys Ala Cys Ala Gly Gly Gly Ala Ala Gly Gly
    4730            4735                4740

Thr Gly Cys Thr Cys Gly Ala Ala Ala Gly Ala Cys Cys Cys Ala
    4745            4750                4755

Ala Gly Ala Gly Cys Ala Ala Gly Ala Thr Gly Ala Ala Gly Ala
    4760            4765                4770

Gly Gly Thr Gly Gly Gly Cys Thr Thr Ala Gly Gly Cys Ala Cys
    4775            4780                4785

Thr Gly Ala Gly Gly Ala Gly Gly Ala Cys Cys Cys Gly Thr Cys
    4790            4795                4800

Cys Cys Thr Thr Cys Cys Gly Cys Cys Cys Thr Cys Cys Thr
    4805            4810                4815

Gly Ala Cys Gly Cys Ala Gly Cys Cys Cys Gly Gly Ala Ala
    4820            4825                4830

Ala Cys Cys Cys Ala Cys Cys Ala Cys Ala Gly Cys Cys Ala
    4835            4840                4845

Gly Gly Ala Gly Cys Cys Cys Ala Gly Gly Gly Cys Cys
    4850            4855                4860

Cys Gly Ala Gly Gly Cys Cys Ala Thr Gly Gly Ala Gly Cys Gly
    4865            4870                4875

Cys Cys Gly Gly Gly Thr Cys Cys Ala Gly Gly Cys Thr Gly Thr
    4880            4885                4890

Gly Cys Gly Thr Gly Ala Gly Ala Thr Cys Cys Ala Cys Cys Cys
    4895            4900                4905

Gly Thr Thr Cys Ala Thr Ala Gly Ala Thr Gly Ala Cys Thr Ala
    4910            4915                4920

Cys Cys Ala Gly Thr Ala Cys Gly Ala Cys Ala Cys Cys Gly Ala
    4925            4930                4935

Gly Gly Ala Gly Ala Gly Cys Cys Thr Gly Thr Gly Gly Thr Gly
    4940            4945                4950
```

```
Cys Cys Ala Gly Gly Thr Gly Ala Cys Ala Gly Thr Gly Ala Ala
    4955                4960                4965
Gly Cys Thr Cys Cys Thr Cys Thr Gly Ala Thr Gly Ala Ala
    4970                4975                4980
Gly Ala Thr Cys Ala Ala Cys Thr Thr Gly Ala Cys Ala Thr
    4985                4990                4995
Gly Ala Gly Cys Thr Cys Cys Thr Gly Gly Thr Ala Gly Thr
    5000                5005                5010
Ala Thr Cys Thr Thr Thr Gly Gly Cys Cys Cys Ala Thr Gly Gly
    5015                5020                5025
Thr Gly Cys Cys Gly Thr Cys Ala Thr Cys Thr Ala Thr Gly Cys
    5030                5035                5040
Gly Ala Cys Cys Ala Ala Gly Gly Gly Cys Ala Thr Cys Ala Cys
    5045                5050                5055
Thr Cys Gly Gly Thr Gly Cys Cys Thr Cys Cys Thr Gly Ala Ala
    5060                5065                5070
Thr Gly Ala Ala Ala Cys Ala Ala Cys Cys Ala Ala Cys Ala Ala
    5075                5080                5085
Thr Ala Ala Gly Ala Ala Cys Gly Ala Gly Ala Ala Gly Gly Ala
    5090                5095                5100
Gly Cys Thr Thr Gly Thr Gly Cys Thr Ala Ala Ala Cys Ala Cys
    5105                5110                5115
Ala Gly Ala Ala Gly Gly Ala Ala Thr Cys Ala Ala Cys Cys Thr
    5120                5125                5130
Cys Cys Cys Ala Gly Ala Gly Cys Thr Ala Thr Thr Cys Ala Ala
    5135                5140                5145
Gly Thr Ala Thr Gly Cys Ala Gly Ala Gly Gly Thr Cys Cys Thr
    5150                5155                5160
Gly Gly Ala Thr Cys Thr Gly Cys Gly Cys Cys Gly Cys Cys Thr
    5165                5170                5175
Cys Thr Ala Cys Thr Cys Cys Ala Ala Cys Gly Ala Cys Ala Thr
    5180                5185                5190
Cys Cys Ala Cys Gly Cys Cys Ala Thr Ala Gly Cys Cys Ala Ala
    5195                5200                5205
Cys Ala Cys Gly Thr Ala Thr Gly Gly Cys Ala Thr Thr Gly Ala
    5210                5215                5220
Gly Gly Cys Cys Gly Cys Gly Cys Thr Gly Cys Gly Gly Gly Thr
    5225                5230                5235
Gly Ala Thr Cys Gly Ala Gly Ala Ala Gly Gly Ala Gly Ala Thr
    5240                5245                5250
Cys Ala Ala Gly Gly Ala Thr Gly Thr Gly Thr Thr Gly Cys
    5255                5260                5265
Cys Gly Thr Gly Thr Ala Thr Gly Gly Cys Ala Thr Cys Gly Cys
    5270                5275                5280
Gly Gly Thr Cys Gly Ala Cys Cys Cys Thr Cys Gly Cys Cys Ala
    5285                5290                5295
Thr Cys Thr Cys Thr Cys Cys Thr Gly Gly Thr Thr Gly Cys
    5300                5305                5310
Thr Gly Ala Thr Thr Ala Thr Ala Thr Gly Thr Gly Cys Thr Thr
    5315                5320                5325
Cys Gly Ala Gly Gly Gly Thr Gly Thr Thr Ala Cys Ala Ala
    5330                5335                5340
Gly Cys Cys Ala Cys Thr Gly Ala Ala Thr Cys Gly Cys Thr Thr
```

```
                  5345                5350                5355
Thr Gly Gly Gly Ala Thr Cys Cys Gly Gly Thr Cys Ala Ala Ala
                  5360                5365                5370
Cys Thr Cys Thr Thr Cys Cys Cys Cys Gly Cys Thr Ala Cys Ala
                  5375                5380                5385
Gly Cys Ala Gly Ala Thr Gly Ala Cys Ala Thr Thr Thr Gly Ala
                  5390                5395                5400
Ala Ala Cys Cys Ala Gly Cys Thr Thr Cys Cys Ala Gly Thr Thr
                  5405                5410                5415
Thr Cys Thr Gly Ala Ala Gly Cys Ala Ala Gly Cys Cys Ala Cys
                  5420                5425                5430
Cys Ala Thr Gly Cys Thr Gly Gly Gly Ala Thr Cys Cys Cys Ala
                  5435                5440                5445
Cys Gly Ala Thr Gly Ala Gly Cys Thr Gly Ala Gly Gly Thr Cys
                  5450                5455                5460
Thr Cys Cys Thr Thr Cys Thr Gly Cys Cys Thr Gly Cys Cys Thr
                  5465                5470                5475
Thr Gly Thr Gly Gly Thr Cys Gly Gly Gly Ala Ala Gly Gly Thr
                  5480                5485                5490
Cys Gly Thr Cys Ala Gly Gly Gly Gly Cys Gly Gly Gly Ala Cys
                  5495                5500                5505
Ala Gly Gly Cys Cys Thr Gly Thr Thr Cys Gly Ala Gly Cys Thr
                  5510                5515                5520
Cys Ala Ala Gly Cys Ala Gly Cys Cys Thr Cys Thr Gly Ala Gly
                  5525                5530                5535
Ala Thr Ala Gly Cys Ala Gly Cys Thr Ala Cys Cys Cys Cys Gly
                  5540                5545                5550
Gly Cys Ala Cys Cys Ala Thr Cys Thr Gly Cys Cys Cys Ala Gly
                  5555                5560                5565
Cys Thr Cys Cys Ala Ala Gly Gly Ala Cys Cys Cys Thr Thr Gly
                  5570                5575                5580
Gly Thr Gly Ala Gly Gly Gly Cys Gly Thr Gly Gly Cys Cys Cys
                  5585                5590                5595
Ala Gly Cys Cys Thr Gly Cys Cys Thr Thr Cys Thr Gly Cys Ala
                  5600                5605                5610
Thr Gly Ala Gly Ala Gly Gly Ala Cys Cys Ala Gly Gly Ala Gly
                  5615                5620                5625
Ala Cys Thr Gly Gly Ala Ala Thr Cys Cys Ala Gly Gly Gly Cys
                  5630                5635                5640
Ala Gly Thr Thr Cys Cys Ala Ala Gly Thr Gly Ala Cys Ala Gly
                  5645                5650                5655
Thr Ala Cys Ala Gly Ala Gly Cys Ala Cys Ala Gly Cys Ala Gly
                  5660                5665                5670
Cys Gly Ala Cys Cys Thr Thr Gly Gly Gly Cys Cys Thr Gly Ala
                  5675                5680                5685
Ala Ala Gly Cys Ala Gly Thr Gly Gly Gly Cys Cys Thr Cys Thr
                  5690                5695                5700
Gly Ala Gly Cys Thr Gly Gly Gly Cys Cys Ala Gly Cys Thr Thr
                  5705                5710                5715
Cys Ala Cys Cys Thr Gly Gly Ala Ala Ala Gly Thr Gly Ala Cys
                  5720                5725                5730
Ala Gly Ala Gly Thr Thr Gly Cys Thr Cys Ala Thr Cys Cys Thr
                  5735                5740                5745
```

```
Thr Gly Cys Cys Cys Cys Thr Cys Cys Thr Gly Thr Cys Thr
    5750                5755            5760

Cys Thr Gly Gly Ala Thr Thr Thr Thr Ala Thr Cys Ala Ala
    5765                5770            5775

Gly Gly Thr Thr Thr Ala Cys Cys Ala Ala Gly Thr Cys Thr Thr
    5780                5785            5790

Cys Thr Gly Ala Gly Thr Cys Cys Cys Cys Thr Gly Ala Gly
    5795                5800            5805

Ala Thr Gly Gly Cys Thr Gly Gly Gly Cys Cys Thr Cys Ala
    5810                5815            5820

Cys Cys Thr Gly Thr Gly Cys Thr Gly Cys Ala Gly Gly Ala Gly
    5825                5830            5835

Gly Cys Cys Thr Cys Thr Gly Thr Gly Gly Cys Ala Thr Ala Ala
    5840                5845            5850

Cys Cys Cys Cys Thr Ala Ala Gly Gly Ala Gly Ala Ala Gly Thr
    5855                5860            5865

Cys Cys Thr Gly Ala Thr Thr Cys Ala Cys Gly Ala Thr Thr Cys
    5870                5875            5880

Ala Cys Thr Gly Ala Gly Ala Ala Gly Ala Cys Cys Ala Ala Gly
    5885                5890            5895

Gly Gly Gly Ala Ala Gly Cys Cys Ala Thr Gly Cys Thr Thr Thr
    5900                5905            5910

Gly Cys Thr Gly Cys Thr Gly Gly Gly Ala Cys Cys Cys Cys
    5915                5920            5925

Ala Gly Gly Cys Ala Cys Cys Thr Cys Cys Ala Gly Ala Gly Thr
    5930                5935            5940

Ala Gly Gly Gly Ala Ala Gly Cys Gly Gly Gly Thr Thr Cys
    5945                5950            5955

Thr Thr Thr Thr Gly Cys Thr Gly Thr Gly Ala Gly Thr Gly Gly
    5960                5965            5970

Cys Cys Ala Gly Gly Gly Ala Cys Ala Ala Cys Ala Gly Ala Cys
    5975                5980            5985

Ala Ala Gly Ala Thr Thr Cys Cys Thr Gly Gly Gly Gly Gly Cys
    5990                5995            6000

Thr Cys Cys Cys Gly Ala Thr Gly Ala Gly Cys Ala Gly Gly Ala
    6005                6010            6015

Ala Cys Gly Thr Gly Gly Ala Gly Cys Cys Thr Gly Cys Thr Gly
    6020                6025            6030

Cys Cys Cys Ala Ala Gly Gly Cys Cys Thr Gly Cys Thr Cys Cys
    6035                6040            6045

Thr Thr Cys Cys Gly Gly Cys Thr Gly Cys Thr Cys Ala Gly
    6050                6055            6060

Cys Cys Cys Cys Thr Gly Gly Gly Gly Cys Ala Gly Ala Gly
    6065                6070            6075

Thr Cys Cys Ala Cys Ala Ala Ala Gly Ala Gly Thr Cys Cys Cys
    6080                6085            6090

Cys Ala Thr Cys Ala Ala Gly Ala Cys Thr Thr Cys Thr Thr Cys
    6095                6100            6105

Cys Cys Thr Gly Ala Gly Thr Cys Ala Ala Gly Thr Ala Cys Ala
    6110                6115            6120

Gly Cys Gly Thr Ala Gly Cys Ala Thr Ala Gly Thr Cys Cys Thr
    6125                6130            6135
```

-continued

```
Cys Cys  Ala Cys Cys Cys  Ala Cys Cys Ala  Ala Cys Cys Thr
    6140              6145              6150

Cys Thr  Cys Thr Gly Cys  Thr Gly Gly Cys  Cys Ala Gly Gly
    6155              6160              6165

Gly Thr  Cys Cys Thr Gly  Gly Cys Cys Cys  Thr Gly Cys Cys Ala
    6170              6175              6180

Cys Thr  Gly Thr Gly Thr  Gly Gly Cys Gly  Ala Gly Gly Thr Gly
    6185              6190              6195

Thr Cys  Cys Thr Thr Cys  Thr Ala Gly Ala  Cys Cys Ala Cys Ala
    6200              6205              6210

Thr Cys  Ala Gly Cys Cys  Cys Ala Ala Gly  Gly Cys Thr Gly
    6215              6220              6225

Gly Gly  Ala Gly Cys Ala  Gly Thr Cys Gly  Cys Thr Cys Cys Ala
    6230              6235              6240

Gly Gly  Gly Cys Cys Gly  Cys Ala Gly Cys  Ala Gly Thr Thr Cys
    6245              6250              6255

Ala Cys  Thr Cys Cys Cys  Ala Cys Ala Cys  Ala Thr Ala Gly Ala
    6260              6265              6270

Ala Cys  Cys Cys Ala Gly  Gly Thr Cys Ala  Cys Thr Gly Cys Thr
    6275              6280              6285

Gly Gly  Gly Gly Cys Gly  Ala Thr Thr Gly  Ala Ala Cys Ala Gly
    6290              6295              6300

Gly Thr  Thr Gly Cys Cys  Thr Gly Gly Cys  Thr Thr Thr Thr Cys
    6305              6310              6315

Thr Cys  Thr Gly Cys Thr  Gly Thr Cys Ala  Gly Thr Thr Thr Gly
    6320              6325              6330

Gly Thr  Gly Thr Gly Gly  Ala Gly Gly Cys  Cys Thr Ala Thr Gly
    6335              6340              6345

Thr Thr  Cys Thr Gly Cys  Cys Cys Cys Ala  Thr Ala Cys Ala Cys
    6350              6355              6360

Cys Cys  Cys Ala Cys Ala  Gly Gly Cys Cys  Cys Thr Gly Cys Thr
    6365              6370              6375

Thr Ala  Thr Gly Gly Gly  Ala Ala Gly Gly  Ala Ala Cys Ala Cys
    6380              6385              6390

Ala Gly  Gly Cys Cys Thr  Cys Cys Ala Gly  Cys Cys Cys Ala Gly
    6395              6400              6405

Ala Gly  Gly Ala Cys Thr  Gly Thr Cys Cys  Cys Gly Cys Cys Cys
    6410              6415              6420

Thr Gly  Thr Thr Cys Thr  Thr Gly Gly Cys  Cys Gly Thr Cys Cys
    6425              6430              6435

Ala Cys  Gly Thr Thr Thr  Cys Thr Cys Thr  Thr Cys Cys Cys Thr
    6440              6445              6450

Cys Thr  Ala Gly Cys Ala  Cys Cys Ala Gly  Cys Ala Ala Thr Ala
    6455              6460              6465

Cys Ala  Thr Thr Thr Cys  Cys Thr Gly Gly  Cys Ala Thr Gly
    6470              6475              6480

Gly Ala  Cys Ala Gly Ala  Ala Ala Ala Gly  Ala Cys Ala Gly Ala
    6485              6490              6495

Gly Ala  Gly Gly Ala Cys  Thr Ala Thr Ala  Cys Ala Ala Ala
    6500              6505              6510

Gly Gly  Cys Thr Thr Gly  Thr Ala Ala Ala  Ala Cys Cys Ala
    6515              6520              6525

Gly Ala  Gly Gly Cys Thr  Ala Gly Cys Thr  Thr Cys Thr Ala Thr
```

```
                6530                6535                6540
Cys Thr Thr Thr Gly Thr Cys Thr Ala Cys Thr Gly Thr Thr Ala
                6545                6550                6555
Thr Thr Thr Cys Ala Gly Cys Thr Cys Ala Gly Gly Gly Cys Gly
                6560                6565                6570
Gly Gly Thr Ala Ala Thr Thr Ala Ala Cys Ala Thr Cys Ala Thr
                6575                6580                6585
Thr Gly Gly Ala Ala Cys Thr Ala Gly Cys Thr Ala Thr Thr Ala
                6590                6595                6600
Gly Gly Ala Ala Ala Gly Ala Ala Ala Ala Ala Ala Ala Ala Cys
                6605                6610                6615
Thr Thr Gly Gly Thr Thr Thr Thr Thr Thr Thr Thr Ala Cys Ala
                6620                6625                6630
Ala Cys Ala Ala
   6635

<210> SEQ ID NO 47
<211> LENGTH: 419
<212> TYPE: PRT
<213> ORGANISM: Homo sapiens

<400> SEQUENCE: 47

Met Ala Ala Glu Val Leu Pro Ser Ala Arg Trp Gln Tyr Cys Gly Ala
1               5                   10                  15

Pro Asp Gly Ser Gln Arg Ala Val Leu Val Gln Phe Ser Asn Gly Lys
            20                  25                  30

Leu Gln Ser Pro Gly Asn Met Arg Phe Thr Leu Tyr Glu Asn Lys Asp
        35                  40                  45

Ser Thr Asn Pro Arg Lys Arg Asn Gln Arg Ile Leu Ala Ala Glu Thr
    50                  55                  60

Asp Arg Leu Ser Tyr Val Gly Asn Asn Phe Gly Thr Gly Ala Leu Lys
65                  70                  75                  80

Cys Asn Thr Leu Cys Arg His Phe Val Gly Ile Leu Asn Lys Thr Ser
                85                  90                  95

Gly Gln Met Glu Val Tyr Asp Ala Glu Leu Phe Asn Met Gln Pro Leu
            100                 105                 110

Phe Ser Asp Val Ser Val Glu Ser Glu Leu Ala Leu Glu Ser Gln Thr
        115                 120                 125

Lys Thr Tyr Arg Glu Lys Met Asp Ser Cys Ile Glu Ala Phe Gly Thr
    130                 135                 140

Thr Lys Gln Lys Arg Ala Leu Asn Thr Arg Arg Met Asn Arg Val Gly
145                 150                 155                 160

Asn Glu Ser Leu Asn Arg Ala Val Ala Lys Ala Glu Thr Ile Ile
                165                 170                 175

Asp Thr Lys Gly Val Thr Ala Leu Val Ser Asp Ala Ile His Asn Asp
            180                 185                 190

Leu Gln Asp Asp Ser Leu Tyr Leu Pro Pro Cys Tyr Asp Ala Ala
        195                 200                 205

Lys Pro Glu Asp Val Tyr Lys Phe Glu Asp Leu Leu Ser Pro Ala Glu
    210                 215                 220

Tyr Glu Ala Leu Gln Ser Pro Ser Glu Ala Phe Arg Asn Val Thr Ser
225                 230                 235                 240

Glu Glu Ile Leu Lys Met Ile Glu Glu Asn Ser His Cys Thr Phe Val
                245                 250                 255
```

```
Ile Glu Ala Leu Lys Ser Leu Pro Ser Asp Val Ser Arg Asp Arg
                260                 265                 270

Gln Ala Arg Cys Ile Trp Phe Leu Asp Thr Leu Ile Lys Phe Arg Ala
            275                 280                 285

His Arg Val Val Lys Arg Lys Ser Ala Leu Gly Pro Gly Val Pro His
        290                 295                 300

Ile Ile Asn Thr Lys Leu Leu Lys His Phe Thr Cys Leu Thr Tyr Asn
305                 310                 315                 320

Asn Gly Arg Leu Arg Asn Leu Ile Ser Asp Ser Met Lys Ala Lys Ile
                325                 330                 335

Thr Ala Tyr Val Ile Ile Leu Ala Leu His Ile His Asp Phe Gln Ile
            340                 345                 350

Asp Leu Thr Val Leu Gln Arg Asp Leu Lys Leu Ser Glu Lys Arg Met
        355                 360                 365

Met Glu Ile Ala Lys Ala Met Arg Leu Lys Ile Ser Lys Arg Arg Val
370                 375                 380

Ser Val Ala Ala Gly Ser Glu Glu Asp His Lys Leu Gly Thr Leu Ser
385                 390                 395                 400

Leu Pro Leu Pro Pro Ala Gln Thr Ser Asp Arg Leu Ala Lys Arg Arg
                405                 410                 415

Lys Ile Thr

<210> SEQ ID NO 48
<211> LENGTH: 851
<212> TYPE: PRT
<213> ORGANISM: Homo sapiens

<400> SEQUENCE: 48

Met Ser Ser Lys Gln Glu Ile Met Ser Asp Gln Arg Phe Arg Arg Val
1               5                   10                  15

Ala Lys Asp Pro Arg Phe Trp Glu Met Pro Glu Lys Asp Arg Lys Val
            20                  25                  30

Lys Ile Asp Lys Arg Phe Arg Ala Met Phe His Asp Lys Lys Phe Lys
        35                  40                  45

Leu Asn Tyr Ala Val Asp Lys Arg Gly Arg Pro Ile Ser His Ser Thr
    50                  55                  60

Thr Glu Asp Leu Lys Arg Phe Tyr Asp Leu Ser Asp Ser Asp Ser Asn
65                  70                  75                  80

Leu Ser Gly Glu Asp Ser Lys Ala Leu Ser Gln Lys Lys Ile Lys Lys
                85                  90                  95

Lys Lys Thr Gln Thr Lys Lys Glu Ile Asp Ser Lys Asn Leu Val Glu
            100                 105                 110

Lys Lys Glu Thr Lys Lys Ala Asn His Lys Gly Ser Glu Asn Lys
        115                 120                 125

Thr Asp Leu Asp Asn Ser Ile Gly Ile Lys Lys Met Lys Thr Ser Cys
130                 135                 140

Lys Phe Lys Ile Asp Ser Asn Ile Ser Pro Lys Lys Asp Ser Lys Glu
145                 150                 155                 160

Phe Thr Gln Lys Asn Lys Lys Glu Lys Lys Asn Ile Val Gln His Thr
                165                 170                 175

Thr Asp Ser Ser Leu Glu Glu Lys Gln Arg Thr Leu Asp Ser Gly Thr
            180                 185                 190

Ser Glu Ile Val Lys Ser Pro Arg Ile Glu Cys Ser Lys Thr Arg Arg
        195                 200                 205
```

```
Glu Met Gln Ser Val Val Gln Leu Ile Met Thr Arg Asp Ser Asp Gly
    210                 215                 220

Tyr Glu Asn Ser Thr Asp Gly Glu Met Cys Asp Lys Asp Ala Leu Glu
225                 230                 235                 240

Glu Asp Ser Glu Ser Val Ser Glu Ile Gly Ser Asp Glu Glu Ser Glu
                245                 250                 255

Asn Glu Ile Thr Ser Val Gly Arg Ala Ser Gly Asp Asp Gly Ser
            260                 265                 270

Glu Asp Glu Glu Glu Asp Glu Glu Glu Asp Glu
            275             280             285

Asp Ser Glu Asp Asp Lys Ser Asp Ser Gly Pro Asp Leu Ala Arg
    290             295             300

Gly Lys Gly Asn Ile Glu Thr Ser Ser Glu Asp Glu Asp Thr Ala
305             310             315             320

Asp Leu Phe Pro Glu Glu Ser Gly Phe Glu His Ala Trp Arg Glu Leu
                325             330             335

Asp Lys Asp Ala Pro Arg Ala Asp Glu Ile Thr Arg Arg Leu Ala Val
            340             345             350

Cys Asn Met Asp Trp Asp Arg Leu Lys Ala Lys Asp Leu Leu Ala Leu
            355             360             365

Phe Asn Ser Phe Lys Pro Lys Gly Val Ile Phe Ser Val Lys Ile
    370             375             380

Tyr Pro Ser Glu Phe Gly Lys Glu Arg Met Lys Glu Glu Gln Val Gln
385             390             395             400

Gly Pro Val Glu Leu Leu Ser Ile Pro Glu Asp Ala Pro Glu Lys Asp
                405             410             415

Trp Thr Ser Arg Glu Lys Leu Arg Asp Tyr Gln Phe Lys Arg Leu Lys
            420             425             430

Tyr Tyr Tyr Ala Val Val Asp Cys Asp Ser Pro Glu Thr Ala Ser Lys
        435             440             445

Ile Tyr Glu Asp Cys Asp Gly Leu Glu Phe Glu Ser Ser Cys Ser Phe
    450             455             460

Ile Asp Leu Arg Phe Ile Pro Asp Asp Ile Thr Phe Asp Asp Glu Pro
465             470             475             480

Lys Asp Val Ala Ser Glu Val Asn Leu Thr Ala Tyr Lys Pro Lys Tyr
            485             490             495

Phe Thr Ser Ala Ala Met Gly Thr Ser Thr Val Glu Ile Thr Trp Asp
            500             505             510

Glu Thr Asp His Glu Arg Ile Thr Met Leu Asn Arg Lys Phe Lys Lys
            515             520             525

Glu Glu Leu Leu Asp Met Asp Phe Gln Ala Tyr Leu Ala Ser Ser Ser
530             535             540

Glu Asp Glu Glu Glu Ile Glu Glu Glu Leu Gln Gly Asp Asp Gly Val
545             550             555             560

Asn Val Glu Glu Asp Gly Lys Thr Lys Ser Gln Lys Asp Asp Glu
            565             570             575

Glu Gln Ile Ala Lys Tyr Arg Gln Leu Leu Gln Val Ile Gln Glu Lys
            580             585             590

Glu Lys Lys Gly Lys Glu Asn Asp Met Glu Met Glu Ile Lys Trp Val
            595             600             605

Pro Gly Leu Lys Glu Ser Ala Glu Glu Met Val Lys Asn Lys Leu Glu
    610             615             620

Gly Lys Asp Lys Leu Thr Pro Trp Glu Gln Phe Leu Glu Lys Lys Lys
```

```
            625                 630                 635                 640
    Glu Lys Lys Arg Leu Lys Arg Lys Gln Lys Ala Leu Ala Glu Ala
                    645                 650                 655

Ser Glu Glu Glu Leu Pro Ser Asp Val Asp Leu Asn Asp Pro Tyr Phe
                660                 665                 670

Ala Glu Val Lys Gln Ile Gly Ile Asn Lys Lys Ser Val Lys Ser
                675                 680                 685

Ala Lys Asp Gly Thr Ser Pro Glu Glu Ile Glu Ile Glu Arg Gln
                690                 695                 700

Lys Ala Glu Met Ala Leu Leu Met Met Asp Glu Asp Glu Asp Ser Lys
    705                 710                 715                 720

Lys His Phe Asn Tyr Asn Lys Ile Val Glu His Gln Asn Leu Ser Lys
                    725                 730                 735

Lys Lys Lys Lys Gln Leu Met Lys Lys Glu Leu Ile Glu Asp Asp
                740                 745                 750

Phe Glu Val Asn Val Asn Asp Ala Arg Phe Gln Ala Met Tyr Thr Ser
                    755                 760                 765

His Leu Phe Asn Leu Asp Pro Ser Asp Pro Asn Phe Lys Lys Thr Lys
    770                 775                 780

Ala Met Glu Lys Ile Leu Glu Glu Lys Ala Arg Gln Arg Glu Arg Lys
    785                 790                 795                 800

Glu Gln Glu Leu Thr Gln Ala Ile Lys Lys Glu Ser Glu Ile Glu
                805                 810                 815

Lys Glu Ser Gln Arg Lys Ser Ile Asp Pro Ala Leu Ser Met Leu Ile
                820                 825                 830

Lys Ser Ile Lys Thr Lys Thr Glu Gln Phe Gln Ala Arg Lys Lys Gln
                835                 840                 845

Lys Val Lys
            850

<210> SEQ ID NO 49
<211> LENGTH: 851
<212> TYPE: PRT
<213> ORGANISM: Homo sapiens

<400> SEQUENCE: 49

Met Ser Ser Lys Gln Glu Ile Met Ser Asp Gln Arg Phe Arg Arg Val
1               5                   10                  15

Ala Lys Asp Pro Arg Phe Trp Glu Met Pro Glu Lys Asp Arg Lys Val
                20                  25                  30

Lys Ile Asp Lys Arg Phe Arg Ala Met Phe His Asp Lys Lys Phe Lys
            35                  40                  45

Leu Asn Tyr Ala Val Asp Lys Arg Gly Arg Pro Ile Ser His Ser Thr
        50                  55                  60

Thr Glu Asp Leu Lys Arg Phe Tyr Asp Leu Ser Asp Ser Asp Ser Asn
65                  70                  75                  80

Leu Ser Gly Glu Asp Ser Lys Ala Leu Ser Gln Lys Lys Ile Lys Lys
                85                  90                  95

Lys Lys Thr Gln Thr Lys Glu Ile Asp Ser Lys Asn Leu Val Glu
                100                 105                 110

Lys Lys Lys Glu Thr Lys Lys Ala Asn His Lys Gly Ser Glu Asn Lys
            115                 120                 125

Thr Asp Leu Asp Asn Ser Ile Gly Ile Lys Lys Met Lys Thr Ser Cys
        130                 135                 140
```

```
Lys Phe Lys Ile Asp Ser Asn Ile Ser Pro Lys Asp Ser Lys Glu
145                 150                 155                 160

Phe Thr Gln Lys Asn Lys Lys Glu Lys Lys Asn Ile Val Gln His Thr
                165                 170                 175

Thr Asp Ser Ser Leu Glu Glu Lys Gln Arg Thr Leu Asp Ser Gly Thr
            180                 185                 190

Ser Glu Ile Val Lys Ser Pro Arg Ile Glu Cys Ser Lys Thr Arg Arg
        195                 200                 205

Glu Met Gln Ser Val Val Gln Leu Ile Met Thr Arg Asp Ser Asp Gly
    210                 215                 220

Tyr Glu Asn Ser Thr Asp Gly Glu Met Cys Asp Lys Asp Ala Leu Glu
225                 230                 235                 240

Glu Asp Ser Glu Ser Val Ser Glu Ile Gly Ser Asp Glu Glu Ser Glu
                245                 250                 255

Asn Glu Ile Thr Ser Val Gly Arg Ala Ser Gly Asp Asp Gly Ser
            260                 265                 270

Glu Asp Asp Glu Glu Asp Glu Asp Glu Glu Asp Glu Asp Glu
        275                 280                 285

Asp Ser Glu Asp Asp Lys Ser Asp Ser Gly Pro Asp Leu Ala Arg
290                 295                 300

Gly Lys Gly Asn Ile Glu Thr Ser Ser Glu Asp Glu Asp Thr Ala
305                 310                 315                 320

Asp Leu Phe Pro Glu Glu Ser Gly Phe Glu His Ala Trp Arg Glu Leu
                325                 330                 335

Asp Lys Asp Ala Pro Arg Ala Asp Glu Ile Thr Arg Leu Ala Val
        340                 345                 350

Cys Asn Met Asp Trp Asp Arg Leu Lys Ala Lys Asp Leu Leu Ala Leu
            355                 360                 365

Phe Asn Ser Phe Lys Pro Lys Gly Gly Val Ile Phe Ser Val Lys Ile
    370                 375                 380

Tyr Pro Ser Glu Phe Gly Lys Glu Arg Met Lys Glu Glu Gln Val Gln
385                 390                 395                 400

Gly Pro Val Glu Leu Leu Ser Ile Pro Glu Asp Ala Pro Glu Lys Asp
                405                 410                 415

Trp Thr Ser Arg Glu Lys Leu Arg Asp Tyr Gln Phe Lys Arg Leu Lys
        420                 425                 430

Tyr Tyr Tyr Ala Val Val Asp Cys Asp Ser Pro Glu Thr Ala Ser Lys
            435                 440                 445

Ile Tyr Glu Asp Cys Asp Gly Leu Glu Phe Glu Ser Ser Cys Ser Phe
    450                 455                 460

Ile Asp Leu Arg Phe Ile Pro Asp Asp Ile Thr Phe Asp Asp Glu Pro
465                 470                 475                 480

Lys Asp Val Ala Ser Glu Val Asn Leu Thr Ala Tyr Lys Pro Lys Tyr
                485                 490                 495

Phe Thr Ser Ala Ala Met Gly Thr Ser Thr Val Glu Ile Thr Trp Asp
        500                 505                 510

Glu Thr Asp His Glu Arg Ile Thr Met Leu Asn Arg Lys Phe Lys Lys
            515                 520                 525

Glu Glu Leu Leu Asp Met Asp Phe Gln Ala Tyr Leu Ala Ser Ser Ser
    530                 535                 540

Glu Asp Glu Glu Glu Ile Glu Glu Leu Gln Gly Asp Asp Gly Val
545                 550                 555                 560

Asn Val Glu Glu Asp Gly Lys Thr Lys Lys Ser Gln Lys Asp Asp Glu
```

565                 570                 575

Glu Gln Ile Ala Lys Tyr Arg Gln Leu Leu Gln Val Ile Gln Glu Lys
                580                 585                 590

Glu Lys Lys Gly Lys Glu Asn Asp Met Glu Met Glu Ile Lys Trp Val
            595                 600                 605

Pro Gly Leu Lys Glu Ser Ala Glu Glu Met Val Lys Asn Lys Leu Glu
        610                 615                 620

Gly Lys Asp Lys Leu Thr Pro Trp Glu Gln Phe Leu Glu Lys Lys Lys
625                 630                 635                 640

Glu Lys Lys Arg Leu Lys Arg Lys Gln Lys Ala Leu Ala Glu Ala
                645                 650                 655

Ser Glu Glu Glu Leu Pro Ser Asp Val Asp Leu Asn Asp Pro Tyr Phe
            660                 665                 670

Ala Glu Glu Val Lys Gln Ile Gly Ile Asn Lys Ser Val Lys Ser
        675                 680                 685

Ala Lys Asp Gly Thr Ser Pro Glu Glu Ile Glu Ile Glu Arg Gln
        690                 695                 700

Lys Ala Glu Met Ala Leu Leu Met Met Asp Glu Asp Glu Asp Ser Lys
705                 710                 715                 720

Lys His Phe Asn Tyr Asn Lys Ile Val Glu His Gln Asn Leu Ser Lys
                725                 730                 735

Lys Lys Lys Lys Gln Leu Met Lys Lys Lys Glu Leu Ile Glu Asp Asp
            740                 745                 750

Phe Glu Val Asn Val Asn Asp Ala Arg Phe Gln Ala Met Tyr Thr Ser
        755                 760                 765

His Leu Phe Asn Leu Asp Pro Ser Asp Pro Asn Phe Lys Lys Thr Lys
        770                 775                 780

Ala Met Glu Lys Ile Leu Glu Glu Lys Ala Arg Gln Arg Glu Arg Lys
785                 790                 795                 800

Glu Gln Glu Leu Thr Gln Ala Ile Lys Lys Lys Glu Ser Glu Ile Glu
                805                 810                 815

Lys Glu Ser Gln Arg Lys Ser Ile Asp Pro Ala Leu Ser Met Leu Ile
            820                 825                 830

Lys Ser Ile Lys Thr Lys Thr Glu Gln Phe Gln Ala Arg Lys Lys Gln
        835                 840                 845

Lys Val Lys
    850

<210> SEQ ID NO 50
<211> LENGTH: 450
<212> TYPE: PRT
<213> ORGANISM: Homo sapiens

<400> SEQUENCE: 50

Met Ser Asp Phe Ser Glu Glu Leu Lys Gly Pro Val Thr Asp Asp Glu
1               5                   10                  15

Glu Val Glu Thr Ser Val Leu Ser Gly Ala Gly Met His Phe Pro Trp
            20                  25                  30

Leu Gln Thr Tyr Val Glu Thr Val Ala Ile Gly Gly Lys Arg Arg Lys
        35                  40                  45

Asp Phe Ala Gln Thr Thr Ser Ala Cys Leu Ser Phe Ile Gln Glu Ala
    50                  55                  60

Leu Leu Lys His Gln Trp Gln Gln Ala Ala Glu Tyr Met Tyr Ser Tyr
65                  70                  75                  80

Phe Gln Thr Leu Glu Asp Ser Asp Ser Tyr Lys Arg Gln Ala Ala Pro
                85                  90                  95

Glu Ile Ile Trp Lys Leu Gly Ser Glu Ile Leu Phe Tyr His Pro Lys
            100                 105                 110

Ser Asn Met Glu Ser Phe Asn Thr Phe Ala Asn Arg Met Lys Asn Ile
            115                 120                 125

Gly Val Met Asn Tyr Leu Lys Ile Ser Leu Gln His Ala Leu Tyr Leu
130                 135                 140

Leu His His Gly Met Leu Lys Asp Ala Lys Arg Asn Leu Ser Glu Ala
145                 150                 155                 160

Glu Thr Trp Arg His Gly Glu Asn Thr Ser Ser Arg Glu Ile Leu Ile
                165                 170                 175

Asn Leu Ile Gln Ala Tyr Lys Gly Leu Leu Gln Tyr Tyr Thr Trp Ser
            180                 185                 190

Glu Lys Lys Met Glu Leu Ser Lys Leu Asp Lys Asp Tyr Ala Tyr
            195                 200                 205

Asn Ala Val Ala Gln Asp Val Phe Asn His Ser Trp Lys Thr Ser Ala
            210                 215                 220

Asn Ile Ser Ala Leu Ile Lys Ile Pro Gly Val Trp Asp Pro Phe Val
225                 230                 235                 240

Lys Ser Tyr Val Glu Met Leu Glu Phe Tyr Gly Asp Arg Asp Gly Ala
                245                 250                 255

Gln Glu Val Leu Thr Asn Tyr Ala Tyr Asp Glu Lys Phe Pro Ser Asn
            260                 265                 270

Pro Asn Ala His Ile Tyr Leu Tyr Asn Phe Leu Lys Arg Gln Lys Ala
            275                 280                 285

Pro Arg Ser Lys Leu Ile Ser Val Leu Lys Ile Leu Tyr Gln Ile Val
290                 295                 300

Pro Ser His Lys Leu Met Leu Glu Phe His Thr Leu Leu Arg Lys Ser
305                 310                 315                 320

Glu Lys Glu Glu His Arg Lys Leu Gly Leu Glu Val Leu Phe Gly Val
                325                 330                 335

Leu Asp Phe Ala Gly Cys Thr Lys Asn Ile Thr Ala Trp Lys Tyr Leu
            340                 345                 350

Ala Lys Tyr Leu Lys Asn Ile Leu Met Gly Asn His Leu Ala Trp Val
            355                 360                 365

Gln Glu Glu Trp Asn Ser Arg Lys Asn Trp Trp Pro Gly Phe His Phe
            370                 375                 380

Ser Tyr Phe Trp Ala Lys Ser Asp Trp Lys Glu Asp Thr Ala Leu Ala
385                 390                 395                 400

Cys Glu Lys Ala Phe Val Ala Gly Leu Leu Leu Gly Lys Gly Cys Arg
                405                 410                 415

Tyr Phe Arg Tyr Ile Leu Lys Gln Asp His Gln Ile Leu Gly Lys Lys
            420                 425                 430

Ile Lys Arg Met Lys Arg Ser Val Lys Lys Tyr Ser Ile Val Asn Pro
            435                 440                 445

Arg Leu
    450

<210> SEQ ID NO 51
<211> LENGTH: 450
<212> TYPE: PRT
<213> ORGANISM: Homo sapiens

<400> SEQUENCE: 51

```
Met Ser Asp Phe Ser Glu Glu Leu Lys Gly Pro Val Thr Asp Asp Glu
1               5                   10                  15

Glu Val Glu Thr Ser Val Leu Ser Gly Ala Gly Met His Phe Pro Trp
            20                  25                  30

Leu Gln Thr Tyr Val Glu Thr Val Ala Ile Gly Gly Lys Arg Arg Lys
            35                  40                  45

Asp Phe Ala Gln Thr Thr Ser Ala Cys Leu Ser Phe Ile Gln Glu Ala
        50                  55                  60

Leu Leu Lys His Gln Trp Gln Gln Ala Ala Glu Tyr Met Tyr Ser Tyr
65                  70                  75                  80

Phe Gln Thr Leu Glu Asp Ser Asp Ser Tyr Lys Arg Gln Ala Ala Pro
            85                  90                  95

Glu Ile Ile Trp Lys Leu Gly Ser Glu Ile Leu Phe Tyr His Pro Lys
            100                 105                 110

Ser Asn Met Glu Ser Phe Asn Thr Phe Ala Asn Arg Met Lys Asn Ile
            115                 120                 125

Gly Val Met Asn Tyr Leu Lys Ile Ser Leu Gln His Ala Leu Tyr Leu
            130                 135                 140

Leu His His Gly Met Leu Lys Asp Ala Lys Arg Asn Leu Ser Glu Ala
145                 150                 155                 160

Glu Thr Trp Arg His Gly Glu Asn Thr Ser Ser Arg Glu Ile Leu Ile
            165                 170                 175

Asn Leu Ile Gln Ala Tyr Lys Gly Leu Leu Gln Tyr Tyr Thr Trp Ser
            180                 185                 190

Glu Lys Lys Met Glu Leu Ser Lys Leu Asp Lys Asp Asp Tyr Ala Tyr
            195                 200                 205

Asn Ala Val Ala Gln Asp Val Phe Asn His Ser Trp Lys Thr Ser Ala
210                 215                 220

Asn Ile Ser Ala Leu Ile Lys Ile Pro Gly Val Trp Asp Pro Phe Val
225                 230                 235                 240

Lys Ser Tyr Val Glu Met Leu Glu Phe Tyr Gly Asp Arg Asp Gly Ala
            245                 250                 255

Gln Glu Val Leu Thr Asn Tyr Ala Tyr Asp Glu Lys Phe Pro Ser Asn
            260                 265                 270

Pro Asn Ala His Ile Tyr Leu Tyr Asn Phe Leu Lys Arg Gln Lys Ala
            275                 280                 285

Pro Arg Ser Lys Leu Ile Ser Val Leu Lys Ile Leu Tyr Gln Ile Val
            290                 295                 300

Pro Ser His Lys Leu Met Leu Glu Phe His Thr Leu Leu Arg Lys Ser
305                 310                 315                 320

Glu Lys Glu Glu His Arg Lys Leu Gly Leu Glu Val Leu Phe Gly Val
            325                 330                 335

Leu Asp Phe Ala Gly Cys Thr Lys Asn Ile Thr Ala Trp Lys Tyr Leu
            340                 345                 350

Ala Lys Tyr Leu Lys Asn Ile Leu Met Gly Asn His Leu Ala Trp Val
            355                 360                 365

Gln Glu Glu Trp Asn Ser Arg Lys Asn Trp Pro Gly Phe His Phe
            370                 375                 380

Ser Tyr Phe Trp Ala Lys Ser Asp Trp Lys Glu Asp Thr Ala Leu Ala
385                 390                 395                 400

Cys Glu Lys Ala Phe Val Ala Gly Leu Leu Leu Gly Lys Gly Cys Arg
            405                 410                 415
```

```
Tyr Phe Arg Tyr Ile Leu Lys Gln Asp His Gln Ile Leu Gly Lys Lys
                420                 425                 430

Ile Lys Arg Met Lys Arg Ser Val Lys Lys Tyr Ser Ile Val Asn Pro
                435                 440                 445

Arg Leu
    450

<210> SEQ ID NO 52
<211> LENGTH: 336
<212> TYPE: PRT
<213> ORGANISM: Homo sapiens

<400> SEQUENCE: 52

Met Glu Ser Phe Asn Thr Phe Ala Asn Arg Met Lys Asn Ile Gly Val
1               5                   10                  15

Met Asn Tyr Leu Lys Ile Ser Leu Gln His Ala Leu Tyr Leu Leu His
            20                  25                  30

His Gly Met Leu Lys Asp Ala Lys Arg Asn Leu Ser Glu Ala Glu Thr
        35                  40                  45

Trp Arg His Gly Glu Asn Thr Ser Ser Arg Glu Ile Leu Ile Asn Leu
    50                  55                  60

Ile Gln Ala Tyr Lys Gly Leu Leu Gln Tyr Tyr Thr Trp Ser Glu Lys
65                  70                  75                  80

Lys Met Glu Leu Ser Lys Leu Asp Lys Asp Tyr Ala Tyr Asn Ala
                85                  90                  95

Val Ala Gln Asp Val Phe Asn His Ser Trp Lys Thr Ser Ala Asn Ile
            100                 105                 110

Ser Ala Leu Ile Lys Ile Pro Gly Val Trp Asp Pro Phe Val Lys Ser
        115                 120                 125

Tyr Val Glu Met Leu Glu Phe Tyr Gly Asp Arg Asp Gly Ala Gln Glu
    130                 135                 140

Val Leu Thr Asn Tyr Ala Tyr Asp Glu Lys Phe Pro Ser Asn Pro Asn
145                 150                 155                 160

Ala His Ile Tyr Leu Tyr Asn Phe Leu Lys Arg Gln Lys Ala Pro Arg
                165                 170                 175

Ser Lys Leu Ile Ser Val Leu Lys Ile Leu Tyr Gln Ile Val Pro Ser
            180                 185                 190

His Lys Leu Met Leu Glu Phe His Thr Leu Leu Arg Lys Ser Glu Lys
        195                 200                 205

Glu Glu His Arg Lys Leu Gly Leu Glu Val Leu Phe Gly Val Leu Asp
    210                 215                 220

Phe Ala Gly Cys Thr Lys Asn Ile Thr Ala Trp Lys Tyr Leu Ala Lys
225                 230                 235                 240

Tyr Leu Lys Asn Ile Leu Met Gly Asn His Leu Ala Trp Val Gln Glu
                245                 250                 255

Glu Trp Asn Ser Arg Lys Asn Trp Pro Gly Phe His Phe Ser Tyr
            260                 265                 270

Phe Trp Ala Lys Ser Asp Trp Lys Glu Asp Thr Ala Leu Ala Cys Glu
        275                 280                 285

Lys Ala Phe Val Ala Gly Leu Leu Leu Gly Lys Gly Cys Arg Tyr Phe
    290                 295                 300

Arg Tyr Ile Leu Lys Gln Asp His Gln Ile Leu Gly Lys Lys Ile Lys
305                 310                 315                 320

Arg Met Lys Arg Ser Val Lys Lys Tyr Ser Ile Val Asn Pro Arg Leu
                325                 330                 335
```

-continued

<210> SEQ ID NO 53
<211> LENGTH: 588
<212> TYPE: PRT
<213> ORGANISM: Homo sapiens

<400> SEQUENCE: 53

Met Asp Leu Glu Glu Ala Glu Phe Lys Glu Arg Cys Thr Gln Cys
1               5                   10                  15

Ala Ala Val Ser Trp Gly Leu Thr Asp Glu Gly Lys Tyr Tyr Cys Thr
                20                  25                  30

Ser Cys His Asn Val Thr Glu Arg Tyr Gln Glu Val Thr Asn Thr Asp
            35                  40                  45

Leu Ile Pro Asn Thr Gln Ile Lys Ala Leu Asn Arg Gly Leu Lys Lys
        50                  55                  60

Lys Asn Asn Thr Glu Lys Gly Trp Asp Trp Tyr Val Cys Glu Gly Phe
65                  70                  75                  80

Gln Tyr Ile Leu Tyr Gln Gln Ala Glu Ala Leu Lys Asn Leu Gly Val
                85                  90                  95

Gly Pro Glu Leu Lys Asn Asp Val Leu His Asn Phe Trp Lys Arg Tyr
            100                 105                 110

Leu Gln Lys Ser Lys Gln Ala Tyr Cys Lys Asn Pro Val Tyr Thr Thr
        115                 120                 125

Gly Arg Lys Pro Thr Val Leu Glu Asp Asn Leu Ser His Ser Asp Trp
130                 135                 140

Ala Ser Glu Pro Glu Leu Leu Ser Asp Val Ser Cys Pro Pro Phe Leu
145                 150                 155                 160

Glu Ser Gly Ala Glu Ser Gln Ser Asp Ile His Thr Arg Lys Pro Phe
                165                 170                 175

Pro Val Ser Lys Ala Ser Gln Ser Glu Thr Ser Val Cys Ser Gly Ser
            180                 185                 190

Leu Asp Gly Val Glu Tyr Ser Gln Arg Lys Glu Lys Gly Ile Val Lys
        195                 200                 205

Met Thr Met Pro Gln Thr Leu Ala Phe Cys Tyr Leu Ser Leu Leu Trp
210                 215                 220

Gln Arg Glu Ala Ile Thr Leu Ser Asp Leu Leu Arg Phe Val Glu Glu
225                 230                 235                 240

Asp His Ile Pro Tyr Ile Asn Ala Phe Gln His Phe Pro Glu Gln Met
                245                 250                 255

Lys Leu Tyr Gly Arg Asp Arg Gly Ile Phe Gly Ile Glu Ser Trp Pro
            260                 265                 270

Asp Tyr Glu Asp Ile Tyr Lys Lys Thr Ile Glu Val Gly Thr Phe Leu
        275                 280                 285

Asp Leu Pro Arg Phe Pro Asp Ile Thr Glu Asp Cys Tyr Leu His Pro
290                 295                 300

Asn Ile Leu Cys Met Lys Tyr Leu Met Glu Val Asn Leu Pro Asp Glu
305                 310                 315                 320

Met His Ser Leu Thr Cys His Val Val Lys Met Thr Gly Met Gly Glu
                325                 330                 335

Val Asp Phe Leu Thr Phe Asp Pro Ile Ala Lys Met Ala Lys Thr Val
            340                 345                 350

Lys Tyr Asp Val Gln Ala Val Ala Ile Ile Val Val Leu Lys Leu
        355                 360                 365

Leu Phe Leu Leu Asp Asp Ser Phe Glu Trp Ser Leu Ser Asn Leu Ala

```
            370                 375                 380
Glu Lys His Asn Glu Lys Asn Lys Lys Asp Lys Pro Trp Phe Asp Phe
385                 390                 395                 400

Arg Lys Trp Tyr Gln Ile Met Lys Lys Ala Phe Asp Glu Lys Lys Gln
                405                 410                 415

Lys Trp Glu Glu Ala Arg Ala Lys Tyr Leu Trp Lys Ser Glu Lys Pro
            420                 425                 430

Leu Tyr Tyr Ser Phe Val Asp Lys Pro Val Ala Tyr Lys Lys Arg Glu
        435                 440                 445

Met Val Val Asn Leu Gln Lys Gln Phe Ser Thr Leu Val Glu Ser Thr
    450                 455                 460

Ala Thr Ala Gly Lys Lys Ser Pro Ser Ser Phe Gln Phe Asn Trp Thr
465                 470                 475                 480

Glu Glu Asp Thr Asp Arg Thr Cys Phe His Gly His Ser Leu Gln Gly
                485                 490                 495

Val Leu Lys Glu Lys Gly Gln Ser Leu Leu Thr Lys Asn Ser Leu Tyr
            500                 505                 510

Trp Leu Ser Thr Gln Lys Phe Cys Arg Cys Tyr Cys Thr His Val Thr
        515                 520                 525

Thr Tyr Glu Glu Ser Asn Tyr Ser Leu Ser Tyr Gln Phe Ile Leu Asn
    530                 535                 540

Leu Phe Ser Phe Leu Leu Arg Ile Lys Thr Ser Leu Leu His Glu Glu
545                 550                 555                 560

Val Ser Leu Val Glu Lys Lys Leu Phe Glu Lys Lys Tyr Ser Val Lys
                565                 570                 575

Arg Lys Lys Ser Arg Ser Lys Lys Val Arg Arg His
            580                 585

<210> SEQ ID NO 54
<211> LENGTH: 843
<212> TYPE: PRT
<213> ORGANISM: Homo sapiens

<400> SEQUENCE: 54

Met Asp Phe Pro Ser Ser Leu Arg Pro Ala Leu Phe Leu Thr Gly Pro
1               5                   10                  15

Leu Gly Leu Ser Asp Val Pro Asp Leu Ser Phe Met Cys Ser Trp Arg
            20                  25                  30

Asp Ala Leu Thr Leu Pro Glu Ala Gln Pro Gln Asn Ser Glu Asn Gly
        35                  40                  45

Ala Leu His Val Thr Lys Asp Leu Leu Trp Glu Pro Ala Thr Pro Gly
    50                  55                  60

Pro Leu Pro Met Leu Pro Pro Leu Ile Asp Pro Trp Asp Pro Gly Leu
65                  70                  75                  80

Thr Ala Arg Asp Leu Leu Phe Arg Gly Gly Tyr Arg Tyr Arg Lys Arg
                85                  90                  95

Pro Arg Val Val Leu Asp Val Thr Glu Gln Ile Ser Arg Phe Leu Leu
            100                 105                 110

Asp His Gly Asp Val Ala Phe Ala Pro Leu Gly Lys Leu Met Leu Glu
        115                 120                 125

Asn Phe Lys Leu Glu Gly Ala Gly Ser Arg Thr Lys Lys Lys Thr Val
    130                 135                 140

Val Ser Val Lys Lys Leu Leu Gln Asp Leu Gly Gly His Gln Pro Trp
145                 150                 155                 160
```

-continued

Gly Cys Pro Trp Ala Tyr Leu Ser Asn Arg Gln Arg Phe Ser Ile
                165                 170                 175

Leu Gly Gly Pro Ile Leu Gly Thr Ser Val Ala Ser His Leu Ala Glu
            180                 185                 190

Leu Leu His Glu Glu Leu Val Leu Arg Trp Glu Gln Leu Leu Leu Asp
        195                 200                 205

Glu Ala Cys Thr Gly Gly Ala Leu Ala Trp Val Pro Gly Arg Thr Pro
210                 215                 220

Gln Phe Gly Gln Leu Val Tyr Pro Ala Gly Ala Gln Asp Arg Leu
225                 230                 235                 240

His Phe Gln Glu Val Leu Thr Pro Gly Asp Asn Pro Gln Phe Leu
            245                 250                 255

Gly Lys Pro Gly Arg Ile Gln Leu Gln Gly Pro Val Arg Gln Val Val
            260                 265                 270

Thr Cys Thr Val Gln Gly Glu Thr Leu Leu Ala Val Arg Ser Asp Tyr
        275                 280                 285

His Cys Ala Val Trp Lys Phe Gly Lys Gln Trp Gln Pro Thr Leu Leu
        290                 295                 300

Gln Ala Met Gln Val Glu Lys Gly Ala Thr Gly Ile Ser Leu Ser Pro
305                 310                 315                 320

His Leu Pro Gly Glu Leu Ala Ile Cys Ser Arg Ser Gly Ala Val Cys
            325                 330                 335

Leu Trp Ser Pro Glu Asp Gly Leu Arg Gln Ile Tyr Arg Asp Pro Glu
            340                 345                 350

Thr Leu Val Phe Arg Asp Ser Ser Trp Arg Trp Ala Asp Phe Thr
            355                 360                 365

Ala His Pro Arg Val Leu Thr Val Gly Asp Arg Thr Gly Val Lys Met
        370                 375                 380

Leu Asp Thr Gln Gly Pro Pro Gly Cys Gly Leu Leu Leu Phe Arg Leu
385                 390                 395                 400

Gly Ala Glu Ala Ser Cys Gln Lys Gly Glu Arg Val Leu Leu Thr Gln
                405                 410                 415

Tyr Leu Gly His Ser Ser Pro Lys Cys Leu Pro Pro Thr Leu His Leu
            420                 425                 430

Val Cys Thr Gln Phe Ser Leu Tyr Leu Val Asp Glu Arg Leu Pro Leu
        435                 440                 445

Val Pro Met Leu Lys Trp Asn His Gly Leu Pro Ser Pro Leu Leu Leu
        450                 455                 460

Ala Arg Leu Leu Pro Pro Arg Pro Ser Cys Val Gln Pro Leu Leu
465                 470                 475                 480

Leu Gly Gly Gln Gly Gly Gln Leu Gln Leu Leu His Leu Ala Gly Glu
            485                 490                 495

Gly Ala Ser Val Pro Arg Leu Ala Gly Pro Pro Gln Ser Leu Pro Ser
            500                 505                 510

Arg Ile Asp Ser Leu Pro Ala Phe Pro Leu Leu Glu Pro Lys Ile Gln
        515                 520                 525

Trp Arg Leu Gln Glu Arg Leu Lys Ala Pro Thr Ile Gly Leu Ala Ala
        530                 535                 540

Val Val Pro Pro Leu Pro Ser Ala Pro Thr Pro Gly Leu Val Leu Phe
545                 550                 555                 560

Gln Leu Ser Ala Ala Gly Asp Val Phe Tyr Gln Gln Leu Arg Pro Gln
                565                 570                 575

Val Asp Ser Ser Leu Arg Arg Asp Ala Gly Pro Pro Gly Asp Thr Gln

```
                    580                 585                 590
Pro Asp Cys His Ala Pro Thr Ala Ser Trp Thr Ser Gln Asp Thr Ala
                595                 600                 605

Gly Cys Ser Gln Trp Leu Lys Ala Leu Leu Lys Val Pro Leu Ala Pro
            610                 615                 620

Pro Val Trp Thr Ala Pro Thr Phe Thr His Arg Gln Met Leu Gly Ser
625                 630                 635                 640

Thr Glu Leu Arg Arg Glu Glu Glu Gly Gln Arg Leu Gly Val Leu
                645                 650                 655

Arg Lys Ala Met Ala Arg Gly Gln Leu Leu Gln Arg Asp Leu Gly
            660                 665                 670

Ser Leu Pro Ala Ala Glu Pro Pro Ala Pro Glu Ser Gly Leu Glu
            675                 680                 685

Asp Lys Leu Ser Glu Arg Leu Gly Glu Ala Trp Ala Gly Arg Gly Ala
            690                 695                 700

Ala Trp Trp Glu Arg Gln Gln Gly Arg Thr Ser Glu Pro Gly Arg Gln
705                 710                 715                 720

Thr Arg Arg Pro Lys Arg Arg Thr Gln Leu Ser Ser Ser Phe Ser Leu
                725                 730                 735

Ser Gly His Val Asp Pro Ser Glu Asp Thr Ser Ser Pro His Ser Pro
            740                 745                 750

Glu Trp Pro Pro Ala Asp Ala Leu Pro Leu Pro Pro Thr Pro Pro
            755                 760                 765

Ser Gln Glu Leu Thr Pro Asp Ala Cys Ala Gln Gly Val Pro Ser Glu
            770                 775                 780

Gln Arg Gln Met Leu Arg Asp Tyr Met Ala Lys Leu Pro Pro Gln Arg
785                 790                 795                 800

Asp Thr Pro Gly Cys Ala Thr Thr Pro Pro His Ser Gln Ala Ser Ser
                805                 810                 815

Val Arg Ala Thr Arg Ser Gln Gln His Thr Pro Val Leu Ser Ser Ser
                820                 825                 830

Gln Pro Leu Arg Lys Pro Arg Met Gly Phe
            835                 840

<210> SEQ ID NO 55
<211> LENGTH: 537
<212> TYPE: PRT
<213> ORGANISM: Homo sapiens

<400> SEQUENCE: 55

Met Gln Val Glu Lys Gly Ala Thr Gly Ile Ser Leu Ser Pro His Leu
1               5                   10                  15

Pro Gly Glu Leu Ala Ile Cys Ser Arg Ser Gly Ala Val Cys Leu Trp
            20                  25                  30

Ser Pro Glu Asp Gly Leu Arg Gln Ile Tyr Arg Asp Pro Glu Thr Leu
        35                  40                  45

Val Phe Arg Asp Ser Ser Ser Trp Arg Trp Ala Asp Phe Thr Ala His
    50                  55                  60

Pro Arg Val Leu Thr Val Gly Asp Arg Thr Gly Val Lys Met Leu Asp
65                  70                  75                  80

Thr Gln Gly Pro Pro Gly Cys Gly Leu Leu Leu Phe Arg Leu Gly Ala
                85                  90                  95

Glu Ala Ser Cys Gln Lys Gly Glu Arg Val Leu Leu Thr Gln Tyr Leu
            100                 105                 110
```

```
Gly His Ser Ser Pro Lys Cys Leu Pro Pro Thr Leu His Leu Val Cys
            115                 120                 125

Thr Gln Phe Ser Leu Tyr Leu Val Asp Glu Arg Leu Pro Leu Val Pro
130                 135                 140

Met Leu Lys Trp Asn His Gly Leu Pro Ser Pro Leu Leu Ala Arg
145                 150                 155                 160

Leu Leu Pro Pro Pro Arg Pro Ser Cys Val Gln Pro Leu Leu Leu Gly
                165                 170                 175

Gly Gln Gly Gly Gln Leu Gln Leu Leu His Leu Ala Gly Glu Gly Ala
            180                 185                 190

Ser Val Pro Arg Leu Ala Gly Pro Gln Ser Leu Pro Ser Arg Ile
            195                 200                 205

Asp Ser Leu Pro Ala Phe Pro Leu Leu Glu Pro Lys Ile Gln Trp Arg
210                 215                 220

Leu Gln Glu Arg Leu Lys Ala Pro Thr Ile Gly Leu Ala Ala Val Val
225                 230                 235                 240

Pro Pro Leu Pro Ser Ala Pro Thr Pro Gly Leu Val Leu Phe Gln Leu
                245                 250                 255

Ser Ala Ala Gly Asp Val Phe Tyr Gln Gln Leu Arg Pro Gln Val Asp
            260                 265                 270

Ser Ser Leu Arg Arg Asp Ala Gly Pro Pro Gly Asp Thr Gln Pro Asp
            275                 280                 285

Cys His Ala Pro Thr Ala Ser Trp Thr Ser Gln Asp Thr Ala Gly Cys
            290                 295                 300

Ser Gln Trp Leu Lys Ala Leu Leu Lys Val Pro Leu Ala Pro Pro Val
305                 310                 315                 320

Trp Thr Ala Pro Thr Phe Thr His Arg Gln Met Leu Gly Ser Thr Glu
                325                 330                 335

Leu Arg Arg Glu Glu Glu Gly Gln Arg Leu Gly Val Leu Arg Lys
            340                 345                 350

Ala Met Ala Arg Gly Gln Leu Leu Leu Gln Arg Asp Leu Gly Ser Leu
            355                 360                 365

Pro Ala Ala Glu Pro Pro Ala Pro Glu Ser Gly Leu Glu Asp Lys
370                 375                 380

Leu Ser Glu Arg Leu Gly Glu Ala Trp Ala Gly Arg Gly Ala Ala Trp
385                 390                 395                 400

Trp Glu Arg Gln Gln Gly Arg Thr Ser Glu Pro Gly Arg Gln Thr Arg
                405                 410                 415

Arg Pro Lys Arg Arg Thr Gln Leu Ser Ser Ser Phe Ser Leu Ser Gly
            420                 425                 430

His Val Asp Pro Ser Glu Asp Thr Ser Ser Pro His Ser Pro Glu Trp
            435                 440                 445

Pro Pro Ala Asp Ala Leu Pro Leu Pro Pro Thr Thr Pro Pro Ser Gln
450                 455                 460

Glu Leu Thr Pro Asp Ala Cys Ala Gln Gly Val Pro Ser Glu Gln Arg
465                 470                 475                 480

Gln Met Leu Arg Asp Tyr Met Ala Lys Leu Pro Pro Gln Arg Asp Thr
                485                 490                 495

Pro Gly Cys Ala Thr Thr Pro His Ser Gln Ala Ser Ser Val Arg
            500                 505                 510

Ala Thr Arg Ser Gln Gln His Thr Pro Val Leu Ser Ser Ser Gln Pro
            515                 520                 525

Leu Arg Lys Lys Pro Arg Met Gly Phe
```

<210> SEQ ID NO 56
<211> LENGTH: 537
<212> TYPE: PRT
<213> ORGANISM: Homo sapiens
<400> SEQUENCE: 56

```
Met Gln Val Glu Lys Gly Ala Thr Gly Ile Ser Leu Ser Pro His Leu
1               5                   10                  15

Pro Gly Glu Leu Ala Ile Cys Ser Arg Ser Gly Ala Val Cys Leu Trp
            20                  25                  30

Ser Pro Glu Asp Gly Leu Arg Gln Ile Tyr Arg Asp Pro Glu Thr Leu
        35                  40                  45

Val Phe Arg Asp Ser Ser Trp Arg Trp Ala Asp Phe Thr Ala His
    50                  55                  60

Pro Arg Val Leu Thr Val Gly Asp Arg Thr Gly Val Lys Met Leu Asp
65                  70                  75                  80

Thr Gln Gly Pro Pro Gly Cys Gly Leu Leu Leu Phe Arg Leu Gly Ala
                85                  90                  95

Glu Ala Ser Cys Gln Lys Gly Glu Arg Val Leu Leu Thr Gln Tyr Leu
            100                 105                 110

Gly His Ser Ser Pro Lys Cys Leu Pro Pro Thr Leu His Leu Val Cys
        115                 120                 125

Thr Gln Phe Ser Leu Tyr Leu Val Asp Glu Arg Leu Pro Leu Val Pro
    130                 135                 140

Met Leu Lys Trp Asn His Gly Leu Pro Ser Pro Leu Leu Leu Ala Arg
145                 150                 155                 160

Leu Leu Pro Pro Arg Pro Ser Cys Val Gln Pro Leu Leu Leu Gly
                165                 170                 175

Gly Gln Gly Gly Gln Leu Gln Leu Leu His Leu Ala Gly Glu Gly Ala
            180                 185                 190

Ser Val Pro Arg Leu Ala Gly Pro Pro Gln Ser Leu Pro Ser Arg Ile
        195                 200                 205

Asp Ser Leu Pro Ala Phe Pro Leu Leu Glu Pro Lys Ile Gln Trp Arg
    210                 215                 220

Leu Gln Glu Arg Leu Lys Ala Pro Thr Ile Gly Leu Ala Ala Val Val
225                 230                 235                 240

Pro Pro Leu Pro Ser Ala Pro Thr Pro Gly Leu Val Leu Phe Gln Leu
                245                 250                 255

Ser Ala Ala Gly Asp Val Phe Tyr Gln Leu Arg Pro Gln Val Asp
            260                 265                 270

Ser Ser Leu Arg Arg Asp Ala Gly Pro Pro Gly Asp Thr Gln Pro Asp
        275                 280                 285

Cys His Ala Pro Thr Ala Ser Trp Thr Ser Gln Asp Thr Ala Gly Cys
    290                 295                 300

Ser Gln Trp Leu Lys Ala Leu Leu Lys Val Pro Leu Ala Pro Pro Val
305                 310                 315                 320

Trp Thr Ala Pro Thr Phe Thr His Arg Gln Met Leu Gly Ser Thr Glu
                325                 330                 335

Leu Arg Arg Glu Glu Glu Gly Gln Arg Leu Gly Val Leu Arg Lys
            340                 345                 350

Ala Met Ala Arg Gly Gln Leu Leu Leu Gln Arg Asp Leu Gly Ser Leu
        355                 360                 365
```

```
Pro Ala Ala Glu Pro Pro Ala Pro Glu Ser Gly Leu Glu Asp Lys
        370                 375                 380

Leu Ser Glu Arg Leu Gly Glu Ala Trp Ala Gly Arg Gly Ala Ala Trp
385                 390                 395                 400

Trp Glu Arg Gln Gln Gly Arg Thr Ser Glu Pro Gly Arg Gln Thr Arg
                405                 410                 415

Arg Pro Lys Arg Arg Thr Gln Leu Ser Ser Ser Phe Ser Leu Ser Gly
                420                 425                 430

His Val Asp Pro Ser Glu Asp Thr Ser Ser Pro His Ser Pro Glu Trp
                435                 440                 445

Pro Pro Ala Asp Ala Leu Pro Leu Pro Pro Thr Thr Pro Pro Ser Gln
450                 455                 460

Glu Leu Thr Pro Asp Ala Cys Ala Gln Gly Val Pro Ser Glu Gln Arg
465                 470                 475                 480

Gln Met Leu Arg Asp Tyr Met Ala Lys Leu Pro Pro Gln Arg Asp Thr
                485                 490                 495

Pro Gly Cys Ala Thr Thr Pro Pro His Ser Gln Ala Ser Ser Val Arg
                500                 505                 510

Ala Thr Arg Ser Gln Gln His Thr Pro Val Leu Ser Ser Ser Gln Pro
                515                 520                 525

Leu Arg Lys Lys Pro Arg Met Gly Phe
530                 535

<210> SEQ ID NO 57
<211> LENGTH: 460
<212> TYPE: PRT
<213> ORGANISM: Homo sapiens

<400> SEQUENCE: 57

Met Leu Asp Thr Gln Gly Pro Pro Gly Cys Gly Leu Leu Leu Phe Arg
1               5                   10                  15

Leu Gly Ala Glu Ala Ser Cys Gln Lys Gly Glu Arg Val Leu Leu Thr
                20                  25                  30

Gln Tyr Leu Gly His Ser Ser Pro Lys Cys Leu Pro Pro Thr Leu His
                35                  40                  45

Leu Val Cys Thr Gln Phe Ser Leu Tyr Leu Val Asp Glu Arg Leu Pro
        50                  55                  60

Leu Val Pro Met Leu Lys Trp Asn His Gly Leu Pro Ser Pro Leu Leu
65                  70                  75                  80

Leu Ala Arg Leu Leu Pro Pro Arg Pro Ser Cys Val Gln Pro Leu
                85                  90                  95

Leu Leu Gly Gly Gln Gly Gly Gln Leu Gln Leu Leu His Leu Ala Gly
                100                 105                 110

Glu Gly Ala Ser Val Pro Arg Leu Ala Gly Pro Gln Ser Leu Pro
                115                 120                 125

Ser Arg Ile Asp Ser Leu Pro Ala Phe Pro Leu Leu Glu Pro Lys Ile
                130                 135                 140

Gln Trp Arg Leu Gln Glu Arg Leu Lys Ala Pro Thr Ile Gly Leu Ala
145                 150                 155                 160

Ala Val Val Pro Pro Leu Pro Ser Ala Pro Thr Pro Gly Leu Val Leu
                165                 170                 175

Phe Gln Leu Ser Ala Ala Gly Asp Val Phe Tyr Gln Gln Leu Arg Pro
                180                 185                 190

Gln Val Asp Ser Ser Leu Arg Arg Asp Ala Gly Pro Pro Gly Asp Thr
                195                 200                 205
```

```
Gln Pro Asp Cys His Ala Pro Thr Ala Ser Trp Thr Ser Gln Asp Thr
    210                 215                 220

Ala Gly Cys Ser Gln Trp Leu Lys Ala Leu Leu Lys Val Pro Leu Ala
225                 230                 235                 240

Pro Pro Val Trp Thr Ala Pro Thr Phe Thr His Arg Gln Met Leu Gly
                245                 250                 255

Ser Thr Glu Leu Arg Arg Glu Glu Glu Gly Gln Arg Leu Gly Val
            260                 265                 270

Leu Arg Lys Ala Met Ala Arg Gly Gln Leu Leu Gln Arg Asp Leu
        275                 280                 285

Gly Ser Leu Pro Ala Ala Glu Pro Pro Ala Pro Glu Ser Gly Leu
    290                 295                 300

Glu Asp Lys Leu Ser Glu Arg Leu Gly Glu Ala Trp Ala Gly Arg Gly
305                 310                 315                 320

Ala Ala Trp Trp Glu Arg Gln Gln Gly Arg Thr Ser Glu Pro Gly Arg
                325                 330                 335

Gln Thr Arg Arg Pro Lys Arg Thr Gln Leu Ser Ser Phe Ser
                340                 345                 350

Leu Ser Gly His Val Asp Pro Ser Glu Asp Thr Ser Ser Pro His Ser
            355                 360                 365

Pro Glu Trp Pro Pro Ala Asp Ala Leu Pro Leu Pro Pro Thr Thr Pro
    370                 375                 380

Pro Ser Gln Glu Leu Thr Pro Asp Ala Cys Ala Gln Gly Val Pro Ser
385                 390                 395                 400

Glu Gln Arg Gln Met Leu Arg Asp Tyr Met Ala Lys Leu Pro Pro Gln
                405                 410                 415

Arg Asp Thr Pro Gly Cys Ala Thr Thr Pro His Ser Gln Ala Ser
                420                 425                 430

Ser Val Arg Ala Thr Arg Ser Gln Gln His Thr Pro Val Leu Ser Ser
            435                 440                 445

Ser Gln Pro Leu Arg Lys Lys Pro Arg Met Gly Phe
    450                 455                 460

<210> SEQ ID NO 58
<211> LENGTH: 392
<212> TYPE: PRT
<213> ORGANISM: Homo sapiens

<400> SEQUENCE: 58

Met Leu Lys Trp Asn His Gly Leu Pro Ser Pro Leu Leu Ala Arg
1               5                   10                  15

Leu Leu Pro Pro Pro Arg Pro Ser Cys Val Gln Pro Leu Leu Leu Gly
                20                  25                  30

Gly Gln Gly Gly Gln Leu Gln Leu Leu His Leu Ala Glu Gly Ala Ser
            35                  40                  45

Val Pro Arg Leu Ala Gly Pro Pro Gln Ser Leu Pro Ser Arg Ile Asp
        50                  55                  60

Ser Leu Pro Ala Phe Pro Leu Leu Glu Pro Lys Ile Gln Trp Arg Leu
65                  70                  75                  80

Gln Glu Arg Leu Lys Ala Pro Thr Ile Gly Leu Ala Ala Val Val Pro
                85                  90                  95

Pro Leu Pro Ser Ala Pro Thr Pro Gly Leu Val Leu Phe Gln Leu Ser
                100                 105                 110

Ala Ala Gly Asp Val Phe Tyr Gln Gln Leu Arg Pro Gln Val Asp Ser
```

```
                      115                 120                 125
Ser Leu Arg Arg Asp Ala Gly Pro Pro Gly Asp Thr Gln Pro Asp Cys
    130                 135                 140

His Ala Pro Thr Ala Ser Trp Thr Ser Gln Asp Thr Ala Gly Cys Ser
145                 150                 155                 160

Gln Trp Leu Lys Ala Leu Leu Lys Val Pro Leu Ala Pro Pro Val Trp
                165                 170                 175

Thr Ala Pro Thr Phe Thr His Arg Gln Met Leu Gly Ser Thr Glu Leu
            180                 185                 190

Arg Arg Glu Glu Glu Gly Gln Arg Leu Gly Val Leu Arg Lys Ala
        195                 200                 205

Met Ala Arg Gly Gln Leu Leu Leu Gln Arg Asp Leu Gly Ser Leu Pro
    210                 215                 220

Ala Ala Glu Pro Pro Ala Pro Glu Ser Gly Leu Glu Asp Lys Leu
225                 230                 235                 240

Ser Glu Arg Leu Gly Glu Ala Trp Ala Gly Arg Gly Ala Ala Trp Trp
                245                 250                 255

Glu Arg Gln Gln Gly Arg Thr Ser Glu Pro Gly Arg Gln Thr Arg Arg
            260                 265                 270

Pro Lys Arg Arg Thr Gln Leu Ser Ser Phe Ser Leu Ser Gly His
        275                 280                 285

Val Asp Pro Ser Glu Asp Thr Ser Ser Pro His Ser Pro Glu Trp Pro
    290                 295                 300

Pro Ala Asp Ala Leu Pro Leu Pro Pro Thr Thr Pro Pro Ser Gln Glu
305                 310                 315                 320

Leu Thr Pro Asp Ala Cys Ala Gln Gly Val Pro Ser Glu Gln Arg Gln
                325                 330                 335

Met Leu Arg Asp Tyr Met Ala Lys Leu Pro Pro Gln Arg Asp Thr Pro
            340                 345                 350

Gly Cys Ala Thr Thr Pro Pro His Ser Gln Ala Ser Val Arg Ala
        355                 360                 365

Thr Arg Ser Gln Gln His Thr Pro Val Leu Ser Ser Ser Gln Pro Leu
    370                 375                 380

Arg Lys Lys Pro Arg Met Gly Phe
385                 390
```

<210> SEQ ID NO 59
<211> LENGTH: 278
<212> TYPE: PRT
<213> ORGANISM: Homo sapiens

<400> SEQUENCE: 59

```
Met Asp Lys Ser Gly Ile Asp Ser Leu Asp His Val Thr Ser Asp Ala
1               5                   10                  15

Val Glu Leu Ala Asn Arg Ser Asp Asn Ser Ser Asp Ser Ser Leu Phe
            20                  25                  30

Lys Thr Gln Cys Ile Pro Tyr Ser Pro Lys Gly Glu Lys Arg Asn Pro
        35                  40                  45

Ile Arg Lys Phe Val Arg Thr Pro Glu Ser Val His Ala Ser Asp Ser
    50                  55                  60

Ser Ser Asp Ser Ser Phe Glu Pro Ile Pro Leu Thr Ile Lys Ala Ile
65                  70                  75                  80

Phe Glu Arg Phe Lys Asn Arg Lys Lys Arg Tyr Lys Lys Lys Lys
                85                  90                  95
```

```
Arg Arg Tyr Gln Pro Thr Gly Arg Pro Arg Gly Pro Glu Gly Arg
                100                 105                 110

Arg Asn Pro Ile Tyr Ser Leu Ile Asp Lys Lys Gln Phe Arg Ser
            115                 120                 125

Arg Gly Ser Gly Phe Pro Phe Leu Glu Ser Glu Asn Glu Lys Asn Ala
130                 135                 140

Pro Trp Arg Lys Ile Leu Thr Phe Glu Gln Ala Val Ala Arg Gly Phe
145                 150                 155                 160

Phe Asn Tyr Ile Glu Lys Leu Lys Tyr Glu His His Leu Lys Glu Ser
                165                 170                 175

Leu Lys Gln Met Asn Val Gly Glu Asp Leu Glu Asn Gly Asp Phe Asp
            180                 185                 190

Ser Arg Arg Tyr Lys Phe Leu Asp Asp Asp Gly Ser Ile Ser Pro Ile
        195                 200                 205

Glu Glu Ser Thr Ala Glu Asp Glu Ala Thr His Leu Glu Asp Asn
    210                 215                 220

Glu Cys Asp Ile Lys Leu Ala Gly Asp Ser Phe Ile Val Ser Ser Glu
225                 230                 235                 240

Phe Pro Val Arg Leu Ser Val Tyr Leu Glu Glu Glu Asp Ile Thr Glu
                245                 250                 255

Glu Ala Ala Leu Ser Lys Lys Arg Ala Thr Lys Ala Lys Asn Thr Gly
            260                 265                 270

Gln Arg Gly Leu Lys Met
            275

<210> SEQ ID NO 60
<211> LENGTH: 727
<212> TYPE: PRT
<213> ORGANISM: Homo sapiens

<400> SEQUENCE: 60

Met Asn Gly Glu Ala Asp Cys Pro Thr Asp Leu Glu Met Ala Ala Pro
1               5                   10                  15

Lys Gly Gln Asp Arg Trp Ser Gln Glu Asp Met Leu Thr Leu Leu Glu
            20                  25                  30

Cys Met Lys Asn Asn Leu Pro Ser Asn Asp Ser Ser Lys Phe Lys Thr
        35                  40                  45

Thr Glu Ser His Met Asp Trp Glu Lys Val Ala Phe Lys Asp Phe Ser
    50                  55                  60

Gly Asp Met Cys Lys Leu Lys Trp Val Glu Ile Ser Asn Glu Val Arg
65                  70                  75                  80

Lys Phe Arg Thr Leu Thr Glu Leu Ile Leu Asp Ala Gln Glu His Val
                85                  90                  95

Lys Asn Pro Tyr Lys Gly Lys Lys Leu Lys Lys His Pro Asp Phe Pro
            100                 105                 110

Lys Lys Pro Leu Thr Pro Tyr Phe Arg Phe Phe Met Glu Lys Arg Ala
        115                 120                 125

Lys Tyr Ala Lys Leu His Pro Glu Met Ser Asn Leu Asp Leu Thr Lys
    130                 135                 140

Ile Leu Ser Lys Lys Tyr Lys Glu Leu Pro Glu Lys Lys Lys Met Lys
145                 150                 155                 160

Tyr Ile Gln Asp Phe Gln Arg Glu Lys Gln Glu Phe Glu Arg Asn Leu
                165                 170                 175

Ala Arg Phe Arg Glu Asp His Pro Asp Leu Ile Gln Asn Ala Lys Lys
            180                 185                 190
```

```
Ser Asp Ile Pro Glu Lys Pro Lys Thr Pro Gln Gln Leu Trp Tyr Thr
        195                 200                 205

His Glu Lys Lys Val Tyr Leu Lys Val Arg Pro Asp Glu Ile Met Arg
        210                 215                 220

Asp Tyr Ile Gln Lys His Pro Glu Leu Asn Ile Ser Glu Glu Gly Ile
225                 230                 235                 240

Thr Lys Ser Thr Leu Thr Lys Ala Glu Arg Gln Leu Lys Asp Lys Phe
            245                 250                 255

Asp Gly Arg Pro Thr Lys Pro Pro Asn Ser Tyr Ser Leu Tyr Cys
                260                 265                 270

Ala Glu Leu Met Ala Asn Met Lys Asp Val Pro Ser Thr Glu Arg Met
            275                 280                 285

Val Leu Cys Ser Gln Gln Trp Lys Leu Leu Ser Gln Lys Glu Lys Asp
        290                 295                 300

Ala Tyr His Lys Lys Cys Asp Gln Lys Lys Asp Tyr Glu Val Glu
305                 310                 315                 320

Leu Leu Arg Phe Leu Glu Ser Leu Pro Glu Glu Gln Gln Arg Val
                325                 330                 335

Leu Gly Glu Glu Lys Met Leu Asn Ile Asn Lys Lys Gln Ala Thr Ser
            340                 345                 350

Pro Ala Ser Lys Lys Pro Ala Gln Glu Gly Gly Lys Gly Gly Ser Glu
        355                 360                 365

Lys Pro Lys Arg Pro Val Ser Ala Met Phe Ile Phe Ser Glu Glu Lys
        370                 375                 380

Arg Arg Gln Leu Gln Glu Arg Pro Glu Leu Ser Glu Ser Glu Leu
385                 390                 395                 400

Thr Arg Leu Leu Ala Arg Met Trp Asn Asp Leu Ser Glu Lys Lys Lys
            405                 410                 415

Ala Lys Tyr Lys Ala Arg Glu Ala Ala Leu Lys Ala Gln Ser Glu Arg
            420                 425                 430

Lys Pro Gly Gly Glu Arg Glu Arg Gly Lys Leu Pro Glu Ser Pro
        435                 440                 445

Lys Arg Ala Glu Glu Ile Trp Gln Gln Ser Val Ile Gly Asp Tyr Leu
        450                 455                 460

Ala Arg Phe Lys Asn Asp Arg Val Lys Ala Leu Lys Ala Met Glu Met
465                 470                 475                 480

Thr Trp Asn Asn Met Glu Lys Lys Glu Lys Leu Met Trp Ile Lys Lys
                485                 490                 495

Ala Ala Glu Asp Gln Lys Arg Tyr Glu Arg Glu Leu Ser Glu Met Arg
            500                 505                 510

Ala Pro Pro Ala Ala Thr Asn Ser Ser Lys Lys Met Lys Phe Gln Gly
            515                 520                 525

Glu Pro Lys Lys Pro Pro Met Asn Gly Tyr Gln Lys Phe Ser Gln Glu
        530                 535                 540

Leu Leu Ser Asn Gly Glu Leu Asn His Leu Pro Leu Lys Glu Arg Met
545                 550                 555                 560

Val Glu Ile Gly Ser Arg Trp Gln Arg Ile Ser Gln Ser Gln Lys Glu
                565                 570                 575

His Tyr Lys Lys Leu Ala Glu Glu Gln Lys Gln Tyr Lys Val His
            580                 585                 590

Leu Asp Leu Trp Val Lys Ser Leu Ser Pro Gln Asp Arg Ala Ala Tyr
            595                 600                 605
```

```
Lys Glu Tyr Ile Ser Asn Lys Arg Lys Ser Met Thr Lys Leu Arg Gly
            610                 615                 620

Pro Asn Pro Lys Ser Ser Arg Thr Thr Leu Gln Ser Lys Ser Glu Ser
625                 630                 635                 640

Glu Glu Asp Asp Glu Glu Asp Glu Asp Glu Asp Glu Asp Glu Glu
            645                 650                 655

Glu Glu Asp Asp Glu Asn Gly Asp Ser Ser Glu Asp Gly Gly Asp Ser
            660                 665                 670

Ser Glu Ser Ser Ser Glu Asp Ser Glu Asp Gly Asp Glu Asn Glu
            675                 680                 685

Glu Asp Asp Glu Asp Glu Asp Asp Glu Asp Asp Glu Asp Glu
690                 695                 700

Asp Asn Glu Ser Glu Gly Ser Ser Ser Ser Ser Ser Ser Gly Asp
705                 710                 715                 720

Ser Ser Asp Ser Asp Ser Asn
            725

<210> SEQ ID NO 61
<211> LENGTH: 727
<212> TYPE: PRT
<213> ORGANISM: Homo sapiens

<400> SEQUENCE: 61

Met Asn Gly Glu Ala Asp Cys Pro Thr Asp Leu Glu Met Ala Ala Pro
1               5                   10                  15

Lys Gly Gln Asp Arg Trp Ser Gln Glu Asp Met Leu Thr Leu Leu Glu
            20                  25                  30

Cys Met Lys Asn Asn Leu Pro Ser Asn Asp Ser Ser Lys Phe Lys Thr
        35                  40                  45

Thr Glu Ser His Met Asp Trp Glu Lys Val Ala Phe Lys Asp Phe Ser
    50                  55                  60

Gly Asp Met Cys Lys Leu Lys Trp Val Glu Ile Ser Asn Glu Val Arg
65                  70                  75                  80

Lys Phe Arg Thr Leu Thr Glu Leu Ile Leu Asp Ala Gln Glu His Val
                85                  90                  95

Lys Asn Pro Tyr Lys Gly Lys Lys Leu Lys Lys His Pro Asp Phe Pro
            100                 105                 110

Lys Lys Pro Leu Thr Pro Tyr Phe Arg Phe Phe Met Glu Lys Arg Ala
        115                 120                 125

Lys Tyr Ala Lys Leu His Pro Glu Met Ser Asn Leu Asp Leu Thr Lys
    130                 135                 140

Ile Leu Ser Lys Lys Tyr Lys Glu Leu Pro Glu Lys Lys Lys Met Lys
145                 150                 155                 160

Tyr Ile Gln Asp Phe Gln Arg Glu Lys Gln Phe Glu Arg Asn Leu
                165                 170                 175

Ala Arg Phe Arg Glu Asp His Pro Asp Leu Ile Gln Asn Ala Lys Lys
            180                 185                 190

Ser Asp Ile Pro Glu Lys Pro Lys Thr Pro Gln Gln Leu Trp Tyr Thr
        195                 200                 205

His Glu Lys Lys Val Tyr Leu Lys Val Arg Pro Asp Glu Ile Met Arg
    210                 215                 220

Asp Tyr Ile Gln Lys His Pro Glu Leu Asn Ile Ser Glu Glu Gly Ile
225                 230                 235                 240

Thr Lys Ser Thr Leu Thr Lys Ala Glu Arg Gln Leu Lys Asp Lys Phe
                245                 250                 255
```

Asp Gly Arg Pro Thr Lys Pro Pro Asn Ser Tyr Ser Leu Tyr Cys
            260             265             270

Ala Glu Leu Met Ala Asn Met Lys Asp Val Pro Ser Thr Glu Arg Met
            275             280             285

Val Leu Cys Ser Gln Gln Trp Lys Leu Leu Ser Gln Lys Glu Lys Asp
290             295             300

Ala Tyr His Lys Lys Cys Asp Gln Lys Lys Asp Tyr Glu Val Glu
305             310             315             320

Leu Leu Arg Phe Leu Glu Ser Leu Pro Glu Glu Gln Gln Arg Val
                325             330             335

Leu Gly Glu Glu Lys Met Leu Asn Ile Asn Lys Lys Gln Ala Thr Ser
            340             345             350

Pro Ala Ser Lys Lys Pro Ala Gln Glu Gly Lys Gly Gly Ser Glu
            355             360             365

Lys Pro Lys Arg Pro Val Ser Ala Met Phe Ile Phe Ser Glu Glu Lys
            370             375             380

Arg Arg Gln Leu Gln Glu Glu Arg Pro Glu Leu Ser Glu Ser Glu Leu
385             390             395             400

Thr Arg Leu Leu Ala Arg Met Trp Asn Asp Leu Ser Glu Lys Lys Lys
            405             410             415

Ala Lys Tyr Lys Ala Arg Glu Ala Ala Leu Lys Ala Gln Ser Glu Arg
            420             425             430

Lys Pro Gly Gly Glu Arg Glu Glu Arg Gly Lys Leu Pro Glu Ser Pro
            435             440             445

Lys Arg Ala Glu Glu Ile Trp Gln Gln Ser Val Ile Gly Asp Tyr Leu
            450             455             460

Ala Arg Phe Lys Asn Asp Arg Val Lys Ala Leu Lys Ala Met Glu Met
465             470             475             480

Thr Trp Asn Asn Met Glu Lys Lys Glu Lys Leu Met Trp Ile Lys Lys
            485             490             495

Ala Ala Glu Asp Gln Lys Arg Tyr Glu Arg Glu Leu Ser Glu Met Arg
            500             505             510

Ala Pro Pro Ala Ala Thr Asn Ser Ser Lys Lys Met Lys Phe Gln Gly
            515             520             525

Glu Pro Lys Lys Pro Pro Met Asn Gly Tyr Gln Lys Phe Ser Gln Glu
            530             535             540

Leu Leu Ser Asn Gly Glu Leu Asn His Leu Pro Leu Lys Glu Arg Met
545             550             555             560

Val Glu Ile Gly Ser Arg Trp Gln Arg Ile Ser Gln Ser Gln Lys Glu
            565             570             575

His Tyr Lys Lys Leu Ala Glu Glu Gln Gln Lys Gln Tyr Lys Val His
            580             585             590

Leu Asp Leu Trp Val Lys Ser Leu Ser Pro Gln Asp Arg Ala Ala Tyr
            595             600             605

Lys Glu Tyr Ile Ser Asn Lys Arg Lys Ser Met Thr Lys Leu Arg Gly
            610             615             620

Pro Asn Pro Lys Ser Ser Arg Thr Thr Leu Gln Ser Lys Ser Glu Ser
625             630             635             640

Glu Glu Asp Asp Glu Glu Asp Glu Asp Glu Asp Glu Asp Glu Glu
            645             650             655

Glu Glu Asp Asp Glu Asn Gly Asp Ser Ser Glu Asp Gly Gly Asp Ser
            660             665             670

```
Ser Glu Ser Ser Ser Glu Asp Glu Ser Asp Gly Asp Glu Asn Glu
            675                 680                 685

Glu Asp Asp Glu Asp Asp Asp Glu Asp Asp Ser Glu Asp Glu
690                 695                 700

Asp Asn Glu Ser Glu Gly Ser Ser Ser Ser Ser Ser Ser Gly Asp
705                 710                 715                 720

Ser Ser Asp Ser Asp Ser Asn
            725

<210> SEQ ID NO 62
<211> LENGTH: 764
<212> TYPE: PRT
<213> ORGANISM: Homo sapiens

<400> SEQUENCE: 62

Met Asn Gly Glu Ala Asp Cys Pro Thr Asp Leu Glu Met Ala Ala Pro
1               5                   10                  15

Lys Gly Gln Asp Arg Trp Ser Gln Glu Asp Met Leu Thr Leu Leu Glu
            20                  25                  30

Cys Met Lys Asn Asn Leu Pro Ser Asn Asp Ser Ser Lys Phe Lys Thr
        35                  40                  45

Thr Glu Ser His Met Asp Trp Glu Lys Val Ala Phe Lys Asp Phe Ser
50                  55                  60

Gly Asp Met Cys Lys Leu Lys Trp Val Glu Ile Ser Asn Glu Val Arg
65                  70                  75                  80

Lys Phe Arg Thr Leu Thr Glu Leu Ile Leu Asp Ala Gln Glu His Val
                85                  90                  95

Lys Asn Pro Tyr Lys Gly Lys Leu Lys Lys His Pro Asp Phe Pro
            100                 105                 110

Lys Lys Pro Leu Thr Pro Tyr Phe Arg Phe Phe Met Glu Lys Arg Ala
        115                 120                 125

Lys Tyr Ala Lys Leu His Pro Glu Met Ser Asn Leu Asp Leu Thr Lys
130                 135                 140

Ile Leu Ser Lys Lys Tyr Lys Glu Leu Pro Glu Lys Lys Lys Met Lys
145                 150                 155                 160

Tyr Ile Gln Asp Phe Gln Arg Glu Lys Gln Glu Phe Glu Arg Asn Leu
                165                 170                 175

Ala Arg Phe Arg Glu Asp His Pro Asp Leu Ile Gln Asn Ala Lys Lys
            180                 185                 190

Ser Asp Ile Pro Glu Lys Pro Lys Thr Pro Gln Gln Leu Trp Tyr Thr
        195                 200                 205

His Glu Lys Lys Val Tyr Leu Lys Val Arg Pro Asp Ala Thr Thr Lys
210                 215                 220

Glu Val Lys Asp Ser Leu Gly Lys Gln Trp Ser Gln Leu Ser Asp Lys
225                 230                 235                 240

Lys Arg Leu Lys Trp Ile His Lys Ala Leu Glu Gln Arg Lys Glu Tyr
                245                 250                 255

Glu Glu Ile Met Arg Asp Tyr Ile Gln Lys His Pro Glu Leu Asn Ile
            260                 265                 270

Ser Glu Glu Gly Ile Thr Lys Ser Thr Leu Thr Lys Ala Glu Arg Gln
        275                 280                 285

Leu Lys Asp Lys Phe Asp Gly Arg Pro Thr Lys Pro Pro Pro Asn Ser
290                 295                 300

Tyr Ser Leu Tyr Cys Ala Glu Leu Met Ala Asn Met Lys Asp Val Pro
305                 310                 315                 320
```

Ser Thr Glu Arg Met Val Leu Cys Ser Gln Gln Trp Lys Leu Leu Ser
            325                 330                 335

Gln Lys Glu Lys Asp Ala Tyr His Lys Lys Cys Asp Gln Lys Lys Lys
            340                 345                 350

Asp Tyr Glu Val Glu Leu Leu Arg Phe Leu Glu Ser Leu Pro Glu Glu
            355                 360                 365

Glu Gln Gln Arg Val Leu Gly Glu Glu Lys Met Leu Asn Ile Asn Lys
        370                 375                 380

Lys Gln Ala Thr Ser Pro Ala Ser Lys Lys Pro Ala Gln Glu Gly Gly
385                 390                 395                 400

Lys Gly Gly Ser Glu Lys Pro Lys Arg Pro Val Ser Ala Met Phe Ile
                405                 410                 415

Phe Ser Glu Glu Lys Arg Arg Gln Leu Gln Glu Glu Arg Pro Glu Leu
            420                 425                 430

Ser Glu Ser Glu Leu Thr Arg Leu Leu Ala Arg Met Trp Asn Asp Leu
            435                 440                 445

Ser Glu Lys Lys Lys Ala Lys Tyr Lys Ala Arg Glu Ala Ala Leu Lys
        450                 455                 460

Ala Gln Ser Glu Arg Lys Pro Gly Gly Glu Arg Glu Glu Arg Gly Lys
465                 470                 475                 480

Leu Pro Glu Ser Pro Lys Arg Ala Glu Glu Ile Trp Gln Gln Ser Val
                485                 490                 495

Ile Gly Asp Tyr Leu Ala Arg Phe Lys Asn Asp Arg Val Lys Ala Leu
            500                 505                 510

Lys Ala Met Glu Met Thr Trp Asn Asn Met Glu Lys Lys Glu Lys Leu
            515                 520                 525

Met Trp Ile Lys Lys Ala Ala Glu Asp Gln Lys Arg Tyr Glu Arg Glu
        530                 535                 540

Leu Ser Glu Met Arg Ala Pro Pro Ala Ala Thr Asn Ser Ser Lys Lys
545                 550                 555                 560

Met Lys Phe Gln Gly Glu Pro Lys Lys Pro Pro Met Asn Gly Tyr Gln
                565                 570                 575

Lys Phe Ser Gln Glu Leu Leu Ser Asn Gly Glu Leu Asn His Leu Pro
            580                 585                 590

Leu Lys Glu Arg Met Val Glu Ile Gly Ser Arg Trp Gln Arg Ile Ser
            595                 600                 605

Gln Ser Gln Lys Glu His Tyr Lys Lys Leu Ala Glu Glu Gln Gln Lys
        610                 615                 620

Gln Tyr Lys Val His Leu Asp Leu Trp Val Lys Ser Leu Ser Pro Gln
625                 630                 635                 640

Asp Arg Ala Ala Tyr Lys Glu Tyr Ile Ser Asn Lys Arg Lys Ser Met
                645                 650                 655

Thr Lys Leu Arg Gly Pro Asn Pro Lys Ser Ser Arg Thr Thr Leu Gln
            660                 665                 670

Ser Lys Ser Glu Ser Glu Glu Asp Glu Glu Asp Glu Asp Glu Asp Glu
            675                 680                 685

Asp Glu Asp Glu Glu Glu Glu Asp Asp Glu Asn Gly Asp Ser Ser Glu
        690                 695                 700

Asp Gly Gly Asp Ser Ser Glu Ser Ser Ser Glu Asp Glu Ser Glu Asp
705                 710                 715                 720

Gly Asp Glu Asn Glu Glu Asp Asp Glu Asp Glu Asp Asp Asp Glu Asp
                725                 730                 735

```
Asp Asp Glu Asp Glu Asp Asn Glu Ser Gly Ser Ser Ser Ser
            740                 745                 750

Ser Ser Ser Gly Asp Ser Asp Ser Asp Ser Asn
        755                 760

<210> SEQ ID NO 63
<211> LENGTH: 390
<212> TYPE: PRT
<213> ORGANISM: Homo sapiens

<400> SEQUENCE: 63

Met Tyr Arg Asp Asp Leu Glu Arg Phe Lys Glu Phe Lys Ala Gln Gly
1               5                   10                  15

Val Ala Ile Lys Phe Gly Lys Phe Ser Val Lys Glu Asn Lys Gln Leu
            20                  25                  30

Glu Lys Asn Val Glu Asp Phe Leu Ala Leu Thr Gly Ile Glu Ser Ala
        35                  40                  45

Asp Lys Leu Leu Tyr Thr Asp Arg Tyr Pro Glu Glu Lys Ser Val Ile
    50                  55                  60

Thr Asn Leu Lys Arg Arg Tyr Ser Phe Arg Leu His Ile Gly Arg Asn
65                  70                  75                  80

Ile Ala Arg Pro Trp Lys Leu Ile Tyr Tyr Arg Ala Lys Lys Met Phe
                85                  90                  95

Asp Val Asn Asn Tyr Lys Gly Arg Tyr Ser Glu Gly Asp Thr Glu Lys
            100                 105                 110

Leu Lys Met Tyr His Ser Leu Leu Gly Asn Asp Trp Lys Thr Ile Gly
        115                 120                 125

Glu Met Val Ala Arg Ser Ser Leu Ser Val Ala Leu Lys Phe Ser Gln
    130                 135                 140

Ile Ser Ser Gln Arg Asn Arg Gly Ala Trp Ser Lys Ser Glu Thr Arg
145                 150                 155                 160

Lys Leu Ile Lys Ala Val Glu Glu Val Ile Leu Lys Lys Met Ser Pro
                165                 170                 175

Gln Glu Leu Lys Glu Val Asp Ser Lys Leu Gln Glu Asn Pro Glu Ser
            180                 185                 190

Cys Leu Ser Ile Val Arg Glu Lys Leu Tyr Lys Gly Ile Ser Trp Val
        195                 200                 205

Glu Val Glu Ala Lys Val Gln Thr Arg Asn Trp Met Gln Cys Lys Ser
    210                 215                 220

Lys Trp Thr Glu Ile Leu Thr Lys Arg Met Thr Asn Gly Arg Arg Ile
225                 230                 235                 240

Tyr Tyr Gly Met Asn Ala Leu Arg Ala Lys Val Ser Leu Ile Glu Arg
                245                 250                 255

Leu Tyr Glu Ile Asn Val Glu Asp Thr Asn Glu Ile Asp Trp Glu Asp
            260                 265                 270

Leu Ala Ser Ala Ile Gly Asp Val Pro Pro Ser Tyr Val Gln Thr Lys
        275                 280                 285

Phe Ser Arg Leu Lys Ala Val Tyr Val Pro Phe Trp Gln Lys Lys Thr
    290                 295                 300

Phe Pro Glu Ile Ile Asp Tyr Leu Tyr Glu Thr Thr Leu Pro Leu Leu
305                 310                 315                 320

Lys Glu Lys Leu Glu Lys Met Met Glu Lys Lys Gly Thr Lys Ile Gln
                325                 330                 335

Thr Pro Ala Ala Pro Lys Gln Val Phe Pro Phe Arg Asp Ile Phe Tyr
            340                 345                 350
```

```
Tyr Glu Asp Asp Ser Glu Gly Glu Asp Ile Glu Lys Glu Ser Glu Gly
        355                 360                 365

Gln Ala Pro Cys Met Ala His Ala Cys Asn Ser Ser Thr Leu Gly Gly
    370                 375                 380

Gln Gly Arg Trp Ile Ile
385                 390

<210> SEQ ID NO 64
<211> LENGTH: 905
<212> TYPE: PRT
<213> ORGANISM: Homo sapiens

<400> SEQUENCE: 64

Met Glu Gly Glu Ser Ser Arg Phe Glu Ile His Thr Pro Val Ser Asp
1               5                   10                  15

Lys Lys Lys Lys Lys Cys Ser Ile His Lys Glu Arg Pro Gln Lys His
                20                  25                  30

Ser His Glu Ile Phe Arg Asp Ser Ser Leu Val Asn Glu Gln Ser Gln
            35                  40                  45

Ile Thr Arg Arg Lys Lys Arg Lys Lys Asp Phe Gln His Leu Ile Ser
        50                  55                  60

Ser Pro Leu Lys Lys Ser Arg Ile Cys Asp Glu Thr Ala Asn Ala Thr
65                  70                  75                  80

Ser Thr Leu Lys Lys Arg Lys Lys Arg Arg Tyr Ser Ala Leu Glu Val
                85                  90                  95

Asp Glu Glu Ala Gly Val Thr Val Val Leu Val Asp Lys Glu Asn Ile
            100                 105                 110

Asn Asn Thr Pro Lys His Phe Arg Lys Asp Val Asp Val Val Cys Val
        115                 120                 125

Asp Met Ser Ile Glu Gln Lys Leu Pro Arg Lys Pro Lys Thr Asp Lys
    130                 135                 140

Phe Gln Val Leu Ala Lys Ser His Ala His Lys Ser Glu Ala Leu His
145                 150                 155                 160

Ser Lys Val Arg Glu Lys Lys Asn Lys Lys His Gln Arg Lys Ala Ala
                165                 170                 175

Ser Trp Glu Ser Gln Arg Ala Arg Asp Thr Leu Pro Gln Ser Glu Ser
            180                 185                 190

His Gln Glu Glu Ser Trp Leu Ser Val Gly Pro Gly Gly Glu Ile Thr
        195                 200                 205

Glu Leu Pro Ala Ser Ala His Lys Asn Lys Ser Lys Lys Lys Lys Lys
    210                 215                 220

Lys Ser Ser Asn Arg Glu Tyr Glu Thr Leu Ala Met Pro Glu Gly Ser
225                 230                 235                 240

Gln Ala Gly Arg Glu Ala Gly Thr Asp Met Gln Glu Ser Gln Pro Thr
                245                 250                 255

Val Gly Leu Asp Asp Glu Thr Pro Gln Leu Leu Gly Pro Thr His Lys
            260                 265                 270

Lys Lys Ser Lys Lys Lys Lys Lys Lys Ser Asn His Gln Glu Phe
        275                 280                 285

Glu Ala Leu Ala Met Pro Glu Gly Ser Gln Val Gly Ser Glu Val Gly
    290                 295                 300

Ala Asp Met Gln Glu Ser Arg Pro Ala Val Gly Leu His Gly Glu Thr
305                 310                 315                 320

Ala Gly Ile Pro Ala Pro Ala Tyr Lys Asn Lys Ser Lys Lys Lys Lys
```

```
                    325                 330                 335
Lys Lys Ser Asn His Gln Glu Phe Glu Ala Val Ala Met Pro Glu Ser
                340                 345                 350
Leu Glu Ser Ala Tyr Pro Glu Gly Ser Gln Val Gly Ser Glu Val Gly
                355                 360                 365
Thr Val Glu Gly Ser Thr Ala Leu Lys Gly Phe Lys Glu Ser Asn Ser
            370                 375                 380
Thr Lys Lys Ser Lys Lys Arg Lys Leu Thr Ser Val Lys Arg Ala
385                 390                 395                 400
Arg Val Ser Gly Asp Asp Phe Ser Val Pro Ser Lys Asn Ser Glu Ser
                405                 410                 415
Thr Leu Phe Asp Ser Val Glu Gly Asp Gly Ala Met Met Glu Glu Gly
                420                 425                 430
Val Lys Ser Arg Pro Arg Gln Lys Lys Thr Gln Ala Cys Leu Ala Ser
                435                 440                 445
Lys His Val Gln Glu Ala Pro Arg Leu Glu Pro Ala Asn Glu Glu His
            450                 455                 460
Asn Val Glu Thr Ala Glu Asp Ser Glu Ile Arg Tyr Leu Ser Ala Asp
465                 470                 475                 480
Ser Gly Asp Ala Asp Asp Ser Asp Ala Asp Leu Gly Ser Ala Val Lys
                485                 490                 495
Gln Leu Gln Glu Phe Ile Pro Asn Ile Lys Asp Arg Ala Thr Ser Thr
                500                 505                 510
Ile Lys Arg Met Tyr Arg Asp Asp Leu Glu Arg Phe Lys Glu Phe Lys
            515                 520                 525
Ala Gln Gly Val Ala Ile Lys Phe Gly Lys Phe Ser Val Lys Glu Asn
            530                 535                 540
Lys Gln Leu Glu Lys Asn Val Glu Asp Phe Leu Ala Leu Thr Gly Ile
545                 550                 555                 560
Glu Ser Ala Asp Lys Leu Leu Tyr Thr Asp Arg Tyr Pro Glu Glu Lys
                565                 570                 575
Ser Val Ile Thr Asn Leu Lys Arg Arg Tyr Ser Phe Arg Leu His Ile
            580                 585                 590
Gly Arg Asn Ile Ala Arg Pro Trp Lys Leu Ile Tyr Arg Ala Lys
            595                 600                 605
Lys Met Phe Asp Val Asn Asn Tyr Lys Gly Arg Tyr Ser Glu Gly Asp
            610                 615                 620
Thr Glu Lys Leu Lys Met Tyr His Ser Leu Leu Gly Asn Asp Trp Lys
625                 630                 635                 640
Thr Ile Gly Glu Met Val Ala Arg Ser Ser Leu Ser Val Ala Leu Lys
                645                 650                 655
Phe Ser Gln Ile Ser Ser Gln Arg Asn Arg Gly Ala Trp Ser Lys Ser
                660                 665                 670
Glu Thr Arg Lys Leu Ile Lys Ala Val Glu Glu Val Ile Leu Lys Lys
            675                 680                 685
Met Ser Pro Gln Glu Leu Lys Glu Val Asp Ser Lys Leu Gln Glu Asn
            690                 695                 700
Pro Glu Ser Cys Leu Ser Ile Val Arg Glu Lys Leu Tyr Lys Gly Ile
705                 710                 715                 720
Ser Trp Val Glu Val Glu Ala Lys Val Gln Thr Arg Asn Trp Met Gln
                725                 730                 735
Cys Lys Ser Lys Trp Thr Glu Ile Leu Thr Lys Arg Met Thr Asn Gly
            740                 745                 750
```

```
Arg Arg Ile Tyr Tyr Gly Met Asn Ala Leu Arg Ala Lys Val Ser Leu
        755                 760                 765

Ile Glu Arg Leu Tyr Glu Ile Asn Val Glu Asp Thr Asn Glu Ile Asp
    770                 775                 780

Trp Glu Asp Leu Ala Ser Ala Ile Gly Asp Val Pro Pro Ser Tyr Val
785                 790                 795                 800

Gln Thr Lys Phe Ser Arg Leu Lys Ala Val Tyr Val Pro Phe Trp Gln
                805                 810                 815

Lys Lys Thr Phe Pro Glu Ile Ile Asp Tyr Leu Tyr Glu Thr Thr Leu
                820                 825                 830

Pro Leu Leu Lys Glu Lys Leu Glu Lys Met Met Glu Lys Lys Gly Thr
                835                 840                 845

Lys Ile Gln Thr Pro Ala Ala Pro Lys Gln Val Phe Pro Phe Arg Asp
                850                 855                 860

Ile Phe Tyr Tyr Glu Asp Asp Ser Glu Gly Glu Asp Ile Glu Lys Glu
865                 870                 875                 880

Ser Glu Gly Gln Ala Pro Cys Met Ala His Ala Cys Asn Ser Ser Thr
                885                 890                 895

Leu Gly Gly Gln Gly Arg Trp Ile Ile
                900                 905

<210> SEQ ID NO 65
<211> LENGTH: 390
<212> TYPE: PRT
<213> ORGANISM: Homo sapiens

<400> SEQUENCE: 65

Met Glu Asp Pro Thr Leu Tyr Ile Val Glu Arg Pro Leu Pro Gly Tyr
1               5                   10                  15

Pro Asp Ala Glu Ala Pro Glu Pro Ser Ser Ala Gly Ala Gln Ala Ala
                20                  25                  30

Glu Glu Pro Ser Gly Ala Gly Ser Glu Glu Leu Ile Lys Ser Asp Gln
            35                  40                  45

Val Asn Gly Val Leu Val Leu Ser Leu Leu Asp Lys Ile Ile Gly Ala
        50                  55                  60

Val Asp Gln Ile Gln Leu Thr Gln Ala Gln Leu Glu Glu Arg Gln Ala
65                  70                  75                  80

Glu Met Glu Gly Ala Val Gln Ser Ile Gln Gly Glu Leu Ser Lys Leu
                85                  90                  95

Gly Lys Ala His Ala Thr Thr Ser Asn Thr Val Ser Lys Leu Leu Glu
                100                 105                 110

Lys Val Arg Lys Val Ser Val Asn Val Lys Thr Val Arg Gly Ser Leu
            115                 120                 125

Glu Arg Gln Ala Gly Gln Ile Lys Lys Leu Glu Val Asn Glu Ala Glu
        130                 135                 140

Leu Leu Arg Arg Arg Asn Phe Lys Val Met Ile Tyr Gln Asp Glu Val
145                 150                 155                 160

Lys Leu Pro Ala Lys Leu Ser Ile Ser Lys Ser Leu Lys Glu Ser Glu
                165                 170                 175

Ala Leu Pro Glu Lys Glu Gly Glu Leu Gly Glu Gly Glu Arg Pro
                180                 185                 190

Glu Glu Asp Ala Ala Ala Leu Glu Leu Ser Ser Asp Glu Ala Val Glu
            195                 200                 205

Val Glu Glu Val Ile Glu Glu Ser Arg Ala Glu Arg Ile Lys Arg Ser
```

-continued

```
                210                 215                 220

Gly Leu Arg Arg Val Asp Asp Phe Lys Ala Phe Ser Lys Glu Lys
225                 230                 235                 240

Met Glu Lys Thr Lys Val Arg Thr Arg Glu Asn Leu Glu Lys Thr Arg
                245                 250                 255

Leu Lys Thr Lys Glu Asn Leu Glu Lys Thr Arg His Thr Leu Glu Lys
                260                 265                 270

Arg Met Asn Lys Leu Gly Thr Arg Leu Val Pro Ala Glu Arg Arg Glu
                275                 280                 285

Lys Leu Lys Thr Ser Arg Asp Lys Leu Arg Lys Ser Phe Thr Pro Asp
                290                 295                 300

His Val Val Tyr Ala Arg Ser Lys Thr Ala Val Tyr Lys Val Pro Pro
305                 310                 315                 320

Phe Thr Phe His Val Lys Lys Ile Arg Glu Gly Gln Val Glu Val Leu
                325                 330                 335

Lys Ala Thr Glu Met Val Glu Val Gly Ala Asp Asp Asp Gly Gly
                340                 345                 350

Ala Glu Arg Gly Glu Ala Gly Asp Leu Arg Arg Gly Ser Ser Pro Asp
                355                 360                 365

Val His Ala Leu Leu Glu Ile Thr Glu Glu Ser Asp Ala Val Leu Val
                370                 375                 380

Asp Lys Ser Asp Ser Asp
385                 390

<210> SEQ ID NO 66
<211> LENGTH: 133
<212> TYPE: PRT
<213> ORGANISM: Homo sapiens

<400> SEQUENCE: 66

Met Arg Pro Leu Thr Glu Glu Thr Arg Val Met Phe Glu Lys Ile
1               5                   10                  15

Ala Lys Tyr Ile Gly Glu Asn Leu Gln Leu Leu Val Asp Arg Pro Asp
                20                  25                  30

Gly Thr Tyr Cys Phe Arg Leu His Asn Asp Arg Val Tyr Tyr Val Ser
                35                  40                  45

Glu Lys Ile Met Lys Leu Ala Ala Asn Ile Ser Gly Asp Lys Leu Val
                50                  55                  60

Ser Leu Gly Thr Cys Phe Gly Lys Phe Thr Lys Thr His Lys Phe Arg
65                  70                  75                  80

Leu His Val Thr Ala Leu Asp Tyr Leu Ala Pro Tyr Ala Lys Gly Phe
                85                  90                  95

Gly Val Ala Ala Lys Ser Thr Gln Asp Cys Arg Lys Val Asp Pro Met
                100                 105                 110

Ala Ile Val Val Phe His Gln Ala Asp Ile Gly Glu Tyr Val Arg His
                115                 120                 125

Glu Glu Thr Leu Thr
        130

<210> SEQ ID NO 67
<211> LENGTH: 180
<212> TYPE: PRT
<213> ORGANISM: Homo sapiens

<400> SEQUENCE: 67

Met Arg Pro Leu Thr Glu Glu Glu Thr Arg Val Met Phe Glu Lys Ile
```

```
            1               5                  10                 15
          Ala Lys Tyr Ile Gly Glu Asn Leu Gln Leu Leu Val Asp Arg Pro Asp
                          20                  25                 30
          Gly Thr Tyr Cys Phe Arg Leu His Asn Asp Arg Val Tyr Tyr Val Ser
                      35                  40                 45
          Glu Lys Ile Met Lys Leu Ala Ala Asn Ile Ser Gly Asp Lys Leu Val
                      50                  55                 60
          Ser Leu Gly Thr Cys Phe Gly Lys Phe Thr Lys Thr His Lys Phe Arg
          65                  70                  75                 80
          Leu His Val Thr Ala Leu Asp Tyr Leu Ala Pro Tyr Ala Lys Tyr Lys
                              85                  90                 95
          Val Trp Ile Lys Pro Gly Ala Glu Gln Ser Phe Leu Tyr Gly Asn His
                          100                 105                110
          Val Leu Lys Ser Gly Leu Gly Arg Ile Thr Glu Asn Thr Ser Gln Tyr
                      115                 120                125
          Gln Gly Val Val Val Tyr Ser Met Ala Asp Ile Pro Leu Gly Phe Gly
                      130                 135                140
          Val Ala Ala Lys Ser Thr Gln Asp Cys Arg Lys Val Asp Pro Met Ala
          145                 150                 155                160
          Ile Val Val Phe His Gln Ala Asp Ile Gly Glu Tyr Val Arg His Glu
                              165                 170                175
          Glu Thr Leu Thr
                      180

<210> SEQ ID NO 68
<211> LENGTH: 13357
<212> TYPE: DNA
<213> ORGANISM: Homo sapiens

<400> SEQUENCE: 68
gctgacacgc tgtcctctgg cgacctgtcg ctggagaggt tgggcctccg gatgcgcgcg      60
gggctctggc ctaccggtga cccggctagc cggccgcgct cctgcttgag ccgcctgccg     120
gggcccgcgg gcctgctgtt ctctcgcgcg tccgagcgtc ccgactcccg gtgccggccc     180
gggtccgggt ctctgacccca cccggggggcg gcggggaagg cggcgagggc caccgtgccc    240
ccgtgcgctc tccgctgcgg gcgcccgggg cggccgcgac aaccccaccc cgctggctcc     300
gtgccgtgcg tgtcaggcgt tctcgtctcc gcggggttgt ccgccgcccc ttccccggag     360
tggggggttg gccggagccg atcggctcgc tggccggccg gccggcctcc gctcccgggg     420
ggctcttcgt gatcgatgtg gtgacgtcgt gctctcccgg gccgggtccg agccgcgacg     480 ggcgagggggc ggacgttcgt ggcgaacggg accgtccttc tcgctccgcc ccgcggggggt    540 ccctcgtct ctcctctccc cgcccgccgg cggtgcgtgt gggaaggcgt ggggtgcgga      600
ccccggcccg acctcgccgt cccgcccgcc gccttctgcg tcgcggggcg ggccggcggg      660
gtcctctgac gcggcagaca gccctcgctg tcgcctccag tggttgtcga cttgcgggcg     720
gcccccctcc gcggcggtgg gggtgccgtc ccgccggccc gtcgtgctgc cctctcgggg     780
ggtttgcgcg agcgtcggct ccgcctgggc ccttgcggtg ctcctggagc gctccggggtt     840 gtccctcagg tgcccgaggc cgaacggtgg tgtgtcgttc ccgcccccgg cgcccccctcc    900 tccggtcgcc gccgcggtgt ccgcgcgtgg gtcctgaggg agctcgtcgg tgtggggttc    960
gaggcggttt gagtgagacg agacgagacg cgccccctccc acgcggggaa gggcgcccgc    1020
ctgctctcgg tgagcgcacg tccgtgctcc ccctctgggg ggtgcgcgcg ggccgtgtga    1080
```

```
gcgatcgcgg tgggttcggg ccggtgtgac gcgtgcgccg gccggccgcc gagggggctgc    1140 cgttctgcct ccgaccggtc gtgtgtgggt tgacttcgga ggcgctctgc ctcggaagga    1200
aggaggtggg tggacggggg ggcctggtgg ggttgcgcgc acgcgcgcac cggccgggcc    1260
cccgccctga acgcgaacgc tcgaggtggc cgcgcgcagg tgtttcctcg taccgcaggg    1320 cccccctccct tccccaggcg tccctcggcg cctctgcggg cccgaggagg agcggctggc    1380
gggtgggggg agtgtgaccc accctcggtg agaaaagcct tctctagcga tctgagaggc    1440
gtgccttggg ggtaccggat cccccgggcc gccgcctctg tctctgcctc cgttatggta    1500
gcgctgccgt agcgacccgc tcgcagagga ccctcctccg cttcccccctc gacggggttg    1560 ggggggagaa gcgagggttc cgccggccac cgcggtggtg gccgagtgcg gctcgtcgcc    1620
tactgtggcc cgcgcctccc ccttccgagt cgggggagga tcccgccggg ccggcccgg    1680 cgttcccagc gggttgggac gcggcggccg gcgggcggtg ggtgtgcgcg cccggcgctc    1740
tgtccggcgc gtgacccccct ccgccgcgag tcggctctcc gcccgctccc gtgccgagtc    1800
gtgaccggtg ccgacgaccg cgtttgcgtg gcacggggtc gggcccgcct ggccctggga    1860
aagcgtccca cggtgggggc gcgccggtct cccggagcgg gaccgggtcg gaggatggac    1920
gagaatcacg agcgacggtg gtgcgggcgt gtcgggttcg tggctgcggt cgctccgggg    1980 ccccccggtgg cggggccccg gggctcgcga ggcggttctc ggtgggggcc gagggccgtc    2040
cggcgtccca ggcggggcgc gcgggaccg ccctcgtgtc tgtggcggtg ggatcccgcg    2100
gccgtgtttt cctggtggcc cggccgtgcc tgaggtttct ccccgagccg ccgcctctgc    2160
gggctcccgg gtgccccttgc cctcgcggtc cccggcccctc gccgtctgt gccctcttcc    2220 ccgcccgccg cccgccgatc ctcttcttcc cccgagcgg ctcaccggct tcacgtccgt    2280
tggtggcccc gcctgggacc gaacccggca ccgcctcgtg gggcgccgcc gccggccact    2340
gatcggcccg gcgtccgcgt ccccggcgc gcgccttggg gaccgggtcg gtggcgcccc    2400 gcgtgggggcc cggtgggctt cccggagggt tccggggtc ggcctgccggc gcgtgcgggg    2460 gaggagacgg ttccggggga ccggccgcga ctgcggcggc ggtggtgggg gcagccgcgg    2520
ggatcgccga gggccggtcg gccgcccgg gtgccgcgcg gtgccgccgg cggcggtgag    2580
gccccgcgcg tgtgtcccgg ccgcggtcgg ccgcgctcga ggggtccccg tggcgtcccc    2640
ttccccgccg gccgccttttc tcgcgccttc ccgtcgccc cggcctcgcc cgtggtctct    2700
cgtcttctcc cggcccgctc ttccgaaccg ggtcggcgcg tccccccgggt gcgcctcgct    2760 tcccgggcct gccgcggccc ttccccgagg cgtccgtccc gggcgtcggc gtcggggaga    2820
gcccgtcctc cccgcgtggc gtcgccccgt tcggcgcgcg cgtgcgcccg agcgcggccc    2880
ggtggtccct gccggacagg cgttcgtgcg acgtgtggcg tgggtcgacc tccgccttgc    2940
cggtcgctcg cccttttcccc gggtcggggg gtggggcccg ggccggggcc tcggcccccgg    3000 tcgcggtccc ccgtcccggg cggggccggg cgcgccggcc ggcctcggtc ggccctccct    3060
tggccgtcgt gtggcgtgtg ccaccccctgc gcccgcgccc ccggcggggg ctcggagccg    3120
ggcttcggcc gggcccccggg ccctcgaccg gaccggtgcg cgggcgctgc ggccgcacgg    3180
cgcgactgtc cccgggccgg gcaccgcggt ccgcctctcg ctcgccgccc ggacgtcggg    3240
gccgccccgc ggggcgggcg gagcgccgtc cccgcctcgc cgccgcccgc gggcgccggc    3300 gcgcgcgcg cgccgcgtgg ccgccggtccc tccggccgc cgggcgcggg tcgggccgtc    3360
cgcctcctcg cggggcgggcg cgacgaagaa gcgtcgcggg tctgtggcgc ggggccccgg    3420
tggtcgtgtc gcgtggggg cgggtggttg gggcgtccgg ttcgccgcgc cccgccccgg    3480
```

```
ccccaccggt cccggccgcc gcccccgcgc ccgctcgctc cctcccgtcc gcccgtccgc   3540
ggcccgtccg tccgtccgtc gtcctcctcg cttgcggggc gccgggcccg tcctcgcgag   3600
gccccccggc cggccgtccg gccgcgtcgg ggcctcgccg cgctctacct tacctacctg   3660
gttgatcctg ccagtagcat atgcttgtct caaagattaa gccatgcatg tctgagtacg   3720
cacggccggt acagtgaaac tgcgaatggc tcattaaatc agttatggtt cctttggtcg   3780
ctcgctcctc tcctacttgg ataactgtgg taattctaga gctaatacat gccgacgggc   3840
gctgacccc  ttcgcggggg ggatgcgtgc atttatcaga tcaaaaccaa cccggtcagc   3900
ccctctccgg ccccggccgg ggggcgggcg ccggcggctt tggtgactct agataacctc   3960
gggccgatcg cacgcccccc gtggcggcga cgacccattc gaacgtctgc cctatcaact   4020
ttcgatggta gtcgccgtgc ctaccatggt gaccacgggt gacggggaat cagggttcga   4080
ttccggagag ggagcctgag aaacggctac cacatccaag gaaggcagca ggcgcgcaaa   4140
ttacccactc ccgacccggg gaggtagtga cgaaaaataa caatacagga ctctttcgag   4200
gccctgtaat tggaatgagt ccactttaaa tcctttaacg aggatccatt ggagggcaag   4260
tctggtgcca gcagccgcgg taattccagc tccaatagcg tatattaaag ttgctgcagt   4320
taaaaagctc gtagttggat cttgggagcg ggcgggcggt ccgccgcgag gcgagccacc   4380
gcccgtcccc gccccttgcc tctcggccgc cctcgatgc  tcttagctga gtgtcccgcg   4440
gggcccgaag cgtttacttt gaaaaaatta gagtgttcaa agcaggcccg agccgcctgg   4500
ataccgcagc taggaataat ggaataggac cgcggttcta ttttgttggt tttcggaact   4560
gaggccatga ttaagaggga cggccggggg cattcgtatt gcgccgctag aggtgaaatt   4620
cttggaccgg cgcaagacgg accagagcga aagcatttgc caagaatgtt ttcattaatc   4680
aagaacgaaa gtcggaggtt cgaagacgat cagataccgt cgtagttccg accataaacg   4740
atgccgaccg gcgatgcggc ggcgttattc ccatgacccg ccgggcagct tccgggaaac   4800
caaagtcttt gggttccggg gggagtatgg ttgcaaagct gaaacttaaa ggaattgacg   4860
gaagggcacc accaggagtg gagcctgcgg cttaatttga ctcaacacgg gaaacctcac   4920
ccggcccgga cacggacagg attgacagat tgatagctct ttctcgattc cgtgggtggt   4980
ggtgcatggc cgttcttagt tggtggagcg atttgtctgg ttaattccga taacgaacga   5040
gactctggca tgctaactag ttacgcgacc cccgagcggt cggcgtcccc caacttctta   5100
gagggacaag tggcgttcag ccacccgaga ttgagcaata acaggtctgt gatgccctta   5160
gatgtccggg gctgcacgcg cgctacactg actggctcag cgtgtgccta ccctacgccg   5220
gcaggcgcgg gtaacccgtt gaaccccatt cgtgatgggg atcggggatt gcaattattc   5280
cccatgaacg aggaattccc agtaagtgcg ggtcataagc ttgcgttgat taagtccctg   5340
cccttgtac  acaccgcccg tcgctactac cgattggatg gtttagtgag gccctcggat   5400
cggcccgcc  ggggtcggcc cacggccctg gcggagcgct gagaagacgg tcgaacttga   5460
ctatctagag gaagtaaaag tcgtaacaag gtttccgtag gtgaacctgc ggaaggatca   5520
ttaacgagc  ccggagggcg aggcccgcgc cggcgccgcc gccgccgcgc gcttccctcc   5580
gcacacccac cccccaccg  cgacgcgcg  cgtgcgcggg cggggcccgc gtgcccgttc   5640
gttcgctcgc tcgttcgttc gccgccggc  cccgccggcc gcgagagccg gagaactcgg   5700
gagggagacg gggagagag  agagagagag agaaagagaa agaagggcgt gtcgttggtg   5760
tgcgcgtgtc gtgggccgg  cgggcggcgg ggagcggtcc ccggccgcgg ccccgacgac   5820
```

```
gtgggtgtcg gcgggcgcgg gggcggttct cggcggcgtc gcggcgggtc tgggggggtc    5880
tcggtgccct cctccccgcc ggggcccgtc gtccggcccc gccgcgccgg ctccccgtct    5940
tcggggccgg ccggattccc gtcgcctccg ccgcgccgct ccgcgccgcc gggcacggcc    6000
ccgctcgctc tccccggcct tcccgctagg gcgtctcgag ggtcggggc cggacgccgg     6060 tccccctcccc cgcctcctcg tccgccccc cgccgtccag gtacctagcg cgttccggcg    6120
cggaggttta aagaccccett gggggatcc cccgtccgcc cgtgggtcgg gggcggtggt    6180
gggcccgcgg gggagtcccg tcgggagggg cccggcccct cccgcgcctc caccgcggac    6240
tccgctcccc ggccggggcc gcgccgccgc cgccgccgcg gcggccgtcg ggtgggggct    6300
ttacccggcg gccgtcgcgc gcctgccgcg cgtgtggcgt gcgccccgcg ccgtggggc     6360 gggaaccccc gggcgcctgt ggggtggtgt ccgcgctcgc ccccgcgtgg gcggcgcgcg    6420
cctccccgtg gtgtgaaacc ttccgacccc tctccggagt ccggtcccgt ttgctgtctc    6480
gtctggccgg cctgaggcaa cccccctctcc tcttgggcgg gggggggggg gacgtgccgc    6540
gccaggaagg gcctcctccc ggtgcgtcgt cgggagcgcc ctcgccaaat cgacctcgta    6600
cgactcttag cggtggatca ctcggctcgt gcgtcgatga agaacgcagc tagctgcgag    6660
aattaatgtg aattgcagga cacattgatc atcgacactt cgaacgcact tgcggccccg    6720
ggttcctccc ggggctacgc ctgtctgagc gtcgcttgcc gatcaatcgc ccccgggggt    6780
gcctccgggc tcctcggggt gcggcggctgg gggttccctc gcagggcccg ccgggggccc    6840
tccgtccccc taagcgcaga cccggcggcg tccgccctcc tcttgccgcc gcgcccgccc    6900
cttccccctc cccccgcggg ccctgcgtgg tcacgcgtcg ggtggcgggg gggagagggg    6960
ggcgcgcccg gctgagagag acggggaggg cggcgccgcc gccgcccgcg aagacggaga    7020
gggaaagaga gagccggctc gggccgagtt cccgtggccg ccgcctgcgg tccgggttcc    7080
tccctcgggg ggctccctcg cgccgcgcgc ggctcggggt tcggggttcg tcggccccgg    7140
ccgggtggaa ggtccgtgc ccgtcgtcgt cgtcgtcgtc gcgcgtcgtc ggcggtgggg     7200
gcgtgttgcg tgcggtgtgg tggtgggga ggaggaaggc gggtccggaa ggggaagggt     7260
gccggcgggg agagagggtc gggggagcgc gtcccggtcg ccgcggttcg ccgcccgccc    7320
ccggtggcgg cccggcgtcc ggccgaccgc cgctcccgcg cccctcctcc tccccgccgc    7380
ccctcctccg aggccccgcc cgtcctcctc gccctccccg cgcgtacgcg cgcccgcccg    7440
cccggctcgc ctcgcggcgc gtcggccggg gccgggagcc cgccccgcgg cccgcccggc    7500
cgcgcccgtg gccgcggcgc cgggggttcgc gtgtccccgg cggcgacccg cgggacgccg    7560
cggtgtcgtc cgccgtcgcg cgcccgcctc cggctcgcgg ccgcgccgcg ccgcgccggg    7620
gccccgtccc gagcttccgc gtcggggcgg ggcggctccg ccgccgcgtc ctcggacccg    7680
tccccccgac ctccgcgggg gagacgggtc ggggcgtgcg gcgcccgtcc cgcccccggc    7740
ccgtgcccct ccctccggtc gtccgctcc ggcggggcgg cgcggggggtg ccgccggccg    7800 cgcgctctct ctcccgtcgc ctctccccct gccggggccc gtctcccgac ggagcgtcgg    7860
gcgggcggtc gggccggcgc gattccgtcc gtccgtccgc cgagcggccc gtccccctcc    7920
gagacgcgac ctcagatcag acgtggcgac ccgctgaatt taagcatatt agtcagcgga    7980
ggagaagaaa ctaaccagga ttccctcagt aacggcgagt gaacagggaa gagcccagcg    8040
ccgaatcccc gcccgcgcgg ggggcgcggg acatgtggcg tacggaagac ccgctccccg    8100
gcgccgctcg tggggggccc aagtccttct gatcgaggcc cagcccgtgg acggtgtgag    8160
gccggtagcg gccccccggcg cgccgggccc gggtcttccc ggagtcgggt tgcttgggaa    8220
```

-continued

```
tgcagcccaa agcgggtggt aaactccatc taaggctaaa taccggcacg agaccgatag    8280
tcaacaagta ccgtaaggga aagttgaaaa gaactttgaa gagagagttc aagagggcgt    8340
gaaaccgtta agaggtaaac gggtggggtc cgcgcagtcc gcccggagga ttcaacccgg    8400
cggcgggtcc ggccgtgtcg gcggcccggc ggatctttcc cgccccccgt tcctcccgac    8460
ccctccaccc gccctccctt ccccgccgc ccctcctcct cctccccgga gggggcgggc     8520
tccggcgggt gcggggtgg gcgggcgggg ccggggtgg ggtcggcggg ggaccgtccc      8580
ccgaccggcg accggccgcc gccgggcgca tttccaccgc ggcggtgcgc cgcgaccggc    8640
tccgggacgg ctgggaaggc ccggcgggga aggtggctcg ggggcccg tccgtccgtc      8700
cgtccgtcct cctcctcccc cgtctccgcc ccccggcccc gcgtcctccc tcgggagggc    8760
gcgcgggtcg gggcggcggc ggcggcggcg gtggcggcgg cggcggcggc ggcgggaccg    8820
aaaccccccc cgagtgttac agcccccccg gcagcagcac tcgccgaatc ccggggccga    8880
gggagcgaga cccgtcgccg cgctctcccc cctccccggcg cccaccccg cggggaatcc    8940
cccgcgaggg gggtctcccc cgcgggggcg cgccggcgtc tcctcgtggg ggggccgggc    9000
caccctcccc acgcgcgac cgctctccca ccctcctcc ccgcgccccc gccccggcga      9060
cggggggggt gccgcgcgcg ggtcggggg cgggcggac tgtccccagt gcgccccggg      9120
cgggtcgcgc cgtcgggccc ggggaggtt ctctcggggc cacgcgcgcg tcccccgaag     9180
aggggacgg cggagcgagc gcacgggtc ggcggcgacg tcggctaccc acccgacccg      9240
tcttgaaaca cggaccaagg agtctaacac gtgcgcgagt cggggctcg cacgaaagcc     9300
gccgtggcgc aatgaaggtg aaggccggcg cgctcgccgg ccgaggtggg atcccgaggc    9360
ctctccagtc cgccgaggc gcaccaccgg cccgtctcgc ccgccgcgcc ggggaggtgg     9420
agcacgagcg cacgtgttag gacccgaaag atggtgaact atgcctgggc agggcgaagc    9480
cagaggaaac tctggtggag gtccgtagcg gtcctgacgt gcaaatcggt cgtccgacct    9540
gggtataggg gcgaaagact aatcgaacca tctagtagct ggttccctcc gaagtttccc    9600
tcaggatagc tggcgctctc gcagacccga cgcacccccg ccacgcagtt ttatccggta    9660
aagcgaatga ttagaggtct tggggccgaa acgatctcaa cctattctca aactttaaat    9720
gggtaagaag cccggctcgc tggcgtggag ccgggcgtgg aatgcgagtg cctagtgggc    9780
cacttttggt aagcagaact ggcgctgcgg gatgaaccga acgccgggtt aaggcgcccg    9840
atgccgacgc tcatcagacc ccagaaaagg tgttggttga tatagacagc aggacggtgg    9900
ccatggaagt cggaatccgc taaggagtgt gtaacaactc acctgccgaa tcaactagcc    9960
ctgaaaatgg atggcgctgg agcgtcgggc ccatacccgg ccgtcgccgg cagtcgagag   10020
tggacgggag cggcggggc ggcgcgcgcg cgcgcgcgtg tggtgtgcgt cggagggcgg    10080
cggcggcggc ggcggcgggg gtgtggggtc cttccccgc cccccccccc acgcctcctc    10140
ccctcctccc gcccacgccc cgctccccgc cccggagcc ccgcggacgc tacgccgcga    10200
cgagtaggag ggccgctgcg gtgagccttg aagcctaggg cgcgggcccg ggtggagccg    10260
ccgcaggtgc agatcttggt ggtagtagca aatattcaaa cgagaacttt gaaggccgaa    10320
gtggagaagg gttccatgtg aacagcagtt gaacatgggt cagtcggtcc tgagagatgg    10380
gcgagcgccg ttccgaaggg acgggcgatg gcctccgttg ccctcggccg atcgaaaggg    10440
agtcgggttc agatccccga atccggagtg gcggagatgg gcgccgcgag gcgtccagtg    10500
cggtaacgcg accgatcccg gagaagccgg cgggagcccc ggggagagtt ctcttttctt    10560
```

```
tgtgaagggc agggcgccct ggaatgggtt cgccccgaga gaggggcccg tgccttggaa    10620
agcgtcgcgg ttccggcggc gtccggtgag ctctcgctgg cccttgaaaa tccgggggag    10680
agggtgtaaa tctcgcgccg ggccgtaccc atatccgcag caggtctcca aggtgaacag    10740
cctctggcat gttggaacaa tgtaggtaag ggaagtcggc aagccggatc cgtaacttcg    10800
ggataaggat tggctctaag ggctgggtcg gtcgggctgg ggcgcgaagc ggggctgggc    10860
gcgcgccgcg gctggacgag gcgccgccgc cccccccacg cccggggcac cccctcgcg    10920 gccctccccc gccccacccc gcgcgcgccg ctcgctccct ccccgccccg cgccctctct    10980
ctctctctct ccccgctcc ccgtcctccc cctcccccgg gggagcgccg cgtgggggcg    11040
gcggcggggg gagaagggtc ggggcggcag gggccggcgg cggcccgccg cggggccccg    11100
gcggcggggg cacggtcccc cgcgaggggg gcccgggcac ccgggggggcc ggcggcggcg    11160 gcgactctgg acgcgagccg ggcccttccc gtggatcgcc ccagctgcgg cgggcgtcgc    11220
ggccgccccc ggggagcccg gcgggcgccg gcgcgccccc cccccaccc cacgtctcgt    11280 cgcgcgcgcg tccgctgggg gcggggagcg gtcgggcggc ggcggtcggc gggcggcggg    11340
gcggggcggt tcgtccccc gccctacccc ccggcccccg tccgccccc gttcccccct    11400 cctcctcggc gcgcggcggc ggcggcggca ggcggcggag gggccgcggg ccggtccccc    11460
ccgccgggtc cgcccccggg gccgcggttc cgcgcggcgc ctcgcctcgg ccggcgccta    11520
gcagccgact tagaactggt gcggaccagg ggaatccgac tgtttaatta aaacaaagca    11580
tcgcgaaggc ccgcggcggg tgttgacgcg atgtgatttc tgcccagtgc tctgaatgtc    11640
aaagtgaaga aattcaatga agcgcgggta acggcgggga gtaactatga ctctcttaag    11700
gtagccaaat gcctcgtcat ctaattagtg acgcgcatga atggatgaac gagattccca    11760
ctgtccctac ctactatcca gcgaaaccac agccaaggga acgggcttgg cggaatcagc    11820
ggggaaagaa gaccctgttg agcttgactc tagtctggca cggtgaagag acatgagagg    11880
tgtagaataa gtgggaggcc cccggcgccc ccccggtgtc cccgcgaggg gcccggggcg    11940
gggtccgccg gccctgcggg ccgccggtga ataccacta ctctgatcgt tttttcactg    12000
acccggtgag gcggggggc gagccccgag gggctctcgc ttctggcgcc aagcgcccgg    12060
ccgcgcgccg gccgggcgcg accccgctccg gggacagtgc caggtgggga gtttgactgg    12120
ggcggtacac ctgtcaaacg gtaacgcagg tgtcctaagg cgagctcagg gaggacagaa    12180
acctcccgtg gagcagaagg gcaaaagctc gcttgatctt gattttcagt acgaatacag    12240
accgtgaaag cggggcctca cgatccttct gacctttttgg gttttaagca ggaggtgtca    12300
gaaaagttac cacagggata actggcttgt ggcggccaag cgttcatagc gacgtcgctt    12360
tttgatcctt cgatgtcggc tcttcctatc attgtgaagc agaattcacc aagcgttgga    12420 tgttcaccc actaataggg aacgtgagct gggtttagac cgtcgtgaga caggttagtt    12480
ttaccctact gatgatgtgt tgttgccatg gtaatcctgc tcagtacgag aggaaccgca    12540
ggttcagaca tttggtgtat gtgcttggct gaggagccaa tggggcgaag ctaccatctg    12600
tgggattatg actgaacgcc tctaagtcag aatcccgccc aggcggaacg atacggcagc    12660
gccgcggagc ctcggttggc ctcggatagc cggtcccccg cctgtccccg ccggcgggcc    12720
gccccccccc tccacgcgcc ccgcgcgcgc gggagggcgc gtgcccgcc gcgcgccggg    12780 accggggtcc ggtgcggagt gcccttcgtc ctgggaaacg gggcgcggcc ggagaggcgg    12840 ccgcccctc gcccgtcacg caccgcacgt tcgtggggaa cctggcgcta aaccattcgt    12900
agacgacctg cttctgggtc ggggtttcgt acgtagcaga gcagctccct cgctgcgatc    12960
```

-continued

```
tattgaaagt cagccctcga cacaagggtt tgtccgcgcg cgcgcgcgcg cgcgcgtgcg   13020
gggggcccgg cggggcgtgc gcgtccggcg ccgtccgtcc ttccgttcgt cttcctccct   13080
cccggcctct cccgccgacc gcgggcgtgg tggtgggggt gtggggggga gggcgcgcga   13140
ccccggtcgg cgcgccccgc ttcttcggtt cccgcctcct ccccgttcac cgccggggcg   13200
gctcgtccgc tccgggccgg gacggggtcc ggggagcgtg gtttgggagc cgcggaggcg   13260
gccgcgccga gccgggcccg tggcccgccg gtccccgtcc cggggttgg ccgcgcgggc    13320 cccggtgggg cggccacccg gggtcccggc cctcgcg                            13357
```

<210> SEQ ID NO 69
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 69

```
tttcttgtaa gcgtcgaggt g                                                21
```

<210> SEQ ID NO 70
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 70

```
agcaggcacc taggagacaa                                                  20
```

<210> SEQ ID NO 71
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 71

```
tcaggcgttc tcgtctcc                                                    18
```

<210> SEQ ID NO 72
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 72

```
caccacatcg atcacgaaga                                                  20
```

<210> SEQ ID NO 73
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 73

```
ctatgcgcac ccgttctc                                                    18
```

<210> SEQ ID NO 74
<211> LENGTH: 18
<212> TYPE: DNA

```
<213> ORGANISM: Artificial sequence
<220> FEATURE:
<223> OTHER INFORMATION: Single strand DNA oligonucleotide

<400> SEQUENCE: 74
gtagcgaagc gagcagga                                                18
```